United States Patent
Umetani et al.

(10) Patent No.: US 11,147,272 B2
(45) Date of Patent: Oct. 19, 2021

(54) PYRIDONE COMPOUNDS AND AGRICULTURAL AND HORTICULTURAL FUNGICIDES COMPRISING THE SAME AS ACTIVE INGREDIENTS

(71) Applicant: MITSUI CHEMICALS AGRO, INC., Tokyo (JP)

(72) Inventors: Hideki Umetani, Ritto (JP); Hideaki Ikishima, Chiba (JP); Akihiro Nishida, Chiba (JP); Shun Okaya, Mobara (JP); Ryohei Naito, Kusatsu (JP); Takeshi Fukumoto, Chiba (JP); Satoshi Yutani, Ratchaburi (TH); Toshiaki Ohara, Moriyama (JP)

(73) Assignee: MITSUI CHEMICALS ARGRO, INC., Tokyo (JP)

( * ) Notice: Subject to any disclaimer, the term of this patent is extended or adjusted under 35 U.S.C. 154(b) by 0 days.

(21) Appl. No.: 16/603,075

(22) PCT Filed: Apr. 10, 2018

(86) PCT No.: PCT/JP2018/015140
§ 371 (c)(1),
(2) Date: Oct. 4, 2019

(87) PCT Pub. No.: WO2018/190350
PCT Pub. Date: Oct. 18, 2018

(65) Prior Publication Data
US 2020/0045963 A1     Feb. 13, 2020

(30) Foreign Application Priority Data

Apr. 10, 2017 (JP) ............... JP2017-077801

(51) Int. Cl.
*A01N 43/40* (2006.01)
*C07D 213/89* (2006.01)

(52) U.S. Cl.
CPC ........... *A01N 43/40* (2013.01); *C07D 213/89* (2013.01)

(58) Field of Classification Search
CPC ..................................... A01N 43/40
USPC ....................................... 546/339
See application file for complete search history.

(56) References Cited

U.S. PATENT DOCUMENTS

| | | | |
|---|---|---|---|
| 6,200,982 B1 | 3/2001 | Collins et al. | |
| 10,299,477 B2 * | 5/2019 | Umetani | A01N 55/00 |
| 2001/0018438 A1 | 8/2001 | Collins et al. | |
| 2010/0222592 A1 | 9/2010 | Takabe et al. | |
| 2017/0217890 A1 | 8/2017 | Johns et al. | |
| 2018/0279614 A1 | 10/2018 | Umetani et al. | |
| 2019/0144459 A1 | 5/2019 | Cacatian et al. | |

FOREIGN PATENT DOCUMENTS

| | | |
|---|---|---|
| EP | 0308020 A2 | 3/1989 |
| JP | H02-121970 A | 5/1990 |
| WO | 9855480 A1 | 12/1998 |
| WO | 2007088876 A1 | 8/2007 |
| WO | 2010093595 A1 | 8/2010 |
| WO | 2016012913 A1 | 1/2016 |
| WO | 2016096942 A1 | 6/2016 |
| WO | 2017061525 A1 | 4/2017 |
| WO | 2017214367 A1 | 12/2017 |

OTHER PUBLICATIONS

Su, Organic Letters (2010), 12(23), 5462-5465.*
Linda Hall, How Herbicides Work, Biology to Application, 2014, Alberta Agriculture and Rural Development, Information Management.*
Zhang, ACS Appl. Mater. Interfaces 2013, 5, 10953-10959.*
Dorwald, Side Reactions in Organic Synthesis, 2005, Wiley: VCH, Weinheim p. IX of Preface p. 1-15.*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Venkatesh, J. Pharm. Sci. 89, 145-154 (2000) (p. 146.*
Liu, Nature, Scientific Reports, 7:42096, 2017, 1-17.*
El-Nawawy, Journal of Microbiology of the United Arab Republic (1967), 2(2), 115-33.*
International Search Report (PCT/ISA/210) dated May 15, 2018, by the Japanese Patent Office as the International Searching Authority for International Application No. PCT/JP2018/015140.
The extended European Search Report dated Jul. 28, 2020, by the European Patent Office in corresponding European Patent Application No. 18784047.5. (8 pages).
"2(1H)-Pyridinone, 5-cyclopropyl-6-(5-fluoro-2-hydroxyphenyl)-1-methyl-", Registry, Chemical Abstracts Service, Columbus, Ohio, US, (Nov. 4, 2011), Database accession No. 1347867-95-1/rn, XP055715791 [X] 1* abstract*.

* cited by examiner

*Primary Examiner* — Nizal S Chandrakumar
(74) *Attorney, Agent, or Firm* — Buchanan Ingersoll & Rooney PC

(57) ABSTRACT

Pyridone compounds of formula (1) and salts thereof:

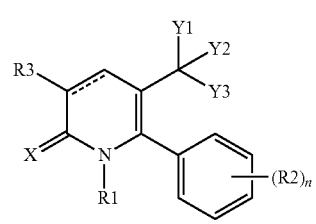

(1)

wherein R1, R2, R3, X, Y1, Y2, Y3 and n are defined. The pyridone compounds can control plant diseases.

5 Claims, No Drawings

PYRIDONE COMPOUNDS AND AGRICULTURAL AND HORTICULTURAL FUNGICIDES COMPRISING THE SAME AS ACTIVE INGREDIENTS

TECHNICAL FIELD

The present invention relates to pyridone compounds and to agricultural chemicals comprising the compounds as active ingredients.

BACKGROUND ART

The protection of agricultural and horticultural crops from diseases is important to ensure stable agricultural production, and various fungicides are used for this purpose. However, fungi become resistant to fungicides due to a long time use of fungicides, and thus, novel fungicides that are effective not only to drug-sensitive fungi but also to drug-resistant fungi are demanded.

1,3,5,6-Substituted-2-pyridone compounds are known in the art. For example, 1,3,5,6-substituted-2-pyridone compounds having an aryl group or a heteroaryl group at the 3-position are disclosed as GABA alpha 2/3 ligands (see, for example, WO 98/55480). 1,3,5,6-Substituted-2-pyridone compounds having a carboxyl group at the 3-position are disclosed as medicaments for treating bacterial infections (see, for example, European Patent No. 0308020). Further, 1,3,5,6-substituted-2-pyridone compounds having 4,4-dimethylpentanoic acid at the 1-position are disclosed as anti-HIV agents (see, for example, WO 2016/012913).

CITATION LIST

Patent Literature

Patent Literature 1: WO 98/55480
Patent Literature 2: European Patent No. 0308020
Patent Literature 3: WO 2016/12913

SUMMARY OF INVENTION

Technical Problem

The compounds described in WO 98/55480, European Patent No. 0308020 and WO 2016/12913 are for medicinal use and do not pertain to the field of art to which the agricultural and horticultural fungicides of the present invention belong.

An object of the present invention is to provide novel pyridone compounds that are effective as agricultural and horticultural fungicides.

Solution to Problem

To achieve the above object, the present inventors carried out extensive studies on 1,3,5,6-substituted-2-pyridone compounds and 1,5,6-substituted-2-pyridone compounds. As a result, the inventors have found that novel compounds, which is synthesized by introducing an alkyl groups and a substituted methyl to the 1-position and the 5-position, respectively, of the 2-pyridone skeleton, show good activity in controlling plant diseases, and thereby, the invention has been completed.

Specifically, the present invention pertains to the following.

[1] A compound of formula (1) or a salt thereof:

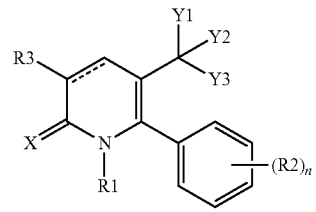

(1)

wherein R1 represents:
  a cyano group,
  a C1-C6 alkyl group optionally substituted with substituent(s) A,
  a C1-C6 haloalkyl group,
  a C3-C8 cycloalkyl group optionally substituted with substituent(s) A,
  a C2-C6 alkenyl group optionally substituted with substituent(s) A,
  a C2-C6 haloalkenyl group,
  a C2-C6 alkynyl group optionally substituted with substituent(s) A,
  a C2-C6 haloalkynyl group,
  a C1-C6 alkoxy group optionally substituted with substituent(s) A,
  a C1-C6 haloalkoxy group,
  a C3-C8 cycloalkoxy group optionally substituted with substituent(s) A,
  a C2-C6 alkenyloxy group optionally substituted with substituent(s) A,
  a C2-C6 haloalkenyloxy group,
  a C3-C6 alkynyloxy group optionally substituted with substituent(s) A, or
  a C3-C6 haloalkynyloxy group;
R2 represents:
  a hydroxy group,
  a cyano group,
  a nitro group,
  a halogen atom,
  a C1-C6 alkyl group optionally substituted with substituent(s) B,
  a C1-C6 haloalkyl group,
  a C3-C8 cycloalkyl group optionally substituted with substituent(s) B,
  a C2-C6 alkenyl group optionally substituted with substituent(s) B,
  a C2-C6 haloalkenyl group,
  a C2-C6 alkynyl group optionally substituted with substituent(s) B,
  a C2-C6 haloalkynyl group,
  a C1-C6 alkoxy group optionally substituted with substituent(s) B,
  a C1-C6 haloalkoxy group,
  a C3-C8 cycloalkoxy group optionally substituted with substituent(s) B,
  a C2-C6 alkenyloxy group optionally substituted with substituent(s) B,
  a C2-C6 haloalkenyloxy group,
  a C3-C6 alkynyloxy group optionally substituted with substituent(s) B,
  a C3-C6 haloalkynyloxy group, RdC(=O)— (wherein Rd represents a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are independent of one another and each represent a hydrogen atom, a C1-C6 alkyl group optionally substituted with substituent(s) C, a C1-C6 haloalkyl group, or a C3-C8 cycloalkyl group, or Ra and Rb, together with the nitrogen atom to which they are bonded, form aziridinyl, azetidinyl, pyrrolidinyl, piperidinyl, homopiperidinyl or azocanyl)), RdC(=O)O— (wherein Rd is the same as defined hereinabove), an aryloxy group optionally substituted with 0 to 5 substituents D, a heteroaryloxy group optionally substituted with 0 to 2 substituents D, an aralkyloxy group optionally substituted with 0 to 5 substituents D, a 3 to 6-membered ring group containing 1 to 2 oxygen atoms, Rc-L- (wherein Rc represents a C1-C6 alkyl group or a C1-C6 haloalkyl group, and L represents S, SO or $SO_2$), RaRbN— (wherein Ra and Rb are the same as defined hereinabove), Rg(RhO)N— (wherein Rg and Rh are independent of one another and each represent a hydrogen atom, a C1-C6 alkyl group optionally substituted with substituent(s) C, a C1-C6 haloalkyl group, or a C3-C8 cycloalkyl group), or ReC(=O)N(Rf)— (wherein Re and Rf are independent of one another and each represent a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove));

R3 represents:
a hydrogen atom,
a cyano group,
a nitro group,
a halogen atom,
a C1-C6 alkyl group optionally substituted with substituent(s) A,
a C1-C6 haloalkyl group,
a C3-C8 cycloalkyl group optionally substituted with substituent(s) A,
a C2-C6 alkenyl group optionally substituted with substituent(s) A,
a C2-C6 haloalkenyl group,
a C2-C6 alkynyl group optionally substituted with substituent(s) A,
a C2-C6 haloalkynyl group,
a C1-C6 alkoxy group optionally substituted with substituent(s) A,
a C1-C6 haloalkoxy group,
a C3-C8 cycloalkoxy group optionally substituted with substituent(s) A,
a C2-C6 alkenyloxy group optionally substituted with substituent(s) A,
a C2-C6 haloalkenyloxy group,
a C3-C6 alkynyloxy group optionally substituted with substituent(s) A,
a C3-C6 haloalkynyloxy group, Rc-L- (wherein Rc and L are the same as defined hereinabove), RaRbN— (wherein Ra and Rb are the same as defined hereinabove), or RiC(=O)— (wherein Ri represents a C1-C6 alkyl group optionally substituted with substituent(s) C, a C1-C6 haloalkyl group, or a C3-C8 cycloalkyl group);

Y1, Y2 and Y3 are independent of one another and each represent:
a hydrogen atom,
a hydroxy group,
a cyano group,
a halogen atom,
a C1-C9 alkyl group optionally substituted with substituent(s) B,
a C1-C6 haloalkyl group,
a C3-C8 cycloalkyl group optionally substituted with substituent(s) B,
a C2-C6 alkenyl group optionally substituted with substituent(s) B,
a C2-C6 haloalkenyl group,
a C2-C6 alkynyl group optionally substituted with substituent(s) B,
a C2-C6 haloalkynyl group,
a C1-C6 alkoxy group optionally substituted with substituent(s) B,
a C1-C6 haloalkoxy group,
a C3-C8 cycloalkoxy group optionally substituted with substituent(s) B,
a C2-C6 alkenyloxy group optionally substituted with substituent(s) B,
a C2-C6 haloalkenyloxy group,
a C3-C6 alkynyloxy group optionally substituted with substituent(s) B,
a C3-C6 haloalkynyloxy group,
RdC(=O)— (wherein Rd is the same as defined hereinabove),
RdC(=O)O— (wherein Rd is the same as defined hereinabove),
an aryloxy group optionally substituted with 0 to 5 substituents D,
a heteroaryloxy group optionally substituted with 0 to 2 substituents D,
an aralkyloxy group optionally substituted with 0 to 5 substituents D,
Rc-L- (wherein Rc and L are the same as defined hereinabove),
RaRbN— (wherein Ra and Rb are the same as defined hereinabove),
Rg(RhO)N— (wherein Rg and Rh are the same as defined hereinabove), or
ReC(=O)N(Rf)— (wherein Re and Rf are the same as defined hereinabove), Y1 and Y2, together with the carbon atom to which Y1, Y2 and Y3 are bonded, form:
a carbonyl group,
a C2-C6 alkenyl group optionally substituted with substituent(s) B,
a C2-C6 haloalkenyl group, or
a C3-C8 cycloalkyl group optionally substituted with substituent(s) B, and Y3 represents:
a hydrogen atom,
a halogen atom,
a C1-C9 alkyl group optionally substituted with substituent(s) B,
a C1-C6 haloalkyl group, a C3-C8 cycloalkyl group optionally substituted with substituent(s) B,
a C2-C6 alkenyl group optionally substituted with substituent(s) B,
a C2-C6 haloalkenyl group,
a C2-C6 alkynyl group optionally substituted with substituent(s) B, or
a C2-C6 haloalkynyl group, or
Y1, Y2 and Y3, together with the carbon atom to which Y1, Y2 and Y3 are bonded, represent:
a cyano group, or
a C2-C6 alkynyl group optionally substituted with substituent(s) B;
n represents an integer of 1 to 5 (with the proviso that when n is 2 or greater, the two or more substituents R2 are independent of one another);
X represents an oxygen atom or a sulfur atom;
the bond with the broken line represents a double bond or a single bond;
the substituent(s) A is at least one selected from the group consisting of hydroxy group, cyano group, C3-C8 cycloalkyl groups, C1-C6 alkoxy groups, C1-C6 haloalkoxy groups, C3-C8 cycloalkoxy groups, RaRbN— (wherein Ra and Rb are the same as defined hereinabove) and Rc-L- (wherein Rc and L are the same as defined hereinabove);
the substituent(s) B is at least one selected from the group consisting of hydroxy group, cyano group, C3-C8 cycloalkyl groups, C1-C6 alkoxy groups, C1-C6 haloalkoxy groups, C3-C8 cycloalkoxy groups, C2-C6 alkoxyalkoxy groups, RaRbN— (wherein Ra and Rb are the same as defined hereinabove), Rc-L- (wherein Rc and L are the same as defined hereinabove), RdC(=O)— (wherein Rd is the same as defined hereinabove) and 3 to 6-membered ring groups containing 1 to 2 oxygen atoms;
the substituent(s) C is at least one selected from the group consisting of cyano group, C1-C6 alkoxy groups, C1-C6 haloalkoxy groups and C3-C8 cycloalkoxy groups; and
the substituent(s) D is at least one selected from the group consisting of halogen atoms, hydroxy group, cyano group, nitro group, C1-C6 alkyl groups optionally substituted with substituent(s) C, C1-C6 haloalkyl groups, C3-C8 cycloalkyl groups, C1-C6 alkoxy groups, C1-C6 haloalkoxy groups and C3-C8 cycloalkoxy groups.

[2] The compound described in [1] or a salt thereof, wherein
R1 represents:
a C1-C6 alkyl group optionally substituted with substituent(s) A,
a C1-C6 haloalkyl group,
a C2-C6 alkenyl group optionally substituted with substituent(s) A,
a C2-C6 haloalkenyl group,
a C2-C6 alkynyl group optionally substituted with substituent(s) A, or
a C2-C6 haloalkynyl group;
R2 represents:
a hydroxy group,
a cyano group,
a halogen atom,
a C1-C6 alkyl group optionally substituted with substituent(s) B,
a C1-C6 haloalkyl group,
a C3-C8 cycloalkyl group optionally substituted with substituent(s) B,
a C1-C6 alkoxy group optionally substituted with substituent(s) B,
a C1-C6 haloalkoxy group,
a C3-C8 cycloalkoxy group optionally substituted with substituent(s) B,
a C2-C6 alkenyloxy group optionally substituted with substituent(s) B,
a C2-C6 haloalkenyloxy group,
a C3-C6 alkynyloxy group optionally substituted with substituent(s) B,
a C3-C6 haloalkynyloxy group,
RdC(=O)O— (wherein Rd represents a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are independent of one another and each represent a hydrogen atom, a C1-C6 alkyl group optionally substituted with substituent(s) C, a C1-C6 haloalkyl group, or a C3-C8 cycloalkyl group, or Ra and Rb, together with the nitrogen atom to which they are bonded, form aziridinyl, azetidinyl, pyrrolidinyl, piperidinyl, homopiperidinyl or azocanyl)), or
Rc-L- (wherein Rc represents a C1-C6 alkyl group or a C1-C6 haloalkyl group, and L represents S, SO or SO2);
R3 represents:
a hydrogen atom,
a halogen atom,
a C1-C6 alkyl group optionally substituted with substituent(s) A,
a C1-C6 alkoxy group optionally substituted with substituent(s) A,
Rc-L- (wherein Rc and L are the same as defined hereinabove), or
RiC(=O)— (wherein Ri represents a C1-C6 alkyl group optionally substituted with substituent(s) C, a C1-C6 haloalkyl group, or a C3-C8 cycloalkyl group);
Y1, Y2 and Y3 are independent of one another and each represent:
a hydrogen atom,
a hydroxy group,
a cyano group,
a halogen atom,
a C1-C9 alkyl group optionally substituted with substituent(s) B,
a C1-C6 haloalkyl group,
a C3-C8 cycloalkyl group optionally substituted with substituent(s) B,
a C2-C6 alkenyl group optionally substituted with substituent(s) B,
a C2-C6 alkynyl group optionally substituted with substituent(s) B,
a C1-C6 alkoxy group optionally substituted with substituent(s) B,
a C1-C6 haloalkoxy group,
a C3-C8 cycloalkoxy group optionally substituted with substituent(s) B,
a C2-C6 alkenyloxy group optionally substituted with substituent(s) B,
a C3-C6 alkynyloxy group optionally substituted with substituent(s) B,
RdC(=O)— (wherein Rd is the same as defined hereinabove),
RdC(=O)O— (wherein Rd is the same as defined hereinabove),
an aryloxy group optionally substituted with 0 to 5 substituents D,
Rc-L- (wherein Rc and L are the same as defined hereinabove), RaRbN— (wherein Ra and Rb are the same as defined hereinabove), Rg(RhO)N— (wherein Rg and Rh are independent of one another and each represent a hydrogen atom, a C1-C6 alkyl group optionally substituted with substituent(s) C, a C1-C6 haloalkyl group, or a C3-C8 cycloalkyl group), or ReC(=O)N(Rf)— (wherein Re and Rf are independent of one another and each represent a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove)), Y1 and Y2, together with the carbon atom to which Y1, Y2 and Y3 are bonded, form:
a carbonyl group,
a C2-C6 alkenyl group optionally substituted with substituent(s) B,
a C2-C6 haloalkenyl group, or
a C3-C8 cycloalkyl group optionally substituted with substituent(s) B, and Y3 represents:
a hydrogen atom,
a halogen atom,
a C1-C9 alkyl group optionally substituted with substituent(s) B,
a C1-C6 haloalkyl group,
a C3-C8 cycloalkyl group optionally substituted with substituent(s) B,
a C2-C6 alkenyl group optionally substituted with substituent(s) B,
a C2-C6 haloalkenyl group,
a C2-C6 alkynyl group optionally substituted with substituent(s) B, or
a C2-C6 haloalkynyl group, or Y1, Y2 and Y3, together with the carbon atom to which Y1, Y2 and Y3 are bonded, represent:
a cyano group, or
a C2-C6 alkynyl group optionally substituted with substituent(s) B.

[3] The compound described in [2] or a salt thereof, wherein
R1 represents:
a C1-C6 alkyl group optionally substituted with substituent(s) A, or
a C1-C6 haloalkyl group;
R2 represents:
a hydroxy group,
a cyano group,
a halogen atom,
a C1-C6 alkyl group optionally substituted with substituent(s) B,
a C1-C6 alkoxy group optionally substituted with substituent(s) B,
a C2-C6 alkenyloxy group optionally substituted with substituent(s) B, or
a C3-C6 alkynyloxy group optionally substituted with substituent(s) B;
R3 represents:
a hydrogen atom,
a halogen atom, or
a C1-C6 alkyl group optionally substituted with substituent(s) A; and Y1, Y2 and Y3 are independent of one another and each represent:
a hydrogen atom,
a hydroxy group,
a halogen atom,
a C1-C9 alkyl group optionally substituted with substituent(s) B,
a C1-C6 haloalkyl group,
a C3-C8 cycloalkyl group optionally substituted with substituent(s) B,
a C2-C6 alkynyl group optionally substituted with substituent(s) B,
a C1-C6 alkoxy group optionally substituted with substituent(s) B,
a C1-C6 haloalkoxy group,
RdC(=O)— (wherein Rd represents a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are independent of one another and each represent a hydrogen atom, a C1-C6 alkyl group optionally substituted with substituent(s) C, a C1-C6 haloalkyl group, or a C3-C8 cycloalkyl group, or Ra and Rb, together with the nitrogen atom to which they are bonded, form aziridinyl, azetidinyl, pyrrolidinyl, piperidinyl, homopiperidinyl or azocanyl)),
RdC(=O)O— (wherein Rd is the same as defined hereinabove),
an aryloxy group optionally substituted with 0 to 5 substituents D,
RaRbN— (wherein Ra and Rb are the same as defined hereinabove),
Rg(RhO)N— (wherein Rg and Rh are independent of one another and each represent a hydrogen atom, a C1-C6 alkyl group optionally substituted with substituent(s) C, a C1-C6 haloalkyl group, or a C3-C8 cycloalkyl group), or
ReC(=O)N(Rf)— (wherein Re and Rf are independent of one another and each represent a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove)), and Y1 and Y2, together with the carbon atom to which Y1, Y2 and Y3 are bonded, form:
a carbonyl group,
a C2-C6 alkenyl group optionally substituted with substituent(s) B,
a C2-C6 haloalkenyl group, or
a C3-C8 cycloalkyl group optionally substituted with substituent(s) B, and Y3 represents:
a hydrogen atom,
a halogen atom,
a C1-C9 alkyl group optionally substituted with substituent(s) B,
a C3-C8 cycloalkyl group optionally substituted with substituent(s) B, or
a C2-C6 alkynyl group optionally substituted with substituent(s) B, or Y1, Y2 and Y3, together with the carbon atom to which Y1, Y2 and Y3 are bonded, represent:
a cyano group, or
a C2-C6 alkynyl group optionally substituted with substituent(s) B.

[4] The compound described in any one of [1] to [3] or a salt thereof, wherein R1 is methyl, ethyl, propyl, or 2,2-difluoroethyl.

[5] The compound described in any one of [1] to [4] or a salt thereof, wherein R2 is a hydroxy group, a cyano group, fluorine atom, chlorine atom, bromine atom, methyl, ethyl, methoxy, cyanomethoxy, cyclopropylmethoxy, methoxymethoxy, methylthiomethoxy, ethoxy, methoxyethoxy, propyloxy, allyloxy, propargyloxy, or 2-butynyloxy.

[6] The compound described in any one of [1] to [4] or a salt thereof, wherein the partial structure (A) in the formula (1):

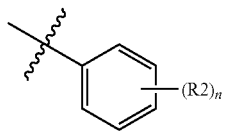

(A)

is 2,4,6-trifluorophenyl, 2,4-dichlorophenyl, 2,4-difluorophenyl, 2,6-difluoro-4-ethoxyphenyl, 2,6-difluoro-4-(methoxyethoxy)phenyl, 2,6-difluoro-4-methoxyphenyl, 2,6-difluorophenyl, 2-bromo-4-fluorophenyl, 2-chloro-4-fluorophenyl, 2-chloro-4-hydroxyphenyl, 2-chloro-4-methoxyphenyl, 2-chlorophenyl, 2-ethyl-4-fluorophenyl, 2-fluoro-4-chlorophenyl, 2-fluoro-4-(cyclopropylmethoxy) phenyl, 2-fluoro-4-ethoxyphenyl, 2-fluoro-4-allyloxyphenyl, 2-fluoro-4-propargyloxyphenyl, 2-fluoro-4-hydroxyphenyl, 2-fluoro-4-(methoxyethoxy)phenyl, 2-fluoro-4-(methoxymethoxy)phenyl, 2-fluoro-4-methoxyphenyl, 2-fluoro-4-methylphenyl, 2-fluoro-4-(methylthiomethoxy)phenyl, 2-fluoro-4-(cyanomethoxy)phenyl, 2-fluoro-4-propyloxyphenyl, 2-fluoro-6-allyloxyphenyl, 2-fluoro-6-propargyloxyphenyl, 2-fluoro-6-hydroxyphenyl, 2-fluoro-6-(methoxymethoxy)phenyl, 2-fluoro-6-methoxyphenyl, 2-fluoro-6-(methylthiomethoxy)phenyl, 2-fluorophenyl, 4-bromo-2-chlorophenyl, 4-bromo-2-fluorophenyl, 4-bromophenyl, 4-fluoro-2-methylphenyl, 4-fluorophenyl, 4-hydroxyphenyl, 4-methoxyphenyl, 4-cyanophenyl, 2-chloro-4-ethoxyphenyl, 2-bromo-4-methoxyphenyl, 4-methoxy-2-methylphenyl, 2,6-difluoro-4-hydroxyphenyl, 2,6-difluoro-4-propargyloxyphenyl, or 2,6-difluoro-4-(2-butynyloxy) phenyl.

[7] The compound described in any one of [1] to [6], or a salt thereof, wherein R3 is a hydrogen atom, chlorine atom, bromine atom, iodine atom, or methyl.

[8] The compound described in any one of [1] to [7], or a salt thereof, wherein Y1, Y2 and Y3 are each independently a hydrogen atom, a hydroxy group, fluorine atom, chlorine atom, bromine atom, methyl, ethyl, propyl, isopropyl, butyl, isobutyl, t-butyl, pentyl, hexyl, heptyl, octyl, trifluoromethyl, cyclopropyl, cyclopentyl, ethynyl, methoxy, ethoxy, propyloxy, isopropyloxy, 2,2-difluoroethoxy, formyl, acetyloxy, phenoxy, 4-chloro-phenoxy, 4-methoxyphenoxy, dimethylamino, isopropyl(methyl)amino, methoxyamino, methoxy(methyl)amino, ethyl(methoxy) amino, acetyl(methoxy)amino, or methoxycarbonyl (methoxy)amino, and Y1 and Y2, together with the carbon atom to which Y1, Y2 and Y3 are bonded, form O=C(Y3)-, CH$_2$=C(Y3)-, CH$_3$CH=C(Y3)-, (CH$_3$)$_2$C=C(Y3)-, N=C—CH=C(Y3)-, ClCH=C(Y3)-, Br$_2$C=C(Y3)-, BrCH=C(Y3)-, 1-(Y3)-cyclopentyl, or 1-(Y3)-cyclohexyl, and Y3 is a hydrogen atom, chlorine atom, bromine atom, methyl, ethyl, butyl, isopropyl, isobutyl, t-butyl, cyclopropyl, cyclopentyl, or ethynyl, or Y1, Y2 and Y3, together with the carbon atom to which Y1, Y2 and Y3 are bonded, form a cyano group, or ethynyl.

[9] The compound described in any one of [1] to [7], or a salt thereof, wherein the partial structure (B) in the formula (1):

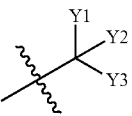

(B)

is methyl, ethyl, propyl, isopropyl, butyl, isobutyl, sec-butyl, t-butyl, pentyl, neopentyl, hexyl, heptyl, octyl, nonyl, hydroxymethyl, methoxymethyl, ethoxymethyl, isopropyloxymethyl, dibromomethyl, phenoxymethyl, (4-chlorophenoxy)methyl, (4-methoxyphenoxy)methyl, Me$_2$N—CH$_2$—, iPr(Me)N—CH$_2$—, MeONH—CH$_2$—, Me(MeO)N—CH$_2$—, Et(MeO)N—CH$_2$—, Ac(MeO)N—CH$_2$—, MeO(O=)C—N(OMe)-CH$_2$—, 1-hydroxyethyl, 1-methoxyethyl, 1-ethoxyethyl, 1-hydroxypropyl, 1-methoxypropyl, 1-hydroxypentyl, HC(=O)CH$_2$—, Me(F$_3$CCH$_2$O)CH—, Me$_2$C(OH)—, Me$_2$C(OMe)-, Me$_2$C(OEt)-, Et(Me)CF—, Et(HO)C(Me)-, Et(MeO)C(Me)-, Et(EtO)C(Me)-, cPr(HO)CH—, cPr(HO)C(Me)-, cPr(AcO)CH—, iPr(HO)CH—, iPr(MeO)CH—, iPr(EtO)CH—, iPr(HO)C(Me)-, iPr(MeO)C(Me)-, iPr(Me)CH—, iPr(Me)CF—, iPr(EtO)C(Me)-, iPr(PrO)C(Me)-, iBu(HO)CH—, iBu(MeO)CH—, iBu(HO)C(Me)-, iBu(MeO)C(Me)-, tBu(HO)CH—, tBu(MeO)CH—, tBu(Cl)CH—, tBu(HO)C(Me)-, F$_3$C(HO)CH—, F$_3$C(MeO)CH—, cPent(HO)CH—, cPent(HO)C(Me)-, cPent(MeO)C(Me)-, cPent(EtO)C(Me)-, cPent(PrO)C(Me)-, HC≡C—(HO)CH—, HC≡C-(MeO)CH—, HC≡C—(F)CH—, formyl, acetyl, propionyl, isobutyryl, 3-methylbutanoyl, pentanoyl, pivaloyl, cyclopentanecarbonyl, cyclopropanecarbonyl, HC≡C—C(=O)—, vinyl, 1,2-dichlorovinyl, 1,2-dibromovinyl, 2-cyanovinyl, 1-propenyl, 2-methyl-1-propenyl, 2,2-dibromovinyl, MeCH=C(Me)-, CH$_2$=C(Et)-, CH$_2$=C(iPr)—, cyclopentyl, cyclohexyl, a cyano group, or ethynyl.

[10] The compound described in any one of [1] to [5] and [7] to [9] or a salt thereof, wherein n is 1.

[11] The compound described in any one of [1] to [5] and [7] to [9] or a salt thereof, wherein n is 2.

[12] The compound described in any one of [1] to [5] and [7] to [9] or a salt thereof, wherein n is 3.

[13] The compound described in any one of [1] to [12] or a salt thereof, wherein X is an oxygen atom.

[14] The compound described in any one of [1] to [12] or a salt thereof, wherein X is a sulfur atom.

[15] The compound described in any one of [1] to [14] or a salt thereof, wherein the bond with the broken line is a double bond.

[16] The compound described in any one of [1] to [14] or a salt thereof, wherein the bond with the broken line is a single bond.

[17] An agricultural and horticultural pest control agent comprising the compound described in any one of [1] to [16] or a salt thereof as an active ingredient.

[18] An agricultural and horticultural fungicide comprising the compound described in any one of [1] to [16] or a salt thereof as an active ingredient.

[19] A method for controlling a plant disease, comprising applying the agricultural and horticultural pest control agent described in [17] to a plant, a plant seed or a soil on which a plant is or is to be cultivated.

[20] A method for controlling a plant disease, comprising applying the agricultural and horticultural fungicide described in [18] to a plant, a plant seed or a soil on which a plant is or is to be cultivated.

[21] Use of the compound described in any one of [1] to [16] as an agricultural and horticultural pest control agent.

[22] Use of the compound described in any one of [1] to [16] as an agricultural and horticultural fungicide.

Advantageous Effects of Invention

The present invention provides the novel compounds that is effective as agricultural and horticultural fungicides.

DESCRIPTION OF EMBODIMENTS

Best mode for carrying out the present invention is hereinbelow described in detail.

The terms used in the claims and the specification have definitions generally used in the technical field unless otherwise mentioned.

The abbreviations used in the specification are described below.

DMF: N,N-dimethylformamide, THF: tetrahydrofuran, Me: methyl, Et: ethyl, Pr: propyl, Bu: butyl, Pent: pentyl, Hex: hexyl, Hept: heptyl, Oct: octyl, Non: nonyl, Ac: acetyl, Ph: phenyl, Py: pyridyl, c: cyclo, i: iso, sec: secondary, t: tertiary, =: double bond, and ≡: triple bond. In the columns of the tables, Pr, Bu, Pent, Hex, Hept, Oct and Non having no prefix mean normal.

The definitions of the terms used in the specification is hereinbelow described.

The expression Cx-Cy means that the number of carbon atoms is from x to y. Here, x and y are integers, and such expression are understood to disclose all individual integers between x and y inclusive. For example, C1-C9 means that the number of carbon atoms is 1, 2, 3, 4, 5, 6, 7, 8 or 9; C1-C6 means that the number of carbon atoms is 1, 2, 3, 4, 5 or 6; C1-C5 means that the number of carbon atoms is 1, 2, 3, 4 or 5; C1-C3 means that the number of carbon atoms t is 1, 2 or 3; C2-C6 means that the number of carbon atoms is 2, 3, 4, 5 or 6; C3-C8 means that the number of carbon atoms is 3, 4, 5, 6, 7 or 8; and C3-C6 means that the number of carbon atoms is 3, 4, 5 or 6.

The phrase "optionally substituted" means that a group, compound or the like may be substituted or unsubstituted. When this phrase is used without explicit indication of the number of substituents, the number of substituents is one.

A C1-C6 alkyl group may be linear or branched. Examples include methyl, ethyl, propyl, isopropyl, butyl, isobutyl, sec-butyl, t-butyl, pentyl, isopentyl, 1-methylbutyl, 2-methylbutyl, neopentyl, 1-ethylpropyl, 1,2-dimethylpropyl, hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, 1-isopropylpropyl, 1,1,2-trimethylpropyl, 1,2,2-trimethylpropyl.

A C1-C9 alkyl group may be linear or branched. Examples include those exemplified in the C1-C6 alkyl groups, and heptyl, 2-methyl-1-isopropylpropyl, 1-t-butyl-propyl, 1-isopropylbutyl, 1,1-dimethylbutyl, 2,2-dimethylpentyl, 3,3-dimethylpentyl, 4,4-dimethylpentyl, 1,2-dimethylpentyl, 1,3-dimethylpentyl, 1,4-dimethylpentyl, 1-methylhexyl, 1-ethylpentyl, 1-propylbutyl, octyl, 1-t-butylbutyl, 1,1-dimethylhexyl, 2,2-dimethylhexyl, 3,3-dimethylhexyl, 4,4-dimethylhexyl, 5,5-dimethylhexyl, 1-methylheptyl, 1-ethylhexyl, 1-propylpentyl, nonyl, 1,1-dimethylheptyl, 2,2-dimethylheptyl, 3,3-dimethylheptyl, 4,4-dimethylheptyl, 5,5-dimethylheptyl, 6,6-dimethylheptyl, 1-methyloctyl, 1-ethylheptyl, 1-propylhexyl, 1-butylpentyl.

Examples of halogen atoms include fluorine atom, chlorine atom, bromine atom, iodine atom.

A C1-C6 haloalkyl group is a group wherein any hydrogen in the C1-C6 alkyl group is replaced with one, or two or more halogen atoms. When the group is substituted with two or more halogen atoms, the halogen atoms may be the same or different from one another, and the number of substitution is not particularly limited as long as such substitution is possible. Specific examples of the C1-C6 haloalkyl groups include monofluoromethyl, difluoromethyl, trifluoromethyl, monochloromethyl, monobromomethyl, monoiodomethyl, chlorodifluoromethyl, bromodifluoromethyl, 1-fluoroethyl, 2-fluoroethyl, 1,1-difluoroethyl, 2,2-difluoroethyl, 2,2,2-trifluoroethyl, 1,1,2,2-tetrafluoroethyl, pentafluoroethyl, 2,2,2-trichloroethyl, 3,3-difluoropropyl, 3,3,3-trifluoropropyl, heptafluoropropyl, heptafluoroisopropyl, 2,2,2-trifluoro-1-(trifluoromethyl)ethyl, nonafluorobutyl, nonafluoro-sec-butyl, 3,3,4,4,5,5,5-heptafluoropentyl, undecafluoropentyl, tridecafluorohexyl.

Examples of C3-C8 cycloalkyl groups include cyclopropyl, cyclobutyl, cyclopentyl, cyclohexyl, cycloheptyl, cyclooctyl.

A C2-C6 alkenyl group is an unsaturated hydrocarbon group which has one, or two or more double bonds and is linear or branched. When the group has geometric isomeric forms, the group may be either E-isomer or Z-isomer, or a mixture containing E-isomer and Z-isomer in any proportions, without limitation as long as within the number of carbon atoms indicated. Specific examples of the C2-C6 alkenyl groups include vinyl, 1-propenyl, allyl, 1-butenyl, 2-butenyl, 3-butenyl, 2-methyl-1-propenyl, 1-pentenyl, 2-pentenyl, 3-pentenyl, 4-pentenyl, 2-methyl-1-butenyl, 3-methyl-2-butenyl, 1-hexenyl, 2-hexenyl, 3-hexenyl, 4-hexenyl, 5-hexenyl, 3-methyl-2-pentenyl, 4-methyl-3-pentenyl.

A C2-C6 haloalkenyl group is a group wherein any hydrogen atom(s) in the C2-C6 alkenyl group is replaced with one, or two or more halogen atoms. When the group is substituted with two or more halogen atoms, the halogen atoms may be the same or different from one another, and the number of substitution is not particularly limited as long as such substitution is possible. Specific examples of the C2-C6 haloalkenyl groups include 2-fluorovinyl, 2-chlorovinyl, 2-bromovinyl, 2-iodovinyl, 1,2-difluorovinyl, 1,2-dichlorovinyl, 1,2-dibromovinyl, 1,2-diiodovinyl, 2,2-difluorovinyl, 2,2-dichlorovinyl, 2,2-dibromovinyl, 2,2-diiodovinyl, 3-fluoroallyl, 3-chloroallyl, 3-bromoallyl, 3,3-difluoroallyl, 3,3-dichloroallyl, 3,3-dibromoallyl, 4,4-difluoro-3-butenyl, 5,5-difluoro-4-pentenyl, 6,6-difluoro-5-hexenyl.

A C2-C6 alkynyl group is an unsaturated hydrocarbon group which has one, or two or more triple bonds and is linear or branched. Specific examples of the C2-C6 alkynyl groups include ethynyl, 1-propynyl, propargyl, 1-butynyl, 2-butynyl, 3-butynyl, 1-pentynyl, 2-pentynyl, 3-pentynyl, 4-pentynyl, 1,1-dimethyl-2-propynyl, 1-hexynyl, 2-hexynyl, 3-hexynyl, 4-hexynyl, 5-hexynyl.

A C2-C6 haloalkynyl group is a group wherein any hydrogen atom(s) in the C2-C6 alkynyl group is replaced with one, or two or more halogen atoms. When the group is substituted with two or more halogen atoms, the halogen atoms may be the same or different from one another, and the number of substituent is not particularly limited as long as such substitution is possible. Specific examples of the C2-C6 haloalkynyl groups include 2-fluoroethynyl, 2-chloroethynyl, 2-bromoethynyl, 2-iodoethynyl, 3,3-difluoro-1-propynyl, 3-chloro-3,3-difluoro-1-propynyl, 3-bromo-3,3-difluoro-1-propynyl, 3,3,3-trifluoro-1-propynyl, 4,4-difluoro-1-butynyl, 4,4-difluoro-2-butynyl, 4-chloro-4,4-difluoro-1-butynyl, 4-chloro-4,4-difluoro-2-butynyl, 4-bromo-4,4-difluoro-1-butynyl, 4-bromo-4,4-difluoro-2-butynyl, 4,4,4-trifluoro-1-butynyl, 4,4,4-trifluoro-2-butynyl, 5,5-difluoro-3-pentynyl, 5-chloro-5,5-difluoro-3-pentynyl, 5-bromo-5,5-difluoro-3-pentynyl, 5,5,5-trifluoro-3-pentynyl, 6,6-difluoro-4-hexynyl, 6-chloro-6,6-difluoro-4-hexynyl, 6-bromo-6,6-difluoro-4-hexynyl, 6,6,6-trifluoro-4-hexynyl.

A C1-C6 alkoxy group is a group resulting from the bonding of an oxygen atom to the C1-C6 alkyl group. Specific examples of the C1-C6 alkoxy groups include methoxy, ethoxy, propyloxy, isopropyloxy, butoxy, isobutoxy, sec-butoxy, t-butoxy, pentyloxy, isopentyloxy, 2-methylbutoxy, neopentyloxy, 1-ethylpropyloxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy.

A C1-C6 haloalkoxy group is a group wherein any hydrogen atom(s) in the C1-C6 alkoxy group is replaced with one, or two or more halogen atoms. When the group is substituted with two or more halogen atoms, the halogen atoms may be the same or different from one another, and the number of substituent is not particularly limited as long as such substitution is possible. Specific examples of the C1-C6 haloalkoxy groups include difluoromethoxy, trifluoromethoxy, chlorodifluoromethoxy, bromodifluoromethoxy, 2-fluoroethoxy, 2,2-difluoroethoxy, 2,2,2-trifluoroethoxy, 1,1,2,2-tetrafluoroethoxy, pentafluoroethoxy, 2,2,2-trichloroethoxy, 3,3-difluoropropyloxy, 3,3,3-trifluoropropyloxy, heptafluoropropyloxy, heptafluoroisopropyloxy, 2,2,2-trifluoro-1-(trifluoromethyl)-ethoxy, nonafluorobutoxy, nonafluoro-sec-butoxy, 3,3,4,4,5,5,5-heptafluoropentyloxy, undecafluoropentyloxy, tridecafluorohexyloxy.

A C3-C8 cycloalkoxy group is a group resulting from the bonding of an oxygen atom to the C3-C8 cycloalkyl group. Specific examples of the C3-C8 cycloalkoxy groups include cyclopropyloxy, cyclobutoxy, cyclopentyloxy, cyclohexyloxy, cycloheptyloxy, cyclooctyloxy.

A C2-C6 alkenyloxy group is a group resulting from the bonding of an oxygen atom to the C2-C6 alkenyl group. When the group has geometric isomeric forms, the group may be either E-isomer or Z-isomer, or a mixture containing E-isomer and Z-isomer in any proportions, without limitation as long as within the number of carbon atoms indicated. Specific examples of the C2-C6 alkenyloxy groups include vinyloxy, 1-propenyloxy, allyloxy, 1-butenyloxy, 2-butenyloxy, 3-butenyloxy, 2-methyl-1-propenyloxy, 1-pentenyloxy, 2-pentenyloxy, 3-pentenyloxy, 4-pentenyloxy, 2-methyl-1-butenyloxy, 3-methyl-2-butenyloxy, 1-hexenyloxy, 2-hexenyloxy, 3-hexenyloxy, 4-hexenyloxy, 5-hexenyloxy, 3-methyl-2-pentenyloxy, 4-methyl-3-pentenyloxy.

A C2-C6 haloalkenyloxy group is a group wherein any hydrogen atom(s) in the C2-C6 alkenyloxy group is replaced with one, or two or more halogen atoms. When the group is substituted with two or more halogen atoms, the halogen atoms may be the same or different from one another, and the number of substituent is not particularly limited as long as such substitution is possible. Specific examples of the C2-C6 haloalkenyloxy groups include 2-fluorovinyloxy, 2,2-difluorovinyloxy, 2,2-dichlorovinyloxy, 3-fluoroallyloxy, 3,3-difluoroallyloxy, 3,3-dichloroallyloxy, 4,4-difluoro-3-butenyloxy, 5,5-difluoro-4-pentenyloxy, 6,6-difluoro-5-hexenyloxy.

A C3-C6 alkynyloxy group is a group resulting from the bonding of an oxygen atom to, among the C2-C6 alkynyl groups, a C3-C6 alkynyl group. Specific examples of the C3-C6 alkynyloxy groups include propargyloxy, 2-butynyloxy, 3-butynyloxy, 2-pentynyloxy, 3-pentynyloxy, 4-pentynyloxy, 1,1-dimethyl-2-propynyloxy, 2-hexynyloxy, 3-hexynyloxy, 4-hexynyloxy, 5-hexynyloxy.

A C3-C6 haloalkynyloxy group is a group wherein any hydrogen atom(s) in the C3-C6 alkynyloxy group is replaced with one, or two or more halogen atoms. When the group is substituted with two or more halogen atoms, the halogen atoms may be the same or different from one another, and the number of substituent is not particularly limited as long as such substitution is possible. Specific examples of the C3-C6 haloalkynyloxy groups include 1,1-difluoro-2-propynyloxy, 4,4-difluoro-2-butynyloxy, 4-chloro-4,4-difluoro-2-butynyloxy, 4-bromo-4,4-difluoro-2-butynyloxy, 4,4,4-trifluoro-2-butynyloxy, 5,5-difluoro-3-pentynyloxy, 5-chloro-5,5-difluoro-3-pentynyloxy, 5-bromo-5,5-difluoro-3-pentynyloxy, 5,5,5-trifluoro-3-pentynyloxy, 6,6-difluoro-4-hexynyloxy, 6-chloro-6,6-difluoro-4-hexynyloxy, 6-bromo-6,6-difluoro-4-hexynyloxy, 6,6,6-trifluoro-4-hexynyloxy.

An aryloxy group is a group resulting from the bonding to an oxygen atom to an aryl group such as phenyl or naphthyl. Specific examples of the aryloxy groups include phenoxy, naphthyloxy.

A heteroaryloxy group is a group resulting from the bonding to an oxygen atom to heteroaryl group such as pyridyl, pyridazinyl, pyrimidinyl, pyrazinyl, triazinyl, tetrazinyl, thienyl, thiazolyl, isothiazolyl, thiadiazolyl, furyl, pyrrolyl, imidazolyl, pyrazolyl, oxazolyl, isoxazolyl, triazolyl, oxadiazolyl, thiadiazolyl or tetrazolyl. Specific examples of the heteroaryloxy groups include pyridyloxy, pyridazinyloxy, pyrimidinyloxy, pyrazinyloxy, triazinyloxy, tetrazinyloxy, thienyloxy, thiazolyloxy, isothiazolyloxy, thiadiazolyloxy, furyloxy, pyrrolyloxy, imidazolyloxy, pyrazolyloxy, oxazolyloxy, isoxazolyloxy, triazolyloxy, oxadiazolyloxy, thiadiazolyloxy, tetrazolyloxy.

An aralkyloxy group is a group resulting from the bonding to an oxygen atom to an aralkyl group, which results from replacing any hydrogen atom(s) in a C1-C3 alkyl group with an aryl group such as phenyl or naphthyl. Specific examples of the aralkyloxy groups include benzyloxy, phenethyloxy, phenylpropyloxy, naphthalenylmethoxy, naphthalenylethoxy, naphthalenylpropoxy.

Specific examples of 3 to 6-membered ring groups containing 1 to 2 oxygen atoms include 1,2-epoxyethanyl, oxetanyl, oxolanyl, oxanyl, 1,3-dioxolanyl, 1,3-dioxanyl, 1,4-dioxanyl.

A C2-C6 alkoxyalkoxy group is a group wherein any hydrogen atom(s) in, among the C1-C6 alkoxy groups, C1-C5 alkoxy group is replaced with one, or two or more C1-C5 alkoxy groups. This alkoxyalkoxy group is not particularly limited as long as within the number of carbon atoms indicated. Specific examples of the C2-C6 alkoxyalkoxy groups include methoxymethoxy, ethoxymethoxy, propyloxymethoxy, isopropyloxymethoxy, methoxyethoxy, ethoxyethoxy, propyloxyethoxy, isopropyloxyethoxy, methoxypropyloxy, ethoxypropyloxy, propyloxypropyloxy, isopropyloxypropyloxy.

The pyridone compounds of the present invention encompass compounds of the following formula (1) and salts thereof (hereinafter, referred to as the "inventive compound(s)")

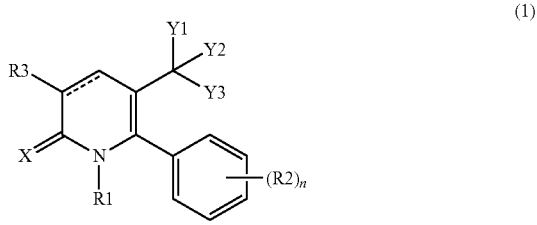

(1)

The formula (1) is hereinbelow described.

In the formula, R1 represents a cyano group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, or a C3-C6 haloalkynyloxy group.

In particular, R1 is preferably a C1-C6 alkyl group optionally substituted with substituent(s) A, a C1-C6 haloalkyl group, a C2-C6 alkenyl group optionally substituted with substituent(s) A, a C2-C6 haloalkenyl group, a C2-C6 alkynyl group optionally substituted with substituent(s) A, or a C2-C6 haloalkynyl group, and R1 is more preferably a C1-C6 alkyl group optionally substituted with substituent(s) A, or a C1-C6 haloalkyl group.

In the formula (1), R1 may represent a cyano group.

In the "C1-C6 alkyl group optionally substituted with substituent(s) A" represented by R1 in the formula (1), the C1-C6 alkyl group is the same as defined hereinabove, and is preferably methyl, ethyl, propyl, isopropyl, butyl or isobutyl, and more preferably methyl, ethyl, propyl or butyl. When this group is substituted with substituent(s) A, any hydrogen atom(s) in the C1-C6 alkyl group is appropriately substituted with substituent(s) A.

The "C1-C6 haloalkyl group" represented by R1 in the formula (1) is the same as defined hereinabove, and is preferably 2-fluoroethyl, 2,2-difluoroethyl, 2,2,2-trifluoroethyl, 3,3-difluoropropyl or 3,3,3-trifluoropropyl, and more preferably 2-fluoroethyl, 2,2-difluoroethyl or 2,2,2-trifluoroethyl.

In the "C3-C8 cycloalkyl group optionally substituted with substituent(s) A" represented by R1 in the formula (1), the C3-C8 cycloalkyl group is the same as defined hereinabove, and is preferably cyclopropyl, cyclobutyl, cyclopentyl or cyclohexyl, and more preferably cyclopropyl or cyclobutyl. When this group is substituted with substituent(s) A, any hydrogen atom(s) in the C3-C8 cycloalkyl group is appropriately substituted with substituent(s) A.

In the "C2-C6 alkenyl group optionally substituted with substituent(s) A" represented by R1 in the formula (1), the C2-C6 alkenyl group is the same as defined hereinabove, and is preferably vinyl, 1-propenyl or allyl, and more preferably vinyl or allyl. When this group is substituted with substituent(s) A, any hydrogen atom(s) in the C2-C6 alkenyl group is appropriately substituted with substituent(s) A.

The "C2-C6 haloalkenyl group" represented by R1 in the formula (1) is the same as defined hereinabove, and is preferably 2-fluorovinyl, 2,2-difluorovinyl, 3-fluoroallyl or 3,3-difluoroallyl, and more preferably 2-fluorovinyl or 2,2-difluorovinyl.

In the "C2-C6 alkynyl group optionally substituted with substituent(s) A" represented by R1 in the formula (1), the C2-C6 alkynyl group is the same as defined hereinabove, and is preferably propargyl, 2-butynyl or 3-butynyl, and more preferably propargyl. When this group is substituted with substituent(s) A, any hydrogen atom(s) in the C2-C6 alkynyl group is appropriately substituted with substituent(s) A.

The "C2-C6 haloalkynyl group" represented by R1 in the formula (1) is the same as defined hereinabove, and is preferably 4,4-difluoro-2-butynyl, 4-chloro-4,4-difluoro-2-butynyl, 4-bromo-4,4-difluoro-2-butynyl or 4,4,4-trifluoro-2-butynyl, and more preferably 4,4-difluoro-2-butynyl or 4,4,4-trifluoro-2-butynyl.

In the "C1-C6 alkoxy group optionally substituted with substituent(s) A" represented by R1 in the formula (1), the C1-C6 alkoxy group is the same as defined hereinabove, and is preferably methoxy, ethoxy, propyloxy, isopropyloxy, butoxy or isobutoxy, and more preferably methoxy or ethoxy. When this group is substituted with substituent(s) A, any hydrogen atom(s) in the C1-C6 alkoxy group is appropriately substituted with substituent(s) A.

The "C1-C6 haloalkoxy group" represented by R1 in the formula (1) is the same as defined hereinabove, and is preferably difluoromethoxy, trifluoromethoxy, 2,2-difluoroethoxy, 2,2,2-trifluoroethoxy, 3,3-difluoropropyloxy or 3,3,3-trifluoropropyloxy, and more preferably difluoromethoxy, trifluoromethoxy, 2,2-difluoroethoxy or 2,2,2-trifluoroethoxy.

In the "C3-C8 cycloalkoxy group optionally substituted with substituent(s) A" represented by R1 in the formula (1), the C3-C8 cycloalkoxy group is the same as defined hereinabove, and is preferably cyclopropyloxy, cyclobutoxy, cyclopentyloxy or cyclohexyloxy, and more preferably cyclopropyloxy or cyclobutoxy. When this group is substituted with substituent(s) A, any hydrogen atom(s) in the C3-C8 cycloalkoxy group is appropriately substituted with substituent(s) A.

In the "C2-C6 alkenyloxy group optionally substituted with substituent(s) A" represented by R1 in the formula (1), the C2-C6 alkenyloxy group is the same as defined hereinabove, and is preferably vinyloxy, 1-propenyloxy or allyloxy, and more preferably vinyloxy. When this group is substituted with substituent(s) A, any hydrogen atom(s) in the C2-C6 alkenyloxy group is appropriately substituted with substituent(s) A.

The "C2-C6 haloalkenyloxy group" represented by R1 in the formula (1) is the same as defined hereinabove, and is preferably 2-fluorovinyloxy, 2,2-difluorovinyloxy, 3-fluoroallyloxy or 3,3-difluoroallyloxy, and more preferably 2-fluorovinyloxy or 2,2-difluorovinyloxy.

In the "C3-C6 alkynyloxy group optionally substituted with substituent(s) A" represented by R1 in the formula (1), the C3-C6 alkynyloxy group is the same as defined hereinabove, and is preferably propargyloxy, 2-butynyloxy or 3-butynyloxy, and more preferably propargyloxy. When this group is substituted with substituent(s) A, any hydrogen atom(s) in the C3-C6 alkynyloxy group is appropriately substituted with substituent(s) A.

The "C3-C6 haloalkynyloxy group" represented by R1 in the formula (1) is the same as defined hereinabove, and is preferably 4,4-difluoro-2-butynyloxy, 4-chloro-4,4-difluoro-2-butynyloxy, 4-bromo-4,4-difluoro-2-butynyloxy or 4,4,4-trifluoro-2-butynyloxy, and more preferably 4,4-difluoro-2-butynyloxy or 4,4,4-trifluoro-2-butynyloxy.

In the formula (1), R2 represents a hydroxy group, a cyano group, a nitro group, a halogen atom, a C1-C6 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, a C2-C6 haloalkynyl group, a C1-C6 alkoxy group optionally substituted with substituent(s) B, a C1-C6 haloalkoxy group, a C3-C8 cycloalkoxy group optionally substituted with substituent(s) B, a C2-C6 alkenyloxy group optionally substituted with substituent(s) B, a C2-C6 haloalkenyloxy group, a C3-C6 alkynyloxy group optionally substituted with substituent(s) B, a C3-C6 haloalkynyloxy group, RdC(=O)— (wherein Rd represents a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are independent of one another and each represent a hydrogen atom, a C1-C6 alkyl group optionally substituted with substituent(s) C, a C1-C6 haloalkyl group, or a C3-C8 cycloalkyl group, or Ra and Rb, together with the nitrogen atom to which they are bonded, form aziridinyl, azetidinyl, pyrrolidinyl, piperidinyl, homopiperidinyl or azocanyl)), RdC(=O)O— (wherein Rd is the same as defined hereinabove), an aryloxy group optionally substituted with 0 to 5 substituents D, a heteroaryloxy group optionally substituted with 0 to 2 substituents D, an aralkyloxy group optionally substituted with 0 to 5 substituents D, a 3 to 6-membered ring group containing 1 to 2 oxygen atoms, Rc-L- (wherein Rc represents a C1-C6 alkyl group or a C1-C6 haloalkyl group, and L represents S, SO or $SO_2$), RaRbN— (wherein Ra and Rb are the same as defined hereinabove), Rg(RhO)N— (wherein Rg and Rh are independent of one another and each represent a hydrogen atom, a C1-C6 alkyl group optionally substituted with substituent(s) C, a C1-C6 haloalkyl group, or a C3-C8 cycloalkyl group), or ReC(=O)N(Rf)— (wherein Re and Rf are independent of one another and each represent a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove)).

In particular, R2 is preferably a hydroxy group, a cyano group, a halogen atom, a C1-C6 alkyl group optionally substituted with substituent(s) B, a C1-C6 haloalkyl group, a C3-C8 cycloalkyl group optionally substituted with substituent(s) B, a C1-C6 alkoxy group optionally substituted with substituent(s) B, a C1-C6 haloalkoxy group, a C3-C8 cycloalkoxy group optionally substituted with substituent(s) B, a C2-C6 alkenyloxy group optionally substituted with substituent(s) B, a C2-C6 haloalkenyloxy group, a C3-C6 alkynyloxy group optionally substituted with substituent(s) B, a C3-C6 haloalkynyloxy group, RdC(=O)O— (wherein Rd is the same as defined hereinabove), or Rc-L- (wherein Rc and L are the same as defined hereinabove), and R2 is more preferably a hydroxy group, a cyano group, a halogen atom, a C1-C6 alkyl group optionally substituted with substituent(s) B, a C1-C6 alkoxy group optionally substituted with substituent(s) B, a C2-C6 alkenyloxy group optionally substituted with substituent(s) B, or a C3-C6 alkynyloxy group optionally substituted with substituent(s) B.

In the formula (1), R2 may represent a hydroxy group, a cyano group or a nitro group.

The halogen atom represented by R2 in the formula (1) is the same as defined hereinabove, and is preferably fluorine atom, chlorine atom, bromine atom or iodine atom.

In the "C1-C6 alkyl group optionally substituted with substituent(s) B" represented by R2 in the formula (1), the C1-C6 alkyl group is the same as defined hereinabove, and is preferably methyl, ethyl, propyl, isopropyl, butyl or isobutyl, and more preferably methyl, ethyl, propyl or isopropyl. When this group is substituted with substituent(s) B, any hydrogen atom(s) in the C1-C6 alkyl group is appropriately substituted with substituent(s) B.

The "C1-C6 haloalkyl group" represented by R2 in the formula (1) is the same as defined hereinabove, and is preferably difluoromethyl, trifluoromethyl, 2,2-difluoroethyl or 2,2,2-trifluoroethyl, and more preferably difluoromethyl or trifluoromethyl.

In the "C3-C8 cycloalkyl group optionally substituted with substituent(s) B" represented by R2 in the formula (1), the C3-C8 cycloalkyl group is the same as defined hereinabove, and is preferably cyclopropyl, cyclobutyl, cyclopentyl or cyclohexyl, and more preferably cyclopropyl or cyclobutyl. When this group is substituted with substituent(s) B, any hydrogen atom(s) in the C3-C8 cycloalkyl group is appropriately substituted with substituent(s) B.

In the "C2-C6 alkenyl group optionally substituted with substituent(s) B" represented by R2 in the formula (1), the C2-C6 alkenyl group is the same as defined hereinabove, and is preferably vinyl, 1-propenyl, allyl, 1-butenyl, 2-butenyl or 3-butenyl, and more preferably vinyl, 1-propenyl or allyl. When this group is substituted with substituent(s) B, any hydrogen atom(s) in the C2-C6 alkenyl group is appropriately substituted with substituent(s) B.

The "C2-C6 haloalkenyl group" represented by R2 in the formula (1) is the same as defined hereinabove, and is preferably 2-fluorovinyl, 2,2-difluorovinyl, 2,2-dichlorovinyl, 3-fluoroallyl, 3,3-difluoroallyl or 3,3-dichloroallyl, and more preferably 2-fluorovinyl or 2,2-difluorovinyl.

In the "C2-C6 alkynyl group optionally substituted with substituent(s) B" represented by R2 in the formula (1), the C2-C6 alkynyl group is the same as defined hereinabove, and is preferably ethynyl, 1-propynyl, propargyl, 1-butynyl, 2-butynyl or 3-butynyl, and more preferably ethynyl, 1-propynyl or propargyl. When this group is substituted with substituent(s) B, any hydrogen atom(s) in the C2-C6 alkynyl group is appropriately substituted with substituent(s) B.

The "C2-C6 haloalkynyl group" represented by R2 in the formula (1) is the same as defined hereinabove, and is preferably 3,3-difluoro-1-propynyl, 3,3,3-trifluoro-1-propynyl, 4,4-difluoro-1-butynyl, 4,4-difluoro-2-butynyl, 4,4,4-trifluoro-1-butynyl or 4,4,4-trifluoro-2-butynyl, and more preferably 3,3-difluoro-1-propynyl or 3,3,3-trifluoro-1-propynyl.

In the "C1-C6 alkoxy group optionally substituted with substituent(s) B" represented by R2 in the formula (1), the C1-C6 alkoxy group is the same as defined hereinabove, and is preferably methoxy, ethoxy, propyloxy, isopropyloxy, butoxy, isobutoxy or pentyloxy, and more preferably methoxy, ethoxy, propyloxy, isopropyloxy or butoxy. When this group is substituted with substituent(s) B, any hydrogen atom(s) in the C1-C6 alkoxy group is appropriately substituted with substituent(s) B.

The "C1-C6 haloalkoxy group" represented by R2 in the formula (1) is the same as defined hereinabove, and is preferably difluoromethoxy, trifluoromethoxy, 2,2-difluoroethoxy, 2,2,2-trifluoroethoxy, 3,3-difluoropropyloxy or 3,3,3-trifluoropropyloxy, and more preferably difluoromethoxy, trifluoromethoxy, 2,2-difluoroethoxy or 2,2,2-trifluoroethoxy.

In the "C3-C8 cycloalkoxy group optionally substituted with substituent(s) B" represented by R2 in the formula (1), the C3-C8 cycloalkoxy group is the same as defined hereinabove, and is preferably cyclopropyloxy, cyclobutoxy, cyclopentyloxy or cyclohexyloxy, and more preferably cyclopropyloxy or cyclobutoxy. When this group is substituted with substituent(s) B, any hydrogen atom(s) in the C3-C8 cycloalkoxy group is appropriately substituted with substituent(s) B.

In the "C2-C6 alkenyloxy group optionally substituted with substituent(s) B" represented by R2 in the formula (1), the C2-C6 alkenyloxy group is the same as defined hereinabove, and is preferably vinyloxy, 1-propenyloxy, allyloxy, 1-butenyloxy, 2-butenyloxy or 3-butenyloxy, and more preferably vinyloxy, 1-propenyloxy or allyloxy. When this group is substituted with substituent(s) B, any hydrogen atom(s) in the C2-C6 alkenyloxy group is appropriately substituted with substituent(s) B.

The "C2-C6 haloalkenyloxy group" represented by R2 in the formula (1) is the same as defined hereinabove, and is preferably 2-fluorovinyloxy, 2,2-difluorovinyloxy, 2,2-dichlorovinyloxy, 3-fluoroallyloxy, 3,3-difluoroallyloxy or 3,3-dichloroallyloxy, and more preferably 2-fluorovinyloxy or 2,2-difluorovinyloxy.

In the "C3-C6 alkynyloxy group optionally substituted with substituent(s) B" represented by R2 in the formula (1), the C3-C6 alkynyloxy group is the same as defined hereinabove, and is preferably propargyloxy, 2-butynyloxy or 3-butynyloxy, and more preferably propargyloxy or 2-butynyloxy. When this group is substituted with substituent(s) B, any hydrogen atom(s) in the C3-C6 alkynyloxy group is appropriately substituted with substituent(s) B.

The "C3-C6 haloalkynyloxy group" represented by R2 in the formula (1) is the same as defined hereinabove, and is preferably 4,4-difluoro-2-butynyloxy, 4-chloro-4,4-difluoro-2-butynyloxy, 4-bromo-4,4-difluoro-2-butynyloxy or 4,4,4-trifluoro-2-butynyloxy, and more preferably 4,4-difluoro-2-butynyloxy or 4,4,4-trifluoro-2-butynyloxy.

In "RdC(=O)—" (wherein Rd represents a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are independent of one another and each represent a hydrogen atom, a C1-C6 alkyl group optionally substituted with substituent(s) C, a C1-C6 haloalkyl group, or a C3-C8 cycloalkyl group, or Ra and Rb, together with the nitrogen atom to which they are bonded, form aziridinyl, azetidinyl, pyrrolidinyl, piperidinyl, homopiperidinyl or azocanyl)) represented by R2 in the formula (1), the terms are the same as defined hereinabove. Where the "C1-C6 alkyl group optionally substituted with substituent(s) C" is substituted with substituent(s) C, any hydrogen atom(s) in the C1-C6 alkyl group is appropriately substituted with substituent(s) C. "RdC(=O)—" is preferably formyl, acetyl, methoxyacetyl, cyanoacetyl, propionyl, difluoroacetyl, trifluoroacetyl, cyclopropanecarbonyl, methoxycarbonyl, ethoxycarbonyl, 2,2-difluoroethoxycarbonyl, 2,2,2-trifluoroethoxycarbonyl, 3,3,3-trifluoropropyloxycarbonyl, cyclopropyloxycarbonyl, aminocarbonyl, methylaminocarbonyl, ethylaminocarbonyl, (methoxymethyl)aminocarbonyl, (2-methoxyethyl)aminocarbonyl, (cyanomethyl)aminocarbonyl, (2-cyanoethyl)aminocarbonyl, dimethyl aminocarbonyl, ethyl(methyl)aminocarbonyl, di ethylaminocarbonyl, (methoxymethyl)methylaminocarbonyl, (2-methoxyethyl)methylaminocarbonyl, (cyanomethyl)methylaminocarbonyl, (2-cyanoethyl)methylaminocarbonyl, 2,2-difluoroethylaminocarbonyl, 2,2,2-trifluoroethylaminocarbonyl, cyclopropylaminocarbonyl, cyclopropyl(methyl)aminocarbonyl, pyrrolidinylcarbonyl or piperidinylcarbonyl, and more preferably acetyl, methoxyacetyl, cyanoacetyl, difluoroacetyl, trifluoroacetyl, methoxycarbonyl, ethoxycarbonyl, aminocarbonyl, dimethylaminocarbonyl, ethyl(methyl)aminocarbonyl or diethylaminocarbonyl.

In "RdC(=O)O—" represented by R2 in the formula (1), Rd is the same as defined hereinabove. "RdC(=O)O—" is preferably formyloxy, acetyloxy, methoxyacetyloxy, cyanoacetyloxy, propionyloxy, difluoroacetyloxy, trifluoroacetyloxy, cyclopropanecarbonyloxy, methoxycarbonyloxy, ethoxycarbonyloxy, 2,2-difluoroethoxycarbonyloxy, 2,2,2-trifluoroethoxycarbonyloxy, 3,3,3-trifluoropropyloxycarbonyloxy, cyclopropyl oxycarbonyloxy, aminocarbonyloxy, methylaminocarbonyloxy, ethylaminocarbonyloxy, (methoxymethyl)aminocarbonyloxy, (2-methoxyethyl)aminocarbonyloxy, (cyanomethyl)aminocarbonyloxy, (2-cyanoethyl)aminocarbonyloxy, dimethylaminocarbonyloxy, ethyl(methyl)aminocarbonyloxy, diethylaminocarbonyloxy, (methoxymethyl)methylaminocarbonyloxy, (2-methoxyethyl)methyl aminocarbonyloxy, (cyanomethyl)methylaminocarbonyloxy, (2-cyanoethyl)methylaminocarbonyloxy, 2,2-difluoroethylaminocarbonyloxy, 2,2,2-trifluoroethylaminocarbonyloxy, cyclopropylaminocarbonyloxy, cyclopropyl(methyl)aminocarbonyloxy, pyrrolidinylcarbonyloxy or piperidinylcarbonyloxy, and more preferably acetyloxy, methoxyacetyloxy, cyanoacetyloxy, difluoroacetyloxy, trifluoroacetyloxy, methoxycarbonyloxy, ethoxycarbonyloxy, aminocarbonyloxy, dimethylaminocarbonyloxy, ethyl(methyl)aminocarbonyloxy or di ethylaminocarbonyloxy.

In the "aryloxy group optionally substituted with 0 to 5 substituents D" represented by R2 in the formula (1), the aryloxy group is the same as defined hereinabove, and is preferably phenoxy or naphthyloxy, and more preferably phenoxy. When this group is substituted with substituent(s) D, any hydrogen atom(s) in the aryloxy group is appropriately substituted with substituent(s) D. Where there are two or more substituents D, they are independent of one another.

In the "heteroaryloxy group optionally substituted with 0 to 2 substituents D" represented by R2 in the formula (1), the heteroaryloxy group is the same as defined hereinabove, and is preferably pyridyloxy, pyridazinyloxy, pyrimidinyloxy, pyrazinyloxy, triazinyloxy, tetrazinyloxy, thienyloxy, thiazolyloxy, isothiazolyloxy or thiadiazolyloxy, and more preferably pyridyloxy, pyridazinyloxy, pyrimidinyloxy or pyrazinyloxy. When this group is substituted with substituent(s) D, any hydrogen atom(s) in the heteroaryloxy group is appropriately substituted with substituent(s) D. Where there are two substituents D, they are independent of one another.

In the "aralkyloxy group optionally substituted with 0 to 5 substituents D" represented by R2 in the formula (1), the aralkyloxy group is the same as defined hereinabove, and is preferably benzyloxy, phenetyloxy or phenylpropyloxy, and more preferably benzyloxy or phenetyloxy. When this group is substituted with substituent(s) D, any hydrogen atom(s) in the aralkyloxy group is appropriately substituted with substituent(s) D. Where there are two or more substituents D, they are independent of one another.

The "3 to 6-membered ring group containing 1 to 2 oxygen atoms" represented by R2 in the formula (1) is the same as defined hereinabove, and is preferably oxolanyl, oxanyl, 1,3-dioxolanyl or 1,3-dioxanyl, and more preferably 1,3-dioxolanyl or 1,3-dioxanyl.

In "Rc-L-" (wherein Rc represents a C1-C6 alkyl group or a C1-C6 haloalkyl group, and L represents S, SO or $SO_2$) represented by R2 in the formula (1), the terms are the same as defined hereinabove. "Rc-L-" is preferably methylthio, methanesulfinyl, methanesulfonyl, trifluoromethylthio, trifluoromethanesulfinyl or trifluoromethanesulfonyl, and more preferably methylthio, methanesulfinyl or methanesulfonyl.

In "RaRbN—" represented by R2 in the formula (1), Ra and Rb are the same as defined hereinabove. "RaRbN—" is preferably amino, methylamino, ethylamino, propyl amino, isopropylamino, (methoxymethyl)amino, (2-methoxyethyl) amino, (cyanomethyl)amino, (2-cyanoethyl)amino, dimethylamino, ethyl(methyl)amino, methyl(propyl)amino, isopropyl(methyl)amino, (methoxymethyl)methyl amino, (2-methoxyethyl)methylamino, (cyanomethyl)methylamino, (2-cyanoethyl)methylamino, diethylamino, ethyl(propyl)amino, ethyl(isopropyl)amino, ethyl(methoxymethyl)amino, ethyl(2-methoxyethyl)amino, (cyanomethyl)ethylamino, (2-cyanoethyl)ethylamino, 2,2-difluoroethylamino, 2,2,2-trifluoroethylamino, cyclopropylamino, (cyclopropyl)methylamino, pyrrolidinyl or piperidinyl, and more preferably dimethylamino, ethyl(methyl)amino, isopropyl(methyl)amino, diethylamino or ethyl(isopropyl)amino.

In "Rg(RhO)N—" (wherein Rg and Rh are independent of one another and each represent a hydrogen atom, a C1-C6 alkyl group optionally substituted with substituent(s) C, a C1-C6 haloalkyl group, or a C3-C8 cycloalkyl group) represented by R2 in the formula (1), the terms are the same as defined hereinabove. Where the "C1-C6 alkyl group optionally substituted with substituent(s) C" is substituted with substituent(s) C, any hydrogen atom(s) in the C1-C6 alkyl group is appropriately substituted with substituent(s) C. "Rg(RhO)N—" is preferably hydroxyamino, methoxyamino, ethoxyamino, propyloxyamino, isopropyloxyamino, methoxy(methyl)amino, ethoxy(methyl)amino, methyl(propyloxy)amino, isopropyloxy(methyl)amino, ethyl(methoxy)amino, ethoxy(ethyl)amino, ethyl(propyloxy)amino, ethyl(isopropyloxy)amino, methoxy(propyl)amino, ethoxy(propyl)amino, propyloxy(propyl)amino, isopropyloxy(propyl)amino, methoxy(trifluoroethyl)amino, ethoxy(trifluoroethyl)amino, propyloxy(trifluoroethyl)amino, isopropyloxy(trifluoroethyl)amino, trifluoroethoxyamino, methyl(trifluoroethoxy)amino, ethyl(trifluoroethoxy)amino, propyl(trifluoroethoxy)amino, isopropyl(trifluoroethoxy)amino, cyclopropyl(methoxy)amino, cyclopropyl(ethoxy)amino, cyclopropyl(propyloxy)amino, cyclopropyl(isopropyloxy)amino, cyclobutyl(methoxy)amino, cyclobutyl(ethoxy)amino, cyclobutyl(propyloxy)amino, cyclobutyl(isopropyloxy)amino, cyclopropyloxy(methyl)amino, cyclopropyloxy(ethyl)amino, cyclopropyloxy(propyl)amino, cyclopropyloxy(isopropyl)amino, cyclobutoxy(methyl)amino, cyclobutoxy(ethyl)amino, cyclobutoxy(propyl)amino, cyclobutoxy(isopropyl)amino, methoxy(methoxymethyl)amino, ethoxy(methoxymethyl)amino, methoxymethyl(propyloxy)amino, isopropyloxy(methoxymethyl)amino, cyanomethyl(methoxy)amino, cyanomethyl(ethoxy)amino, cyanomethyl(propyloxy)amino or cyanomethyl(isopropyloxy)amino, and more preferably methoxyamino, ethoxyamino, methoxy(methyl)amino, ethoxy(methyl)amino, ethyl(methoxy)amino or ethoxy(ethyl)amino.

In "ReC(=O)N(Rf)—" (wherein Re and Rf are independent of one another and each represent a hydrogen atom, a C1-C6 alkyl group optionally substituted with substituent(s) C, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove)) represented by R2 in the formula (1), the terms are the same as defined hereinabove. Where the "C1-C6 alkyl group optionally substituted with substituent(s) C" is substituted with substituent(s) C, any hydrogen atom(s) in the C1-C6 alkyl group is appropriately substituted with substituent(s) C. "ReC(=O)N(Rf)—" is preferably formylamino, acetylamino, methoxyacetylamino, cyanoacetylamino, propionylamino, difluoroacetylamino, trifluoroacetylamino, cyclopropanecarbonylamino, methoxycarbonylamino, ethoxycarbonyl amino, 2,2-difluoroethoxycarbonylamino, 2,2,2-trifluoroethoxycarbonyl amino, 3,3,3-trifluoropropyloxycarbonylamino, cyclopropyloxycarbonylamino, aminocarbonylamino, methylaminocarbonylamino, ethylaminocarbonylamino, (methoxymethyl)aminocarbonylamino, (2-methoxyethyl)aminocarbonyl amino, (cyanomethyl)aminocarbonylamino, (2-cyanoethyl)aminocarbonylamino, dimethylaminocarbonylamino, ethyl(methyl)aminocarbonylamino, di ethylaminocarbonylamino, (methoxymethyl)methylaminocarbonylamino, (2-methoxyethyl)methylaminocarbonylamino, (cyanomethyl)methylaminocarbonylamino, (2-cyanoethyl)methylaminocarbonylamino, 2,2-difluoroethylaminocarbonylamino, 2,2,2-trifluoroethylaminocarbonylamino, cyclopropylaminocarbonyl amino, cyclopropyl(methyl)aminocarbonylamino, pyrrolidinylcarbonylamino, piperidinylcarbonylamino, formyl(methyl)amino, acetyl(methyl)amino, methoxyacetyl(methyl)amino, cyanoacetyl(methyl)amino, propionyl(methyl)amino, difluoroacetyl(methyl)amino, trifluoroacetyl(methyl)amino, cyclopropanecarbonyl(methyl)amino, methoxycarbonyl(methyl)amino, ethoxycarbonyl(methyl)amino, 2,2-difluoroethoxycarbonyl(methyl)amino, 2,2,2-trifluoroethoxycarbonyl(methyl)amino, 3,3,3-trifluoropropyloxycarbonyl(methyl)amino, cyclopropyloxycarbonyl(methyl)amino, aminocarbonyl(methyl)amino, methylaminocarbonyl(methyl)amino, ethyl aminocarbonyl(methyl)amino, (methoxymethyl)aminocarbonyl(methyl)amino, (2-methoxyethyl)aminocarbonyl(methyl)amino, (cyanomethyl)aminocarbonyl(methyl)amino, (2-cyanoethyl)aminocarbonyl(methyl)amino, dimethylaminocarbonyl(methyl)amino, ethyl(methyl)aminocarbonyl(methyl)amino, diethylaminocarbonyl(methyl)amino, (methoxymethyl)methylaminocarbonyl(methyl)amino, (2-methoxyethyl)methylaminocarbonyl(methyl)amino, (cyanomethyl)methylaminocarbonyl(methyl)amino, (2-cyanoethyl)methylaminocarbonyl(methyl)amino, 2,2-difluoroethylaminocarbonyl(methyl)amino, 2,2,2-trifluoroethylaminocarbonyl(methyl)amino, cyclopropylaminocarbonyl(methyl)amino, cyclopropyl(methyl)aminocarbonyl(methyl)amino, pyrrolidinylcarbonyl(methyl)amino, piperidinylcarbonyl(methyl)amino, formyl(ethyl)amino, acetyl(ethyl)amino, methoxyacetyl(ethyl)amino, cyanoacetyl(ethyl)amino, propionyl(ethyl)amino, difluoroacetyl(ethyl)amino, trifluoroacetyl(ethyl)amino, cyclopropanecarbonyl(ethyl)amino, methoxycarbonyl(ethyl)amino, ethoxycarbonyl(ethyl)amino, 2,2-difluoroethoxycarbonyl(ethyl)amino, 2,2,2-trifluoroethoxycarbonyl(ethyl)amino, 3,3,3-trifluoropropyloxycarbonyl(ethyl)amino, cyclopropyloxycarbonyl(ethyl)amino, aminocarbonyl(ethyl)amino, methylaminocarbonyl(ethyl)amino, ethylaminocarbonyl(ethyl)amino, (methoxymethyl)aminocarbonyl(ethyl)amino, (2-methoxyethyl)aminocarbonyl(ethyl)amino, (cyanomethyl)aminocarbonyl(ethyl)amino, (2-cyanoethyl)aminocarbonyl(ethyl)amino, dimethylaminocarbonyl(ethyl)amino, ethyl(methyl)aminocarbonyl(ethyl)amino, diethylaminocarbonyl(ethyl)amino, (methoxymethyl)methylaminocarbonyl(ethyl)amino, (2-methoxyethyl)methylaminocarbonyl(ethyl)amino, (cyanomethyl)methylaminocarbonyl(ethyl)amino, (2-cyanoethyl)methylaminocarbonyl(ethyl)amino, 2,2-difluoroethylaminocarbonyl(ethyl)amino, 2,2,2-trifluoroethylaminocarbonyl(ethyl)amino, cyclopropylaminocarbonyl(ethyl)amino, cyclopropyl(methyl)aminocarbonyl(ethyl)amino, pyrrolidinylcarbonyl(ethyl)amino, piperidinylcarbonyl(ethyl)amino, formyl(methoxy)amino, acetyl(methoxy)amino, methoxyacetyl(methoxy)amino, cyanoacetyl(methoxy)amino, propionyl(methoxy)amino, difluoroacetyl(methoxy)amino, trifluoroacetyl(methoxy)amino, cyclopropanecarbonyl(methoxy)amino, methoxycarbonyl(methoxy)amino, ethoxycarbonyl(methoxy)amino, 2,2-difluoroethoxycarbonyl(methoxy)amino, 2,2,2-trifluoroethoxycarbonyl(methoxy)amino, 3,3,3-trifluoropropyloxycarbonyl(methoxy)amino, cyclopropyloxycarbonyl(methoxy)amino, aminocarbonyl(methoxy)amino, methylaminocarbonyl(methoxy)amino, ethylaminocarbonyl(methoxy)amino, (methoxymethyl)aminocarbonyl(methoxy)amino, (2-methoxyethyl)aminocarbonyl(methoxy)amino, (cyanomethyl)aminocarbonyl(methoxy)amino, (2-cyanoethyl)aminocarbonyl(methoxy)amino, dimethylaminocarbonyl(methoxy)amino, ethyl(methyl)aminocarbonyl(methoxy)amino, diethylaminocarbonyl(methoxy)amino, (methoxymethyl)methyl aminocarbonyl(methoxy)amino, (2-methoxyethyl)methylaminocarbonyl(methoxy)amino, (cyanomethyl)methylaminocarbonyl(methoxy)amino, (2-cyanoethyl)methylaminocarbonyl(methoxy)amino, 2,2-difluoroethylaminocarbonyl(methoxy)amino, 2,2,2-trifluoroethylaminocarbonyl(methoxy)amino, cyclopropylaminocarbonyl(methoxy)amino, cyclopropyl(methyl)aminocarbonyl(methoxy)amino, pyrrolidinylcarbonyl(methoxy)amino, piperidinylcarbonyl(methoxy)amino, formyl(ethoxy)amino, acetyl(ethoxy)amino, methoxyacetyl(ethoxy)amino, cyanoacetyl(ethoxy)amino, propionyl(ethoxy)amino, difluoroacetyl(ethoxy)amino, trifluoroacetyl(ethoxy)amino, cyclopropanecarbonyl(ethoxy)amino, methoxycarbonyl(ethoxy)amino, ethoxycarbonyl(ethoxy)amino, 2,2-difluoroethoxycarbonyl(ethoxy)amino, 2,2,2-trifluoroethoxycarbonyl(ethoxy)amino, 3,3,3-trifluoropropyloxycarbonyl(ethoxy)amino, cyclopropyloxycarbonyl(ethoxy)amino, aminocarbonyl(ethoxy)amino, methylaminocarbonyl(ethoxy)amino, ethylaminocarbonyl(ethoxy)amino, (methoxymethyl)aminocarbonyl(ethoxy)amino, (2-methoxyethyl)aminocarbonyl(ethoxy)amino, (cyanomethyl)aminocarbonyl(ethoxy)amino, (2-cyanoethyl)aminocarbonyl(ethoxy)amino, dimethylaminocarbonyl(ethoxy)amino, ethyl(methyl)aminocarbonyl(ethoxy)amino, diethylaminocarbonyl(ethoxy)amino, (methoxymethyl)methylaminocarbonyl(ethoxy)amino, (2-methoxyethyl)methylaminocarbonyl(ethoxy)amino, (cyanomethyl)methylaminocarbonyl(ethoxy)amino, (2-cyanoethyl)methylaminocarbonyl(ethoxy)amino, 2,2-difluoroethylaminocarbonyl(ethoxy)amino, 2,2,2-trifluoroethylaminocarbonyl(ethoxy)amino, cyclopropylaminocarbonyl(ethoxy)amino, cyclopropyl(methyl)aminocarbonyl(ethoxy)amino, pyrrolidinylcarbonyl(ethoxy)amino or piperidinylcarbonyl(ethoxy)amino, and more preferably acetyl amino, acetyl(methyl)amino, acetyl(ethyl)amino, acetyl(methoxy)amino, acetyl(ethoxy)amino, methoxycarbonylamino, ethoxycarbonylamino, methoxycarbonyl(methyl)amino, ethoxycarbonyl(methyl)amino, methoxycarbonyl(ethyl)amino, ethoxycarbonyl(ethyl)amino, methoxycarbonyl(methoxy)amino, ethoxycarbonyl(methoxy)amino, methoxycarbonyl(ethoxy)amino or ethoxycarbonyl(ethoxy)amino.

In the formula, R3 represents a hydrogen atom, a cyano group, a nitro group, a halogen atom, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, Rc-L- (wherein Rc and L are the same as defined hereinabove), RaRbN— (wherein Ra and Rb are the same as defined hereinabove), or RiC(=O)— (wherein Ri represents a C1-C6 alkyl group optionally substituted with substituent(s) C, a C1-C6 haloalkyl group, or a C3-C8 cycloalkyl group).

In particular, R3 is preferably a hydrogen atom, a halogen atom, a C1-C6 alkyl group optionally substituted with substituent(s) A, a C1-C6 alkoxy group optionally substituted with substituent(s) A, Rc-L- (wherein Rc and L are the same as defined hereinabove), or RiC(=O)— (wherein Ri is the same as defined hereinabove), and more preferably a hydrogen atom, a halogen atom, or a C1-C6 alkyl group optionally substituted with substituent(s) A.

In the formula (1), R3 may represent a hydrogen atom, a cyano group or a nitro group.

The halogen atom represented by R3 in the formula (1) is the same as defined hereinabove, and is preferably fluorine atom, chlorine atom, bromine atom or iodine atom.

In the "C1-C6 alkyl group optionally substituted with substituent(s) A" represented by R3 in the formula (1), the C1-C6 alkyl group is the same as defined hereinabove, and is preferably methyl, ethyl, propyl, isopropyl, butyl or isobutyl, and more preferably methyl or ethyl. When this group is substituted with substituent(s) A, any hydrogen atom(s) in the C1-C6 alkyl group is appropriately substituted with substituent(s) A.

The "C1-C6 haloalkyl group" represented by R3 in the formula (1) is the same as defined hereinabove, and is preferably difluoromethyl, trifluoromethyl, 2,2-difluoroethyl, 2,2,2-trifluoroethyl, 3,3-difluoropropyl or 3,3,3-trifluoropropyl, and more preferably difluoromethyl, trifluoromethyl, 2,2-difluoroethyl or 2,2,2-trifluoroethyl.

In the "C3-C8 cycloalkyl group optionally substituted with substituent(s) A" represented by R3 in the formula (1), the C3-C8 cycloalkyl group is the same as defined hereinabove, and is preferably cyclopropyl, cyclobutyl, cyclopentyl or cyclohexyl, and more preferably cyclopropyl or cyclobutyl. When this group is substituted with substituent(s) A, any hydrogen atom(s) in the C3-C8 cycloalkyl group is appropriately substituted with substituent(s) A.

In the "C2-C6 alkenyl group optionally substituted with substituent(s) A" represented by R3 in the formula (1), the C2-C6 alkenyl group is the same as defined hereinabove, and is preferably vinyl, 1-propenyl, allyl, 1-butenyl, 2-butenyl or 3-butenyl, and more preferably vinyl, 1-propenyl or allyl. When this group is substituted with substituent(s) A, any hydrogen atom(s) in the C2-C6 alkenyl group is appropriately substituted with substituent(s) A.

The "C2-C6 haloalkenyl group" represented by R3 in the formula (1) is the same as defined hereinabove, and is preferably 2-fluorovinyl, 2,2-difluorovinyl, 2,2-dichlorovinyl, 3-fluoroallyl, 3,3-difluoroallyl or 3,3-dichloroallyl, and more preferably 2-fluorovinyl or 2,2-difluorovinyl.

In the "C2-C6 alkynyl group optionally substituted with substituent(s) A" represented by R3 in the formula (1), the C2-C6 alkynyl group is the same as defined hereinabove, and is preferably ethynyl, 1-propynyl, propargyl, 1-butynyl, 2-butynyl or 3-butynyl, and more preferably ethynyl, 1-propynyl or propargyl. When this group is substituted with substituent(s) A, any hydrogen atom(s) in the C2-C6 alkynyl group is appropriately substituted with substituent(s) A.

The "C2-C6 haloalkynyl group" represented by R3 in the formula (1) is the same as defined hereinabove, and is preferably 3,3-difluoro-1-propynyl, 3,3,3-trifluoro-1-propynyl, 4,4-difluoro-1-butynyl, 4,4-difluoro-2-butynyl, 4,4,4-trifluoro-1-butynyl or 4,4,4-trifluoro-2-butynyl, and more preferably 3,3-difluoro-1-propynyl or 3,3,3-trifluoro-1-propynyl.

In the "C1-C6 alkoxy group optionally substituted with substituent(s) A" represented by R3 in the formula (1), the C1-C6 alkoxy group is the same as defined hereinabove, and is preferably methoxy, ethoxy, propyloxy, isopropyloxy, butoxy or isobutoxy, and more preferably methoxy, ethoxy, propyloxy or isopropyloxy. When this group is substituted with substituent(s) A, any hydrogen atom(s) in the C1-C6 alkoxy group is appropriately substituted with substituent(s) A.

The "C1-C6 haloalkoxy group" represented by R3 in the formula (1) is the same as defined hereinabove, and is preferably difluoromethoxy, trifluoromethoxy, 2,2-difluoroethoxy, 2,2,2-trifluoroethoxy, 3,3-difluoropropyloxy or 3,3,3-trifluoropropyloxy, and more preferably difluoromethoxy, trifluoromethoxy, 2,2-difluoroethoxy or 2,2,2-trifluoroethoxy.

In the "C3-C8 cycloalkoxy group optionally substituted with substituent(s) A" represented by R3 in the formula (1), the C3-C8 cycloalkoxy group is the same as defined hereinabove, and is preferably cyclopropyloxy, cyclobutoxy, cyclopentyloxy or cyclohexyloxy, and more preferably cyclopropyloxy or cyclobutoxy. When this group is substituted with substituent(s) A, any hydrogen atom(s) in the C3-C8 cycloalkoxy group is appropriately substituted with substituent(s) A.

In the "C2-C6 alkenyloxy group optionally substituted with substituent(s) A" represented by R3 in the formula (1), the C2-C6 alkenyloxy group is the same as defined hereinabove, and is preferably vinyloxy, 1-propenyloxy, allyloxy, 1-butenyloxy, 2-butenyloxy or 3-butenyloxy, and more preferably vinyloxy, 1-propenyloxy or allyloxy. When this group is substituted with substituent(s) A, any hydrogen atom(s) in the C2-C6 alkenyloxy group is appropriately substituted with substituent(s) A.

The "C2-C6 haloalkenyloxy group" represented by R3 in the formula (1) is the same as defined hereinabove, and preferably 2-fluorovinyloxy, 2,2-difluorovinyloxy, 2,2-dichlorovinyloxy, 3-fluoroallyloxy, 3,3-difluoroallyloxy or 3,3-dichloroallyloxy, and more preferably 2-fluorovinyloxy or 2,2-difluorovinyloxy.

In the "C3-C6 alkynyloxy group optionally substituted with substituent(s) A" represented by R3 in the formula (1), the C3-C6 alkynyloxy group is the same as defined hereinabove, and is preferably propargyloxy, 2-butynyloxy or 3-butynyloxy, and more preferably propargyloxy. When this group is substituted with substituent(s) A, any hydrogen atom(s) in the C3-C6 alkynyloxy group is appropriately substituted with substituent(s) A.

The "C3-C6 haloalkynyloxy group" represented by R3 in the formula (1) is the same as defined hereinabove, and is preferably 4,4-difluoro-2-butynyloxy, 4-chloro-4,4-difluoro-2-butynyloxy, 4-bromo-4,4-difluoro-2-butynyloxy or 4,4,4-trifluoro-2-butynyloxy, and more preferably 4,4-difluoro-2-butynyloxy or 4,4,4-trifluoro-2-butynyloxy.

In "Rc-L-" represented by R3 in the formula (1), Rc and L are the same as defined hereinabove. "Rc-L-" is preferably methylthio, methanesulfinyl, methanesulfonyl, trifluoromethylthio, trifluoromethanesulfinyl or trifluoromethanesulfonyl, and more preferably methylthio, methanesulfinyl or methanesulfonyl.

In "RaRbN—" represented by R3 in the formula (1), Ra and Rb are the same as defined hereinabove. "RaRbN—" is preferably amino, methylamino, ethylamino, propyl amino, isopropylamino, (methoxymethyl)amino, (2-methoxyethyl)amino, (cyanomethyl)amino, (2-cyanoethyl)amino, dimethylamino, ethyl(methyl)amino, methyl(propyl)amino, isopropyl(methyl)amino, diethylamino, ethyl(propyl)amino, ethyl(isopropyl)amino, (methoxymethyl)methylamino, (2-methoxyethyl)methylamino, (cyanomethyl)methylamino, (2-methoxyethyl)methylamino, (cyanomethyl)methylamino, (2-cyanoethyl)methylamino, 2,2-difluoroethylamino, 2,2,2-trifluoroethylamino, cyclopropylamino, (cyclopropyl)methylamino, pyrrolidinyl or piperidinyl, and more preferably dimethylamino, ethyl(methyl)amino or diethylamino.

In "RiC(=O)—" (wherein Ri represents a C1-C6 alkyl group optionally substituted with substituent(s) C, a C1-C6 haloalkyl group, or a C3-C8 cycloalkyl group) represented by R3 in the formula (1), the terms are the same as defined hereinabove. Where the "C1-C6 alkyl group optionally substituted with substituent(s) C" is substituted with substituent(s) C, any hydrogen atom(s) in the C1-C6 alkyl group is appropriately substituted with substituent(s) C. "RiC(=O)—" is preferably acetyl, methoxyacetyl, cyanoacetyl, propionyl, difluoroacetyl, trifluoroacetyl or cyclopropanecarbonyl, and more preferably acetyl, methoxyacetyl, cyanoacetyl, difluoroacetyl or trifluoroacetyl.

Y1, Y2 and Y3 are independent of one another and each represent a hydrogen atom, a hydroxy group, a cyano group, a halogen atom, a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, a C2-C6 haloalkynyl group, a C1-C6 alkoxy group optionally substituted with substituent(s) B, a C1-C6 haloalkoxy group, a C3-C8 cycloalkoxy group optionally substituted with substituent(s) B, a C2-C6 alkenyloxy group optionally substituted with substituent(s) B, a C2-C6 haloalkenyloxy group, a C3-C6 alkynyloxy group optionally substituted with substituent(s) B, a C3-C6 haloalkynyloxy group, RdC(=O)— (wherein Rd is the same as defined hereinabove), RdC(=O)O— (wherein Rd is the same as defined hereinabove), an aryloxy group optionally substituted with 0 to 5 substituents D, a heteroaryloxy group optionally substituted with 0 to 2 substituents D, an aralkyloxy group optionally substituted with 0 to 5 substituents D, Rc-L- (wherein Rc and L are the same as defined hereinabove), RaRbN— (wherein Ra and Rb are the same as defined hereinabove), Rg(RhO)N— (wherein Rg and Rh are the same as defined hereinabove), or ReC(=O)N(Rf)— (wherein Re and Rf are the same as defined hereinabove), Y1 and Y2, together with the carbon atom to which Y1, Y2 and Y3 are bonded, form a carbonyl group, a C2-C6 alkenyl group optionally substituted with substituent(s) B, a C2-C6 haloalkenyl group, or a C3-C8 cycloalkyl group optionally substituted with substituent(s) B, and Y3 represents a hydrogen atom, a halogen atom, a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, or a C2-C6 haloalkynyl group, or Y1, Y2 and Y3, together with the carbon atom to which Y1, Y2 and Y3 are bonded, represent a cyano group, or a C2-C6 alkynyl group optionally substituted with substituent(s) B.

In particular, Y1, Y2 and Y3 are independent of one another and each preferably represent a hydrogen atom, a hydroxy group, a cyano group, a halogen atom, a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 alkynyl group optionally substituted with substituent(s) B, a C1-C6 alkoxy group optionally substituted with substituent(s) B, a C1-C6 haloalkoxy group, a C3-C8 cycloalkoxy group optionally substituted with substituent(s) B, a C2-C6 alkenyloxy group optionally substituted with substituent(s) B, a C3-C6 alkynyloxy group optionally substituted with substituent(s) B, RdC(=O)— (wherein Rd is the same as defined hereinabove), RdC(=O)O— (wherein Rd is the same as defined hereinabove), an aryloxy group optionally substituted with 0 to 5 substituents D, Rc-L- (wherein Rc and L are the same as defined hereinabove), RaRbN— (wherein Ra and Rb are the same as defined hereinabove), Rg(RhO)N— (wherein Rg and Rh are the same as defined hereinabove), or ReC(=O)N(Rf)— (wherein Re and Rf are the same as defined hereinabove), Y1 and Y2, together with the carbon atom to which Y1, Y2 and Y3 are bonded, form a carbonyl group, a C2-C6 alkenyl group optionally substituted with substituent(s) B, a C2-C6 haloalkenyl group, or a C3-C8 cycloalkyl group optionally substituted with substituent(s) B, and Y3 represents a hydrogen atom, a halogen atom, a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, or a C2-C6 haloalkynyl group, or Y1, Y2 and Y3, together with the carbon atom to which Y1, Y2 and Y3 are bonded, represent a cyano group, or a C2-C6 alkynyl group optionally substituted with substituent(s) B; and more preferably, Y1, Y2 and Y3 are independent of one another and each represent a hydrogen atom, a hydroxy group, a halogen atom, a C1-C9 alkyl group optionally substituted with substituent(s) B, a C1-C6 haloalkyl group, a C3-C8 cycloalkyl group optionally substituted with substituent(s) B, a C2-C6 alkynyl group optionally substituted with substituent(s) B, a C1-C6 alkoxy group optionally substituted with substituent(s) B, a C1-C6 haloalkoxy group, RdC(=O)— (wherein Rd is the same as defined hereinabove), RdC(=O)O— (wherein Rd is the same as defined hereinabove), an aryloxy group optionally substituted with 0 to 5 substituents D, RaRbN— (wherein Ra and Rb are the same as defined hereinabove), Rg(RhO)N— (wherein Rg and Rh are the same as defined hereinabove), or ReC(=O)N(Rf)— (wherein Re and Rf are the same as defined hereinabove), Y1 and Y2, together with the carbon atom to which Y1, Y2 and Y3 are bonded, form a carbonyl group, a C2-C6 alkenyl group optionally substituted with substituent(s) B, a C2-C6 haloalkenyl group, or a C3-C8 cycloalkyl group optionally substituted with substituent(s) B, and Y3 represents a hydrogen atom, a halogen atom, a C1-C9 alkyl group optionally substituted with substituent(s) B, a C3-C8 cycloalkyl group optionally substituted with substituent(s) B, or a C2-C6 alkynyl group optionally substituted with substituent(s) B, or Y1, Y2 and Y3, together with the carbon atom to which Y1, Y2 and Y3 are bonded, represent a cyano group, or a C2-C6 alkynyl group optionally substituted with substituent(s) B.

In the formula (1), Y1 may represent a hydrogen atom, a hydroxy group or a cyano group.

The halogen atom represented by Y1 in the formula (1) is the same as defined hereinabove, and is preferably fluorine atom, chlorine atom, bromine atom or iodine atom.

In the "C1-C9 alkyl group optionally substituted with substituent(s) B" represented by Y1 in the formula (1), the C1-C9 alkyl group is the same as defined hereinabove, and is preferably methyl, ethyl, propyl, isopropyl, butyl, isobutyl, sec-butyl, t-butyl, pentyl, isopentyl, neopentyl, hexyl, heptyl, octyl or nonyl, and more preferably methyl, ethyl, propyl, isopropyl, butyl, isobutyl, sec-butyl, t-butyl, pentyl, hexyl, heptyl or octyl. When this group is substituted with substituent(s) B, any hydrogen atom(s) in the C1-C9 alkyl group is appropriately substituted with substituent(s) B.

The "C1-C6 haloalkyl group" represented by Y1 in the formula (1) is the same as defined hereinabove, and is preferably difluoromethyl, trifluoromethyl, 2,2-difluoroethyl, 2,2,2-trifluoroethyl, 3,3-difluoropropyl or 3,3,3-trifluoropropyl, and more preferably difluoromethyl, trifluoromethyl, 2,2-difluoroethyl or 2,2,2-trifluoroethyl.

In the "C3-C8 cycloalkyl group optionally substituted with substituent(s) B" represented by Y1 in the formula (1), the C3-C8 cycloalkyl group is the same as defined hereinabove, and is preferably cyclopropyl, cyclobutyl, cyclopentyl, cyclohexyl or cycloheptyl, and more preferably cyclopropyl, cyclobutyl, cyclopentyl or cyclohexyl. When this group is substituted with substituent(s) B, any hydrogen atom(s) in the C3-C8 cycloalkyl group is appropriately substituted with substituent(s) B.

In the "C2-C6 alkenyl group optionally substituted with substituent(s) B" represented by Y1 in the formula (1), the C2-C6 alkenyl group is the same as defined hereinabove, and is preferably vinyl, 1-propenyl, allyl, 1-butenyl, 2-butenyl or 3-butenyl, and more preferably vinyl, 1-propenyl or allyl. When this group is substituted with substituent(s) B, any hydrogen atom(s) in the C2-C6 alkenyl group is appropriately substituted with substituent(s) B.

The "C2-C6 haloalkenyl group" represented by Y1 in the formula (1) is the same as defined hereinabove, and is preferably 2-fluorovinyl, 3-fluoroallyl, 1,2-difluorovinyl, 1,2-dichlorovinyl, 1,2-dibromovinyl, 2,2-difluorovinyl, 2,2-dichlorovinyl, 2,2-dibromovinyl, 3,3-difluoroallyl, 3,3-dichloroallyl or 3,3-dibromoallyl, and more preferably 1,2-difluorovinyl, 1,2-dichlorovinyl, 1,2-dibromovinyl, 2,2-difluorovinyl, 2,2-dichlorovinyl or 2,2-dibromovinyl.

In the "C2-C6 alkynyl group optionally substituted with substituent(s) B" represented by Y1 in the formula (1), the C2-C6 alkynyl group is the same as defined hereinabove, and is preferably ethynyl, 1-propynyl, propargyl, 1-butynyl, 2-butynyl or 3-butynyl, and more preferably ethynyl, 1-propynyl or propargyl. When this group is substituted with substituent(s) B, any hydrogen atom(s) in the C2-C6 alkynyl group is appropriately substituted with substituent(s) B.

The "C2-C6 haloalkynyl group" represented by Y1 in the formula (1) is the same as defined hereinabove, and is preferably 3,3-difluoro-1-propynyl, 3,3,3-trifluoro-1-propynyl, 4,4-difluoro-1-butynyl, 4,4-difluoro-2-butynyl, 4,4,4-trifluoro-1-butynyl or 4,4,4-trifluoro-2-butynyl, and more preferably 3,3-difluoro-1-propynyl or 3,3,3-trifluoro-1-propynyl.

In the "C1-C6 alkoxy group optionally substituted with substituent(s) B" represented by Y1 in the formula (1), the C1-C6 alkoxy group is the same as defined hereinabove, and is preferably methoxy, ethoxy, propyloxy, isopropyloxy, butoxy, isobutoxy, sec-butoxy, t-butoxy, pentyloxy, isopentyloxy or neopentyloxy, and more preferably methoxy, ethoxy, propyloxy, isopropyloxy, butoxy, isobutoxy, sec-butoxy, t-butoxy or pentyloxy. When this group is substituted with substituent(s) B, any hydrogen atom(s) in the C1-C6 alkoxy group is appropriately substituted with substituent(s) B.

The "C1-C6 haloalkoxy group" represented by Y1 in the formula (1) is the same as defined hereinabove, and is preferably difluoromethoxy, trifluoromethoxy, 2,2-difluoroethoxy, 2,2,2-trifluoroethoxy, 3,3-difluoropropyloxy or 3,3,3-trifluoropropyloxy, and more preferably difluoromethoxy, trifluoromethoxy, 2,2-difluoroethoxy or 2,2,2-trifluoroethoxy.

In the "C3-C8 cycloalkoxy group optionally substituted with substituent(s) B" represented by Y1 in the formula (1), the C3-C8 cycloalkoxy group is the same as defined hereinabove, and is preferably cyclopropyloxy, cyclobutoxy, cyclopentyloxy, cyclohexyloxy or cycloheptyloxy, and more preferably cyclopropyloxy, cyclobutoxy, cyclopentyloxy or cyclohexyloxy. When this group is substituted with substituent(s) B, any hydrogen atom(s) in the C3-C8 cycloalkoxy group is appropriately substituted with substituent(s) B.

In the "C2-C6 alkenyloxy group optionally substituted with substituent(s) B" represented by Y1 in the formula (1), the C2-C6 alkenyloxy group is the same as defined hereinabove, and is preferably vinyloxy, 1-propenyloxy, allyloxy, 1-butenyloxy, 2-butenyloxy or 3-butenyloxy, and more preferably vinyloxy, 1-propenyloxy or allyloxy. When this group is substituted with substituent(s) B, any hydrogen atom(s) in the C2-C6 alkenyloxy group is appropriately substituted with substituent(s) B.

The "C2-C6 haloalkenyloxy group" represented by Y1 in the formula (1) is the same as defined hereinabove, and is preferably 2-fluorovinyloxy, 3-fluoroallyloxy, 1,2-difluorovinyloxy, 1,2-dichlorovinyloxy, 1,2-dibromovinyloxy, 2,2-difluorovinyloxy, 2,2-dichlorovinyloxy, 2,2-dibromovinyloxy, 3,3-difluoroallyloxy, 3,3-dichloroallyloxy or 3,3-dibromoallyloxy, and more preferably 1,2-difluorovinyloxy, 1,2-dichlorovinyloxy, 1,2-dibromovinyloxy, 2,2-difluorovinyloxy, 2,2-dichlorovinyloxy or 2,2-dibromovinyloxy.

In the "C3-C6 alkynyloxy group optionally substituted with substituent(s) B" represented by Y1 in the formula (1), the C3-C6 alkynyloxy group is the same as defined hereinabove, and is preferably propargyloxy, 2-butynyloxy or 3-butynyloxy, and more preferably propargyloxy. When this group is substituted with substituent(s) B, any hydrogen atom(s) in the C3-C6 alkynyloxy group is appropriately substituted with substituent(s) B.

The "C3-C6 haloalkynyloxy group" represented by Y1 in the formula (1) is the same as defined hereinabove, and is preferably 4,4-difluoro-2-butynyloxy, 4-chloro-4,4-difluoro-2-butynyloxy, 4-bromo-4,4-difluoro-2-butynyloxy or 4,4,4-trifluoro-2-butynyloxy, and more preferably 4,4-difluoro-2-butynyloxy or 4,4,4-trifluoro-2-butynyloxy.

In "RdC(=O)—" represented by Y1 in the formula (1), Rd is the same as defined hereinabove. Rd is preferably a hydrogen atom, a C1-C6 alkyl group optionally substituted with substituent(s) C, or a C1-C6 alkoxy group, and more preferably a hydrogen atom, or a C1-C6 alkyl group optionally substituted with substituent(s) C. "RdC(=O)—" is preferably formyl, acetyl, methoxyacetyl, cyanoacetyl, propionyl, difluoroacetyl, trifluoroacetyl, cyclopropanecarbonyl, methoxycarbonyl, ethoxycarbonyl, 2,2-difluoroethoxycarbonyl, 2,2,2-trifluoroethoxycarbonyl, 3,3,3-trifluoropropyloxycarbonyl, cyclopropyloxycarbonyl, aminocarbonyl, methylaminocarbonyl, ethylaminocarbonyl, (methoxymethyl)aminocarbonyl, (2-methoxyethyl)aminocarbonyl, (cyanomethyl)aminocarbonyl, (2-cyanoethyl)aminocarbonyl, dimethyl aminocarbonyl, ethyl(methyl)aminocarbonyl, di ethylaminocarbonyl, (methoxymethyl)methylaminocarbonyl, (2-methoxyethyl)methylaminocarbonyl, (cyanomethyl)methylaminocarbonyl, (2-cyanoethyl)methylaminocarbonyl, 2,2-difluoroethylaminocarbonyl, 2,2,2-trifluoroethylaminocarbonyl, cyclopropylaminocarbonyl, cyclopropyl(methyl)aminocarbonyl, pyrrolidinylcarbonyl or piperidinylcarbonyl, and more preferably formyl, acetyl or propionyl.

In "RdC(=O)O—" represented by Y1 in the formula (1), Rd is the same as defined hereinabove. Rd is preferably a hydrogen atom, a C1-C6 alkyl group optionally substituted with substituent(s) C, or a C1-C6 haloalkyl group, and more preferably a C1-C6 alkyl group optionally substituted with substituent(s) C. "RdC(=O)O—" is preferably formyloxy, acetyloxy, methoxyacetyloxy, cyanoacetyloxy, propionyloxy, difluoroacetyloxy, trifluoroacetyloxy, cyclopropanecarbonyloxy, methoxycarbonyloxy, ethoxycarbonyloxy, 2,2-difluoroethoxycarbonyloxy, 2,2,2-trifluoroethoxycarbonyloxy, 3,3,3-trifluoropropyloxycarbonyloxy, cyclopropyloxycarbonyloxy, aminocarbonyloxy, methylaminocarbonyloxy, ethylaminocarbonyloxy, (methoxymethyl)aminocarbonyloxy, (2-methoxyethyl)aminocarbonyloxy, (cyanomethyl)aminocarbonyloxy, (2-cyanoethyl)aminocarbonyloxy, dimethylaminocarbonyloxy, ethyl(methyl)aminocarbonyloxy, (methoxymethyl)methylaminocarbonyloxy, (2-methoxyethyl)methyl aminocarbonyloxy, (cyanomethyl)methylaminocarbonyloxy, (2-cyanoethyl)methylaminocarbonyloxy, 2,2-difluoroethylaminocarbonyloxy, 2,2,2-trifluoroethylaminocarbonyloxy, cyclopropylaminocarbonyloxy, cyclopropyl(methyl)aminocarbonyloxy, pyrrolidinylcarbonyloxy or piperidinylcarbonyloxy, and more preferably acetyloxy, methoxyacetyloxy, cyanoacetyloxy or propionyloxy.

In the "aryloxy group optionally substituted with 0 to 5 substituents D" represented by Y1 in the formula (1), the aryloxy group is the same as defined hereinabove, and is preferably phenoxy or naphthyloxy, and more preferably phenoxy. When this group is substituted with substituent(s) D, any hydrogen atom(s) in the aryloxy group is appropriately substituted with substituent(s) D. Where there are two or more substituents D, they are independent of one another.

In the "heteroaryloxy group optionally substituted with 0 to 2 substituents D" represented by Y1 in the formula (1), the heteroaryloxy group is the same as defined hereinabove, and is preferably pyridyloxy, pyridazinyloxy, pyrimidinyloxy, pyrazinyloxy, triazinyloxy, tetrazinyloxy, thienyloxy, thiazolyloxy, isothiazolyloxy or thiadiazolyloxy, and more preferably pyridyloxy, pyridazinyloxy, pyrimidinyloxy or pyrazinyloxy. When this group is substituted with substituent(s) D, any hydrogen atom(s) in the heteroaryloxy group is appropriately substituted with substituent(s) D. Where there are two substituents D, they are independent of one another.

In the "aralkyloxy group optionally substituted with 0 to 5 substituents D" represented by Y1 in the formula (1), the aralkyloxy group is the same as defined hereinabove, and is preferably benzyloxy, phenetyloxy or phenylpropyloxy, and more preferably benzyloxy or phenetyloxy. When this group is substituted with substituent(s) D, any hydrogen atom(s) in the aralkyloxy group is appropriately substituted with substituent(s) D. Where there are two or more substituents D, they are independent of one another.

In "Rc-L-" represented by Y1 in the formula (1), Rc and L are the same as defined hereinabove. "Rc-L-" is preferably methylthio, methanesulfinyl, methanesulfonyl, trifluoromethylthio, trifluoromethanesulfinyl or trifluoromethanesulfonyl, and more preferably methylthio, methanesulfinyl or methanesulfonyl.

In "RaRbN—" represented by Y1 in the formula (1), Ra and Rb are the same as defined hereinabove. Ra and Rb preferably represent a C1-C6 alkyl group optionally substituted with substituent(s) C, or a C1-C6 haloalkyl group, or Ra and Rb preferably, together with the nitrogen atom to which they are bonded, form pyrrolidinyl or piperidinyl. Ra and Rb are more preferably a C1-C6 alkyl group optionally substituted with substituent(s) C. Ra and Rb are independent of one another, and the same applies to preferred embodiments. "RaRbN—" is preferably amino, methylamino, ethylamino, propyl amino, isopropylamino, (methoxymethyl) amino, (2-methoxyethyl)amino, (cyanomethyl)amino, (2-cyanoethyl)amino, dimethylamino, ethyl(methyl)amino, methyl(propyl)amino, isopropyl(methyl)amino, (methoxymethyl)methyl amino, (2-methoxyethyl)methylamino, (cyanomethyl)methylamino, (2-cyanoethyl)methylamino, diethylamino, ethyl(propyl)amino, ethyl(isopropyl)amino, ethyl(methoxymethyl)amino, ethyl(2-methoxyethyl)amino, (cyanomethyl)ethylamino, (2-cyanoethyl)ethyl amino, 2,2-difluoroethylamino, 2,2,2-trifluoroethylamino, cyclopropylamino, (cyclopropyl)methylamino, pyrrolidinyl or piperidinyl, and more preferably dimethylamino, ethyl (methyl)amino, isopropyl(methyl)amino, diethylamino or ethyl(isopropyl)amino.

In "Rg(RhO)N—" represented by Y1 in the formula (1), Rg and Rh are the same as defined hereinabove. Rg and Rh are preferably a hydrogen atom, or a C1-C6 alkyl group optionally substituted with substituent(s) C. Ra and Rb are independent of one another, and the same applies to preferred embodiments. "Rg(RhO)N—" is preferably hydroxyamino, methoxyamino, ethoxyamino, propyloxyamino, isopropyloxyamino, methoxy(methyl)amino, ethoxy(methyl)amino, methyl(propyloxy)amino, isopropyloxy(methyl)amino, ethyl(methoxy)amino, ethoxy(ethyl) amino, ethyl(propyloxy)amino, ethyl(isopropyloxy)amino, methoxy(propyl)amino, ethoxy(propyl)amino, propyloxy (propyl)amino, isopropyloxy(propyl)amino, methoxy(trifluoroethyl)amino, ethoxy(trifluoroethyl)amino, propyloxy (trifluoroethyl)amino, isopropyloxy(trifluoroethyl)amino, methyl(trifluoroethoxy)amino, ethyl(trifluoroethoxy)amino, propyl(trifluoroethoxy)amino, isopropyl(trifluoroethoxy) amino, cyclopropyl(methoxy)amino, cyclopropyl(ethoxy) amino, cyclopropyl(propyloxy)amino, cyclopropyl(isopropyloxy)amino, cyclobutyl(methoxy)amino, cyclobutyl (ethoxy)amino, cyclobutyl(propyloxy)amino, cyclobutyl (isopropyloxy)amino, cyclopropyloxy(methyl)amino, cyclopropyloxy(ethyl)amino, cyclopropyloxy(propyl) amino, cyclopropyloxy(isopropyl)amino, cyclobutoxy (methyl)amino, cyclobutoxy(ethyl)amino, cyclobutoxy(propyl)amino, cyclobutoxy(isopropyl)amino, methoxy (methoxymethyl)amino, ethoxy(methoxymethyl)amino, methoxymethyl(propyloxy)amino, isopropyloxy (methoxymethyl)amino, cyanomethyl(methoxy)amino, cyanomethyl(ethoxy)amino, cyanomethyl(propyloxy)amino or cyanomethyl(isopropyloxy)amino, and more preferably methoxyamino, ethoxyamino, methoxy(methyl)amino, ethoxy(methyl)amino, ethyl(methoxy)amino or ethoxy(ethyl)amino.

In "ReC(=O)N(Rf)—" represented by Y1 in the formula (1), Re and Rf are the same as defined hereinabove. Re and Rf are preferably a hydrogen atom, a C1-C6 alkyl group optionally substituted with substituent(s) C, a C1-C6 haloalkyl group, a C1-C6 alkoxy group, or a C1-C6 haloalkoxy group, and more preferably a hydrogen atom, a C1-C6 alkyl group optionally substituted with substituent(s) C, or a C1-C6 alkoxy group. Re and Rf are independent of one another, and the same applies to preferred embodiments. "ReC(=O)N(Rf)—" is preferably formylamino, acetylamino, methoxyacetylamino, cyanoacetyl amino, propionylamino, difluoroacetylamino, trifluoroacetylamino, cyclopropanecarbonylamino, methoxycarbonylamino, ethoxycarbonylamino, 2,2-difluoroethoxycarbonylamino, 2,2,2-trifluoroethoxycarbonylamino, 3,3,3-trifluoropropyloxycarbonylamino, cyclopropyloxycarbonylamino, aminocarbonylamino, methylaminocarbonylamino, ethylaminocarbonylamino, (methoxymethyl)aminocarbonylamino, (2-methoxyethyl)aminocarbonylamino, (cyanomethyl)aminocarbonylamino, (2-cyanoethyl)aminocarbonylamino, dimethylaminocarbonylamino, ethyl(methyl)aminocarbonylamino, diethylaminocarbonylamino, (methoxymethyl) methylaminocarbonylamino, (2-methoxyethyl)methylaminocarbonylamino, (cyanomethyl) methylaminocarbonylamino, (2-cyanoethyl) methylaminocarbonylamino, 2,2-difluoroethylaminocarbonylamino, 2,2,2-trifluoroethylaminocarbonylamino, cyclopropylaminocarbonyl amino, cyclopropyl(methyl)aminocarbonylamino, pyrrolidinylcarbonylamino, piperidinylcarbonylamino, formyl(methyl)amino, acetyl(methyl) amino, methoxyacetyl(methyl)amino, cyanoacetyl(methyl) amino, propionyl(methyl)amino, difluoroacetyl(methyl) amino, trifluoroacetyl(methyl)amino, cyclopropanecarbonyl (methyl)amino, methoxycarbonyl(methyl)amino, ethoxycarbonyl(methyl)amino, 2,2-difluoroethoxycarbonyl (methyl)amino, 2,2,2-trifluoroethoxycarbonyl(methyl) amino, 3,3,3-trifluoropropyloxycarbonyl(methyl)amino, cyclopropyloxycarbonyl(methyl)amino, aminocarbonyl(methyl)amino, methylaminocarbonyl(methyl)amino, ethyl aminocarbonyl(methyl)amino, (methoxymethyl)aminocarbonyl(methyl)amino, (2-methoxyethyl)aminocarbonyl (methyl)amino, (cyanomethyl)aminocarbonyl(methyl) amino, (2-cyanoethyl)aminocarbonyl(methyl)amino, dimethylaminocarbonyl(methyl)amino, ethyl(methyl)aminocarbonyl(methyl)amino, diethylaminocarbonyl(methyl) amino, (methoxymethyl)methylaminocarbonyl(methyl) amino, (2-methoxyethyl)methylaminocarbonyl(methyl) amino, (cyanomethyl)methylaminocarbonyl(methyl)amino, (2-cyanoethyl)methylaminocarbonyl(methyl)amino, 2,2-difluoroethylaminocarbonyl(methyl)amino, 2,2,2-trifluoroethylaminocarbonyl(methyl)amino, cyclopropylaminocarbonyl (methyl)amino, cyclopropyl(methyl)aminocarbonyl (methyl)amino, pyrrolidinylcarbonyl(methyl)amino, piperidinylcarbonyl(methyl)amino, formyl(ethyl)amino, acetyl(ethyl)amino, methoxyacetyl(ethyl)amino, cyanoacetyl(ethyl)amino, propionyl(ethyl)amino, difluoroacetyl(ethyl)amino, trifluoroacetyl(ethyl)amino, cyclopropanecarbonyl(ethyl)amino, methoxycarbonyl(ethyl)amino, ethoxycarbonyl(ethyl)amino, 2,2-difluoroethoxycarbonyl(ethyl)amino, 2,2,2-trifluoroethoxycarbonyl(ethyl)amino, 3,3,3-trifluoropropyloxycarbonyl(ethyl)amino, cyclopropyloxycarbonyl(ethyl)amino, aminocarbonyl(ethyl)amino, methylaminocarbonyl(ethyl)amino, ethylaminocarbonyl(ethyl)amino, (methoxymethyl)aminocarbonyl(ethyl)amino, (2-methoxyethyl)aminocarbonyl(ethyl)amino, (cyanomethyl)aminocarbonyl(ethyl)amino, (2-cyanoethyl)aminocarbonyl(ethyl)amino, dimethylaminocarbonyl(ethyl)amino, ethyl(methyl)aminocarbonyl(ethyl)amino, diethylaminocarbonyl(ethyl)amino, (methoxymethyl)methylaminocarbonyl(ethyl)amino, (2-methoxyethyl)methylaminocarbonyl(ethyl)amino, (cyanomethyl)methylaminocarbonyl(ethyl)amino, (2-cyanoethyl)methylaminocarbonyl(ethyl)amino, 2,2-difluoroethylaminocarbonyl(ethyl)amino, 2,2,2-trifluoroethylaminocarbonyl(ethyl)amino, cyclopropylaminocarbonyl(ethyl)amino, cyclopropyl(methyl)aminocarbonyl(ethyl)amino, pyrrolidinylcarbonyl(ethyl)amino, piperidinylcarbonyl(ethyl)amino, formyl(methoxy)amino, acetyl(methoxy)amino, methoxyacetyl(methoxy)amino, cyanoacetyl(methoxy)amino, propionyl(methoxy)amino, difluoroacetyl(methoxy)amino, trifluoroacetyl(methoxy)amino, cyclopropanecarbonyl(methoxy)amino, methoxycarbonyl(methoxy)amino, ethoxycarbonyl(methoxy)amino, 2,2-difluoroethoxycarbonyl(methoxy)amino, 2,2,2-trifluoroethoxycarbonyl(methoxy)amino, 3,3,3-trifluoropropyloxycarbonyl(methoxy)amino, cyclopropyloxycarbonyl(methoxy)amino, aminocarbonyl(methoxy)amino, methylaminocarbonyl(methoxy)amino, ethylaminocarbonyl(methoxy)amino, (methoxymethyl)aminocarbonyl(methoxy)amino, (2-methoxyethyl)aminocarbonyl(methoxy)amino, (cyanomethyl)aminocarbonyl(methoxy)amino, (2-cyanoethyl)aminocarbonyl(methoxy)amino, dimethylaminocarbonyl(methoxy)amino, ethyl(methyl)aminocarbonyl(methoxy)amino, diethylaminocarbonyl(methoxy)amino, (methoxymethyl)methyl aminocarbonyl(methoxy)amino, (2-methoxyethyl)methylaminocarbonyl(methoxy)amino, (cyanomethyl)methylaminocarbonyl(methoxy)amino, (2-cyanoethyl)methylaminocarbonyl(methoxy)amino, 2,2-difluoroethylaminocarbonyl(methoxy)amino, 2,2,2-trifluoroethylaminocarbonyl(methoxy)amino, cyclopropylaminocarbonyl(methoxy)amino, cyclopropyl(methyl)aminocarbonyl(methoxy)amino, pyrrolidinylcarbonyl(methoxy)amino, piperidinylcarbonyl(methoxy)amino, formyl(ethoxy)amino, acetyl(ethoxy)amino, methoxyacetyl(ethoxy)amino, cyanoacetyl(ethoxy)amino, propionyl(ethoxy)amino, difluoroacetyl(ethoxy)amino, trifluoroacetyl(ethoxy)amino, cyclopropanecarbonyl(ethoxy)amino, methoxycarbonyl(ethoxy)amino, ethoxycarbonyl(ethoxy)amino, 2,2-difluoroethoxycarbonyl(ethoxy)amino, 2,2,2-trifluoroethoxycarbonyl(ethoxy)amino, 3,3,3-trifluoropropyloxycarbonyl(ethoxy)amino, cyclopropyloxycarbonyl(ethoxy)amino, aminocarbonyl(ethoxy)amino, methylaminocarbonyl(ethoxy)amino, ethylaminocarbonyl(ethoxy)amino, (methoxymethyl)aminocarbonyl(ethoxy)amino, (2-methoxyethyl)aminocarbonyl(ethoxy)amino, (cyanomethyl)aminocarbonyl(ethoxy)amino, (2-cyanoethyl)aminocarbonyl(ethoxy)amino, dimethylaminocarbonyl(ethoxy)amino, ethyl(methyl)aminocarbonyl(ethoxy)amino, diethylaminocarbonyl(ethoxy)amino, (methoxymethyl)methylaminocarbonyl(ethoxy)amino, (2-methoxyethyl)methylaminocarbonyl(ethoxy)amino, (cyanomethyl)methylaminocarbonyl(ethoxy)amino, (2-cyanoethyl)methylaminocarbonyl(ethoxy)amino, 2,2-difluoroethylaminocarbonyl(ethoxy)amino, 2,2,2-trifluoroethylaminocarbonyl(ethoxy)amino, cyclopropylaminocarbonyl(ethoxy)amino, cyclopropyl(methyl)aminocarbonyl(ethoxy)amino, pyrrolidinylcarbonyl(ethoxy)amino or piperidinylcarbonyl(ethoxy)amino, and more preferably acetyl amino, acetyl(methyl)amino, acetyl(ethyl)amino, acetyl(methoxy)amino, acetyl(ethoxy)amino, methoxycarbonylamino, ethoxycarbonylamino, methoxycarbonyl(methyl)amino, ethoxycarbonyl(methyl)amino, methoxycarbonyl(ethyl)amino, ethoxycarbonyl(ethyl)amino, methoxycarbonyl(methoxy)amino, ethoxycarbonyl(methoxy)amino, methoxycarbonyl(ethoxy)amino or ethoxycarbonyl(ethoxy)amino.

In the formula (1), the definition of Y2 is the same as that of Y1.

In the formula (1), the definition of Y3 is the same as that of Y1.

In the formula (1), Y1, Y2 and Y3 are independent of one another and may be the same or different from one another without limitation.

When "Y1 and Y2, together with the carbon atom to which Y1, Y2 and Y3 are bonded, form a carbonyl group", the formula (1) is of formula (1a):

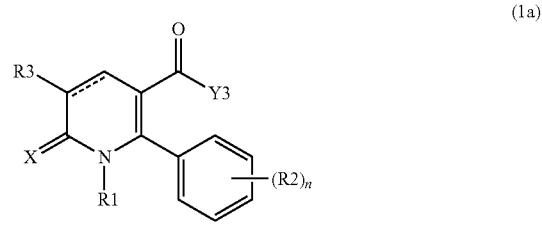

(1a)

In the formula (1a), Y3 is preferably a hydrogen atom, a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, or a C2-C6 alkynyl group optionally substituted with substituent(s) B, and more preferably a hydrogen atom, a C1-C9 alkyl group optionally substituted with substituent(s) B, a C3-C8 cycloalkyl group optionally substituted with substituent(s) B, or a C2-C6 alkynyl group optionally substituted with substituent(s) B.

Preferred specific examples of Y3 in the formula (1a) include a hydrogen atom, methyl, ethyl, propyl, isopropyl, butyl, isobutyl, sec-butyl, t-butyl, pentyl, isopentyl, trifluoromethyl, cyclopropyl, cyclobutyl, cyclopentyl, cyclohexyl, vinyl, allyl, ethynyl and 1-propynyl. More preferred specific examples include a hydrogen atom, methyl, ethyl, propyl, isopropyl, butyl, isobutyl, t-butyl, cyclopropyl, cyclobutyl, cyclopentyl, ethynyl and 1-propynyl.

In "Y1 and Y2, together with the carbon atom to which Y1, Y2 and Y3 are bonded, form a C2-C6 alkenyl group optionally substituted with substituent(s) B" in the formula (1), C2-C6 alkenyl group is the same as defined hereinabove; however, examples listed below are limited to ones having a double bond at the 1-position. Preferable examples include vinyl, 1-propenyl, 1-butenyl, 2-methyl-1-propenyl, 1-pentenyl and 2-methyl-1-butenyl, and more preferable examples include vinyl, 1-propenyl, 1-butenyl and 2-methyl-1-propenyl. When, for example, "Y1 and Y2, together with the carbon atom to which Y1, Y2 and Y3 are bonded, form a C2-C6 alkenyl group optionally substituted with substituent(s) B" is 2-methyl-1-propenyl, the compound is of formula (1b):

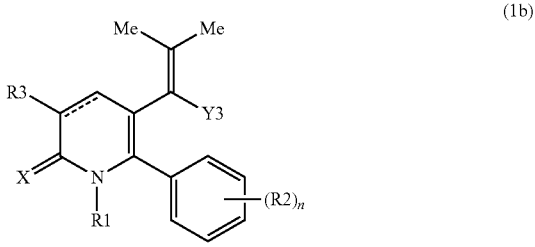

When this group is substituted with substituent(s) B, any hydrogen atom(s) in the C2-C6 alkenyl group is appropriately substituted with substituent(s) B.

In "Y1 and Y2, together with the carbon atom to which Y1, Y2 and Y3 are bonded, form a C2-C6 alkenyl group optionally substituted with substituent(s) B" in the formula (1), Y3 is preferably a hydrogen atom, a halogen atom, a C1-C9 alkyl group optionally substituted with substituent(s) B, a C1-C6 haloalkyl group, or a C3-C8 cycloalkyl group optionally substituted with substituent(s) B, and more preferably a hydrogen atom, or a C1-C9 alkyl group optionally substituted with substituent(s) B.

In "Y1 and Y2, together with the carbon atom to which Y1, Y2 and Y3 are bonded, form a C2-C6 alkenyl group optionally substituted with substituent(s) B" in the formula (1), Y3 may be preferably a hydrogen atom, fluorine atom, chlorine atom, bromine atom, iodine atom, methyl, ethyl, propyl, isopropyl, trifluoromethyl, cyclopropyl or cyclopropyl, and more preferably a hydrogen atom, methyl, ethyl, propyl or isopropyl.

In "Y1 and Y2, together with the carbon atom to which Y1, Y2 and Y3 are bonded, form a C2-C6 haloalkenyl group" in the formula (1), the C2-C6 haloalkenyl group is the same as defined hereinabove; however, examples listed below are limited to ones having a double bond at the 1-position. Preferred examples include 2-fluorovinyl, 2-chlorovinyl, 2-bromovinyl, 2-iodovinyl, 2,2-difluorovinyl, 2,2-dichlorovinyl, 2,2-dibromovinyl and 2,2-diiodovinyl, and more preferred examples include 2-fluorovinyl, 2-chlorovinyl, 2-bromovinyl, 2,2-difluorovinyl, 2,2-dichlorovinyl and 2,2-dibromovinyl. When, for example, "Y1 and Y2, together with the carbon atom to which Y1, Y2 and Y3 are bonded, form a C2-C6 haloalkenyl group" is 2,2-dibromovinyl, the compound is of formula (1b'):

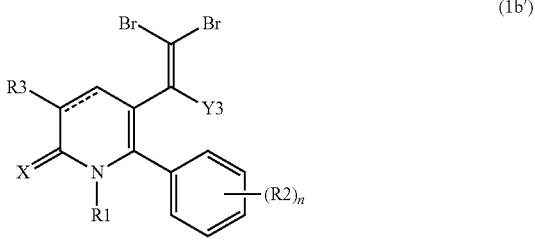

In "Y1 and Y2, together with the carbon atom to which Y1, Y2 and Y3 are bonded, form a C2-C6 haloalkenyl group" in the formula (1), Y3 is preferably a hydrogen atom, a halogen atom, a C1-C9 alkyl group optionally substituted with substituent(s) B, a C1-C6 haloalkyl group, or a C3-C8 cycloalkyl group optionally substituted with substituent(s) B, and more preferably a hydrogen atom, or a halogen atom.

In "Y1 and Y2, together with the carbon atom to which Y1, Y2 and Y3 are bonded, form a C2-C6 haloalkenyl group" in the formula (1), Y3 preferably includes a hydrogen atom, fluorine atom, chlorine atom, bromine atom, iodine atom, methyl, ethyl, propyl, isopropyl, trifluoromethyl, cyclopropyl or cyclopropyl, and more preferably includes a hydrogen atom, fluorine atom, chlorine atom, bromine atom, or iodine atom.

In "Y1 and Y2, together with the carbon atom to which Y1, Y2 and Y3 are bonded, form a C3-C8 cycloalkyl group optionally substituted with substituent(s) B" in the formula (1), the C3-C8 cycloalkyl group is the same as defined hereinabove. Preferred examples include cyclopropyl, cyclobutyl, cyclopentyl, cyclohexyl and cyclohexyl, and more preferred examples include cyclopropyl, cyclobutyl, cyclopentyl and cyclohexyl. When, for example, "Y1 and Y2, together with the carbon atom to which Y1, Y2 and Y3 are bonded, form a C3-C8 cycloalkyl group optionally substituted with substituent(s) B" is cyclopentyl, the compound is of formula (1c):

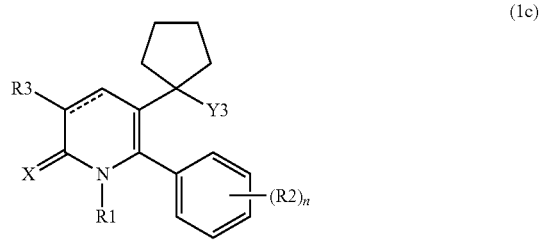

When this group is substituted with substituent(s) B, any hydrogen atom(s) in the C3-C8 cycloalkyl group is appropriately substituted with substituent(s) B.

In "Y1 and Y2, together with the carbon atom to which Y1, Y2 and Y3 are bonded, form a C3-C8 cycloalkyl group optionally substituted with substituent(s) B" in the formula (1), Y3 is preferably a hydrogen atom, a halogen atom, or a C1-C9 alkyl group optionally substituted with substituent(s) B, and more preferably a hydrogen atom, or a halogen atom.

In "Y1 and Y2, together with the carbon atom to which Y1, Y2 and Y3 are bonded, form a C3-C8 cycloalkyl group optionally substituted with substituent(s) B" in the formula (1), preferred Y3 include a hydrogen atom, fluorine atom, chlorine atom, bromine atom, iodine atom, methyl or ethyl, and more preferred Y3 is a hydrogen atom, fluorine atom, or chlorine atom.

In the formula (1), Y1 and Y2, together with the carbon atom to which Y1, Y2 and Y3 are bonded, may form a carbonyl group, a C2-C6 alkenyl group optionally substituted with substituent(s) B, or a C3-C8 cycloalkyl group optionally substituted with substituent(s) B, and Y3 may represent a hydrogen atom, a "halogen atom", a "C1-C9 alkyl group optionally substituted with substituent(s) B", a "C1-C6 haloalkyl group", a "C3-C8 cycloalkyl group optionally substituted with substituent(s) B", a "C2-C6 alkenyl group optionally substituted with substituent(s) B", a "C2-C6 haloalkenyl group", a "C2-C6 alkynyl group optionally substituted with substituent(s) B", or a "C2-C6 haloalkynyl group". In this case, the definitions of terms used for Y3 are the same as those of Y1 in the formula (1).

When "Y1, Y2 and Y3, together with the carbon atom to which Y1, Y2 and Y3 are bonded, represent a cyano group", the formula (1) is of formula (1d):

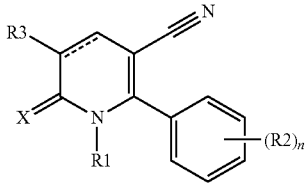

(1d)

In "Y1, Y2 and Y3, together with the carbon atom to which Y1, Y2 and Y3 are bonded, represent a C2-C6 alkynyl group optionally substituted with substituent(s) B" in the formula (1), the C2-C6 alkynyl group is the same as defined hereinabove; however, examples listed below are ones having a triple bond at the 1-position. Preferred examples include ethynyl, 1-propynyl, 1-butynyl, 1-pentynyl and 1-hexynyl, and more preferred examples include ethynyl, 1-propynyl and 1-butynyl. When, for example, "Y1, Y2 and Y3, together with the carbon atom to which Y1, Y2 and Y3 are bonded, represent a C2-C6 alkynyl group optionally substituted with substituent(s) B" is 1-propynyl, the compound is of formula (1e):

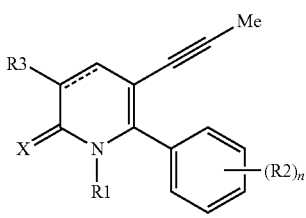

(1e)

When this group is substituted with substituent(s) B, any hydrogen atom(s) in the C2-C6 alkynyl group is appropriately substituted with substituent(s) B.

In the formula (1), n represents an integer of 1 to 5. Here, it is understood that all the integers between 1 and 5 inclusive, i.e. 1, 2, 3, 4 and 5, are disclosed individually. When n is 2 or greater, the two or more substituents R2 are independent of one another.

In the formula (1), X represents an oxygen atom or a sulfur atom. X is preferably an oxygen atom.

The bond with the broken line in the formula (1) is represented by: ----

The bond with the broken line in the formula (1) is a double bond or a single bond.

When the bond with the broken line is a double bond, the formula (1) represents a compound of a formula (1f) or a salt thereof:

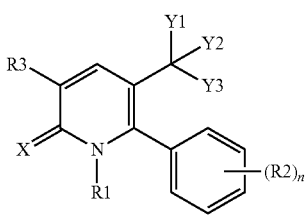

(1f)

wherein, R1, R2, R3, Y1, Y2, Y3, X and n are the same as defined in the formula (1).

When the bond with the broken line is a single bond, the formula (1) represents a compound of formula (1g) or a salt thereof:

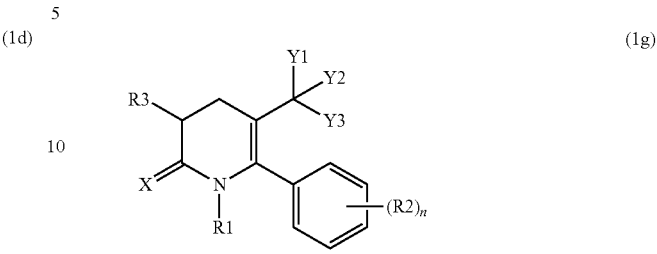

(1g)

wherein, R1, R2, R3, Y1, Y2, Y3, X and n are the same as defined in the formula (1).

When R3 in the formula (1g) is a substituent other than hydrogen, the compound is either R-isomer or S-isomer, or a mixture containing R-isomer and S-isomer in any proportions.

The compound of formula (1) may have a chiral axis. In such a case, the compound may be any single isomer or a mixture of isomers in any proportions without limitation.

The compound of formula (1) may have a chiral atom. In such a case, the compound may be any single isomer or a mixture of isomers in any proportions without limitation.

The compound of formula (1) may have geometric isomeric forms. In such a case, the compound may be any single isomer or a mixture of isomers in any proportions without limitation.

The compound of formula (1) may form a salt with, for example, an acid such as hydrochloric acid, sulfuric acid, acetic acid, fumaric acid or maleic acid, a metal such as sodium, potassium or calcium. The form of the salt is not particularly limited to the above examples as long as the salt may be used as an agricultural and horticultural fungicide.

The substituent(s) A is at least one selected from the group consisting of hydroxy group, cyano group, C3-C8 cycloalkyl groups, C1-C6 alkoxy groups, C1-C6 haloalkoxy groups, C3-C8 cycloalkoxy groups, RaRbN— (wherein Ra and Rb are the same as defined hereinabove) and Rc-L- (wherein Rc and L are the same as defined hereinabove).

In particular, the substituent(s) A is preferably a cyano group, a C1-C6 alkoxy group, or Rc-L- (wherein Rc and L are the same as defined hereinabove), and more preferably a cyano group or a C1-C6 alkoxy group.

The terms used in association with the substituent(s) A are the same as defined hereinabove.

Specifically, preferred examples of the substituents A include hydroxy group; cyano group;

C3-C8 cycloalkyl groups such as cyclopropyl, cyclobutyl, cyclopentyl and cyclohexyl;

C1-C6 alkoxy groups such as methoxy, ethoxy, propyloxy and isopropyloxy;

C1-C6 haloalkoxy groups such as difluoromethoxy, trifluoromethoxy, 2,2-difluoroethoxy, 2,2,2-trifluoroethoxy, 3,3-difluoropropyloxy and 3,3,3-trifluoropropyloxy;

C3-C8 cycloalkoxy groups such as cyclopropyloxy, cyclobutoxy, cyclopentyloxy and cyclohexyloxy;

RaRbN— (wherein Ra and Rb are the same as defined hereinabove) such as amino, methylamino, ethylamino, propylamino, isopropylamino, (methoxymethyl)amino, (2-methoxyethyl)amino, (cyanomethyl)amino, (2-cyanoethyl)amino, dimethylamino, ethyl(methyl)amino, methyl(propyl)amino, isopropyl(methyl)amino, (methoxymethyl)methylamino, (2-methoxyethyl)methylamino, (cyanomethyl)methylamino, (2-cyanoethyl)methylamino, diethylamino, ethyl(propyl)amino, ethyl(isopropyl)amino, ethyl(methoxymethyl)amino, ethyl(2-methoxyethyl)amino, (cyanomethyl)ethylamino, (2-cyanoethyl)ethylamino, 2,2-difluoroethylamino, 2,2,2-trifluoroethylamino, cyclopropylamino, (cyclopropyl)methylamino, pyrrolidinyl and piperidinyl; and Rc-L- (wherein Rc and L are the same as defined hereinabove) such as methylthio, methanesulfinyl, methanesulfonyl, trifluoromethylthio, trifluoromethanesulfinyl and trifluoromethanesulfonyl.

Specifically, more preferred examples of the substituents A include hydroxy group; cyano group;

C3-C8 cycloalkyl groups such as cyclopropyl and cyclobutyl;

C1-C6 alkoxy groups such as methoxy and ethoxy;

C1-C6 haloalkoxy groups such as difluoromethoxy, trifluoromethoxy, 2,2-difluoroethoxy and 2,2,2-trifluoroethoxy;

C3-C8 cycloalkoxy groups such as cyclopropyloxy and cyclobutoxy;

RaRbN— (wherein Ra and Rb are the same as defined hereinabove) such as dimethylamino, ethyl(methyl)amino and diethylamino; and Rc-L- (wherein Rc and L are the same as defined hereinabove) such as methylthio, methanesulfinyl and methanesulfonyl.

The "substituent(s) B" in the formula (1) is at least one selected from the group consisting of hydroxy group, cyano group, C3-C8 cycloalkyl groups, C1-C6 alkoxy groups, C1-C6 haloalkoxy groups, C3-C8 cycloalkoxy groups, C2-C6 alkoxyalkoxy groups, RaRbN— (wherein Ra and Rb are the same as defined hereinabove), Rc-L-(wherein Rc and L are the same as defined hereinabove), RdC(=O)— (wherein Rd is the same as defined hereinabove) and 3 to 6-membered ring groups containing 1 to 2 oxygen atoms.

In particular, the substituent(s) B is preferably a cyano group, a C3-C8 cycloalkyl group, a C1-C6 alkoxy group, a C1-C6 haloalkoxy group, a C3-C8 cycloalkoxy group, Rc-L- (wherein Rc and L are the same as defined hereinabove), or RdC(=O)— (wherein Rd is the same as defined hereinabove), and more preferably a cyano group, a C3-C8 cycloalkoxy group, a C1-C6 alkoxy group, or Rc-L- (wherein Rc and L are the same as defined hereinabove).

The terms used in association with the substituent(s) B are the same as defined hereinabove.

Specifically, preferred examples of the substituents B include hydroxy group; cyano group;

C3-C8 cycloalkyl groups such as cyclopropyl, cyclobutyl, cyclopentyl and cyclohexyl;

C1-C6 alkoxy groups such as methoxy, ethoxy, propyloxy, isopropyloxy, butoxy, isobutoxy and t-butoxy;

C1-C6 haloalkoxy groups such as difluoromethoxy, trifluoromethoxy, 2,2-difluoroethoxy, 2,2,2-trifluoroethoxy, 3,3-difluoropropyloxy and 3,3,3-trifluoropropyloxy;

C3-C8 cycloalkoxy groups such as cyclopropyloxy, cyclobutoxy, cyclopentyloxy and cyclohexyloxy;

C2-C6 alkoxyalkoxy groups such as methoxymethoxy, ethoxymethoxy, methoxyethoxy, ethoxyethoxy and methoxypropyloxy;

RaRbN— (wherein Ra and Rb are the same as defined hereinabove) such as amino, methylamino, ethylamino, propylamino, isopropylamino, (methoxymethyl)amino, (2-methoxyethyl)amino, (cyanomethyl)amino, (2-cyanoethyl)amino, dimethylamino, ethyl(methyl)amino, methyl(propyl)amino, isopropyl(methyl)amino, (methoxymethyl)methylamino, (2-methoxyethyl)methylamino, (cyanomethyl)methylamino, (2-cyanoethyl)methylamino, diethylamino, ethyl(propyl)amino, ethyl(isopropyl)amino, ethyl(methoxymethyl)amino, ethyl(2-methoxyethyl)amino, (cyanomethyl)ethylamino, (2-cyanoethyl)ethylamino, 2,2-difluoroethylamino, 2,2,2-trifluoroethylamino, cyclopropylamino, (cyclopropyl)methylamino, pyrrolidinyl, and piperidinyl;

Rc-L- (wherein Rc and L are the same as defined hereinabove) such as methylthio, methanesulfinyl, methanesulfonyl, trifluoromethylthio, trifluoromethanesulfinyl and trifluoromethanesulfonyl;

RdC(=O)— (wherein Rd is the same as defined hereinabove) such as formyl, acetyl, methoxyacetyl, cyanoacetyl, propionyl, difluoroacetyl, trifluoroacetyl, cyclopropanecarbonyl, methoxycarbonyl, ethoxycarbonyl, 2,2-difluoroethoxycarbonyl, 2,2,2-trifluoroethoxycarbonyl, 3,3,3-trifluoropropyloxycarbonyl, cyclopropyloxycarbonyl, aminocarbonyl, methylaminocarbonyl, ethylaminocarbonyl, (methoxymethyl)aminocarbonyl, (2-methoxyethyl)aminocarbonyl, (cyanomethyl)aminocarbonyl, (2-cyanoethyl)aminocarbonyl, dimethylaminocarbonyl, ethyl(methyl)aminocarbonyl, diethyl aminocarbonyl, (methoxymethyl)methylaminocarbonyl, (2-methoxyethyl)methylaminocarbonyl, (cyanomethyl)methylaminocarbonyl, (2-cyanoethyl)methylaminocarbonyl, 2,2-difluoroethylaminocarbonyl, 2,2,2-trifluoroethylaminocarbonyl, cyclopropylaminocarbonyl, (cyclopropyl)methylaminocarbonyl, pyrrolidinyl carbonyl, and piperidinylcarbonyl; and 3 to 6-membered ring groups containing 1 to 2 oxygen atoms such as oxolanyl, oxanyl, 1,3-dioxolanyl and 1,3-dioxanyl.

Specifically, more preferred examples of the substituents B include hydroxy group; cyano group;

C3-C8 cycloalkyl groups such as cyclopropyl and cyclobutyl;

C1-C6 alkoxy groups such as methoxy and ethoxy;

C1-C6 haloalkoxy groups such as difluoromethoxy, trifluoromethoxy, 2,2-difluoroethoxy and 2,2,2-trifluoroethoxy;

C3-C8 cycloalkoxy groups such as cyclopropyloxy and cyclobutoxy;

C2-C6 alkoxyalkoxy groups such as methoxymethoxy, ethoxymethoxy, methoxyethoxy and ethoxyethoxy;

RaRbN— (wherein Ra and Rb are the same as defined hereinabove) such as dimethylamino, ethyl(methyl)amino and di ethyl amino;

Rc-L- (wherein Rc and L are the same as defined hereinabove) such as methylthio, methanesulfinyl and methanesulfonyl;

RdC(=O)— (wherein Rd is the same as defined hereinabove) such as formyl, acetyl, methoxyacetyl, cyanoacetyl, difluoroacetyl, trifluoroacetyl, methoxycarbonyl, ethoxycarbonyl, aminocarbonyl, dimethylaminocarbonyl, ethyl(methyl)aminocarbonyl, and diethylaminocarbonyl; and 3 to 6-membered ring groups containing 1 to 2 oxygen atoms such as 1,3-dioxolanyl and 1,3-di oxanyl.

The "substituent(s) C" in the formula (1) is at least one selected from the group consisting of cyano group, C1-C6 alkoxy groups, C1-C6 haloalkoxy groups and C3-C8 cycloalkoxy groups.

In particular, the substituent(s) C is preferably a cyano group or a C1-C6 alkoxy group.

The terms used in association with the substituent(s) C are the same as defined hereinabove.

Specifically, preferred examples of the substituents C include cyano group;

C1-C6 alkoxy groups such as methoxy, ethoxy, propyloxy and isopropyloxy;

C1-C6 haloalkoxy groups such as difluoromethoxy, trifluoromethoxy, 2,2-difluoroethoxy, 2,2,2-trifluoroethoxy, 3,3-difluoropropyloxy and 3,3,3-trifluoropropyloxy; and C3-C8 cycloalkoxy groups such as cyclopropyloxy, cyclobutoxy, cyclopentyloxy and cyclohexyloxy.

Specifically, more preferred examples of the substituents C include cyano group;

C1-C6 alkoxy groups such as methoxy and ethoxy;

C1-C6 haloalkoxy groups such as difluoromethoxy, trifluoromethoxy, 2,2-difluoroethoxy and 2,2,2-trifluoroethoxy; and C3-C8 cycloalkoxy groups such as cyclopropyloxy and cyclobutoxy.

The "substituent(s) D" in the formula (1) is at least one selected from the group consisting of halogen atoms, hydroxy group, cyano group, nitro group, C1-C6 alkyl groups optionally substituted with substituent(s) C, C1-C6 haloalkyl groups, C3-C8 cycloalkyl groups, C1-C6 alkoxy groups, C1-C6 haloalkoxy groups and C3-C8 cycloalkoxy groups.

In particular, the substituent(s) D is preferably a halogen atom, a cyano group, a C1-C6 alkyl group optionally substituted with substituent(s) C, a C1-C6 haloalkyl group, a C1-C6 alkoxy group, or a C1-C6 haloalkoxy group, and more preferably a halogen atom, a C1-C6 alkyl group optionally substituted with substituent(s) C, a C1-C6 alkoxy group, or a C1-C6 haloalkoxy group.

The terms used in association with the substituent(s) D are the same as defined hereinabove. When the substituent(s) D is a "C1-C6 alkyl group optionally substituted with substituent(s) C", and this group is substituted with substituent(s) C, any hydrogen atom(s) in the C1-C6 alkyl group is appropriately substituted with substituent(s) C.

Specifically, preferred examples of the substituents D include:

halogen atoms such as fluorine atom, chlorine atom, bromine atom and iodine atom;

hydroxy group; cyano group; nitro group;

C1-C6 alkyl groups optionally substituted with substituent(s) C, such as methyl, methoxymethyl, ethoxymethyl, cyanomethyl, ethyl, 2-methoxyethyl, 2-ethoxyethyl, 2-cyanoethyl, propyl, isopropyl, butyl and isobutyl;

C1-C6 haloalkyl groups such as difluoromethyl, trifluoromethyl, 2,2-difluoroethyl, 2,2,2-trifluoroethyl, 3,3-difluoropropyl and 3,3,3-trifluoropropyl;

C3-C8 cycloalkyl groups such as cyclopropyl, cyclobutyl, cyclopentyl and cyclohexyl;

C1-C6 alkoxy groups such as methoxy, ethoxy, propyloxy, isopropyloxy, butoxy, isobutoxy and t-butoxy;

C1-C6 haloalkoxy groups such as difluoromethoxy, trifluoromethoxy, 2,2-difluoroethoxy, 2,2,2-trifluoroethoxy, 3,3-difluoropropyloxy and 3,3,3-trifluoropropyloxy; and C3-C8 cycloalkoxy groups such as cyclopropyloxy, cyclobutoxy, cyclopentyloxy and cyclohexyloxy.

Specifically, more preferred examples of the substituents D include:

halogen atoms such as fluorine atom, chlorine atom and bromine atom;

hydroxy group; cyano group; nitro group;

C1-C6 alkyl groups optionally substituted with substituent(s) C, such as methyl, methoxymethyl, ethoxymethyl, cyanomethyl, ethyl, 2-methoxyethyl, 2-ethoxyethyl and 2-cyanoethyl;

C1-C6 haloalkyl groups such as difluoromethyl, trifluoromethyl, 2,2-difluoroethyl and 2,2,2-trifluoroethyl;

C3-C8 cycloalkyl groups such as cyclopropyl and cyclobutyl;

C1-C6 alkoxy groups such as methoxy, ethoxy, propyloxy and isopropyloxy;

C1-C6 haloalkoxy groups such as difluoromethoxy, trifluoromethoxy, 2,2-difluoroethoxy and 2,2,2-trifluoroethoxy; and C3-C8 cycloalkoxy groups such as cyclopropyloxy and cyclobutoxy.

All the compounds resulting from any combination of preferred R1, R2, R3, X, Y1, Y2, Y3, n, the broken line, the substituents A, the substituents B, the substituents C and the substituents D described hereinabove are incorporated herein as the compounds of formula (1) according to the present invention.

Specific compounds of the present invention is represented by combinations of the structural formulae shown in Table 1, Y shown in Table 2, and X that is an oxygen atom or a sulfur atom. Y in Table 1 means any of the substituents Y-1 to Y-699 shown in Table 2, and Pyd in Table 2 means any of the structural formulae Pyd-1 to Pyd-1425 shown in Table 1. Such compounds are only illustrative, and the scope of the present invention is not limited to such compounds.

TABLE 1

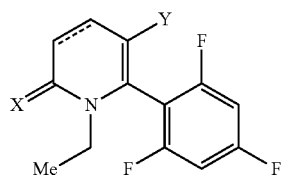

Pyd-1

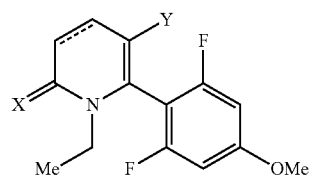

Pyd-2

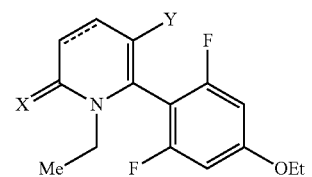

Pyd-3

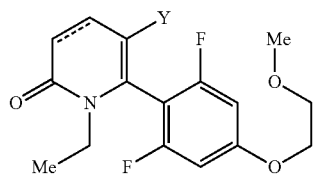

Pyd-4

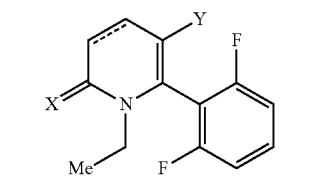

Pyd-5

TABLE 1-continued
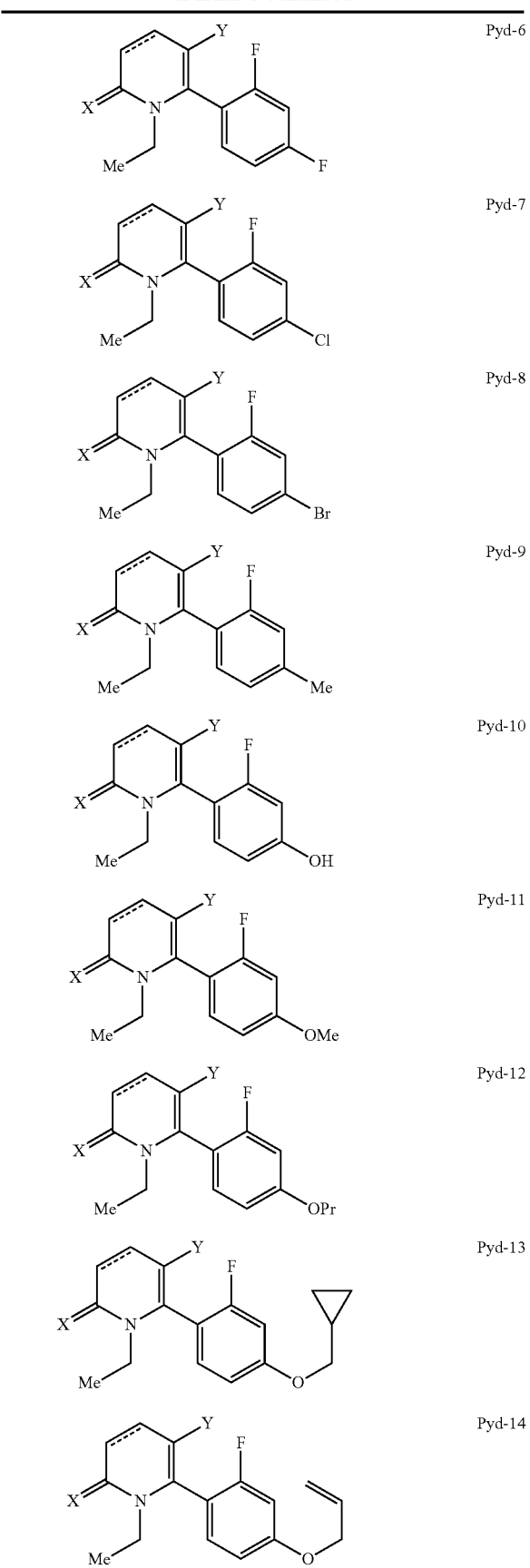
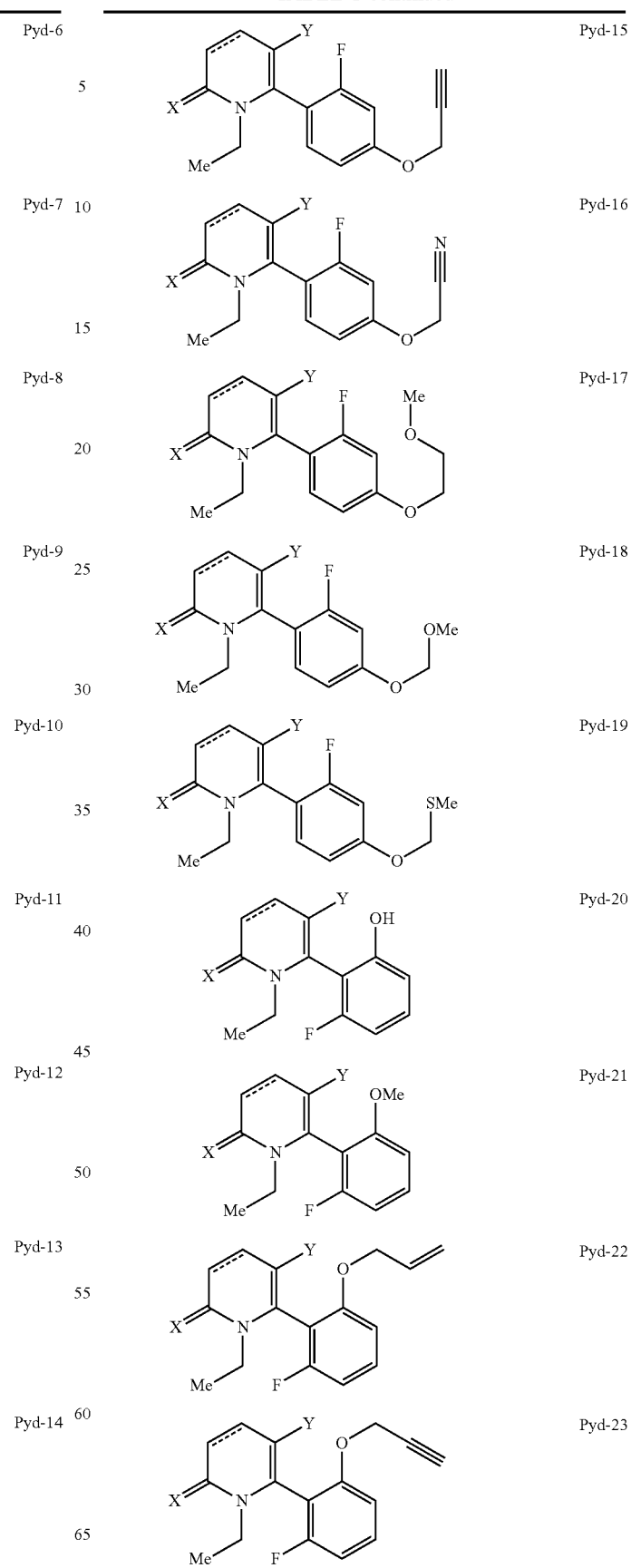

TABLE 1-continued
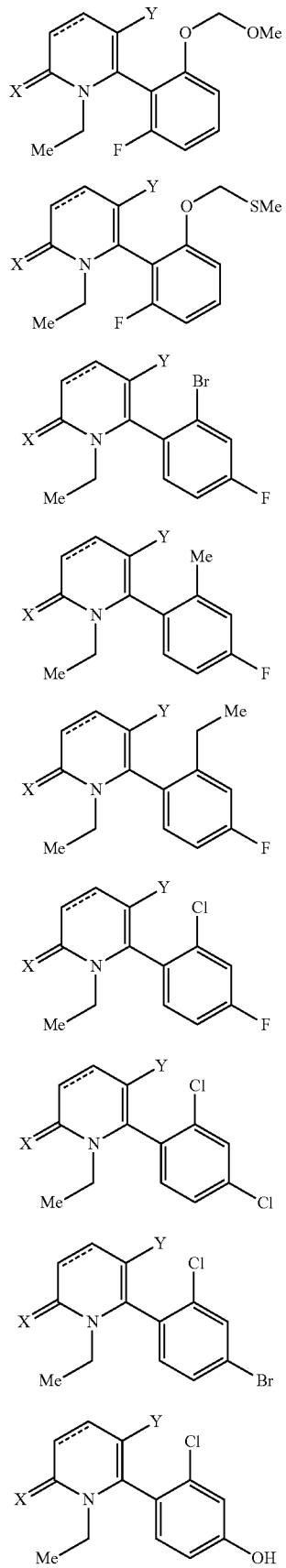
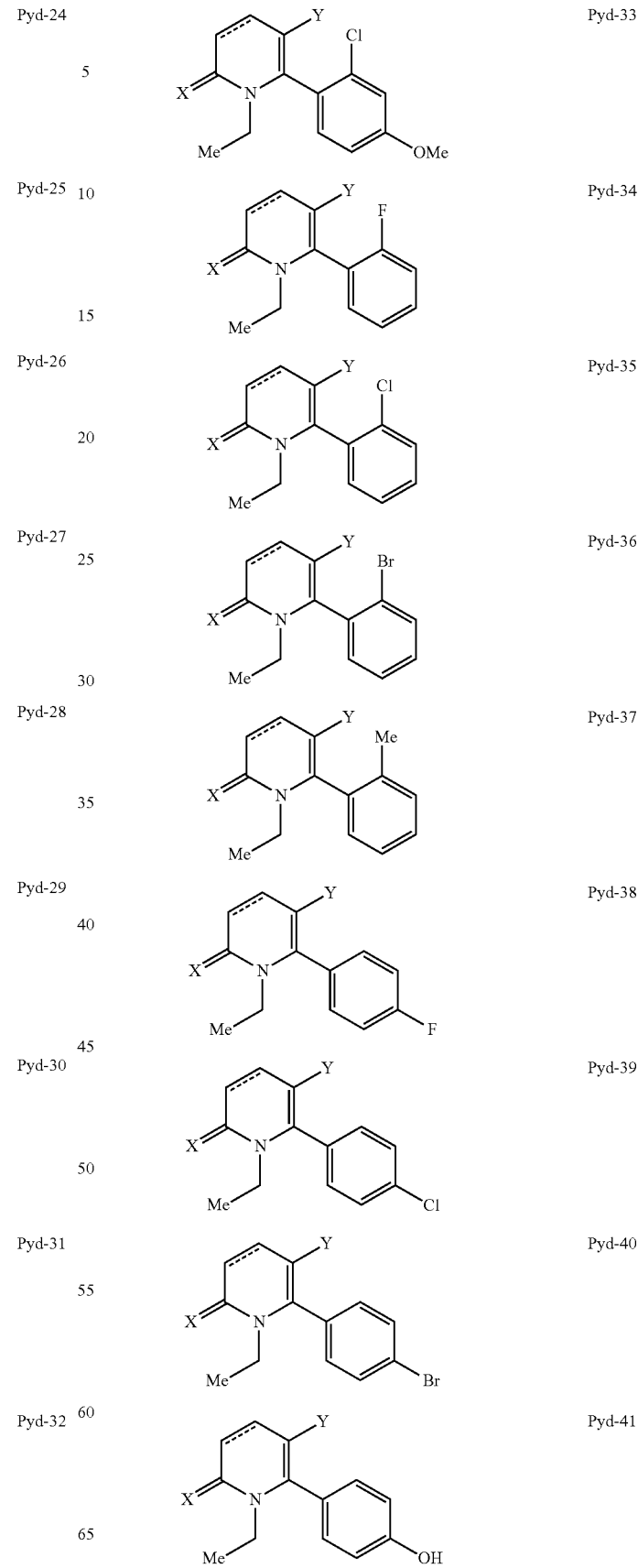

TABLE 1-continued
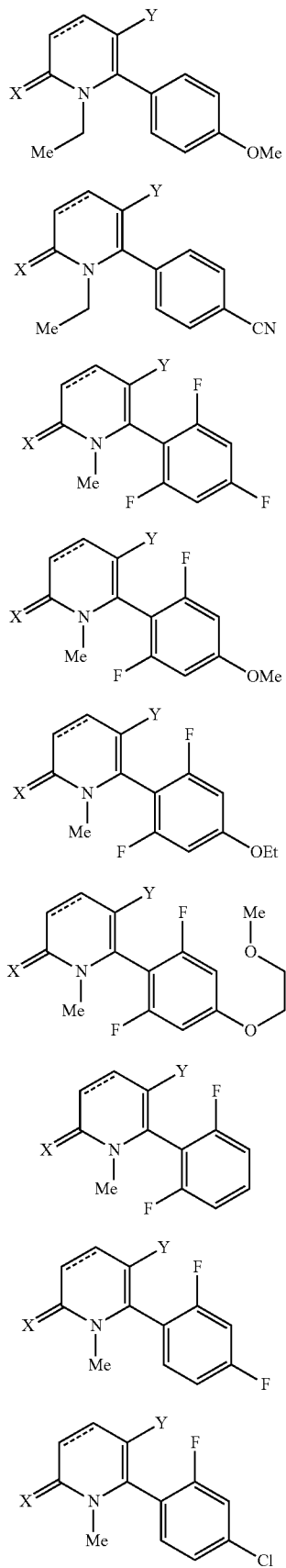
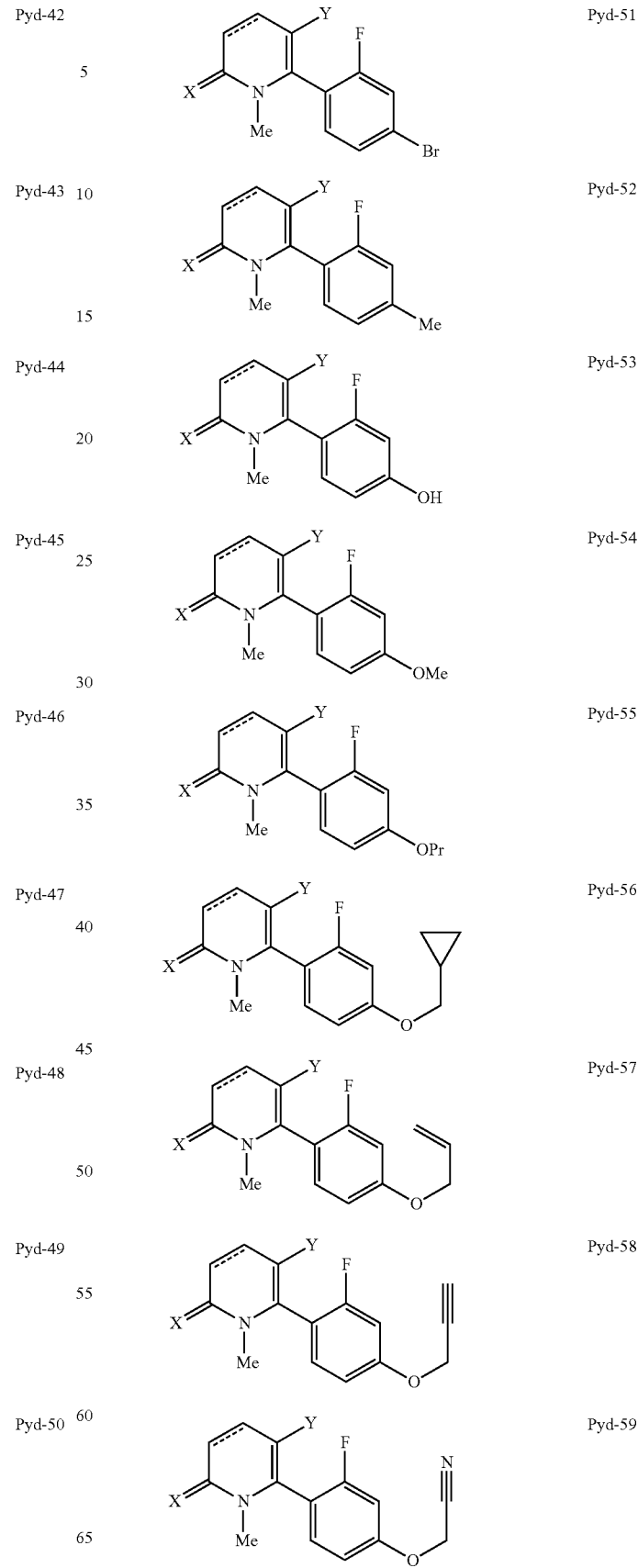

TABLE 1-continued
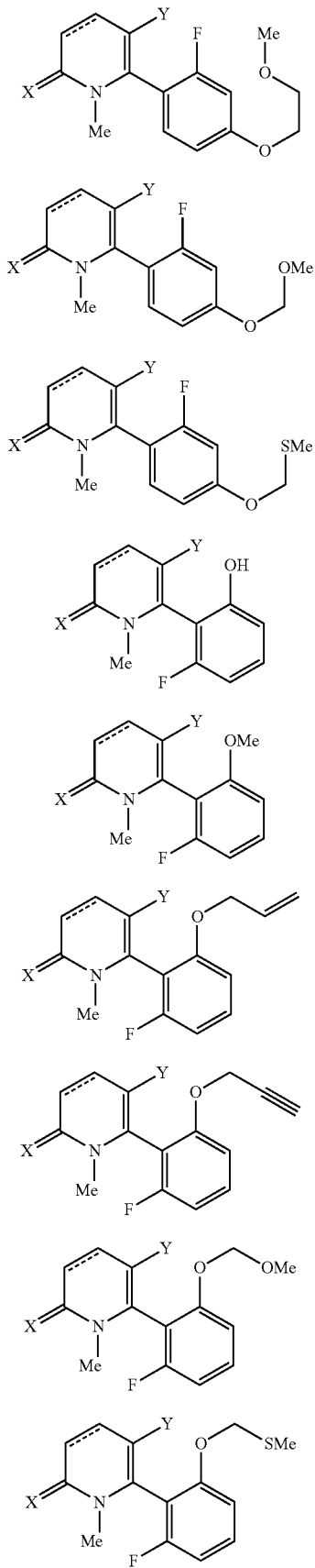
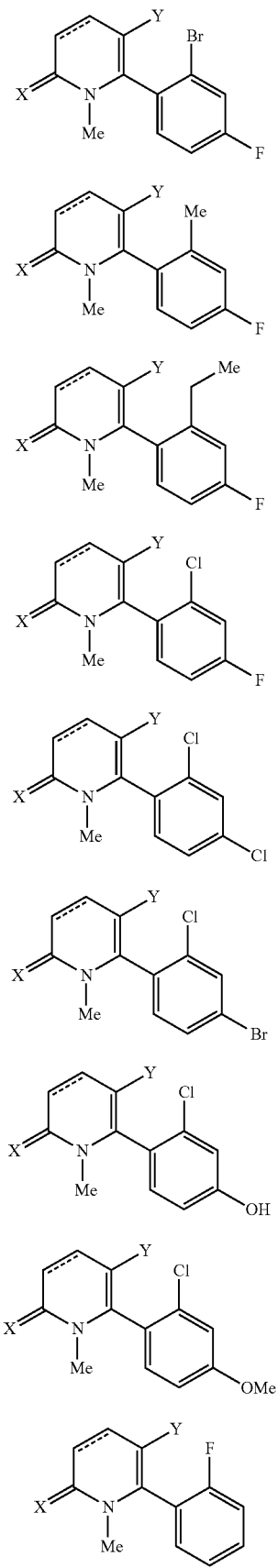

TABLE 1-continued
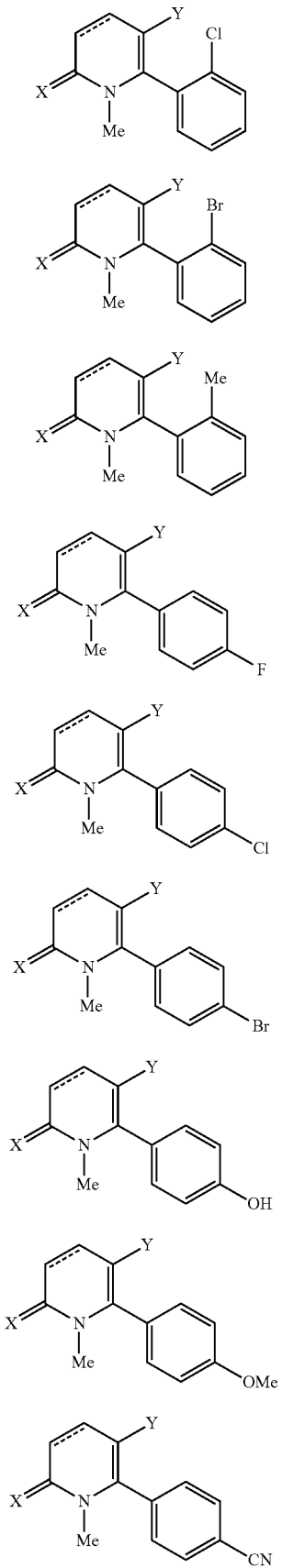
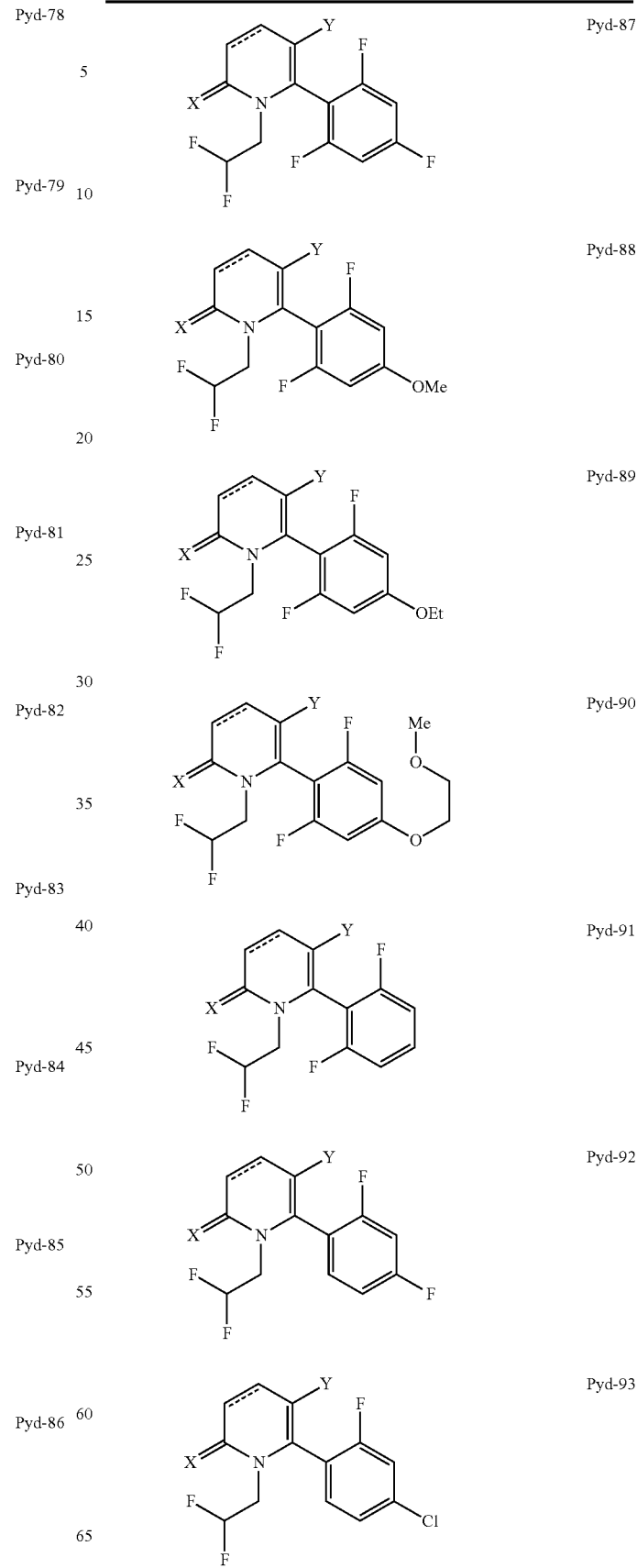

TABLE 1-continued
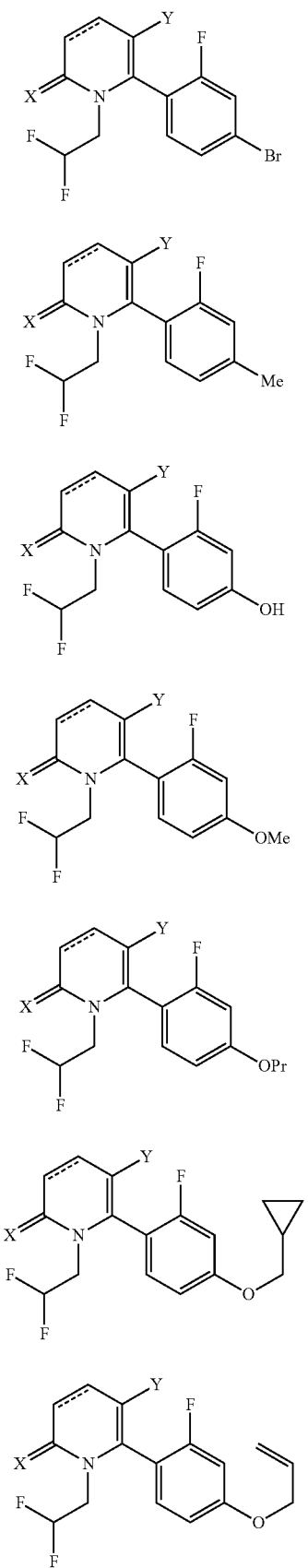
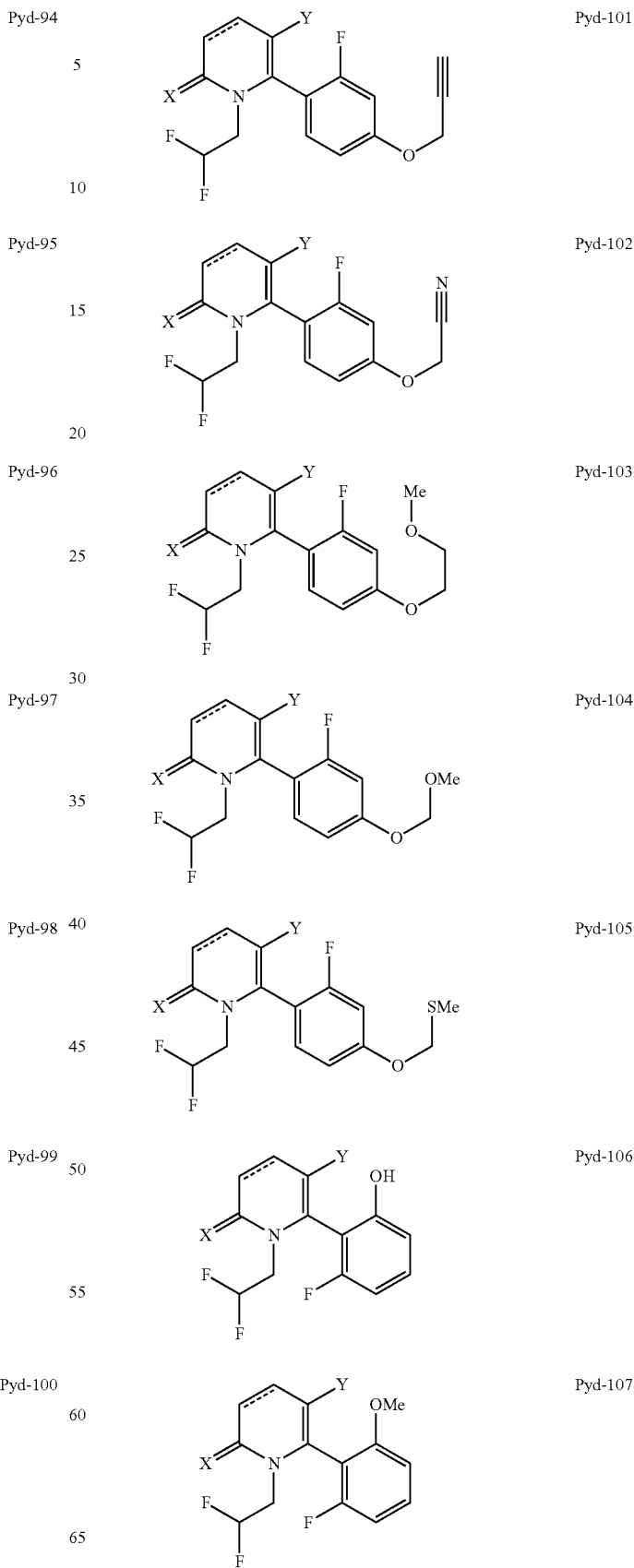

TABLE 1-continued
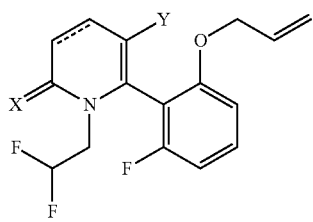 Pyd-108
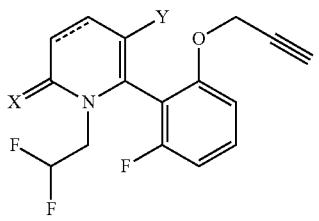 Pyd-109
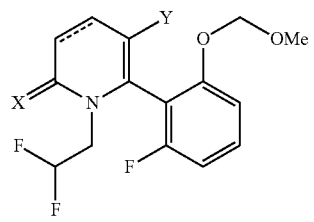 Pyd-110
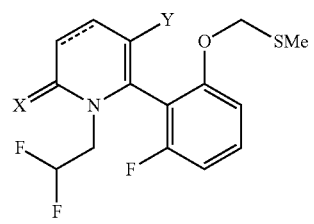 Pyd-111
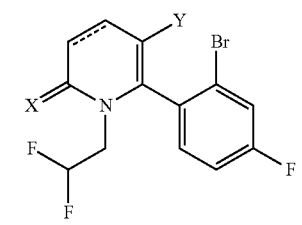 Pyd-112
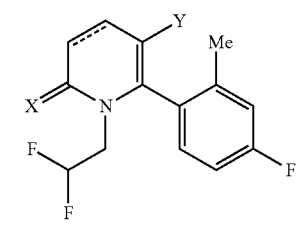 Pyd-113
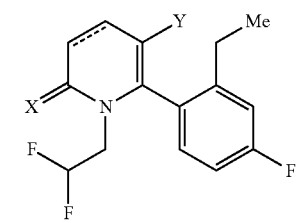 Pyd-114
TABLE 1-continued
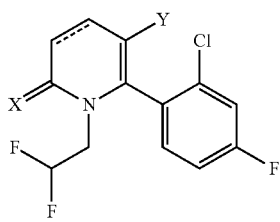 Pyd-115
 Pyd-116
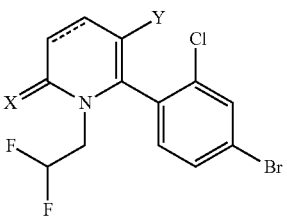 Pyd-117
 Pyd-118
 Pyd-119
 Pyd-120
 Pyd-121

TABLE 1-continued
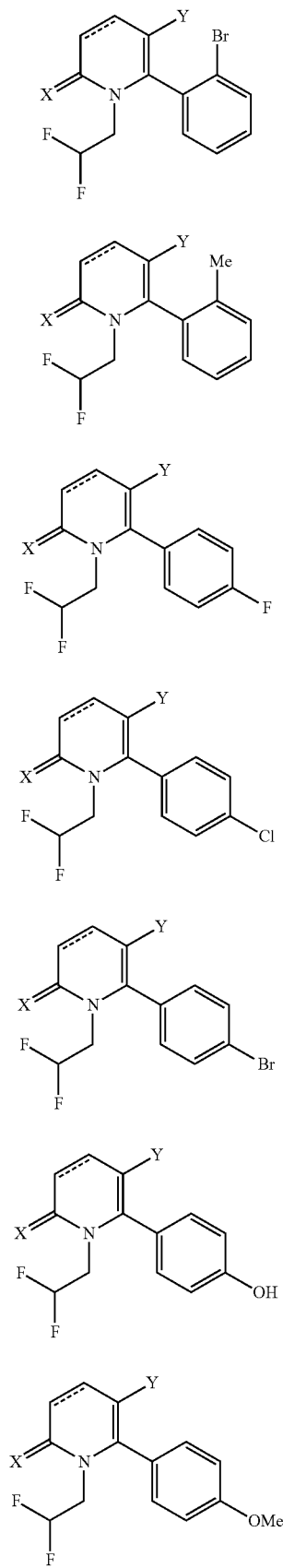
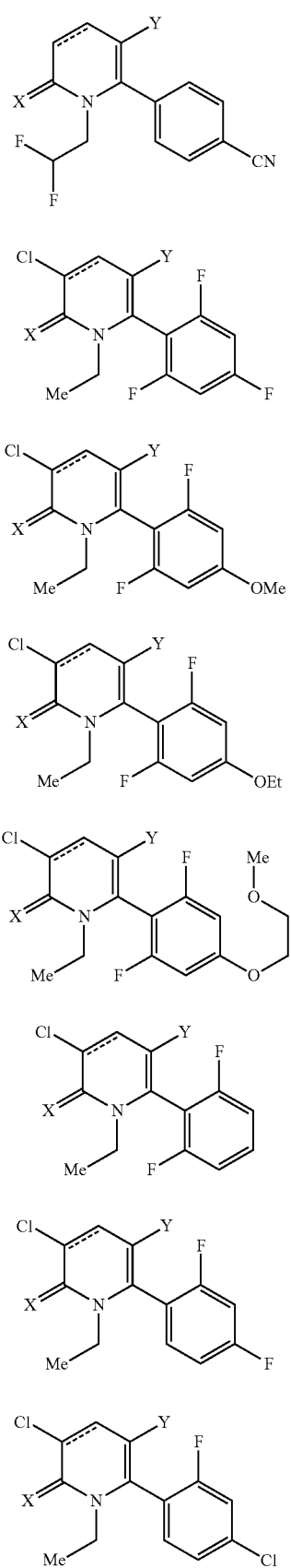

TABLE 1-continued
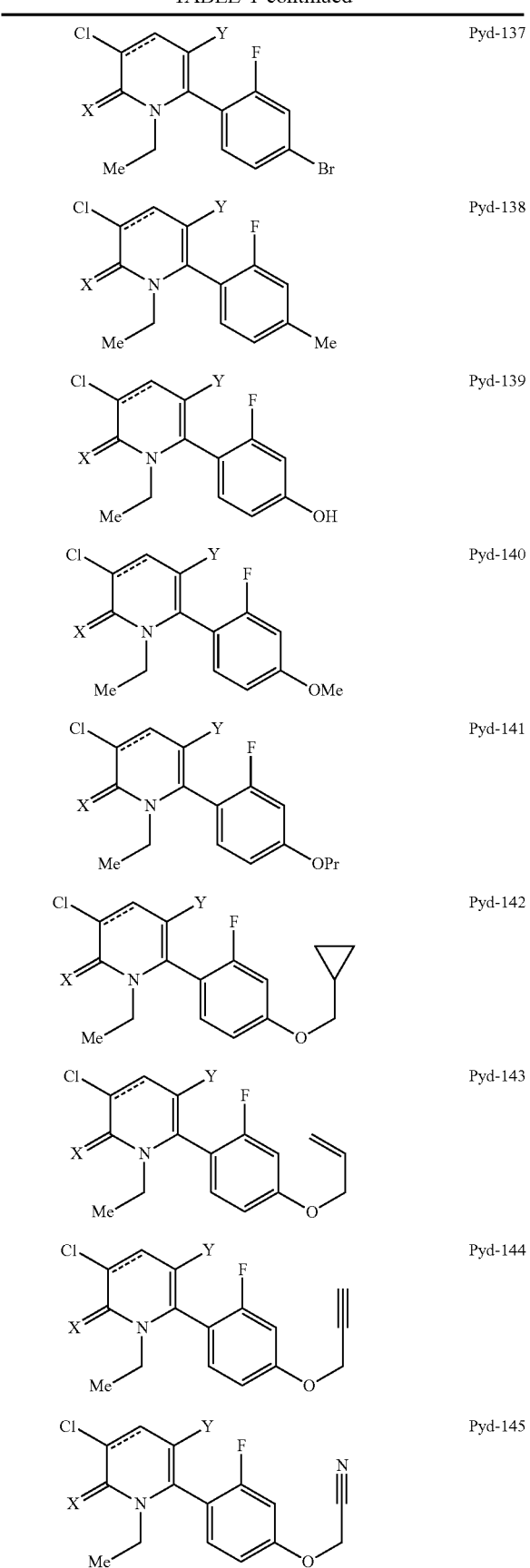
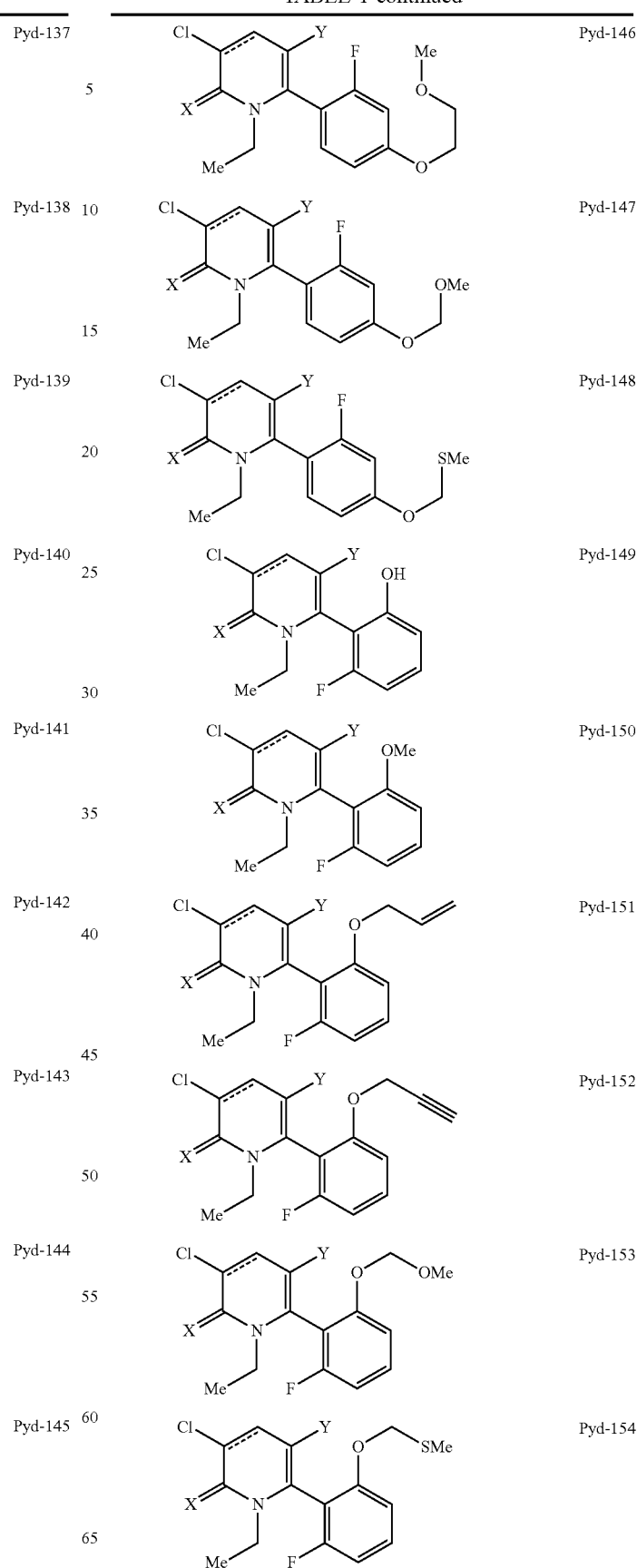

TABLE 1-continued
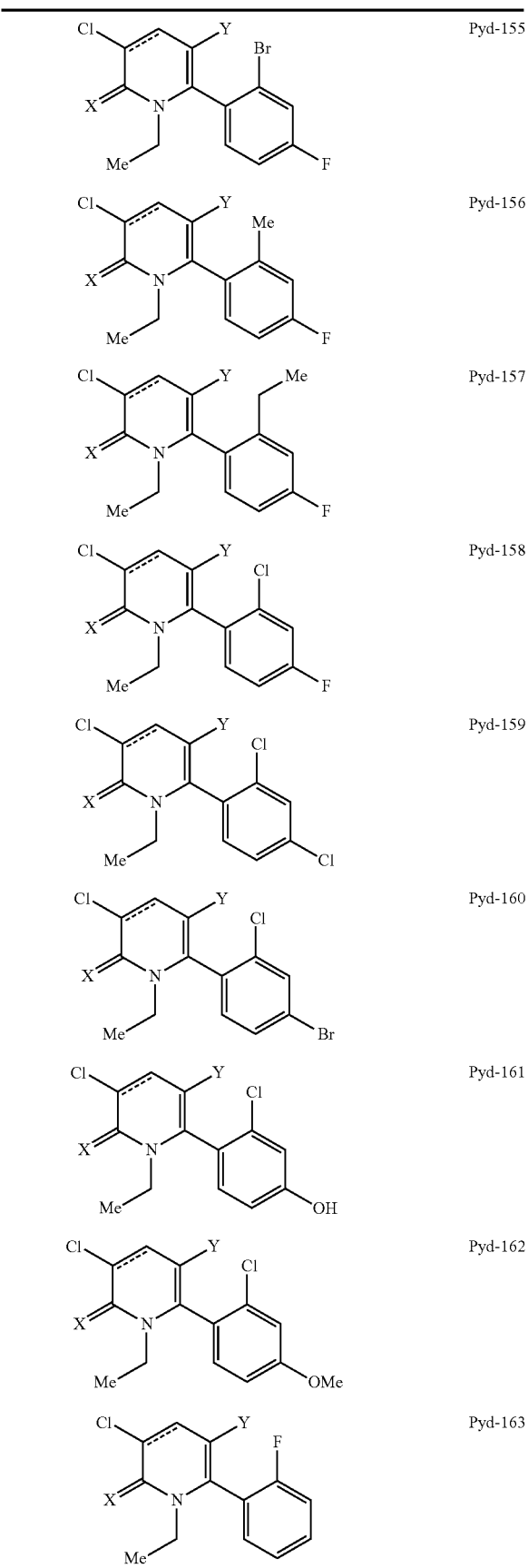
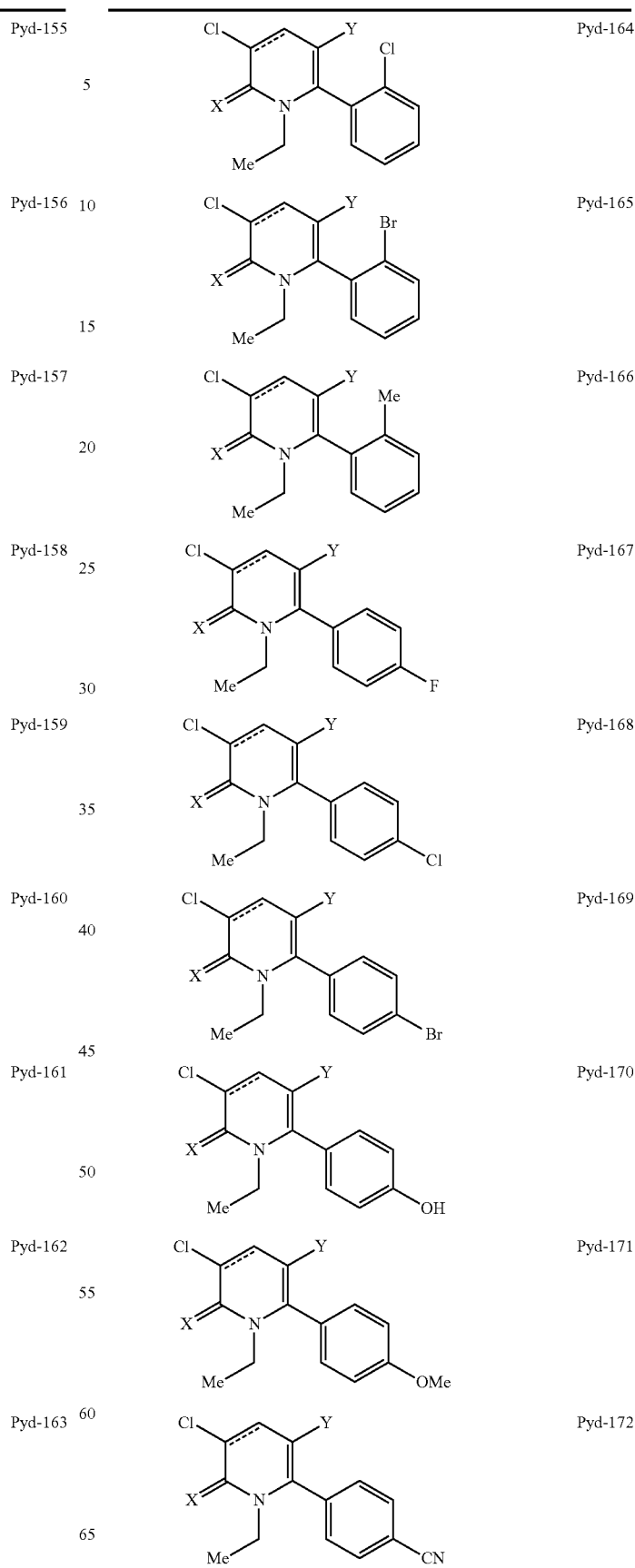

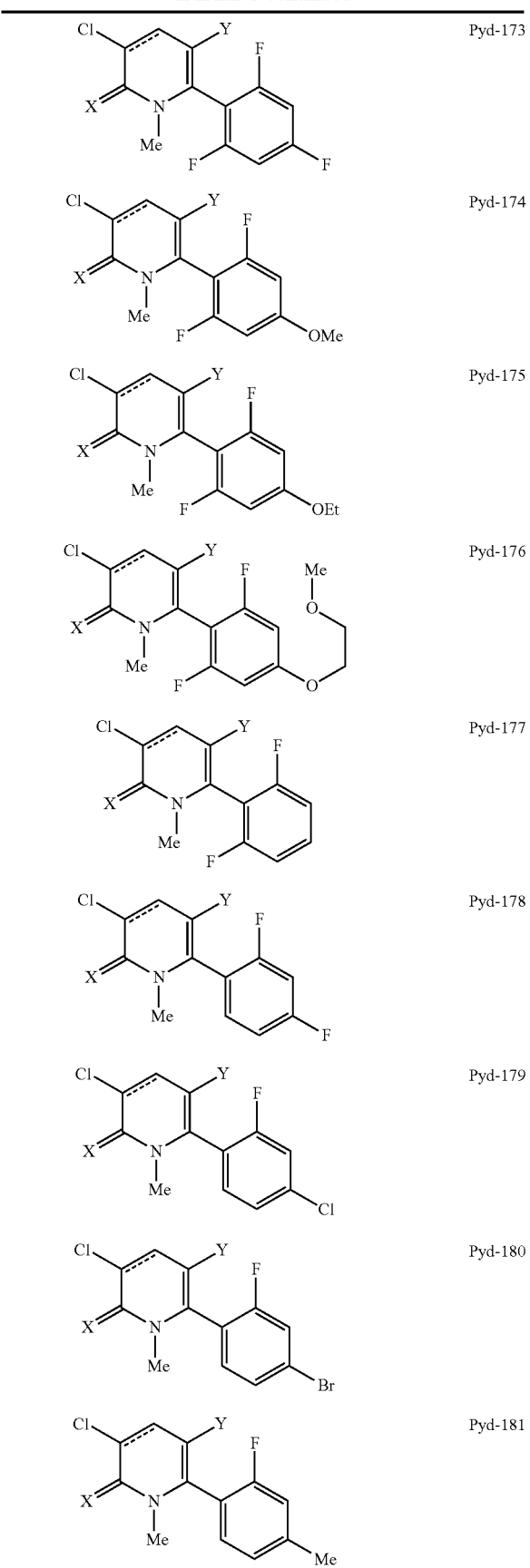
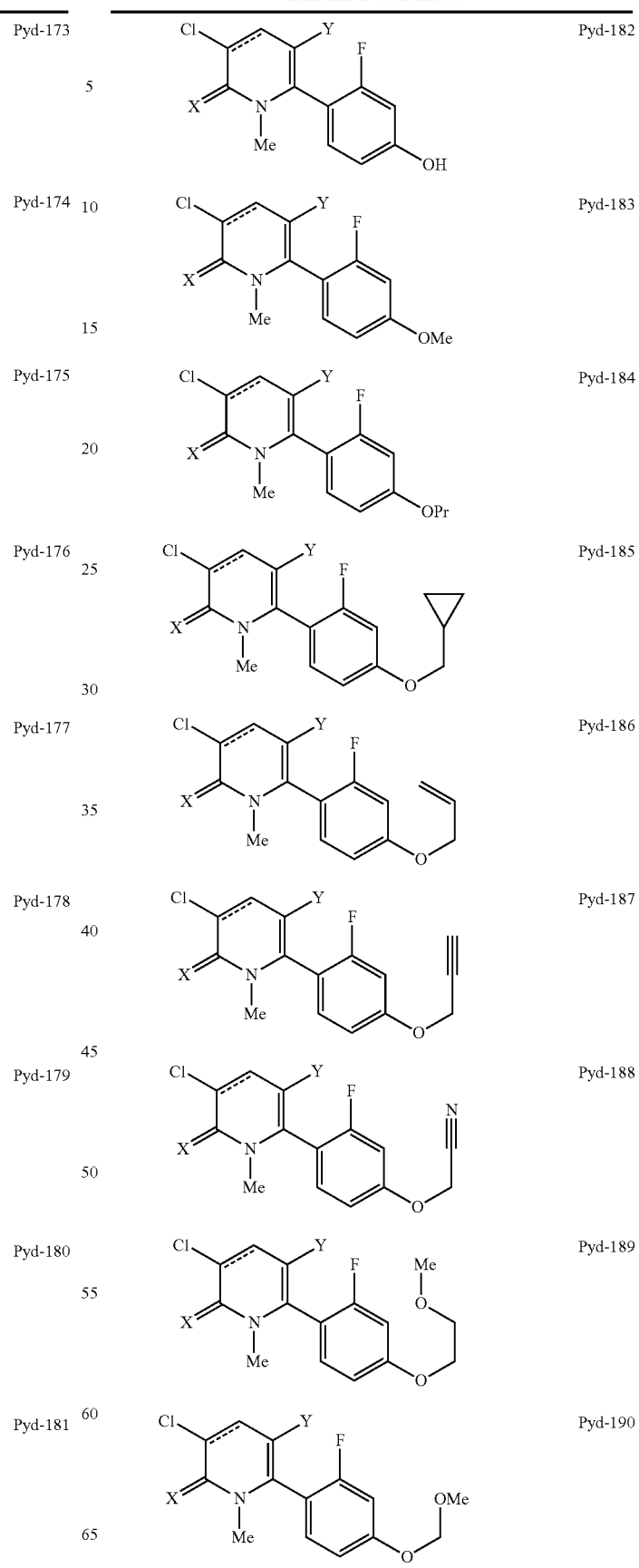

TABLE 1-continued
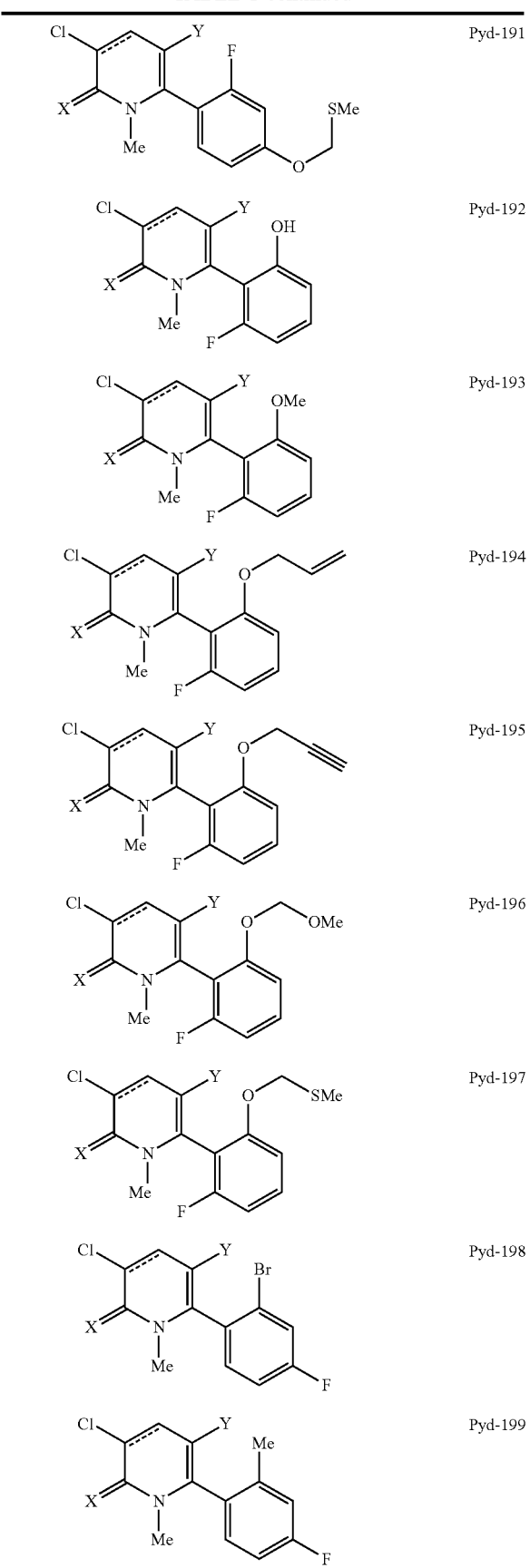
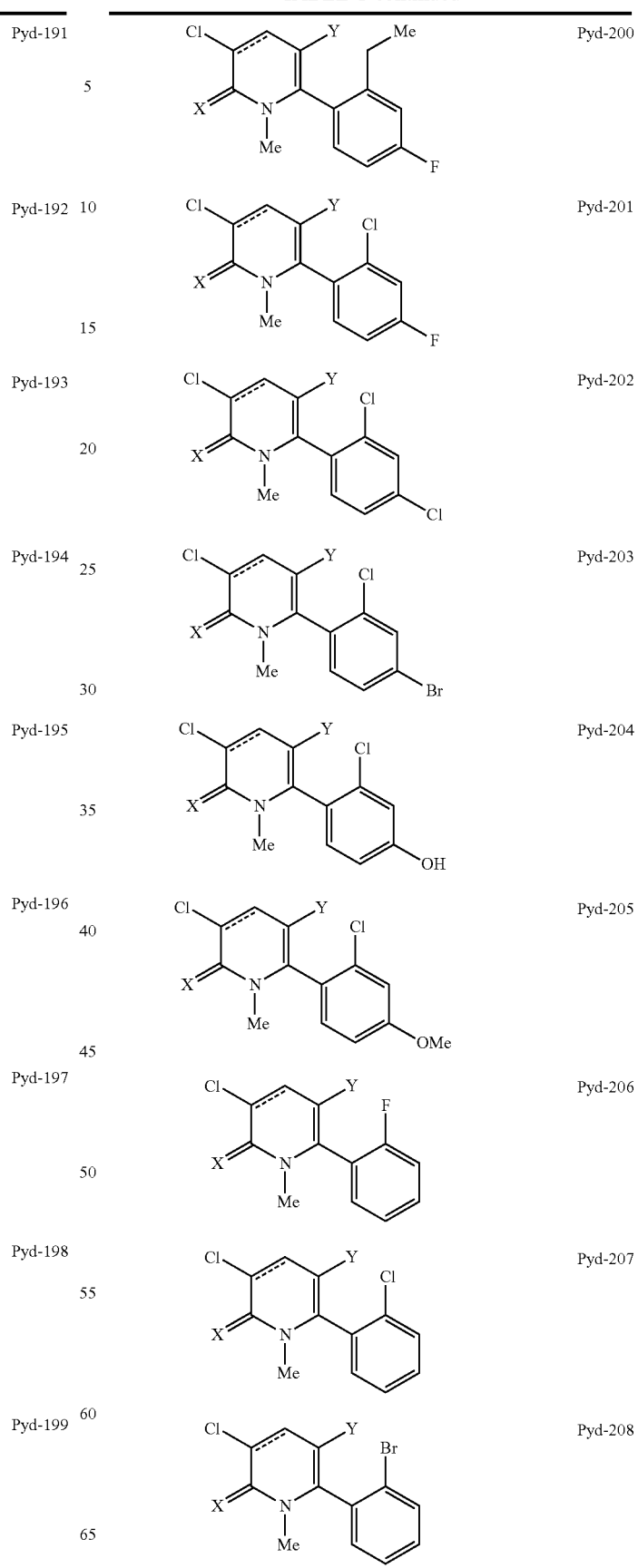

TABLE 1-continued
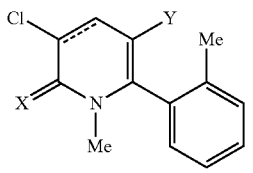 Pyd-209
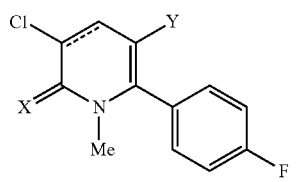 Pyd-210
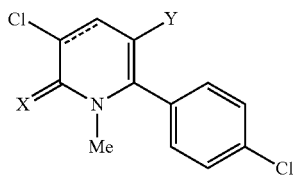 Pyd-211
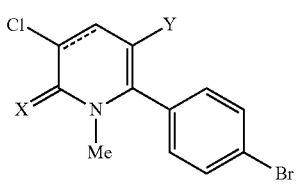 Pyd-212
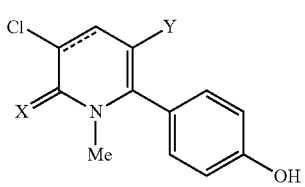 Pyd-213
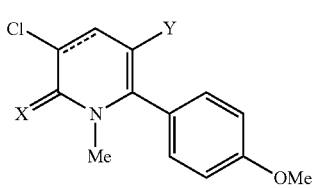 Pyd-214
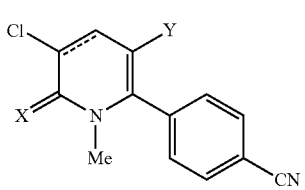 Pyd-215
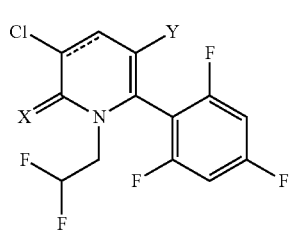 Pyd-216
TABLE 1-continued
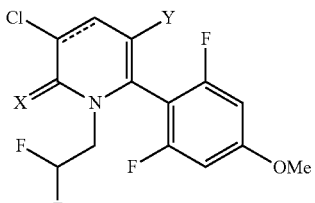 Pyd-217
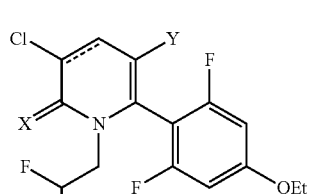 Pyd-218
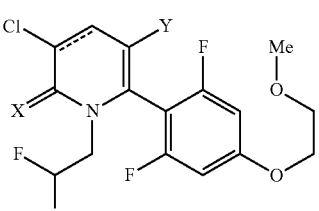 Pyd-219
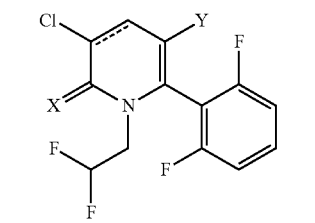 Pyd-220
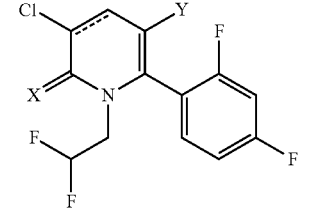 Pyd-221
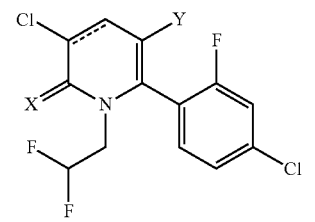 Pyd-222
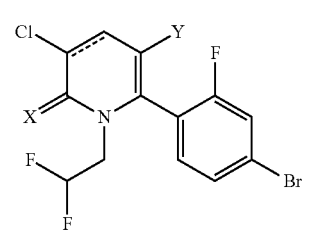 Pyd-223

TABLE 1-continued
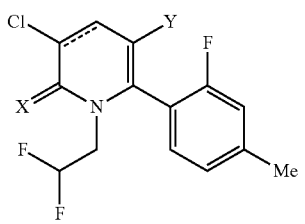 Pyd-224
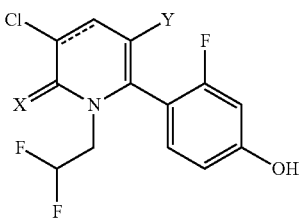 Pyd-225
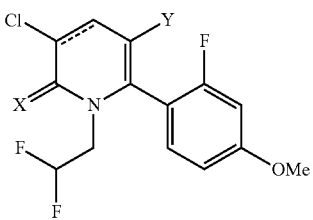 Pyd-226
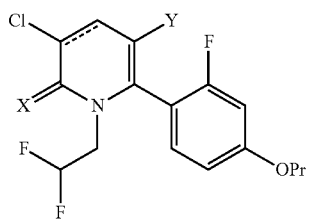 Pyd-227
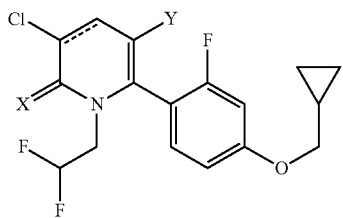 Pyd-228
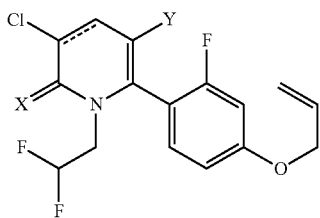 Pyd-229
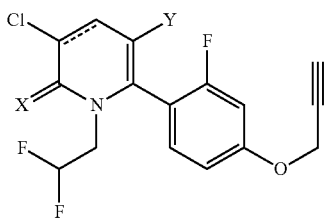 Pyd-230
TABLE 1-continued
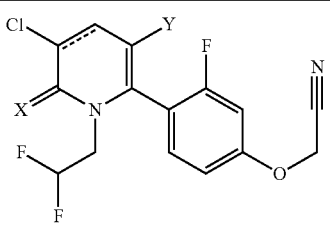 Pyd-231
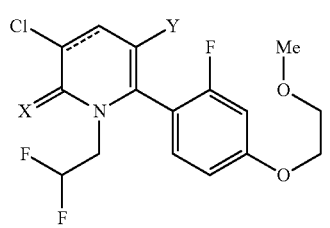 Pyd-232
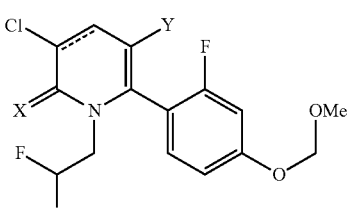 Pyd-233
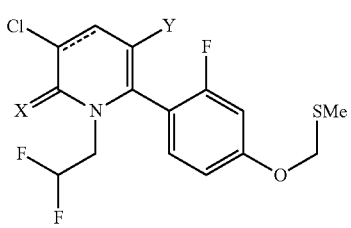 Pyd-234
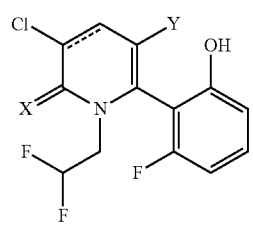 Pyd-235
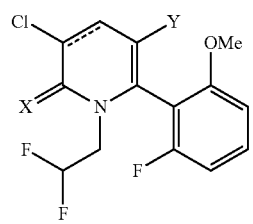 Pyd-236
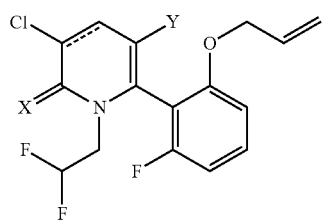 Pyd-237

TABLE 1-continued
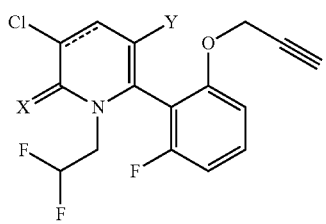 Pyd-238
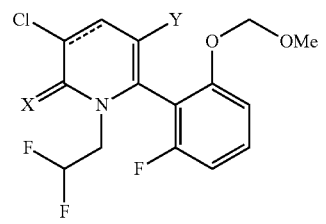 Pyd-239
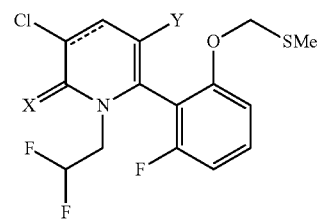 Pyd-240
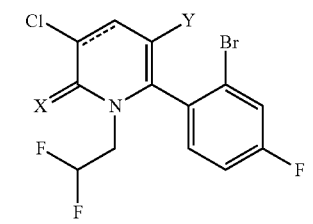 Pyd-241
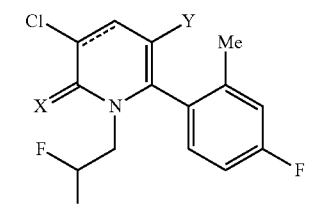 Pyd-242
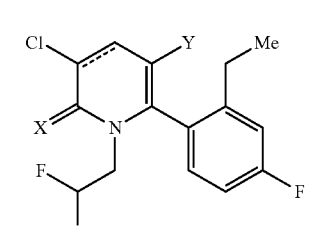 Pyd-243
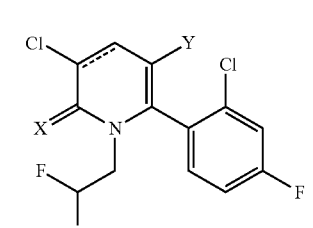 Pyd-244
TABLE 1-continued
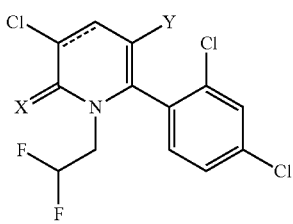 Pyd-245
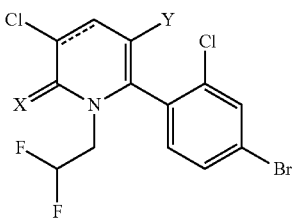 Pyd-246
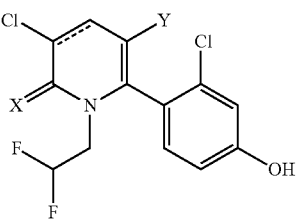 Pyd-247
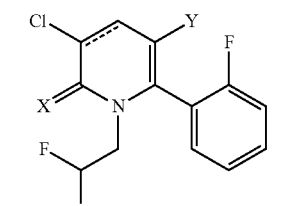 Pyd-248
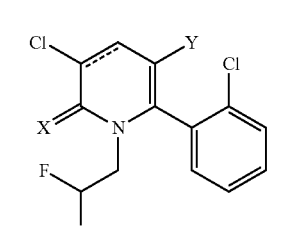 Pyd-249
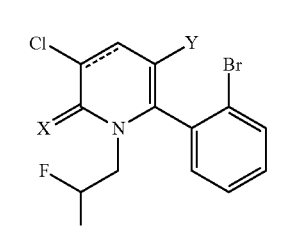 Pyd-250
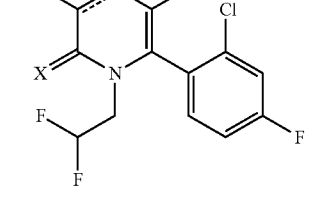 Pyd-251

TABLE 1-continued
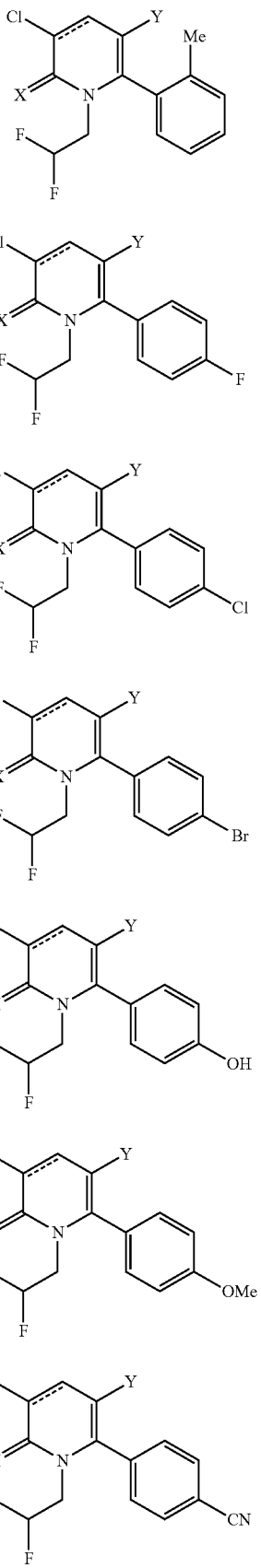
| | |
|---|---|
| | Pyd-252 |
| | Pyd-253 |
| | Pyd-254 |
| | Pyd-255 |
| | Pyd-256 |
| | Pyd-257 |
| | Pyd-258 |
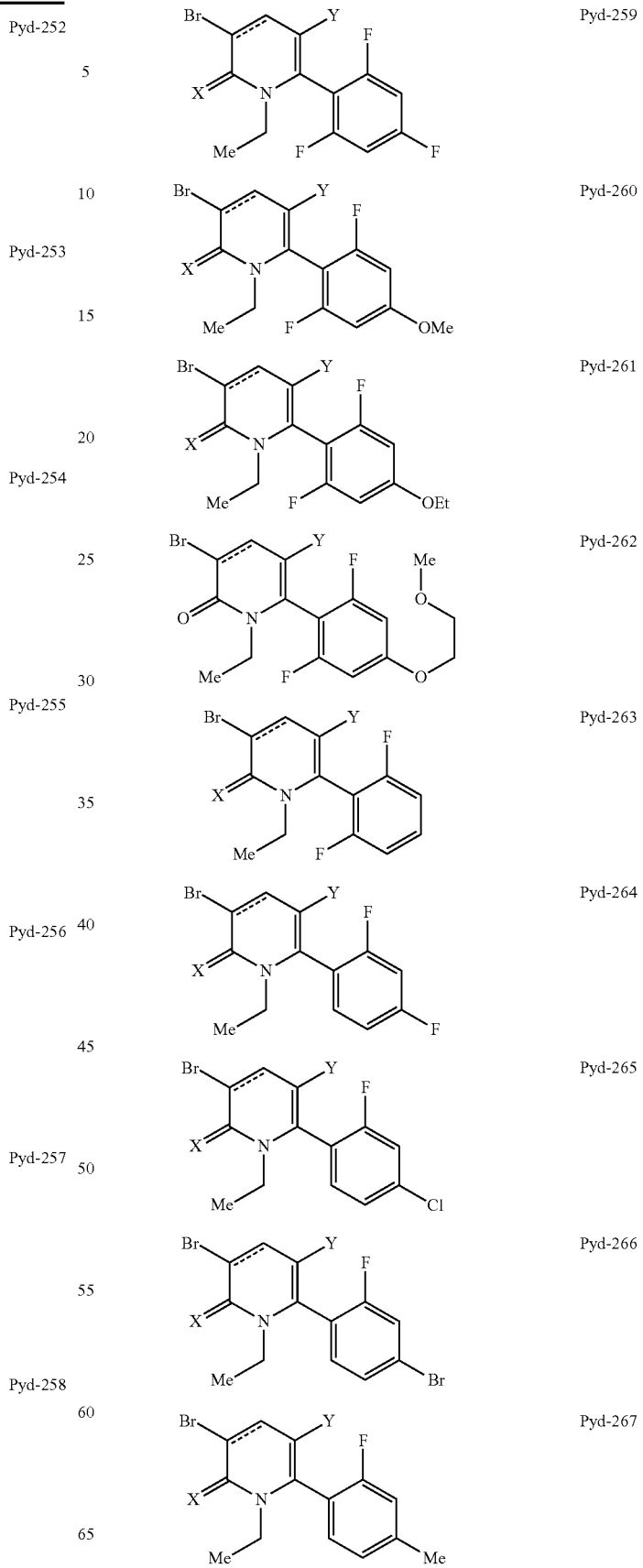
| | |
|---|---|
| | Pyd-259 |
| | Pyd-260 |
| | Pyd-261 |
| | Pyd-262 |
| | Pyd-263 |
| | Pyd-264 |
| | Pyd-265 |
| | Pyd-266 |
| | Pyd-267 |

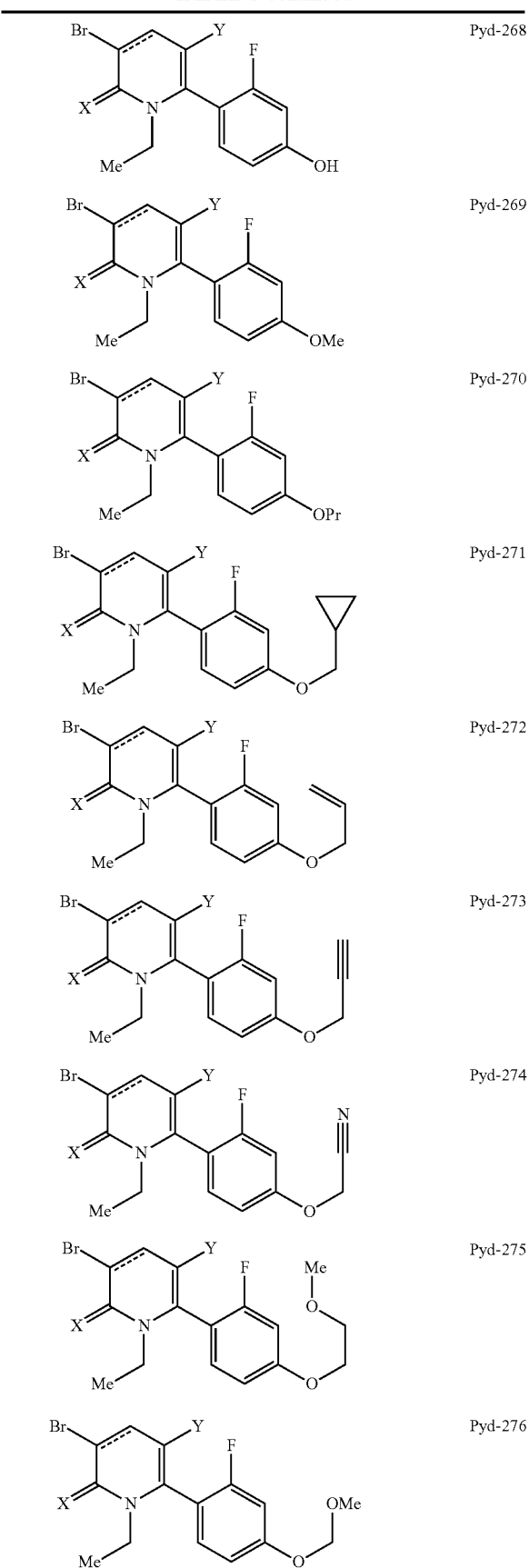
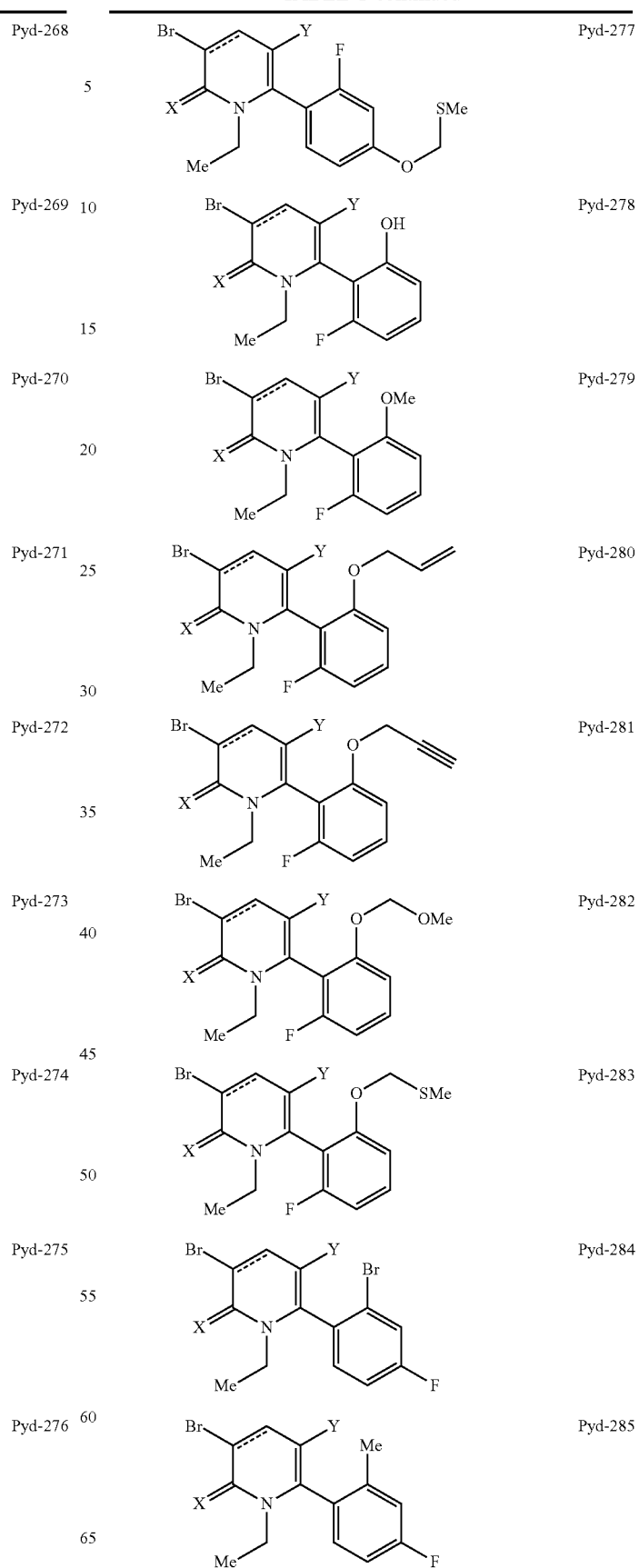

TABLE 1-continued

| Compound | Structure description |
|---|---|
| Pyd-286 | 3-Br, 5-Y, 6-(2-ethyl-4-fluorophenyl), 1-ethyl, 2-X pyridine |
| Pyd-287 | 3-Br, 5-Y, 6-(2-chloro-4-fluorophenyl), 1-ethyl, 2-X pyridine |
| Pyd-288 | 3-Br, 5-Y, 6-(2,4-dichlorophenyl), 1-ethyl, 2-X pyridine |
| Pyd-289 | 3-Br, 5-Y, 6-(2-chloro-4-bromophenyl), 1-ethyl, 2-X pyridine |
| Pyd-290 | 3-Br, 5-Y, 6-(2-chloro-4-hydroxyphenyl), 1-ethyl, 2-X pyridine |
| Pyd-291 | 3-Br, 5-Y, 6-(2-chloro-4-methoxyphenyl), 1-ethyl, 2-X pyridine |
| Pyd-292 | 3-Br, 5-Y, 6-(2-fluorophenyl), 1-ethyl, 2-X pyridine |
| Pyd-293 | 3-Br, 5-Y, 6-(2-chlorophenyl), 1-ethyl, 2-X pyridine |
| Pyd-294 | 3-Br, 5-Y, 6-(2-bromophenyl), 1-ethyl, 2-X pyridine |
| Pyd-295 | 3-Br, 5-Y, 6-(2-methylphenyl), 1-methyl, 2-X pyridine |
| Pyd-296 | 3-Br, 5-Y, 6-(4-fluorophenyl), 1-ethyl, 2-X pyridine |
| Pyd-297 | 3-Br, 5-Y, 6-(4-chlorophenyl), 1-ethyl, 2-X pyridine |
| Pyd-298 | 3-Br, 5-Y, 6-(4-bromophenyl), 1-ethyl, 2-X pyridine |
| Pyd-299 | 3-Br, 5-Y, 6-(4-hydroxyphenyl), 1-ethyl, 2-X pyridine |
| Pyd-300 | 3-Br, 5-Y, 6-(4-methoxyphenyl), 1-ethyl, 2-X pyridine |
| Pyd-301 | 3-Br, 5-Y, 6-(4-cyanophenyl), 1-ethyl, 2-X pyridine |
| Pyd-302 | 3-Br, 5-Y, 6-(2,4,6-trifluorophenyl), 1-methyl, 2-X pyridine |
| Pyd-303 | 3-Br, 5-Y, 6-(2,6-difluoro-4-methoxyphenyl), 1-methyl, 2-X pyridine |

TABLE 1-continued

| Structure | ID |
|---|---|
| Pyd-304 | 3-Br, 6-(2,6-difluoro-4-ethoxyphenyl), N-Me pyridine |
| Pyd-305 | 3-Br, 6-(2,6-difluoro-4-(2-methoxyethoxy)phenyl), N-Me pyridine |
| Pyd-306 | 3-Br, 6-(2,6-difluorophenyl), N-Me pyridine |
| Pyd-307 | 3-Br, 6-(2,4-difluorophenyl), N-Me pyridine |
| Pyd-308 | 3-Br, 6-(2-fluoro-4-chlorophenyl), N-Me pyridine |
| Pyd-309 | 3-Br, 6-(2-fluoro-4-bromophenyl), N-Me pyridine |
| Pyd-310 | 3-Br, 6-(2-fluoro-4-methylphenyl), N-Me pyridine |
| Pyd-311 | 3-Br, 6-(2-fluoro-4-hydroxyphenyl), N-Me pyridine |
| Pyd-312 | 3-Br, 6-(2-fluoro-4-methoxyphenyl), N-Me pyridine |
| Pyd-313 | 3-Br, 6-(2-fluoro-4-propoxyphenyl), N-Me pyridine |
| Pyd-314 | 3-Br, 6-(2-fluoro-4-(cyclopropylmethoxy)phenyl), N-Me pyridine |
| Pyd-315 | 3-Br, 6-(2-fluoro-4-allyloxyphenyl), N-Me pyridine |
| Pyd-316 | 3-Br, 6-(2-fluoro-4-propargyloxyphenyl), N-Me pyridine |
| Pyd-317 | 3-Br, 6-(2-fluoro-4-(cyanomethoxy)phenyl), N-Me pyridine |
| Pyd-318 | 3-Br, 6-(2-fluoro-4-(2-methoxyethoxy)phenyl), N-Me pyridine |
| Pyd-319 | 3-Br, 6-(2-fluoro-4-(methoxymethoxy)phenyl), N-Me pyridine |
| Pyd-320 | 3-Br, 6-(2-fluoro-4-(methylthiomethoxy)phenyl), N-Me pyridine |
| Pyd-321 | 3-Br, 6-(2-hydroxy-6-fluorophenyl), N-Me pyridine |

| | |
|---|---|
| 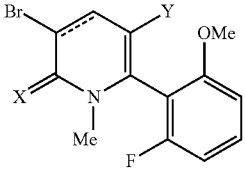 Pyd-322 | 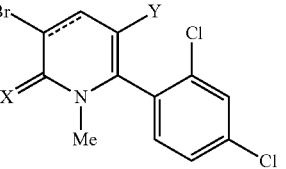 Pyd-331 |
| 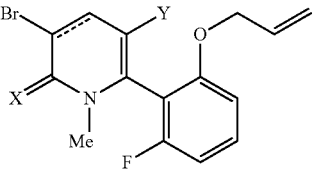 Pyd-323 | 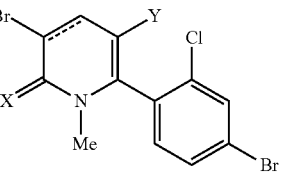 Pyd-332 |
| 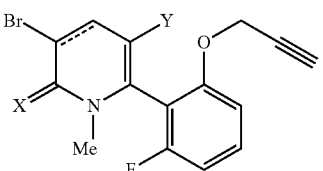 Pyd-324 | 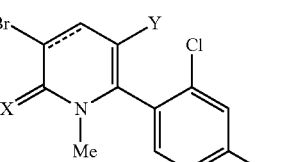 Pyd-333 |
| 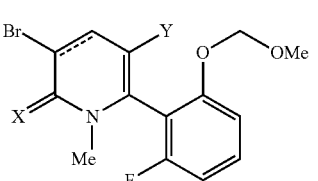 Pyd-325 | 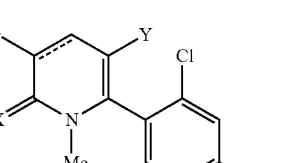 Pyd-334 |
| 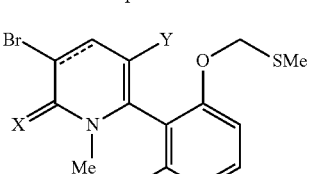 Pyd-326 | 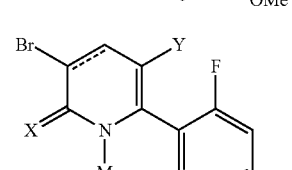 Pyd-335 |
| 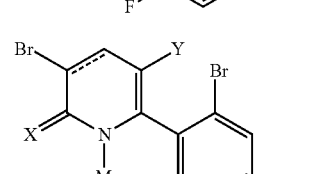 Pyd-327 | 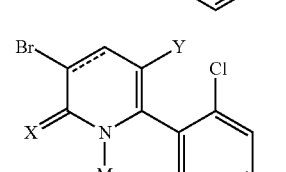 Pyd-336 |
|  Pyd-328 | 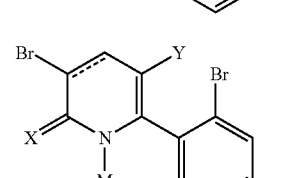 Pyd-337 |
| 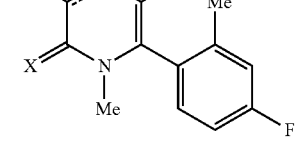 Pyd-329 | 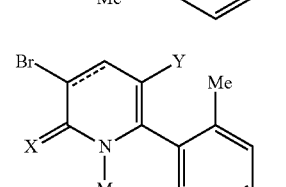 Pyd-338 |
| 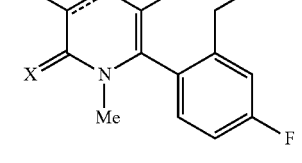 Pyd-330 | 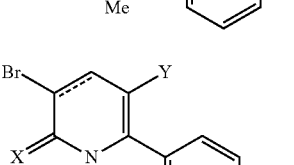 Pyd-339 |

TABLE 1-continued
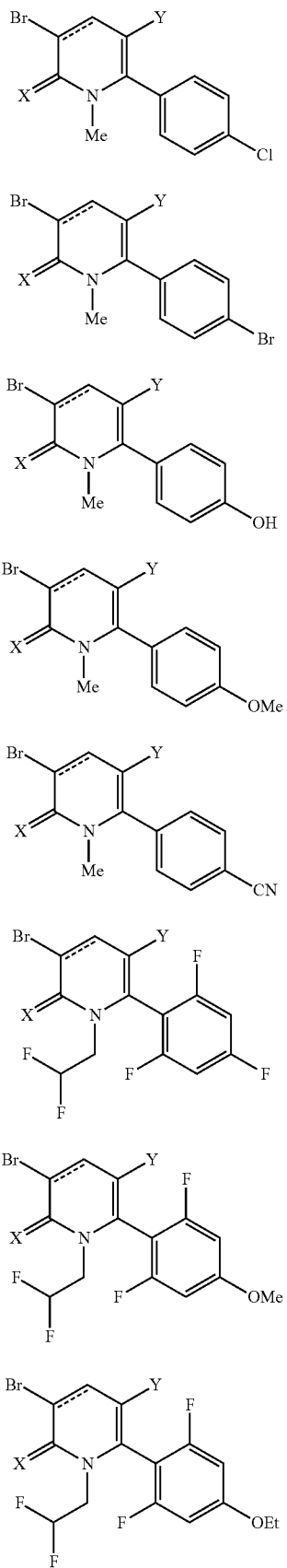
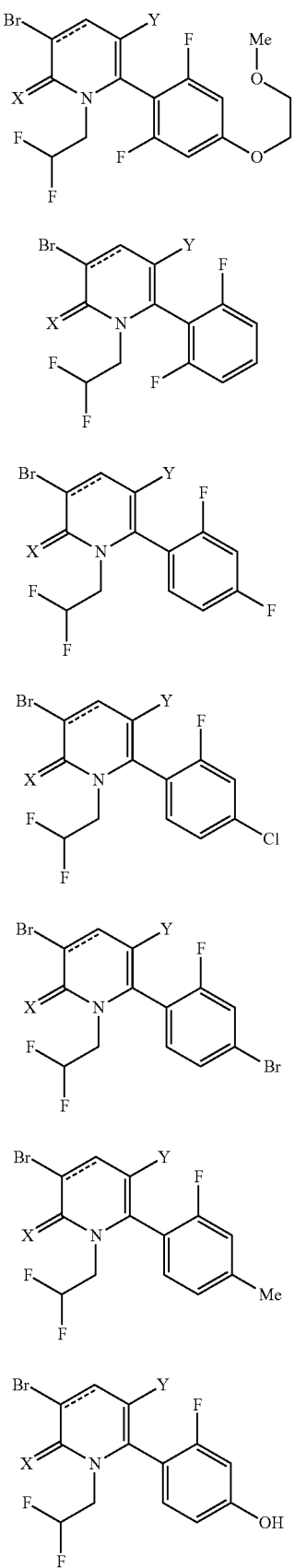

| | |
|---|---|
| 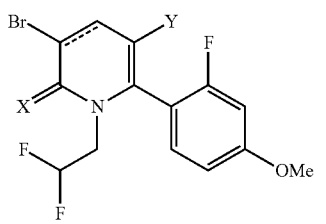 Pyd-355 | 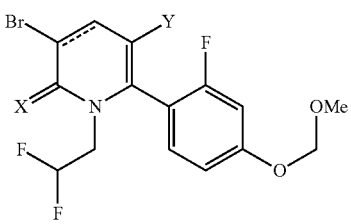 Pyd-362 |
| 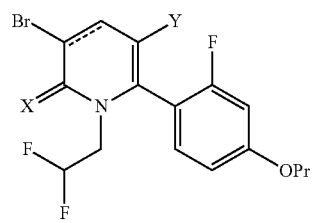 Pyd-356 | 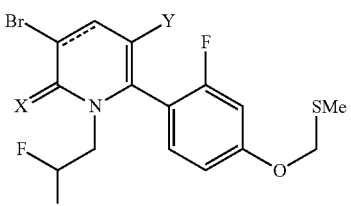 Pyd-363 |
| 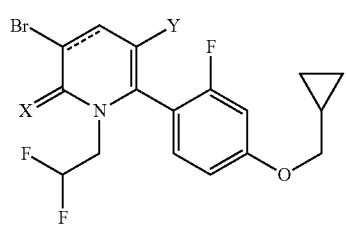 Pyd-357 | 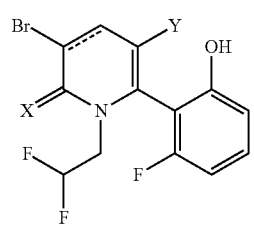 Pyd-364 |
| 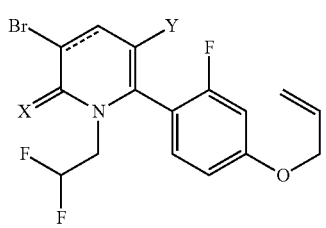 Pyd-358 | 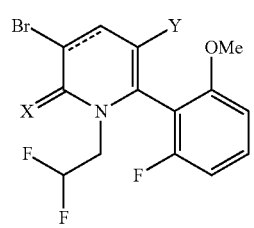 Pyd-365 |
| 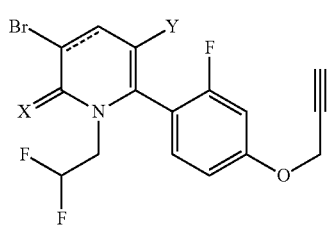 Pyd-359 | 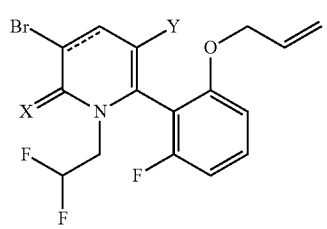 Pyd-366 |
| 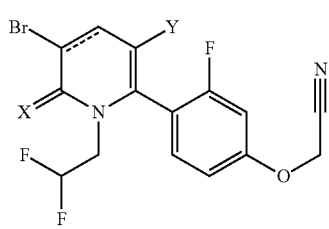 Pyd-360 | 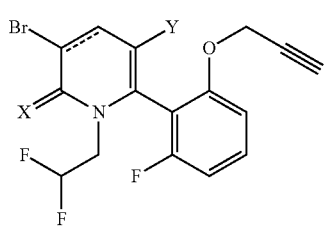 Pyd-367 |
| 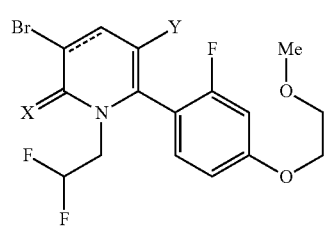 Pyd-361 | 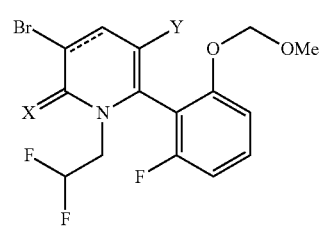 Pyd-368 |

TABLE 1-continued
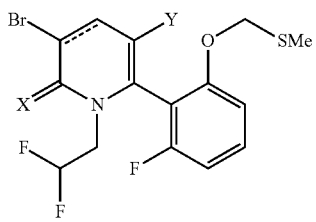 Pyd-369
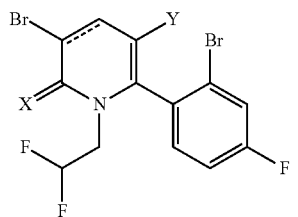 Pyd-370
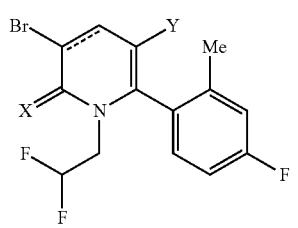 Pyd-371
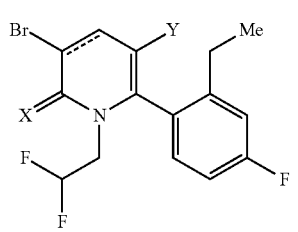 Pyd-372
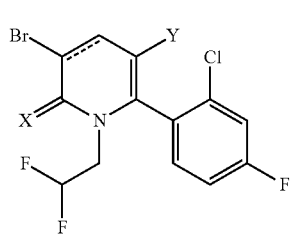 Pyd-373
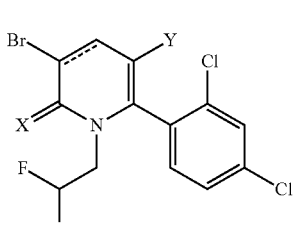 Pyd-374
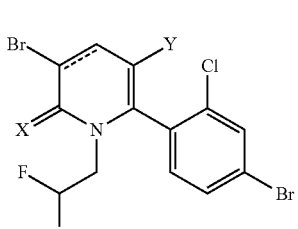 Pyd-375
TABLE 1-continued
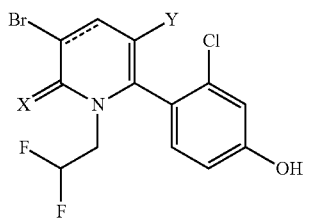 Pyd-376
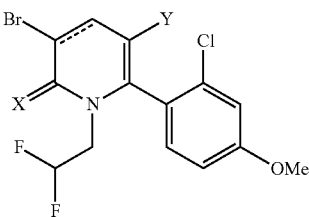 Pyd-377
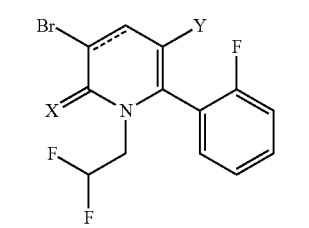 Pyd-378
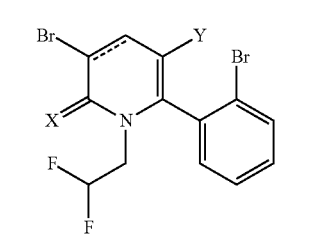 Pyd-379
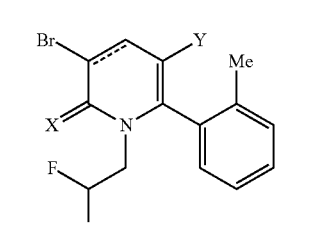 Pyd-380
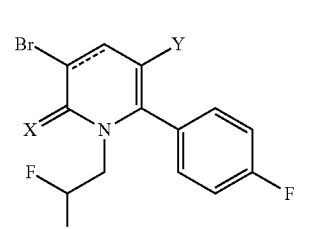 Pyd-381
 Pyd-382

TABLE 1-continued
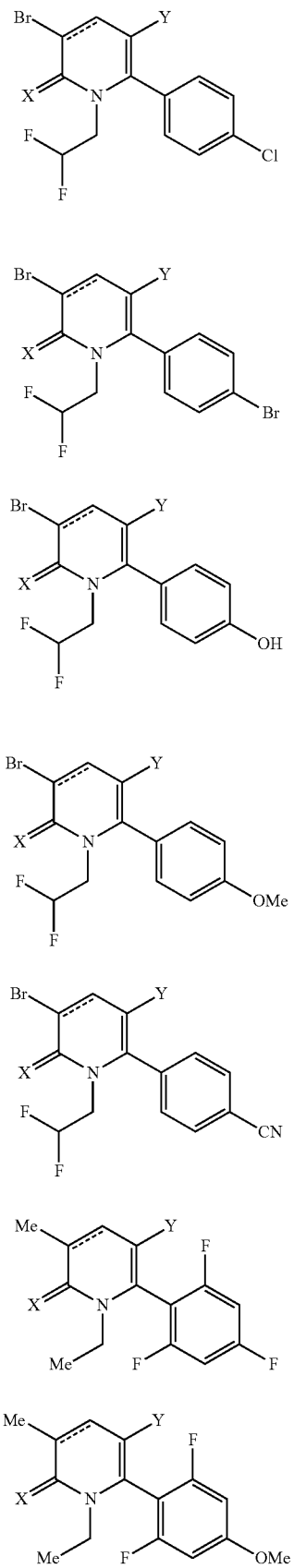
Pyd-383
Pyd-384
Pyd-385
Pyd-386
Pyd-387
Pyd-388
Pyd-389
TABLE 1-continued
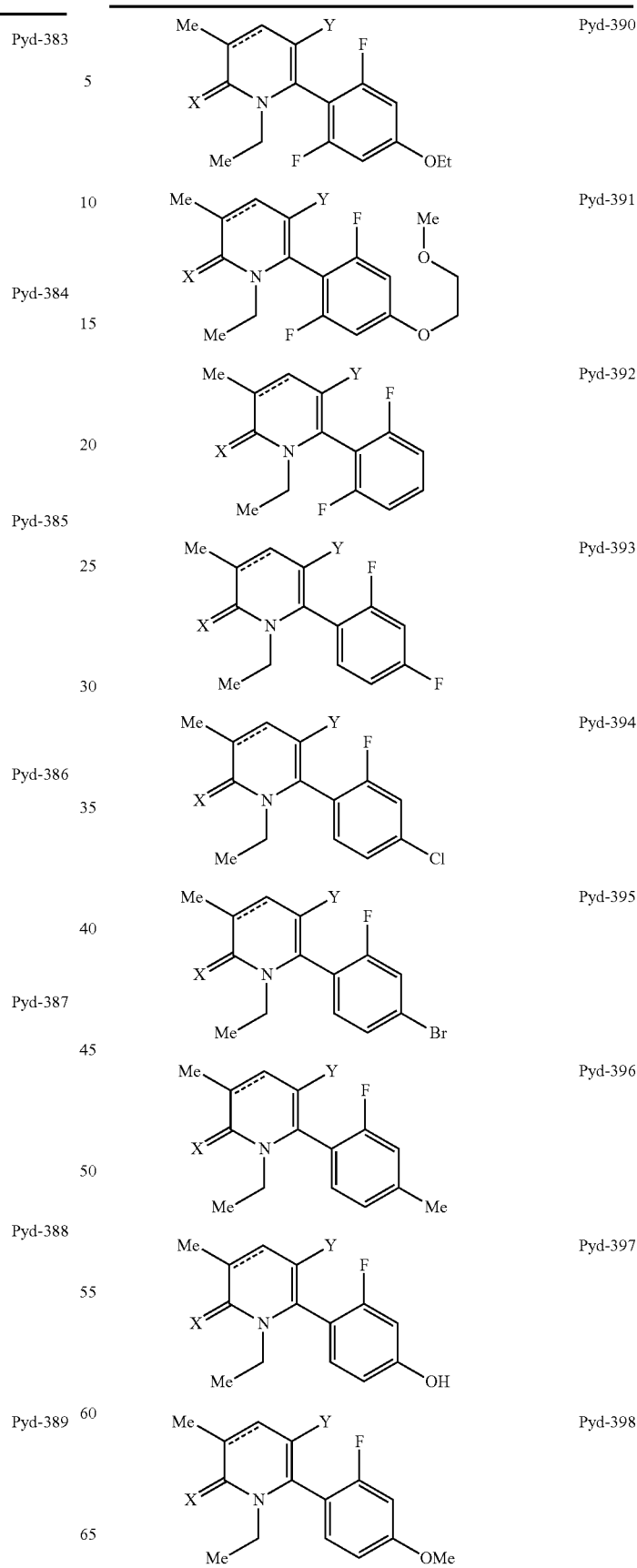
Pyd-390
Pyd-391
Pyd-392
Pyd-393
Pyd-394
Pyd-395
Pyd-396
Pyd-397
Pyd-398

TABLE 1-continued
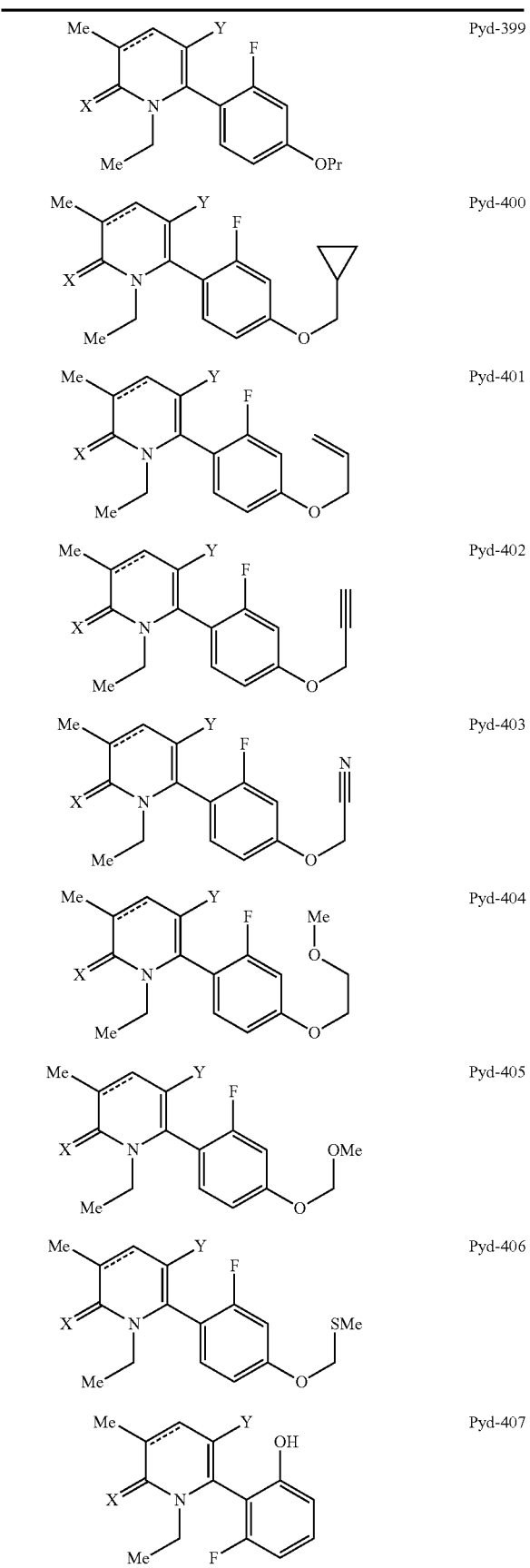
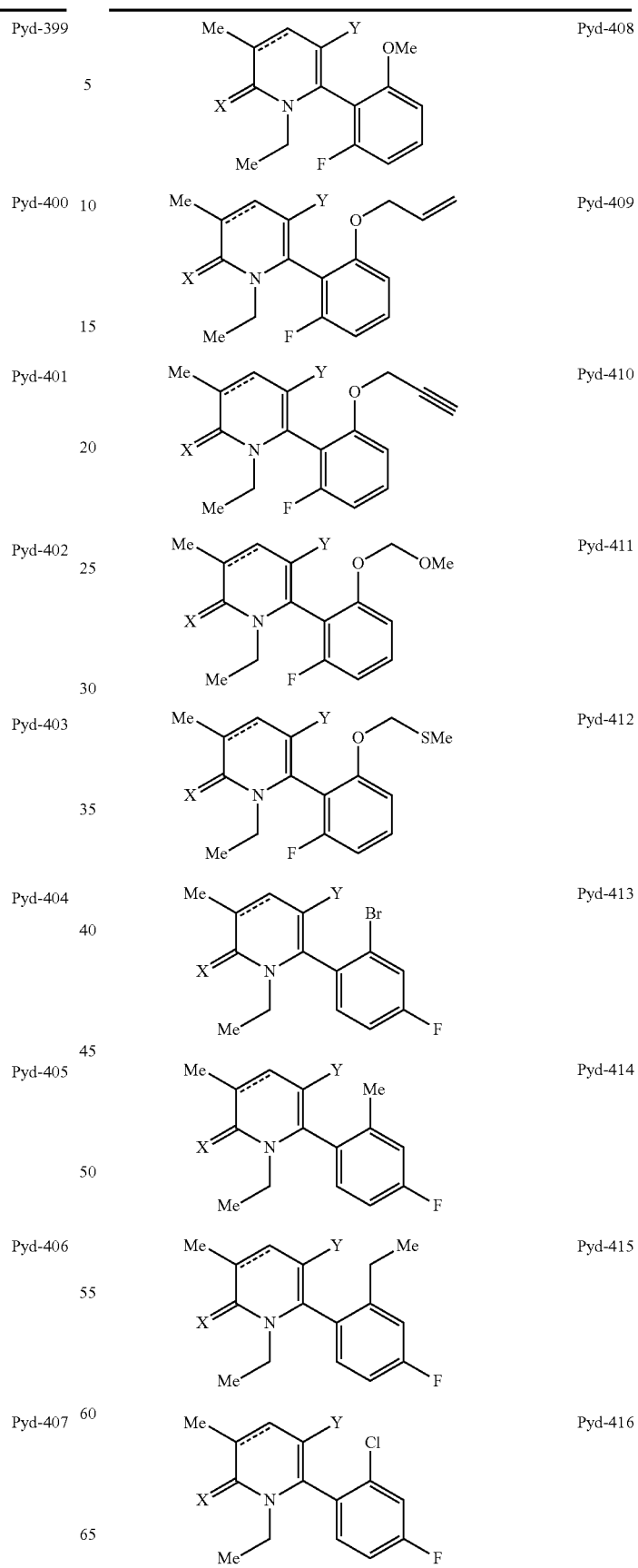

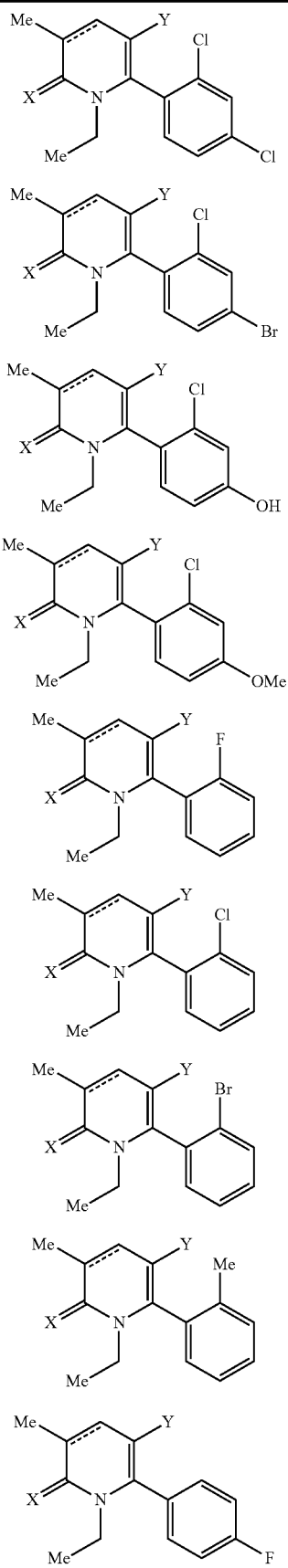
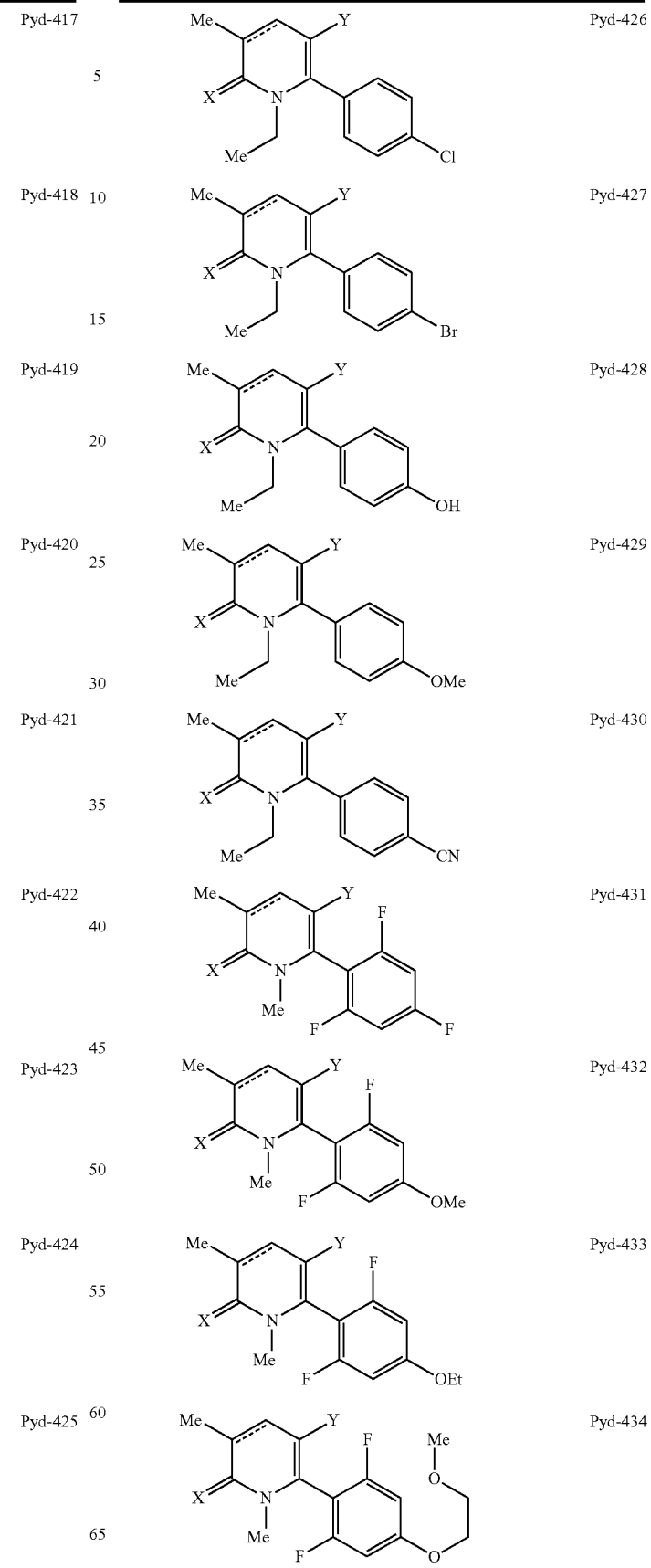

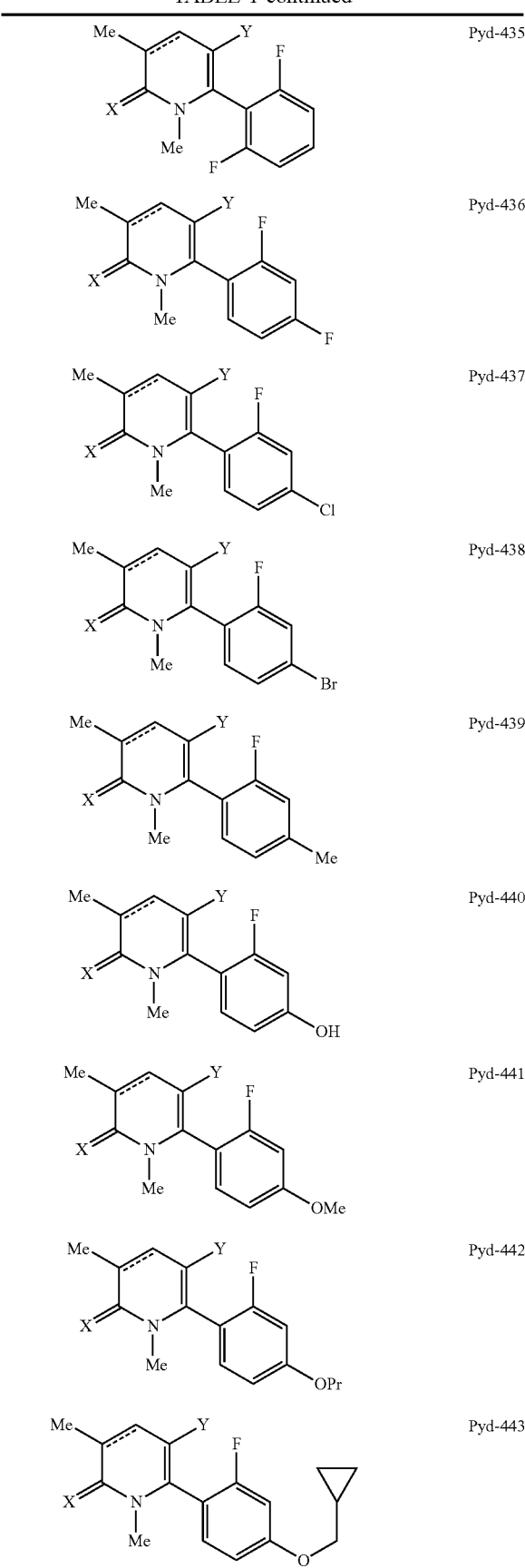
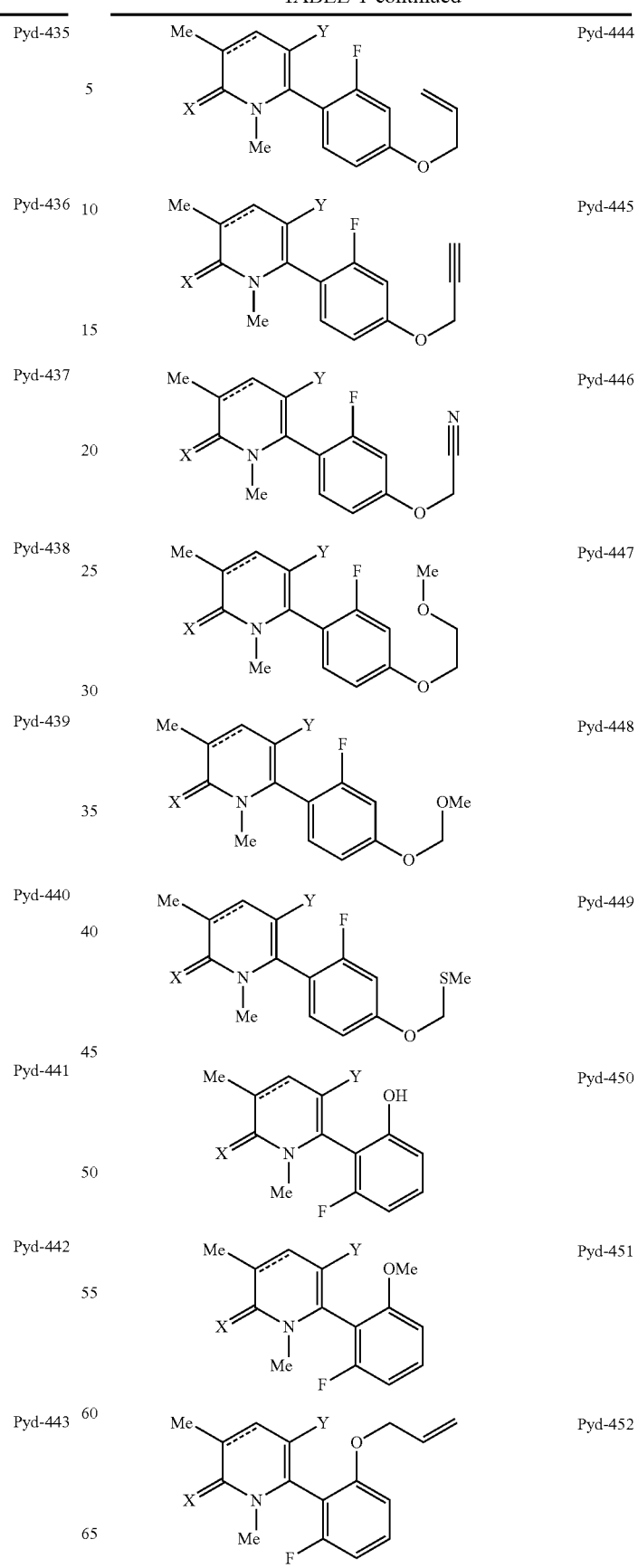

TABLE 1-continued
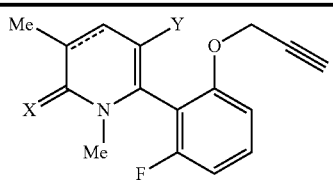 Pyd-453
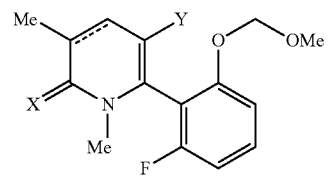 Pyd-454
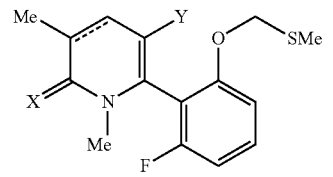 Pyd-455
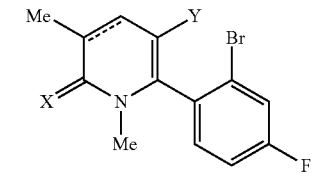 Pyd-456
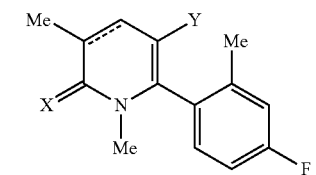 Pyd-457
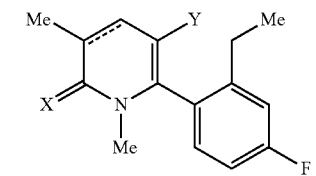 Pyd-458
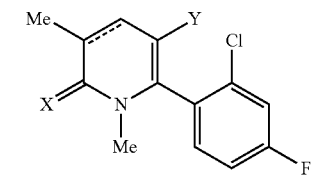 Pyd-459
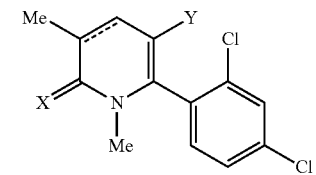 Pyd-460
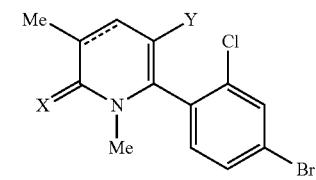 Pyd-461
TABLE 1-continued
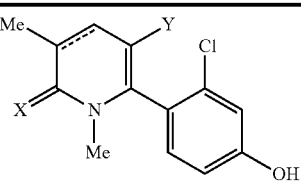 Pyd-462
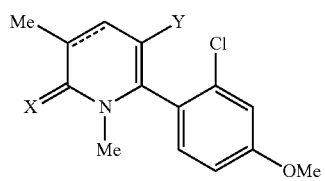 Pyd-463
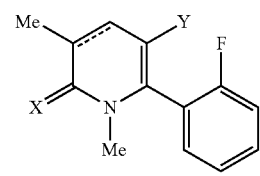 Pyd-464
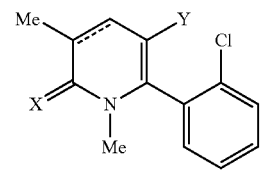 Pyd-465
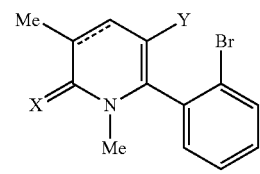 Pyd-466
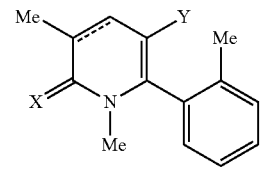 Pyd-467
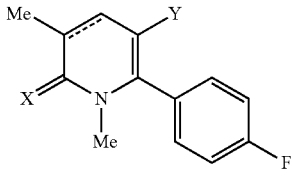 Pyd-468
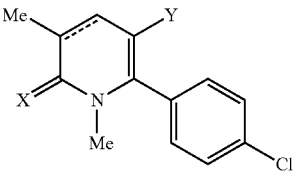 Pyd-469
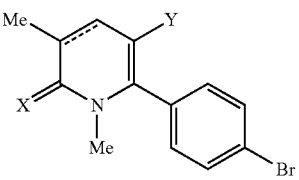 Pyd-470

TABLE 1-continued
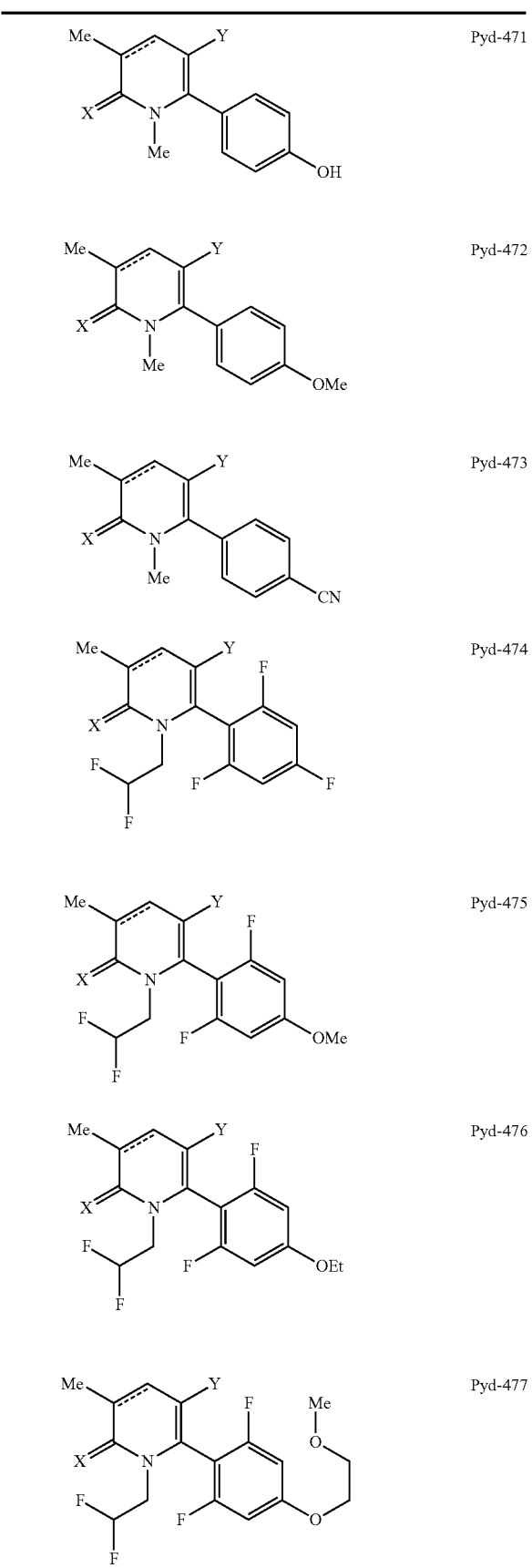
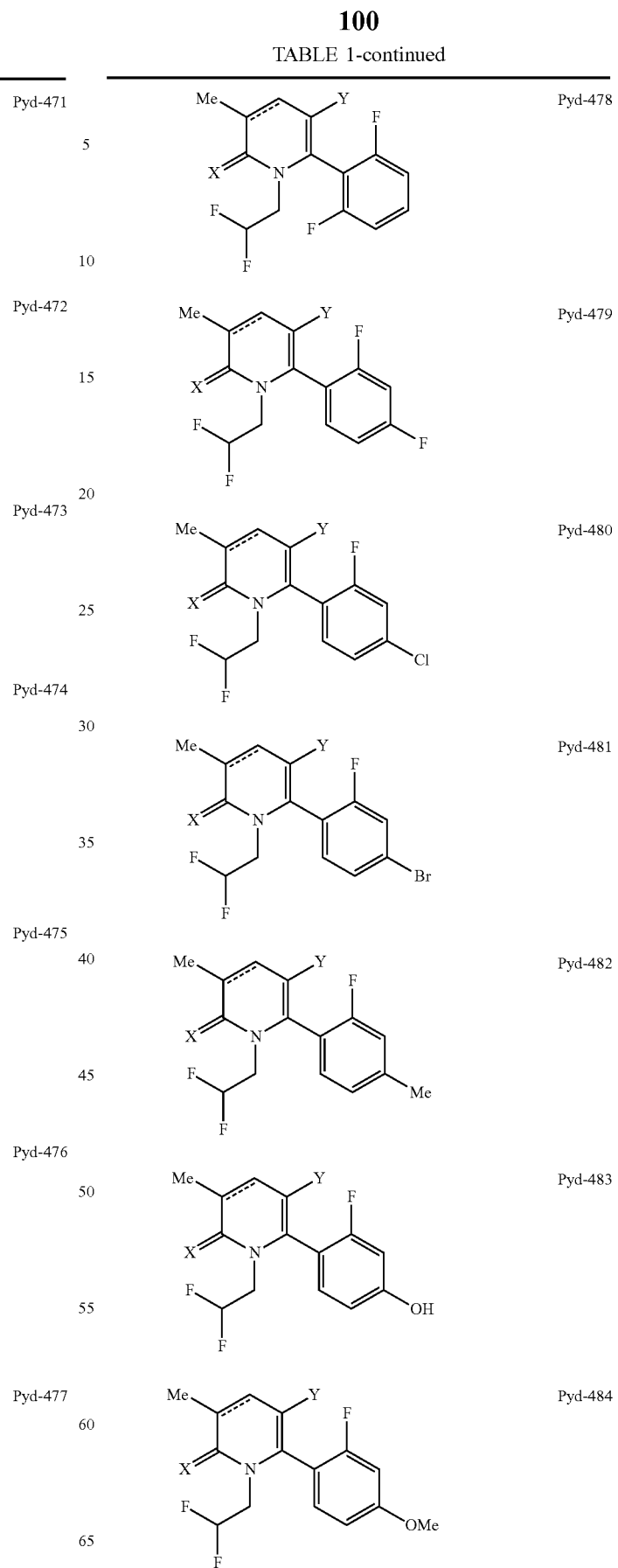

TABLE 1-continued
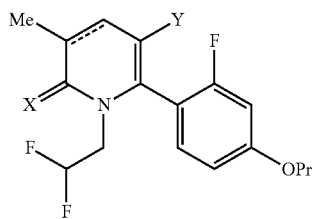 Pyd-485
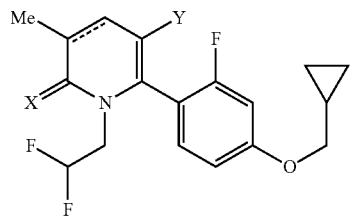 Pyd-486
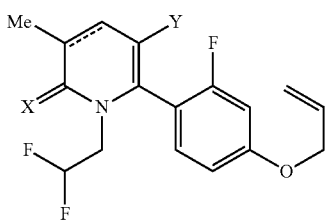 Pyd-487
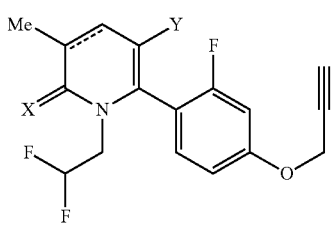 Pyd-488
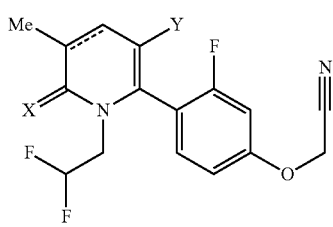 Pyd-489
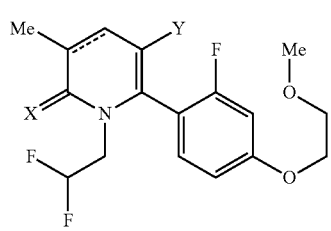 Pyd-490
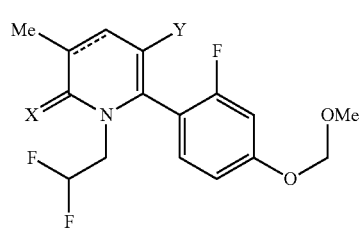 Pyd-491
TABLE 1-continued
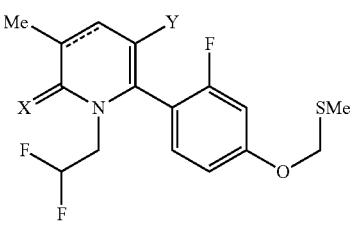 Pyd-492
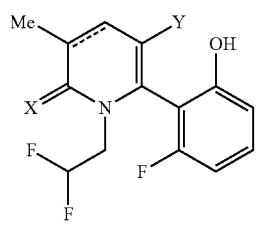 Pyd-493
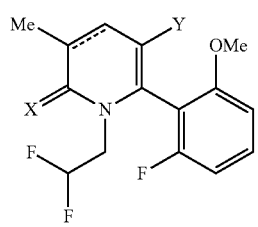 Pyd-494
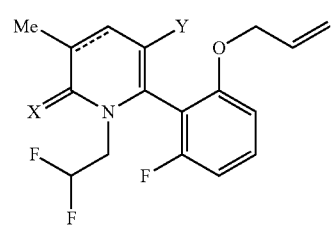 Pyd-495
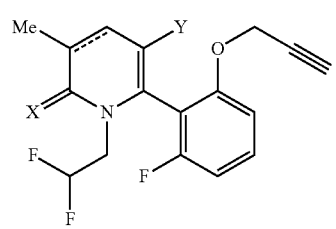 Pyd-496
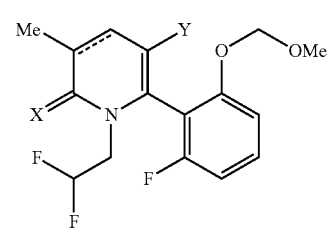 Pyd-497
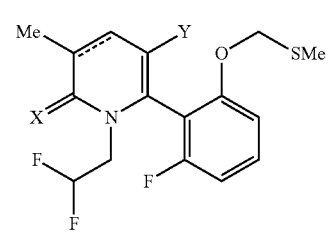 Pyd-498

TABLE 1-continued
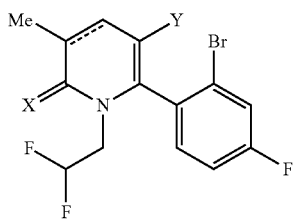 Pyd-499
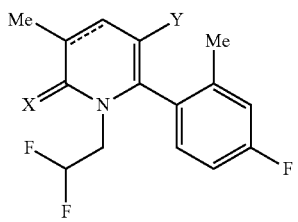 Pyd-500
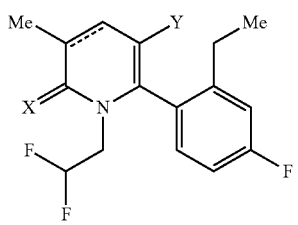 Pyd-501
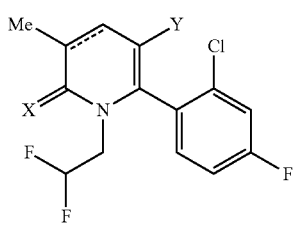 Pyd-502
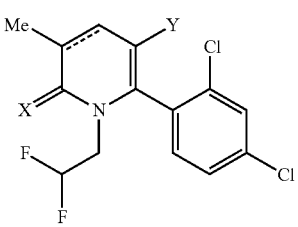 Pyd-503
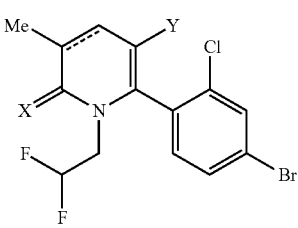 Pyd-504
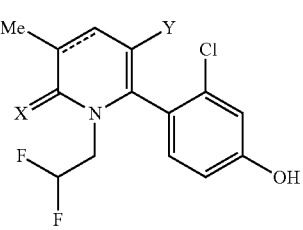 Pyd-505
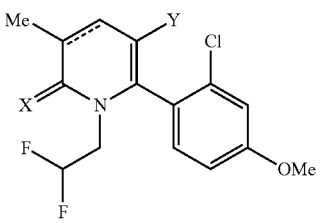 Pyd-506
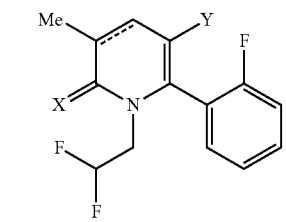 Pyd-507
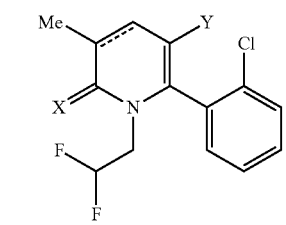 Pyd-508
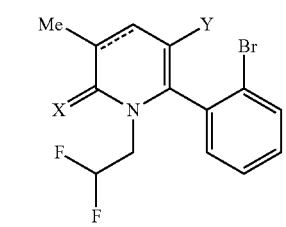 Pyd-509
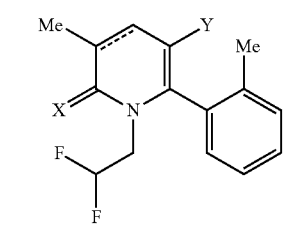 Pyd-510
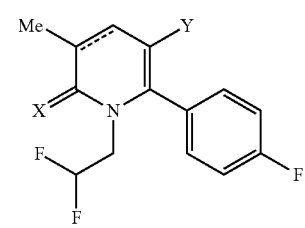 Pyd-511
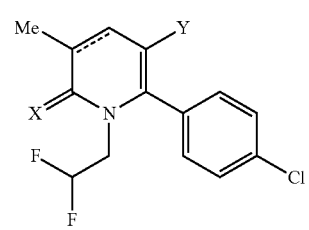 Pyd-512

TABLE 1-continued
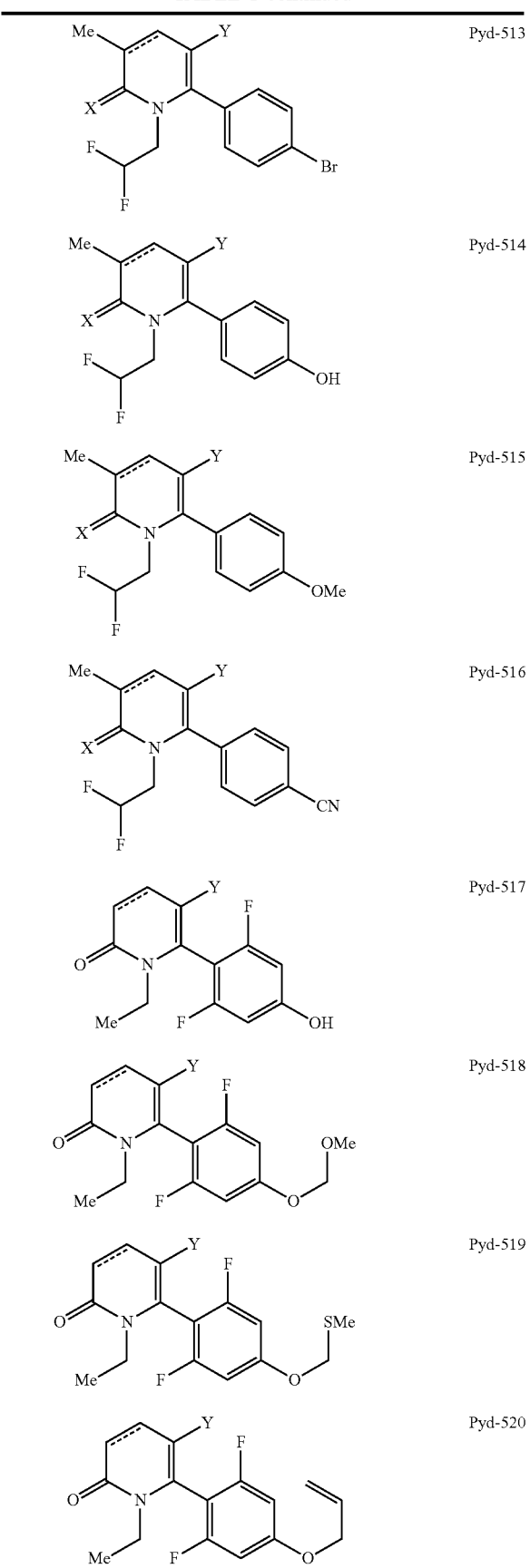
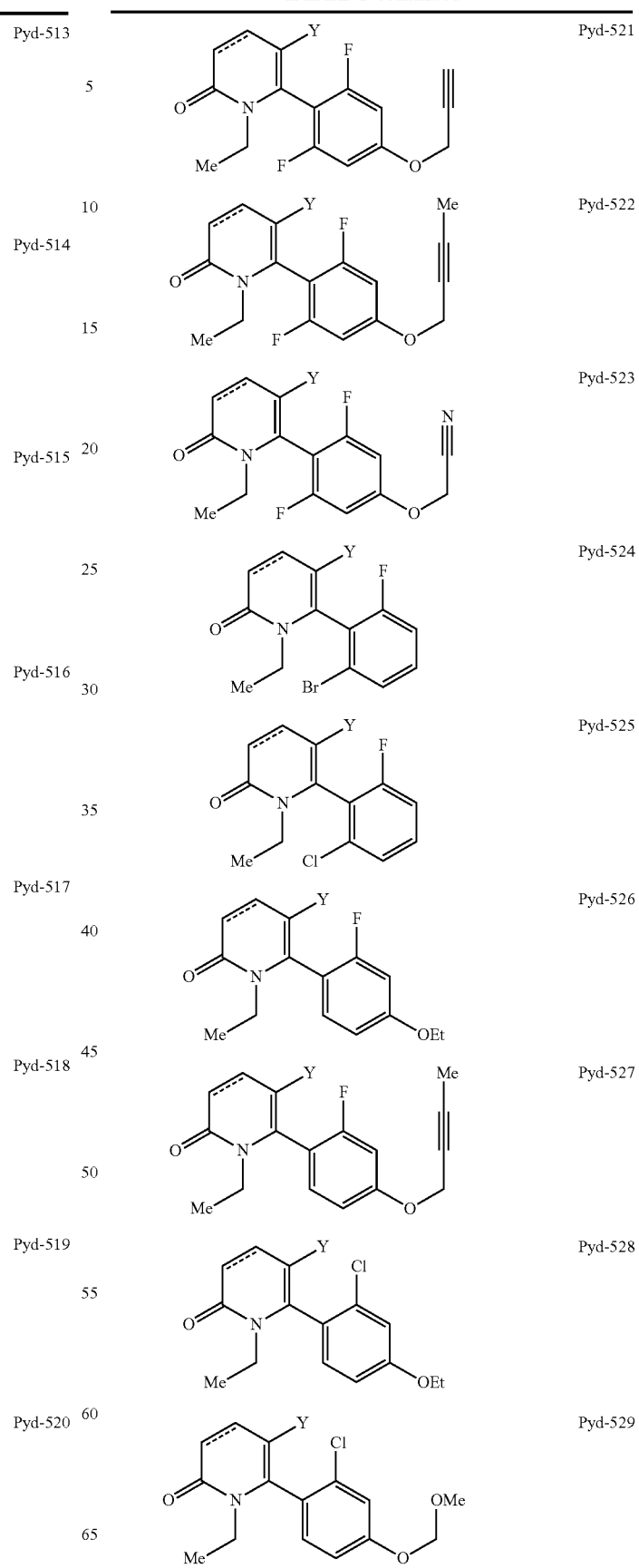

TABLE 1-continued
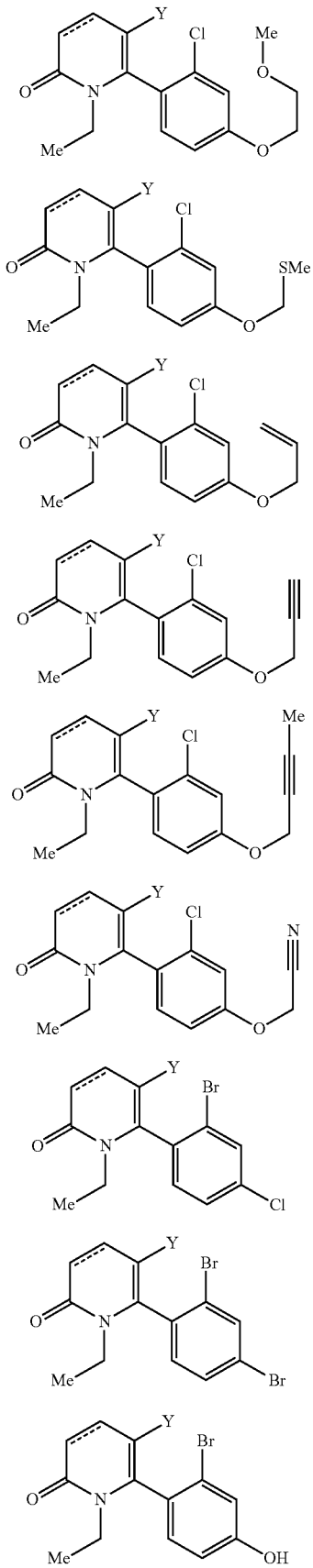
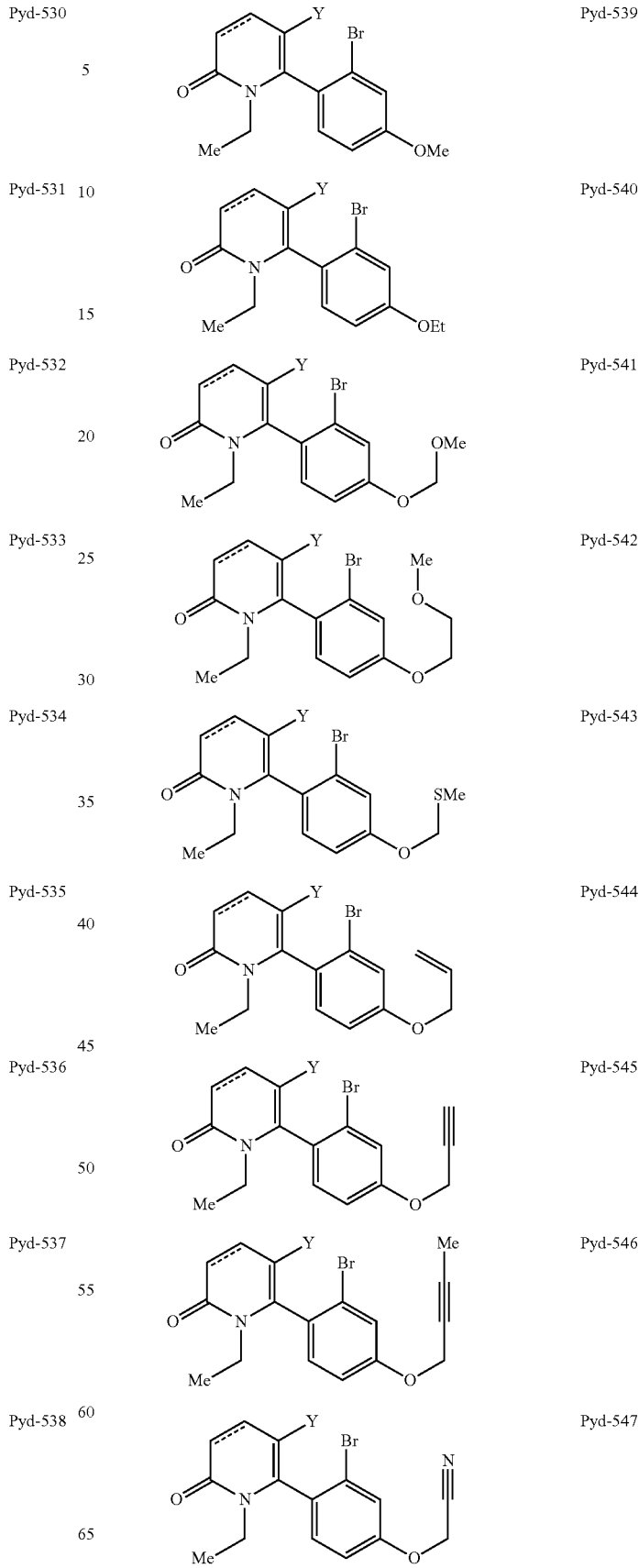

TABLE 1-continued
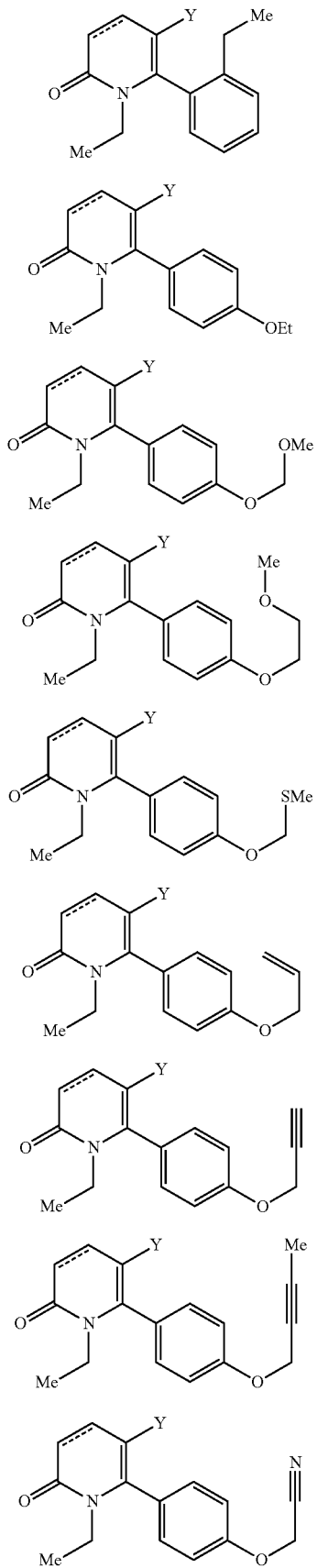
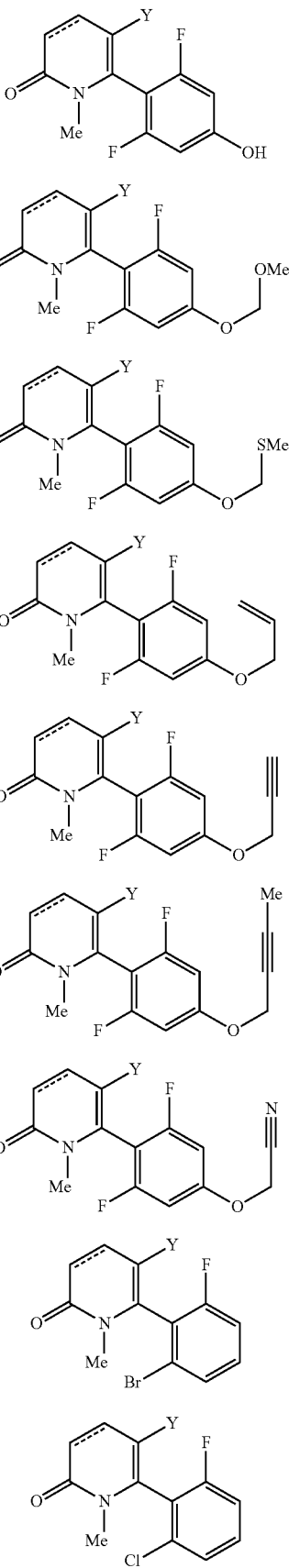

TABLE 1-continued
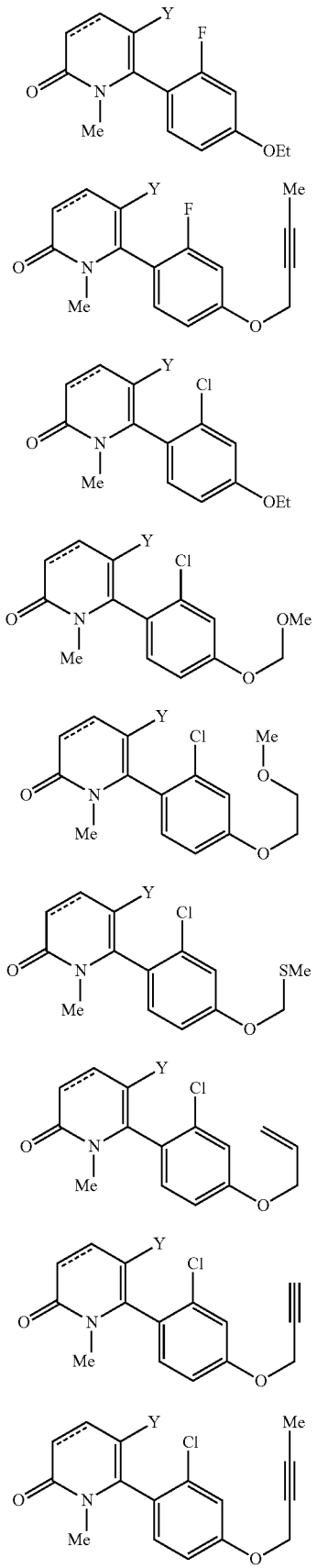
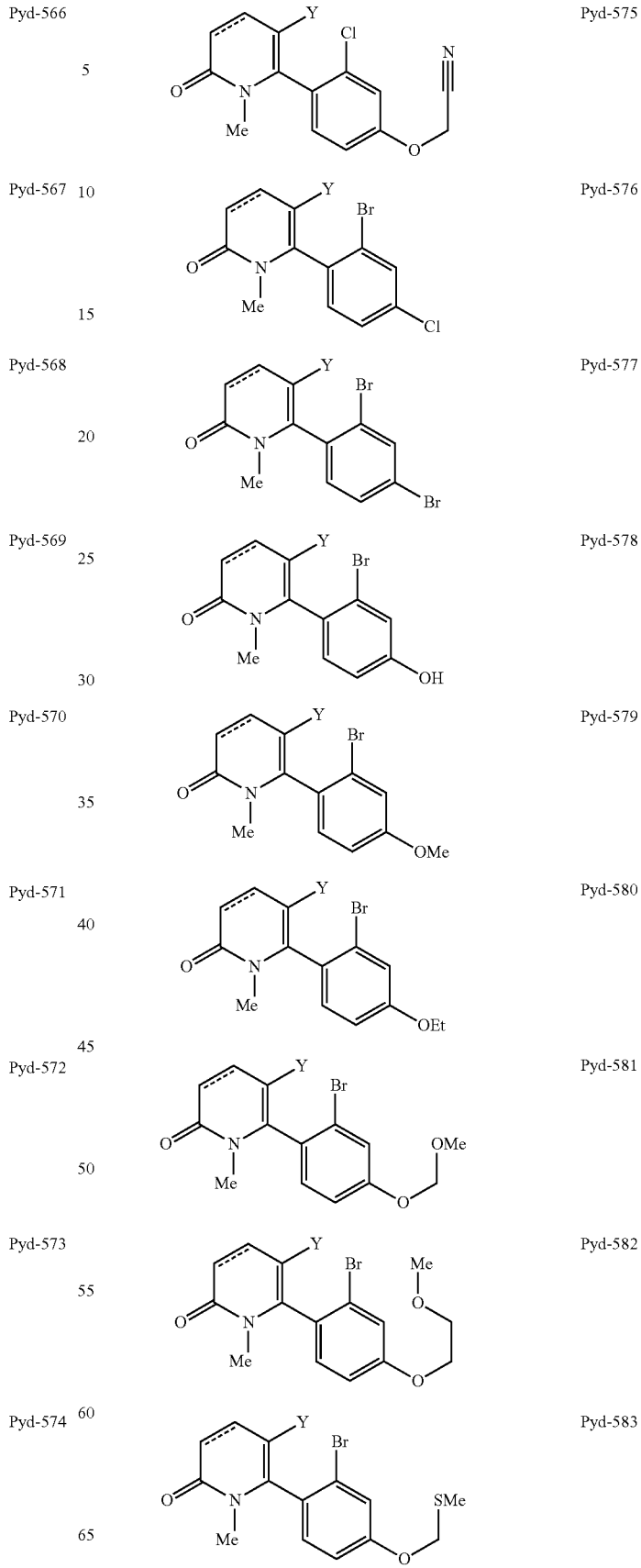

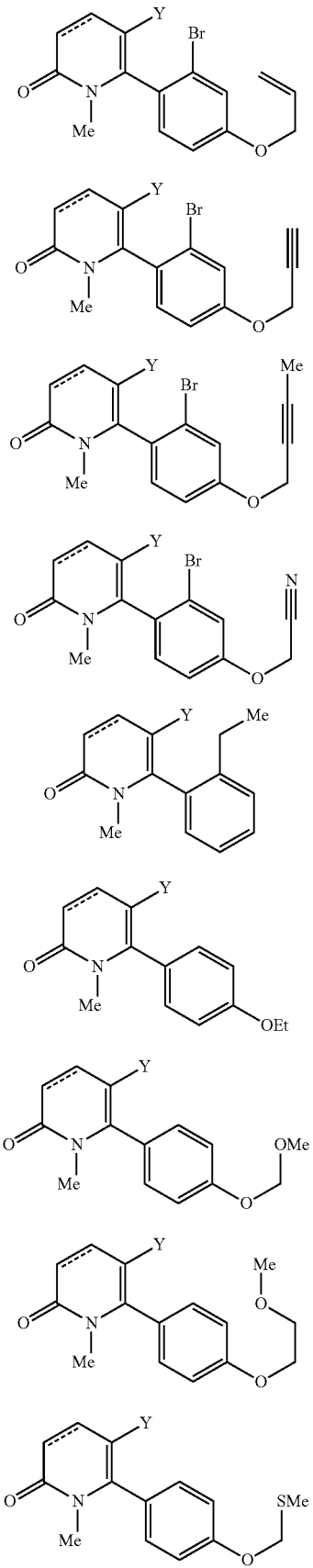
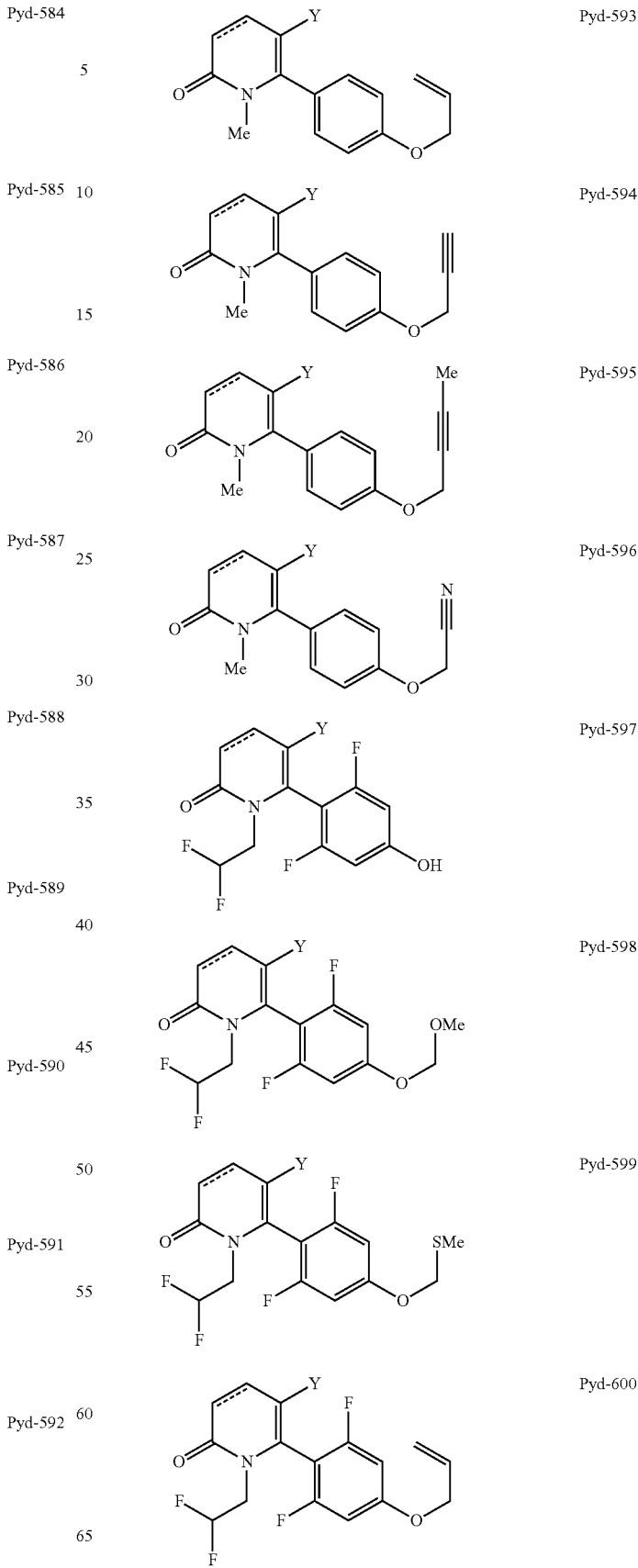

TABLE 1-continued
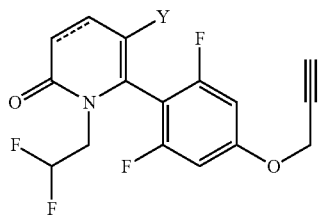 Pyd-601
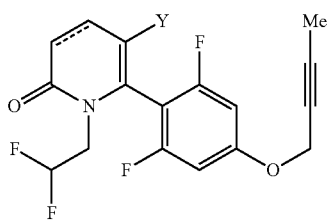 Pyd-602
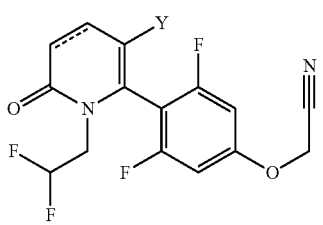 Pyd-603
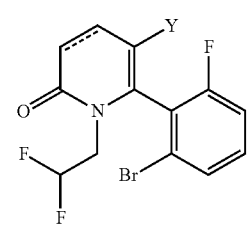 Pyd-604
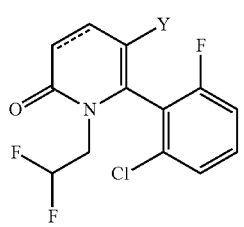 Pyd-605
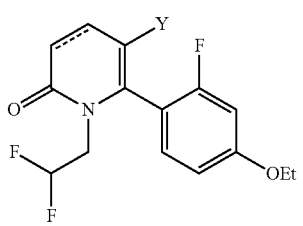 Pyd-606
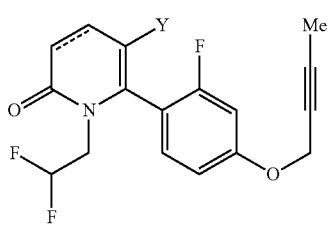 Pyd-607
TABLE 1-continued
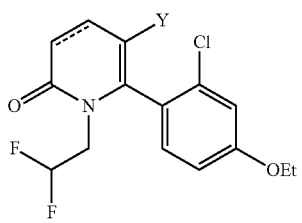 Pyd-608
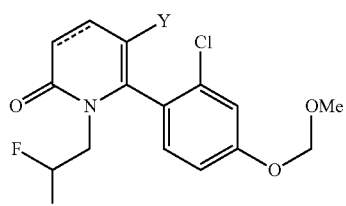 Pyd-609
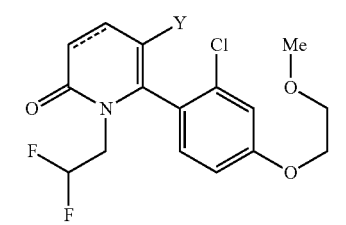 Pyd-610
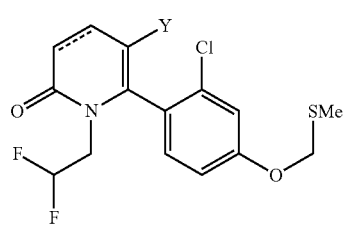 Pyd-611
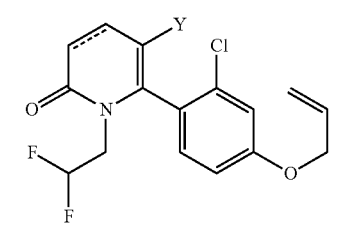 Pyd-612
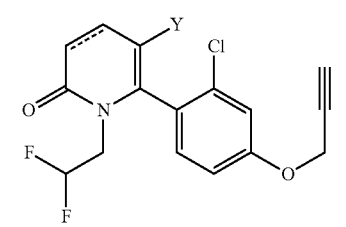 Pyd-613
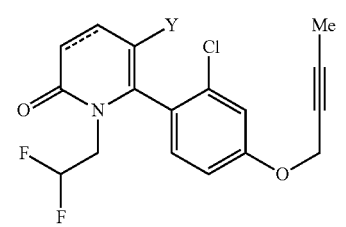 Pyd-614

TABLE 1-continued
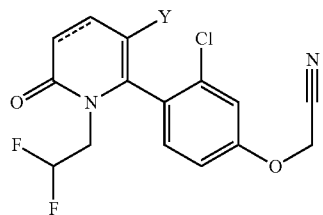 Pyd-615
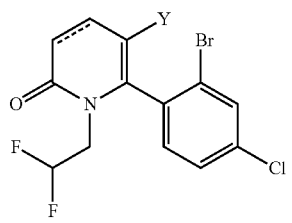 Pyd-616
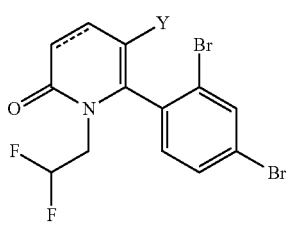 Pyd-617
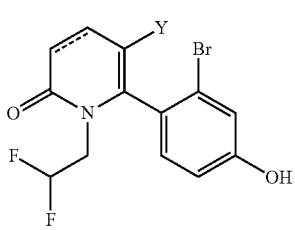 Pyd-618
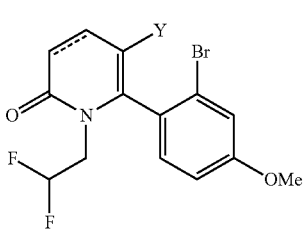 Pyd-619
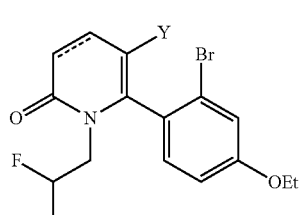 Pyd-620
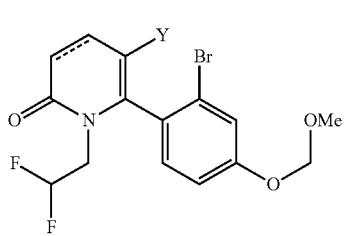 Pyd-621
TABLE 1-continued
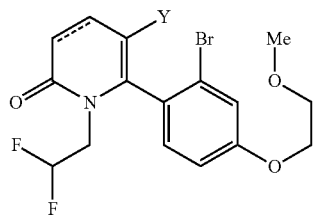 Pyd-622
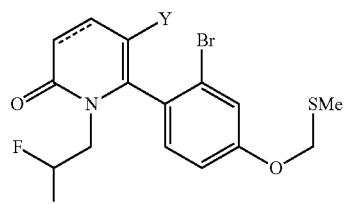 Pyd-623
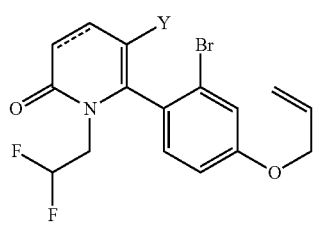 Pyd-624
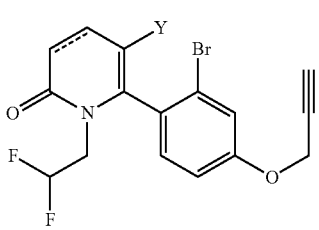 Pyd-625
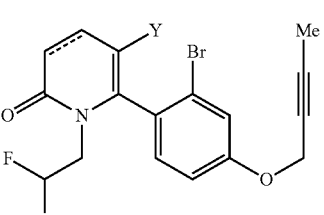 Pyd-626
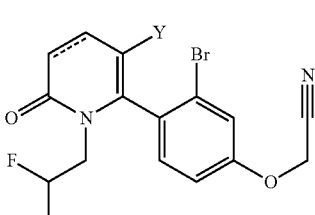 Pyd-627
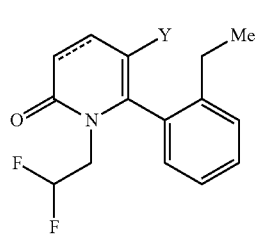 Pyd-628

TABLE 1-continued
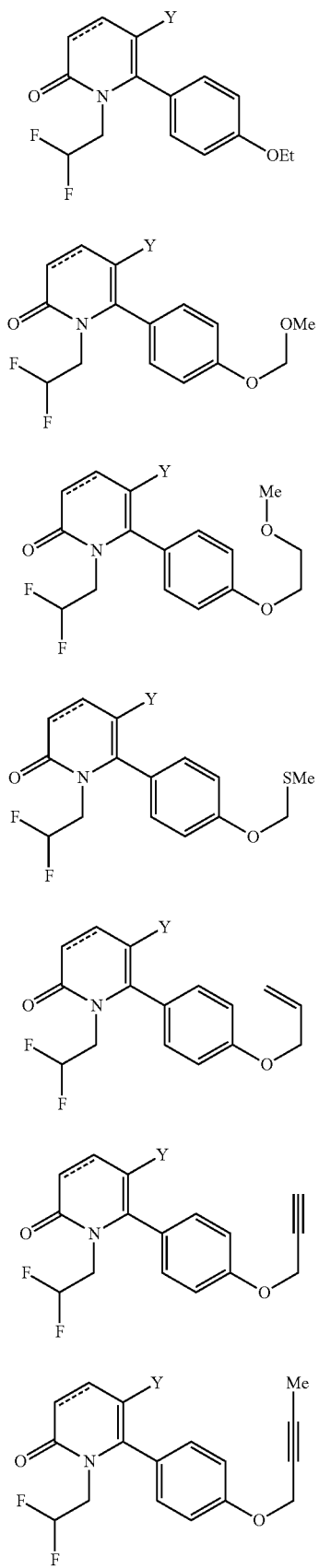
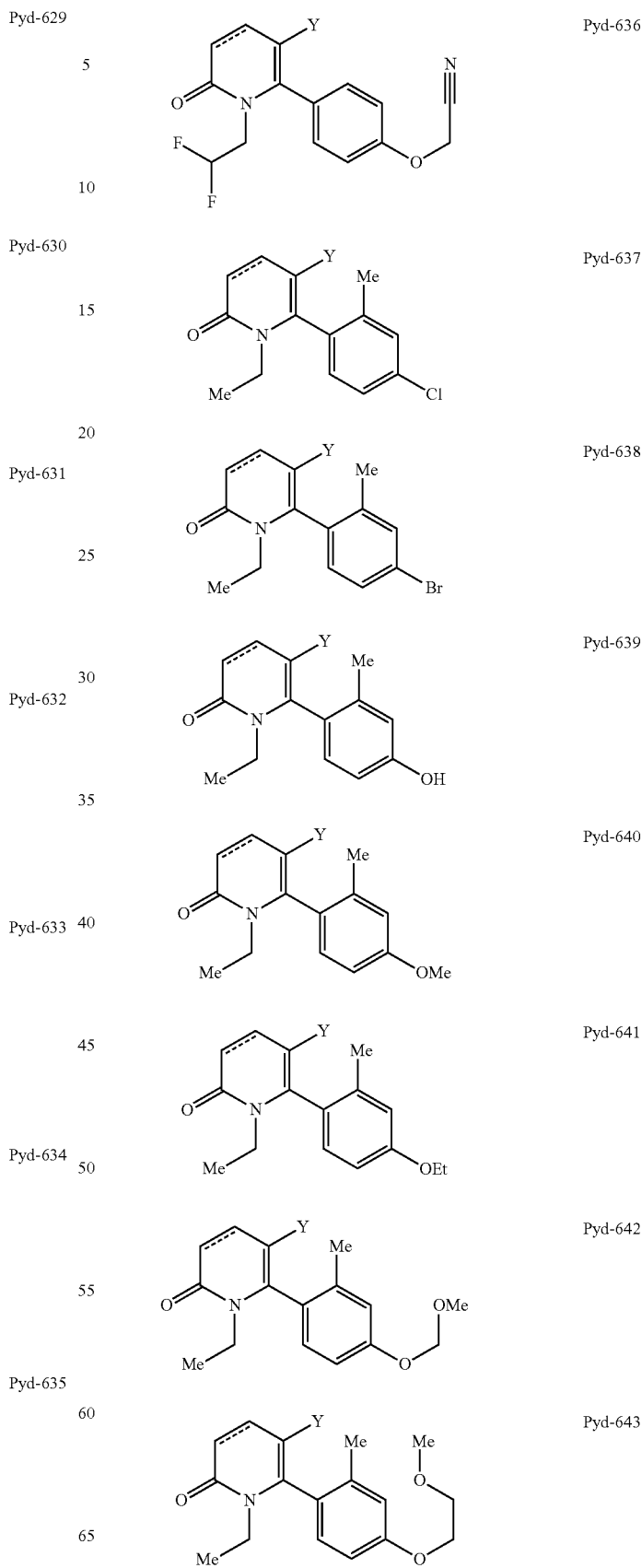

TABLE 1-continued
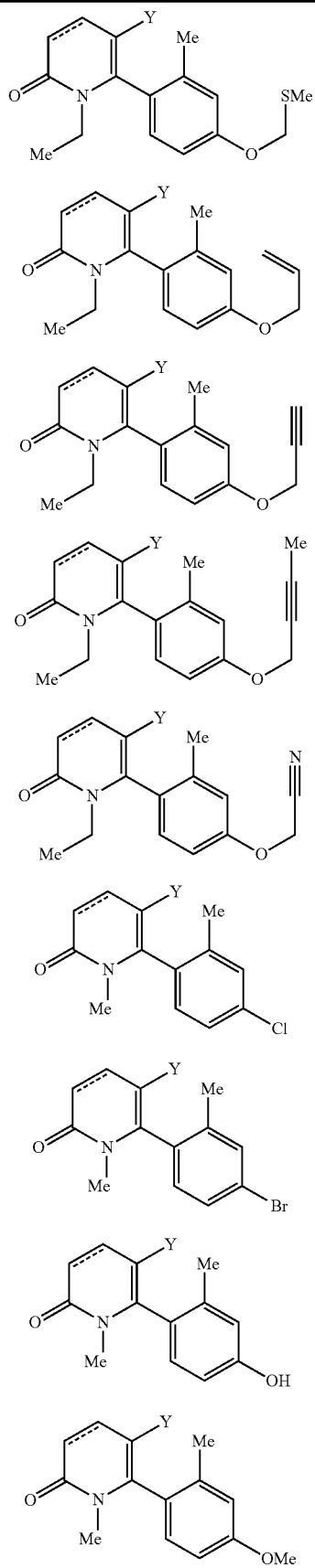
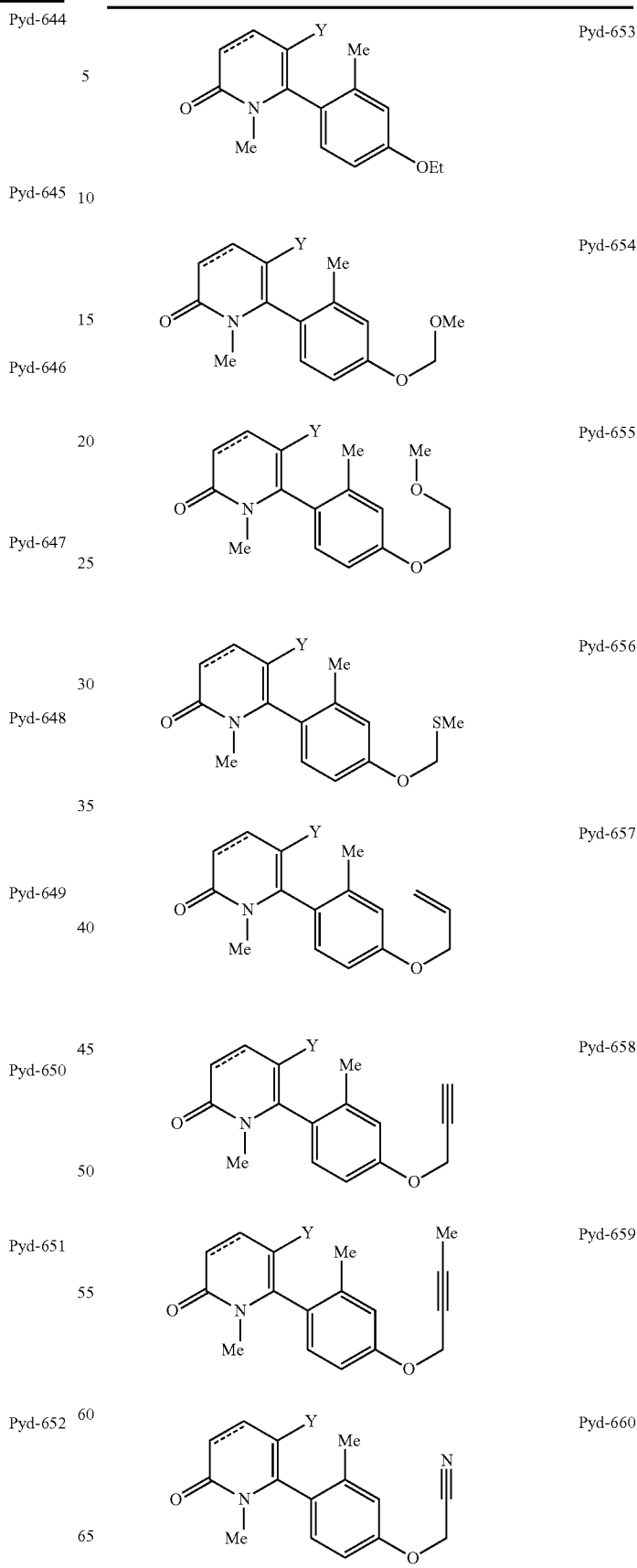

TABLE 1-continued
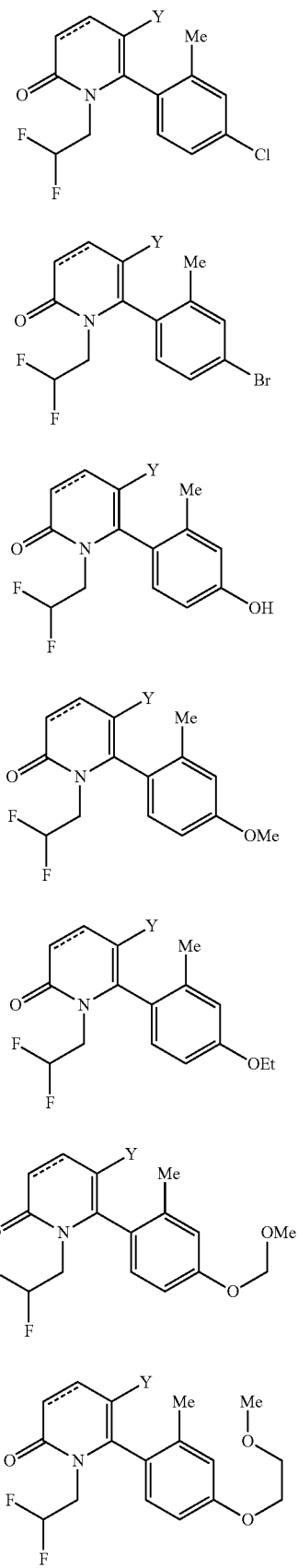
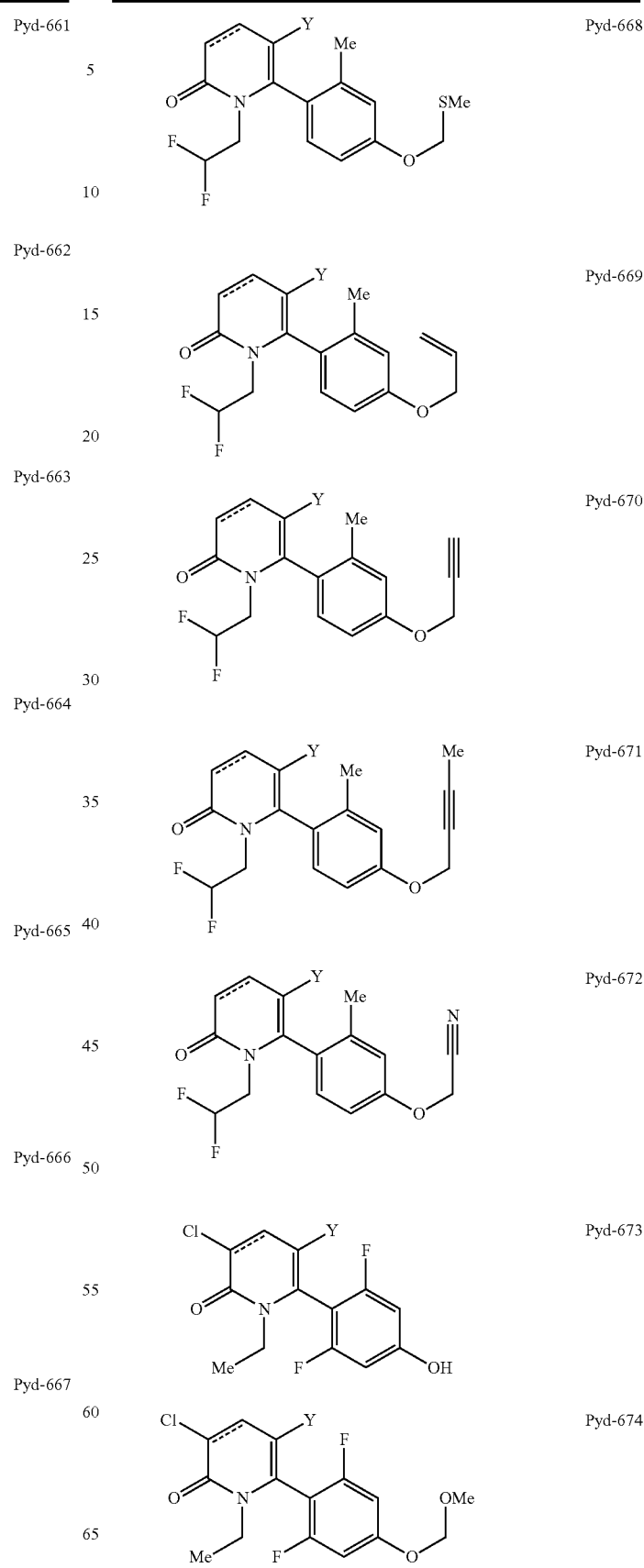

TABLE 1-continued
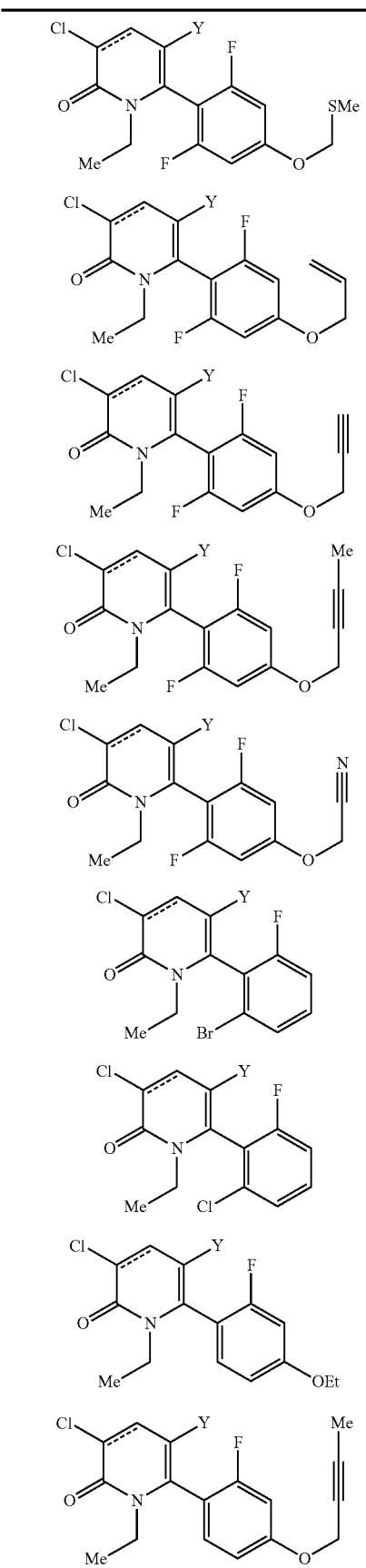
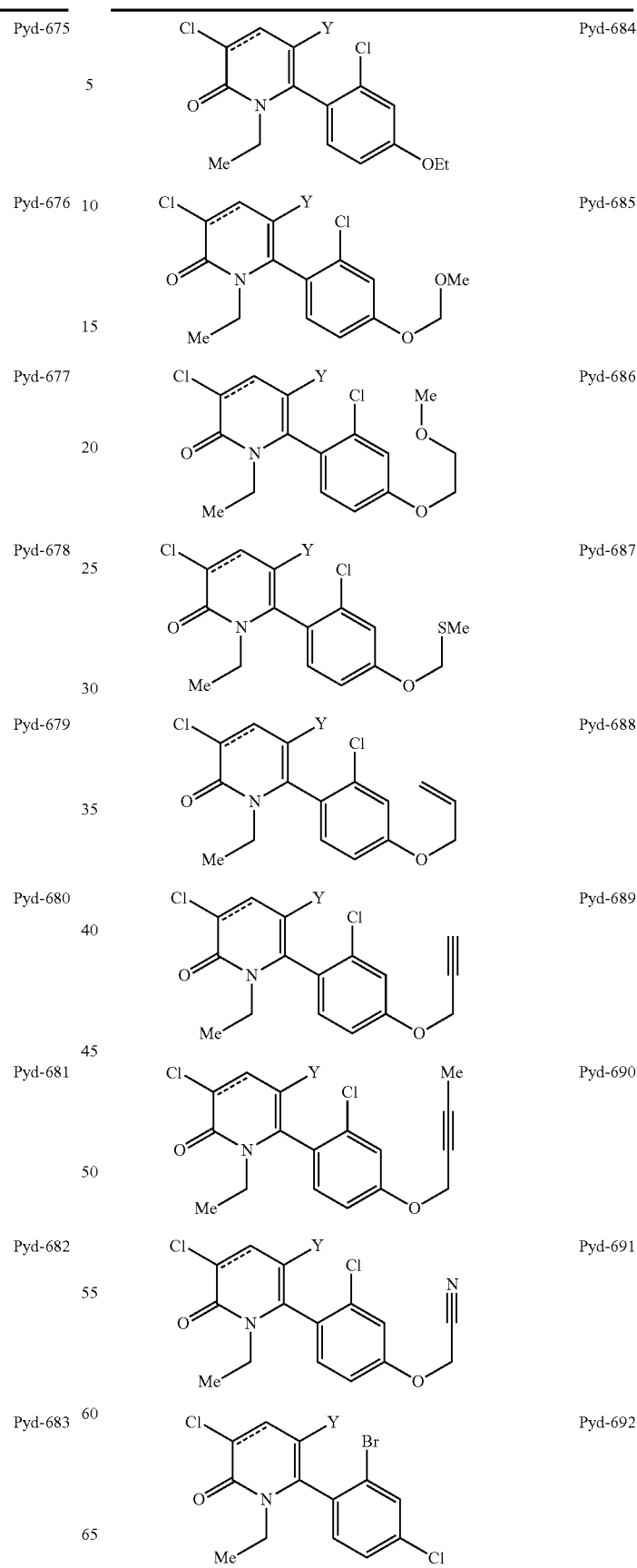

TABLE 1-continued
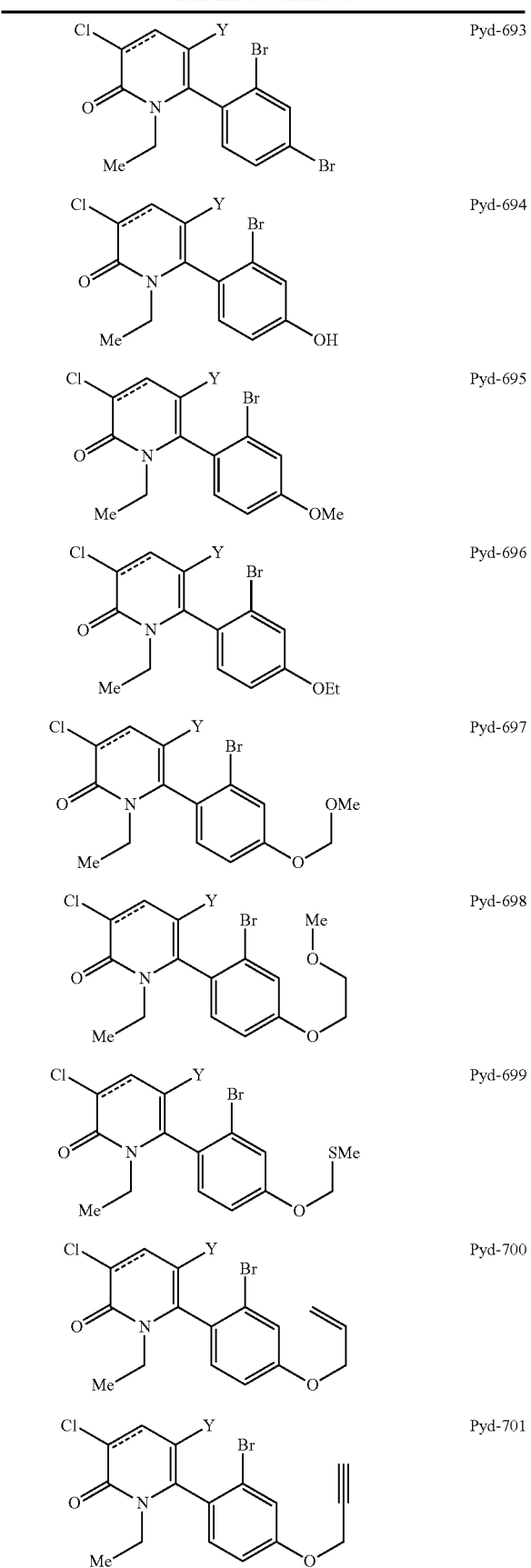
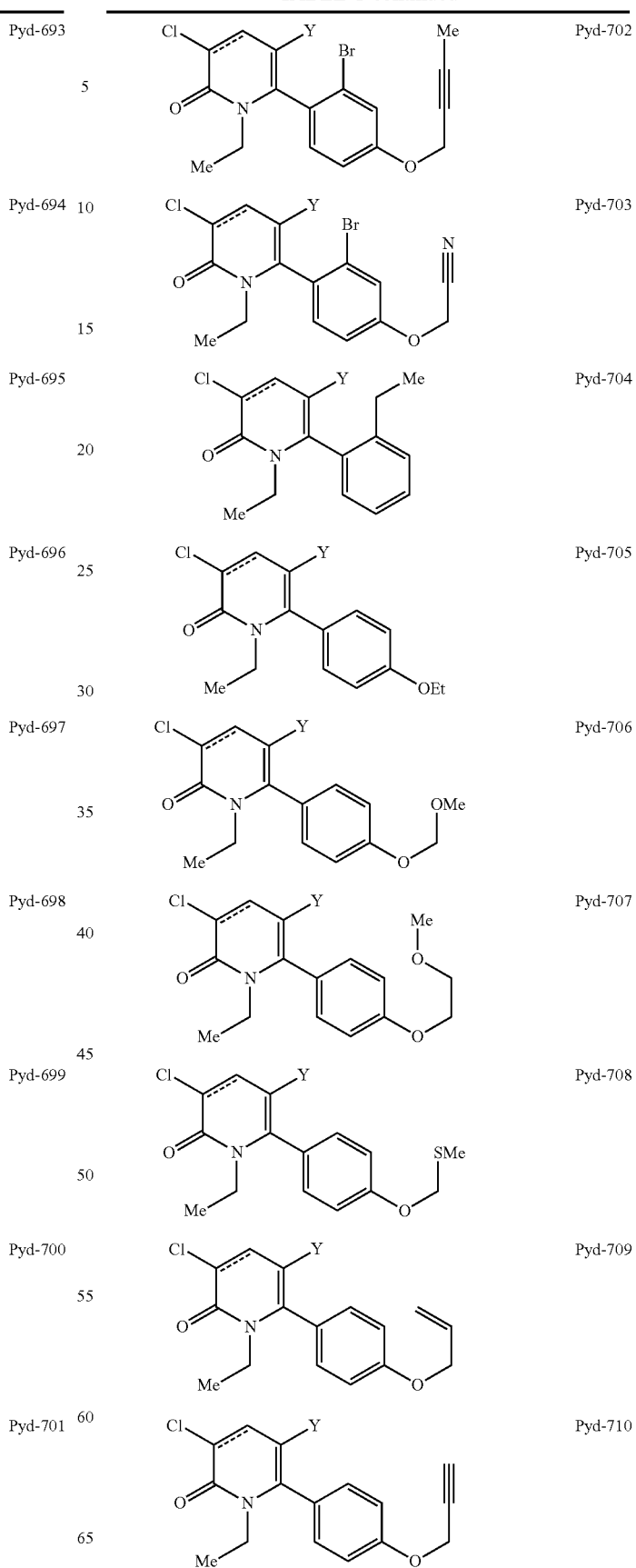

TABLE 1-continued
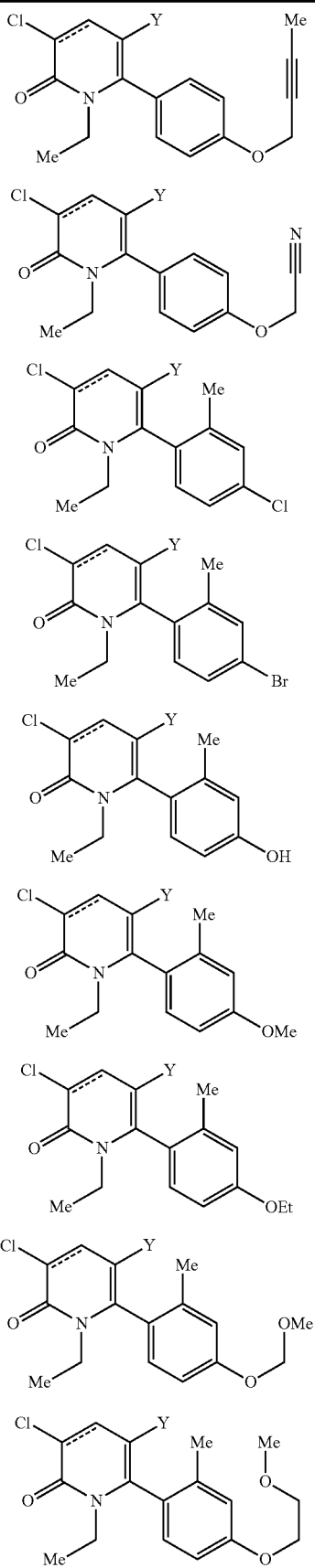
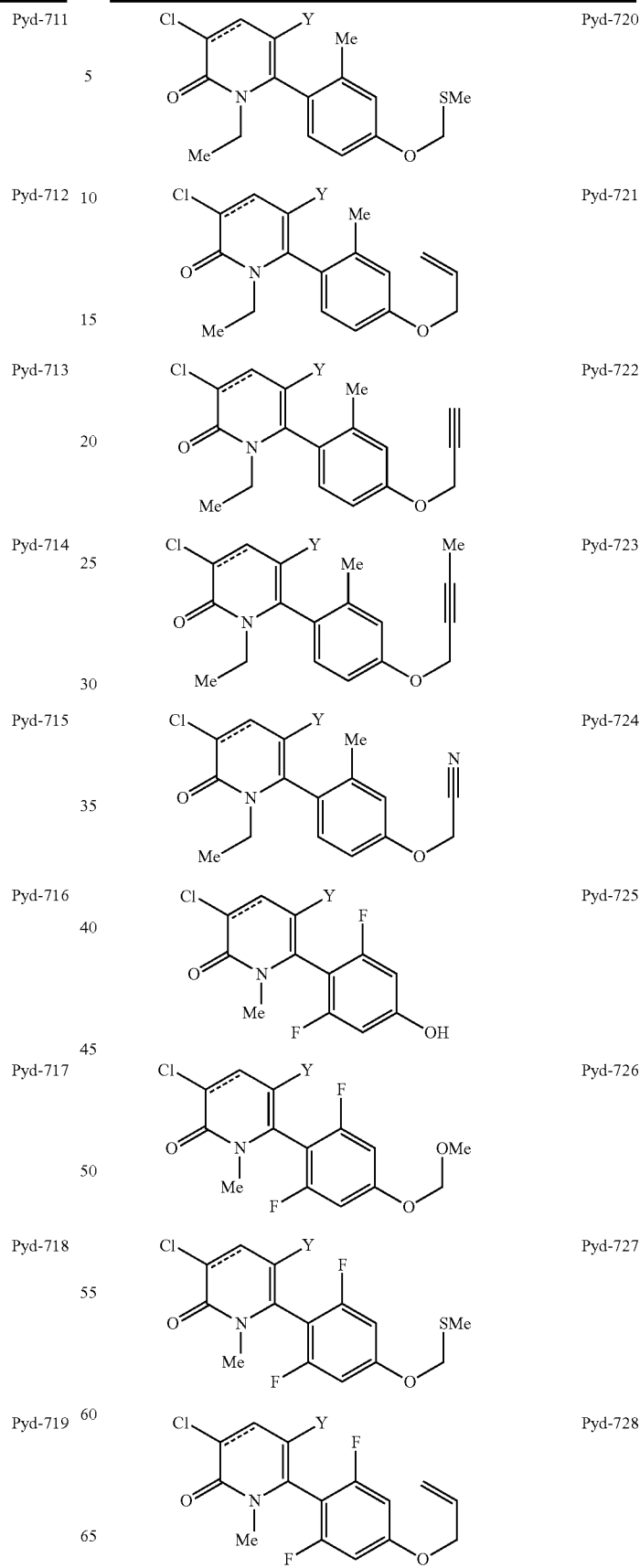

TABLE 1-continued
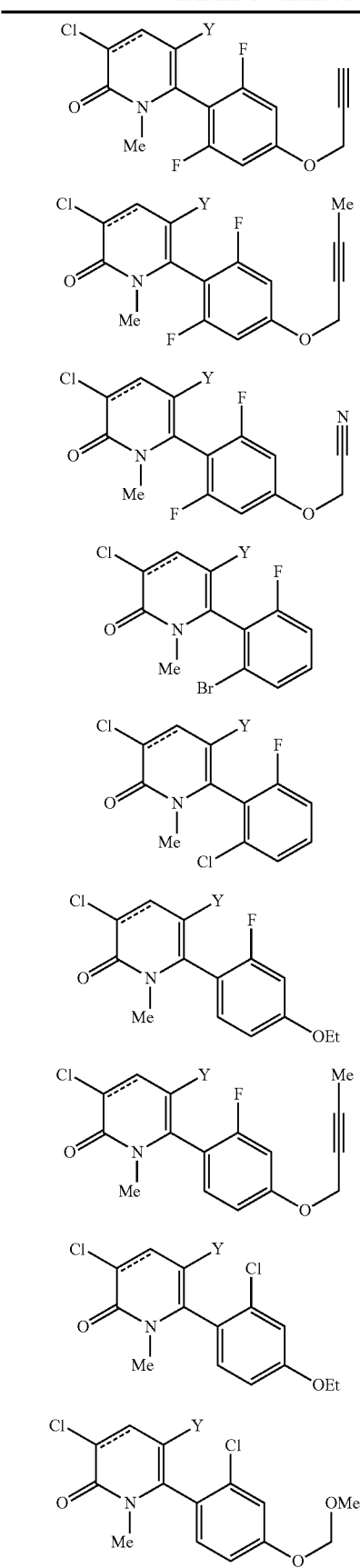
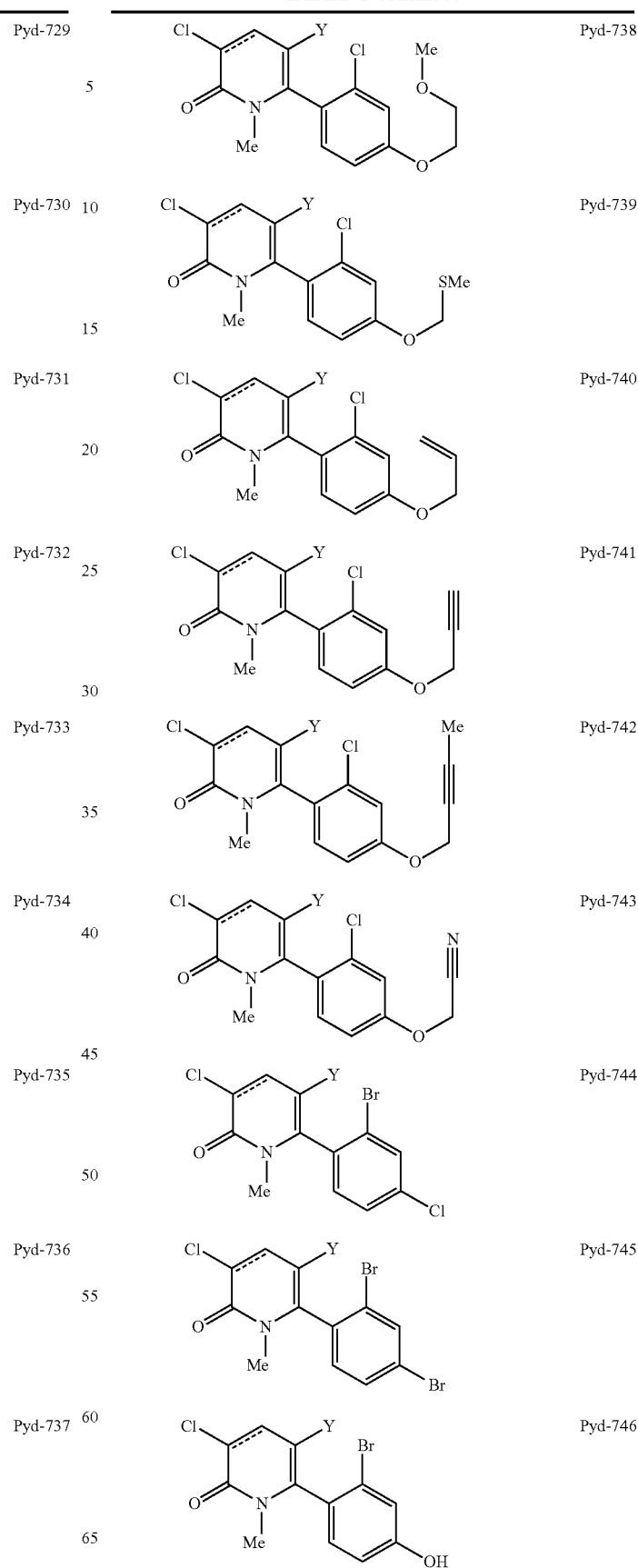

TABLE 1-continued
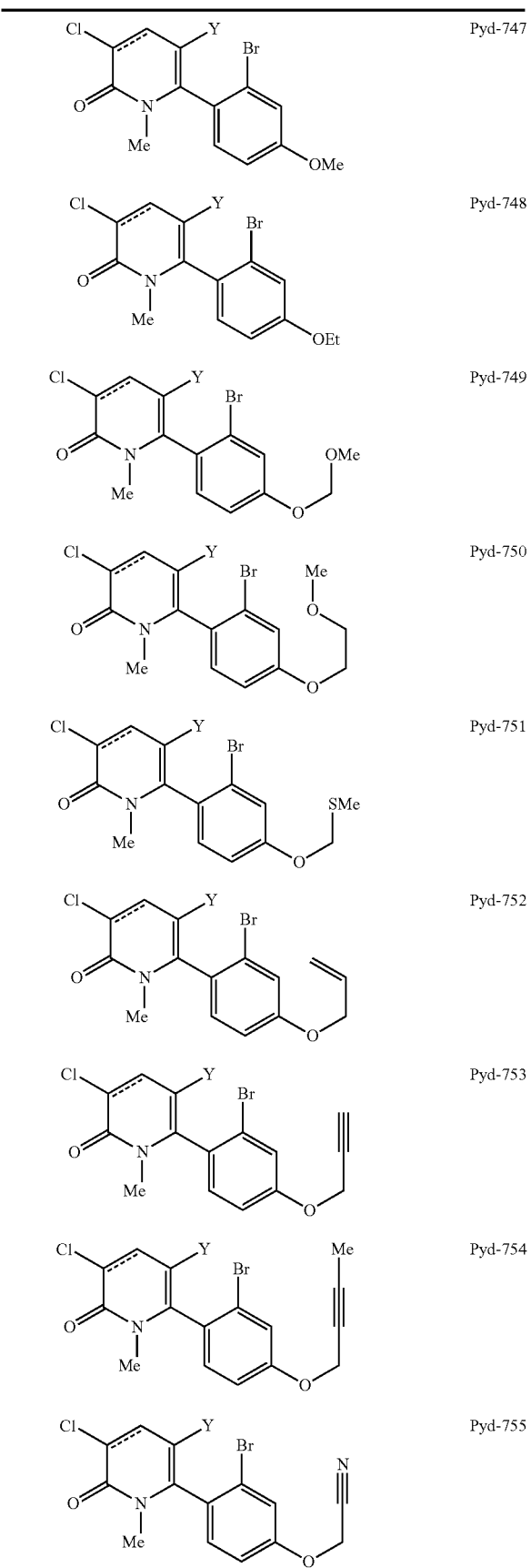
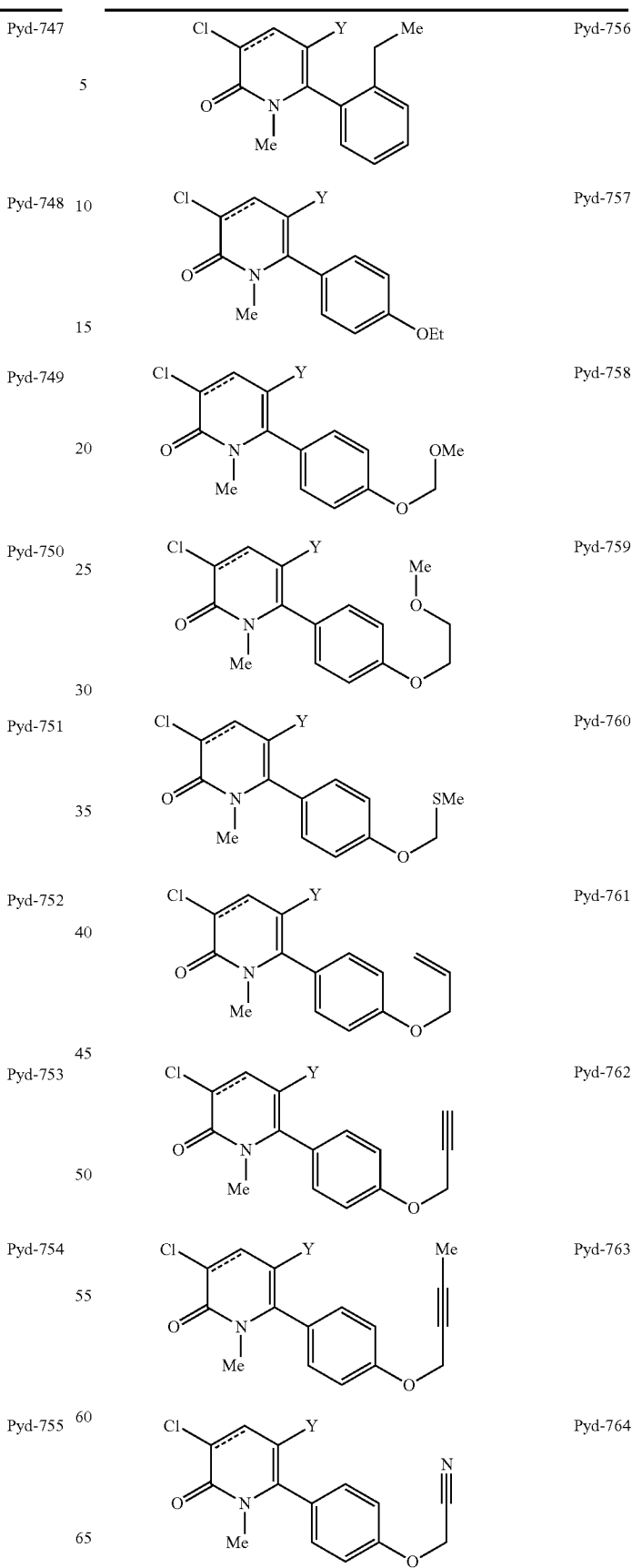

TABLE 1-continued

TABLE 1-continued
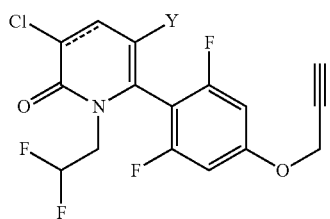 Pyd-781
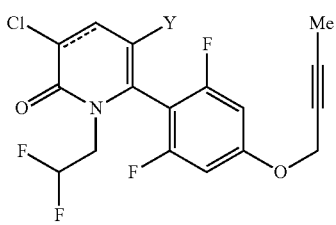 Pyd-782
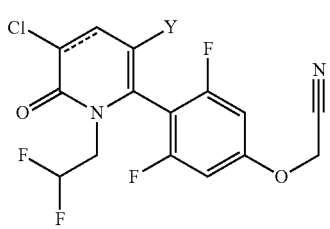 Pyd-783
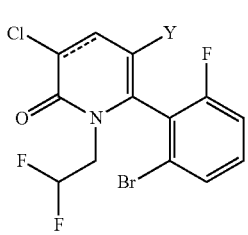 Pyd-784
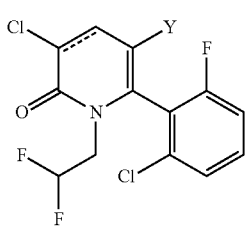 Pyd-785
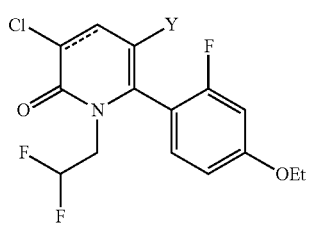 Pyd-786
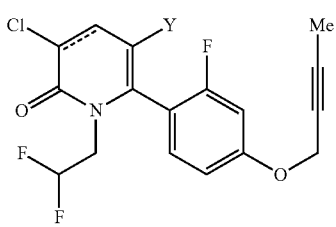 Pyd-787
TABLE 1-continued
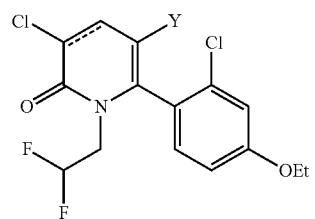 Pyd-788
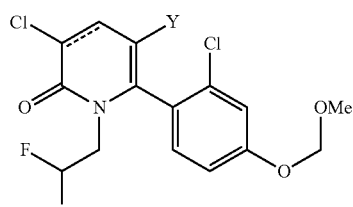 Pyd-789
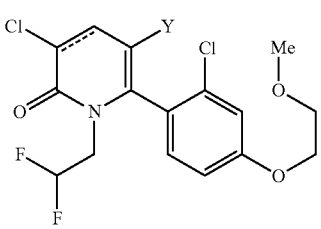 Pyd-790
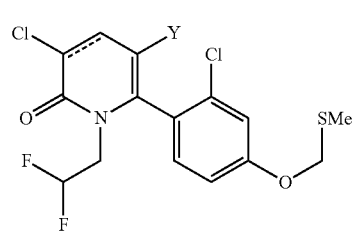 Pyd-791
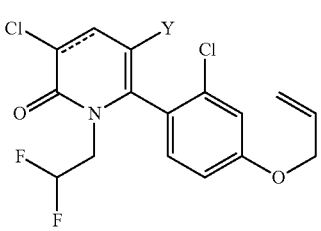 Pyd-792
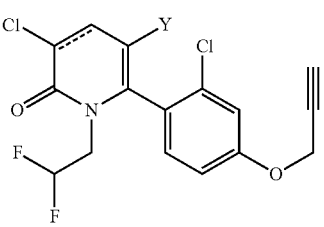 Pyd-793
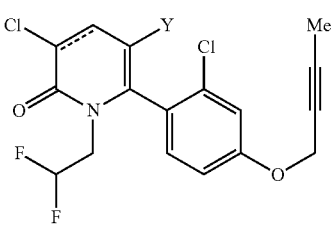 Pyd-794

TABLE 1-continued
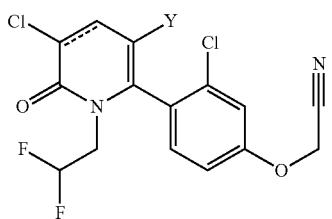 Pyd-795
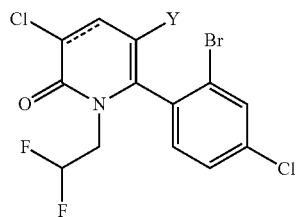 Pyd-796
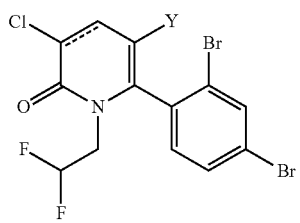 Pyd-797
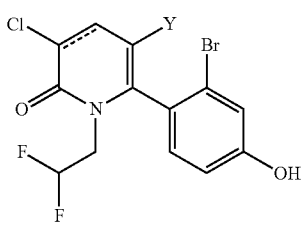 Pyd-798
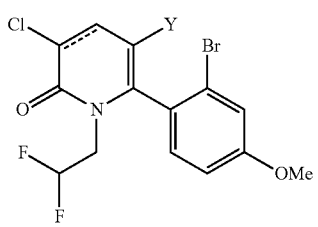 Pyd-799
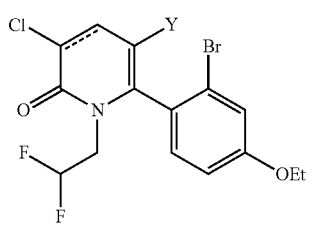 Pyd-800
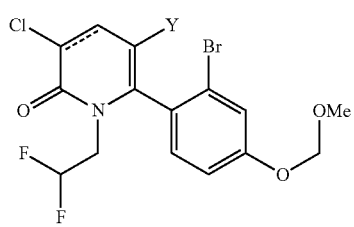 Pyd-801
TABLE 1-continued
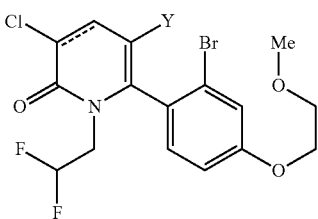 Pyd-802
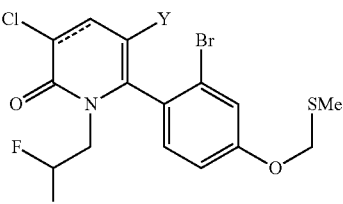 Pyd-803
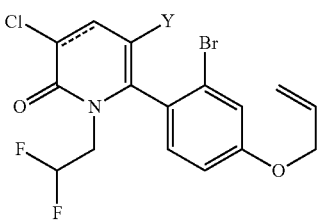 Pyd-804
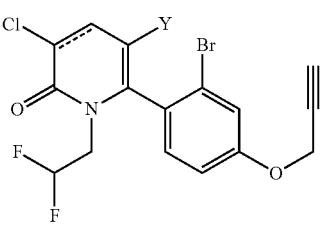 Pyd-805
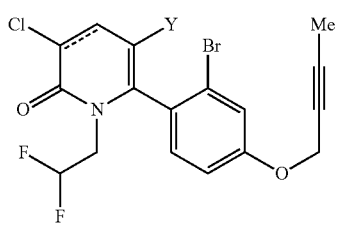 Pyd-806
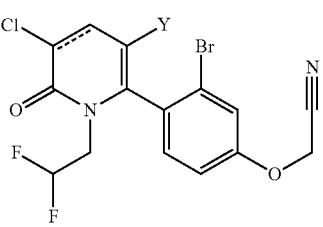 Pyd-807
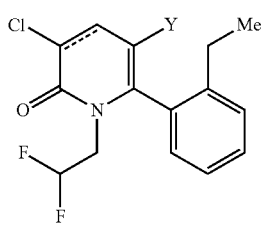 Pyd-808

TABLE 1-continued
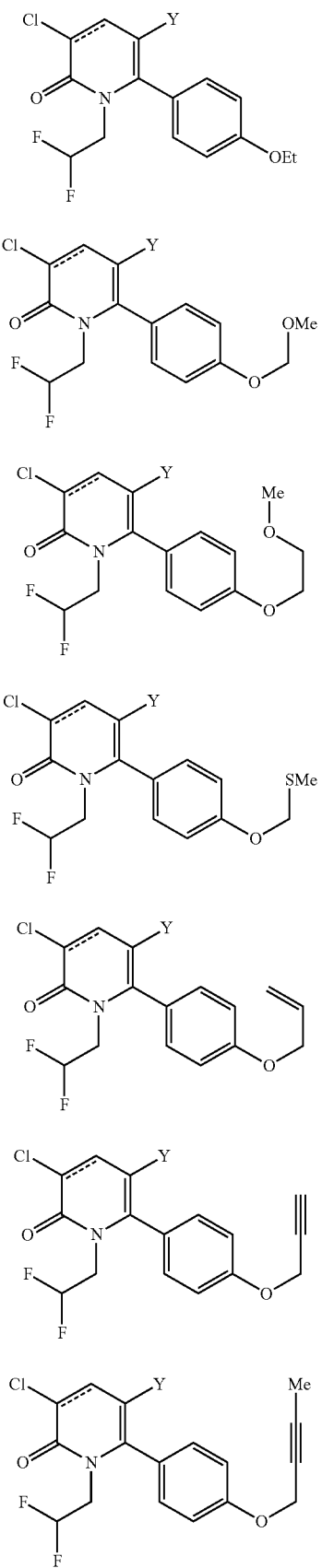
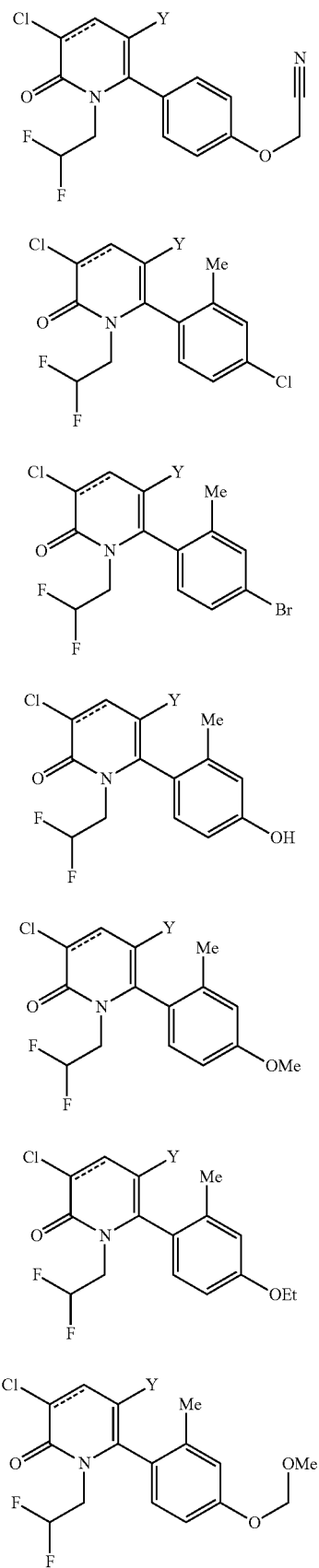

TABLE 1-continued
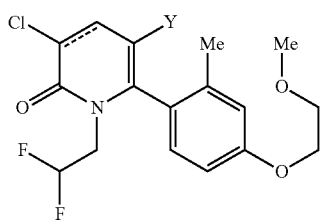 Pyd-823
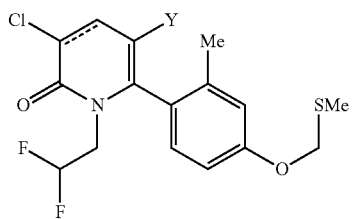 Pyd-824
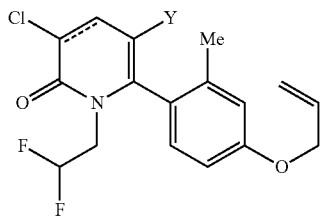 Pyd-825
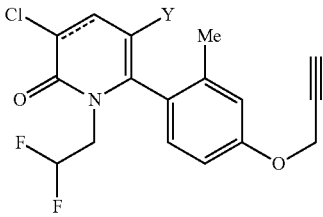 Pyd-826
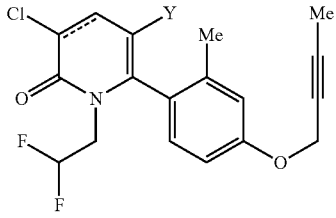 Pyd-827
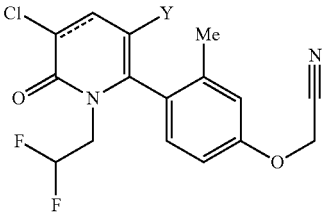 Pyd-828
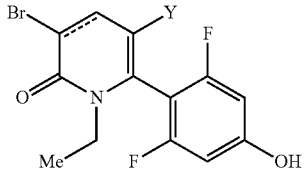 Pyd-829
TABLE 1-continued
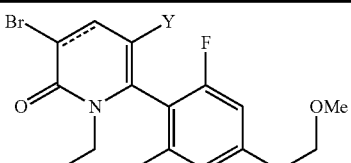 Pyd-830
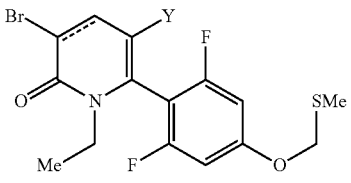 Pyd-831
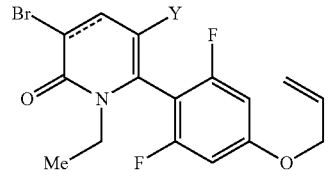 Pyd-832
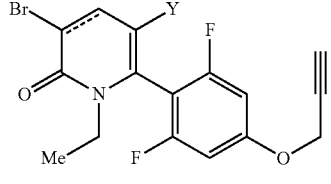 Pyd-833
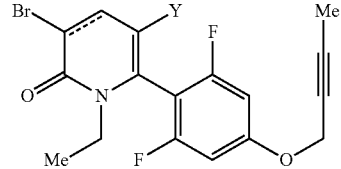 Pyd-834
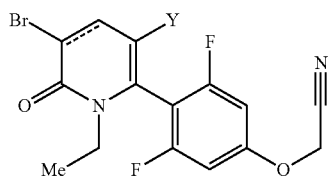 Pyd-835
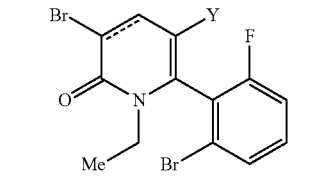 Pyd-836
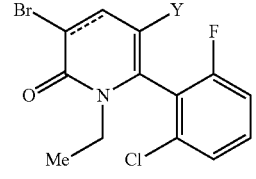 Pyd-837
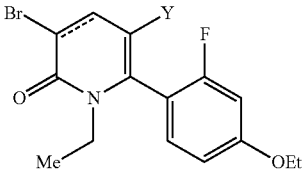 Pyd-838

TABLE 1-continued
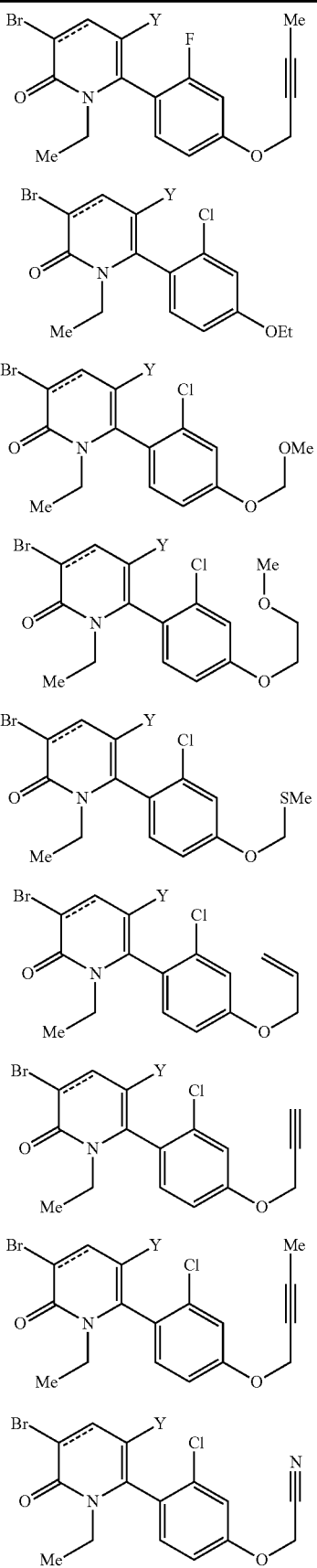
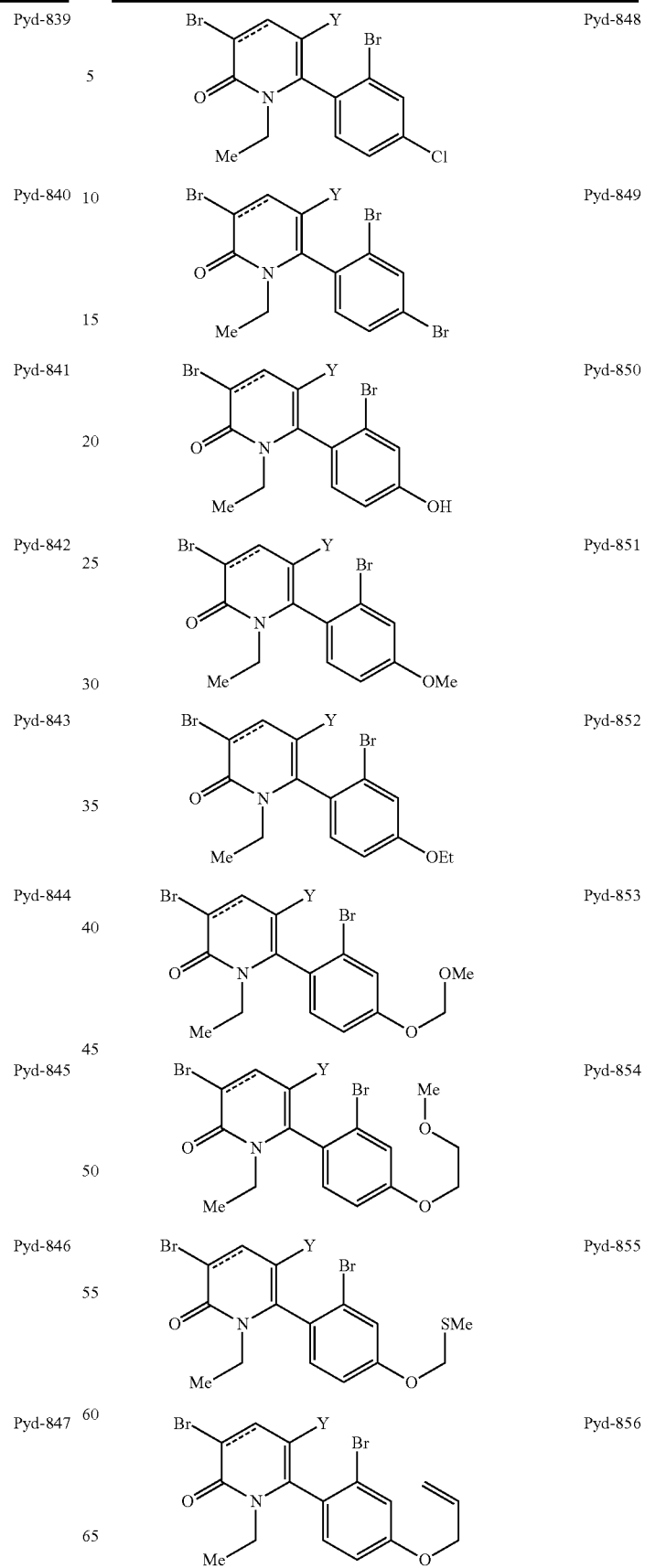

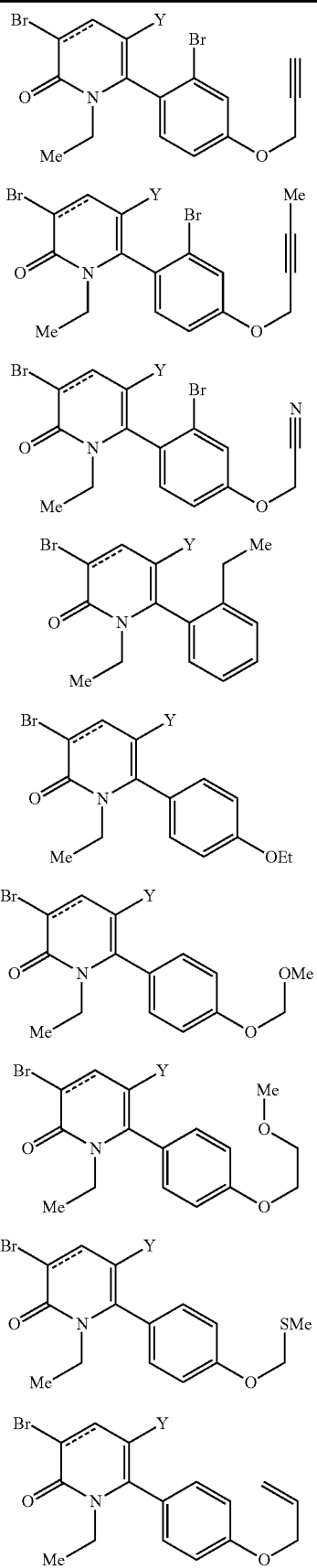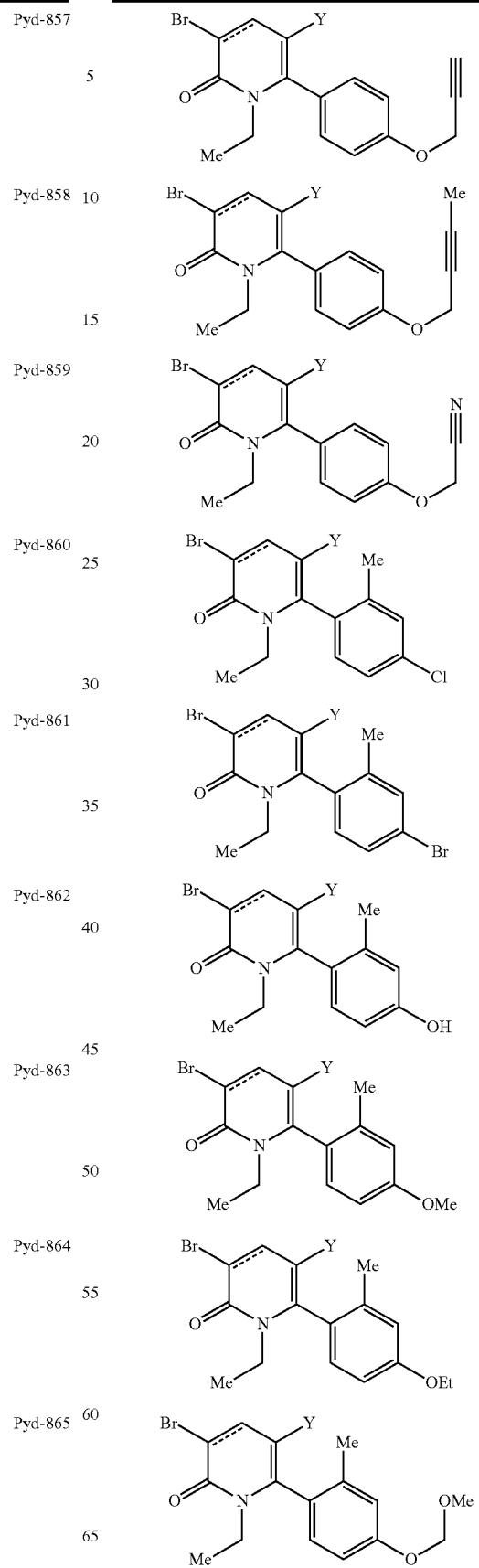

TABLE 1-continued
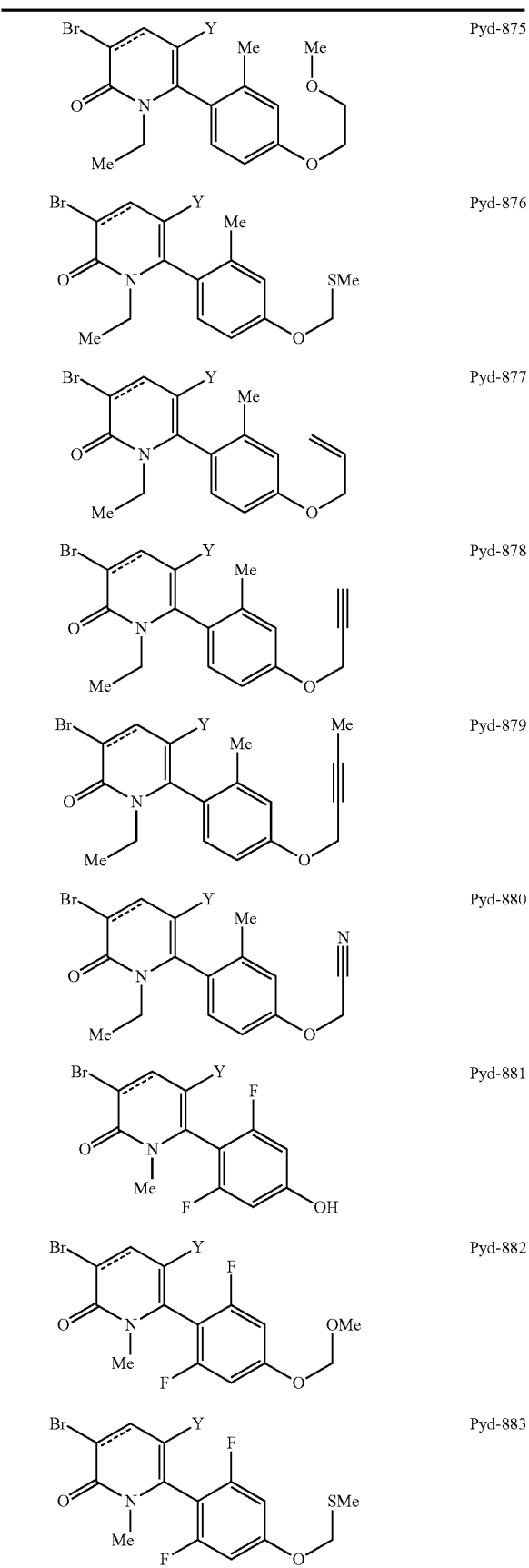
Pyd-875
Pyd-876
Pyd-877
Pyd-878
Pyd-879
Pyd-880
Pyd-881
Pyd-882
Pyd-883
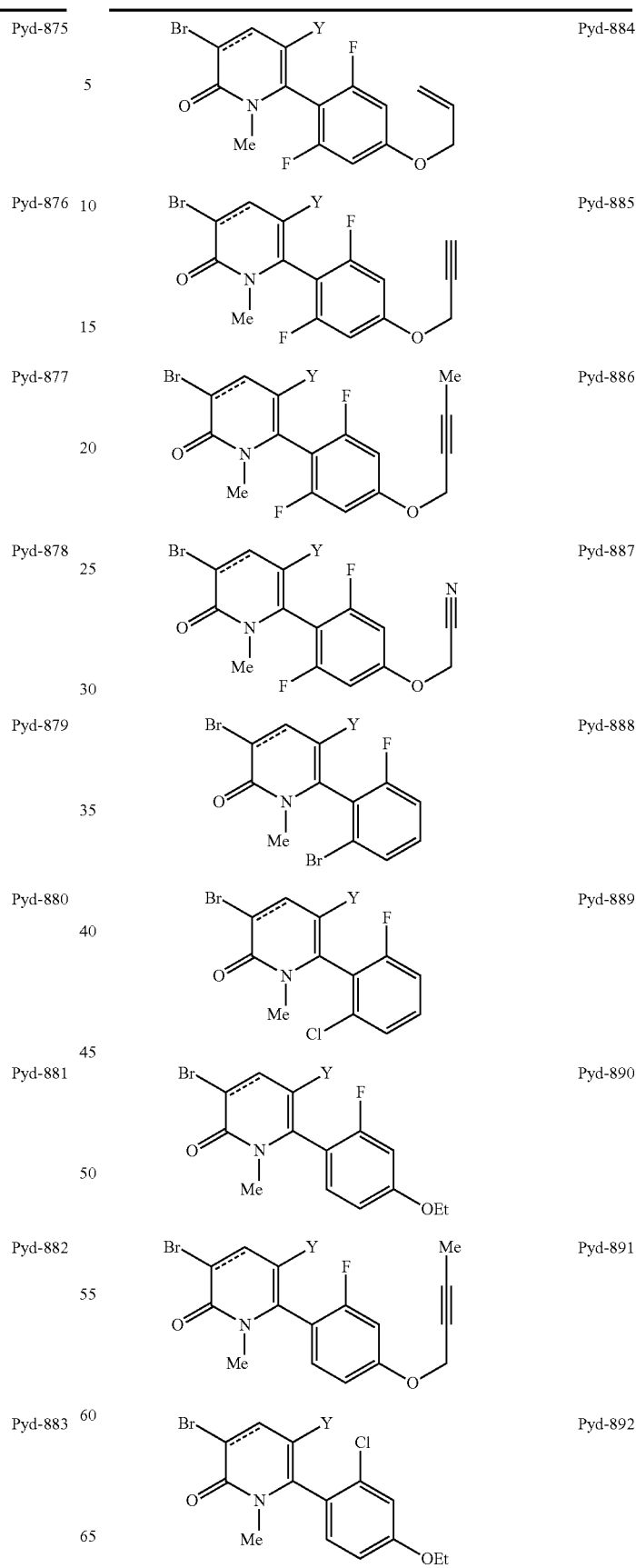
Pyd-884
Pyd-885
Pyd-886
Pyd-887
Pyd-888
Pyd-889
Pyd-890
Pyd-891
Pyd-892

TABLE 1-continued
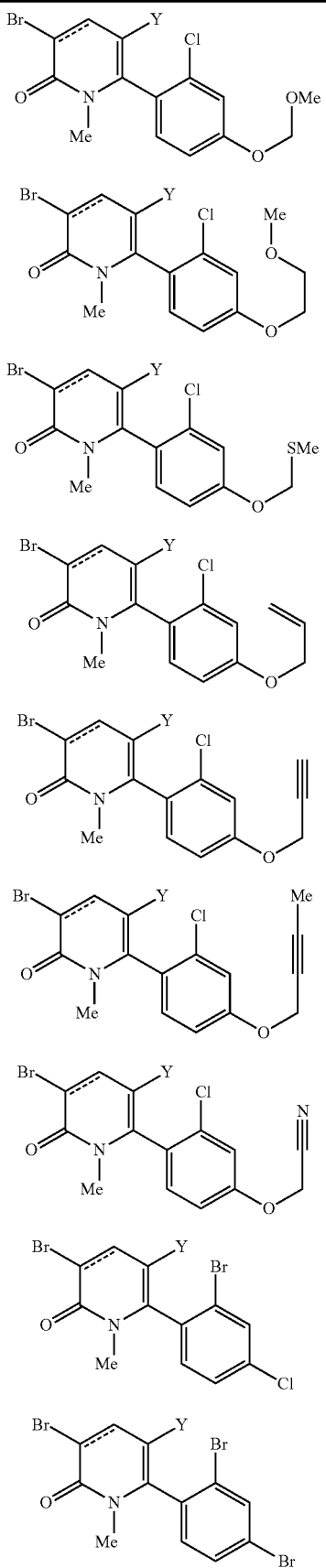
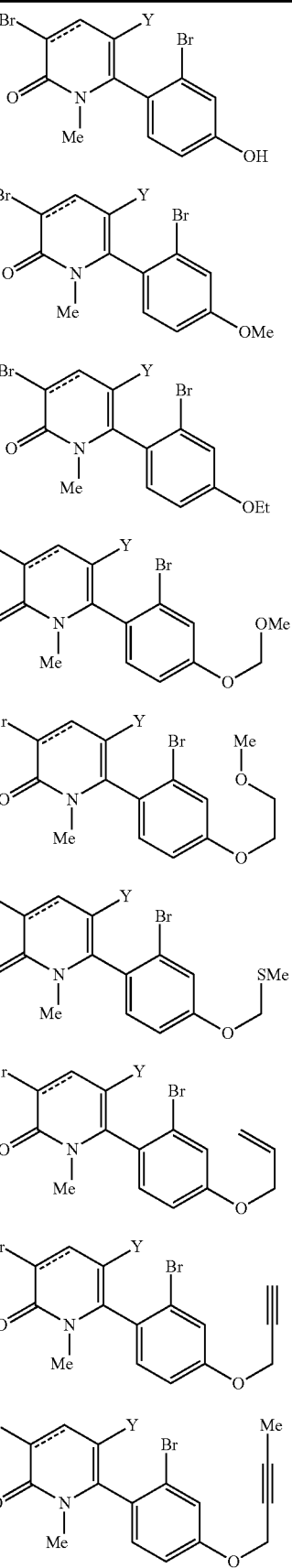

TABLE 1-continued
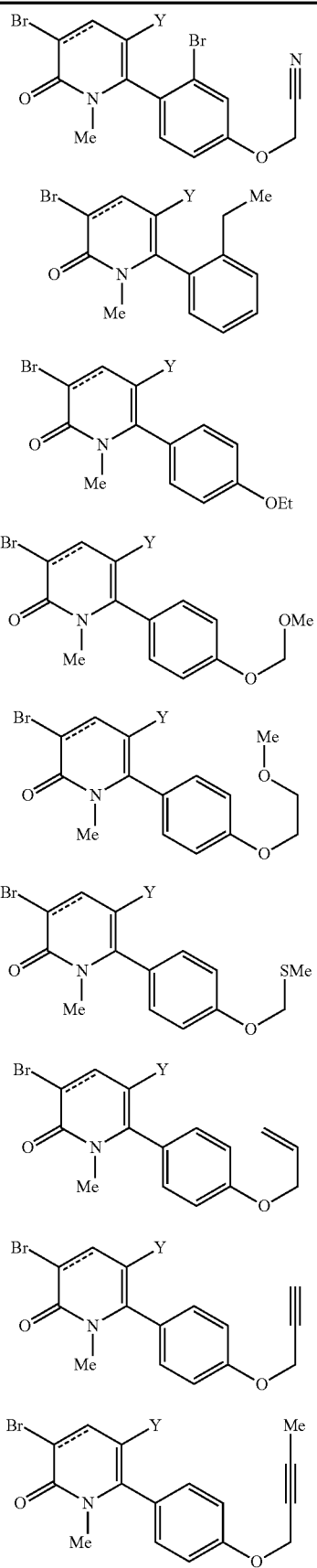
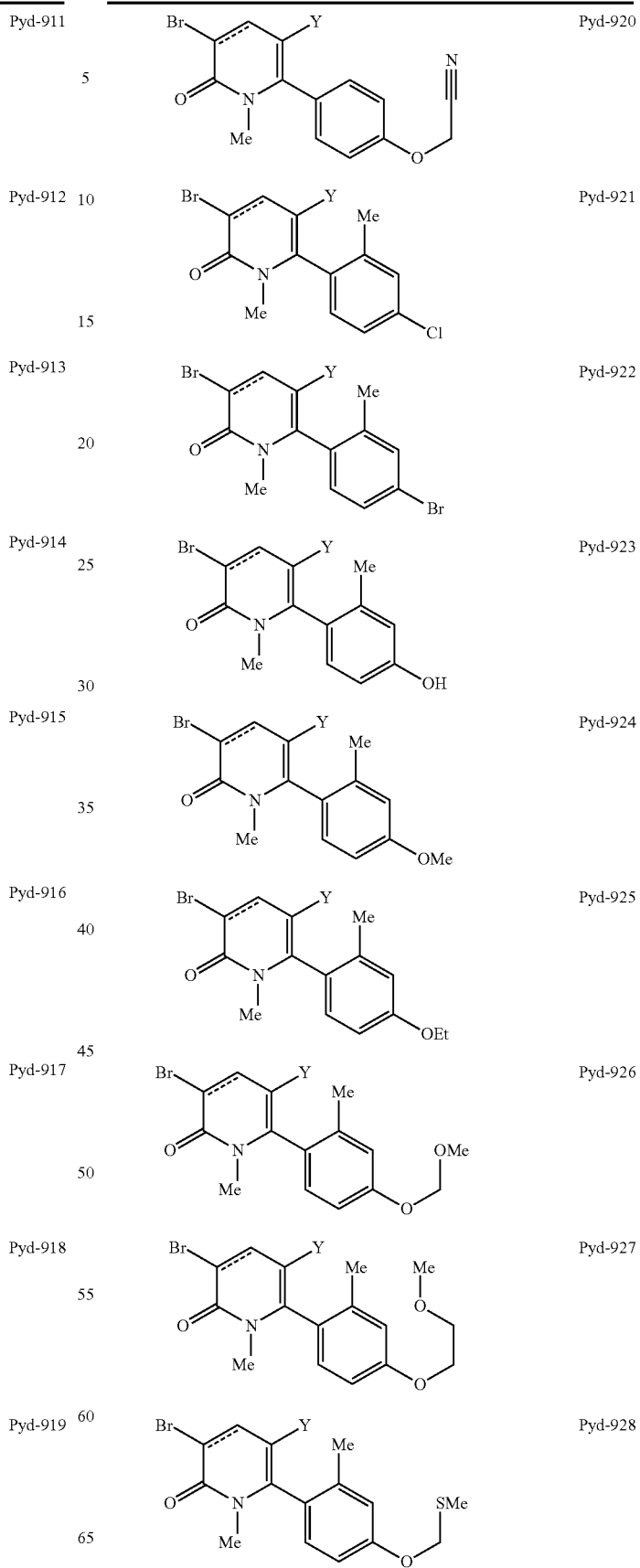

TABLE 1-continued
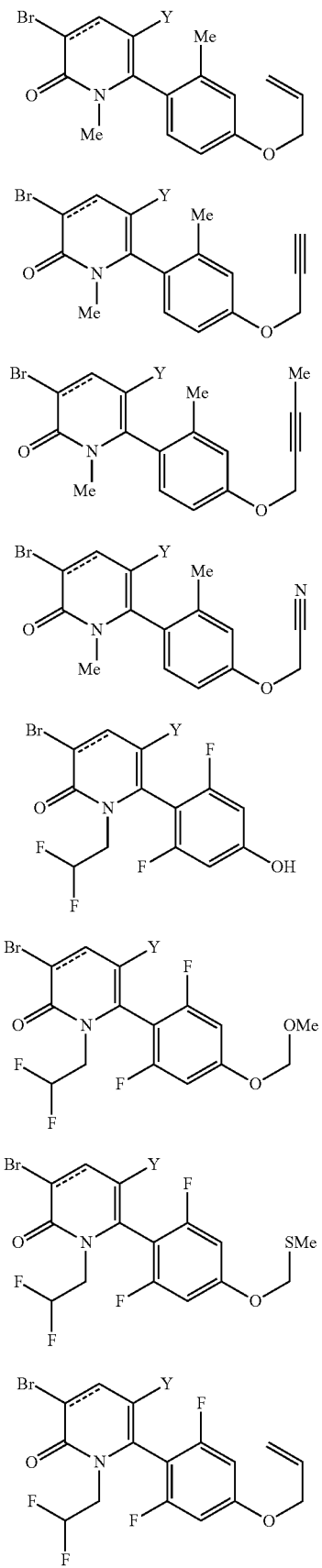
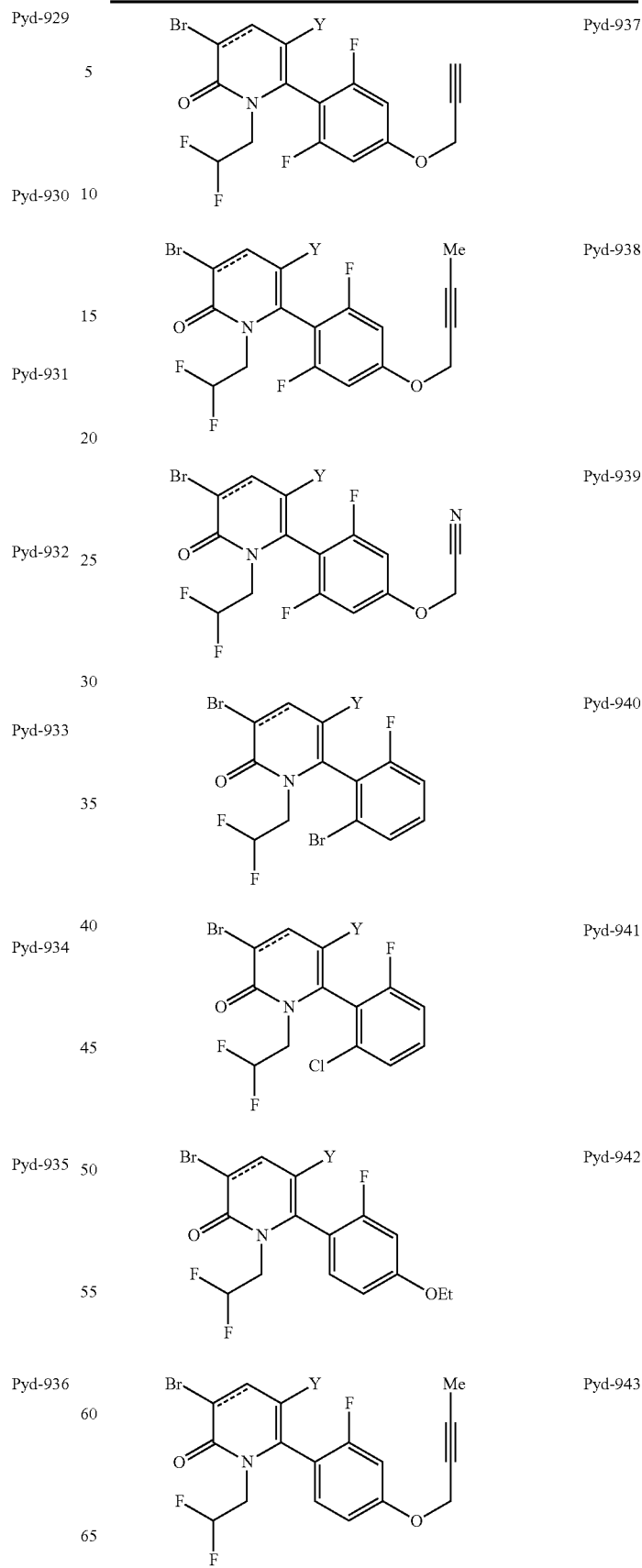

TABLE 1-continued
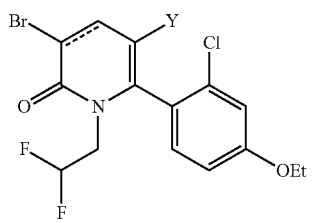 Pyd-944
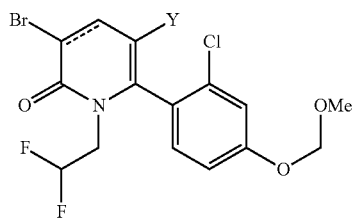 Pyd-945
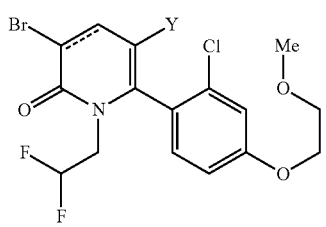 Pyd-946
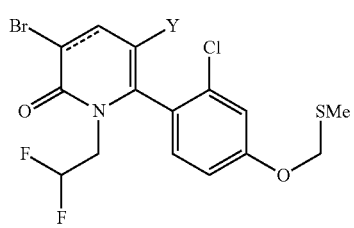 Pyd-947
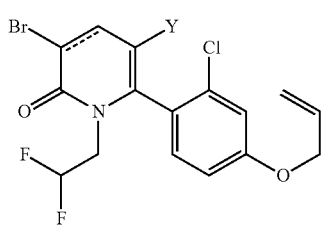 Pyd-948
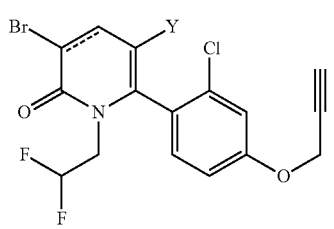 Pyd-949
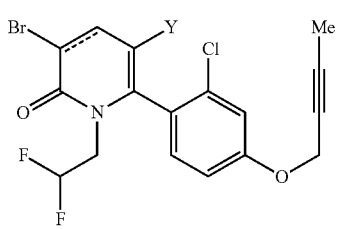 Pyd-950
TABLE 1-continued
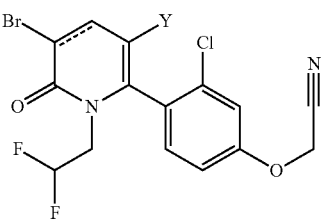 Pyd-951
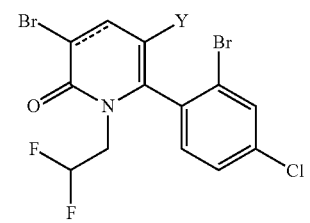 Pyd-952
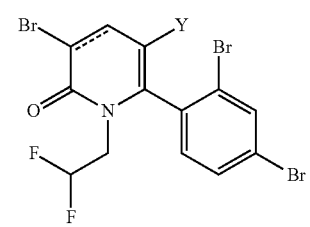 Pyd-953
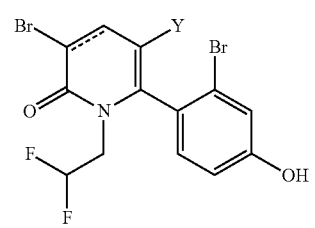 Pyd-954
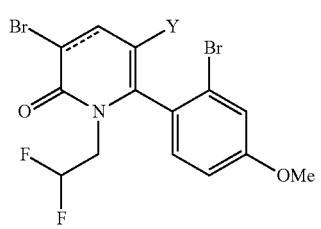 Pyd-955
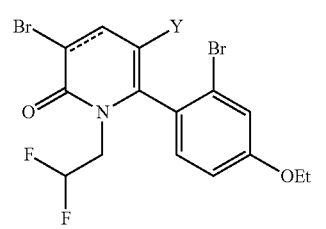 Pyd-956
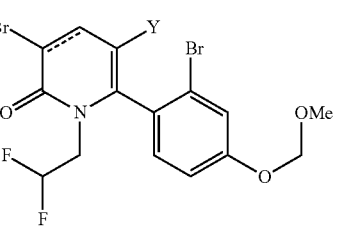 Pyd-957

TABLE 1-continued
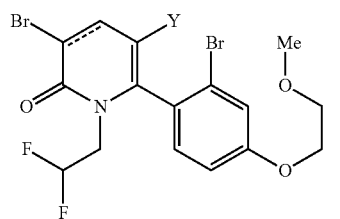 Pyd-958
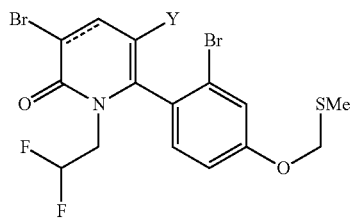 Pyd-959
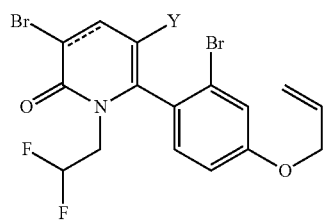 Pyd-960
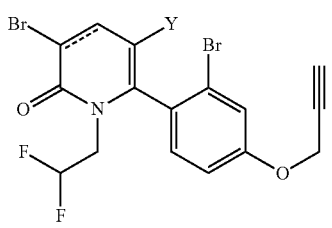 Pyd-961
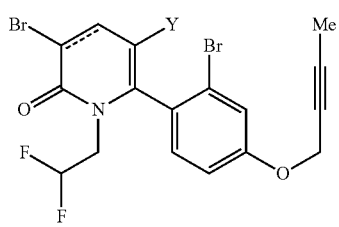 Pyd-962
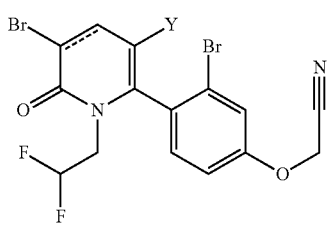 Pyd-963
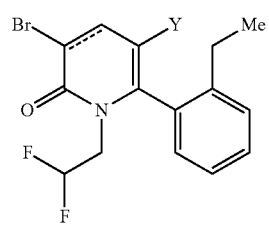 Pyd-964
TABLE 1-continued
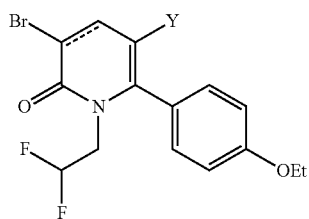 Pyd-965
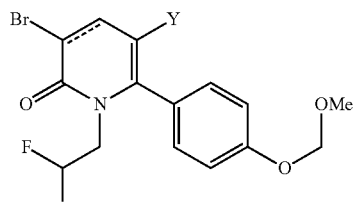 Pyd-966
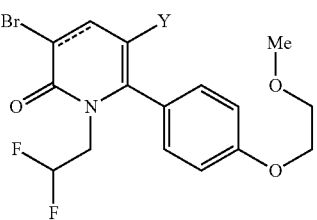 Pyd-967
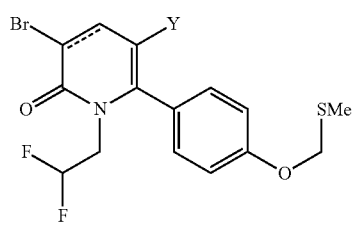 Pyd-968
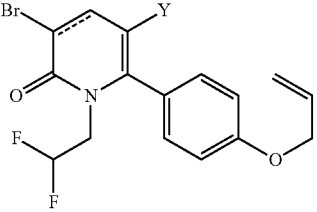 Pyd-969
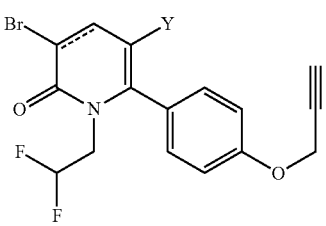 Pyd-970
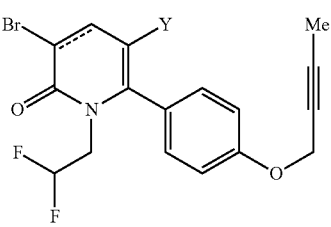 Pyd-971

TABLE 1-continued
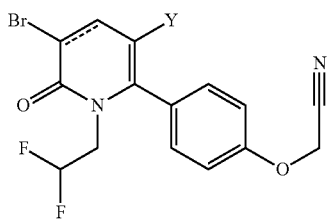 Pyd-972
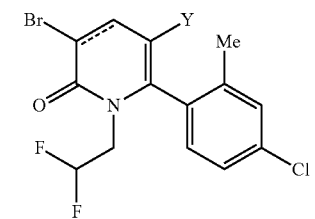 Pyd-973
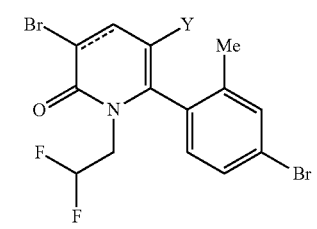 Pyd-974
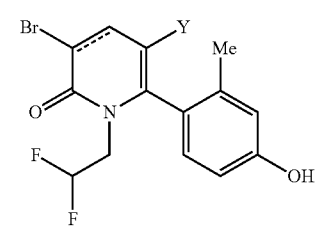 Pyd-975
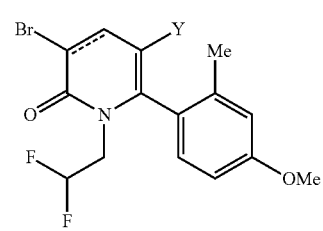 Pyd-976
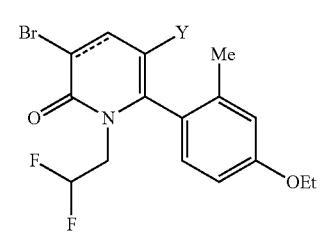 Pyd-977
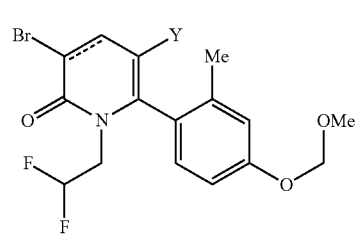 Pyd-978
TABLE 1-continued
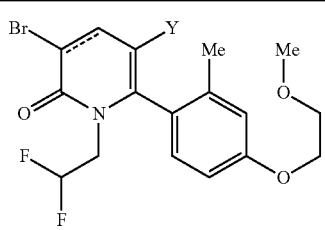 Pyd-979
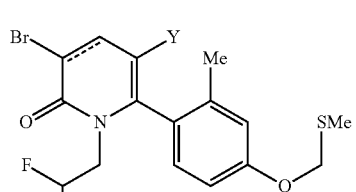 Pyd-980
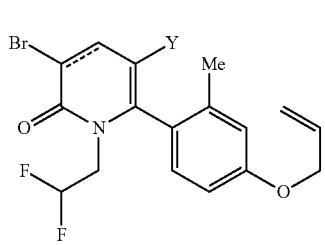 Pyd-981
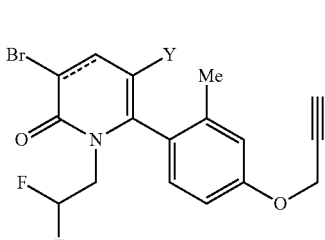 Pyd-982
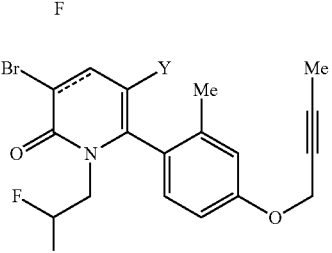 Pyd-983
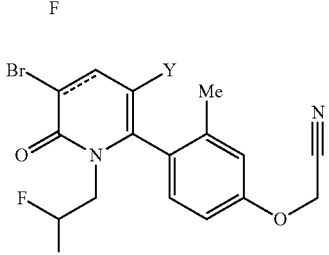 Pyd-984
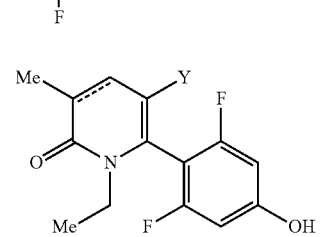 Pyd-985

TABLE 1-continued
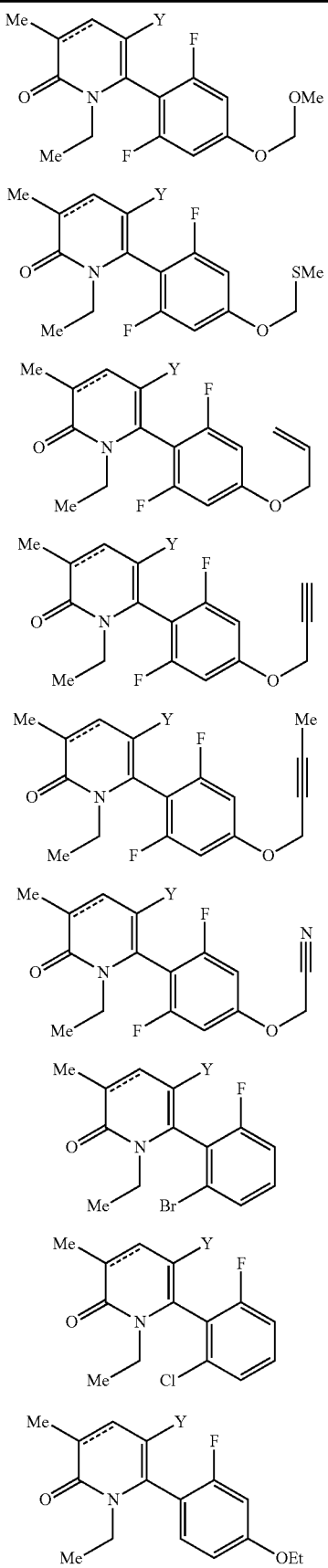
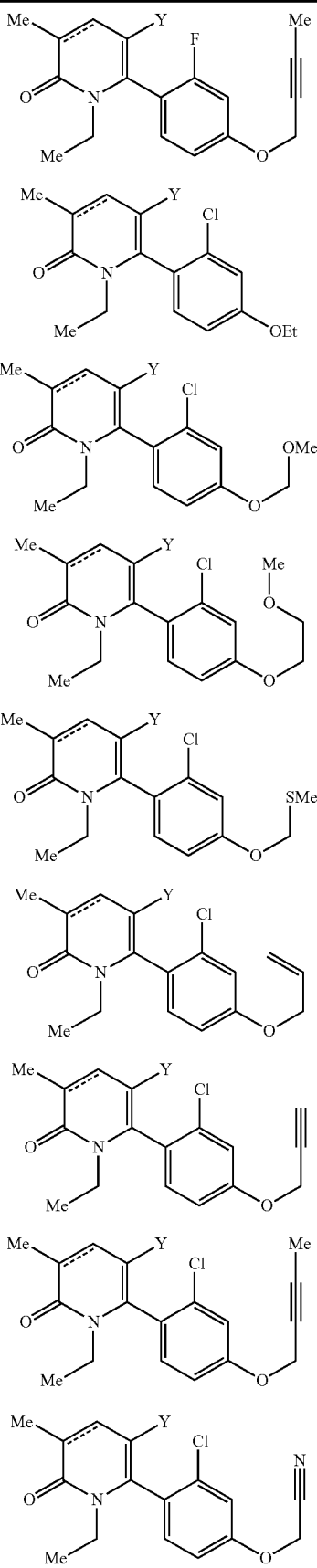

TABLE 1-continued

| Structure | ID |
|---|---|
| (Pyd-1004) 3-Me, 1-Et pyridinone with 2-Br-4-Cl-phenyl | Pyd-1004 |
| (Pyd-1005) 3-Me, 1-Et pyridinone with 2,4-diBr-phenyl | Pyd-1005 |
| (Pyd-1006) 3-Me, 1-Et pyridinone with 2-Br-4-OH-phenyl | Pyd-1006 |
| (Pyd-1007) 3-Me, 1-Et pyridinone with 2-Br-4-OMe-phenyl | Pyd-1007 |
| (Pyd-1008) 3-Me, 1-Et pyridinone with 2-Br-4-OEt-phenyl | Pyd-1008 |
| (Pyd-1009) 3-Me, 1-Et pyridinone with 2-Br-4-OCH2OMe-phenyl | Pyd-1009 |
| (Pyd-1010) 3-Me, 1-Et pyridinone with 2-Br-4-OCH2CH2OMe-phenyl | Pyd-1010 |
| (Pyd-1011) 3-Me, 1-Et pyridinone with 2-Br-4-OCH2SMe-phenyl | Pyd-1011 |
| (Pyd-1012) 3-Me, 1-Et pyridinone with 2-Br-4-OCH2CH=CH2-phenyl | Pyd-1012 |
| (Pyd-1013) 3-Me, 1-Et pyridinone with 2-Br-4-OCH2C≡CH-phenyl | Pyd-1013 |
| (Pyd-1014) 3-Me, 1-Et pyridinone with 2-Br-4-OCH2C≡CMe-phenyl | Pyd-1014 |
| (Pyd-1015) 3-Me, 1-Et pyridinone with 2-Br-4-OCH2CN-phenyl | Pyd-1015 |
| (Pyd-1016) 3-Me, 1-Et pyridinone with 2-Et-phenyl | Pyd-1016 |
| (Pyd-1017) 3-Me, 1-Et pyridinone with 4-OEt-phenyl | Pyd-1017 |
| (Pyd-1018) 3-Me, 1-Et pyridinone with 4-OCH2OMe-phenyl | Pyd-1018 |
| (Pyd-1019) 3-Me, 1-Et pyridinone with 4-OCH2CH2OMe-phenyl | Pyd-1019 |
| (Pyd-1020) 3-Me, 1-Et pyridinone with 4-OCH2SMe-phenyl | Pyd-1020 |
| (Pyd-1021) 3-Me, 1-Et pyridinone with 4-OCH2CH=CH2-phenyl | Pyd-1021 |

TABLE 1-continued
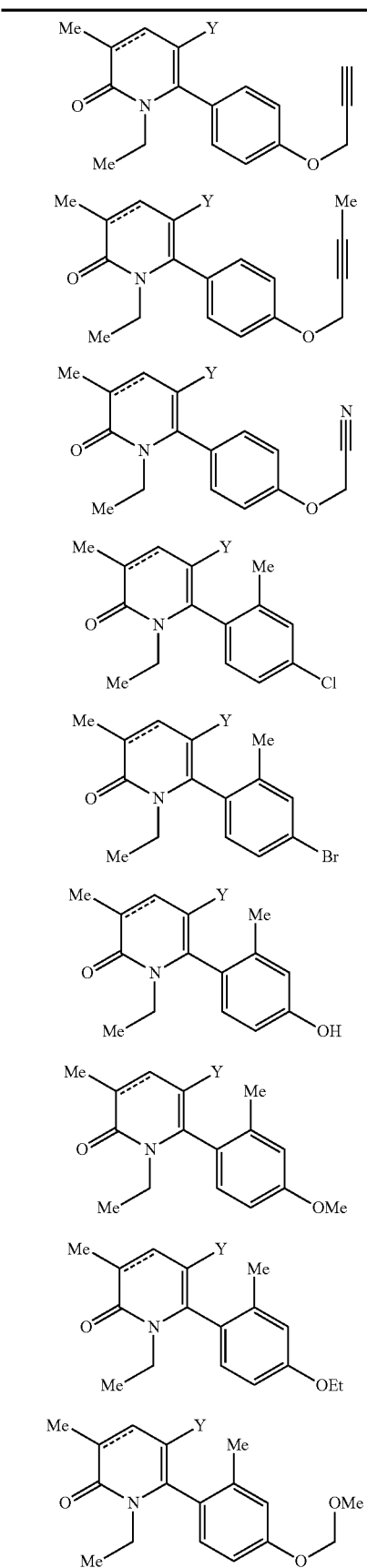
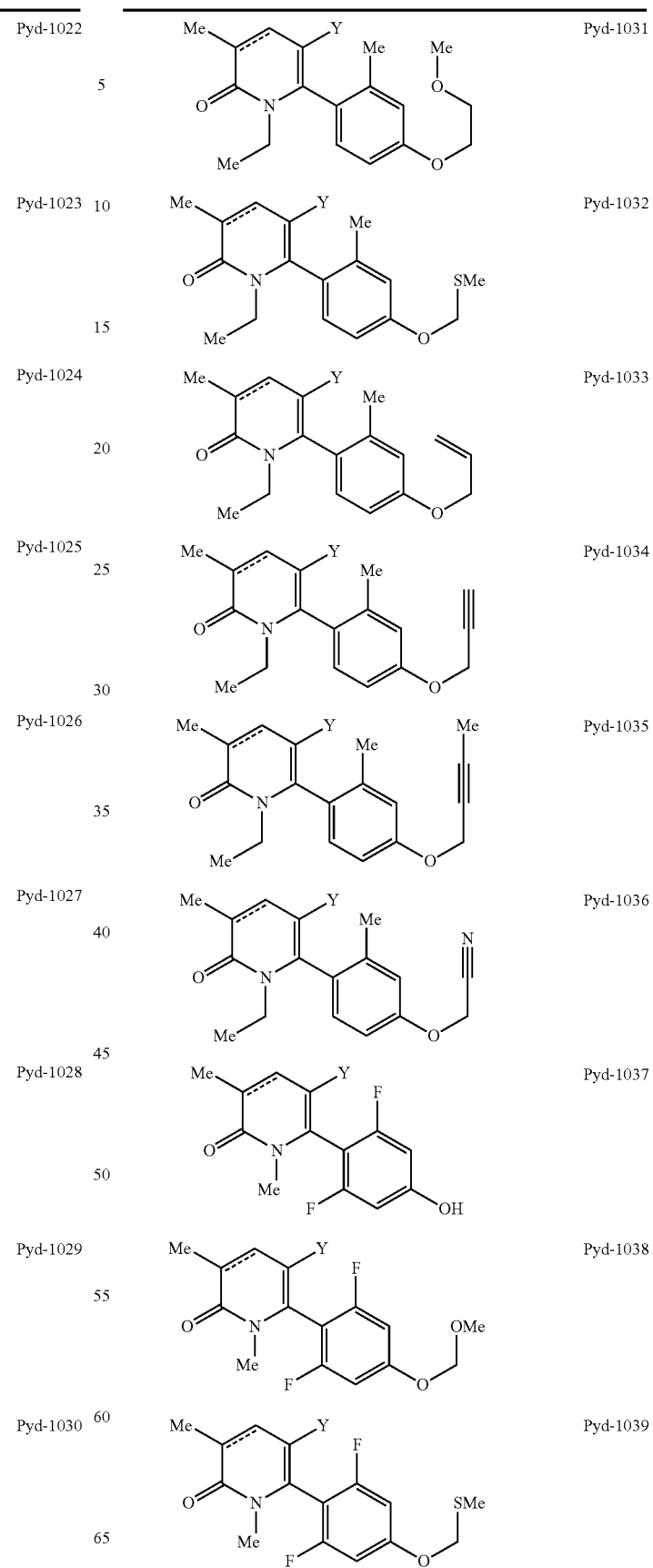

TABLE 1-continued
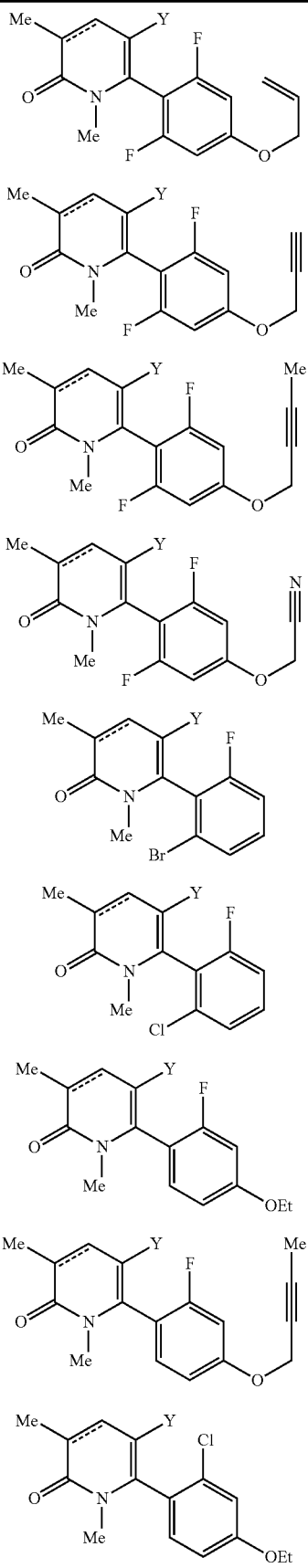
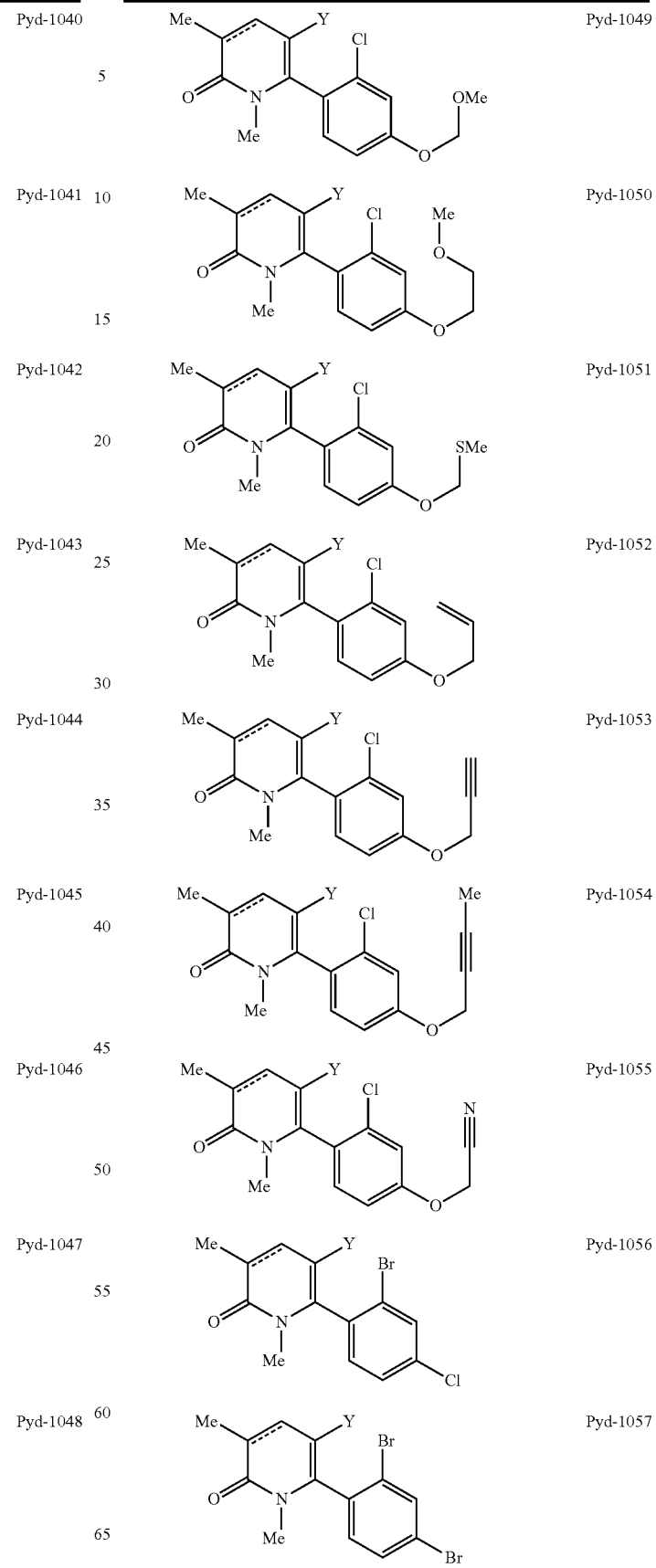

TABLE 1-continued
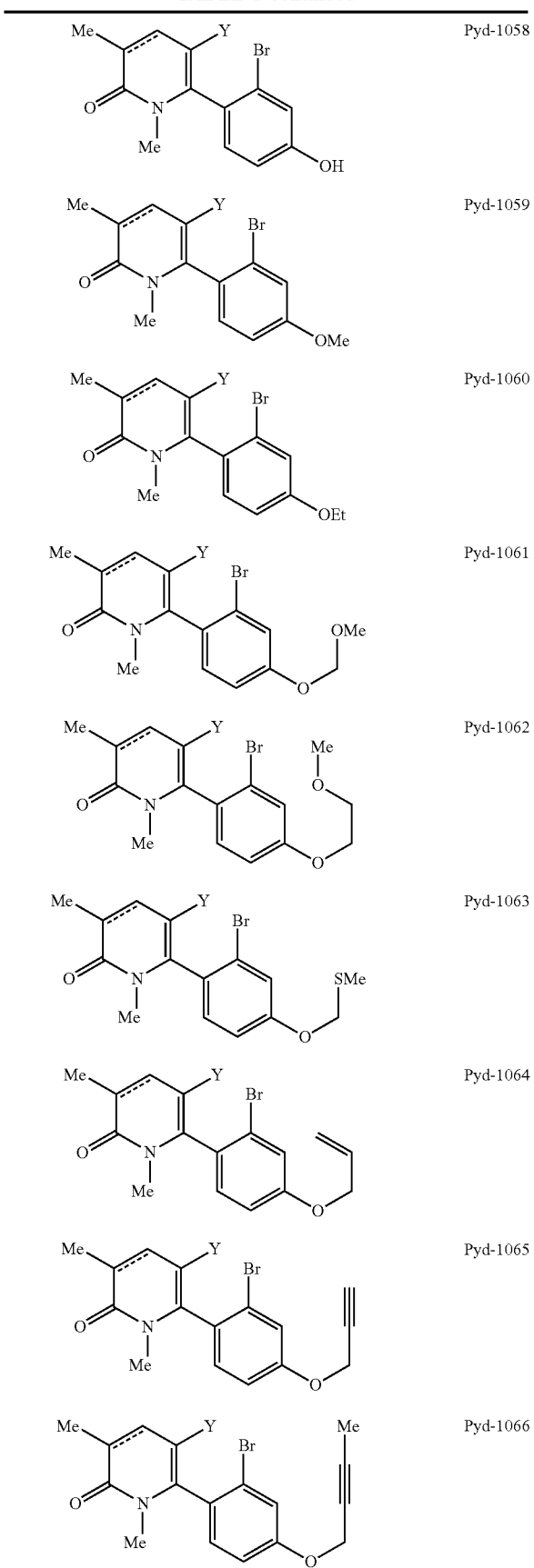
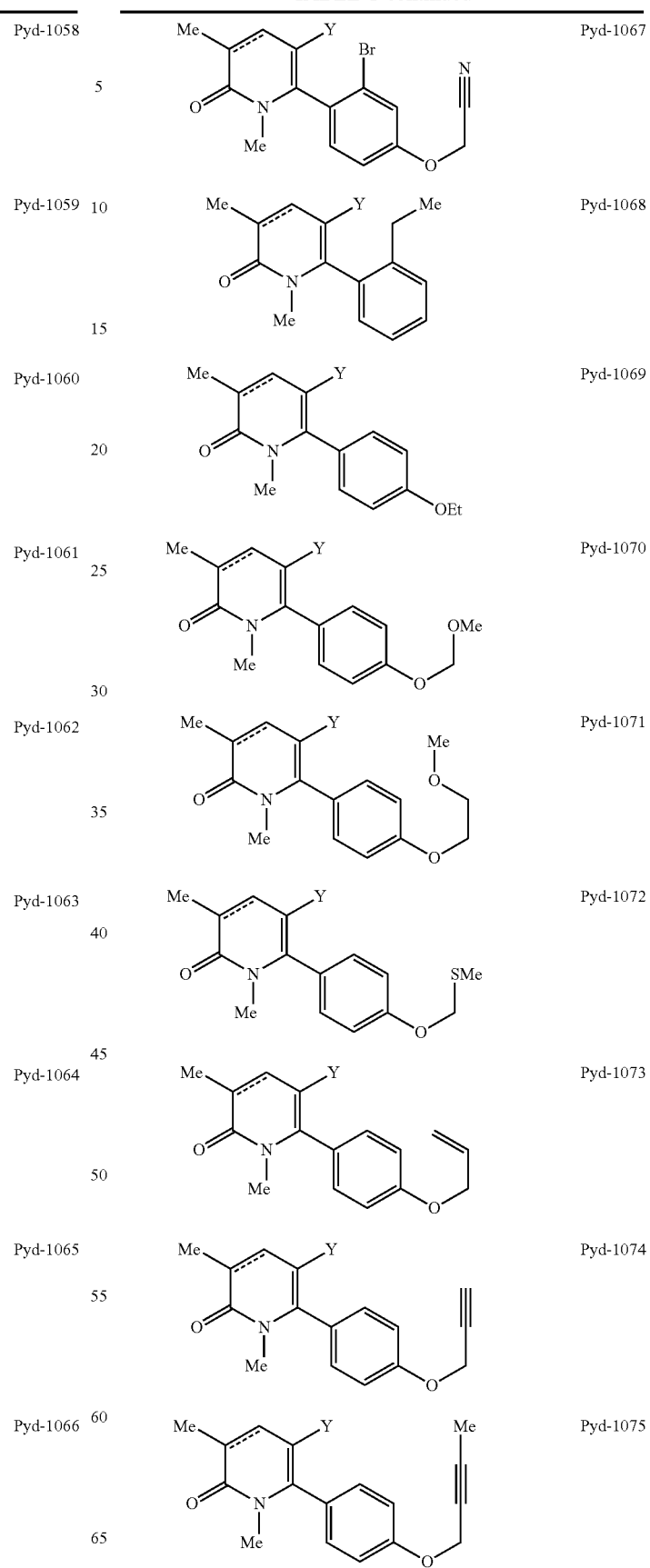

TABLE 1-continued
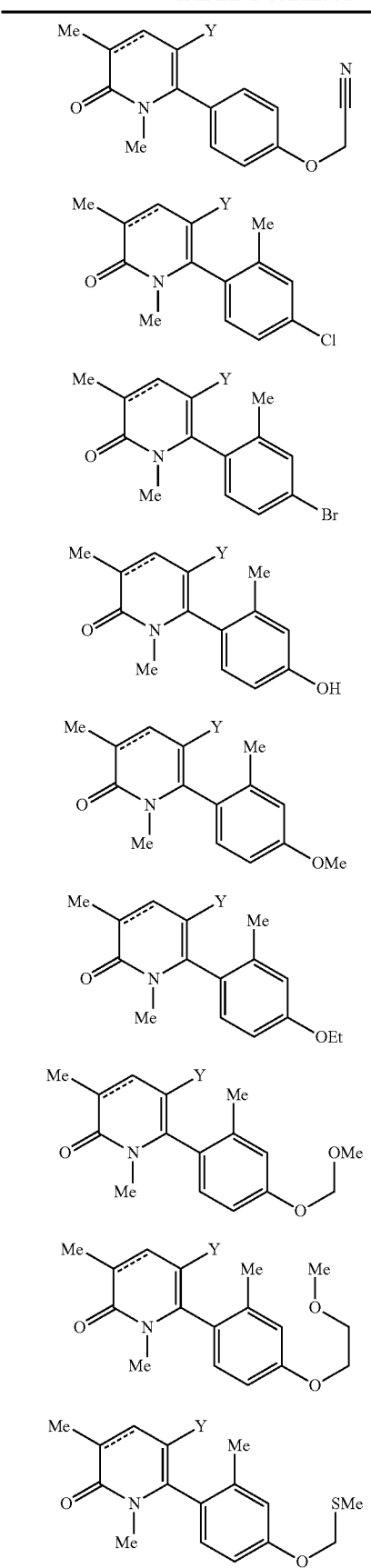
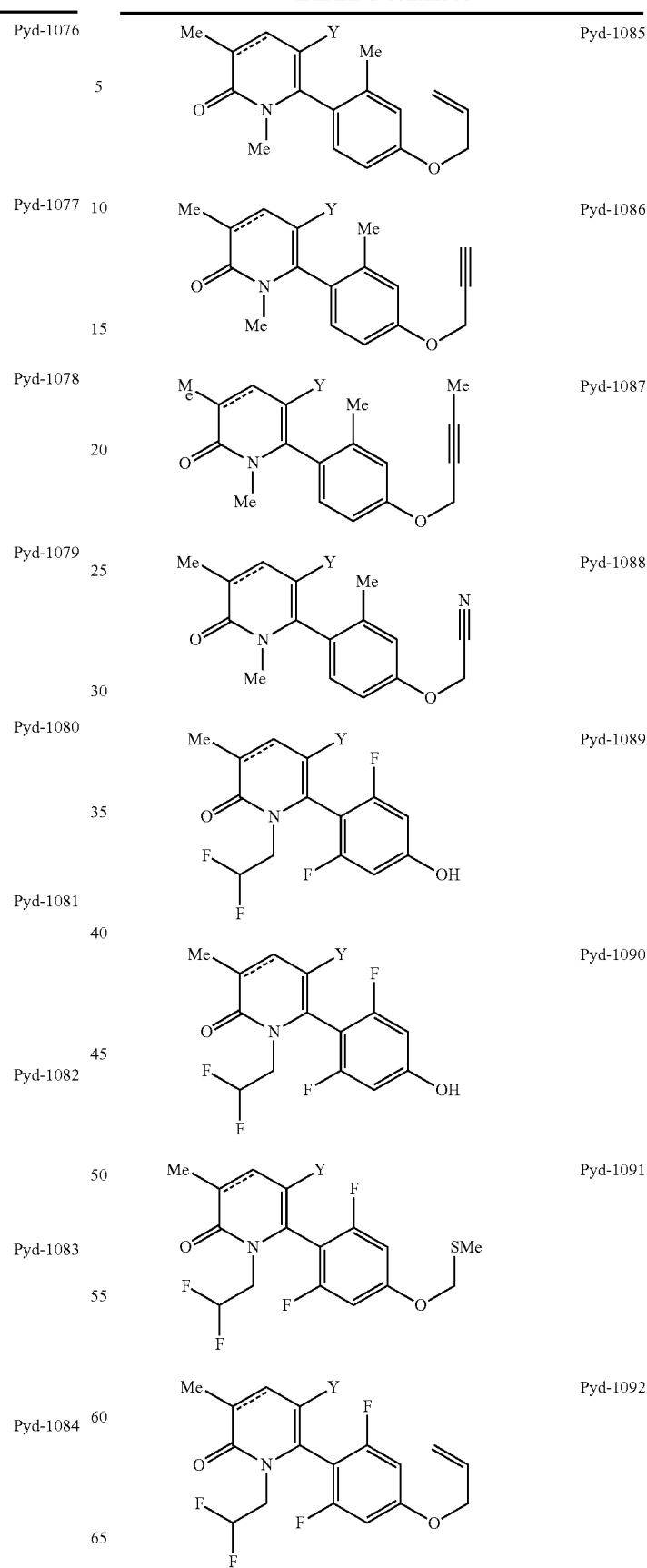

TABLE 1-continued
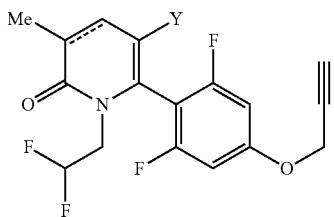 Pyd-1093
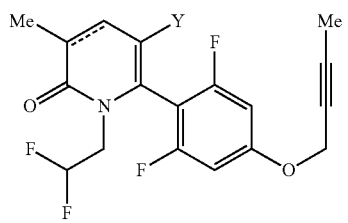 Pyd-1094
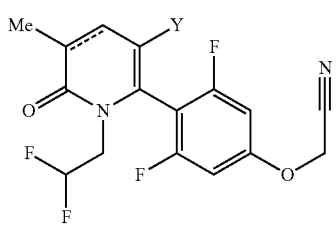 Pyd-1095
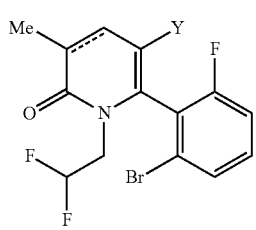 Pyd-1096
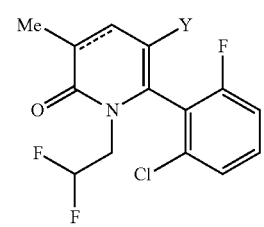 Pyd-1097
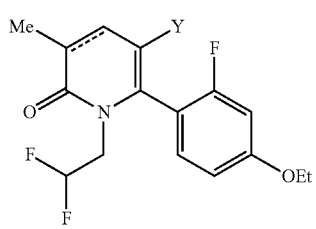 Pyd-1098
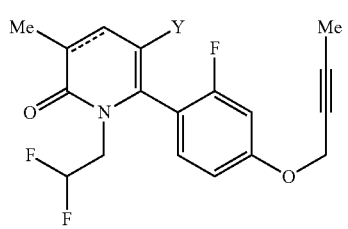 Pyd-1099
TABLE 1-continued
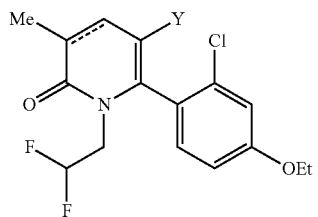 Pyd-1100
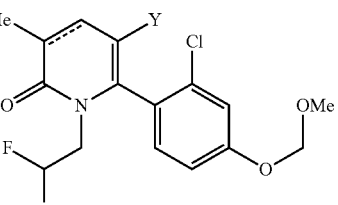 Pyd-1101
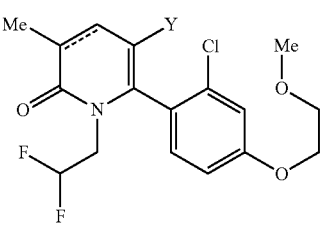 Pyd-1102
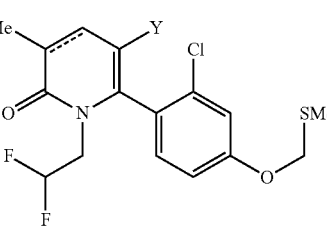 Pyd-1103
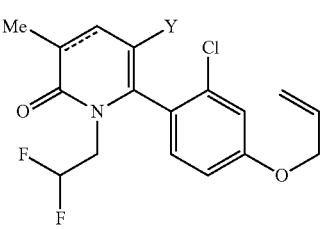 Pyd-1104
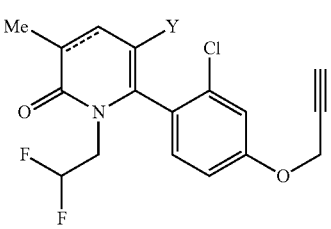 Pyd-1105
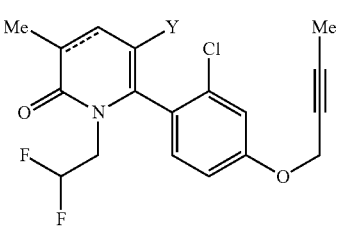 Pyd-1106

TABLE 1-continued

TABLE 1-continued
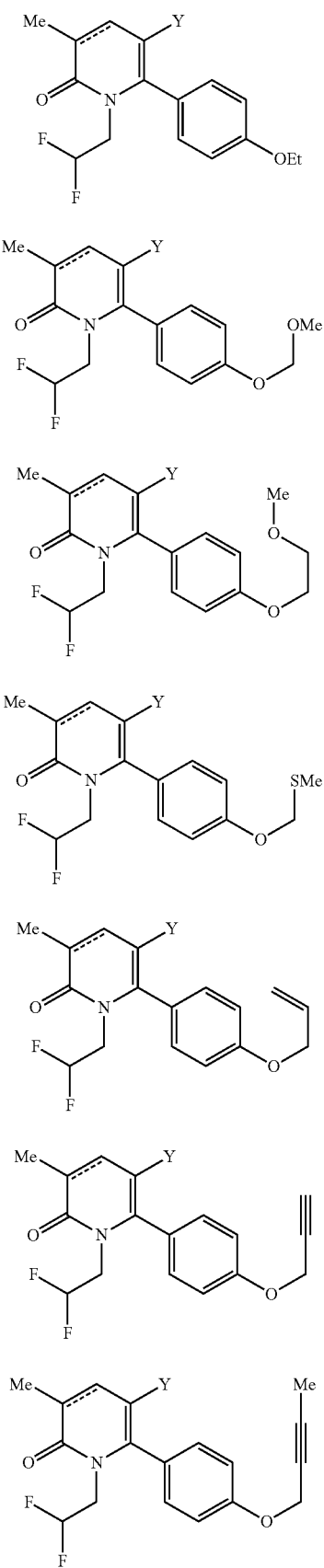
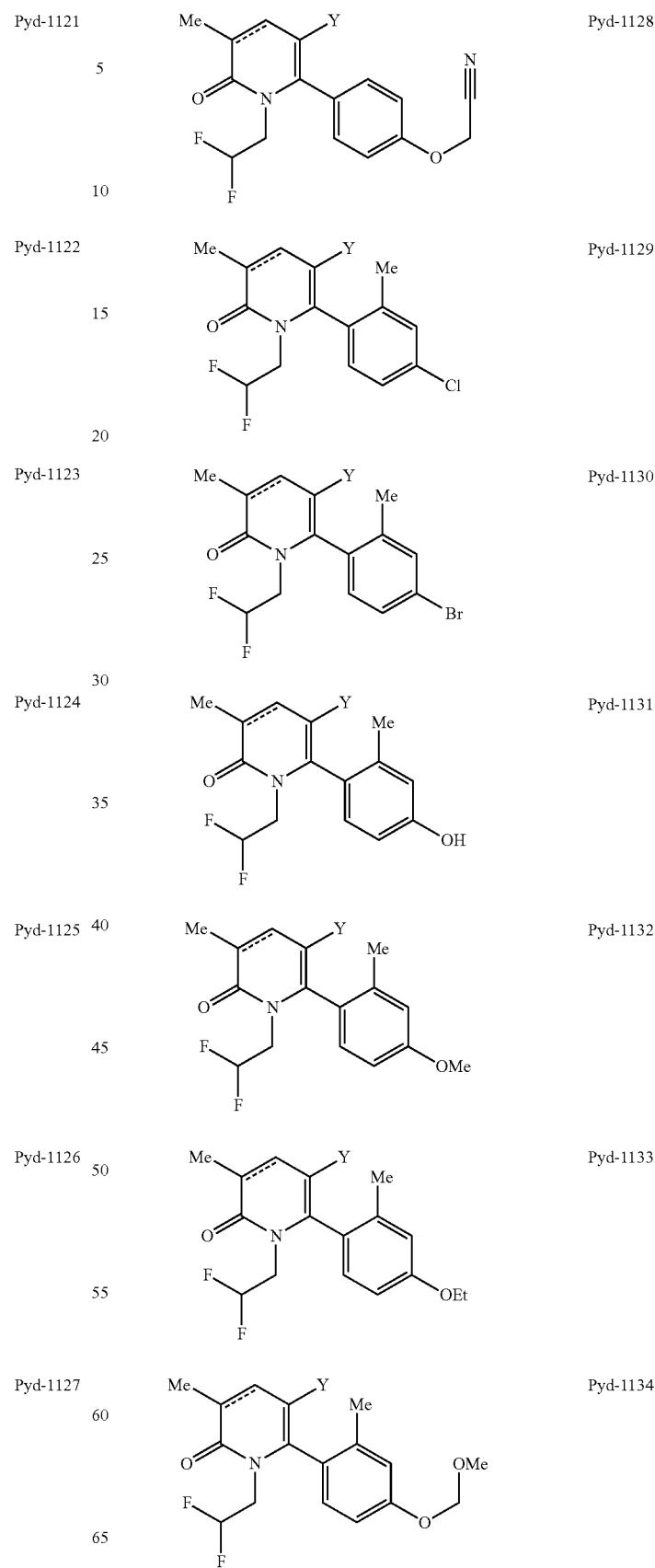

TABLE 1-continued
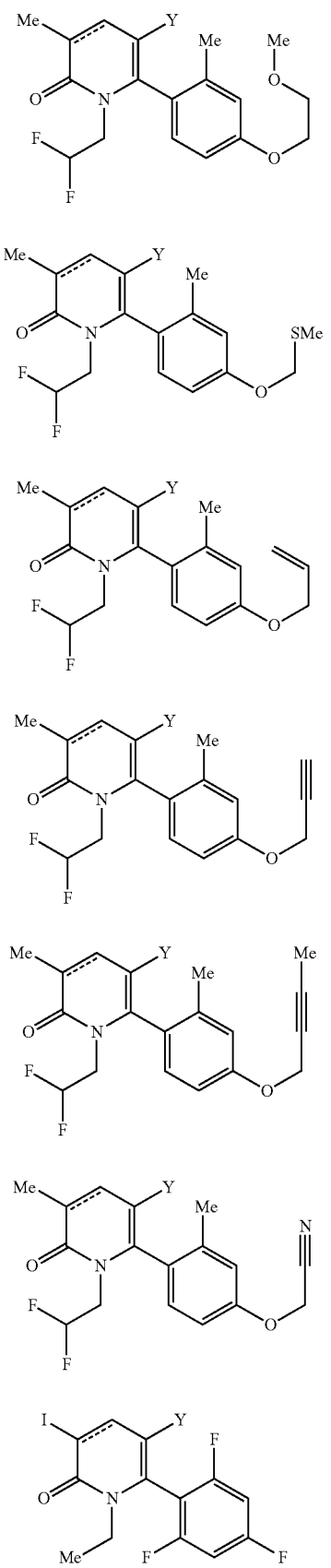
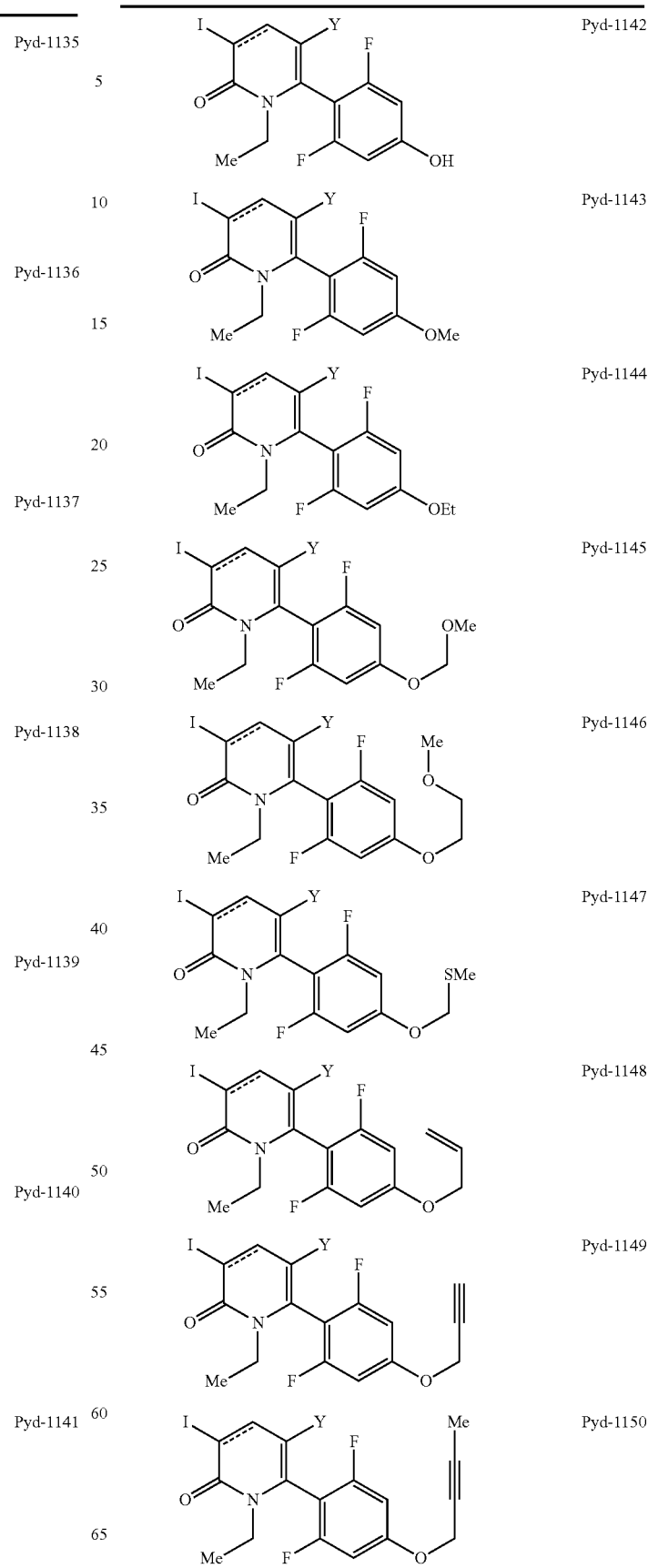

TABLE 1-continued
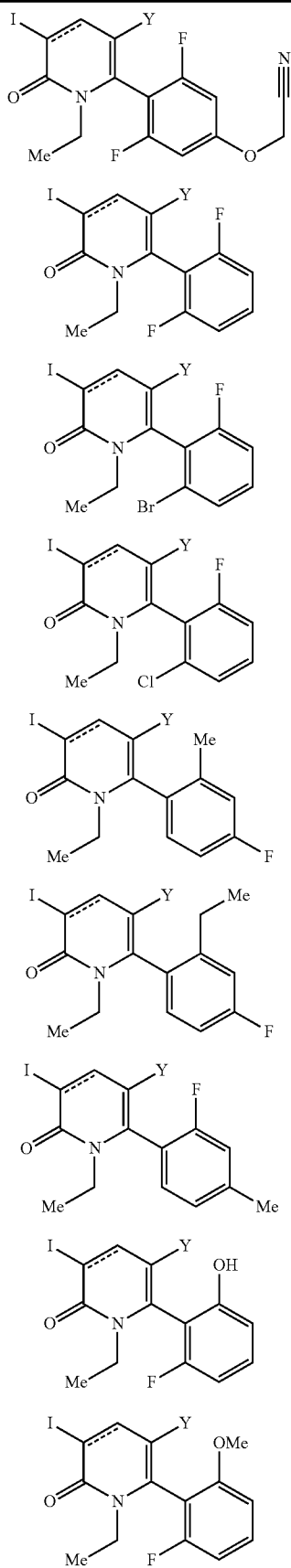
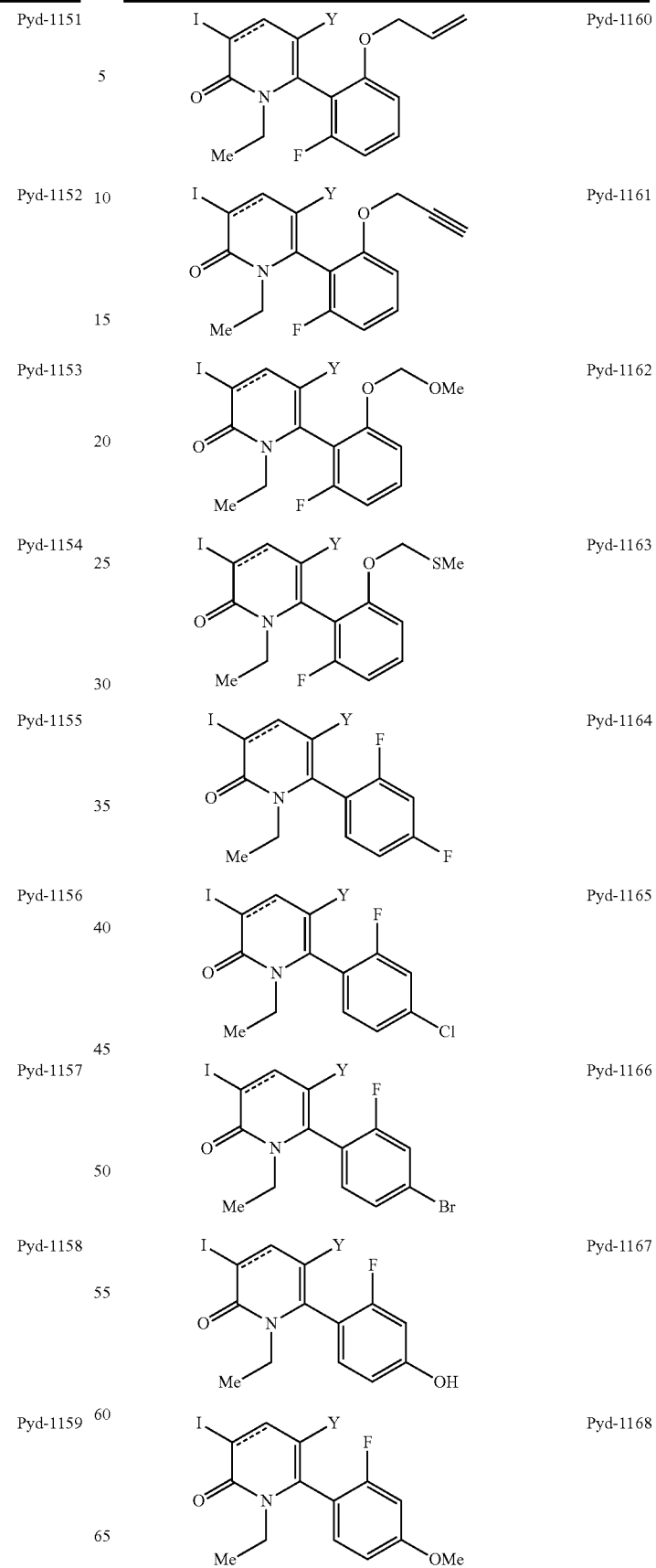

TABLE 1-continued
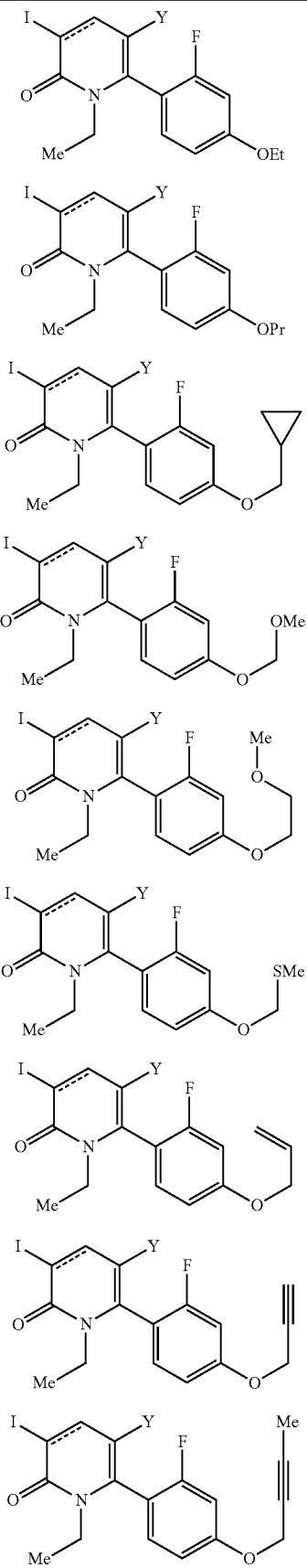
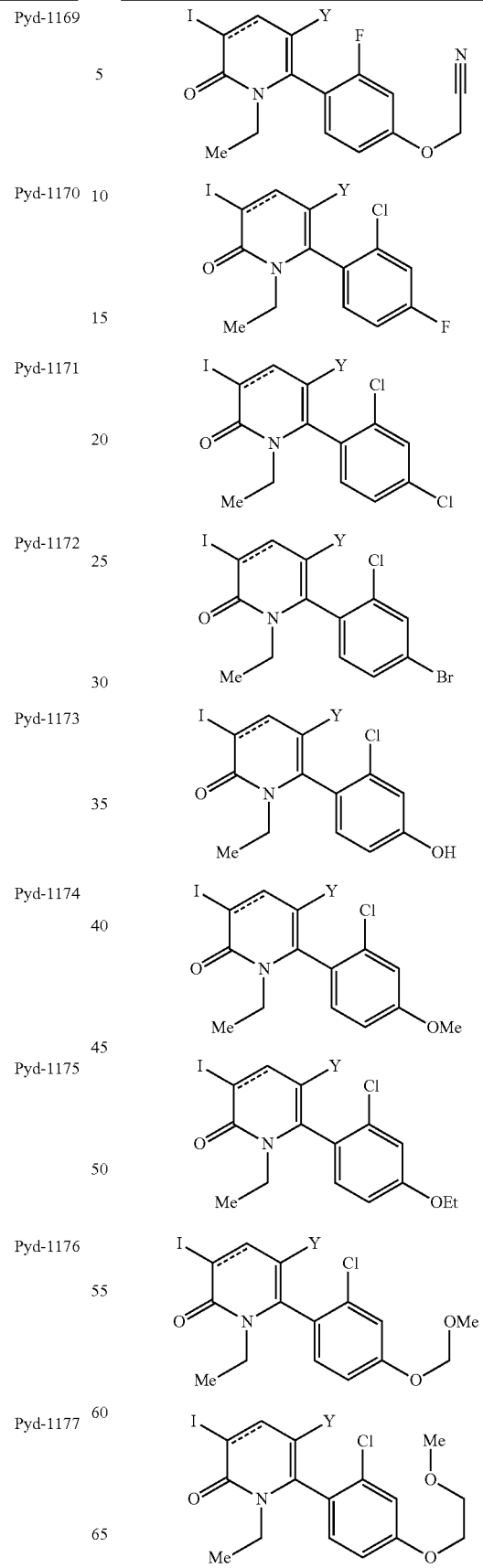

TABLE 1-continued
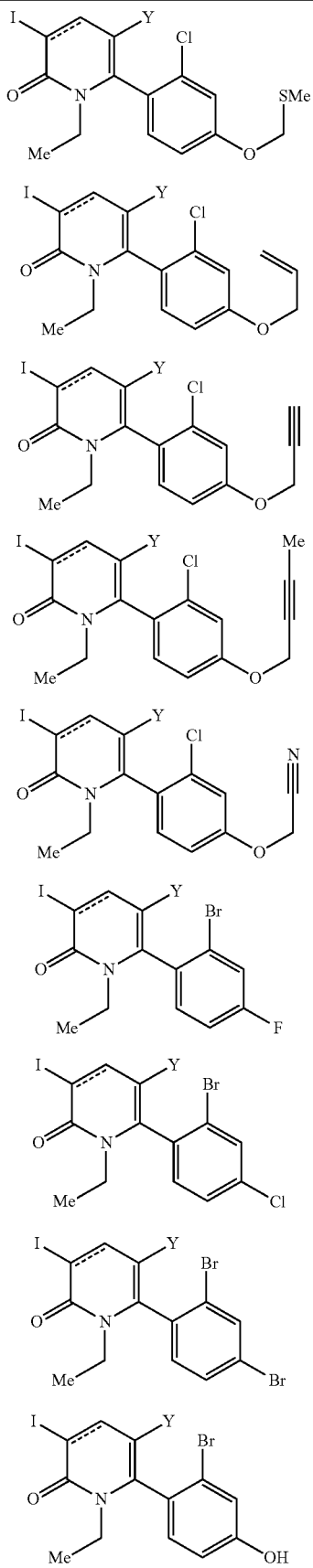
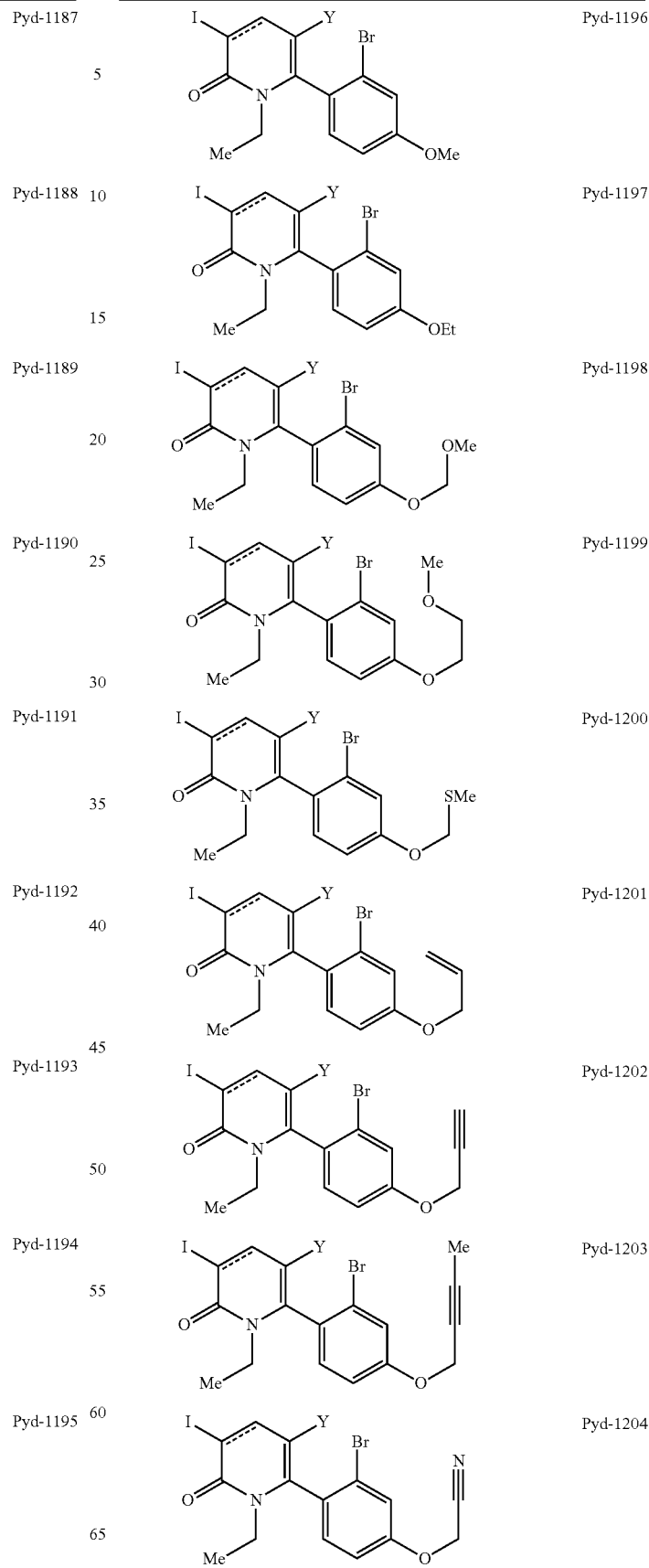

TABLE 1-continued
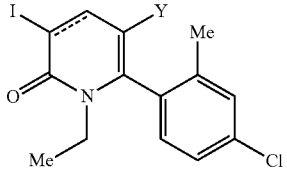 Pyd-1205
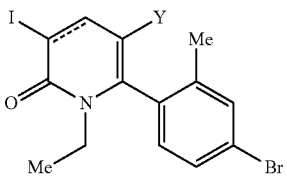 Pyd-1206
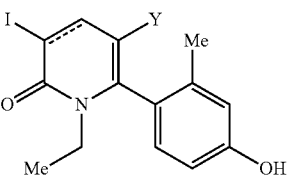 Pyd-1207
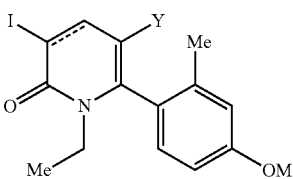 Pyd-1208
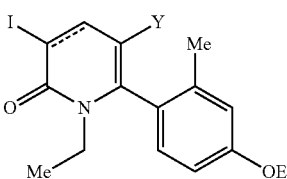 Pyd-1209
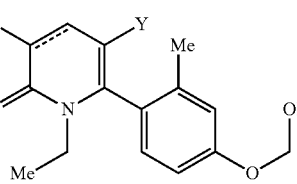 Pyd-1210
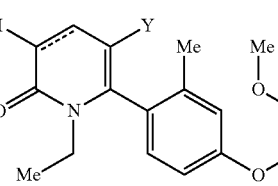 Pyd-1211
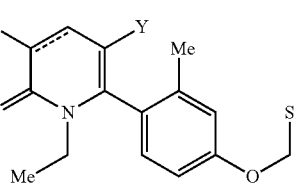 Pyd-1212
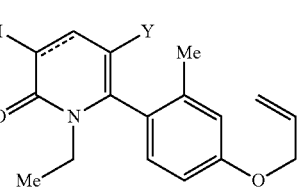 Pyd-1213
TABLE 1-continued
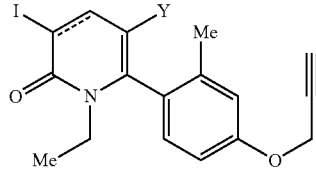 Pyd-1214
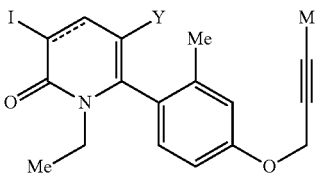 Pyd-1215
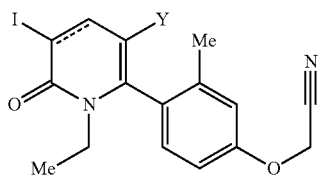 Pyd-1216
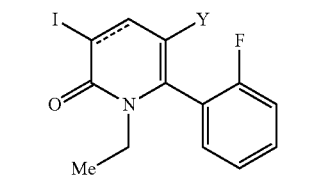 Pyd-1217
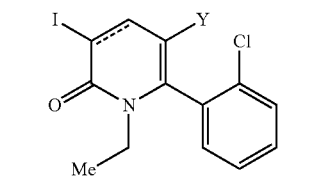 Pyd-1218
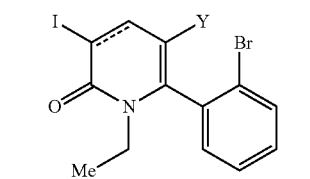 Pyd-1219
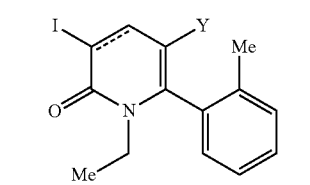 Pyd-1220
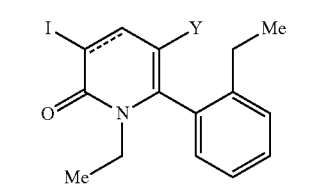 Pyd-1221
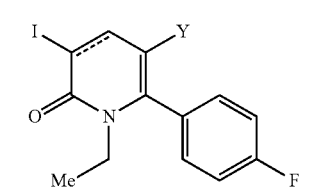 Pyd-1222

TABLE 1-continued
| | |
|---|---|
| 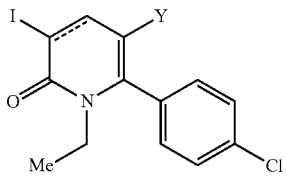 | Pyd-1223 |
| 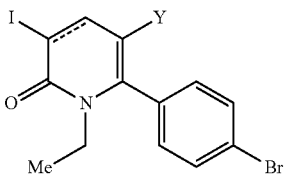 | Pyd-1224 |
| 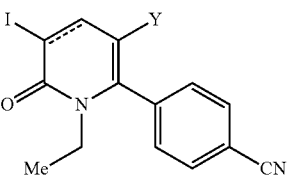 | Pyd-1225 |
| 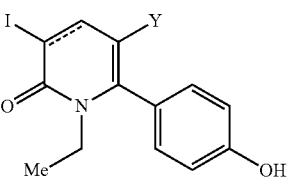 | Pyd-1226 |
| 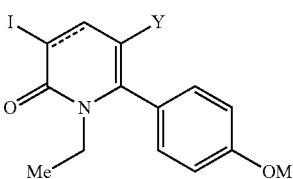 | Pyd-1227 |
| 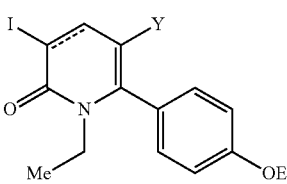 | Pyd-1228 |
| 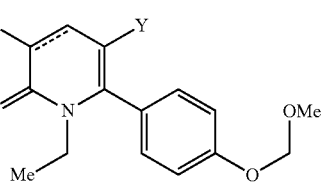 | Pyd-1229 |
| 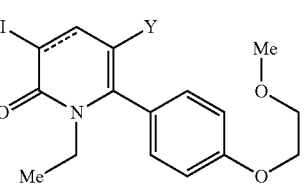 | Pyd-1230 |
| 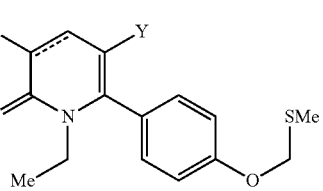 | Pyd-1231 |
TABLE 1-continued
| | |
|---|---|
| 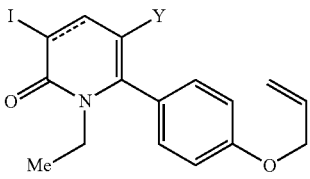 | Pyd-1232 |
| 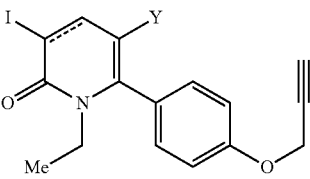 | Pyd-1233 |
| 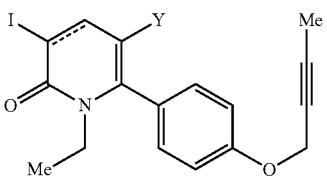 | Pyd-1234 |
| 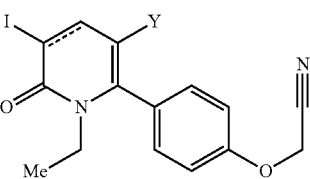 | Pyd-1235 |
| 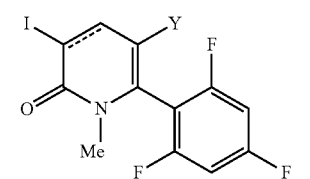 | Pyd-1236 |
| 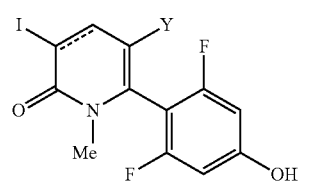 | Pyd-1237 |
| 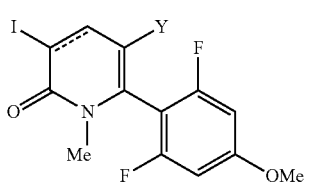 | Pyd-1238 |
| 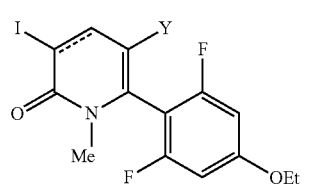 | Pyd-1239 |
| 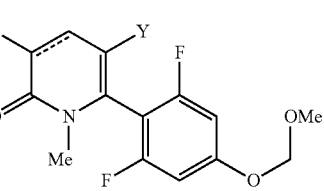 | Pyd-1240 |

TABLE 1-continued
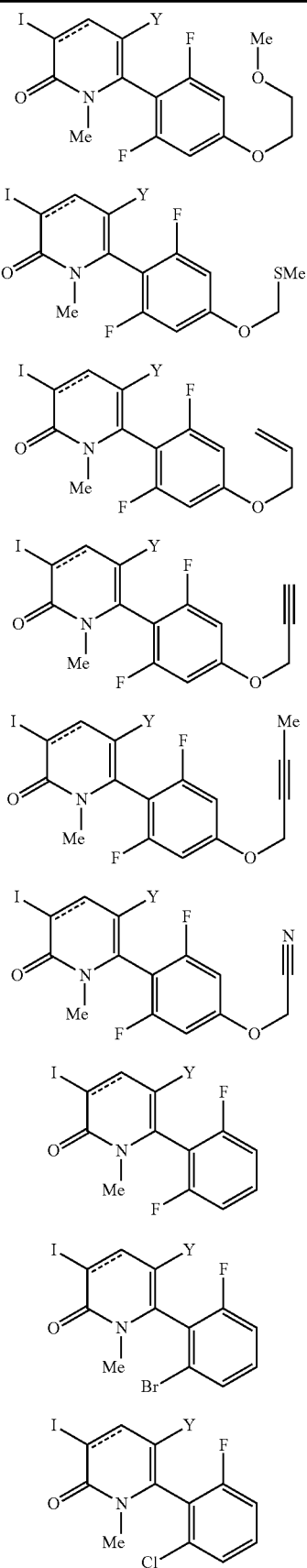
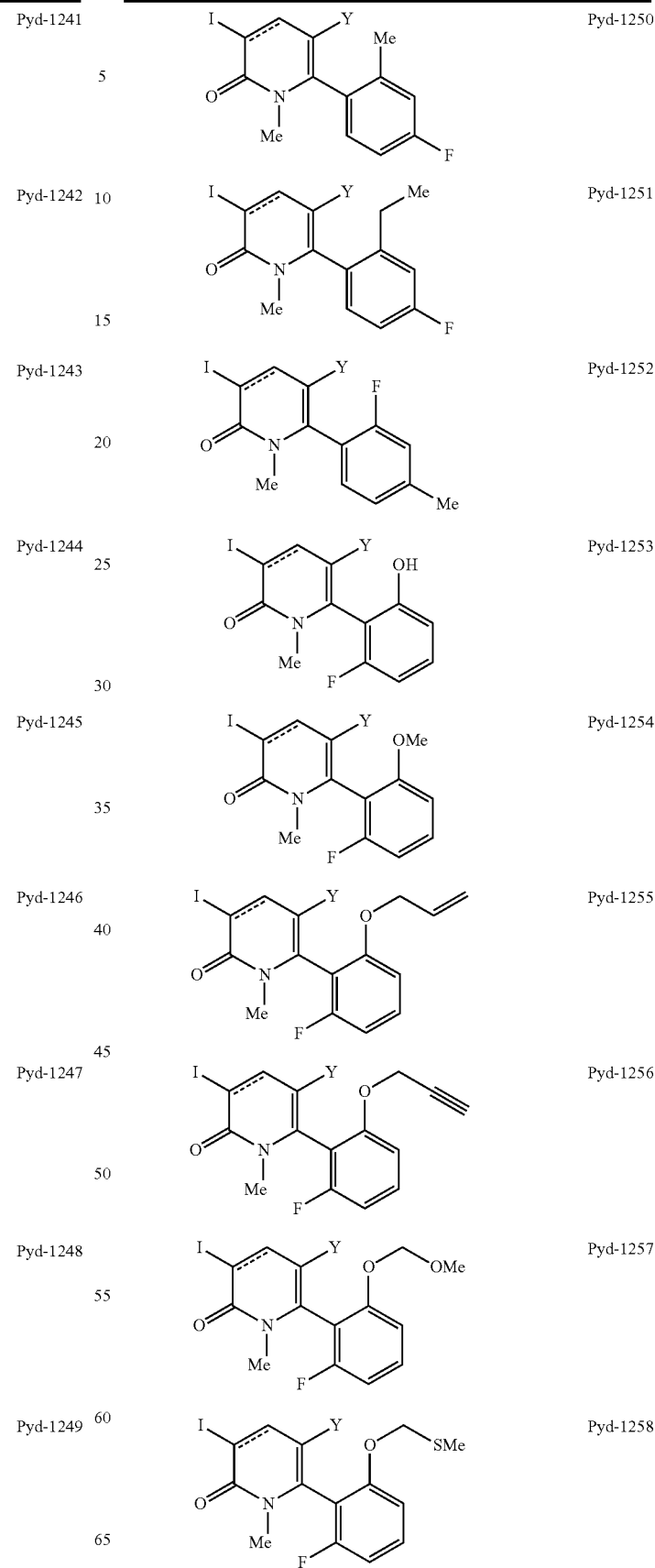

TABLE 1-continued
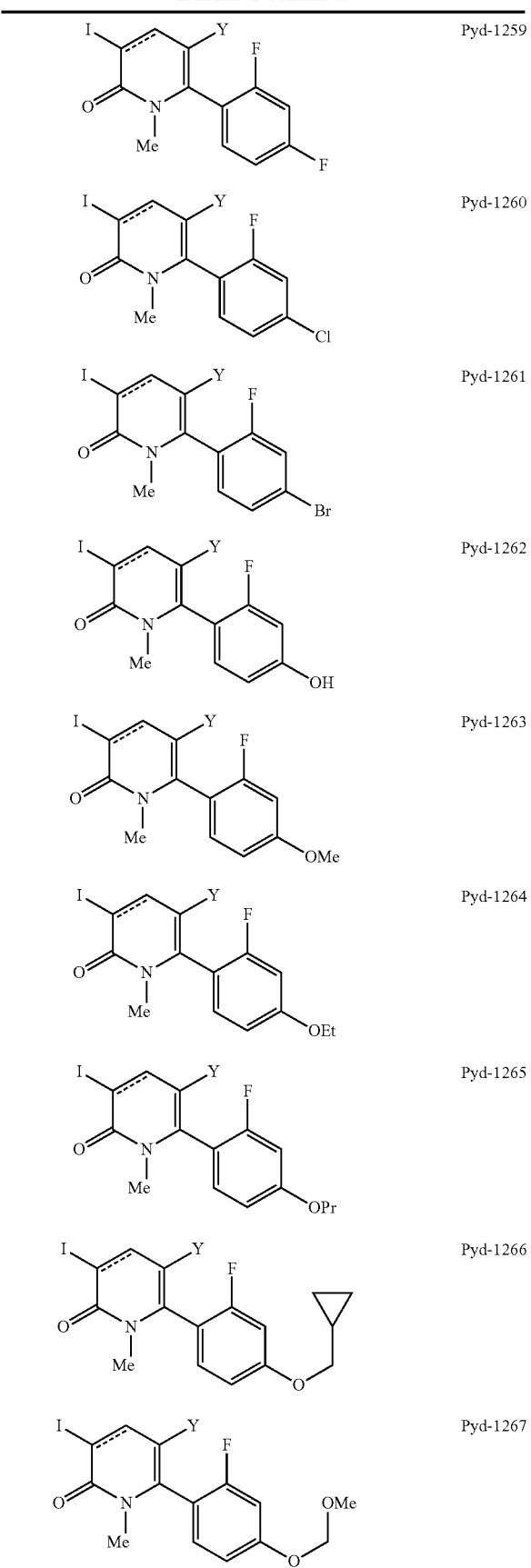
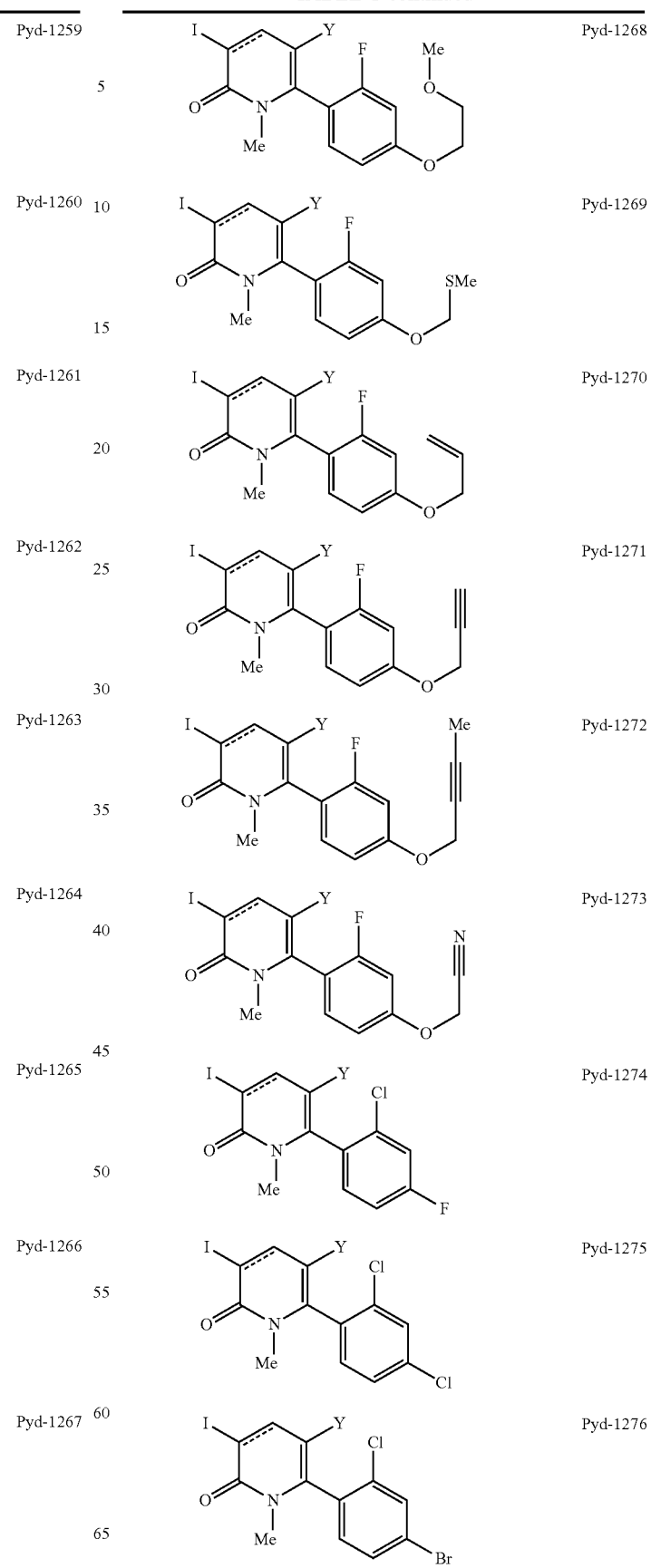

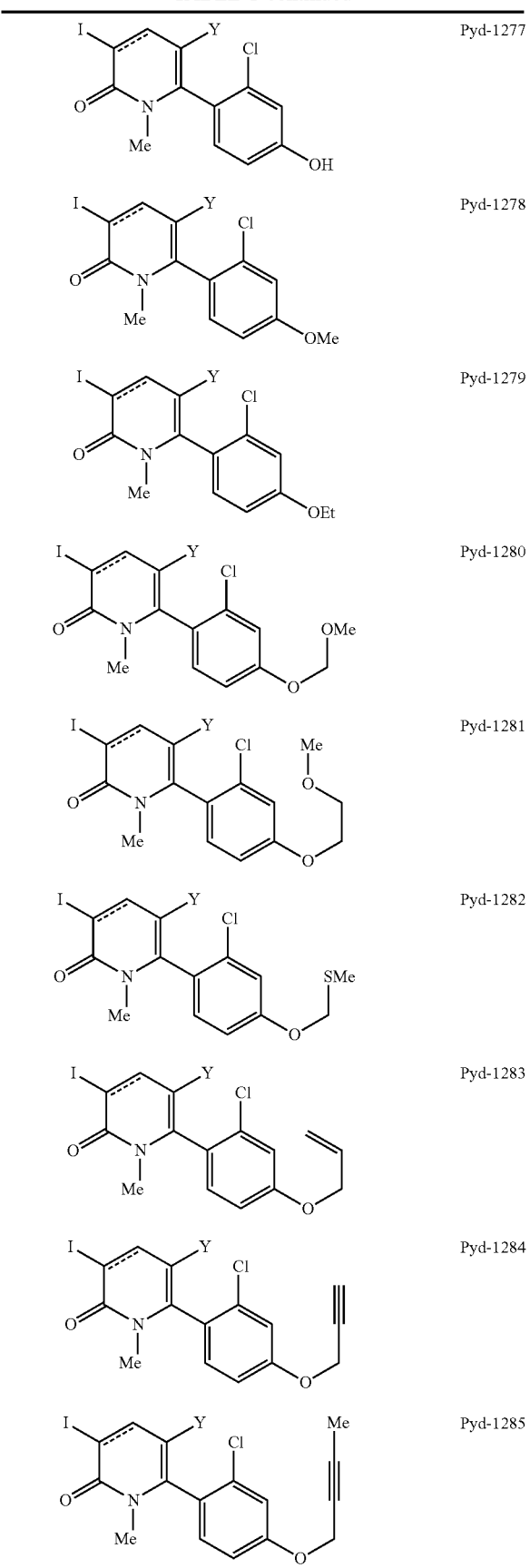

TABLE 1-continued
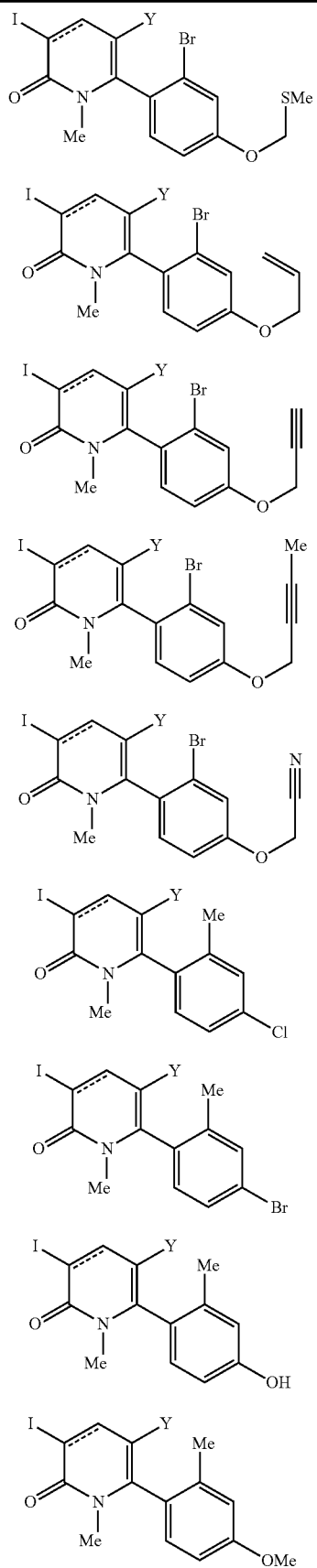
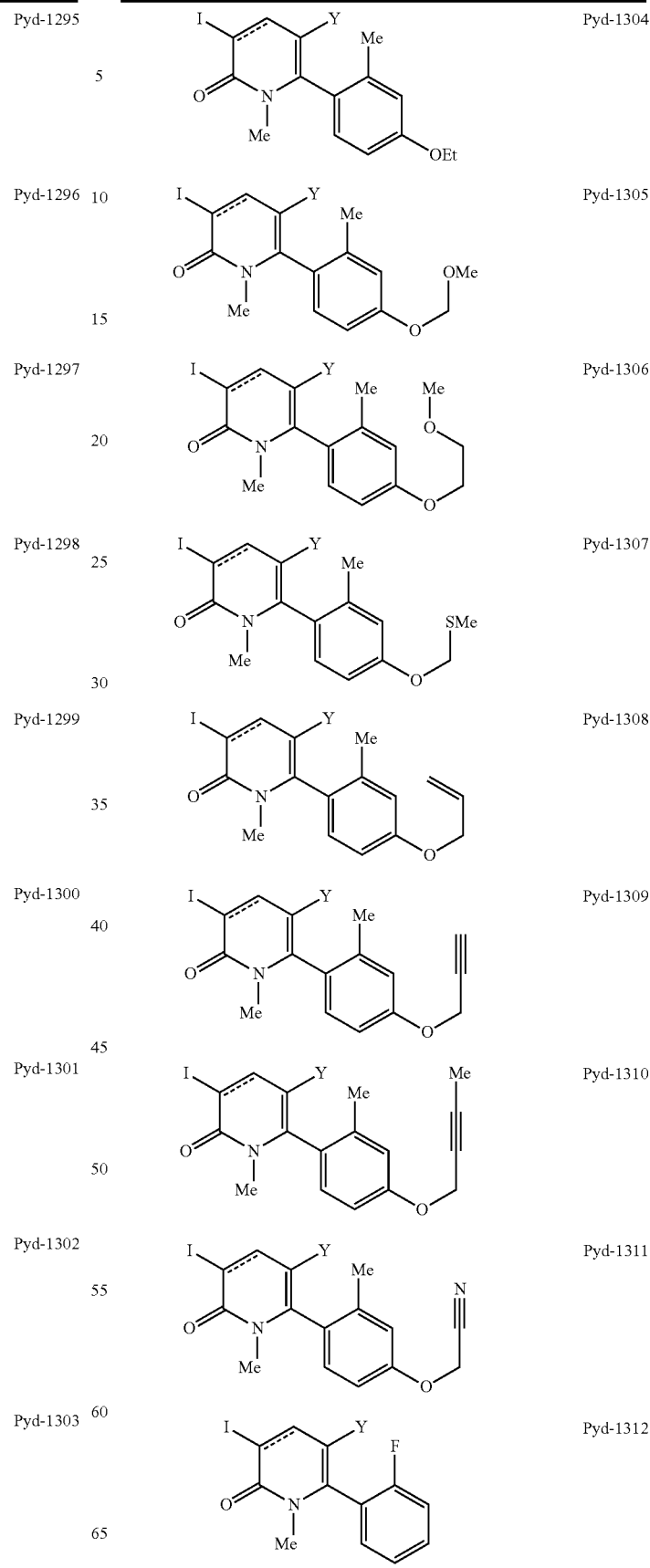

TABLE 1-continued
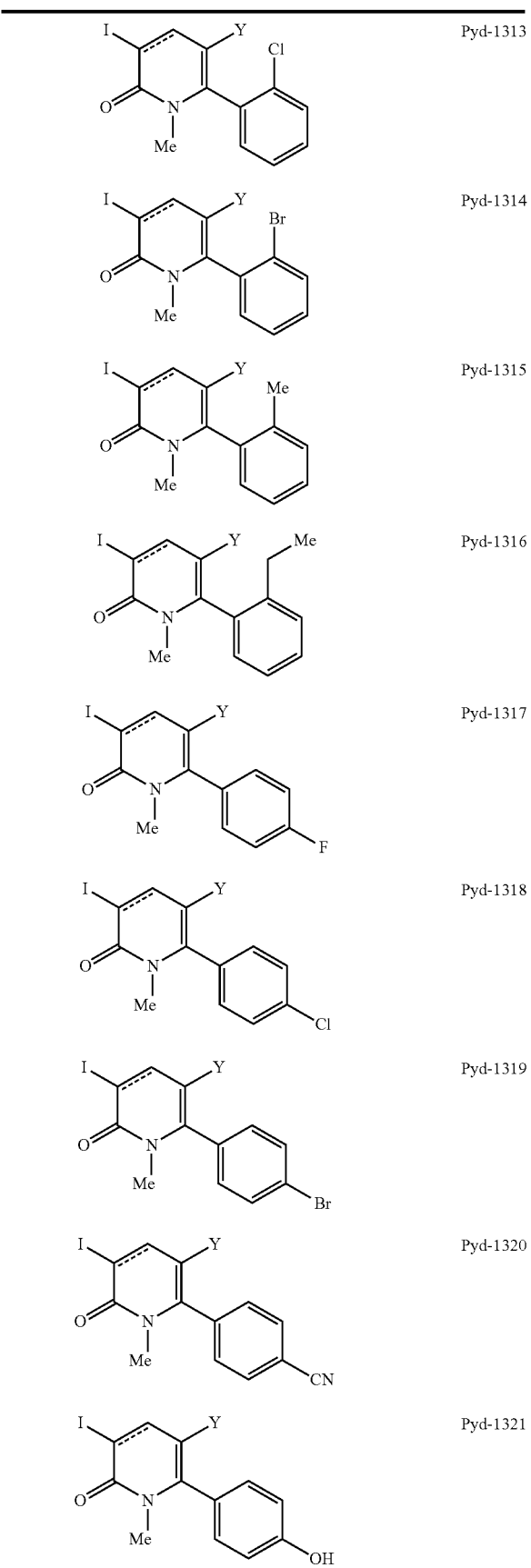
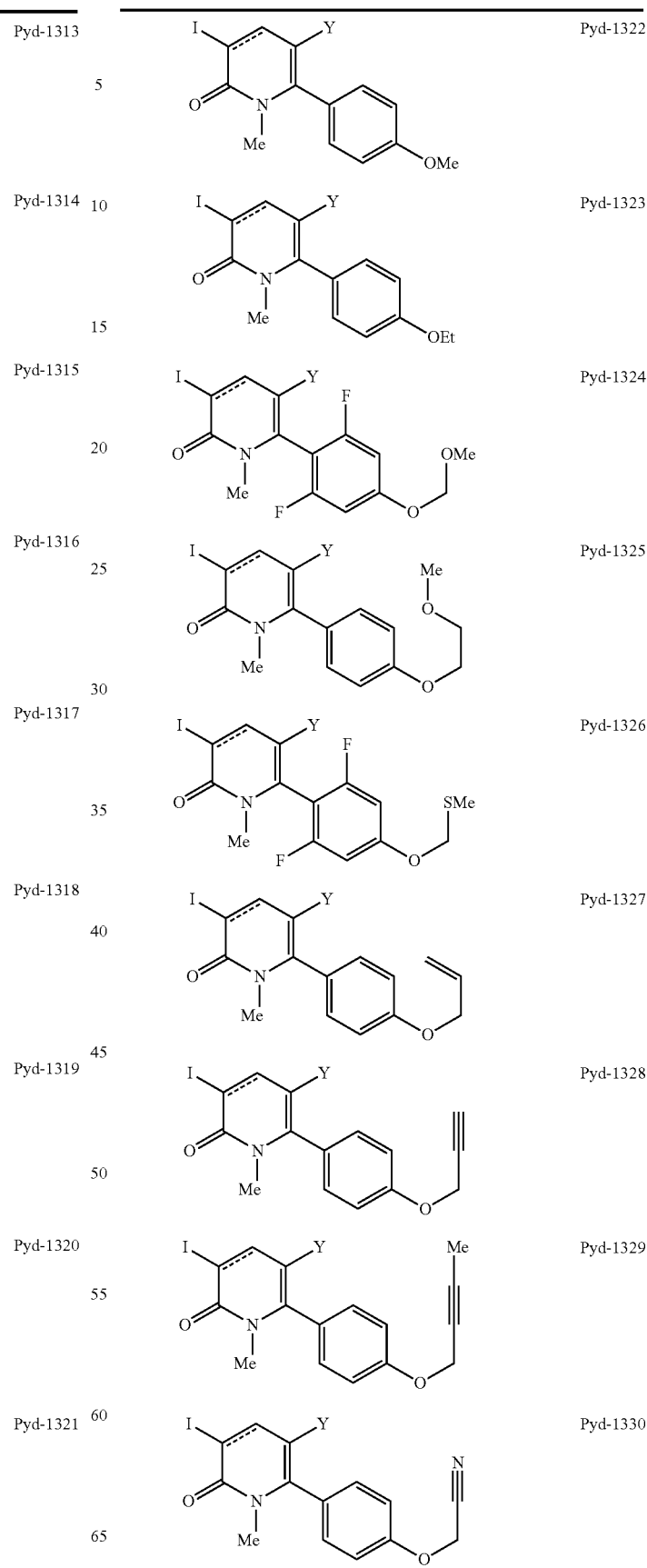

TABLE 1-continued

| Structure | ID |
|---|---|
| (structure) | Pyd-1331 |
| (structure) | Pyd-1332 |
| (structure) | Pyd-1333 |
| (structure) | Pyd-1334 |
| (structure) | Pyd-1335 |
| (structure) | Pyd-1336 |
| (structure) | Pyd-1337 |
| (structure) | Pyd-1338 |
| (structure) | Pyd-1339 |
| (structure) | Pyd-1340 |
| (structure) | Pyd-1341 |
| (structure) | Pyd-1342 |
| (structure) | Pyd-1343 |
| (structure) | Pyd-1344 |

TABLE 1-continued

| Compound |
|---|
| Pyd-1345 |
| Pyd-1346 |
| Pyd-1347 |
| Pyd-1348 |
| Pyd-1349 |
| Pyd-1350 |
| Pyd-1351 |
| Pyd-1352 |
| Pyd-1353 |
| Pyd-1354 |
| Pyd-1355 |
| Pyd-1356 |
| Pyd-1357 |
| Pyd-1358 |

TABLE 1-continued
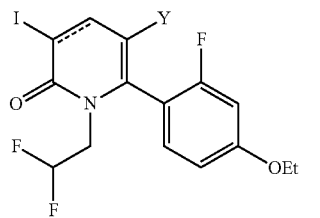 Pyd-1359
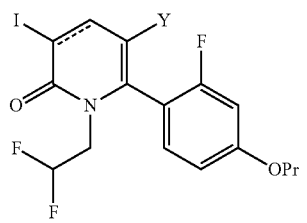 Pyd-1360
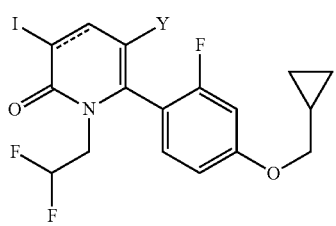 Pyd-1361
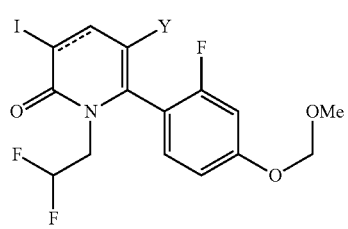 Pyd-1362
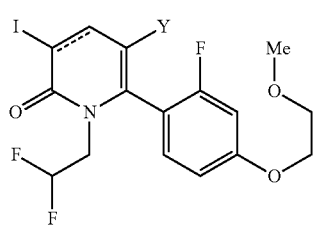 Pyd-1363
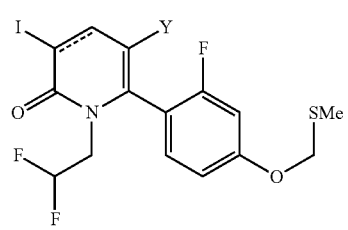 Pyd-1364
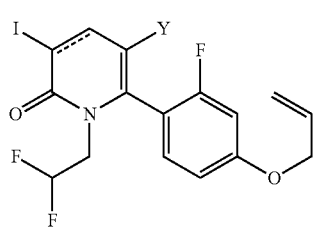 Pyd-1365
TABLE 1-continued
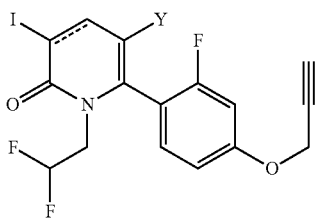 Pyd-1366
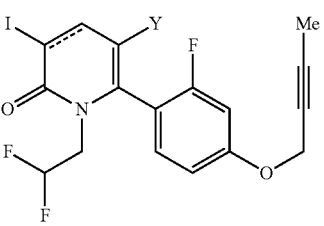 Pyd-1367
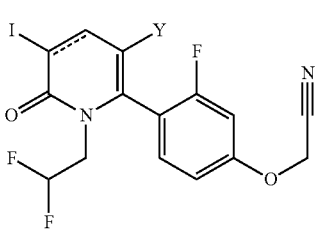 Pyd-1368
 Pyd-1369
 Pyd-1370
Pyd-1371
Pyd-1372

TABLE 1-continued
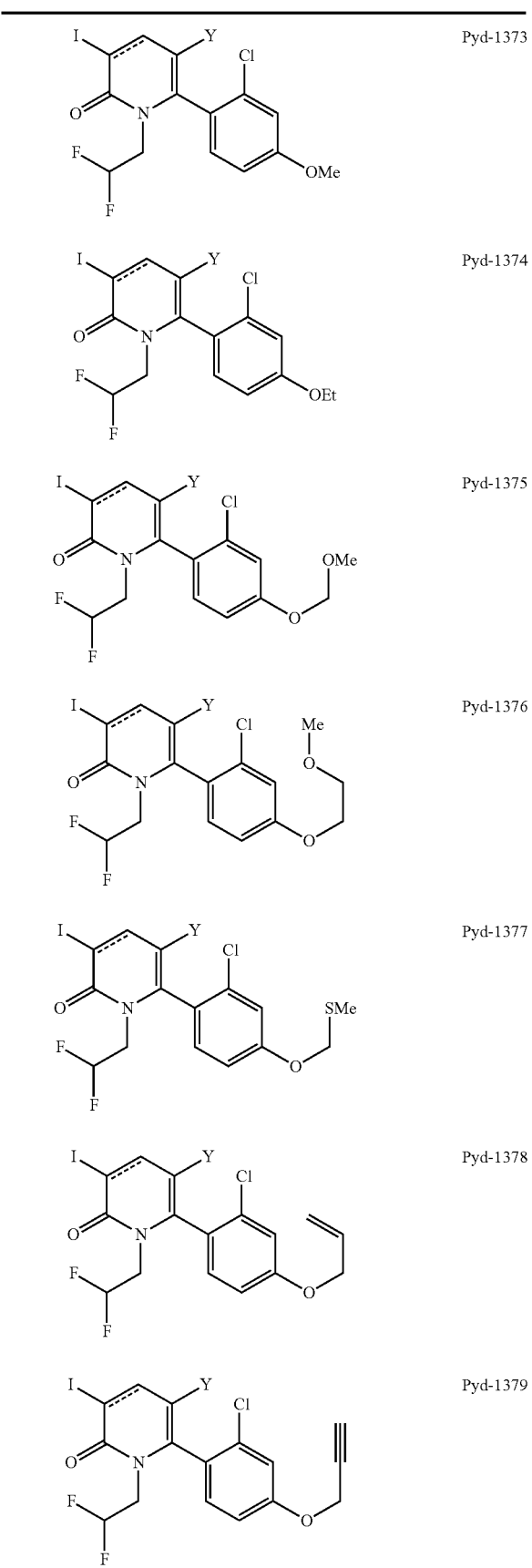
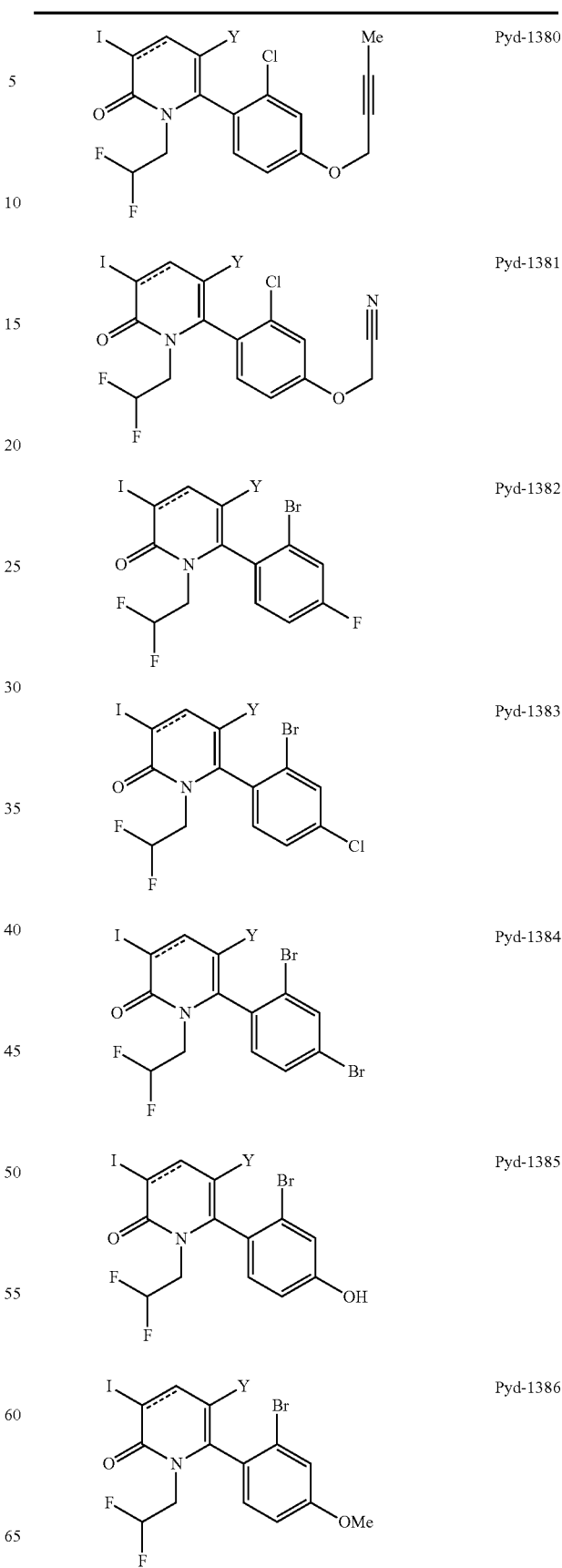

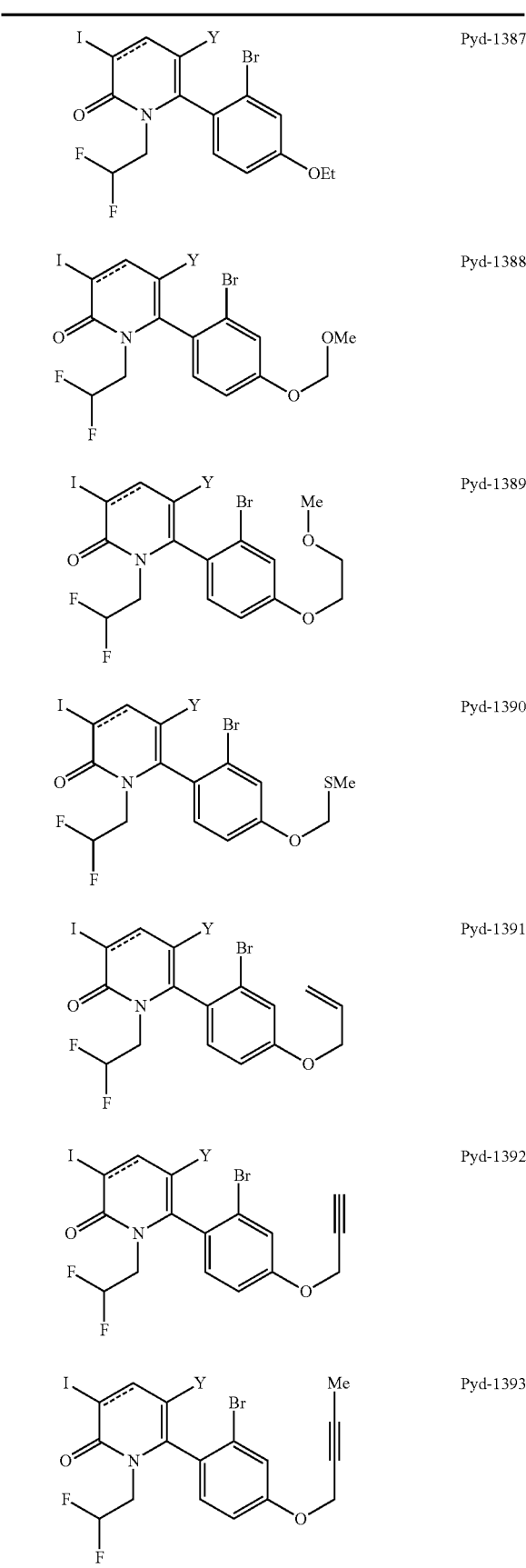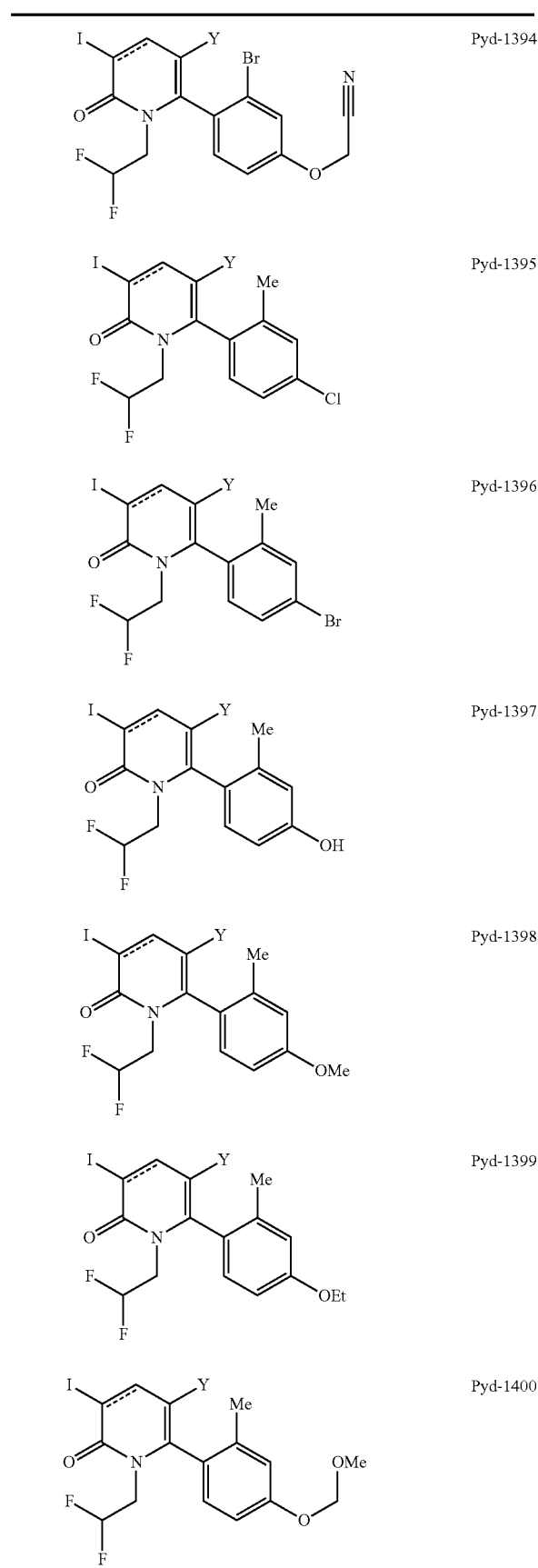

TABLE 1-continued
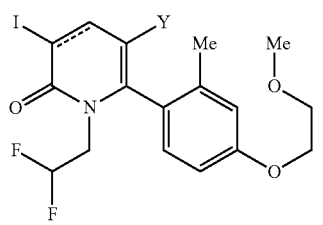 Pyd-1401
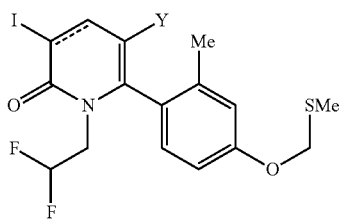 Pyd-1402
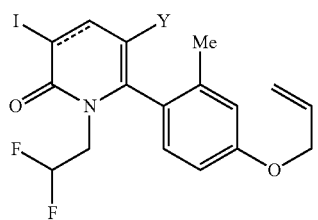 Pyd-1403
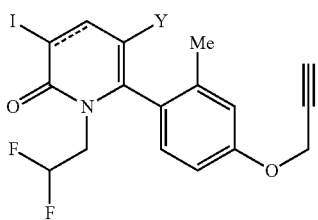 Pyd-1404
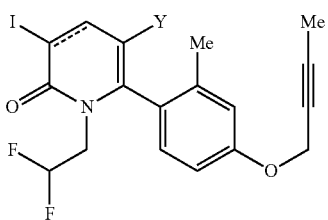 Pyd-1405
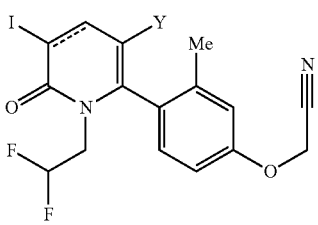 Pyd-1406
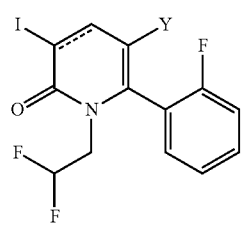 Pyd-1407
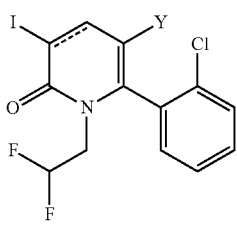 Pyd-1408
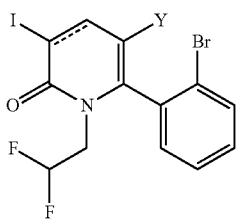 Pyd-1409
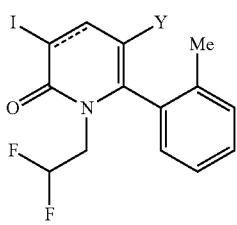 Pyd-1410
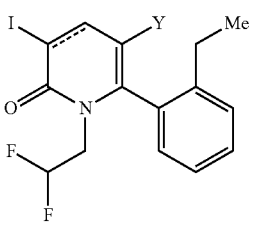 Pyd-1411
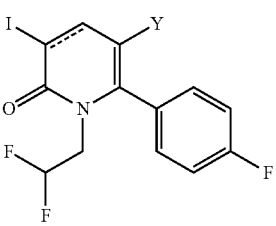 Pyd-1412
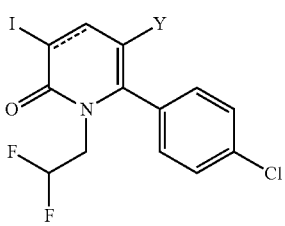 Pyd-1413
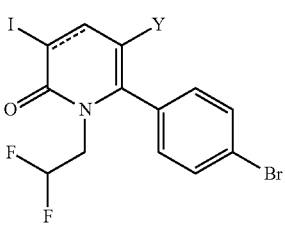 Pyd-1414

TABLE 1-continued
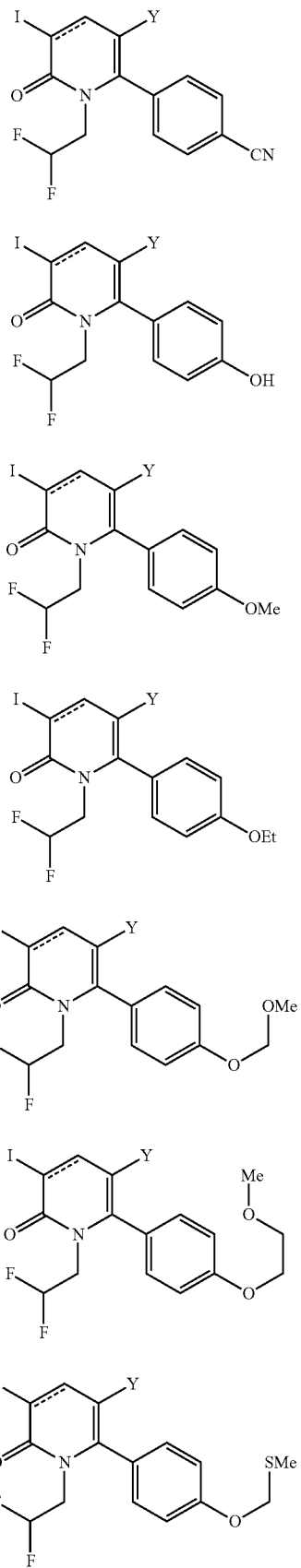
| | |
|---|---|
| | Pyd-1415 |
| | Pyd-1416 |
| | Pyd-1417 |
| | Pyd-1418 |
| | Pyd-1419 |
| | Pyd-1420 |
| | Pyd-1421 |
TABLE 1-continued
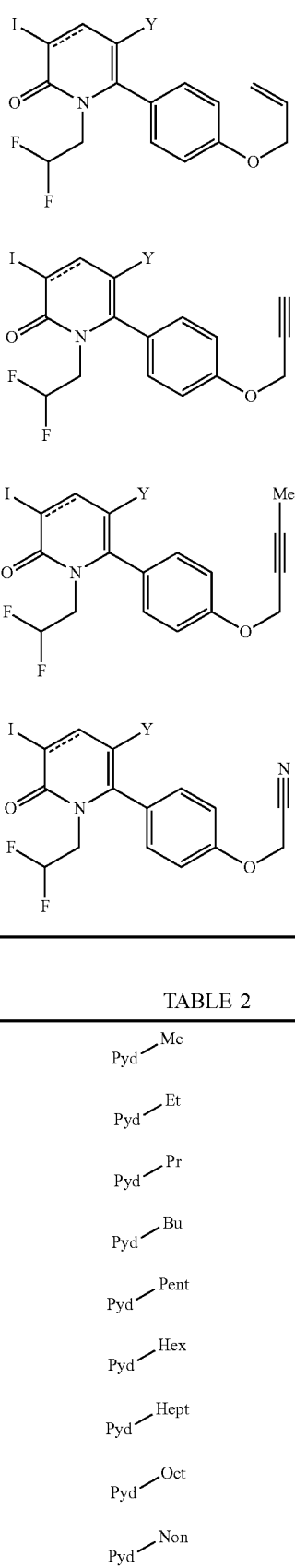
| | |
|---|---|
| | Pyd-1422 |
| | Pyd-1423 |
| | Pyd-1424 |
| | Pyd-1425 |
TABLE 2
| | |
|---|---|
| Pyd—Me | Y-1 |
| Pyd—Et | Y-2 |
| Pyd—Pr | Y-3 |
| Pyd—Bu | Y-4 |
| Pyd—Pent | Y-5 |
| Pyd—Hex | Y-6 |
| Pyd—Hept | Y-7 |
| Pyd—Oct | Y-8 |
| Pyd—Non | Y-9 |

TABLE 2-continued
| | | |
|---|---|---|
| 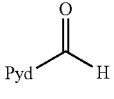 | Y-10 | |
| 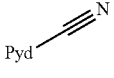 | Y-11 | |
| 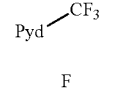 | Y-12 | |
| 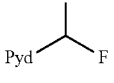 | Y-13 | |
| 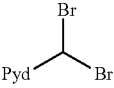 | Y-14 | |
| 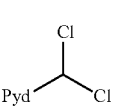 | Y-15 | |
| 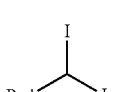 | Y-16 | |
| 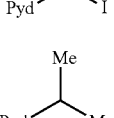 | Y-17 | |
| 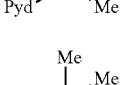 | Y-18 | |
| 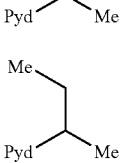 | Y-19 | |
| 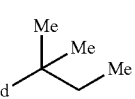 | Y-20 | |
| 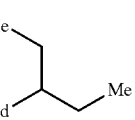 | Y-21 | |
| 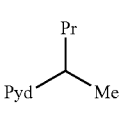 | Y-22 | |
| 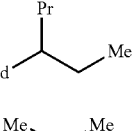 | Y-23 | |
| 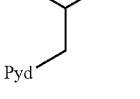 | Y-24 | |
| 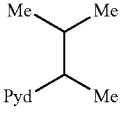 | Y-25 | |
| 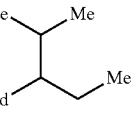 | Y-26 | |
| 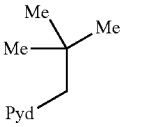 | Y-27 | |
| 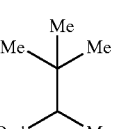 | Y-28 | |
| 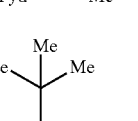 | Y-29 | |
| 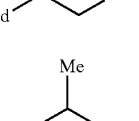 | Y-30 | |
| 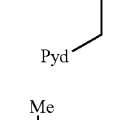 | Y-31 | |
| 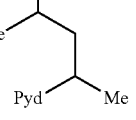 | Y-32 | |
| 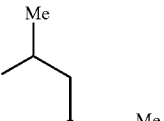 | Y-33 | |
| 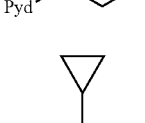 | Y-34 | |
| 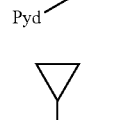 | Y-35 | |

TABLE 2-continued
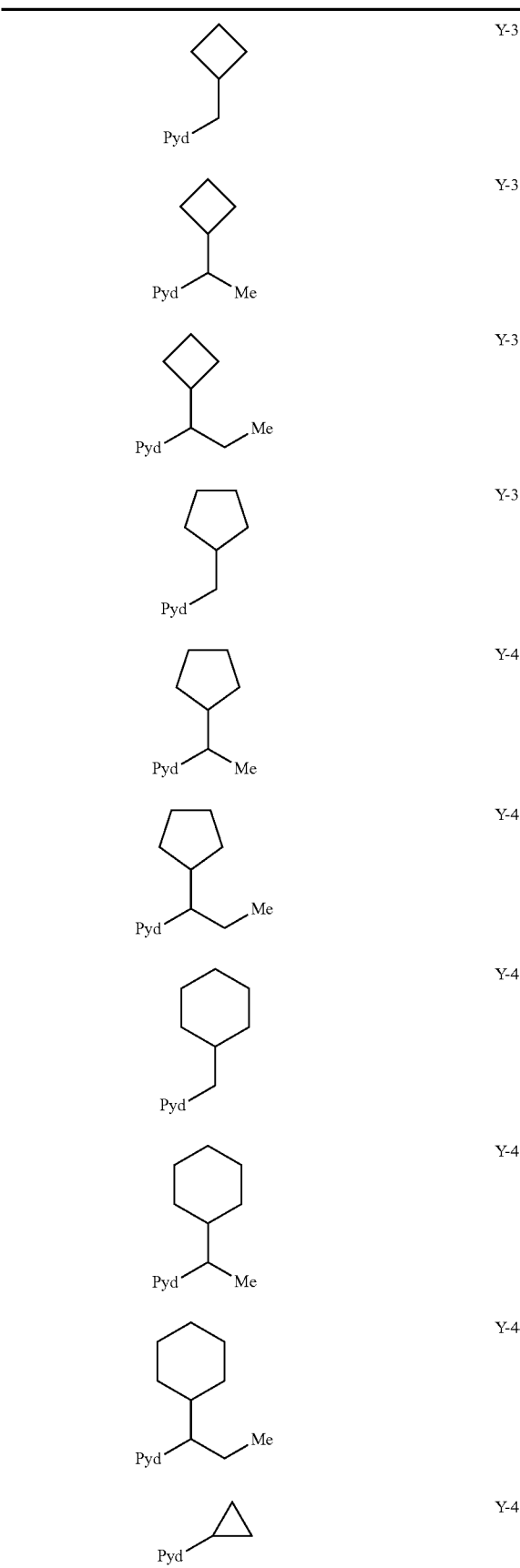
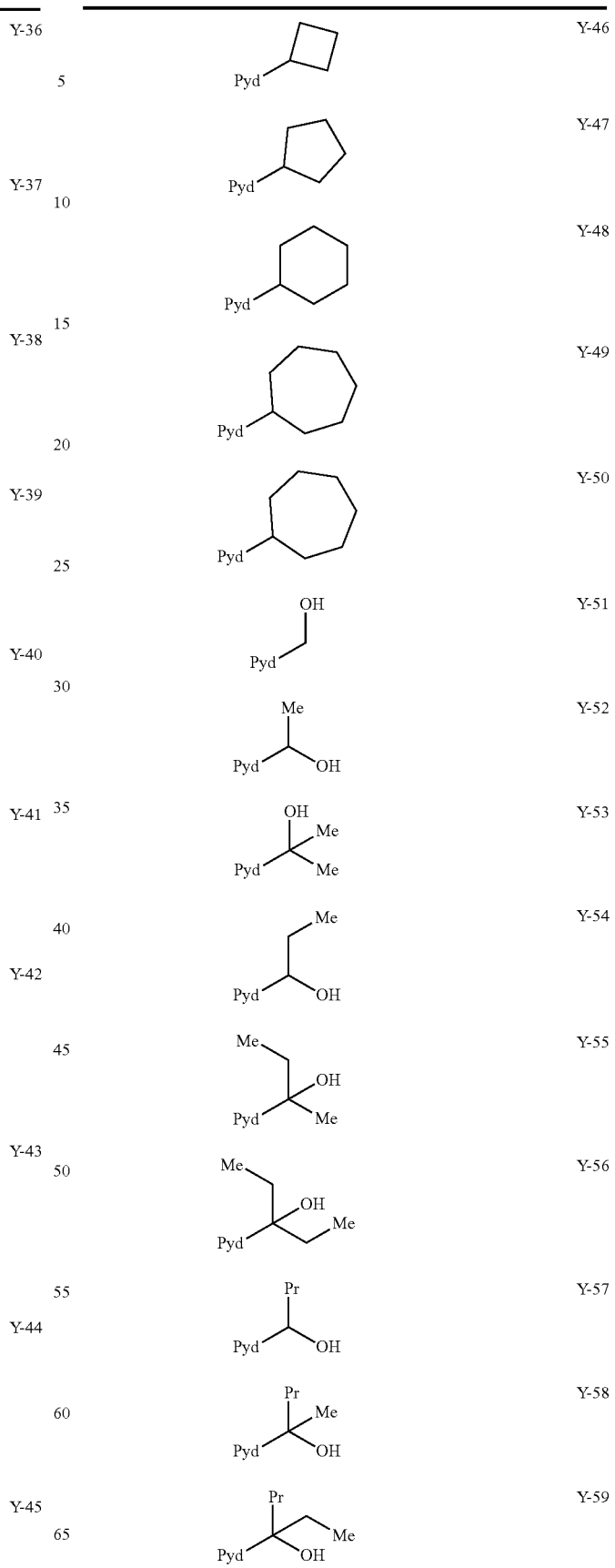

TABLE 2-continued

| Structure | Label |
|---|---|
| Pyd-CH(Bu)-OH | Y-60 |
| Pyd-C(Bu)(Me)-OH | Y-61 |
| Pyd-C(Bu)(Et)-OH | Y-62 |
| Pyd-CH(Pent)-OH | Y-63 |
| Pyd-CH(Hex)-OH | Y-64 |
| Pyd-CH(Hept)-OH | Y-65 |
| Pyd-CH(Oct)-OH | Y-66 |
| Pyd-CH(OH)-CH(Me)Me | Y-67 |
| Pyd-C(Me)(OH)-CH(Me)Me | Y-68 |
| Pyd-C(OH)(Et)-CH(Me)Me | Y-69 |
| Pyd-CH(OH)-C(Me)(Me)Me | Y-70 |
| Pyd-C(Me)(OH)-C(Me)(Me)Me | Y-71 |
| Pyd-C(OH)(Et)-C(Me)(Me)Me | Y-72 |

TABLE 2-continued

| Structure | Label |
|---|---|
| Pyd-CH(OH)-CH2-CH(Me)Me | Y-73 |
| Pyd-C(Me)(OH)-CH2-CH(Me)Me | Y-74 |
| Pyd-C(Et)(OH)-CH2-CH(Me)Me | Y-75 |
| Pyd-CH(OH)-cyclopropyl | Y-76 |
| Pyd-C(Me)(OH)-cyclopropyl | Y-77 |
| Pyd-C(Et)(OH)-cyclopropyl | Y-78 |
| Pyd-CH(OH)-cyclobutyl | Y-79 |
| Pyd-C(Me)(OH)-cyclobutyl | Y-80 |
| Pyd-C(Et)(OH)-cyclobutyl | Y-81 |
| Pyd-CH(OH)-cyclopentyl | Y-82 |

TABLE 2-continued

| Structure | Label |
|---|---|
| Pyd-C(OH)(Me)-cyclopentyl | Y-83 |
| Pyd-C(OH)(Et)-cyclopentyl | Y-84 |
| Pyd-CH(OH)-cyclohexyl | Y-85 |
| Pyd-C(OH)(Me)-cyclohexyl | Y-86 |
| Pyd-C(OH)(Et)-cyclohexyl | Y-87 |
| Pyd-CH2-OMe | Y-88 |
| Pyd-CH(Me)(OMe) | Y-89 |
| Pyd-C(Me)2(OMe) | Y-90 |
| Pyd-CH(OMe)-Et | Y-91 |
| Pyd-C(Me)(OMe)-Et | Y-92 |
| Pyd-C(Me)(OMe)-Pr (with Et branch) | Y-93 |

TABLE 2-continued

| Structure | Label |
|---|---|
| Pyd-CH(Pr)(OMe) | Y-94 |
| Pyd-C(Pr)(Me)(OMe) | Y-95 |
| Pyd-C(Pr)(Me)-CH2OMe | Y-96 |
| Pyd-CH(Bu)(OMe) | Y-97 |
| Pyd-C(Bu)(Me)(OMe) | Y-98 |
| Pyd-C(Bu)(Me)-CH2OMe | Y-99 |
| Pyd-CH(Pent)(OMe) | Y-100 |
| Pyd-CH(Hex)(OMe) | Y-101 |
| Pyd-CH(Hept)(OMe) | Y-102 |
| Pyd-CH(Oct)(OMe) | Y-103 |
| Pyd-CH(OMe)-CH(Me)2 | Y-104 |
| Pyd-C(Me)(OMe)-CH(Me)2 | Y-105 |
| Pyd-C(OMe)(Me)-CH(Me)2 | Y-106 |
| Pyd-CH(OMe)-C(Me)3 | Y-107 |

TABLE 2-continued
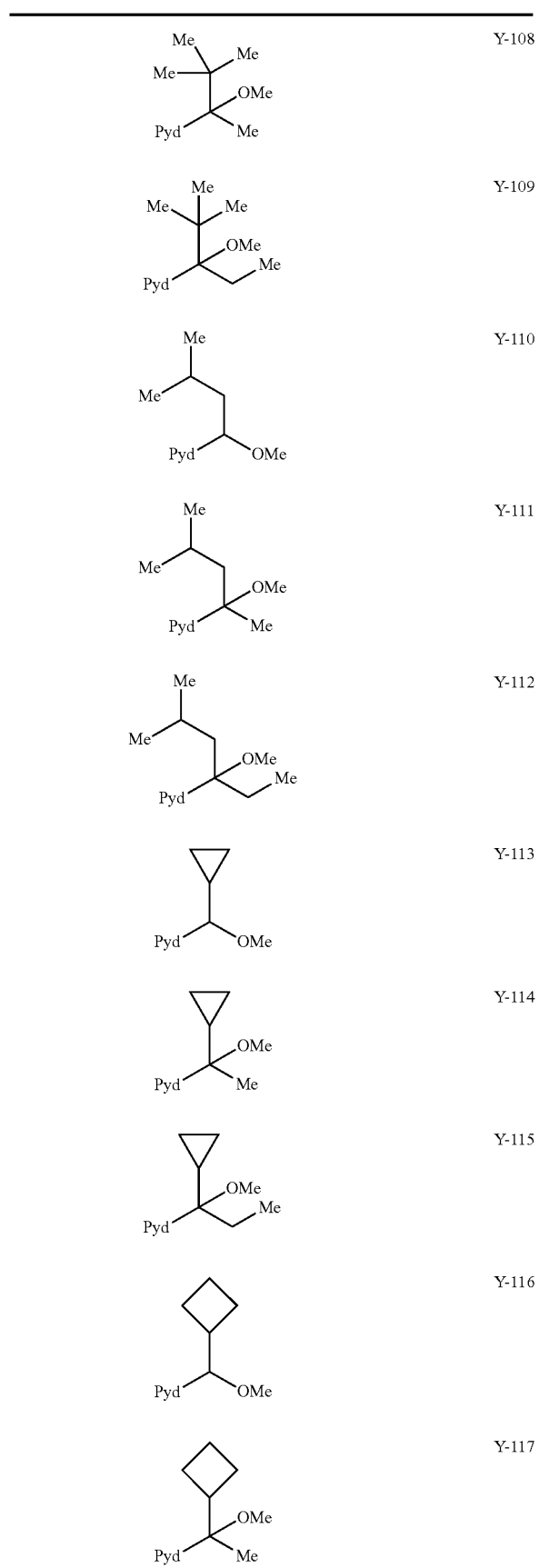
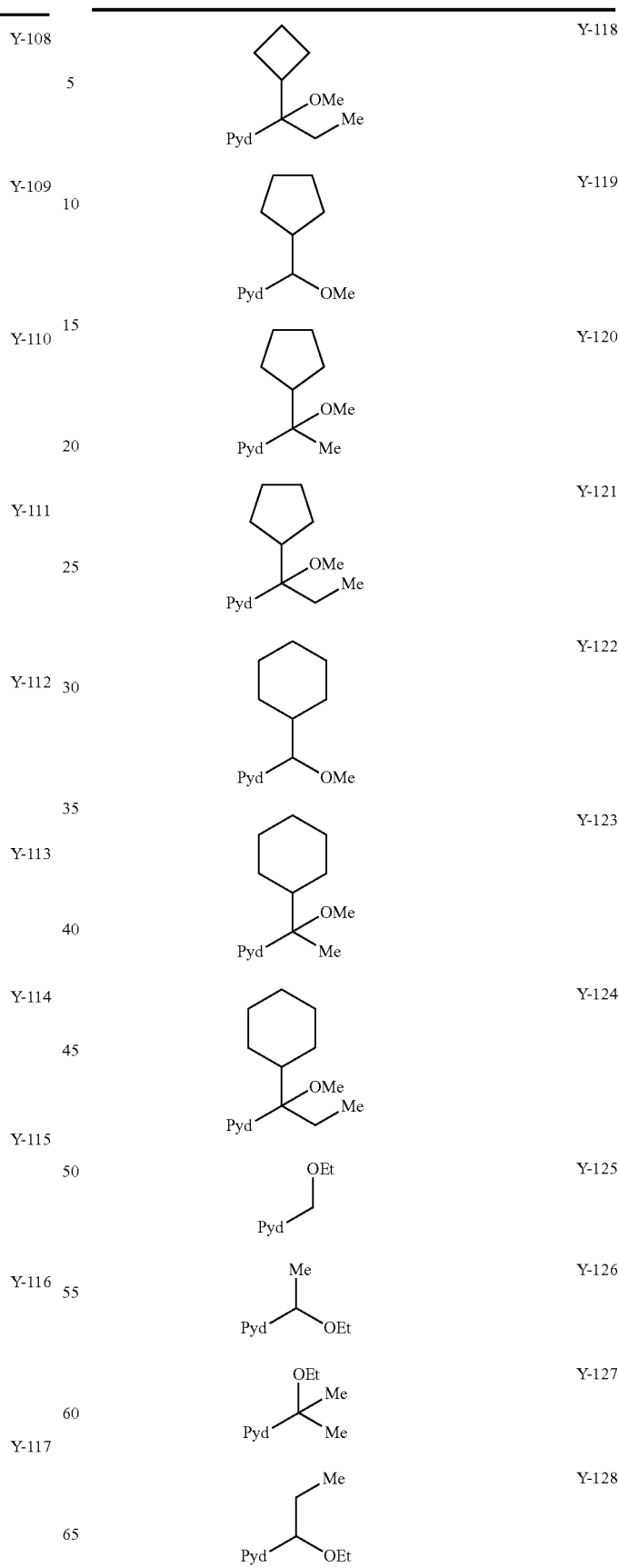

TABLE 2-continued

| Structure | Label |
|---|---|
| Pyd-C(Me)(Me)(OEt)-CH2Me (Me, Et, OEt, Me on central C with Pyd) | Y-129 |
| Pyd-CH(CH2Me)-C(OEt)(Me)- ... | Y-130 |
| Pyd-CH(Pr)(OEt) | Y-131 |
| Pyd-C(Pr)(Me)(OEt) | Y-132 |
| Pyd-C(Pr)(Me)(OEt) | Y-133 |
| Pyd-CH(Bu)(OEt) | Y-134 |
| Pyd-C(Bu)(Me)(OEt) | Y-135 |
| Pyd-C(Bu)(Me)(OEt) (with Et) | Y-136 |
| Pyd-CH(Pent)(OEt) | Y-137 |
| Pyd-CH(Hex)(OEt) | Y-138 |
| Pyd-CH(Hept)(OEt) | Y-139 |
| Pyd-CH(Oct)(OEt) | Y-140 |
| Pyd-CH(CH(Me)2)(OEt) | Y-141 |
| Pyd-C(CH(Me)2)(Me)(OEt) | Y-142 |

TABLE 2-continued

| Structure | Label |
|---|---|
| Pyd-CH(CH(Me)2)(OEt)CH2Me | Y-143 |
| Pyd-CH(C(Me)3)(OEt) | Y-144 |
| Pyd-C(C(Me)3)(Me)(OEt) | Y-145 |
| Pyd-C(C(Me)3)(OEt)CH2Me | Y-146 |
| Pyd-CH(CH2CH(Me)2)(OEt) | Y-147 |
| Pyd-C(CH2CH(Me)2)(Me)(OEt) | Y-148 |
| Pyd-C(CH2CH(Me)2)(OEt)CH2Me | Y-149 |
| Pyd-CH(cyclopropyl)(OEt) | Y-150 |
| Pyd-C(cyclopropyl)(Me)(OEt) | Y-151 |
| Pyd-C(cyclopropyl)(OEt)CH2Me | Y-152 |
| Pyd-CH(cyclobutyl)(OEt) | Y-153 |

TABLE 2-continued

| Structure | ID |
|---|---|
| Pyd—C(Me)(OEt)—cyclobutyl | Y-154 |
| Pyd—CH(cyclobutyl)—CH(Me)(OEt) | Y-155 |
| Pyd—CH(OEt)—cyclopentyl | Y-156 |
| Pyd—C(Me)(OEt)—cyclopentyl | Y-157 |
| Pyd—CH(cyclopentyl)—CH(Me)(OEt) | Y-158 |
| Pyd—CH(OEt)—cyclohexyl | Y-159 |
| Pyd—C(Me)(OEt)—cyclohexyl | Y-160 |
| Pyd—CH(cyclohexyl)—CH(Me)(OEt) | Y-161 |
| Pyd—CH2—OPr | Y-162 |
| Pyd—CH(Me)—OPr | Y-163 |
| Pyd—C(Me)(Me)—OPr | Y-164 |
| Pyd—CH(Me)—CH2—OPr | Y-165 |
| Pyd—C(Me)(Me)—OPr (branched) | Y-166 |
| Pyd—C(CH2Me)(CH2Me)—OPr with Me | Y-167 |
| Pyd—CH(Pr)—OPr | Y-168 |
| Pyd—C(Pr)(Me)—OPr | Y-169 |
| Pyd—C(Pr)(Me)(CH2)—OPr | Y-170 |
| Pyd—CH(Bu)—OPr | Y-171 |
| Pyd—C(Bu)(Me)—OPr | Y-172 |
| Pyd—C(Bu)(Me)(CH2)—OPr | Y-173 |
| Pyd—CH(Pent)—OPr | Y-174 |
| Pyd—CH(Hex)—OPr | Y-175 |
| Pyd—CH(Hept)—OPr | Y-176 |
| Pyd—CH(Oct)—OPr | Y-177 |

TABLE 2-continued

| Structure | ID |
|---|---|
| Pyd-CH(OPr)-CH(Me)Me | Y-178 |
| Pyd-C(Me)(OPr)-CH(Me)Me | Y-179 |
| Pyd-C(Me)(CH2Me)-C(Me)(OPr)... | Y-180 |
| Pyd-CH(OPr)-C(Me)(Me)Me | Y-181 |
| Pyd-C(Me)(OPr)-C(Me)(Me)Me | Y-182 |
| Pyd-C(Me)(OPr)(CH2Me)-C(Me)(Me)Me | Y-183 |
| Pyd-CH(OPr)-CH2-CH(Me)Me | Y-184 |
| Pyd-C(Me)(OPr)-CH2-CH(Me)Me | Y-185 |
| Pyd-C(Et)(OPr)-CH2-CH(Me)Me | Y-186 |
| Pyd-CH(OPr)-cyclopropyl | Y-187 |
| Pyd-C(Me)(OPr)-cyclopropyl | Y-188 |
| Pyd-CH(cyclopropyl)(OPr)... | Y-189 |
| Pyd-CH(OPr)-cyclobutyl | Y-190 |
| Pyd-C(Me)(OPr)-cyclobutyl | Y-191 |
| Pyd-CH(cyclobutyl)-CH(Me)(OPr) | Y-192 |
| Pyd-CH(OPr)-cyclopentyl | Y-193 |
| Pyd-C(Me)(OPr)-cyclopentyl | Y-194 |
| Pyd-C(cyclopentyl)(OPr)-Me | Y-195 |
| Pyd-CH(OPr)-cyclohexyl | Y-196 |
| Pyd-C(Me)(OPr)-cyclohexyl | Y-197 |
| Pyd-C(cyclohexyl)(OPr)-CH2Me | Y-198 |

TABLE 2-continued

| Structure | ID |
|---|---|
| Pyd-CH(OiPr) attached to CH2 with OiPr (Pyd-CH2-CH(OiPr)... ) — OiPr/Pyd | Y-199 |
| Pyd-CH(Me)-OiPr | Y-200 |
| Pyd-C(OiPr)(Me)(Me) | Y-201 |
| Pyd-CH(Me)-CH(OiPr) pattern | Y-202 |
| Pyd-C(Me)(Me)-OiPr variant | Y-203 |
| Pyd-C(OiPr)(CH2Me)(CH2Me) | Y-204 |
| Pyd-CH(Pr)-OiPr | Y-205 |
| Pyd-C(Pr)(Me)-OiPr | Y-206 |
| Pyd-C(Pr)(OiPr)-Me | Y-207 |
| Pyd-CH(Bu)-OiPr | Y-208 |
| Pyd-C(Bu)(Me)-OiPr | Y-209 |
| Pyd-C(Bu)(OiPr)-Me | Y-210 |
| Pyd-CH(Pent)-OiPr | Y-211 |
| Pyd-CH(Hex)-OiPr | Y-212 |
| Pyd-CH(Hept)-OiPr | Y-213 |

TABLE 2-continued

| Structure | ID |
|---|---|
| Pyd-CH(Oct)-OiPr | Y-214 |
| Pyd-CH(OiPr)-CH(Me)(Me) | Y-215 |
| Pyd-C(OiPr)(Me)-CH(Me)(Me) | Y-216 |
| Pyd-C(OiPr)(Me)-CH(Me)(Me) variant | Y-217 |
| Pyd-CH(OiPr)-C(Me)(Me)(Me) | Y-218 |
| Pyd-C(OiPr)(Me)-C(Me)(Me)(Me) | Y-219 |
| Pyd-C(OiPr)(Me)-C(Me)(Me)(Me) variant | Y-220 |
| Pyd-CH(OiPr)-CH2-CH(Me)(Me) | Y-221 |
| Pyd-C(OiPr)(Me)-CH2-CH(Me)(Me) | Y-222 |
| Pyd-C(OiPr)(Me)-CH2-CH(Me)(Me) variant | Y-223 |
| Pyd-CH(OiPr)-cyclopropyl | Y-224 |

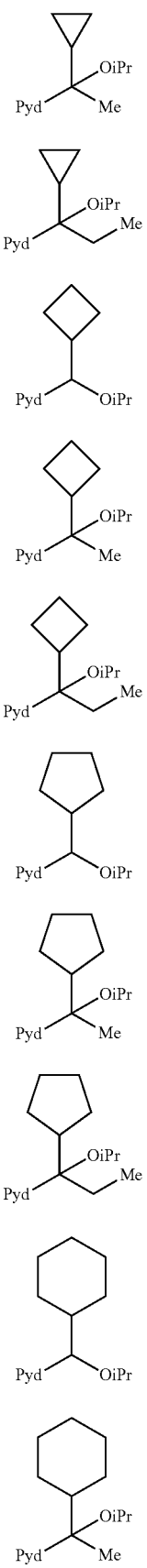
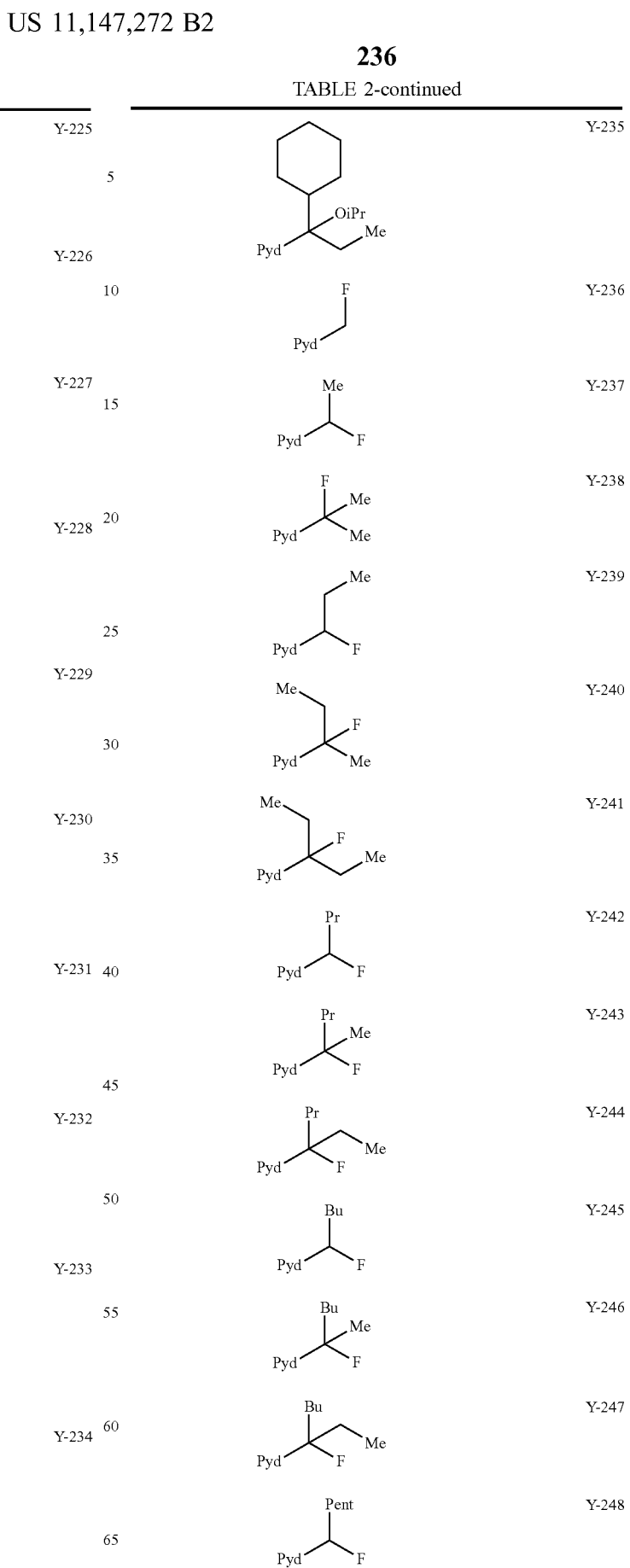

TABLE 2-continued

| Structure | ID |
|---|---|
| Pyd-CHF-Hex | Y-249 |
| Pyd-CHF-Hept | Y-250 |
| Pyd-CHF-Oct | Y-251 |
| Pyd-CHF-CH(Me)₂ | Y-252 |
| Pyd-CF(Me)-CH(Me)₂ | Y-253 |
| Pyd-CH(Me)-CF(Me)-Me | Y-254 |
| Pyd-CHF-C(Me)₃ | Y-255 |
| Pyd-CF(Me)-C(Me)₃ | Y-256 |
| Pyd-C(Me)(Et)-CF(Me)-Me... | Y-257 |
| Pyd-CHF-CH₂-CH(Me)₂ | Y-258 |
| Pyd-CF(Me)-CH₂-CH(Me)-Me | Y-259 |
| Pyd-CF(Et)-CH₂-CH(Me)-Me | Y-260 |
| Pyd-CHF-cyclopropyl | Y-261 |
| Pyd-CF(Me)-cyclopropyl | Y-262 |
| Pyd-CF(CH₂Me)-cyclopropyl | Y-263 |
| Pyd-CHF-cyclobutyl | Y-264 |
| Pyd-CF(Me)-cyclobutyl | Y-265 |
| Pyd-CF(CH₂Me)-cyclobutyl | Y-266 |
| Pyd-CHF-cyclopentyl | Y-267 |
| Pyd-CF(Me)-cyclopentyl | Y-268 |
| Pyd-CF(CH₂Me)-cyclopentyl | Y-269 |
| Pyd-CHF-cyclohexyl | Y-270 |

TABLE 2-continued
| | |
|---|---|
| 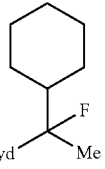 | Y-271 |
| 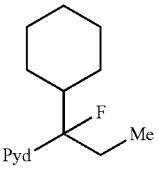 | Y-272 |
|  | Y-273 |
| 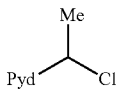 | Y-274 |
| 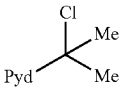 | Y-275 |
| 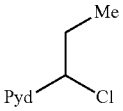 | Y-276 |
| 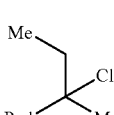 | Y-277 |
| 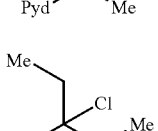 | Y-278 |
| 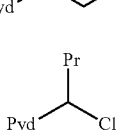 | Y-279 |
| 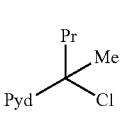 | Y-280 |
| 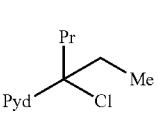 | Y-281 |
| 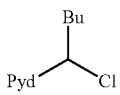 | Y-282 |
| 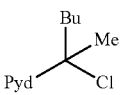 | Y-283 |
| 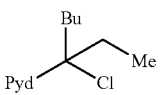 | Y-284 |
| 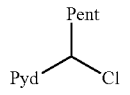 | Y-285 |
| 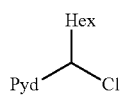 | Y-286 |
| 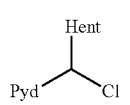 | Y-287 |
| 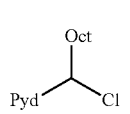 | Y-288 |
| 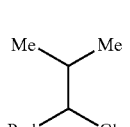 | Y-289 |
| 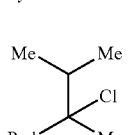 | Y-290 |
| 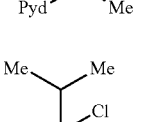 | Y-291 |
| 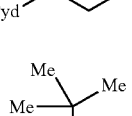 | Y-292 |
| 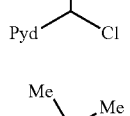 | Y-293 |
| 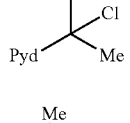 | Y-294 |
| 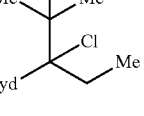 | Y-295 |

TABLE 2-continued

| Structure | ID |
|---|---|
| Pyd-C(Me)(Cl)-CH2-CH(Me)2 | Y-296 |
| Pyd-C(Et)(Cl)-CH2-CH(Me)2 | Y-297 |
| Pyd-CH(Cl)-cyclopropyl | Y-298 |
| Pyd-C(Me)(Cl)-cyclopropyl | Y-299 |
| Pyd-C(Et)(Cl)-cyclopropyl | Y-300 |
| Pyd-CH(Cl)-cyclobutyl | Y-301 |
| Pyd-C(Me)(Cl)-cyclobutyl | Y-302 |
| Pyd-C(Et)(Cl)-cyclobutyl | Y-303 |
| Pyd-CH(Cl)-cyclopentyl | Y-304 |
| Pyd-C(Me)(Cl)-cyclopentyl | Y-305 |
| Pyd-C(Me)(Cl)-CH2-cyclopentyl | Y-306 |
| Pyd-CH(Cl)-cyclohexyl | Y-307 |
| Pyd-C(Me)(Cl)-cyclohexyl | Y-308 |
| Pyd-C(Et)(Cl)-cyclohexyl | Y-309 |
| Pyd-C≡CH | Y-310 |
| Pyd-C≡C-Me | Y-311 |
| Pyd-CH=CH2 | Y-312 |
| Pyd-C(Me)=CH2 | Y-313 |
| Pyd-CH=CH-Me (E) | Y-314 |
| Pyd-CH=CH-Me (Z) | Y-315 |
| Pyd-CH=C(Me)2 | Y-316 |
| Pyd-C(Me)=CH-Me | Y-317 |

TABLE 2-continued
| Structure | Label |
|---|---|
| 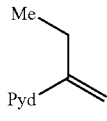 | Y-318 |
| 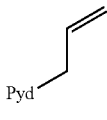 | Y-319 |
| 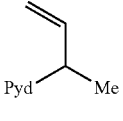 | Y-320 |
| 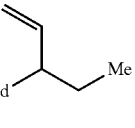 | Y-321 |
| 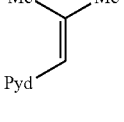 | Y-322 |
| 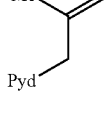 | Y-323 |
| 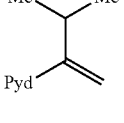 | Y-324 |
| 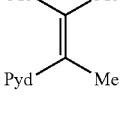 | Y-325 |
| 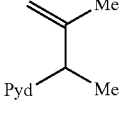 | Y-326 |
| 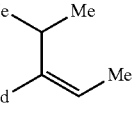 | Y-327 |
| 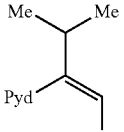 | Y-328 |
| 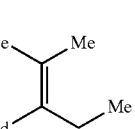 | Y-329 |
| 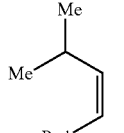 | Y-330 |
| 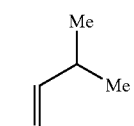 | Y-331 |
| 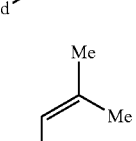 | Y-332 |
| 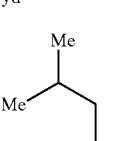 | Y-333 |
| 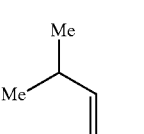 | Y-334 |
| 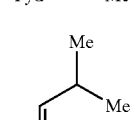 | Y-335 |
| 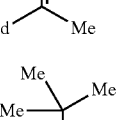 | Y-336 |
| 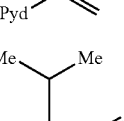 | Y-337 |
| 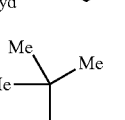 | Y-338 |
| 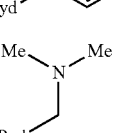 | Y-339 |
| 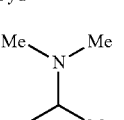 | Y-340 |

TABLE 2-continued

| Structure | ID |
|---|---|
| Me-N(Me)-CH(Me)-Pyd | Y-341 |
| Me-N(Me)-CH(Et)-Pyd (Et shown as CH2Me) | Y-342 |
| Me-N(Et)-CH(Me)-Pyd | Y-343 |
| Me-N(Et)-CH(Et)-Pyd | Y-344 |
| Me-N(iPr)-CH2-Pyd | Y-345 |
| Me-N(iPr)-CH(Me)-Pyd | Y-346 |
| Me-N(iPr)-CH(Et)-Pyd | Y-347 |
| HN(OMe)-CH2-Pyd | Y-348 |
| HN(OEt)-CH2-Pyd | Y-349 |
| HN(OiPr)-CH2-Pyd | Y-350 |
| Me-N(OMe)-CH2-Pyd | Y-351 |
| Me-N(OEt)-CH2-Pyd | Y-352 |
| Me-N(OiPr)-CH2-Pyd | Y-353 |
| Et-N(OMe)-CH2-Pyd | Y-354 |
| Et-N(OEt)-CH2-Pyd | Y-355 |
| Et-N(OiPr)-CH2-Pyd | Y-356 |
| MeC(O)-N(OMe)-CH2-Pyd | Y-357 |
| MeC(O)-N(OEt)-CH2-Pyd | Y-358 |
| MeC(O)-N(OiPr)-CH2-Pyd | Y-359 |
| MeOC(O)-N(OMe)-CH2-Pyd | Y-360 |
| MeOC(O)-N(OEt)-CH2-Pyd | Y-361 |
| MeOC(O)-N(OiPr)-CH2-Pyd | Y-362 |

TABLE 2-continued

| Structure | ID |
|---|---|
| EtO-C(O)-N(OMe)-CH2-Pyd | Y-363 |
| EtO-C(O)-N(OEt)-CH2-Pyd | Y-364 |
| EtO-C(O)-N(OiPr)-CH2-Pyd | Y-365 |
| iPrO-C(O)-N(OMe)-CH2-Pyd | Y-366 |
| iPrO-C(O)-N(OEt)-CH2-Pyd | Y-367 |
| iPrO-C(O)-N(OiPr)-CH2-Pyd | Y-368 |
| Pyd-CH2-C≡CH | Y-369 |
| Pyd-CH(Me)-C≡CH | Y-370 |
| Pyd-CH(CH2Me)-C≡CH | Y-371 |
| Pyd-CH(OMe)-C≡CH | Y-372 |
| Pyd-C(OH)(Me)-CH2-C≡CH | Y-373 |
| Pyd-CH(OH)-C≡CH | Y-374 |
| Pyd-C(OH)(Me)-C≡CH | Y-375 |
| Pyd-C(OMe)(Me)-CH2-C≡CH | Y-376 |
| Pyd-C(OMe)(Me)-C≡CH | Y-377 |
| Pyd-CH(OEt)-C≡CH | Y-378 |
| Pyd-C(OEt)(Me)-C≡CH | Y-379 |
| Pyd-C(OEt)(Me)-CH2-C≡CH | Y-380 |
| Pyd-CH(OiPr)-C≡CH | Y-381 |
| Pyd-C(OiPr)(Me)-C≡CH | Y-382 |
| Pyd-C(OiPr)(Me)-CH2-C≡CH | Y-383 |

TABLE 2-continued

| Structure | Label |
|---|---|
| Pyd−C≡CH with F | Y-384 |
| Pyd−C(Me)(F)−C≡CH | Y-385 |
| Pyd−CH(Et)(F)... C≡CH with Me | Y-386 |
| Pyd−CH(Cl)−C≡CH | Y-387 |
| Pyd−C(Me)(Cl)−C≡CH | Y-388 |
| Pyd−C(Et)(Cl)(Me)−C≡CH | Y-389 |
| Pyd−C(OH)(Me)−CH=CH2 | Y-390 |
| Pyd−C(OH)(Et)(Me)−CH=CH2 | Y-391 |
| Pyd−CH(OMe)−CH=CH2 | Y-392 |
| Pyd−C(OMe)(Me)−CH=CH2 | Y-393 |
| Pyd−C(OMe)(Et)(Me)−CH=CH2 | Y-394 |
| Pyd−CH(OEt)−CH=CH2 | Y-395 |
| Pyd−C(OEt)(Me)−CH=CH2 | Y-396 |
| Pyd−C(OEt)(Et)(Me)−CH=CH2 | Y-397 |
| Pyd−CH(OiPr)−CH=CH2 | Y-398 |
| Pyd−C(OiPr)(Me)−CH=CH2 | Y-399 |
| Pyd−C(OiPr)(Et)(Me)−CH=CH2 | Y-400 |
| Pyd−CH(F)−CH=CH2 | Y-401 |
| Pyd−C(F)(Me)−CH=CH2 | Y-402 |
| Pyd−C(F)(Et)(Me)−CH=CH2 | Y-403 |
| Pyd−CH(Cl)−CH=CH2 | Y-404 |
| Pyd−C(Cl)(Me)−CH=CH2 | Y-405 |
| Pyd−C(Cl)(Et)(Me)−CH=CH2 | Y-406 |
| Pyd−CH2CH2−CH=CH2 | Y-407 |
| Pyd−CH(OH)−CH2−CH=CH2 | Y-408 |

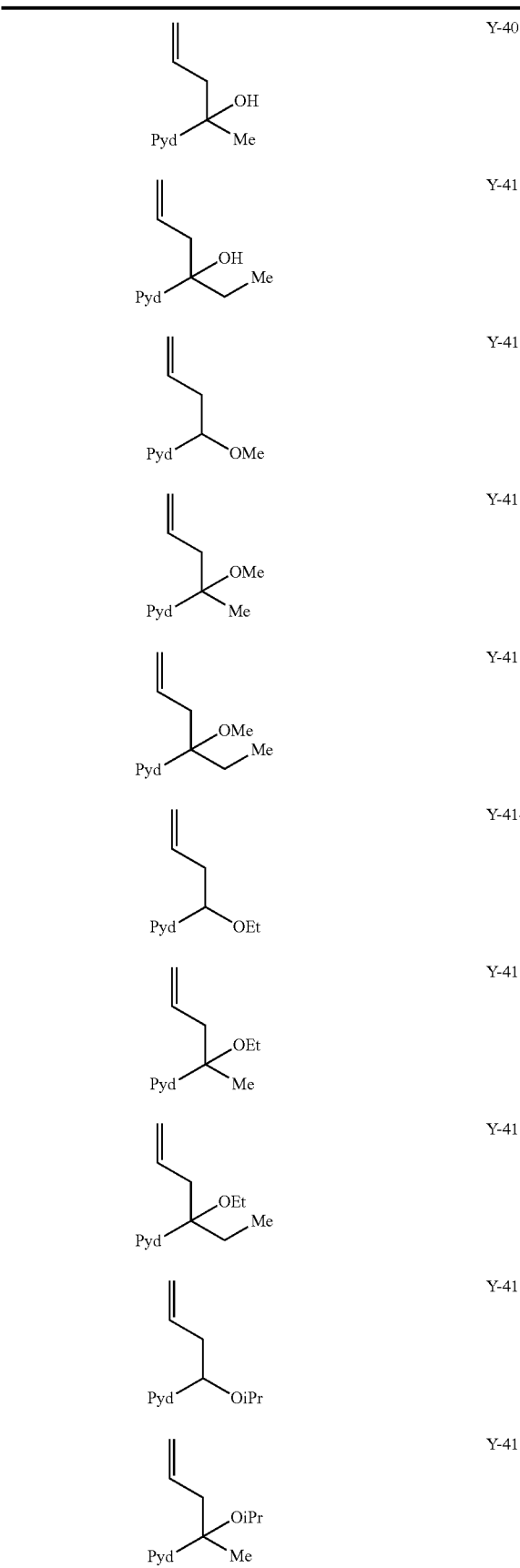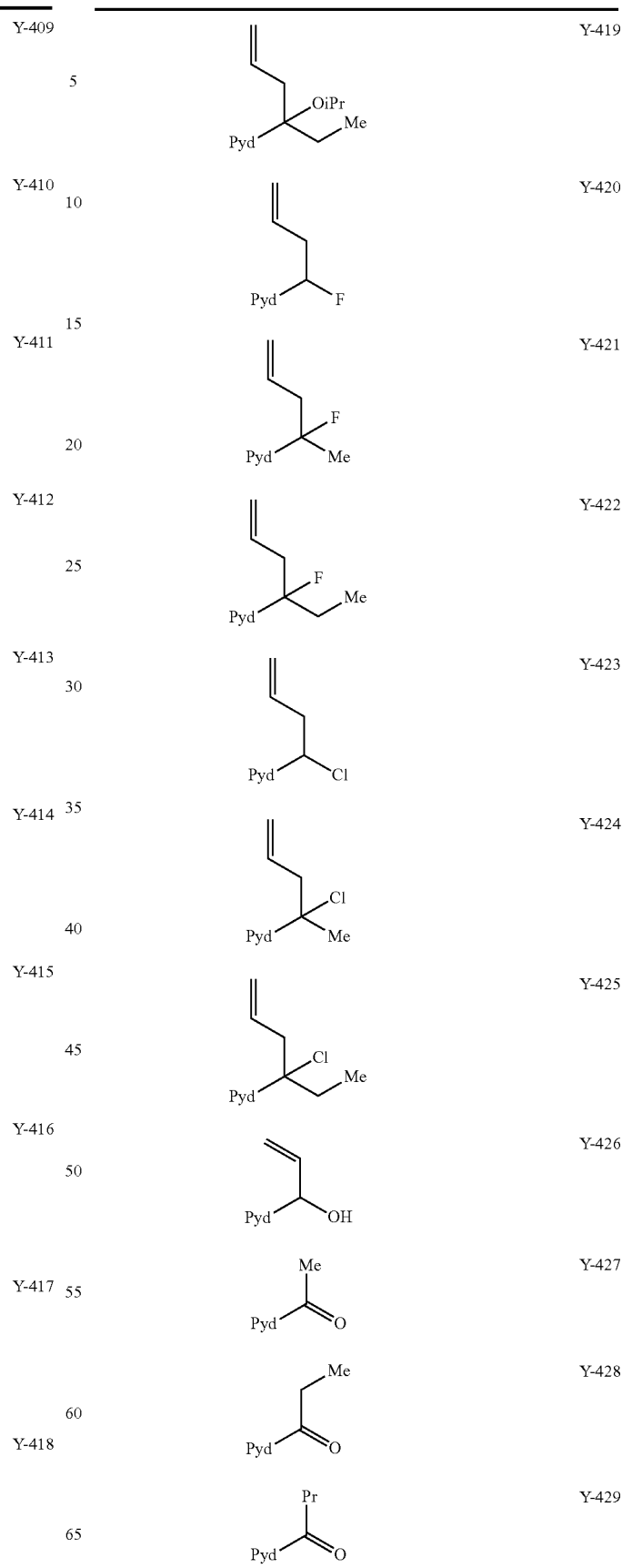

TABLE 2-continued
| | |
|---|---|
| 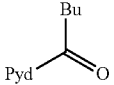 | Y-430 |
| 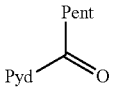 | Y-431 |
| 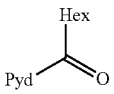 | Y-432 |
| 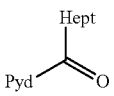 | Y-433 |
| 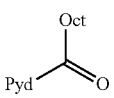 | Y-434 |
| 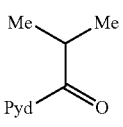 | Y-435 |
| 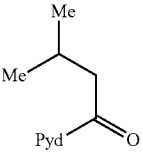 | Y-436 |
| 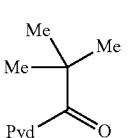 | Y-437 |
| 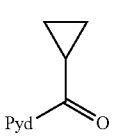 | Y-438 |
| 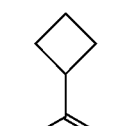 | Y-439 |
| 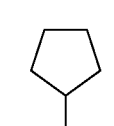 | Y-440 |
| 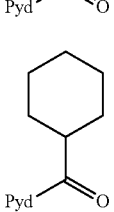 | Y-441 |
TABLE 2-continued
| | |
|---|---|
|  | Y-442 |
| 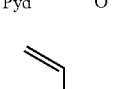 | Y-443 |
| 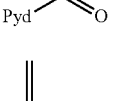 | Y-444 |
| 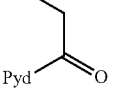 | Y-445 |
| 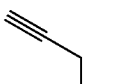 | Y-446 |
| 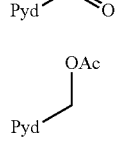 | Y-447 |
| 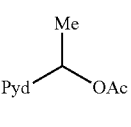 | Y-448 |
| 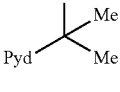 | Y-449 |
| 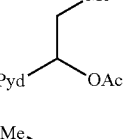 | Y-450 |
| 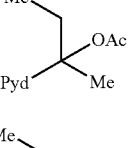 | Y-451 |
| 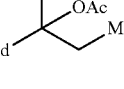 | Y-452 |
| 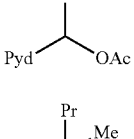 | Y-453 |
| 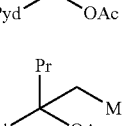 | Y-454 |

TABLE 2-continued
| | |
|---|---|
| 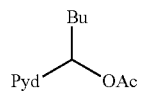 | Y-455 |
| 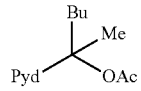 | Y-456 |
| 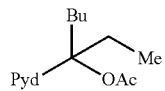 | Y-457 |
| 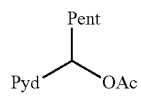 | Y-458 |
| 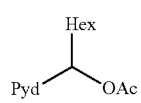 | Y-459 |
| 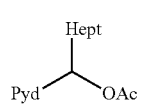 | Y-460 |
| 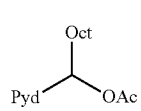 | Y-461 |
| 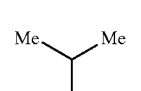 | Y-462 |
| 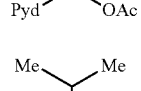 | Y-463 |
| 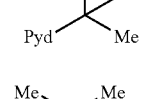 | Y-464 |
| 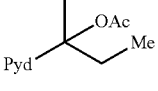 | Y-465 |
| 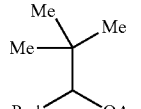 | Y-466 |
| 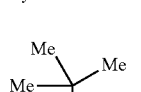 | Y-467 |
TABLE 2-continued
| | |
|---|---|
| 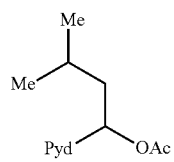 | Y-468 |
| 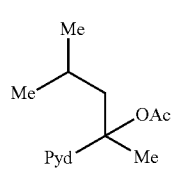 | Y-469 |
| 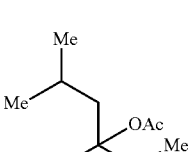 | Y-470 |
| 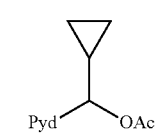 | Y-471 |
| 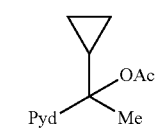 | Y-472 |
| 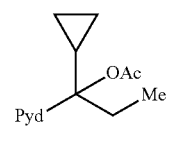 | Y-473 |
| 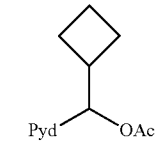 | Y-474 |
| 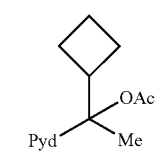 | Y-475 |
| 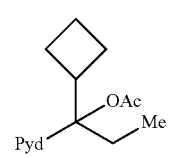 | Y-476 |
| 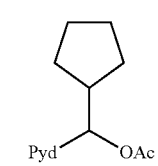 | Y-477 |

TABLE 2-continued

| Structure | ID |
|---|---|
| Pyd-C(cyclopentyl)(OAc)(Me) | Y-478 |
| Pyd-CH2-C(cyclopentyl)(OAc)(Me) (Et variant) | Y-479 |
| Pyd-CH(cyclohexyl)(OAc) | Y-480 |
| Pyd-C(cyclohexyl)(OAc)(Me) | Y-481 |
| Pyd-C(cyclohexyl)(OAc)(Et) | Y-482 |
| Pyd-CH(C≡CH)(OAc) | Y-483 |
| Pyd-C(C≡CH)(OAc)(Me) | Y-484 |
| Pyd-C(C≡CH)(OAc)(Et) | Y-485 |
| Pyd-CH(CH=CH2)(OAc) | Y-486 |
| Pyd-C(CH=CH2)(OAc)(Me) | Y-487 |
| Pyd-C(CH=CH2)(OAc)(Et) | Y-488 |
| Pyd-CH(CH2CH=CH2)(OAc) | Y-489 |
| Pyd-C(CH2CH=CH2)(OAc)(Me) | Y-490 |
| Pyd-C(CH2CH=CH2)(OAc)(Et) | Y-491 |
| Pyd-CH2-F | Y-492 |
| Pyd-CH2-Br | Y-493 |
| Pyd-CH2-Cl | Y-494 |
| Pyd-CH2-I | Y-495 |
| Pyd-CH=CF2 | Y-496 |
| Pyd-CH=CCl2 | Y-497 |
| Pyd-CH=CBr2 | Y-498 |
| Pyd-CH=CI2 | Y-499 |
| Pyd-CF=CHF | Y-500 |
| Pyd-CF=CHF (isomer) | Y-501 |
| Pyd-CBr=CHBr | Y-502 |

TABLE 2-continued

| Structure | Label |
|---|---|
| Pyd-C(Br)=CBr₂ | Y-503 |
| Pyd-C(Cl)=CHCl (E) | Y-504 |
| Pyd-C(Cl)=CHCl (Z) | Y-505 |
| Pyd-C(I)=CHI (E) | Y-506 |
| Pyd-C(I)=CHI (Z) | Y-507 |
| Pyd-CH=CH-CN (E) | Y-508 |
| Pyd-CH=CH-CN (Z) | Y-509 |
| Pyd-CH₂-CHO | Y-510 |
| Pyd-CH₂-O-C₆H₅ | Y-511 |
| Pyd-CH₂-O-C₆H₄-4-F | Y-512 |
| Pyd-CH₂-O-C₆H₄-3-F | Y-513 |
| Pyd-CH₂-O-C₆H₄-2-F | Y-514 |
| Pyd-CH₂-O-C₆H₄-4-Cl | Y-515 |
| Pyd-CH₂-O-C₆H₄-3-Cl | Y-516 |
| Pyd-CH₂-O-C₆H₄-2-Cl | Y-517 |
| Pyd-CH₂-O-C₆H₄-4-Br | Y-518 |
| Pyd-CH₂-O-C₆H₄-3-Br | Y-519 |
| Pyd-CH₂-O-C₆H₄-2-Br | Y-520 |
| Pyd-CH₂-O-C₆H₄-4-I | Y-521 |
| Pyd-CH₂-O-C₆H₄-3-I | Y-522 |
| Pyd-CH₂-O-C₆H₄-2-I | Y-523 |
| Pyd-CH₂-O-C₆H₄-4-OMe | Y-524 |
| Pyd-CH₂-O-C₆H₄-3-OMe | Y-525 |
| Pyd-CH₂-O-C₆H₄-2-OMe | Y-526 |
| Pyd-C(=O)-CF₃ | Y-527 |
| Pyd-CH₂-O-CH₂-CF₃ | Y-528 |

TABLE 2-continued

| Structure | Label |
|---|---|
| Pyd-CH(Me)-O-CH2-CF3 | Y-529 |
| F3C-CH2-O-C(Me)(Me)-Pyd | Y-530 |
| Pyd-CH(CH2Me)-O-CH2-CF3 | Y-531 |
| Pyd-C(Me)(CH2-CF3)-O-Me | Y-532 |
| Y-533 | |
| Pyd-CH(Pr)-O-CH2-CF3 | Y-534 |
| Y-535 | |
| Y-536 | |
| Pyd-CH(Bu)-O-CH2-CF3 | Y-537 |
| Y-538 | |
| Y-539 | |
| Pyd-CH(Pent)-O-CH2-CF3 | Y-540 |
| Pyd-CH(Hex)-O-CH2-CF3 | Y-541 |
| Pyd-CH(Hept)-O-CH2-CF3 | Y-542 |
| Pyd-CH(Oct)-O-CH2-CF3 | Y-543 |
| Y-544 | |
| Y-545 | |
| Y-546 | |
| Y-547 | |
| Y-548 | |
| Y-549 | |
| Y-550 | |

TABLE 2-continued
| | |
|---|---|
| 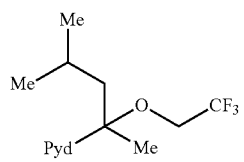 | Y-551 |
| 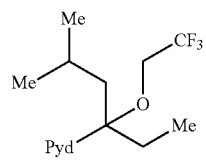 | Y-552 |
| 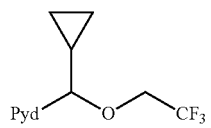 | Y-553 |
| 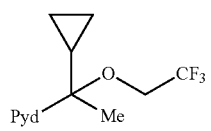 | Y-554 |
| 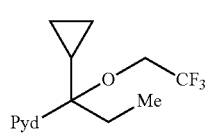 | Y-555 |
| 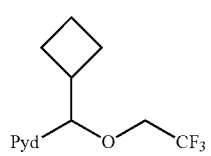 | Y-556 |
| 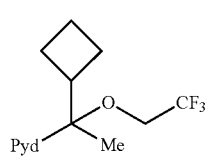 | Y-557 |
| 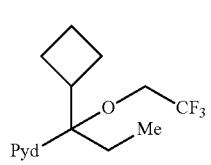 | Y-558 |
| 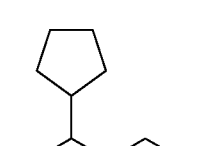 | Y-559 |
| 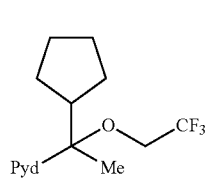 | Y-560 |
TABLE 2-continued
| | |
|---|---|
| 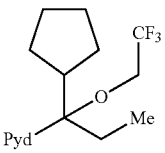 | Y-561 |
| 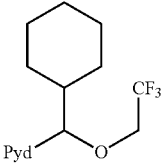 | Y-562 |
| 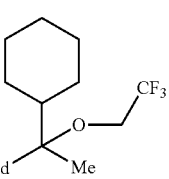 | Y-563 |
| 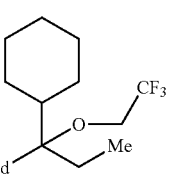 | Y-564 |
| 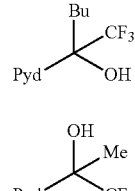 | Y-565 |
| 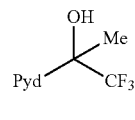 | Y-566 |
| 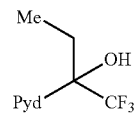 | Y-567 |
| 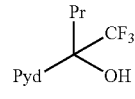 | Y-568 |
| 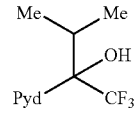 | Y-569 |
| 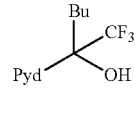 | Y-570 |
| 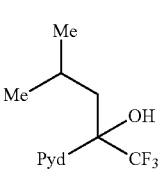 | Y-571 |

TABLE 2-continued

| Structure | ID |
|---|---|
| Pyd-C(Me)(CMe₂Me)(OH)(CF₃) | Y-572 |
| Pyd-C(cyclopropyl)(OH)(CF₃) | Y-573 |
| Pyd-C(cyclobutyl)(OH)(CF₃) | Y-574 |
| Pyd-C(cyclopentyl)(OH)(CF₃) | Y-575 |
| Pyd-C(cyclohexyl)(OH)(CF₃) | Y-576 |
| Pyd-C(CF₃)(OH)(C≡CH) | Y-577 |
| Pyd-C(CF₃)(OH)(CH=CH₂) | Y-578 |
| Pyd-C(CF₃)(OH)(CH₂CH=CH₂) | Y-579 |
| Pyd-CH(CF₃)(OMe) | Y-580 |
| Pyd-C(OMe)(Me)(CF₃) | Y-581 |
| Pyd-C(CH₂Me)(OMe)(CF₃) | Y-582 |
| Pyd-C(Pr)(CH₃)(OMe) | Y-583 |
| Pyd-C(Me)(CHMe)(OMe)(CF₃) | Y-584 |
| Pyd-C(Bu)(CF₃)(OMe) | Y-585 |
| Pyd-C(CH₂CHMe₂)(OMe)(CF₃) | Y-586 |
| Pyd-C(CMe₃)(OMe)(CF₃) | Y-587 |
| Pyd-C(cyclopropyl)(OMe)(CF₃) | Y-588 |
| Pyd-C(cyclobutyl)(OMe)(CF₃) | Y-589 |
| Pyd-C(cyclopentyl)(OMe)(CF₃) | Y-590 |
| Pyd-C(cyclohexyl)(OMe)(CF₃) | Y-591 |
| Pyd-C(CF₃)(C≡CH)(OMe) | Y-592 |
| Pyd-C(CF₃)(CH=CH₂)(OMe) | Y-593 |
| Pyd-C(CF₃)(CH₂CH=CH₂)(OMe) | Y-594 |
| Pyd-CH(CF₃)(OEt) | Y-595 |

TABLE 2-continued
| | |
|---|---|
| 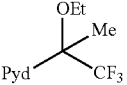 | Y-596 |
| 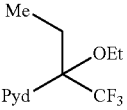 | Y-597 |
| 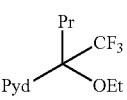 | Y-598 |
| 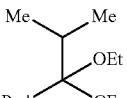 | Y-599 |
| 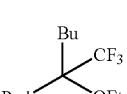 | Y-600 |
| 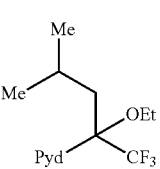 | Y-601 |
| 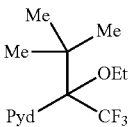 | Y-602 |
| 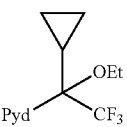 | Y-603 |
| 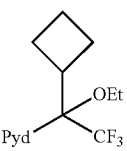 | Y-604 |
| 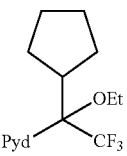 | Y-605 |
| 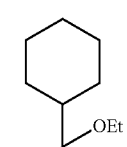 | Y-606 |
| 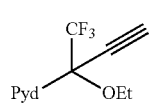 | Y-607 |
| 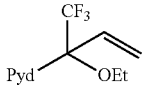 | Y-608 |
| 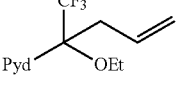 | Y-609 |
| 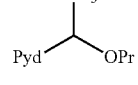 | Y-610 |
| 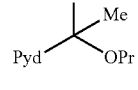 | Y-611 |
| 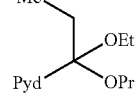 | Y-612 |
| 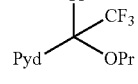 | Y-613 |
| 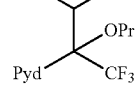 | Y-614 |
| 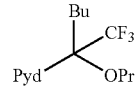 | Y-615 |
| 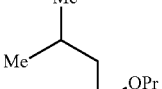 | Y-616 |
| 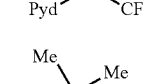 | Y-617 |
| 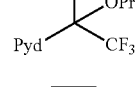 | Y-618 |
| 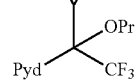 | Y-619 |
| 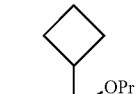 | Y-620 |

TABLE 2-continued

| Structure | ID |
|---|---|
| Pyd-C(OPr)(CF₃)-cyclohexyl | Y-621 |
| Pyd-C(OPr)(CF₃)-C≡CH | Y-622 |
| Pyd-C(OPr)(CF₃)-CH=CH₂ | Y-623 |
| Pyd-C(OPr)(CF₃)-CH₂-CH=CH₂ | Y-624 |
| Pyd-CH(OiPr)(CF₃) | Y-625 |
| Pyd-C(OiPr)(Me)(CF₃) | Y-626 |
| Pyd-C(CH₂Me)(OiPr)(CF₃) | Y-627 |
| Pyd-C(Pr)(CF₃)(OiPr) | Y-628 |
| Pyd-C(CH(Me)₂)(OiPr)(CF₃) | Y-629 |
| Pyd-C(Bu)(CF₃)(OiPr) | Y-630 |
| Pyd-C(CH₂CH(Me)₂)(OiPr)(CF₃) | Y-631 |
| Pyd-C(C(Me)₂Me)(OiPr)(CF₃) | Y-632 |
| Pyd-C(cyclopropyl)(OiPr)(CF₃) | Y-633 |

TABLE 2-continued

| Structure | ID |
|---|---|
| Pyd-C(OiPr)(CF₃)-cyclobutyl | Y-634 |
| Pyd-C(OiPr)(CF₃)-cyclopentyl | Y-635 |
| Pyd-C(OiPr)(CF₃)-cyclohexyl | Y-636 |
| Pyd-C(OiPr)(CF₃)-C≡CH | Y-637 |
| Pyd-C(OiPr)(CF₃)-CH=CH₂ | Y-638 |
| Pyd-C(OiPr)(CF₃)-CH₂-CH=CH₂ | Y-639 |
| Pyd-CH(CF₃)(OAc) | Y-640 |
| Pyd-C(OAc)(Me)(CF₃) | Y-641 |
| Pyd-C(CH₂Me)(OAc)(CF₃) | Y-642 |
| Pyd-C(Pr)(CF₃)(OAc) | Y-643 |
| Pyd-C(CH(Me)₂)(OAc)(CF₃) | Y-644 |
| Pyd-C(Bu)(CF₃)(OAc) | Y-645 |

TABLE 2-continued

| Structure | ID |
|---|---|
| Pyd-C(Me)(CH2CH(Me)2)(OAc)(CF3) | Y-646 |
| Pyd-C(C(Me)2Me)(OAc)(CF3) | Y-647 |
| Pyd-C(cyclopropyl)(OAc)(CF3) | Y-648 |
| Pyd-C(cyclobutyl)(OAc)(CF3) | Y-649 |
| Pyd-C(cyclopentyl)(OAc)(CF3) | Y-650 |
| Pyd-C(cyclohexyl)(OAc)(CF3) | Y-651 |
| Pyd-C(C≡CH)(CF3)(OAc) | Y-652 |
| Pyd-C(CH=CH2)(CF3)(OAc) | Y-653 |
| Pyd-C(CH2CH=CH2)(CF3)(OAc) | Y-654 |
| Pyd-CH(F)(CF3) | Y-655 |
| Pyd-C(F)(Me)(CF3) | Y-656 |
| Pyd-C(CH2Me)(F)(CF3) | Y-657 |
| Pyd-C(Pr)(F)(CF3) | Y-658 |
| Pyd-C(CH(Me)2)(F)(CF3) | Y-659 |
| Pyd-C(Bu)(F)(CF3) | Y-660 |
| Pyd-C(CH2CH(Me)2)(F)(CF3) | Y-661 |
| Pyd-C(C(Me)2Me)(F)(CF3) | Y-662 |
| Pyd-C(cyclopropyl)(F)(CF3) | Y-663 |
| Pyd-C(cyclobutyl)(F)(CF3) | Y-664 |
| Pyd-C(cyclopentyl)(F)(CF3) | Y-665 |
| Pyd-C(cyclohexyl)(F)(CF3) | Y-666 |
| Pyd-C(C≡CH)(CF3)(F) | Y-667 |
| Pyd-C(CH=CH2)(CF3)(F) | Y-668 |
| Pyd-C(CH2CH=CH2)(CF3)(F) | Y-669 |

TABLE 2-continued

| Structure | ID |
|---|---|
| Pyd-C(CF3)(H)-Cl | Y-670 |
| Pyd-C(Cl)(Me)-CF3 | Y-671 |
| Pyd-C(CH2Me)(Cl)-CF3 | Y-672 |
| Pyd-C(Pr)(CF3)-Cl | Y-673 |
| Pyd-C(CH(Me)2)(Cl)-CF3 | Y-674 |
| Pyd-C(Bu)(CF3)-Cl | Y-675 |
| Pyd-C(CH2CH(Me)2)(Cl)-CF3 | Y-676 |
| Pyd-C(CMe3)(Cl)-CF3 | Y-677 |
| Pyd-C(cyclopropyl)(Cl)-CF3 | Y-678 |
| Pyd-C(cyclobutyl)(Cl)-CF3 | Y-679 |
| Pyd-C(cyclopentyl)(Cl)-CF3 | Y-680 |
| Pyd-C(cyclohexyl)(Cl)-CF3 | Y-681 |

TABLE 2-continued

| Structure | ID |
|---|---|
| Pyd-C(C≡CH)(CF3)-Cl | Y-682 |
| Pyd-C(CH=CH2)(CF3)-Cl | Y-683 |
| Pyd-C(CH2CH=CH2)(CF3)-Cl | Y-684 |
| Pyd-CH(CF3)-O-CH2CF3 | Y-685 |
| Pyd-C(Me)(CF3)-O-CH2CF3 | Y-686 |
| Pyd-C(Et)(CF3)-O-CH2CF3 | Y-687 |
| Pyd-C(Pr)(CF3)-O-CH2CF3 | Y-688 |
| Pyd-C(CH(Me)2)(CF3)-O-CH2CF3 | Y-689 |
| Pyd-C(Bu)(CF3)-O-CH2CF3 | Y-690 |
| Pyd-C(CH2CH(Me)2)(CF3)-O-CH2CF3 | Y-691 |
| Pyd-C(CMe3)(CF3)-O-CH2CF3 | Y-692 |
| Pyd-C(cyclopropyl)(CF3)-O-CH2CF3 | Y-693 |
| Pyd-C(cyclobutyl)(CF3)-O-CH2CF3 | Y-694 |

TABLE 2-continued

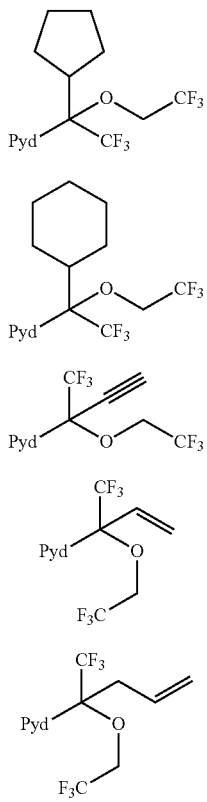

| | |
|---|---|
| | Y-695 |
| | Y-696 |
| | Y-697 |
| | Y-698 |
| | Y-699 |

Production Process A to Production Process AJ for producing the compounds of formula (1) is hereinbelow described. These processes are only illustrative, and the production of the compounds of the present invention is not limited to these processes.

[Production Process A]

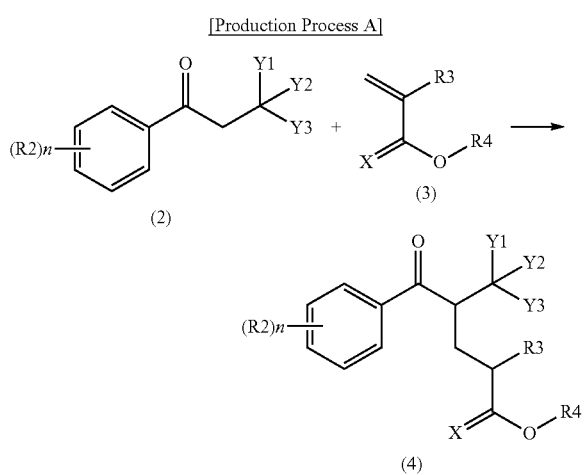

wherein, R4 represents a hydrogen atom or a C1-C6 alkyl group, and R2, R3, Y1, Y2, Y3 and n are the same as defined hereinabove.

Production Process A is a method for obtaining an intermediate of formula (4), comprising reacting a compound of formula (2) with a compound of formula (3) in a solvent in the presence of a base.

The compound of formula (2) used in the reaction may be commercially available or produced in accordance with Reference Example or by a known method.

The compound of formula (3) used in the reaction may be commercially available or produced by a known method.

The amount of the compound of formula (3) used in the reaction is at least 1 equivalent amount relative to the compound of formula (2), and is not particularly limited as long as the target reaction takes place. The amount is usually from 1 equivalent amount to 3 equivalent amounts.

Examples of the bases used in the reaction include inorganic bases such as sodium carbonate, potassium carbonate, cesium carbonate and tripotassium phosphate, metal alkoxides such as sodium methoxide, sodium ethoxide and potassium t-butoxide.

The amount of the base used in the reaction is not particularly limited as long as the target reaction takes place, and is usually from 0.01 equivalent amount to 3 equivalent amounts relative to the compound of formula (2).

Examples of the solvents used in the reaction include, for example ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (2).

The temperature of the reaction is not particularly limited as long as the target reaction takes place, and is usually from −50° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (4) may be dried with a desiccant such as sodium sulfate or magnesium sulfate. This drying process may be omitted.

The reaction mixture comprising the compound of formula (4) may be distilled under reduced pressure to remove the solvent as long as the compound do not decompose.

After the distillation, the reaction mixture comprising the compound of formula (4) may be purified by, for example, washing, reprecipitation, recrystallization or column chromatography using an appropriate solvent. The purification process may be selected appropriately in accordance with the desired purity.

[Production Process B]

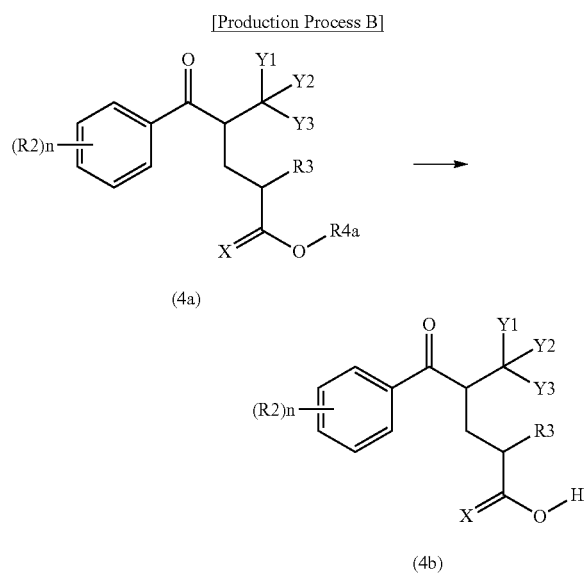

wherein, R4a represents a C1-C6 alkyl group, and R2, R3, Y1, Y2, Y3, X and n are the same as defined hereinabove.

Production Process B is a method for obtaining, among the compound of formula (4), an intermediate of formula (4b). This production process comprises reacting a compound of formula (4a) under acidic conditions or basic conditions in a solvent.

First, the reaction under acidic conditions is described.

Examples of the acids used in the reaction include inorganic acids such as hydrochloric acid, hydrobromic acid and phosphoric acid, organic acids such as acetic acid, methanesulfonic acid, p-toluenesulfonic acid and trifluoroacetic acid.

The amount of the acid used in the reaction may be a catalytic amount, and is not particularly limited as long as the target reaction takes place. The amount is usually not less than 0.01 equivalent amount relative to the compound of formula (4a). A liquid acid may also serve as a solvent.

The solvent used in the reaction is not particularly limited as long as the target reaction takes place. Examples of the solvents include water solvent, acidic solvents such as acetic acid and methanesulfonic acid, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (4a).

The temperature of the reaction is not particularly limited as long as the target reaction takes place, and is usually from 0° C. to 180° C. or is not more than the boiling point of the solvent.

Next, the reaction under basic conditions is described.

Examples of the bases used in the reaction include inorganic bases such as lithium hydroxide, sodium hydroxide and potassium hydroxide.

The amount of the base used in the reaction is at least 1 equivalent amount relative to the compound of formula (4a), and is not particularly limited as long as the target reaction takes place. The amount is usually from 1 equivalent amount to 30 equivalent amounts.

The solvent used in the reaction is not particularly limited as long as the target reaction takes place. Examples of the solvents include water solvent, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (4a).

The temperature of the reaction is not particularly limited as long as the target reaction takes place, and is usually from −20° C. to 180° C. or is not more than the boiling point of the solvent.

The type of post treatment may be common to the reaction under acidic conditions and the reaction under basic conditions. Water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (4b) may be dried with a desiccant such as sodium sulfate or magnesium sulfate. This drying process may be omitted.

The reaction mixture comprising the compound of formula (4b) may be distilled under reduced pressure to remove the solvent as long as the compound do not decompose.

After the distillation, the reaction mixture comprising the compound of formula (4b) may be purified by, for example, washing, reprecipitation, recrystallization or column chromatography using an appropriate solvent. The purification process may be selected appropriately in accordance with the desired purity.

The compounds of formula (4b) encompass isomers of formula (4b'):

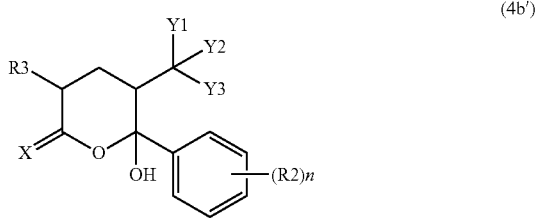

wherein, R2, R3, Y1, Y2, Y3, X and n are the same as defined hereinabove.

The compounds of formula (4b') may be handled similarly to the compounds of formula (4b), and may be produced by, for example, Production Process C. The compound of formula (4b') includes a chiral carbon atom, and may be any single isomer or a mixture of isomers in any proportions. The compound may be a mixture of a compound of formula (4b) and a compound of formula (4b'), and each of the compounds may be any single isomer or a mixture of isomers in any proportions.

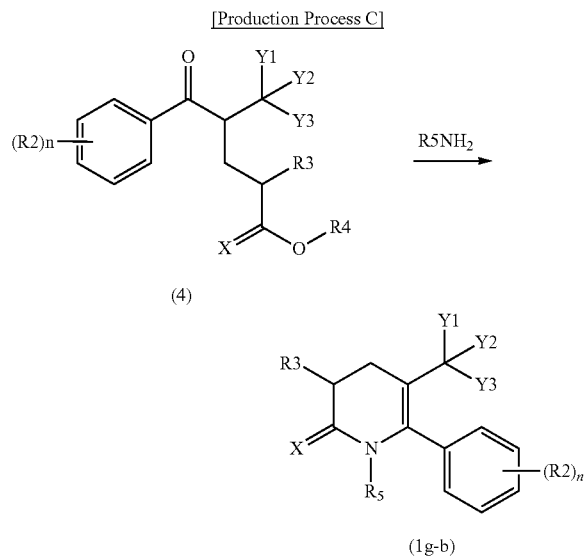

wherein, R5 represents a hydrogen atom, a cyano group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, or a C3-C6 haloalkynyloxy group, and R2, R3, R4, Y1, Y2, Y3, X and n are the same as defined hereinabove.

Production Process C is a method for obtaining a compound of formula (1g-b) which is an inventive compound and also an intermediate of an inventive compound. This production process comprises reacting a compound of formula (4) with $R5NH_2$ in the presence of an acid.

$R5NH_2$ used in the reaction may be commercially available or produced by a known method. $R5NH_2$ may be in the form of a salt with an acidic compound such as hydrochloric acid or acetic acid, and is not particularly limited as long as the target reaction takes place.

The amount of $R5NH_2$ used in the reaction is at least 1 equivalent amount relative to the compound of formula (4), and is not particularly limited as long as the target reaction takes place. The amount is usually from 1 equivalent amount to 200 equivalent amounts.

Examples of the acids used in the reaction include inorganic acids such as hydrochloric acid and sulfuric acid, organic acids such as acetic acid, methanesulfonic acid and p-toluenesulfonic acid. The acid is not particularly limited as long as the target reaction takes place, and acetic acid is preferable. Where $R5NH_2$ is used as a salt with an acidic compound, the acid may not be used.

The amount of the acid used in the reaction is at least 1 equivalent amount relative to $R5NH_2$, and is not particularly limited as long as the target reaction takes place. The amount is usually from 1 equivalent amount to 200 equivalent amounts. A liquid acid may also serve as a solvent.

The reaction may involve a solvent, but the use of a solvent may be dispensable.

The solvent used in the reaction is not particularly limited as long as the target reaction takes place. Examples of the solvents include acidic solvents such as acetic acid and methanesulfonic acid, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride. The solvents may be used singly, or two or more of these solvents may be mixed in any proportions and used. The solvent is preferably an acidic solvent, and more preferably acetic acid.

The amount of the solvent used in the reaction is not particularly limited as long as the target reaction takes place, and is usually from 3 to 200 times the weight of the compound of formula (4).

The temperature of the reaction is not particularly limited as long as the target reaction takes place, and is usually from 50° C. to 180° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1g-b) may be dried with a desiccant such as sodium sulfate or magnesium sulfate. This drying process may be omitted.

The reaction mixture comprising the compound of formula (1g-b) may be distilled under reduced pressure to remove the solvent as long as the compound do not decompose.

After the distillation, the reaction mixture comprising the compound of formula (1g-b) may be purified by, for example, washing, reprecipitation, recrystallization or column chromatography using an appropriate solvent. The purification process may be selected appropriately in accordance with the desired purity.

According to Production Process A, a compound of formula (1g-b) wherein R5 is a hydrogen atom, i.e. a compound of formula (1g-a), may be produced. This compound may be a useful intermediate for the production of an inventive compound of formula (1g)

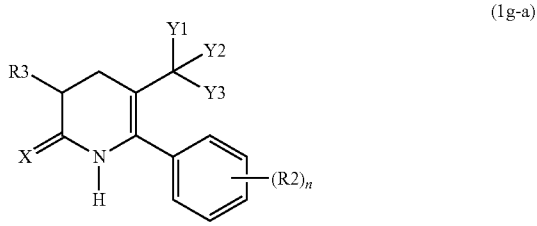

(1g-a)

wherein, R2, R3, Y1, Y2, Y3, X and n are the same as defined hereinabove.

[Production Process D]

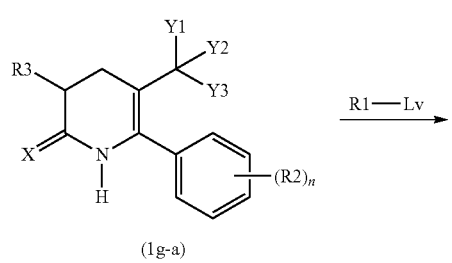

(1g-a)

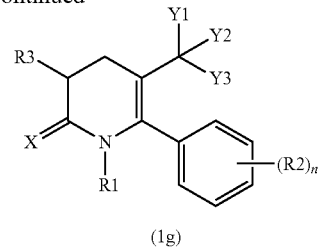

(1g)

wherein, Lv represents a leaving group such as methanesulfonyl, trifluoromethanesulfonyl, p-toluenesulfonyl or a halogen atom, and R1, R2, R3, Y1, Y2, Y3, X and n are the same as defined hereinabove.

Production Process D is a method for obtaining a compound of formula (1g), comprising reacting an intermediate of the formula (1g-a) with R1-Lv in a solvent in the presence of a base.

The compound of formula (1g-a) which is a raw material of the present invention may be synthesized by Production Process C or with reference to non-patent literature such as Journal of Heterocyclic Chemistry, vol. 20, pp. 65-67 (1983).

R1-Lv used in the reaction may be commercially available or produced by a known method.

The amount of the R1-Lv used in the reaction is at least 1 equivalent amount relative to the compound of formula (1g-a), and is not particularly limited as long as the target reaction takes place. The amount is usually from 1 equivalent amount to 10 equivalent amounts.

Examples of the bases used in the reaction include inorganic bases such as sodium hydroxide, potassium hydroxide, sodium carbonate, potassium carbonate, cesium carbonate and sodium hydride.

The amount of the base used in the reaction is at least 1 equivalent amount relative to the compound of formula (1g-a), and is not particularly limited as long as the target reaction takes place. The amount is usually from 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1g-a).

The temperature of the reaction is not particularly limited as long as the target reaction takes place, and is usually from 0° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1g) may be dried with a desiccant such as sodium sulfate or magnesium sulfate. This drying process may be omitted.

The reaction mixture comprising the compound of formula (1g) may be distilled under reduced pressure to remove the solvent as long as the compound do not decompose.

After the distillation, the reaction mixture comprising the compound of formula (1g) may be purified by, for example, washing, reprecipitation, recrystallization or column chromatography using an appropriate solvent. The purification process may be selected appropriately in accordance with the desired purity.

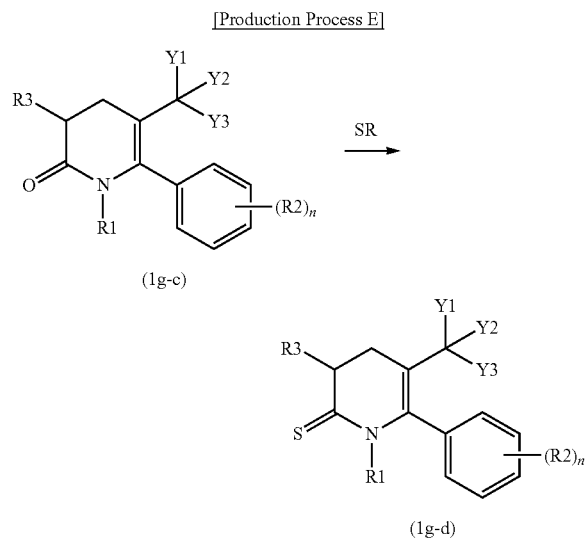

(1g-c)

(1g-d)

wherein, SR represents a sulfurizing reagent, and R1, R2, R3, Y1, Y2, Y3 and n are the same as defined hereinabove.

Production Process E is a method for obtaining, among the compound of formula (1g), a compound of formula (1g-d). This production process comprises reacting a compound of formula (1g-c) with a sulfurizing reagent (SR) in a solvent.

Examples of the sulfurizing reagents used in the reaction include Lawesson's reagent (2,4-bis(4-methoxyphenyl)-1,3-dithia-2,4-diphosphetane-2,4-disulfide).

The amount of the sulfurizing reagent used in the reaction is at least 0.5 equivalent amounts relative to the compound of formula (1g-c), and is not particularly limited as long as the target reaction takes place. The amount is usually from 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1g-c).

The temperature of the reaction is not particularly limited as long as the target reaction takes place, and is usually from 50° C. to 180° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield. In this reaction, the separation may be omitted.

The reaction mixture comprising the compound of formula (1g-d) may be dried with a desiccant such as sodium sulfate or magnesium sulfate. This drying process may be omitted.

The reaction mixture comprising the compound of formula (1g-d) may be distilled under reduced pressure to remove the solvent as long as the compound do not decompose.

After the distillation, the reaction mixture comprising the compound of formula (1g-d) may be purified by, for example, washing, reprecipitation, recrystallization or column chromatography using an appropriate solvent. The purification process may be selected appropriately in accordance with the desired purity.

[Production Process F]

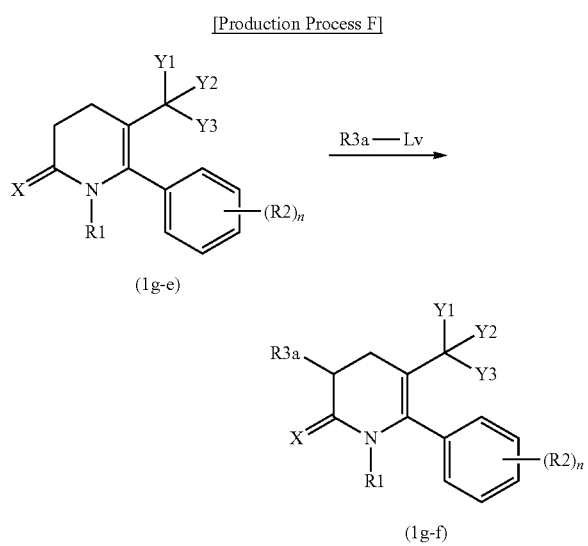

wherein, R3a represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, or a C2-C6 haloalkynyl group, and Lv, R1, R2, Y1, Y2, Y3, X and n are the same as defined hereinabove.

Production Process F is a method for obtaining, among a compound of formula (1g), a compound of formula (1g-f) wherein R3a is a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, or a C2-C6 haloalkynyl group. This production process comprises reacting a compound of formula (1g-e) with R3a-Lv in a solvent in the presence of a base.

R3a-Lv used in the reaction may be commercially available or produced by a known method.

The amount of R3a-Lv used in the reaction is at least 1 equivalent amount relative to the compound of formula (1g-e), and is not particularly limited as long as the target reaction takes place. The amount is usually from 1 equivalent amount to 1.8 equivalent amounts.

Examples of the bases used in the reaction include metal hydrides such as sodium hydride, organic lithiums such as methyllithium, butyllithium, sec-butyllithium, t-butyllithium and hexyllithium, metal amides such as lithium diisopropylamide, hexamethyldisilazane lithium, hexamethyldisilazane sodium and hexamethyldisilazane potassium.

The amount of the base used in the reaction is at least 1 equivalent amount relative to the compound of formula (1g-e), and is not particularly limited as long as the target reaction takes place. The amount is usually from 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1g-e).

The temperature of the reaction is not particularly limited as long as the target reaction takes place, and is usually from −80° C. to 100° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane and chloroform, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1g-f) may be dried with a desiccant such as sodium sulfate or magnesium sulfate. This drying process may be omitted.

The reaction mixture comprising the compound of formula (1g-f) may be distilled under reduced pressure to remove the solvent as long as the compound do not decompose.

After the distillation, the reaction mixture comprising the compound of formula (1g-f) may be purified by, for example, washing, reprecipitation, recrystallization or column chromatography using an appropriate solvent. The purification process may be selected appropriately in accordance with the desired purity.

[Production Process G]

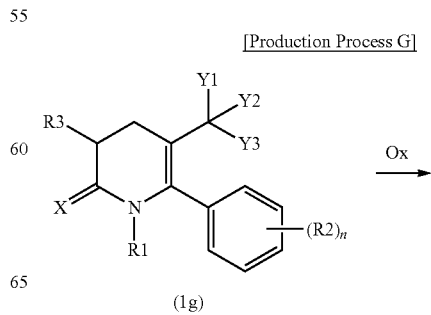

-continued

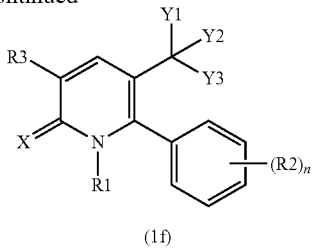

(1f)

wherein, Ox represents an oxidizer, and R1, R2, R3, Y1, Y2, Y3, X and n are the same as defined hereinabove.

Production Process G is a method for obtaining a compound of formula (1f), comprising reacting a compound of formula (1g) with an oxidizer (Ox) in a solvent.

The oxidizer used in the reaction may be, for example, a metal oxide such as manganese dioxide, a benzoquinone such as 2,3-dichloro-5,6-dicyano-p-benzoquinone, or a combination of a radical initiator such as azobisisobutyronitrile or benzoyl peroxide with a halogenating reagent such as N-chlorosuccinimide, N-bromosuccinimide, N-iodosuccinimide, 1,3-dichloro-5,5-dimethylhydantoin, 1,3-dibromo-5,5-dimethylhydantoin or 1,3-diiodo-5,5-dimethylhydantoin.

The process using a metal oxide as the oxidizer is hereinbelow described.

The amount of the oxidizer used in the reaction is at least 1 equivalent amount relative to the compound of formula (1g), and is not particularly limited as long as the target reaction takes place. The amount is usually from 1 equivalent amount to 200 equivalent amounts.

The solvent used in the reaction is not particularly limited as long as the target reaction takes place. Examples of the solvents include benzene-based solvents such as benzene, toluene, xylene, mesitylene, chlorobenzene and dichlorobenzene, halogen solvents such as dichloromethane, dichloroethane, chloroform and carbon tetrachloride. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1g).

The temperature of the reaction is not particularly limited as long as the target reaction takes place, and is usually from 0° C. to 150° C. or is not more than the boiling point of the solvent.

As post-treatment, insoluble metals may be removed by filtration. Further, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield. In this reaction, the separation may be omitted.

The reaction mixture comprising the compound of formula (1f) may be dried with a desiccant such as sodium sulfate or magnesium sulfate. This drying process may be omitted.

The reaction mixture comprising the compound of formula (1f) may be distilled under reduced pressure to remove the solvent as long as the compound do not decompose.

After the distillation, the reaction mixture comprising the compound of formula (1f) may be purified by, for example, washing, reprecipitation, recrystallization or column chromatography using an appropriate solvent. The purification process may be selected appropriately in accordance with the desired purity.

The process using a benzoquinone as the oxidizer is hereinbelow described.

The amount of the oxidizer used in the reaction is at least 1 equivalent amount relative to the compound of formula (1g), and is not particularly limited as long as the target reaction takes place. The amount is usually from 1 equivalent amount to 20 equivalent amounts.

The solvent used in the reaction is not particularly limited as long as the target reaction takes place. Examples of the solvents include benzene-based solvents such as benzene, toluene, xylene, mesitylene, chlorobenzene and dichlorobenzene, halogen solvents such as dichloromethane, dichloroethane, chloroform and carbon tetrachloride. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1g).

The temperature of the reaction is not particularly limited as long as the target reaction takes place, and is usually from 0° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield. In this reaction, the separation may be omitted.

The reaction mixture comprising the compound of formula (1f) may be dried with a desiccant such as sodium sulfate or magnesium sulfate. This drying process may be omitted.

The reaction mixture comprising the compound of formula (1f) may be distilled under reduced pressure to remove the solvent as long as the compound do not decompose.

After the distillation, the reaction mixture comprising the compound of formula (1f) may be purified by, for example, washing, reprecipitation, recrystallization or column chromatography using an appropriate solvent. The purification process may be selected appropriately in accordance with the desired purity.

The process using a combination of a radical initiator and a halogenating reagent as the oxidizer is hereinbelow described.

The amount of the radical initiator and that of the halogenating reagent used in the reaction are at least 0.01 equivalent amount and at least 1.0 equivalent amount, respectively, relative to the compound of formula (1g), and are not particularly limited as long as the target reaction takes place. Usually, the amount of the radical initiator is 0.01 equivalent amount to 1 equivalent amount, and the amount of the halogenating reagent is 1 equivalent amount to 3 equivalent amounts. Where the halogenating reagent contains hydantoin, the amount thereof is at least 0.5 equivalent amounts and is usually from 1 equivalent amount to 1.5 equivalent amounts, although the amounts are not particularly limited as long as the target reaction takes place.

The solvent used in the reaction is not particularly limited as long as the target reaction takes place. Examples of the solvents include halogenated benzene-based solvents such as chlorobenzene and dichlorobenzene, ester solvents such as ethyl acetate, isopropyl acetate and butyl acetate, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1g).

The temperature of the reaction is not particularly limited as long as the target reaction takes place, and is usually from 20° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane and chloroform, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f) may be dried with a desiccant such as sodium sulfate or magnesium sulfate. This drying process may be omitted.

The reaction mixture comprising the compound of formula (1f) may be distilled under reduced pressure to remove the solvent as long as the compound do not decompose.

After the distillation, the reaction mixture comprising the compound of formula (1f) may be purified by, for example, washing, reprecipitation, recrystallization or column chromatography using an appropriate solvent. The purification process may be selected appropriately in accordance with the desired purity.

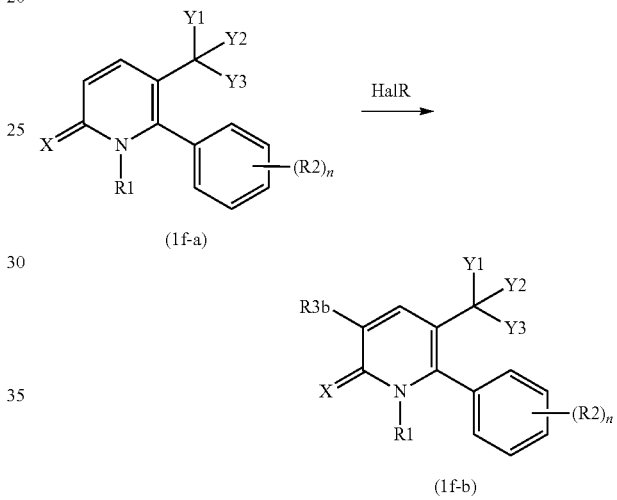

[Production Process H]

wherein, R3b represents a halogen atom, HalR represents a halogenating reagent, and R1, R2, Y1, Y2, Y3 and n are the same as defined hereinabove.

Production Process H is a method for obtaining, among a compound of formula (1f), a compound of formula (1f-b) wherein R3b represents a halogen atom. This production process comprises reacting a compound of formula (1f-a) with a halogenating reagent (HalR) in a solvent.

Examples of the halogenating reagents used in the reaction include Selectfluor (N-fluoro-N'-triethylenediamine bis (tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine.

The amount of the halogenating reagent used in the reaction is at least 1 equivalent amount relative to the compound of formula (1f-a), and is not particularly limited as long as the target reaction takes place. The amount is usually from 1 equivalent amount to 10 equivalent amounts. Where the halogenating reagent contains hydantoin, the amount thereof is at least 0.5 equivalent amounts and is usually from 1 equivalent amount to 5 equivalent amounts, although the amount is not particularly limited as long as the target reaction takes place.

When the halogenating reagent used in the reaction is an iodizing reagent, an acid may be added, with examples including inorganic acids such as hydrochloric acid and sulfuric acid, and organic acids such as acetic acid, trifluoroacetic acid, methanesulfonic acid and trifluoromethanesulfonic acid.

When the halogenating reagent is an iodizing reagent, the amount of the acid used in the reaction is at least 0.01 equivalent amount relative to the compound of formula (1f-a), and is not particularly limited as long as the target reaction takes place. The amount is usually 0.1 equivalent amount to 3 equivalent amounts.

The solvent used in the reaction is not particularly limited as long as the target reaction takes place. Examples of the solvents include acidic solvents such as sulfuric acid, acetic acid, trifluoroacetic acid, methanesulfonic acid and trifluoromethanesulfonic acid, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-a).

The temperature of the reaction is not particularly limited as long as the target reaction takes place, and is usually from 0° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-b) may be dried with a desiccant such as sodium sulfate or magnesium sulfate. This drying process may be omitted.

The reaction mixture comprising the compound of formula (1f-b) may be distilled under reduced pressure to remove the solvent as long as the compound do not decompose.

After the distillation, the reaction mixture comprising the compound of formula (1f-b) may be purified by, for example, washing, reprecipitation, recrystallization or column chromatography using an appropriate solvent. The purification process may be selected appropriately in accordance with the desired purity.

[Production Process I]

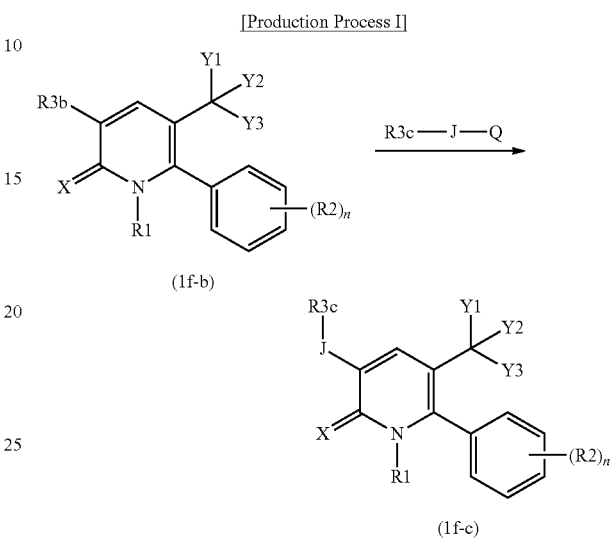

wherein, J represents an oxygen atom or a sulfur atom; when J is an oxygen atom, R3c represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, or a C2-C6 haloalkynyl group; when J is a sulfur atom, R3c represents a C1-C6 alkyl group or a C1-C6 haloalkyl group; Q represents a hydrogen atom or a metal; and R1, R2, R3b, Y1, Y2, Y3, X and n are the same as defined hereinabove.

Production Process I is a method for obtaining, among a compound of formula (1f), a compound of formula (1f-c) wherein J represents an oxygen atom or a sulfur atom; when J is an oxygen atom, R3c represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, or a C2-C6 haloalkynyl group; and when J is a sulfur atom, R3c represents a C1-C6 alkyl group or a C1-C6 haloalkyl group. This production process comprises a coupling reaction, i.e. reacting a compound of formula (1f-b) with R3c-J-Q in a solvent in the presence of a transition metal and a base.

In the compound of formula (1f-b), R3b is preferably chlorine atom, bromine atom, or iodine atom.

R3c-J-Q used in the reaction may be commercially available or produced by a known method. Q is preferably a hydrogen atom, or alkali metals such as sodium or potassium.

The amount of R3c-J-Q used in the reaction is at least 1 equivalent amount relative to the compound of formula (1f-b), and is not particularly limited as long as the target reaction takes place. Where Q is a hydrogen atom, this compound may be used also as a solvent.

The transition metal used in the reaction may have a ligand. Examples include palladiums such as palladium acetate, [1,1'-bis(diphenylphosphino)ferrocene]palladium dichloride, tris(dibenzylideneacetone)dipalladium, tetrakis(triphenylphosphine)palladium, and bis(triphenylphosphine)palladium dichloride.

The amount of the transition metal used in the reaction is usually from 0.001 equivalent amount to 1 equivalent amount relative to the compound of formula (1f-b), but is not particularly limited thereto as long as the target reaction takes place.

To allow the reaction to proceed efficiently, a phosphine ligand such as triphenylphosphine, 1,1'-bis(diphenylphosphino)ferrocene, 2-dicyclohexylphosphino-2',4',6'-triisopropylbiphenyl or 2-di-t-butylphosphino-2',4',6'-triisopropylbiphenyl may be added.

The amount of the phosphine ligand used in the reaction is usually from 0.001 equivalent amount to 1 equivalent amount relative to the compound of formula (1f-b), but is not particularly limited thereto as long as the target reaction takes place.

Examples of bases used in the reaction include inorganic bases such as sodium carbonate, potassium carbonate and cesium carbonate, organic bases such as triethylamine, tributylamine and diisopropylethylamine.

The amount of the base used in the reaction is at least 1 equivalent amount relative to the compound of formula (1f-b), and is not particularly limited as long as the target reaction takes place. The amount is usually from 1 equivalent amount to 50 equivalent amounts.

The solvent used in the reaction is not particularly limited as long as the target reaction takes place. Examples of the solvents include alcohol solvents of R3c-J-H (wherein R3c is the same as defined hereinabove, and J is an oxygen atom), ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-b).

The temperature of the reaction is not particularly limited as long as the target reaction takes place, and is usually from 30° C. to 200° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield. Further, insolubles may be removed by filtration, but this operation may be dispensable.

The reaction mixture comprising the compound of formula (1f-c) may be distilled under reduced pressure to remove the solvent as long as the compound do not decompose.

After the distillation, the reaction mixture comprising the compound of formula (1f-c) may be purified by, for example, washing, reprecipitation, recrystallization or column chromatography using an appropriate solvent. The purification process may be selected appropriately in accordance with the desired purity.

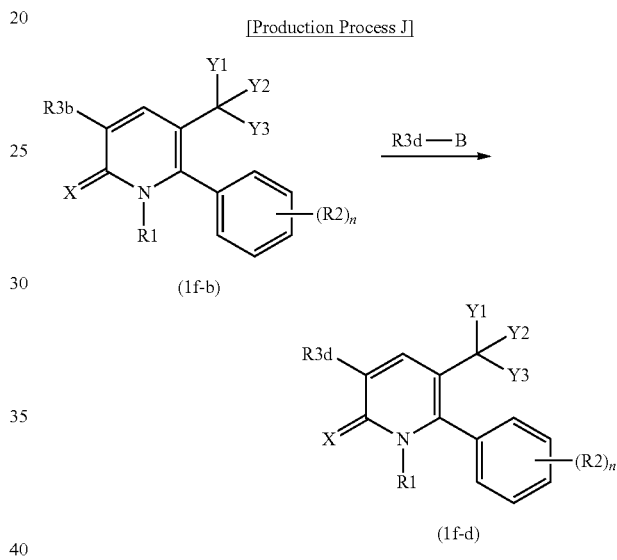

[Production Process J]

(1f-b)

(1f-d)

wherein, R3d represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, or a C2-C6 haloalkenyl group, R3d-B represents an organoboronic acids, and R1, R2, R3b, Y1, Y2, Y3, X and n are the same as defined hereinabove.

Production Process J is a method for obtaining, among a compound of formula (1f), a compound of formula (1f-d) wherein R3d is a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, or a C2-C6 haloalkenyl group. This production process comprises the Suzuki-Miyaura coupling, i.e. reacting a compound of formula (1f-b) with an organoboronic acids (R3d-B) in a solvent in the presence of a transition metal and a base.

In the formula (1f-b), R3b is preferably chlorine atom, bromine atom or iodine atom.

R3d-B used in the reaction represents an organoboronic acid such as an organic boronic acid or an organic boronate ester, and may be commercially available or produced by a known method.

The amount of R3d-B used in the reaction is at least 1 equivalent amount relative to the compound of formula (1f-b), and is not particularly limited as long as the target reaction takes place. The amount is usually from 1 equivalent amount to 10 equivalent amounts.

The transition metal used in the reaction may be, for example, palladium, nickel or ruthenium, and may have a ligand. Preferably, this includes palladiums, for example palladium acetate, [1,1'-bis(diphenylphosphino)ferrocene] palladium dichloride, tris(dibenzylideneacetone)dipalladium, tetrakis(triphenylphosphine)palladium and bis(triphenylphosphine)palladium dichloride.

The amount of the transition metal used in the reaction is usually from 0.001 equivalent amount to 1 equivalent amount relative to the compound of formula (1f-b), but is not particularly limited thereto as long as the target reaction takes place.

To allow the reaction to proceed efficiently, a phosphine ligand such as triphenylphosphine or tricyclohexylphosphine may be added.

The amount of the phosphine ligand used in the reaction is usually from 0.001 equivalent amount to 1 equivalent amount relative to the compound of formula (1f-b), but is not particularly limited thereto as long as the target reaction takes place.

Examples of the bases used in the reaction include inorganic bases such as sodium carbonate, potassium carbonate, cesium carbonate and tripotassium phosphate, metal alkoxides such as sodium methoxide, sodium ethoxide and potassium t-butoxide.

The amount of the base used in the reaction is at least 1 equivalent amount relative to the compound of formula (1f-b), and is not particularly limited as long as the target reaction takes place. The amount is usually from 1 equivalent amount to 50 equivalent amounts.

The solvent used in the reaction is not particularly limited as long as the target reaction takes place. Examples of the solvents include water solvent, ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-b).

The temperature of the reaction is not particularly limited as long as the target reaction takes place, and is usually from 30° C. to 200° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield. Further, insolubles may be removed by filtration, but this operation may be dispensable.

The reaction mixture comprising the compound of formula (1f-d) may be distilled under reduced pressure to remove the solvent as long as the compound do not decompose.

After the distillation, the reaction mixture comprising the compound of formula (1f-d) may be purified by, for example, washing, reprecipitation, recrystallization or column chromatography using an appropriate solvent. The purification process may be selected appropriately in accordance with the desired purity.

[Production Process K]

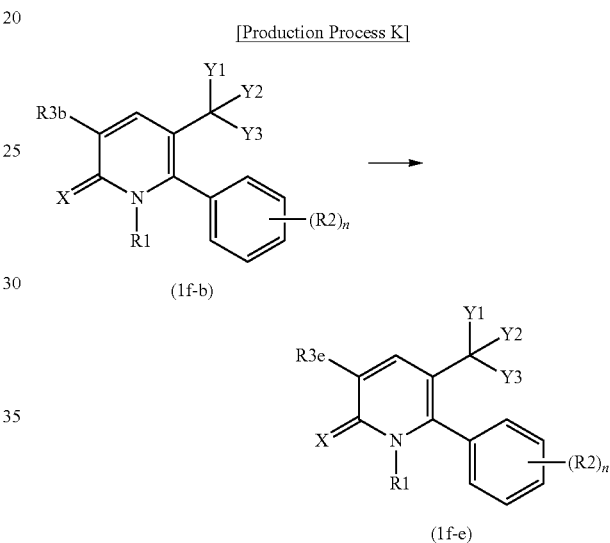

wherein, R3e represents a C2-C6 alkynyl group optionally substituted with substituent(s) A, or a C2-C6 haloalkynyl group, and R1, R2, R3b, Y1, Y2, Y3, X and n are the same as defined hereinabove.

Production Process K is a method for obtaining, among a compound of formula (1f), a compound of formula (1f-e) wherein R3e is a C2-C6 alkynyl group optionally substituted with substituent(s) A, or a C2-C6 haloalkynyl group. This production process comprises the Sonogashira coupling reaction, i.e. reacting a compound of formula (1f-b) with an alkyne-terminated compound in a solvent in the presence of transition metals and a base.

In the formula (1f-b), R3b is preferably chlorine atom, bromine atom or iodine atom.

The alkyne-terminated compound used in the reaction may be commercially available or produced by a known method. Trimethylsilylacetylene can also be used as the alkyne-terminated compound. In this case, a trimethylsilylethynyl is introduced into the compound of formula (1f-b), before the compound is desilylated. The desilylation may be performed with reference to non-patent literature such as Journal of the American Chemical Society, vol. 131, No. 2, pp. 634-643 (2009) and Journal of Organometallic Chemistry, vol. 696, No. 25, pp. 4039-4045 (2011).

The amount of the alkyne-terminated compound used in the reaction is at least 1 equivalent amount relative to the compound of formula (1f-b), and is not particularly limited as long as the target reaction takes place. The amount is usually from 1 equivalent amount to 10 equivalent amounts.

The transition metals used in the reaction may have a ligand. Examples include palladiums such as palladium acetate, [1,1'-bis(diphenylphosphino)ferrocene]palladium dichloride, tris(dibenzylideneacetone)dipalladium, tetrakis (triphenylphosphine)palladium and bis(triphenylphosphine) palladium dichloride. Coppers such as copper chloride, copper bromide and copper iodide are used simultaneously.

For the amounts of the transition metals used in the reaction, the palladiums or the like, and the copper are usually each at least 0.001 equivalent amount relative to the compound of formula (1f-b). The amounts are not particularly limited as long as the target reaction takes place. The amounts are both preferably 0.001 equivalent amount to 1 equivalent amount.

Examples of the bases used in the reaction include organic amines such as triethylamine, tributylamine, isopropylamine, diethylamine, diisopropylamine and diisopropylethylamine, inorganic bases such as sodium carbonate, potassium carbonate and cesium carbonate.

The amount of the base used in the reaction is at least 1 equivalent amount relative to the compound of formula (1f-b), and is not particularly limited as long as the target reaction takes place. The amount is usually from 1 equivalent amount to 50 equivalent amounts. A liquid organic base may also serve as a solvent.

To allow the reaction to proceed efficiently, a phosphine ligand such as tri-t-butylphosphine or 2-dicyclohexylphosphino-2',4',6'-triisopropylbiphenyl may be added, although the use of such a ligand may be dispensable.

The amount of the phosphine ligand used in the reaction is usually from 0.001 equivalent amount to 1 equivalent amount relative to the compound of formula (1f-b), but is not particularly limited thereto as long as the target reaction takes place.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, organic amine solvents such as triethylamine, tributylamine, isopropylamine, diethylamine, diisopropylamine and diisopropylethylamine. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-b).

The temperature of the reaction is not particularly limited as long as the target reaction takes place, and is usually from 0° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield. Further, insolubles may be removed by filtration, but this operation may be dispensable.

The reaction mixture comprising the compound of formula (1f-e) may be distilled under reduced pressure to remove the solvent as long as the compound do not decompose.

After the distillation, the reaction mixture comprising the compound of formula (1f-e) may be purified by, for example, washing, reprecipitation, recrystallization or column chromatography using an appropriate solvent. The purification process may be selected appropriately in accordance with the desired purity.

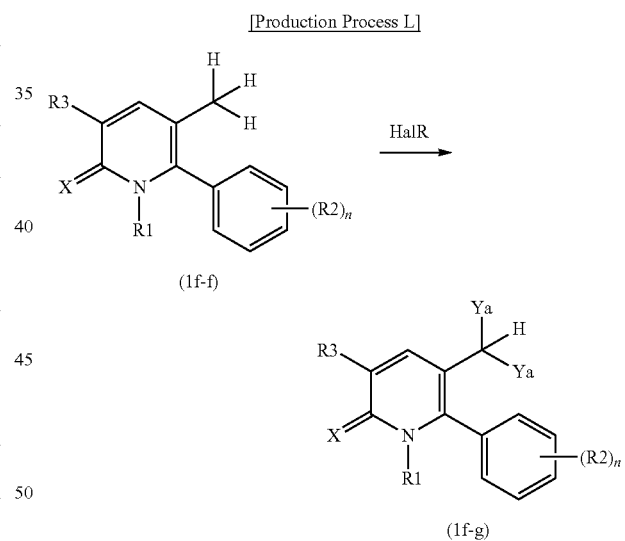

wherein, Ya represents a halogen atom, and HalR, R1, R2, R3, X and n are the same as defined hereinabove.

Production Process L is a method for obtaining, among a compound of formula (1f), a compound of formula (1f-g) wherein Ya is a halogen atom. This production process comprises reacting a compound of formula (1f-f) using a radical initiator and a halogenating reagent (HalR) in a solvent.

In the formula (1f-g), Ya is preferably chlorine atom, bromine atom, or iodine atom.

Examples of the radical initiators used in the reaction include azobisisobutyronitrile, benzoyl peroxide.

The amount of the radical initiator used in the reaction is not particularly limited as long as the target reaction takes place, and is usually from 0.01 equivalent amount to 1.0 equivalent amount relative to the compound of formula (1f-f).

Examples of the halogenating reagents used in the reaction include N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin.

The amount of the halogenating reagent used in the reaction is at least 2 equivalent amounts relative to the compound of formula (1f-f), and is not particularly limited as long as the target reaction takes place. The amount is usually from 2 equivalent amounts to 2.8 equivalent amounts. Where the halogenating reagent contains hydantoin, the amount thereof is at least 1 equivalent amount and is usually from 1 equivalent amount to 1.4 equivalent amounts, although the amount is not particularly limited as long as the target reaction takes place.

The solvent used in the reaction is not particularly limited as long as the target reaction takes place. Examples of the solvents include halogenated benzene-based solvents such as chlorobenzene and dichlorobenzene, ester solvents such as ethyl acetate, isopropyl acetate and butyl acetate, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-f).

The temperature of the reaction is not particularly limited as long as the target reaction takes place, and is usually from 20° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane and chloroform, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-g) may be dried with a desiccant such as sodium sulfate or magnesium sulfate. This drying process may be omitted.

The reaction mixture comprising the compound of formula (1f-g) may be distilled under reduced pressure to remove the solvent as long as the compound do not decompose.

After the distillation, the reaction mixture comprising the compound of formula (1f-g) may be purified by, for example, washing, reprecipitation, recrystallization or column chromatography using an appropriate solvent. The purification process may be selected appropriately in accordance with the desired purity.

[Production Process M]

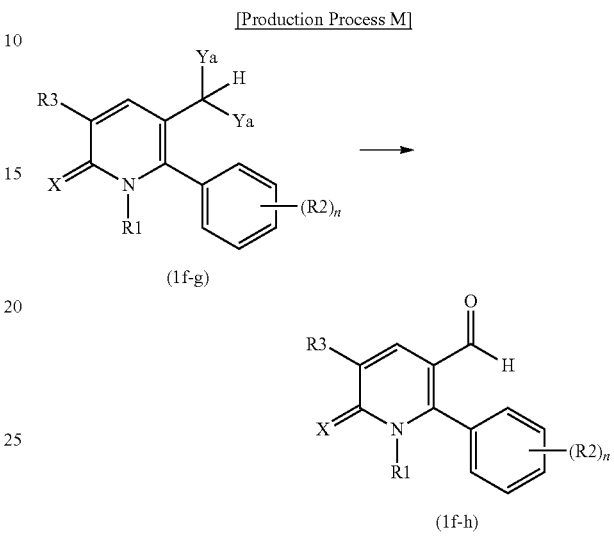

wherein, Ya, R1, R2, R3, X and n are the same as defined hereinabove.

Production Process M is a method for obtaining, among the compound of formula (1f), a compound of formula (1f-h), comprising hydrolyzing a compound of formula (1f-g) in a solvent in the presence of water.

In the formula (1f-g), Ya is preferably chlorine atom, bromine atom, or iodine atom.

Water is essential in this reaction. Silver nitrate may be used to allow the reaction to take place smoothly.

The amount of water used in the reaction is at least 1 equivalent amount relative to the compound of formula (1f-g), and is not particularly limited as long as the target reaction takes place. Water may also serve as a solvent.

The amount of silver nitrate used in the reaction is at least 2 equivalent amounts relative to the compound of formula (1f-g), and is not particularly limited as long as the target reaction takes place. The amount is usually from 2 equivalent amounts to 10 equivalent amounts.

The solvent used in the reaction is not particularly limited as long as the target reaction takes place. Examples of the solvents include water solvent, ether solvents such as diethyl ether, diisopropyl ether, methyl t-butyl ether, dimethoxyethane, tetrahydrofuran and dioxane, nitrile solvents such as acetonitrile. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-g).

The temperature of the reaction is not particularly limited as long as the target reaction takes place, and is usually from –10° C. to 100° C. or is not more than the boiling point of the solvent.

As post-treatment, insoluble metals may be removed by filtration. Further, water or an appropriate aqueous solution may be added to the reaction mixture to perform separation.

The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-h) may be dried with a desiccant such as sodium sulfate or magnesium sulfate. This drying process may be omitted.

The reaction mixture comprising the compound of formula (1f-h) may be distilled under reduced pressure to remove the solvent as long as the compound do not decompose.

After the distillation, the reaction mixture comprising the compound of formula (1f-h) may be purified by, for example, washing, reprecipitation, recrystallization or column chromatography using an appropriate solvent. The purification process may be selected appropriately in accordance with the desired purity.

The inventive compound of formula (1f-h) may be used as an intermediate.

[Production Process N]

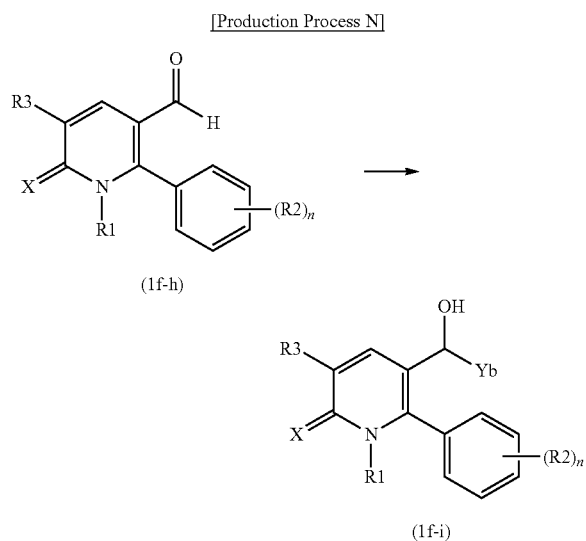

wherein, Yb represents a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, or a C2-C6 haloalkynyl group, and R1, R2, R3, X and n are the same as defined hereinabove.

Production Process N is a method for obtaining, among a compound of formula (1f), a compound of formula (1f-i) wherein Yb is a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, or a C2-C6 haloalkynyl group. This production process comprises reacting a compound of formula (1f-h) with an organometallic reagent in a solvent.

Examples of the organometallic reagents used in the reaction include organomagnesium halides (Yb—Mg-Hal wherein Hal represents a halogen atom, and Yb is the same as defined hereinabove), organolithium reagents (Yb—Li wherein Yb is the same as defined hereinabove), organomagnesium halide-zinc (II) ate complex reagents ([(Yb)$_3$-Zn]$^-$[Mg-Hal]$^+$[Mg-(Hal)$_2$]$_2$ wherein Yb and Hal are the same as defined hereinabove). The organometallic reagent may be commercially available or produced by a known method.

The amount of the organometallic reagent used in the reaction is at least 1 equivalent amount relative to the compound of formula (1f-h), and is not particularly limited as long as the target reaction takes place. The amount is usually from 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-h).

The temperature of the reaction is not particularly limited as long as the target reaction takes place, and is usually from −80° C. to 100° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane and chloroform, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-i) may be dried with a desiccant such as sodium sulfate or magnesium sulfate. This drying process may be omitted.

The reaction mixture comprising the compound of formula (1f-i) may be distilled under reduced pressure to remove the solvent as long as the compound do not decompose.

After the distillation, the reaction mixture comprising the compound of formula (1f-i) may be purified by, for example, washing, reprecipitation, recrystallization or column chromatography using an appropriate solvent. The purification process may be selected appropriately in accordance with the desired purity.

[Production Process O]

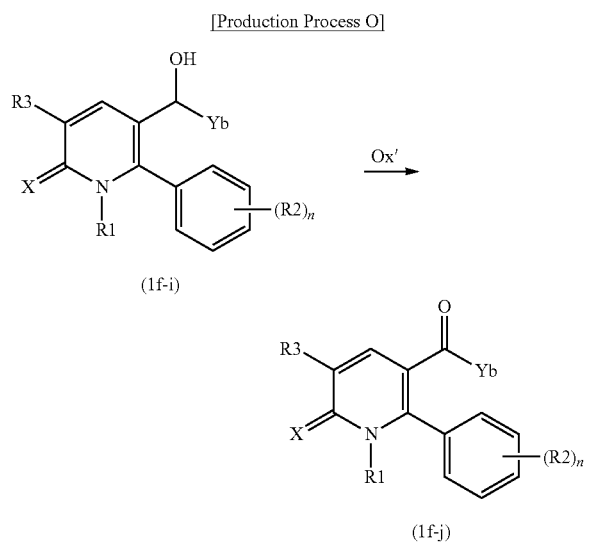

wherein, Ox' represents an oxidizer, and R1, R2, R3, Yb, X and n are the same as defined hereinabove.

Production Process O is a method for obtaining, among the compound of formula (1f), a compound of formula (1f-j), comprising reacting a compound of formula (1f-i) with an oxidizer (Ox') in a solvent.

This production process may be performed by an oxidation technique usually used by a skilled person, such as Dess-Martin oxidation, Swern oxidation or Parikh-Doering oxidation. The oxidation reaction is not particularly limited as long as the target reaction takes place. Here, the Parikh-Doering oxidation process using dimethylsulfoxide, pyridine-sulfur trioxide complex and a base in a solvent is described.

The amount of the dimethylsulfoxide used in the reaction is at least 1 equivalent amount relative to the compound of formula (1f-i), and is not particularly limited as long as the target reaction takes place. The dimethylsulfoxide may also be used as a solvent.

The amount of the pyridine-sulfur trioxide complex used in the reaction is at least 1 equivalent amount relative to the compound of formula (1f-i), and is not particularly limited as long as the target reaction takes place. The amount is usually from 1 equivalent amount to 20 equivalent amounts.

Examples of the bases used in the reaction include organoamines such as triethylamine, tributylamine and diisopropylethylamine.

The amount of the base used in the reaction is at least 1 equivalent amount relative to the compound of formula (1f-i), and is not particularly limited as long as the target reaction takes place. The amount is usually from 1 equivalent amount to 50 equivalent amounts.

The solvent used in the reaction is not particularly limited as long as the target reaction takes place. Examples of the solvents include halogen solvents such as dichloromethane, dichloroethane, chloroform and carbon tetrachloride, sulfur solvents such as dimethylsulfoxide. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-i).

The temperature of the reaction is not particularly limited as long as the target reaction takes place, and is usually from −10° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane and chloroform, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-j) may be dried with a desiccant such as sodium sulfate or magnesium sulfate. This drying process may be omitted.

The reaction mixture comprising the compound of formula (1f-j) may be distilled under reduced pressure to remove the solvent as long as the compound do not decompose.

After the distillation, the reaction mixture comprising the compound of formula (1f-j) may be purified by, for example, washing, reprecipitation, recrystallization or column chromatography using an appropriate solvent. The purification process may be selected appropriately in accordance with the desired purity.

[Production Process P]

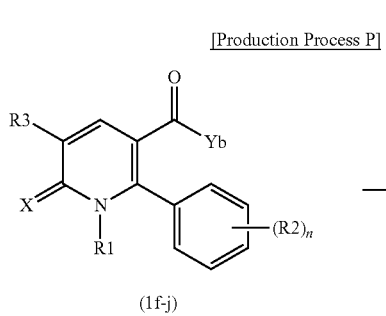

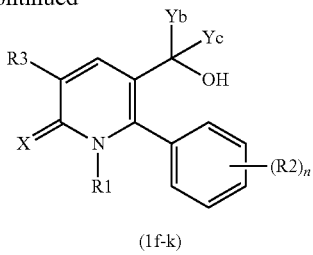

(1f-k)

wherein, Yb and Yc are independent of one another and each represent a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, or a C2-C6 haloalkynyl group, and R1, R2, R3, X and n are the same as defined hereinabove.

Production Process P is a method for obtaining, among a compound of the general formula (1f), a compound of formula (1f-k) wherein Yb and Yc are each independently a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, or a C2-C6 haloalkynyl group. This production process comprises reacting a compound of formula (1f-j) with an organometallic reagent in a solvent.

Production Process P may be carried out according to Production Process N by replacing the compound of formula (1f-h) in Production Process N with the compound of formula (1f-j).

[Production Process Q]

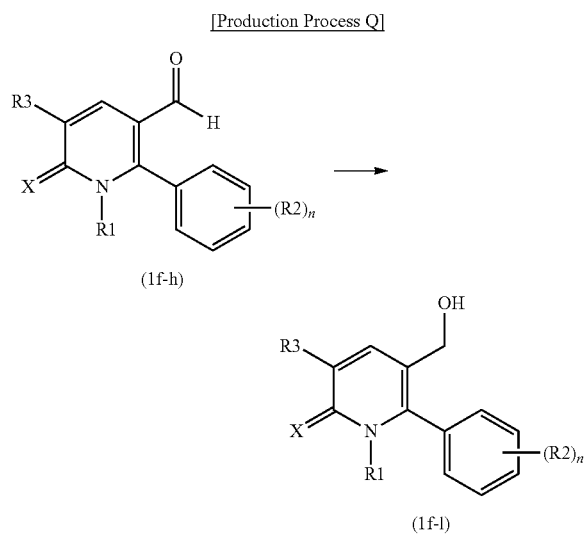

wherein, R1, R2, R3, X and n are the same as defined hereinabove.

Production Process Q is a method for obtaining, among a compound of formula (1f), a compound of formula (1f-1) having hydroxyl group. This production process comprises reacting a compound of formula (1f-h) with a hydride reagent in a solvent.

Examples of the hydride reagents used in the reaction include boron compounds such as sodium borohydride.

The amount of the hydride reagent used in the reaction is at least 1 equivalent amount in terms of hydride relative to the compound of formula (1f-h), and is not particularly limited as long as the target reaction takes place. The amount is usually from 1 equivalent amount to 40 equivalent amounts.

The solvent used in the reaction is not particularly limited as long as the target reaction takes place. Examples of the solvents include water solvent, ether solvents such as diethyl ether, diisopropyl ether, methyl t-butyl ether, dimethoxyethane, tetrahydrofuran and dioxane, alcohol solvents such as methanol, ethanol and isopropanol. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-h).

The temperature of the reaction is not particularly limited as long as the target reaction takes place, and is usually from −20° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-1) may be dried with a desiccant such as sodium sulfate or magnesium sulfate. This drying process may be omitted.

The reaction mixture comprising the compound of formula (1f-1) may be distilled under reduced pressure to remove the solvent as long as the compound do not decompose.

After the distillation, the reaction mixture comprising the compound of formula (1f-1) may be purified by, for example, washing, reprecipitation, recrystallization or column chromatography using an appropriate solvent. The purification process may be selected appropriately in accordance with the desired purity.

[Production Process R]

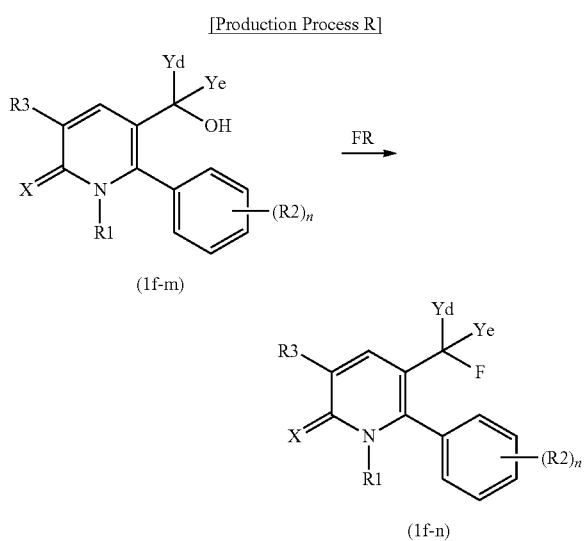

wherein, FR represents a fluorinating reagent, Yd and Ye are independent of one another and each represent a hydrogen atom, a C1-C9 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, or a C2-C6 haloalkynyl group, and R1, R2, R3, X and n are the same as defined hereinabove.

Production Process R is a method for obtaining, among a compound of formula (1f), a compound of formula (1f-n) having fluorine atom(s). This production process comprises reacting a compound of formula (1f-m) with a fluorinating reagent (FR) in a solvent.

Examples of the fluorinating reagents used in the reaction include (diethylamino)sulfur trifluoride, bis(2-methoxyethyl)aminosulfur trifluoride, N,N-diethyl-1,1,2,3,3,3-hexafluoropropylamine, 2,2-difluoro-1,3-dimethylimidazolidine.

The amount of the fluorinating reagent used in the reaction is at least 1 equivalent amount relative to the compound of formula (1f-m), and is not particularly limited as long as the target reaction takes place. The amount is usually from 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-m).

The temperature of the reaction is not particularly limited as long as the target reaction takes place, and is usually from −80° C. to 100° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-n) may be dried with a desiccant such as sodium sulfate or magnesium sulfate. This drying process may be omitted.

The reaction mixture comprising the compound of formula (1f-n) may be distilled under reduced pressure to remove the solvent as long as the compound do not decompose.

After the distillation, the reaction mixture comprising the compound of formula (1f-n) may be purified by, for example, washing, reprecipitation, recrystallization or column chromatography using an appropriate solvent. The purification process may be selected appropriately in accordance with the desired purity.

[Production Process S]

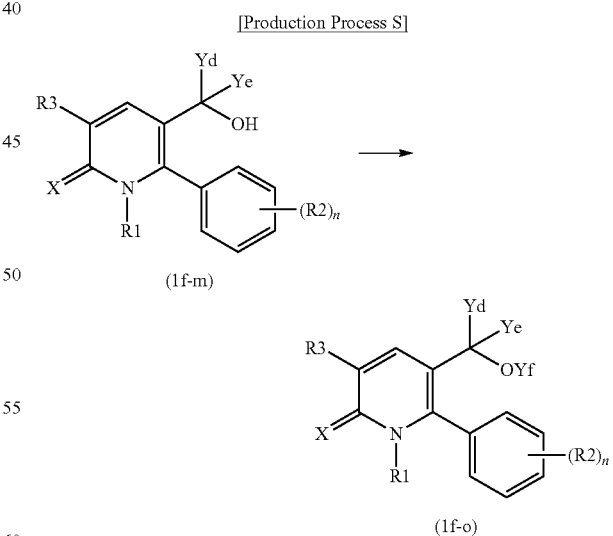

wherein, Yf represents a C1-C6 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, or a C2-C6 haloalkynyl group, and Yd, Ye, R1, R2, R3, X and n are the same as defined hereinabove.

Production Process S is a method for obtaining, among a compound of formula (1f), a compound of formula (1f-o) wherein Yf is a C1-C6 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, or a C2-C6 haloalkynyl group. This production process comprises reacting a compound of formula (1f-m) with orthoesters in a solvent in the presence of an acid.

The orthoesters used in the reaction is preferably an orthoformate ester, and may be commercially available or produced by a known method.

The amount of the orthoesters used in the reaction is at least 1 equivalent amount relative to the compound of formula (1f-m), and is not particularly limited as long as the target reaction takes place. The amount is usually from 1 equivalent amount to 30 equivalent amounts. The orthoesters may also serve as a solvent.

An alcohol of YfOH (Yb is the same as defined hereinabove) may be added to allow the reaction to take place smoothly. Such an alcohol may also serve as a solvent.

The amount of the alcohol YfOH (Yb is the same as defined hereinabove) used in the reaction is not particularly limited as long as the target reaction takes place, and is usually not more than 50 equivalent amounts relative to the compound of formula (1f-m). The use of the alcohol may be dispensable.

Examples of the acids used in the reaction include inorganic acids such as hydrochloric acid and sulfuric acid, organic acids such as trifluoroacetic acid, methanesulfonic acid, p-toluenesulfonic acid and trifluoromethanesulfonic acid.

The amount of the acid used in the reaction is at least 0.01 equivalent amount relative to the compound of formula (1f-m), and is not particularly limited as long as the target reaction takes place. The amount is usually from 0.01 equivalent amount to 1 equivalent amount.

The solvent used in the reaction is not particularly limited as long as the target reaction takes place. Examples of the solvents include alcohol solvents of YfOH (Yb is the same as defined hereinabove), nitro solvents such as nitromethane and nitrobenzene, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually not more than 200 times the weight of the compound of formula (1f-m). The use of the solvent may be dispensable.

The temperature of the reaction is not particularly limited as long as the target reaction takes place, and is usually from −30° C. to 100° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-o) may be dried with a desiccant such as sodium sulfate or magnesium sulfate. This drying process may be omitted.

The reaction mixture comprising the compound of formula (1f-o) may be distilled under reduced pressure to remove the solvent as long as the compound do not decompose.

After the distillation, the reaction mixture comprising the compound of formula (1f-o) may be purified by, for example, washing, reprecipitation, recrystallization or column chromatography using an appropriate solvent. The purification process may be selected appropriately in accordance with the desired purity.

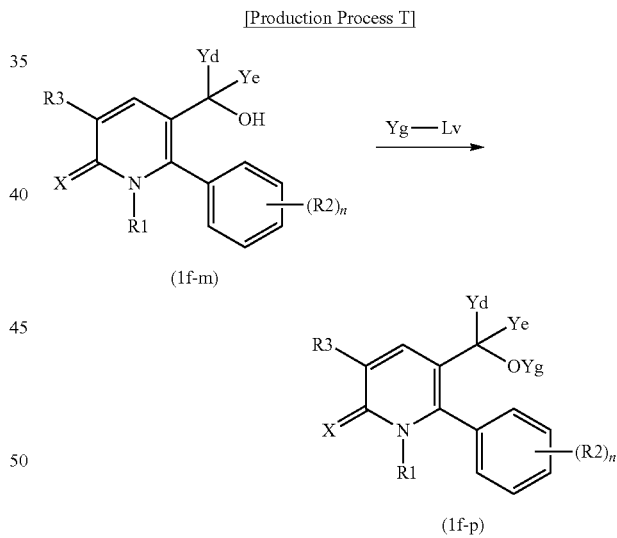

wherein, Yg represents a C1-C6 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C2-C6 alkynyl group optionally substituted with substituent(s) B, a C2-C6 haloalkynyl group, RdC(=O) (Rd is the same as defined hereinabove), an aryl group optionally substituted with 0 to 5 substituents D, a heteroaryl group optionally substituted with 0 to 2 substituents D, or an aralkyl group optionally substituted with 0 to 5 substituents D, and Yd, Ye, Lv, R1, R2, R3, X and n are the same as defined hereinabove.

Production Process T is a method for obtaining, among a compound of formula (1f), a compound of formula (1f-p) wherein Yg is a C1-C6 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C3-C6 alkynyl group optionally substituted with substituent(s) B, a C3-C6 haloalkynyl group, RdC(=O) (Rd is the same as defined hereinabove), an aryl group optionally substituted with 0 to 5 substituents D, a heteroaryl group optionally substituted with 0 to 2 substituents D, or an aralkyl group optionally substituted with 0 to 5 substituents D. This production process comprises reacting a compound of formula (1f-m) with Yg-Lv in a solvent in the presence of a base.

Yg-Lv used in the reaction may be commercially available or produced by a known method.

The amount of Yg-Lv used in the reaction is at least 1 equivalent amount relative to the compound of formula (1f-m), and is not particularly limited as long as the target reaction takes place. The amount is usually from 1 equivalent amount to 30 equivalent amounts.

Examples of the bases used in the reaction include inorganic bases such as sodium carbonate, potassium carbonate, cesium carbonate, sodium hydride and silver (I) oxide, organic bases such as triethylamine, tributylamine, diisopropylethylamine, pyridine, 4-dimethylaminopyridine, collidine and lutidine.

The amount of the base used in the reaction is at least 1 equivalent amount relative to the compound of formula (1f-m), and is not particularly limited as long as the target reaction takes place. The amount is usually from 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-m).

The temperature of the reaction is not particularly limited as long as the target reaction takes place, and is usually from −20° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-p) may be dried with a desiccant such as sodium sulfate or magnesium sulfate. This drying process may be omitted.

The reaction mixture comprising the compound of formula (1f-p) may be distilled under reduced pressure to remove the solvent as long as the compound do not decompose.

After the distillation, the reaction mixture comprising the compound of formula (1f-p) may be purified by, for example, washing, reprecipitation, recrystallization or column chromatography using an appropriate solvent. The purification process may be selected appropriately in accordance with the desired purity.

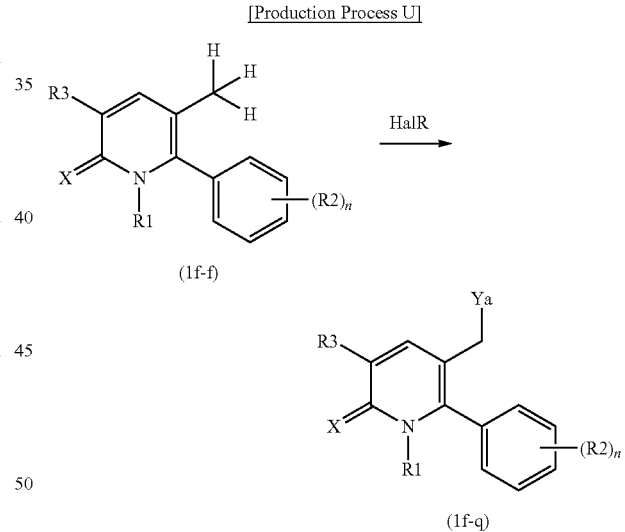

[Production Process U]

wherein, Ya, HalR, R1, R2, R3, X and n are the same as defined hereinabove.

Production Process U is a method for obtaining, among a compound of formula (1f), a compound of formula (1f-q) wherein Ya is a halogen atom. This production process comprises reacting a compound of formula (1f-f) using a radical initiator and a halogenating reagent (HalR) in a solvent.

In the formula (1f-q), Ya is preferably chlorine atom, bromine atom, or iodine atom.

The amount of the halogenating reagent used in the reaction is at least 1 equivalent amount relative to the compound of formula (1f-f), and is not particularly limited as long as the target reaction takes place. The amount is usually from 1 equivalent amount to 1.5 equivalent amounts. Where the halogenating reagent contains hydantoin, the amount thereof is at least 0.5 equivalent amounts and is usually from 0.5 equivalent amounts to 0.75 equivalent amounts, although not particularly limited as long as the target reaction takes place.

Production Process U may be carried out according to Production Process L by changing the amount of the halogenating reagent in Production Process L as described above.

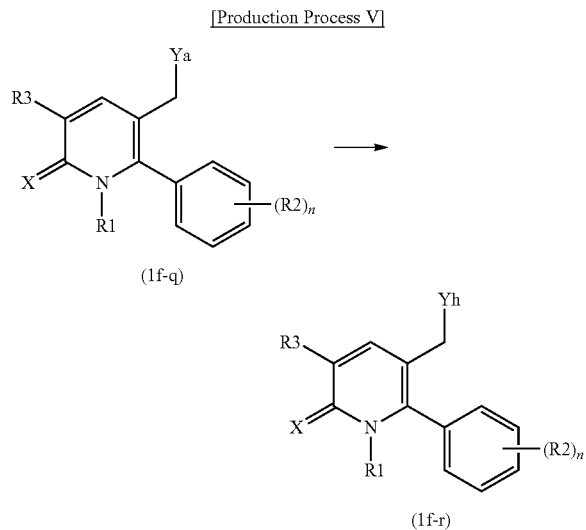

[Production Process V]

(1f-q)

(1f-r)

wherein, Yh represents RaRbN— (Ra and Rb are the same as defined hereinabove), Rg(RhO)N— (Rg and Rh are the same as defined hereinabove), or ReC(=O)N(Rf)— (Re and Rf are the same as defined hereinabove), and Ya, R1, R2, R3, X and n are the same as defined hereinabove.

Production Process V is a method for obtaining, among a compound of formula (1f), a compound of formula (1f-r) wherein Yh is RaRbN— (Ra and Rb are the same as defined hereinabove), Rg(RhO)N— (Rg and Rh are the same as defined hereinabove), or ReC(=O)N(Rf)— (Re and Rf are the same as defined hereinabove). This production process comprises reacting a compound of formula (1f-q) with RaRbN—H (Ra and Rb are the same as defined hereinabove), Rg(RhO)N—H (Rg and Rh are the same as defined hereinabove), or ReC(=O)N(Rf)—H (Re and Rf are the same as defined hereinabove) in a solvent in the presence of a base.

In the formula (1f-q), Ya is preferably chlorine atom, bromine atom, or iodine atom.

RaRbN—H (Ra and Rb are the same as defined hereinabove), Rg(RhO)N—H (Rg and Rh are the same as defined hereinabove), or ReC(=O)N(Rf)—H (Re and Rf are the same as defined hereinabove) used in the reaction may be commercially available or produced by a known method.

RaRbN—H (Ra and Rb are the same as defined hereinabove), or Rg(RhO)N—H (Rg and Rh are the same as defined hereinabove) used in the reaction may be in the form of a salt with an acidic substance such as hydrochloric acid or sulfuric acid. In this case, the acid may be desalted by a known method, and the resultant amines may be used. Alternatively, the amine salt may be used directly in the reaction by adding at least 1 equivalent amount of a base relative to the acidic substance forming the salt.

The amount of RaRbN—H (Ra and Rb are the same as defined hereinabove), Rg(RhO)N—H (Rg and Rh are the same as defined hereinabove), or ReC(=O)N(Rf)—H (Re and Rf are the same as defined hereinabove) used in the reaction is at least 1 equivalent amount relative to the compound of formula (1f-q), and is not particularly limited as long as the target reaction takes place. The amount is usually from 1 equivalent amount to 20 equivalent amounts.

Examples of the bases used in the reaction include inorganic bases such as sodium carbonate, potassium carbonate, cesium carbonate and sodium hydride, organic bases such as triethylamine, tributylamine, diisopropylethylamine, pyridine, 4-dimethylaminopyridine, collidine and lutidine.

The amount of the base used in the reaction is at least 1 equivalent amount relative to the compound of formula (1f-q), and is not particularly limited as long as the target reaction takes place. The amount is usually from 1 equivalent amount to 20 equivalent amounts. Where RaRbN—H (Ra and Rb are the same as defined hereinabove) or Rg(RhO)N—H (Rg and Rh are the same as defined hereinabove) that forms a salt with an acidic substance is used, the amount is preferably from 2 equivalent amounts to 40 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-q).

The temperature of the reaction is not particularly limited as long as the target reaction takes place, and is usually from 0° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-r) may be dried with a desiccant such as sodium sulfate or magnesium sulfate. This drying process may be omitted.

The reaction mixture comprising the compound of formula (1f-r) may be distilled under reduced pressure to remove the solvent as long as the compound do not decompose.

After the distillation, the reaction mixture comprising the compound of formula (1f-r) may be purified by, for example, washing, reprecipitation, recrystallization or column chromatography using an appropriate solvent. The purification process may be selected appropriately in accordance with the desired purity.

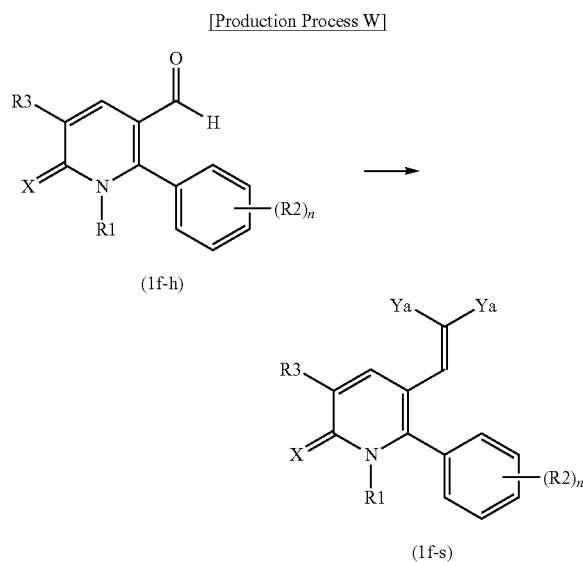

[Production Process W]

(1f-h)

(1f-s)

wherein, Ya, R1, R2, R3, X and n are the same as defined hereinabove.

Production Process W is a method for obtaining, among the compound of formula (1f), a compound of formula (1f-s). This production process comprises reacting a compound of formula (1f-h) in a solvent using a tetrahalomethane and an organophosphorus reagent.

In the formula (1f-s), Ya is preferably chlorine atom, bromine atom, or iodine atom.

Examples of the tetrahalomethanes used in the reaction include carbon tetrachloride, carbon tetrabromide, carbon tetraiodide.

The amount of the tetrahalomethane used in the reaction is at least 1 equivalent amount relative to the compound of formula (1f-h), and is not particularly limited as long as the target reaction takes place. The amount is usually from 1 equivalent amount to 10 equivalent amounts.

Examples of the organophosphorus reagents used in the reaction include triphenylphosphine.

The amount of the organophosphorus reagent used in the reaction is at least 1 equivalent amount relative to the compound of formula (1f-h), and is not particularly limited as long as the target reaction takes place. The amount is usually from 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as toluene, xylene, benzene, chlorobenzene and dichlorobenzene, nitrile solvents such as acetonitrile, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-h).

The temperature of the reaction is not particularly limited as long as the target reaction takes place, and is usually from 0° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-s) may be dried with a desiccant such as sodium sulfate or magnesium sulfate. This drying process may be omitted.

The reaction mixture comprising the compound of formula (1f-s) may be distilled under reduced pressure to remove the solvent as long as the compound do not decompose.

After the distillation, the reaction mixture comprising the compound of formula (1f-s) may be purified by, for example, washing, reprecipitation, recrystallization or column chromatography using an appropriate solvent. The purification process may be selected appropriately in accordance with the desired purity.

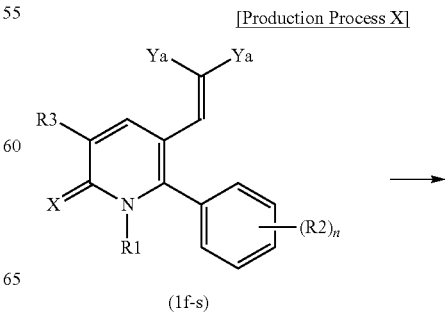

[Production Process X]

(1f-s)

-continued

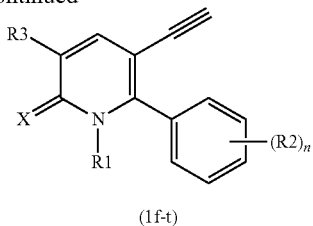

(1f-t)

wherein, Ya, R1, R2, R3, X and n are the same as defined hereinabove.

Production Process X is a method for obtaining, among a compound of formula (1f), a compound of formula (1f-t) having alkynyl group. This production process comprises converting a compound of formula (1f-s) in a solvent in the presence of a base.

Examples of the bases used in the reaction include organolithiums such as methyllithium, butyllithium, sec-butyllithium, t-butyllithium and hexyllithium, lithiumamides such as lithium diisopropylamide and hexamethyldisilazane lithium.

The amount of the base used in the reaction is at least 2 equivalent amounts relative to the compound of formula (1f-s), and is not particularly limited as long as the target reaction takes place. The amount is usually from 2 equivalent amounts to 5 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-s).

The temperature of the reaction is not particularly limited as long as the target reaction takes place, and is usually from −80° C. to 100° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-t) may be dried with a desiccant such as sodium sulfate or magnesium sulfate. This drying process may be omitted.

The reaction mixture comprising the compound of formula (1f-t) may be distilled under reduced pressure to remove the solvent as long as the compound do not decompose.

After the distillation, the reaction mixture comprising the compound of formula (1f-t) may be purified by, for example, washing, reprecipitation, recrystallization or column chromatography using an appropriate solvent. The purification process may be selected appropriately in accordance with the desired purity.

[Production Process Y]

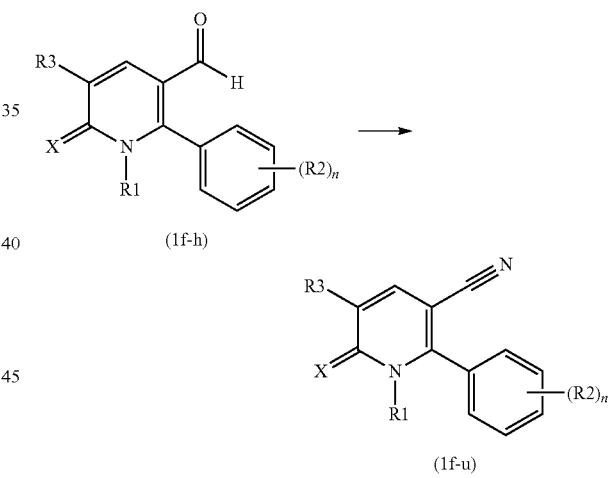

wherein, R1, R2, R3, X and n are the same as defined hereinabove.

Production Process Y is a method for obtaining, among a compound of formula (1f), a compound of formula (1f-u) having cyano group. This production process comprises reacting a compound of formula (1f-h) with hydroxylamine-O-sulfonic acid in a solvent.

The amount of the hydroxylamine-O-sulfonic acid used in the reaction is at least 1 equivalent amount relative to the compound of formula (1f-h), and is not particularly limited as long as the target reaction takes place. The amount is usually from 1 equivalent amount to 5 equivalent amounts.

An acid may be added to allow the reaction to take place smoothly.

Examples of the acids used in the reaction include organic acids such as acetic acid, methanesulfonic acid, p-toluenesulfonic acid and trifluoroacetic acid.

The amount of the acid used in the reaction may be a catalytic amount, and is not particularly limited as long as the target reaction takes place. The amount is usually not less than 0.1 equivalent amount relative to the compound of formula (1f-h). A liquid acid may also serve as a solvent.

The solvent used in the reaction is not particularly limited as long as the target reaction takes place. Examples of the solvents include water solvent, acidic solvents such as acetic acid and methanesulfonic acid, nitrile solvents such as acetonitrile, halogen solvents such as dichloromethane, dichloroethane, chloroform and carbon tetrachloride, sulfur solvents such as dimethylsulfoxide and sulfolane. The solvents may be used singly, or two or more of these solvents may be mixed in any proportions and used.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-u) may be dried with a desiccant such as sodium sulfate or magnesium sulfate. This drying process may be omitted.

The reaction mixture comprising the compound of formula (1f-u) may be distilled under reduced pressure to remove the solvent as long as the compound do not decompose.

After the distillation, the reaction mixture comprising the compound of formula (1f-u) may be purified by, for example, washing, reprecipitation, recrystallization or column chromatography using an appropriate solvent. The purification process may be selected appropriately in accordance with the desired purity.

The inventive compound of formula (1f-u) may also be used as an intermediate.

[Production Process Z]

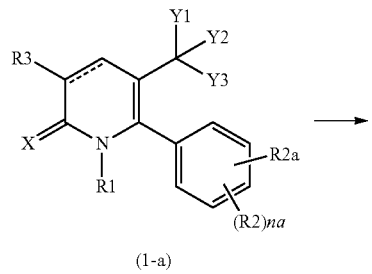

(1-a)

-continued

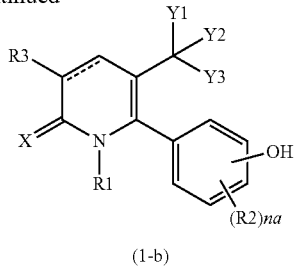

(1-b)

wherein, R2a represents a C1-C6 alkoxy group, na represents an integer of 0 to 4 (with the proviso that when na is 2 or greater, the two or more substituents R2 are independent of one another), and Y1, Y2, Y3, R1, R2, R3, X and the broken line are the same as defined hereinabove.

Production Process Z is a method for obtaining, among a compound of formula (1), a compound of formula (1-b) having hydroxyl group. This production process comprises reacting a compound of formula (1-a) with an acid in a solvent.

Examples of the acids used in the reaction include boron halides such as boron trichloride and boron tribromide.

The amount of the acid used in the reaction is at least 1 equivalent amount relative to the compound of formula (1-a), and is not particularly limited as long as the target reaction takes place. The amount is usually from 1 equivalent amount to 10 equivalent amounts.

The solvent used in the reaction is not particularly limited as long as the target reaction takes place. Examples of the solvents include benzene-based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1-a).

The temperature of the reaction is not particularly limited as long as the target reaction takes place, and is usually from −80° C. to 100° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1-b) may be dried with a desiccant such as sodium sulfate or magnesium sulfate. This drying process may be omitted.

The reaction mixture comprising the compound of formula (1-b) may be distilled under reduced pressure to remove the solvent as long as the compound do not decompose.

After the distillation, the reaction mixture comprising the compound of formula (1-b) may be purified by, for example, washing, reprecipitation, recrystallization or column chromatography using an appropriate solvent. The purification process may be selected appropriately in accordance with the desired purity.

[Production Process AA]

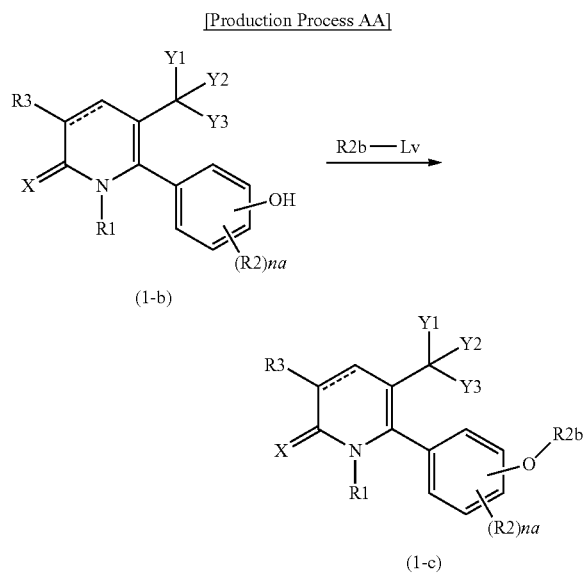

wherein, R2b represents a C1-C6 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C3-C6 alkynyl group optionally substituted with substituent(s) B, a C3-C6 haloalkynyl group, RdC(=O) (Rd is the same as defined hereinabove), an aryl group optionally substituted with 0 to 5 substituents D, a heteroaryl group optionally substituted with 0 to 2 substituents D, or an aralkyl group optionally substituted with 0 to 5 substituents D, and Lv, Y1, Y2, Y3, R1, R2, R3, X, na and the broken line are the same as defined hereinabove.

Production Process AA is a method for obtaining, among a compound of formula (1), a compound of formula (1-c) wherein R2b is a C1-C6 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, a C2-C6 haloalkenyl group, a C3-C6 alkynyl group optionally substituted with substituent(s) B, a C3-C6 haloalkynyl group, RdC(=O) (Rd is the same as defined hereinabove), an aryl group optionally substituted with 0 to 5 substituents D, a heteroaryl group optionally substituted with 0 to 2 substituents D, or an aralkyl group optionally substituted with 0 to 5 substituents D. This production process comprises reacting a compound of formula (1-b) with R2b-Lv in a solvent in the presence of a base.

R2b-Lv used in the reaction may be commercially available or produced by a known method.

Production Process AA may be carried out according to Production Process T by replacing the compound of formula (1f-m) and Yg-Lv in Production Process T with the compound of formula (1-b) and R2b-Lv, respectively.

[Production Process AB]

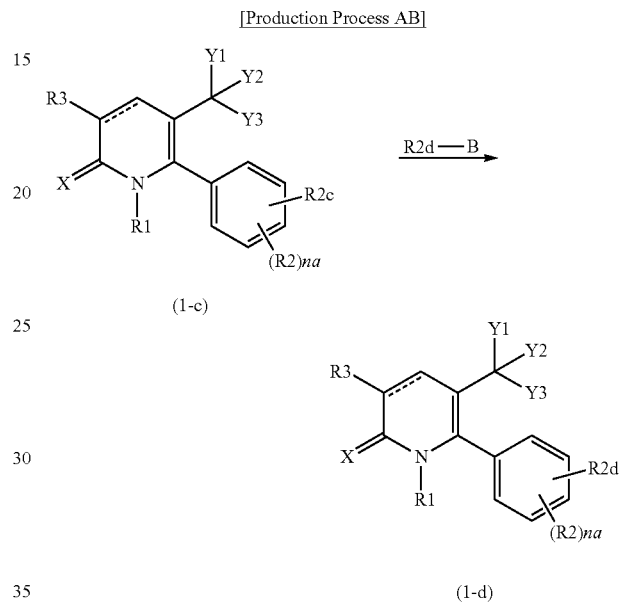

wherein, R2c represents a halogen atom, R2d represents a C1-C6 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, or a C2-C6 haloalkenyl group, R2d-B represents organoboronic acids, and Y1, Y2, Y3, R1, R3, X, na and the broken line are the same as defined hereinabove.

Production Process AB is a method for obtaining, among a compound of formula (1), a compound of formula (1-d) wherein R2d is a C1-C6 alkyl group optionally substituted with substituent(s) B, a C1-C6 haloalkyl group, a C3-C8 cycloalkyl group optionally substituted with substituent(s) B, a C2-C6 alkenyl group optionally substituted with substituent(s) B, or a C2-C6 haloalkenyl group. This production process comprises the Suzuki-Miyaura coupling reaction, i.e. reacting a compound of formula (1-c) with organoboronic acids (R2d-B) in a solvent in the presence of a transition metal and a base.

In the formula (1-c), R2c is preferably chlorine atom, bromine atom, or iodine atom.

R2d-B used in the reaction represents organoboronic acids such as an organic boronic acid or an organic boronate ester, and may be commercially available or produced by a known method.

Production Process AB may be carried out according to Production Process J by replacing the compound of formula (1f-b) and R3d-B in Production Process J with the compound of formula (1-c) and R2d-B, respectively.

[Production Process AC]

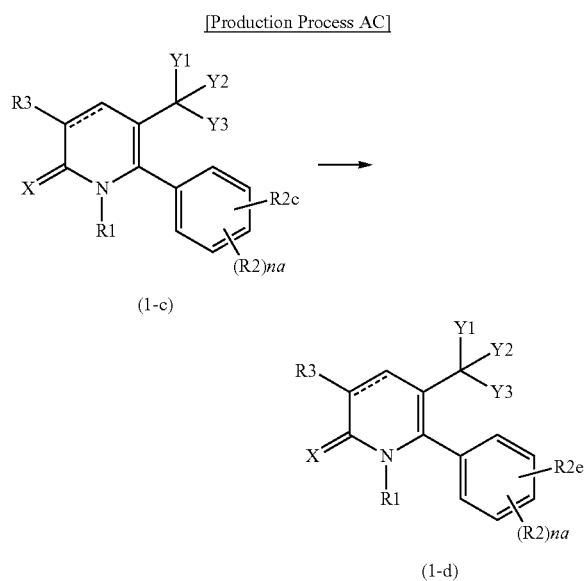

wherein, R2e represents a C2-C6 alkynyl group optionally substituted with substituent(s) B, or a C2-C6 haloalkynyl group, and R2c, Y1, Y2, Y3, R1, R3, X, na and the broken line are the same as defined hereinabove.

Production Process AC is a method for obtaining, among a compound of formula (1), a compound of formula (1-d) wherein R2e is a C2-C6 alkynyl group optionally substituted with substituent(s) B, or a C2-C6 haloalkynyl group. This production process comprises the Sonogashira coupling reaction, i.e. reacting a compound of formula (1-c) with an alkyne-terminated compound in a solvent in the presence of a transition metal and a base.

In the formula (1-c), R2c is preferably chlorine atom, bromine atom, or iodine atom.

The alkyne-terminated compound used in the reaction may be commercially available or produced by a known method. Trimethylsilylacetylene may also be used as the alkyne-terminated compound.

Production Process AC may be carried out according to Production Process K by replacing the compound of formula (1f-b) in Production Process K with the compound of formula (1-c).

[Production Process AD]

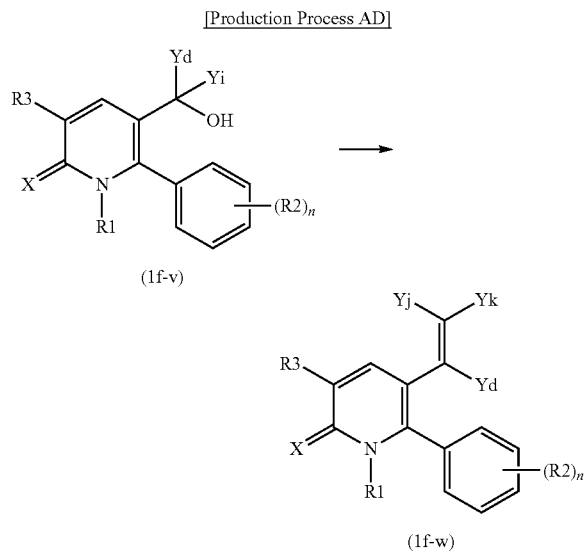

wherein, Yi represents a C1-C5 alkyl group optionally substituted with substituent(s) B, Yj and Yk are independent of one another and each represent a hydrogen atom or a C1-C4 alkyl group optionally substituted with substituent(s) B (wherein the total number of carbon atoms in Yj and Yk is 0 to 4), and R1, R2, R3, Yd, X and n are the same as defined hereinabove.

Production Process AD is a method for obtaining, among a compound of the formula (1f), a compound of formula (1f-w) having double bonds. This production process comprises reacting a compound of formula (1f-v) with an acid in a solvent.

Examples of the acids used in the reaction include inorganic acids such as hydrochloric acid, hydrobromic acid, phosphoric acid and boron trifluoride, organic acids such as acetic acid, methanesulfonic acid, p-toluenesulfonic acid and trifluoroacetic acid.

The amount of the acid used in the reaction may be a catalytic amount, and is not particularly limited as long as the target reaction takes place. The amount is usually at least 0.01 equivalent amount relative to the compound of formula (1f-v). A liquid acid may also serve as a solvent.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-v).

The temperature of the reaction is not particularly limited as long as the target reaction takes place, and is usually from −80° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-w) may be dried with a desiccant such as sodium sulfate or magnesium sulfate. This drying process may be omitted.

The reaction mixture comprising the compound of formula (1f-w) may be distilled under reduced pressure to remove the solvent as long as the compound do not decompose.

After the distillation, the reaction mixture comprising the compound of formula (1f-w) may be purified by, for example, washing, reprecipitation, recrystallization or column chromatography using an appropriate solvent. The purification process may be selected appropriately in accordance with the desired purity.

When the compound of formula (1f-w) has geometric isomeric forms, the compound may be either of E-isomer, Z-isomer or a mixture containing E-isomer and Z-isomer in any proportions without limitation.

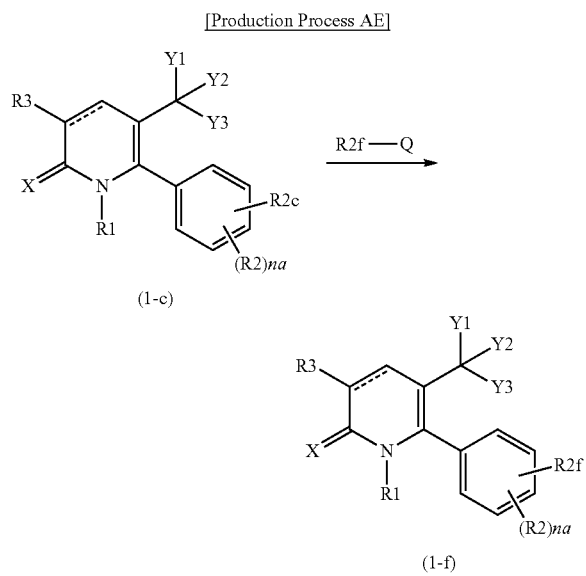

wherein, R2f represents a C1-C6 alkoxy group optionally substituted with substituent(s) B, a C1-C6 haloalkoxy group, a C3-C8 cycloalkoxy group optionally substituted with substituent(s) B, a C2-C6 alkenyloxy group optionally substituted with substituent(s) B, a C2-C6 haloalkenyloxy group, a C3-C6 alkynyloxy group optionally substituted with substituent(s) B, or a C3-C6 haloalkynyloxy group, and R2c, Y1, Y2, Y3, R1, R3, X, na, Q and the broken line are the same as defined hereinabove.

Production Process AD is a method for obtaining, among a compound of formula (1), a compound of formula (1-f) wherein R2f is a C1-C6 alkoxy group optionally substituted with substituent(s) B, a C1-C6 haloalkoxy group, a C3-C8 cycloalkoxy group optionally substituted with substituent(s) B, a C2-C6 alkenyloxy group optionally substituted with substituent(s) B, a C2-C6 haloalkenyloxy group, a C3-C6 alkynyloxy group optionally substituted with substituent(s) B, or a C3-C6 haloalkynyloxy group. This production process comprises reacting a compound of formula (1-c) with R2d-Q in a solvent.

R2f-Q used in the reaction may be commercially available or produced by a known method. Q is preferably a hydrogen atom, or alkali metals such as sodium or potassium.

The amount of R2f-Q used in the reaction is at least 1 equivalent amount relative to the compound of formula (1-c), and is not particularly limited as long as the target reaction takes place. The amount is usually from 1 equivalent amount to 30 equivalent amounts. When Q represents a hydrogen atom, R2f-Q may be used as a solvent.

The reaction may involve a base, for example inorganic bases such as sodium carbonate, potassium carbonate, cesium carbonate and sodium hydride. When Q is alkali metals, the base may not be used.

The amount of the base used in the reaction is at least 1 equivalent amount relative to the compound of formula (1-c), and is not particularly limited as long as the target reaction takes place. The amount is usually from 1 equivalent amount to 30 equivalent amounts.

The solvent used in the reaction is not particularly limited as long as the target reaction takes place. Examples of the solvents include alcohol solvents of R2f-H, ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1-c).

The temperature of the reaction is not particularly limited as long as the target reaction takes place, and is usually from 0° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid or sulfuric acid, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1-f) may be dried with a desiccant such as sodium sulfate or magnesium sulfate. This drying process may be omitted.

The reaction mixture comprising the compound of formula (1-f) may be distilled under reduced pressure to remove the solvent as long as the compound do not decompose.

After the distillation, the reaction mixture comprising the compound of formula (1-f) may be purified by, for example, washing, reprecipitation, recrystallization or column chromatography using an appropriate solvent. The purification process may be selected appropriately in accordance with the desired purity.

[Production Process AF]

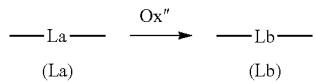

wherein, La represents S, Lb represents SO or $SO_2$, and Ox″ represents an oxidizer.

Production Process AF is a method for obtaining, among a compound of formula (1), a compound of formula (Lb) wherein Lb in R1, R2, R3, Y1, Y2 and Y3 is SO or $SO_2$. This production process comprises reacting, among a compound of formula (1), a compound of formula (La) wherein La in R1, R2, R3, Y1, Y2 and Y3 is S, with an oxidizer (Ox″) in a solvent.

The oxidizer used in the reaction may be, for example peroxides such as hydrogen peroxide solution or m-chloroperbenzoic acid. Transition metals such as sodium tungstate may be added.

When producing SO, the amount of the oxidizer used in the reaction is usually 1.0 equivalent amount to 1.2 equivalent amounts relative to the compound of formula (La). When producing $SO_2$, the amount is usually from 2 equivalent amounts to 10 equivalent amounts relative to the compound of formula (La). When a transition metal is added, the amount thereof is usually from 0.001 equivalent amount to 1 equivalent amount.

The solvent used in the reaction is not particularly limited as long as the target reaction takes place. Examples of the solvents include water solvent, acidic solvents such as acetic acid, benzene-based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (La).

The temperature of the reaction is not particularly limited as long as the target reaction takes place, and is usually from −10° C. to 120° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid or sulfuric acid, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (Lb) may be dried with a desiccant such as sodium sulfate or magnesium sulfate. This drying process may be omitted.

The reaction mixture comprising the compound of formula (Lb) may be distilled under reduced pressure to remove the solvent as long as the compound do not decompose.

After the distillation, the reaction mixture comprising the compound of formula (Lb) may be purified by, for example, washing, reprecipitation, recrystallization or column chromatography using an appropriate solvent. The purification process may be selected appropriately in accordance with the desired purity.

[Production Process AG]

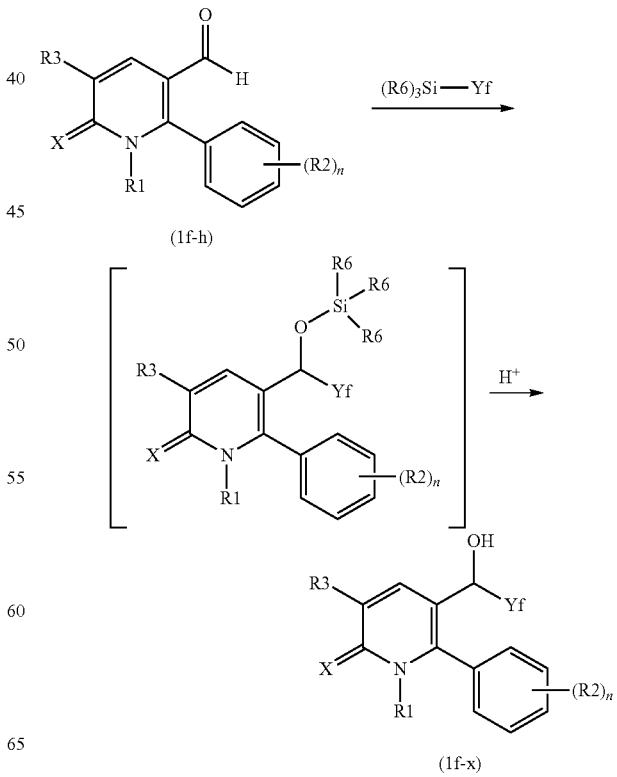

In the formula, R6 represents a C1-C6 alkyl group, Yf represents a C1-C6 haloalkyl group, and R1, R2, R3, X and n are the same as defined hereinabove.

Production Process AG is a method for obtaining, among a compound of formula (1f), a compound of formula (1f-x) wherein Yf is a haloalkyl group. This production process comprises reacting a compound of formula (1f-h) with (R6)$_3$Si-Yf in a solvent in the presence of a base.

(R6)$_3$Si-Yf used in the reaction may be commercially available or produced by a known method.

The amount of (R6)$_3$Si-Yf used in the reaction is at least 1 equivalent amount relative to the compound of formula (1f-h), and is not particularly limited as long as the target reaction takes place. The amount is usually from 1 equivalent amount to 10 equivalent amounts.

Examples of the bases used in the reaction include inorganic bases such as sodium carbonate, potassium carbonate, cesium carbonate, lithium carbonate, ammonium carbonate, sodium hydrogen carbonate, potassium hydrogen carbonate, tripotassium phosphate, dipotassium hydrogen phosphate, potassium dihydrogen phosphate, potassium fluoride and cesium fluoride, organic bases such as trimethylamine N-oxide, pyridine N-oxide and tetrabutylammonium fluoride.

The amount of the base used in the reaction may be a catalytic amount, and is not particularly limited as long as the target reaction takes place. The amount is usually not less than 0.01 equivalent amount relative to the compound of formula (1f-h).

An acid such as hydrochloric acid, sulfuric acid or trifluoroacetic acid may be added to perform desilylation.

The amount of the acid used for the desilylation is at least 1 equivalent amount relative to the compound of formula (1f-h), and is not particularly limited as long as the target reaction takes place.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-h).

The temperature of the reaction is not particularly limited as long as the target reaction takes place, and is usually from −80° C. to 100° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-x) may be dried with a desiccant such as sodium sulfate or magnesium sulfate. This drying process may be omitted.

The reaction mixture comprising the compound of formula (1f-x) may be distilled under reduced pressure to remove the solvent as long as the compound do not decompose.

After the distillation, the reaction mixture comprising the compound of formula (1f-x) may be purified by, for example, washing, reprecipitation, recrystallization or column chromatography using an appropriate solvent. The purification process may be selected appropriately in accordance with the desired purity.

[Production Process AH]

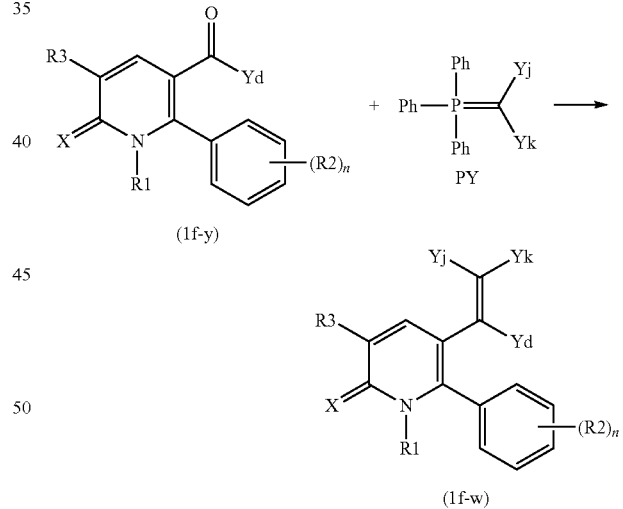

wherein, R1, R2, R3, Yd, Yj, Yk, X and n are the same as defined hereinabove.

Production Process AH is a method for obtaining, among a compound of the formula (1f), a compound of formula (1f-w) having double bonds. This production process comprises the Wittig reaction, i.e. reacting a compound of formula (1f-y) with phosphorus ylides (PY) in a solvent.

The phosphorus ylides used in the reaction may be prepared by treating a phosphonium salt (commercially available or produced by a known method) with a base. The phosphorus ylides thus prepared may be used directly in Production Process AH without isolation.

The amount of the phosphorus ylides used in the reaction is at least 1 equivalent amount relative to the compound of formula (1f-y), and is not particularly limited as long as the target reaction takes place. The amount is usually from 1 equivalent amount to 20 equivalent amounts.

Examples of the bases used in the preparation of the phosphorus ylides include inorganic bases such as sodium carbonate, potassium carbonate, cesium carbonate and sodium hydride, metal alkoxides such as sodium methoxide, sodium ethoxide and potassium t-butoxide, organolithiums such as methyllithium, butyllithium, sec-butyllithium, t-butyllithium and hexyllithium, lithiumamides such as lithium diisopropylamide and hexamethyldisilazane lithium.

The amount of the base used in the preparation of the phosphorus ylides is at least 1 equivalent amount relative to the phosphonium salt and is not particularly limited as long as the target reaction takes place. The amount is usually from 1 equivalent amount to 20 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-y).

The temperature of the reaction is not particularly limited as long as the target reaction takes place, and is usually from −80° C. to 100° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-w) may be dried with a desiccant such as sodium sulfate or magnesium sulfate. This drying process may be omitted.

The reaction mixture comprising the compound of formula (1f-w) may be distilled under reduced pressure to remove the solvent as long as the compound do not decompose.

After the distillation, the reaction mixture comprising the compound of formula (1f-w) may be purified by, for example, washing, reprecipitation, recrystallization or column chromatography using an appropriate solvent. The purification process may be selected appropriately in accordance with the desired purity.

[Production Process AI]

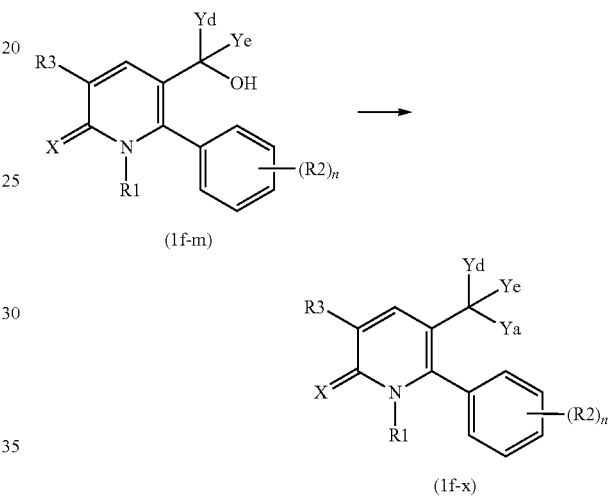

wherein, R1, R2, R3, Ya, Yd, Ye, X and n are the same as defined hereinabove.

Production Process AI is a method for obtaining, among a compound of formula (1f), a compound of formula (1f-x) wherein Ya is a halogen atom. This production process comprises reacting a compound of formula (1f-m) in a solvent using a tetrahalomethane and an organophosphorus reagent.

In the formula (1f-x), Ya is preferably chlorine atom, or bromine atom.

Examples of the tetrahalomethanes used in the reaction include carbon tetrachloride, carbon tetrabromide.

The amount of the tetrahalomethane used in the reaction is at least 1 equivalent amount relative to the compound of formula (1f-m), and is not particularly limited as long as the target reaction takes place. The amount is usually from 1 equivalent amount to 30 equivalent amounts. Carbon tetrachloride may also be used as a solvent and may be used in large excess amount.

Examples of the organophosphorus reagents used in the reaction include triphenylphosphine.

The amount of the organophosphorus reagent used in the reaction is at least 1 equivalent amount relative to the compound of formula (1f-m), and is not particularly limited as long as the target reaction takes place. The amount is usually from 1 equivalent amount to 30 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as toluene, xylene, benzene, chlorobenzene and dichlorobenzene, nitrile solvents such as acetonitrile, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-m).

The temperature of the reaction is not particularly limited as long as the target reaction takes place, and is usually from 0° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-x) may be dried with a desiccant such as sodium sulfate or magnesium sulfate. This drying process may be omitted.

The reaction mixture comprising the compound of formula (1f-x) may be distilled under reduced pressure to remove the solvent as long as the compound do not decompose.

After the distillation, the reaction mixture comprising the compound of formula (1f-x) may be purified by, for example, washing, reprecipitation, recrystallization or column chromatography using an appropriate solvent. The purification process may be selected appropriately in accordance with the desired purity.

[Production Process AJ]

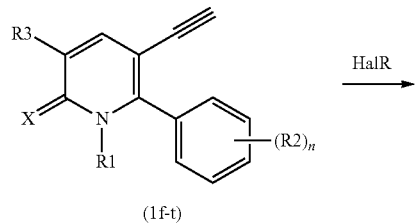

(1f-t)

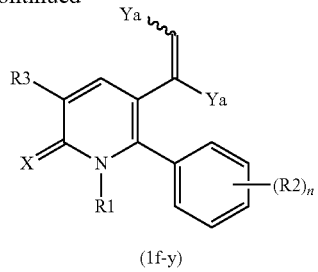

(1f-y)

wherein, R1, R2, R3, Ya, X and n are the same as defined hereinabove.

Production Process AJ is a method for obtaining, among a compound of formula (1f), a compound of formula (1f-y) wherein Ya is a halogen atom.

This production process comprises reacting a compound of formula (1f-t) with a halogenating reagent (HalR) in a solvent.

In the formula (1f-y), Ya is preferably chlorine atom, or bromine atom.

Examples of the halogenating reagents used in the reaction include N-chlorosuccinimide, N-bromosuccinimide, 1,3-dichloro-5,5-dimethylhydantoin, 1,3-dibromo-5,5-dimethylhydantoin, chlorine, bromine, sulfuryl chloride.

The amount of the halogenating reagent used in the reaction is at least 2 equivalent amounts relative to the compound of formula (1f-t), and is not particularly limited as long as the target reaction takes place. The amount is usually from 2 equivalent amounts to 20 equivalent amounts. Where the halogenating reagent is chlorine, bromine or sulfuryl chloride, or contains hydantoin, the amount of the halogenating reagent is at least 1 equivalent amount and is usually from 1 equivalent amount to 10 equivalent amounts, although the amount is not particularly limited as long as the target reaction takes place.

The solvent used in the reaction is not particularly limited as long as the target reaction takes place. Examples of the solvents include acidic solvents such as acetic acid, ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, halogen solvents such as dichloromethane, dichloroethane, chloroform and carbon tetrachloride. The solvents may be used singly, or two or more of these solvents may be mixed in any proportions and used.

The amount of the solvent used in the reaction is not particularly limited as long as the target reaction takes place, and is usually from 3 to 200 times the weight of the compound of formula (1f-t).

The temperature of the reaction is not particularly limited as long as the target reaction takes place, and is usually from −80° C. to 150° C. or is not more than the boiling point of the solvent.

As post-treatment, water or an appropriate aqueous solution may be added to the reaction mixture to perform separation. The aqueous solution that is used here may be, for example, an aqueous solution of acids such as hydrochloric acid, sulfuric acid or ammonium chloride, an aqueous solution of alkalis such as potassium hydroxide, sodium hydroxide, sodium carbonate, potassium carbonate, sodium hydrogen carbonate or potassium hydrogen carbonate, an aqueous solution of a sulfur-containing salt such as sodium thiosulfate or sodium sulfite, or brine. During the separation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane. The solvents may be used singly, or two or more of these solvents may be mixed in any proportions and used. The number of separation is not particularly limited and may be determined in accordance with the desired purity or yield.

The reaction mixture comprising the compound of formula (1f-y) may be dried with a desiccant such as sodium sulfate or magnesium sulfate. This drying process may be omitted.

The reaction mixture comprising the compound of formula (1f-y) may be distilled under reduced pressure to remove the solvent as long as the compound do not decompose.

After the distillation, the reaction mixture comprising the compound of formula (1f-y) may be purified by, for example, washing, reprecipitation, recrystallization or column chromatography using an appropriate solvent. The purification process may be selected appropriately in accordance with the desired purity.

When the compound of formula (1f-y) has geometric isomeric forms, the compound may be either of E-isomer or Z-isomer, or a mixture containing E-isomer and Z-isomer in any proportions without limitation.

The compounds of formula (1) may be produced by an appropriate combination of Production Process A to Production Process AJ described hereinabove. The compounds of formula (1) may also be produced by an appropriate combination of a known process and any of Production Process A to Production Process AJ.

The inventive compounds can protect plants from pests, and thus, may be used as agricultural chemicals, particularly as agricultural and horticultural pest control agents. Specific examples include fungicides, insecticides, herbicides, plant growth regulators, with fungicides being preferable.

The inventive compounds may be used as agricultural and horticultural fungicides in, for example farms, paddy fields, tea gardens, orchards, meadows, grasses, forests, gardens, roadside trees for controlling plant diseases.

Plant diseases in the present invention means that systemic abnormal pathological states such as wilting, damping-off, yellowing, dwarfism and spindly growth, or partial pathological states such as spotting, leaf blight, mosaic pattern, leaf rolling, die back, root rot, clubroot and knotting, are induced in plants such as crops, flowering plants, flowering trees and shrubs, and trees. In other words, the term means that plants become or have become ill. Some main pathogens that cause plant diseases include fungi, bacteria, spiroplasmas, phytoplasmas, viruses, viroids, parasitic higher plants and nematodes. The inventive compounds are effective against, but not limited to, fungi.

Diseases caused by fungi are mainly fungal diseases. Examples of the fungi (pathogens) that cause fungal diseases include *Plasmodiophora*, Oomycetes, Zygomycetes, Ascomycetes, Basidiomycetes, Deuteromycetes. Examples of the *Plasmodiophora* include clubroot fungus, potato powdery scab fungus, beet necrotic yellow vein virus. Examples of the Oomycetes include blight fungus, downy mildew fungus, *Pythium* species, *Aphanomyces* species. Examples of the Zygomycetes include *Rhizopus* species. Examples of the Ascomycetes include peach leaf curl fungus, corn southern leaf blight fungus, rice blast fungus, powdery mildew fungus, anthracnose fungus, *fusarium* head blight fungus, bakanae fungus, stem rot fungus. Examples of the Basidiomycetes include rust fungus, smut fungus, violet root rot fungus, blister blight fungus, rice sheath blight fungus. Examples of the Deuteromycetes include gray mold fungus, *Alternaria* species, *Fusarium* species, *Penicillium* species, *Rhizoctonia* species, southern blight fungus.

The inventive compounds are effective against various plant diseases. The following provides specific examples of disease names and pathogens thereof.

Rice: blast (*Magnaporthe grisea*), sheath blight (*Thanatephorus cucumeris*), brown sclerotial disease (*Ceratobasidium setariae*), brown small sclerotial disease (*Waitea circinata*), brown sheath blight (*Thanatephorus cucumeris*), globular sclerotial disease (*Sclerotium hydrophilum*), red sclerotial disease (*Wairea circinata*), black leaf blight (*Entyloma dactylidis*), stem rot (*Magnaporthe salvinii*), gray sclerotial disease (*Ceratobasidium cornigerum*), brown spot (*Cochliobolus miyabeanus*), cercospora leaf spot (*Sphaerulina oryzina*), bakanae disease (*Gibberella fujikuroi*), seedling blight (*Pythium* spp., *Fusarium* spp., *Trichoderma* spp., *Rhizopus* spp., *Rhizoctonia solani*, *Mucor* sp., *Phoma* sp.), seedling rot (*Pythium* spp., *Achlya* spp., *Dictyuchus* spp.), rice false smut (*Claviceps virens*), kernel smut (*Tilletia barclayana*), discolored rice grains (*Curvularia* spp., *Alternaria* spp.), crazy top (*Sclerophthora macrospora*), bacterial leaf blight (*Xanthomonas oryzae* pv. *oryzae*), bacterial brown stripe (*Acidovorax avenae* subsp. *avenae*), bacterial palea browning (*Erwinia ananas*), bacterial seeding blight (*Burkholderia plantarii*), bacterial grain rot (*Burkholderia glumae*), sheath brown rot (*Pseudomonas fuscovaginae*), bacterial halo blight (*Pseudomonas syringae* pv. *oryzae*), bacterial foot rot (*Erwinia chrysanthemi*), yellow dwarf (*Phytoplasma oryzae*), rice stripe (Rice stripe tenuivirus), rice dwarf (Rice dwarf reovirus);

wheat and barley: powdery mildew (*Blumeria graminis* f sp. *hordei*; f sp. *tritici*), rust (*Puccinia striiformis*, *Puccinia graminis*, *Puccinia recondita*, *Puccinia hordei*), leaf blotch (*Pyrenophora graminea*), net blotch (*Pyrenophora teres*), Fusarium head blight (*Gibberella zeae*, *Fusarium culmorum*, *Fusarium avenaceum*, *Monographella nivalis*), *Typhula* snow blight (*Typhula incarnata*, *Typhula ishikariensis*, *Monographella nivalis*), loose smut (*Ustilago nuda*), stinking smut (*Tilletia caries*, *Tilletia controversa*), eye spot (*Pseudocercosporella herpotrichoides*), foot rot (*Ceratobasidium gramineum*), leaf scald (*Rhynchosporium secalis*), speckled leaf blotch (*Septoria tritici*), glume blotch (*Phaeosphaeria nodorum*), damping-off (*Fusarium* spp., *Pythium* spp., *Rhizoctonia* spp., *Septoria* spp., *Pyrenophora* spp.), take-all (*Gaeumannomyces graminis*), anthracnose (*Colletotrichum graminicola*), ergot (*Claviceps purpurea*), leaf spot (*Cochliobolus sativus*), bacterial black node (*Pseudomonas syringae* pv. *syringae*);

corn: *Fusarium* blight (*Gibberella zeae*, etc.), damping-off (*Fusarium avenaceum*, *Penicillium* spp., *Pythium* spp., *Rhizoctonia* spp.), rust (*Puccinia sorghi*), brown spot (*Cochliobolus heterostrophus*), smut (*Ustilago maydis*), anthracnose (*Colletotrichum graminicola*), northern leaf spot (*Cochliobolus carbonum*), bacterial brown stripe (*Acidovorax avenae* subsp. *avenae*), bacterial stripe (*Burkholderia andropogonis*), bacterial stalk rot (*Erwinia chrysanthemi* pv. *zeae*), bacterial wilt (*Erwinia stewartii*); grapes: downy mildew (*Plasmopara viticola*), rust (*Physopella ampelopsidis*), powdery mildew (*Uncinula necator*), scab (*Elsinoe ampelina*), ripe rot (*Glomerella cingulata*, *Colletotrichum*

*acutatum*), black rot (*Guignardia bidwellii*), Phomopsis leaf spot (*Phomopsis viticola*), fly speck (*Zygophiala jamaicensis*), gray mold (*Botrytis cinerea*), twig blight (*Diaporthe medusaea*), violet root rot (*Helicobasidium mompa*), white root rot (*Rosellinia necatrix*), crown gall (*Agrobacterium vitis*); apples: powdery mildew (*Podosphaera leucotricha*), black spot disease (*Venturia inaequalis*), Alternaria leaf spot (*Alternaria mali*), rust (*Gymnosporangium yamadae*), blossom blight (*Monilinia mali*), apple canker (*Valsa ceratosperma*), ring spot (*Botryosphaeria berengeriana*), anthracnose (*Colletotrichum acutatum, Glomerella cingulata*), fly speck (*Zygophiala jamaicensis*), sooty spot (*Gloeodes pomigena*), fruit spot (*Mycosphaerella pomi*), violet root rot (*Helicobasidium mompa*), white root rot (*Rosellinia necatrix*), canker (*Phomopsis mali, Diaporthe tanakae*), apple blotch (*Diplocarpon mali*), fire blight (*Erwinia amylovora*), crown gall (*Agrobacterium tumefaciens*), hairy root disease (*Agrobacterium rhizogenes*);

Japanese pears: black spot (*Alternaria kikuchiana*), pear scab (*Venturia nashicola*), rust (*Gymnosporangium asiaticum*), ring spot (*Botryosphaeria berengeriana* f. sp. *piricola*), pear canker (*Phomopsis fukushii*), bacterial shoot blight (*Erwinia* sp.), crown gall (*Agrobacterium tumefaciens*), rusty canker (*Erwinia chrysanthemi* pv. *chrysanthemi*), bacterial petal blight (*Pseudomonas syringae* pv. *syringae*); European pears: blight (*Phytophthora cactorum, Phytophthora syringae*), bacterial shoot blight (*Erwinia* sp.); peaches: black spot (*Cladosporium carpophilum*), Phomopsis rot (*Phomopsis* sp.), blight (*Phytophthora* sp.), anthracnose (*Colletotrichum gloeosporioides*), leaf curl (*Taphrina deformans*), bacterial shot hole (*Xhanthomonas campestris* pv. *pruni*), crown gall (*Agrobacterium tumefaciens*); cherries: anthracnose (*Glomerella cingulata*), young fruit sclerotial disease (*Monilinia kusanoi*), gray spot (*Monilinia fructicola*), crown gall (*Agrobacterium tumefaciens*), bacterial gummosis (*Pseudomonas syringae* pv. *syringae*); persimmons: anthracnose (*Glomerella cingulata*), leaf spot (*Cercospora kaki; Mycosphaerella nawae*), powdery mildew (*Phyllactinia kakikora*), crown gall (*Agrobacterium tumefaciens*); citrus fruits: melanose (*Diaporthe citri*), green mold disease (*Penicillium digitatum*), blue mold disease (*Penicillium italicum*), scab (*Elsinoe fawcettii*), brown rot (*Phytophthora citrophthora*), canker (*Xhanthomonas campestris* pv. *citri*), bacterial brown spot (*Pseudomonas syringae* pv. *syringae*), greening disease (*Liberibactor asiaticus*), crown gall (*Agrobacterium tumefaciens*);

tomatoes, cucumbers, beans, strawberries, potatoes, cabbage, eggplants, lettuce and the like: gray mold (*Botrytis cinerea*); tomatoes, cucumbers, beans, strawberries, potatoes, rapeseed, cabbage, eggplants, lettuce and the like: sclerotial disease (*Sclerotinia sclerotiorum*); various vegetables such as tomatoes, cucumbers, beans, Japanese radishes, watermelons, eggplants, rapeseed, green peppers, spinach and beets: seedling damping-off (*Rhizoctonia* spp., *Pythium* spp., *Fusarium* spp., *Phythophthora* spp., *Sclerotinia sclerotiorum*, etc.); solanaceous plants: bacterial wilt (*Ralstonia solanacearum*); Cucurbitaceae: downy mildew (*Pseudoperonospora cubensis*), powdery mildew (*Sphaerotheca fuliginea*), anthracnose (*Colletotrichum orbiculare*), gummy stem blight (*Didymella bryoniae*), stem rot (*Fusarium oxysporum*), late blight (*Phytophthora parasitica, Phytophthora melonis, Phytophthora nicotianae, Phytophthora drechsleri, Phytophthora capsici*, etc.), bacterial brown spot (*Xhanthomonas campestris* pv. *cucurbitae*), soft rot (*Erwinia carotovora* subsp. *carotovora*), bacterial spot (*Pseudomonas syringae* pv. *lachrymans*), marginal blight (*Pseudomonas marginalis* pv. *marginalis*), canker (*Streptomyces* sp.), hairy root disease (*Agrobacterium rhizogenes*), cucumber mosaic virus (Cucumber mosaic virus);

tomatoes: ring spot (*Alternaria solani*), leaf mold (*Fulvia fulva*), late blight (*Phytophthora infestans*), wilt disease (*Fusarium oxysporum*), root rot (*Pythium myriotylum, Pythium dissotocum*), anthracnose (*Colletotrichum gloeosporioides*), canker (*Clavibacter michiganensis*), pith necrosis (*Pseudomonas corrugata*), bacterial black spot (*Pseudomonas viridiflava*), soft rot (*Envinia carotovora* subsp. *carotovora*), bacterial leaf gall (*Crynebacterium* sp.), yellowing wilt (*Phytoplasma asteris*), yellow dwarfism (Tobacco leaf curl, subgroup III geminivirus); eggplants: powdery mildew (*Sphaerotheca fuliginea* etc.), leaf mold (*Mycovellosiella nattrassii*), blight (*Phytophthora infestans*), brown rot (*Phytophthora capsici*), bacterial brown spot (*Pseudomonas cichorii*), necrotic leaf spot (*Pseudomonas corrugata*), bacterial stem rot (*Envinia chrysanthemi*), soft rot (*Envinia carotovora* subsp. *carotovora*), bacterial spot (*Pseudomonas* sp.); rapeseed: black spot (*Alternaria brassicae*), black rot (*Xhanthomonas campestris* pv. *campestris*), bacterial black spot (*Pseudomonas syringae* pv. *maculicola*), soft rot (*Envinia carotovora*); cruciferous vegetables: black spot (*Alternaria brassicae* etc.), white spot (*Cercosporella brassicae*), black leg (*Phoma lingam*), clubroot (*Plasmodiophora brassicae*), downy mildew (*Peronospora parasitica*), black rot (*Xanthomonas campestris* pv. *campestris*), bacterial black spot (*Pseudomonas syringae* pv. *maculicola*), soft rot (*Envinia carotovora* subsp. *carotovora*);

cabbage: club foot (*Thanatephorus cucumeris*), yellowing wilt (*Fusarium oxysporum*), alternaria sooty spot (*Alternaria brassisicola*); Chinese cabbage: bottom rot (*Rhizoctonia solani*), yellowing (*Verticillium dahliae*); green onions: rust (*Puccinia allii*), black spot (*Alternaria porri*), southern blight (*Sclerotium rolfsii*), white rot (*Phytophthora porri*), black rot (*Sclerotium cepivorum*); onions: canker (*Curtobacterium flaccumfaciens*), soft rot (*Erwinia carotovora* subsp. *carotovora*), bacterial spot (*Pseudomonas syringae* pv. *syringae*), rot (*Erwinia rhapontici*), scale rot (*Burkholderia gladioli*), yellowing wilt (*Phytoplasma asteris*); garlic: soft rot (*Erwinia carotovora* subsp. *carotovora*), spring rot (*Pseudomonas marginalis* pv. *marginalis*); soybeans: purple seed stain (*Cercospora kikuchii*), scab (*Elsinoe glycines*), black spot (*Diaporthe phaseolorum*), Rhizoctonia root rot (*Rhizoctonia solani*), stem rot (*Phytophthora sojae*), downy mildew (*Peronospora manshurica*), rust (*Phakopsora pachyrhizi*), anthracnose (*Colletotrichum truncatum* etc.), leaf scald (*Xhanthomonas campestris* pv. *glycines*), bacterial spot (*Pseudomonas syringae* pv. *glycinea*); kidney beans: anthracnose (*Colletotrichum lindemuthianum*), bacterial wilt (*Ralstonia solanacearum*), halo blight (*Pseudomonas syringae* pv. *phaseolicola*), bacterial brown spot (*Pseudomonas viridiflava*), leaf scald (*Xhanthomonas campestris* pv. *phaseoli*);

peanuts: leaf spot (*Mycosphaerella berkeleyi*), brown spot (*Mycosphaerella arachidis*), bacterial wilt (*Ralstonia solanacearum*); garden peas: powdery mildew (*Erysiphe pisi*), downy mildew (*Peronospora pisi*), bacterial stem blight (*Pseudomonas syringae* pv. *pisi*), bacterial stem rot (*Xhanthomonas campestris* pv. *pisi*); broad beans: downy mildew (*Peronospora viciae*), blight (*Phytophthora nicotianae*); potatoes: early blight (*Alternaria solani*), black scurf (*Thanatephorus cucumeris*), blight (*Phytophthora infestans*), silver scurf (*Helminthosporium solani*), soft rot (*Fusarium oxysporum, Fusarium solani*), powdery scab (*Spongospora subterranea*), bacterial wilt (*Ralstonia solan-*

*acearum*), black foot disease (*Erwinia carotovora* subsp. *atroseptica*), common scab (*Streptomyces scabies, Streptomyces acidiscabies*), soft rot (*Erwinia carotovora* subsp. *carotovora*), slimy rot (*Crostridium* spp.), ring rot (*Clavibacter michiganensis* subsp. *sepedonicus*); sweet potatoes: damping-off (*Streptomyces ipomoeae*); sugar beets: brown spot (*Cercospora beticola*), downy mildew (*Peronospora schachtii*), black root rot (*Aphanomyces cochioides*), leaf spot (*Phoma betae*), crown gall (*Agrobacterium tumefaciens*), scab (*Streptomyces scabies*), bacterial spot (*Pseudomonas syringae* pv. *aptata*);

carrots: leaf blight (*Alternaria dauci*), bacterial gall (*Rhizobacter dauci*), crown gall (*Agrobacterium tumefaciens*), *Streptomyces* scab (*Streptomyces* spp.), soft rot (*Erwinia carotovora* subsp. *carotovora*); strawberries: powdery mildew (*Sphaerotheca aphanis* var. *aphanis*), blight (*Phytophthora nicotianae* etc.), anthracnose (*Glomerella cingulata*), fruit rot (*Pythium ultimum*), bacterial wilt (*Ralstonia solanacearum*), angular leaf spot (*Xhanthomonas campestris*), bacterial bud blight (*Pseudomonas marginalis* pv. *marginalis*); tea: net blister blight (*Exobasidium reticulatum*), white scab (*Elsinoe leucospila*), anthracnose (*Colletotrichum theae-sinensis*), ring spot (*Pestalotiopsis longiseta*), red blight (*Pseudomonas syringae* pv. *theae*), canker (*Xhanthomonas campestris* pv. *theicola*), witch's broom (*Pseudomonas* sp.); tobacco: red spot (*Alternaria alternata*), powdery mildew (*Erysiphe cichoracearum*), anthracnose (*Colletotrichum gloeosporioides*), blight (*Phytophthora nicotianae*), wildfire (*Pseudomonas syringae* pv. *tabaci*), bacterial leaf spot (*Pseudomonas syringae* pv. *mellea*), hollow root (*Erwinia carotovora* subsp. *carotovora*), bacterial wilt (*Ralstonia solanacearum*), Tobacco mosaic virus (Tobacco mosaic virus);

coffee: rust (*Hemileia vastatrix*); banana: black sigatoka (*Mycosphaerella fijiensis*), panama disease (*Fusarium oxysporum* f. sp *cubense*); cotton: damping-off (*Fusarium oxysporum*), frosty mildew (*Ramularia areola*); sunflowers: sclerotial disease (*Sclerotinia sclerotiorum*), angular leaf spot (*Xhanthomonas campestris* pv. *malvacearum*), hollow root (*Erwinia carotovora* subsp. *carotovora*), bacterial spot (*Pseudomonas syringae* pv. *helianthi*); roses: black spot (*Diplocarpon rosae*), powdery mildew (*Sphaerotheca pannosa* etc.), blight (*Phytophthora megasperma*), downy mildew (*Peronospora sparsa*), crown gall (*Agrobacterium tumefaciens*); chrysanthemums: brown spot (*Septoria obesa*), white rust (*Puccinia horiana*), blight (*Phytophthora cactorum*), bacterial spot (*Pseudomonas cichorii*), soft rot (*Erwinia carotovora* subsp. *carotovora*), crown gall (*Agrobacterium tumefaciens*), hairy root disease (*Agrobacterium rhizogenes*), chrysanthemum virescence (*Phytoplasma aurantifolia*); grasses: brown patch disease (*Rhizoctonia solani*), dollar spot disease (*Sclerotinia homoeocarpa*), curvularia leaf blight (*Curvularia* sp.), rust (*Puccinia zoysiae*), helminthosporium leaf blight (*Cochliobolus* sp.), scald (*Rhynchosporium secalis*), take-all (*Gaeumannomyces graminis*), anthracnose (*Colletotrichum* sp.), typhula brown snow blight (*Typhula incarnata*), typhula black snow blight (*Typhula ishikariensis*), Sclerotinia (*Myriosclerotinia borealis*), fairy ring disease (*Marasmius oreades* etc.), *Pythium* blight (*Pythium aphanidermatum* etc.), blast (*Pyricularia grisea*).

The inventive compounds may be used singly, and may be preferably used as compositions such as powders, water-dispersible powders, water-dispersible granules, water-soluble powders, water-soluble granules, granules, emulsions, solutions, microemulsions, aqueous suspension preparations, aqueous emulsion preparations and suspoemulsion preparations by being mixed with, for example solid carriers, liquid carriers, gas carriers, surfactants, binders, dispersants, stabilizers. The form is not limited to such compositions as long as remaining the effects of the inventive compounds.

Some specific formulating examples are described below without limiting the scope of the invention thereto.

Preparation Example 1: Flowables

The inventive compound (10 parts by mass), a sodium salt of naphthalene sulfonate formaldehyde condensate (5 parts by mass), polyoxyethylene aryl phenyl ether (1 part by mass), propylene glycol (5 parts by mass), a silicone antifoaming agent (0.1 part by mass), xanthan gum (0.2 parts by mass), and ion exchanged water (78.7 parts by mass) are mixed to give a slurry. The slurry is wet milled using Dyno-Mill KDL with glass beads having a diameter of 1.0 mm to give flowables.

Preparation Example 2: Emulsions

The inventive compound (5 parts by mass) is dissolved into a mixed solution of xylene (40 parts by mass) and cyclohexane (35 parts by mass). The resultant solution is added Tween 20 (20 parts by mass) and mixed to give emulsions.

Preparation Example 3: Water-Dispersible Powders

The inventive compound (10 parts by mass), white carbon (10 parts by mass), polyvinyl alcohol (2 parts by mass), sodium dioctylsulfosuccinate (0.5 parts by mass), sodium alkylbenzenesulfonate (5 parts by mass), calcined diatomaceous earth (10 parts by mass), and kaolinite clay (62.5 parts by mass) are mixed thoroughly, and the mixture is milled with an air mill to give water-dispersible powders.

A method of applying compositions comprising the inventive compounds (such as agricultural and horticultural pest control agents, and agricultural and horticultural fungicides) is hereinbelow described.

For example, a composition comprising the inventive compound may be applied by being brought into contact with plant bodies or seeds, or by being added to cultivation soil and brought into contact with the roots or underground stems of plants. Specific examples for methods of applying the composition include spraying onto the stem and leaves of an individual plant, injection treatment, seedling nursery box treatment, cell tray treatment, spraying to plant seeds, plant seed coating treatment, plant seed immersion treatment, plant seed dressing treatment, spraying onto the surface of soil, spraying onto the surface of soil followed by mixing into the soil, injection into soil, injection and subsequent mixing into soil, irrigation to soil, irrigation and subsequent mixing into soil. The compositions usually offer sufficient effects when applied by any methods used by a person skilled in the art.

The term "plant" used in the present invention refers to a living thing that thrives by photosynthesis without moving. Specific examples include, for example rice, wheat, barley, corn, coffee, bananas, grapes, apples, pears, peaches, cherries, persimmons, citrus fruits, soybeans, kidney beans, cotton, strawberries, potatoes, cabbage, lettuce, tomatoes, cucumbers, eggplants, watermelons, sugar beets, spinach, field peas, squash, sugar cane, tobacco, green peppers, sweet potatoes, taro potatoes, konjak, cotton, sunflowers, roses, tulips, chrysanthemums, grasses, and for example F1 hybrids thereof. Examples further include gene recombinant crops that are created by genetic or other artificial manipulation and are inherently not present in nature, with specific examples including agricultural and horticultural crops, for examples soybeans, corn, cotton imparted with resistance to herbicides, for example rice, tobacco acclimated to cold climates, for example corn, cotton given the ability to produce insecticidal substances. Examples further include trees such as pines, ash trees, ginkgoes, maples, evergreen oaks, poplars and zelkova trees. The term "plant body", "plant bodies" used in the present invention is a generic term for all portions that constitute an individual plant, for example, stems, leaves, roots, seeds, flowers, fruits.

The term "seed" used in the present invention refers to a thing that stores nutrients for the germination of seedlings and is used for agricultural production. Specific examples include seeds of, for example corn, soybeans, cotton, rice, sugar beets, wheat, barley, sunflowers, tomatoes, cucumbers, eggplants, spinach, field peas, squash, sugar cane, tobacco, green peppers, rape; seeds of, for example F1 hybrids of the above plants; seed tubers of, for example taro potatoes, potatoes, sweet potatoes, konjak; bulbs of, for example edible lilies, tulips; seed bulbs of, for example scallions; seeds and tubers of, for example gene recombinant crops.

The amount and concentration of the composition comprising the inventive compound applied may vary depending on factors such as the type of target crops, the type of target diseases, the degree of the occurrence of diseases, the form of the formulation comprising the compound, the method of applying and various environmental conditions. In the case of spraying or irrigation, an appropriate amount of active ingredient applied is from 0.1 to 10,000 g per hectare, and preferably from 10 to 1,000 g per hectare. In the case of seeds treatment, an amount of active ingredient used is from 0.0001 to 1,000 g, and preferably from 0.001 to 100 g per kg of seeds. Where the composition comprising the inventive compound is sprayed to the stem and leaves of an individual plant, is sprayed to the surface of soil, is injected into the soil or is irrigated to the soil, the treatment may be carried out after the composition is diluted to an appropriate concentration with an appropriate carrier. When the composition comprising the inventive compound is brought into contact with plant seeds, the plant seeds may be immersed, dressed, sprayed or coated after the composition is diluted to an appropriate concentration. In the immersion, dressing, spraying or coating treatment, the amount of the composition in terms of active ingredient is usually from about 0.05 to 50% of the dry weight of the plant seeds, and is preferably from 0.1 to 30%, but is not limited thereto and may be determined appropriately depending on the form of the composition and the type of plant seeds to be treated.

Where necessary, the compositions comprising the inventive compounds may be used as mixtures with or may be used simultaneously with other agricultural chemicals, for example, agricultural chemicals such as fungicides, insecticides, miticides, nematicides, herbicides, biological agrochemicals and plant growth regulators; disease control agents comprising nucleic acids as active ingredients (WO 2014/062775); soil improvers; and fertilizing substances. A mixture of the inventive compound and other agricultural chemicals may be, for example, used by formulating the inventive compound and the agricultural chemical into a single preparation; formulated into a distinct preparation and mixed them together before use; or formulated into a distinct preparation and they are used simultaneously or successively.

Specific examples of ingredients that may be contained in fungicides and mixed with the inventive compounds are illustrated in the following Group b, and salts, isomers and N-oxides thereof are also encompassed. However, known fungicides are not limited thereto.

Group b:

b-1: Phenylamide Fungicides

Examples of the phenylamide fungicides include [b-1.1] benalaxyl, [b-1.2] benalaxyl-M or kiralaxyl, [b-1.3] furalaxyl, [b-1.4] metalaxyl, [b-1.5] metalaxyl-M or mefenoxam, [b-1.6] oxadixyl, [b-1.7] ofurace.

b-2: Mitosis Inhibitors and Cell Division Inhibitors

Examples of the mitosis inhibitors and cell division inhibitors include [b-2.1] benomyl, [b-2.2] carbendazim, [b-2.3] fuberidazole, [b-2.4] thiabendazole, [b-2.5] thiophanate, [b-2.6] thiophanate-methyl, [b-2.7] diethofencarb, [b-2.8] zoxamide, [b-2.9] ethaboxam, [b-2.10] pencycuron, [b-2.11] fluopicolide, [b-2.12] phenamacril.

b-3: Succinic Dehydrogenase Inhibitors (SDHI)

Examples of the succinic dehydrogenase inhibitors (SDHI) include [b-3.1] benodanil, [b-3.2] benzovindiflupyr, [b-3.3] bixafen, [b-3.4] boscalid, [b-3.5] carboxin, [b-3.6] fenfuram, [b-3.7] fluopyram, [b-3.8] flutolanil, [b-3.9] fluxapyroxad, [b-3.10] furametpyr, [b-3.11] isofetamid, [b-3.12] isopyrazam, [b-3.13] mepronil, [b-3.14] oxycarboxin, [b-3.15] penthiopyrad, [b-3.16] penflufen, [b-3.17] pydiflumetofen, [b-3.18] sedaxane, [b-3.19] thifluzamide, [b-3.20] pyraziflumid.

b-4: Quinone Outside Inhibitors (QoI)

Examples of the quinone outside inhibitors (QoI) include [b-4.1] azoxystrobin, [b-4.2] coumoxystrobin, [b-4.3] dimoxystrobin, [b-4.4] enoxastrobin, [b-4.5] famoxadone, [b-4.6] fenamidone, [b-4.7] fenaminstrobin, [b-4.8] flufenoxystrobin, [b-4.9] fluoxastrobin, [b-4.10] kresoxim-methyl, [b-4.11] mandestrobin, [b-4.12] metominostrobin, [b-4.13] orysastrobin, [b-4.14] picoxystrobin, [b-4.15] pyraclostrobin, [b-4.16] pyrametostrobin, [b-4.17] pyraoxystrobin, [b-4.18] pyribencarb, [b-4.19] triclopyricarb, [b-4.20] trifloxystrobin.

b-5: Quinone Inside Inhibitors (QiI)

Examples of the quinone inside inhibitors (QiI) include [b-5.1] cyazofamid, [b-5.2] amisulbrom.

b-6: Oxidative Phosphorylation Uncoupling Inhibitors

Examples of the oxidative phosphorylation uncoupling inhibitors include [b-6.1] binapacryl, [b-6.2] meptyldinocap, [b-6.3] dinocap, [b-6.4] fluazinam.

b-7: Quinone Outside Stigmatellin Binding Subsite Inhibitors (QoSI)

Examples of the quinone outside stigmatellin binding subsite inhibitors (QoSI) include [b-7.1] ametoctradin.

b-8: Amino Acid Biosynthesis Inhibitors

Examples of the amino acid biosynthesis inhibitors include [b-8.1] cyprodinil, [b-8.2] mepanipyrim, [b-8.3] pyrimethanil.

b-9: Protein Biosynthesis Inhibitors

Examples of the protein biosynthesis inhibitors include [b-9.1] streptomycin, [b-9.2] blasticidin-S, [b-9.3] kasugamycin, [b-9.4] oxytetracycline.

b-10: Signal Transduction Inhibitors

Examples of the signal transduction inhibitors include [b-10.1] fenpiclonil, [b-10.2] fludioxonil, [b-10.3] quinoxyfen, [b-10.4] proquinazid, [b-10.5] chlozolinate, [b-10.6] dimethachlone, [b-10.7] iprodione, [b-10.8] procymidone, [b-10.9] vinclozolin.

b-11: Lipid and Cell Membrane Biosynthesis Inhibitors

Examples of the lipid and cell membrane biosynthesis inhibitors include [b-11.1] edifenphos, [b-11.2] iprobenfos,

[b-11.3] pyrazophos, [b-11.4] isoprothiolane, [b-11.5] biphenyl, [b-11.6] chloroneb, [b-11.7] dicloran, [b-11.8] quintozene, [b-11.9] tecnazene, [b-11.10] tolclofos-methyl, [b-11.11] echlomezol or etridiazole, [b-11.12] iodocarb, [b-11.13] propamocarb, [b-11.14] prothiocarb.

b-12: Demethylation Inhibitors (DMI)

Examples of the demethylation inhibitors (DMI) include [b-12.1] azaconazole, [b-12.2] bitertanol, [b-12.3] bromuconazole, [b-12.4] cyproconazole, [b-12.5] difenoconazole, [b-12.6] diniconazole, [b-12.7] diniconazole-M, [b-12.8] epoxiconazole, [b-12.9] etaconazole, [b-12.10] fenarimol, [b-12.11] fenbuconazole, [b-12.12] fluquinconazole, [b-12.13] quinconazole, [b-12.14] flusilazole, [b-12.15] flutriafol, [b-12.16] hexaconazole, [b-12.17] imazalil, [b-12.18] imibenconazole, [b-12.19] ipconazole, [b-12.20] metconazole, [b-12.21] myclobutanil, [b-12.22] nuarimol, [b-12.23] oxpoconazole, [b-12.24] oxpoconazole fumarate, [b-12.25] pefurazoate, [b-12.26] penconazole, [b-12.27] prochloraz, [b-12.28] propiconazole, [b-12.29] prothioconazole, [b-12.30] pyrifenox, [b-12.31] pyrisoxazole, [b-12.32] simeconazole, [b-12.33] tebuconazole, [b-12.34] tetraconazole, [b-12.35] triadimefon, [b-12.36] triadimenol, [b-12.37] triflumizole, [b-12.38] triforine, [b-12.39] triticonazole, [b-12.40] mefentrifluconazole, [b-12.41] ipfentrifluconazole.

b-13: Amine Fungicides

Examples of the amine fungicides include [b-13.1] aldimorph, [b-13.2] dodemorph, [b-13.3] fenpropimorph, [b-13.4] tridemorph, [b-13.5] fenpropidin, [b-13.6] piperalin, [b-13.7] spiroxamine.

b-14: 3-Keto Reductase Inhibitors in C4-Demethylation in Sterol Biosynthesis

Examples of the 3-keto reductase inhibitors in C4-demethylation in sterol biosynthesis include [b-14.1] fenhexamid, [b-14.2] fenpyrazamine.

b-15: Squalene Epoxidase Inhibitors in Sterol Biosynthesis

Examples of the squalene epoxidase inhibitors in sterol biosynthesis include [b-15.1] pyributicarb, [b-15.2] naftifine, [b-15.3] terbinafine.

b-16: Cell Wall Biosynthesis Inhibitors

Examples of the cell wall biosynthesis inhibitors include [b-16.1] polyoxins, [b-16.2] dimethomorph, [b-16.3] flumorph, [b-16.4] pyrimorph, [b-16.5] benthiavalicarb, [b-16.6] benthiavalicarb-isopropyl, [b-16.7] iprovalicarb, [b-16.8] mandipropamid, [b-17.9] valifenalate.

b-17: Melanin Biosynthesis Inhibitors

Examples of the melanin biosynthesis inhibitors include [b-17.1] phthalide or fthalide, [b-17.2] pyroquilone, [b-17.3] tricyclazole, [b-17.4] carpropamid, [b-17.5] diclocymet, [b-17.6] fenoxanil, [b-17.7] tolprocarb.

b-18: Host Plant Resistance Inducers Examples of the host plant resistance inducers include [b-18.1] acibenzolar-S-methyl, [b-18.2] probenazole, [b-18.3] tiadinil, [b-18.4] isotianil, [b-18.5] laminarin.

b-19: Dithiocarbamate Fungicides

Examples of the dithiocarbamate fungicides include [b-19.1] mancozeb or manzeb, [b-19.2] maneb, [b-19.3] metiram, [b-19.4] propineb, [b-19.5] thiram, [b-19.6] zineb, [b-19.7] ziram, [b-19.8] ferbam.

b-20: Phthalimide Fungicides

Examples of the phthalimide fungicides include [b-20.1] captan, [b-20.2] captafol, [b-20.3] folpet, [b-20.4] fluorofolpet.

b-21: Guanidine Fungicides

Examples of the guanidine fungicides include [b-21.1] guazatine, [b-21.2] iminoctadine, [b-21.3] iminoctadine albesilate, [b-21.4] iminoctadine triacetate.

b-22: Multi-Site Contact Active Fungicides

Examples of the multi-site contact active fungicides include [b-22.1] copper oxychloride, [b-22.2] copper (II) hydroxide, [b-22.3] copper hydroxide sulfate, [b-22.4] organocopper compound, [b-22.5] dodecylbenzenesulphonic acid bisethylenediamine copper [II] salt, DBEDC, [b-22.6] sulphur, [b-22.7] fluoroimide, [b-22.8] chlorothalonil, [b-22.9] dichlofluanid, [b-22.10] tolylfluanid, [b-22.11] anilazine, [b-22.12] dithianon, [b-22.13] chinomethionat or quinomethionate, [b-22.14] extracts from lupine seedling cotyledons (BLAD).

b-23: Other Fungicides

Examples of other fungicides include [b-23.1] dichlobentiazox, [b-23.2] fenpicoxamid, [b-23.3] dipymetitrone, [b-23.4] bupirimate, [b-23.5] dimethirimol, [b-23.6] ethirimol, [b-23.7] fentin acetate, [b-23.8] fentin chloride, [b-23.9] fentin hydroxide, [b-23.10] oxolinic acid, [b-23.11] hymexazol, [b-23.12] octhilinone, [b-23.13] fosetyl, [b-23.14] phosphorous acid, [b-23.15] sodium phosphite, [b-23.16] ammonium phosphite, [b-23.17] potassium phosphite, [b-23.18] tecloftalam, [b-23.19] triazoxide, [b-23.20] flusulfamide, [b-23.21] diclomezine, [b-23.22] silthiofam, [b-23.23] diflumetorim, [b-23.24] methasulfocarb, [b-23.25] cyflufenamid, [b-23.26] metrafenone, [b-23.27] pyriofenone, [b-23.28] dodine, [b-23.29] flutianil, [b-23.30] ferimzone, [b-23.31] oxathiapiprolin, [b-23.32] tebufloquin, [b-23.33] picarbutrazox, [b-23.34] validamycins, [b-23.35] cymoxanil, [b-23.36] quinofumelin,

[b-23.37] a Compound of Formula (s1):

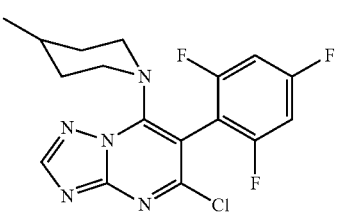

(s1)

(see WO 98/046607),

[b-23.38] a Compound of Formula (s2):

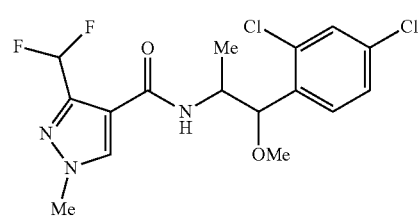

(s2)

(see WO 08/148570),

[b-23.39] a Compound of Formula (s3):
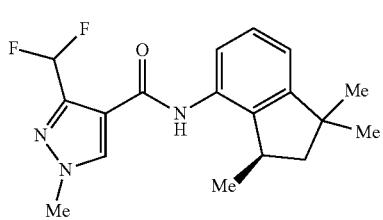
(see WO 92/012970),
[b-23.40] a Compound of Formula (s4):
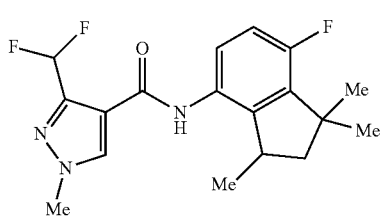
(see WO 12/084812),
[b-23.41] a Compound of Formula (s5):
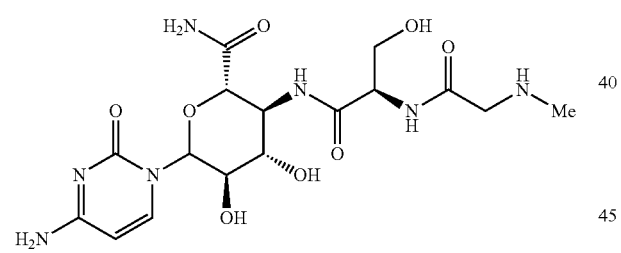
(gougerotin),
[b-23.42] a Compound of Formula (s6):
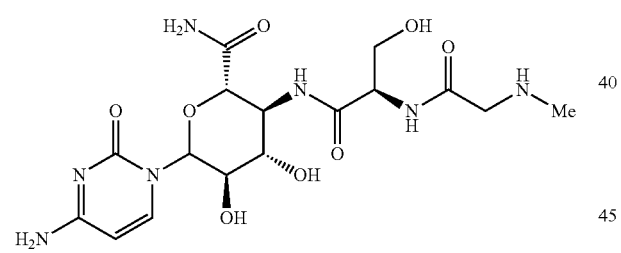
(ningnanmycin),
[b-23.43] a Compound of Formula (s7):
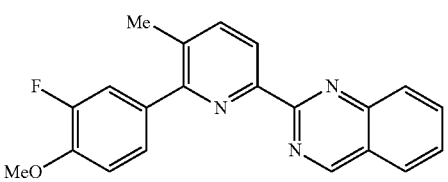
(see WO 10/136475),
[b-23.44] a Compound of Formula (s8):
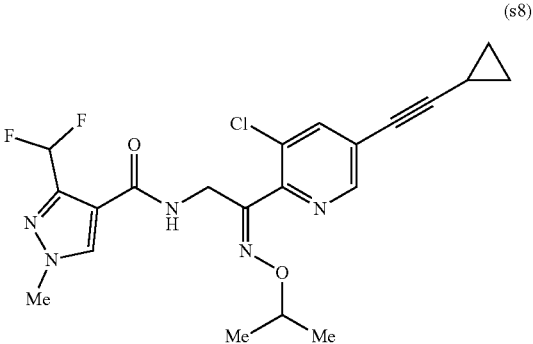 [SMILES: CC(C)O/N=C(/CNC(=O)c1cn(C)nc1C(F)F)c1ncc(C#CC2CC2)cc1Cl]
(see WO 14/010737),
[b-23.45] a Compound of Formula (s9):
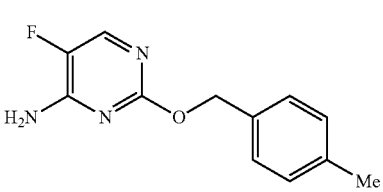
(see WO 11/085084),
[b-23.46] a Compound of Formula (s10):
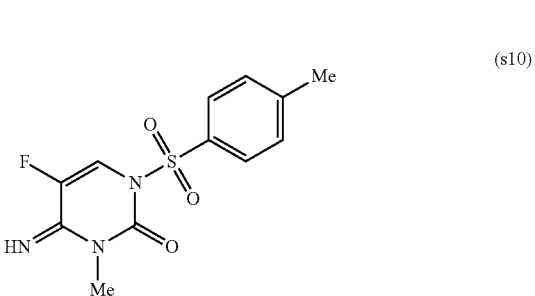 [SMILES: Cc1ccc(S(=O)(=O)n2cc(F)c(=N)n(C)c2=O)cc1]
(see WO 11/137002),

[b-23.47] a Compound of Formula (s11):

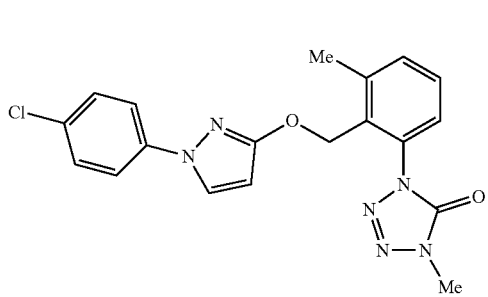
(s11)

(see WO 13/162072),
[b-23.48] a Compound of Formula (s12):

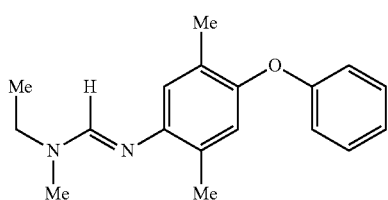
(s12)

(see WO 08/110313),
[b-23.49] a Compound of Formula (s13):

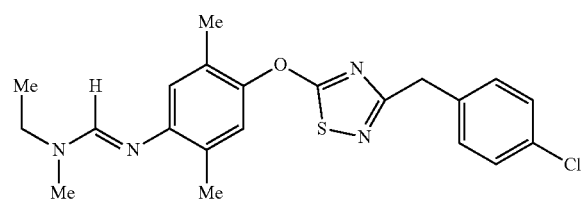
(s13)

(see WO 09/156098),
[b-23.50] a Compound of Formula (s14):

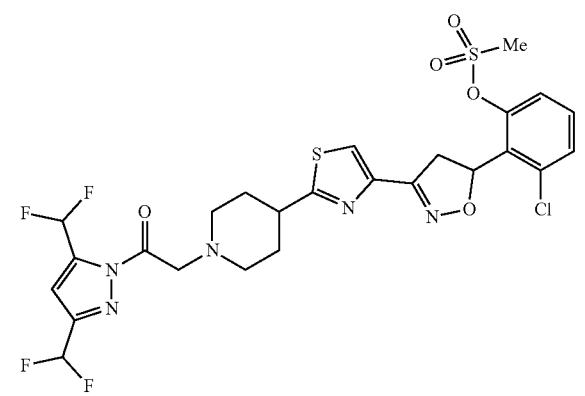
(s14)

(see WO 12/025557),

[b-23.51] a Compound of Formula (s15):

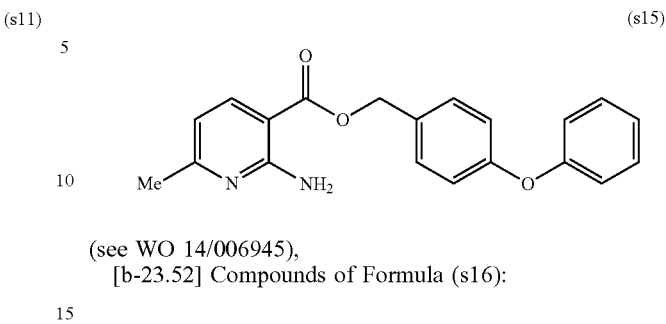
(s15)

(see WO 14/006945),
[b-23.52] Compounds of Formula (s16):

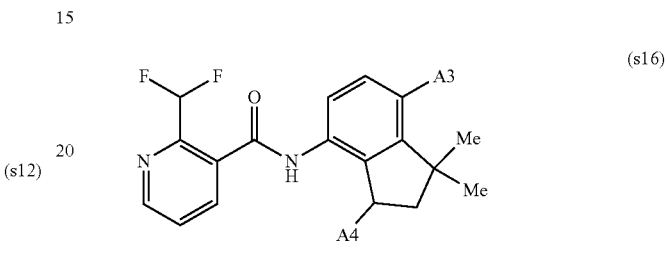
(s16)

wherein A3 represents a hydrogen atom, a halogen atom, a C1-C6 alkyl group, a C1-C6 haloalkyl group or a cyano group, and A4 represents a hydrogen atom, a C1-C6 alkyl group, a C1-C6 haloalkyl group or a C3-C8 cycloalkyl group (see WO 14/095675),
[b-23.53] Compounds of Formula (s17):

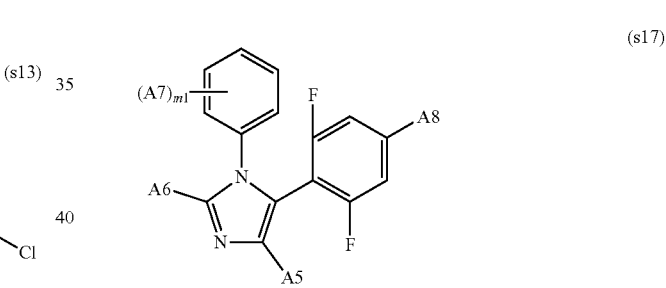
(s17)

wherein m1 represents an integer of 0 to 3, A5 and A6 are independent of one another and each represent a halogen atom or a C1-C6 alkyl group, A7 and A8 are independent of one another and each represent a halogen atom or a C1-C6 alkoxy group, wherein when m1 is 2 or greater, the two or more substituents A7 are independent of one another and may be the same or different from one another (see WO 09/137538 and International Patent No. 09/137651),
[b-23.54] Compounds of Formula (s18):

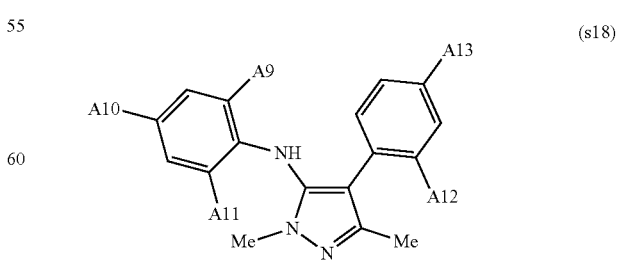
(s18)

wherein A9 and A10 are independent of one another and each represent a hydrogen atom or a halogen atom, A11 represents a halogen atom, A12 represents a halogen atom or a C1-C6 alkyl group, and A13 represents a halogen atom, a cyano group, a C1-C6 alkyl group or a C1-C6 alkoxy group (see WO 12/031061),

[b-23.55] Compounds of Formula (s19):

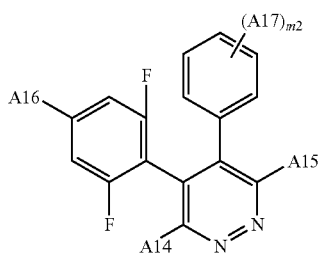

(s19)

wherein m2 represents an integer of 0 to 6, A14 and A15 are independent of one another and each represent a halogen atom, a cyano group or a C1-C6 alkyl group, A16 represents a hydrogen atom, a halogen atom or a C1-C6 alkoxy group, A17 represents a halogen atom or a C1-C6 alkoxy group, wherein when m2 is 2 or greater, the two or more substituents A17 are independent of one another and may be the same or different from one another (see WO 05/121104),

[b-23.56] Compounds of Formula (s20):

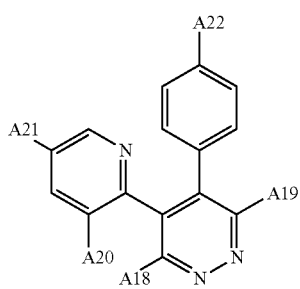

(s20)

wherein A18 and A19 are independent of one another and each represent a halogen atom, a cyano group or a C1-C6 alkyl group, and A20, A21 and A22 are independent of one another and each represent a hydrogen atom, a halogen atom or a C1-C6 alkoxy group (see WO 07/066601),

[b-23.57] Compounds of Formula (s21):

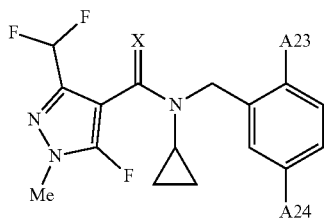

(s21)

wherein A23 and A24 are independent of one another and each represent a hydrogen atom, a halogen atom, a C1-C6 alkyl group or a C3-C8 cycloalkyl group, and X represents an oxygen atom or a sulfur atom (see WO 07/087906, International Patent No. 09/016220 and International Patent No. 10/130767),

[b-23.58] Compounds of Formula (s22):

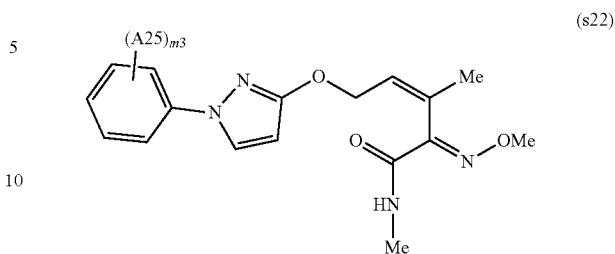

(s22)

wherein m3 represents an integer of 0 to 5, A25 represents a halogen atom, a C1-C6 alkyl group, a C1-C6 haloalkyl group, a C1-C6 alkoxy group, a C1-C6 haloalkoxy group or a C3-C8 cycloalkyl group, wherein when m3 is 2 or greater, the two or more substituents A25 are independent of one another and may be the same or different from one another (see WO 13/092224),

[b-23.59] Compounds of Formula (s23):

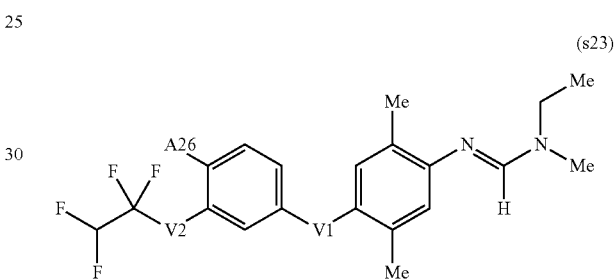

(s23)

wherein A26 represents a hydrogen atom or a halogen atom, and V1 and V2 are independent of one another and each represent an oxygen atom or a sulfur atom (see WO 12/025450),

[b-23.60] Compounds of Formula (s24) or the formula (s25):

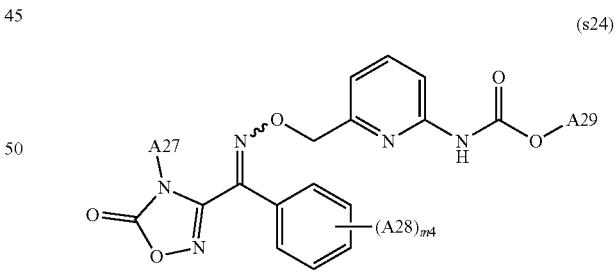

(s24)

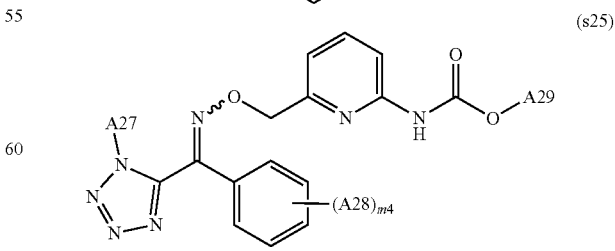

(s25)

wherein m4 represents an integer of 0 to 5, A27 represents a C1-C6 alkyl group, A28 represents a halogen atom, a cyano group, a C1-C6 alkyl group or a C1-C6 haloalkyl group, wherein when m4 is 2 or greater, the two or more substituents A28 are independent of one another and may be the same or different from one another, and A29 represents a C1-C6 alkyl group, a C2-C6 alkenyl group or a C3-C6 alkynyl group (see WO 13/037717),

[b-23.61] Compounds of Formula (s26) or (s27):

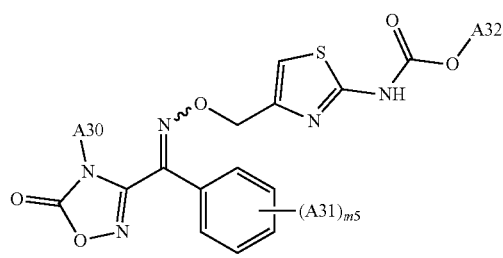

(s26)

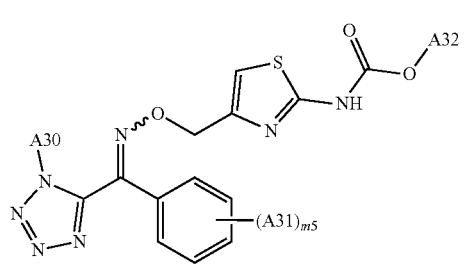

(s27)

wherein m5 represents an integer of 0 to 5, A30 represents a C1-C6 alkyl group, A31 represents a halogen atom, a cyano group, a C1-C6 alkyl group or a C1-C6 haloalkyl group wherein when m5 is 2 or greater, the two or more substituents A31 are independent of one another and may be the same or different from one another, and A32 represents a C1-C6 alkyl group, a C2-C6 alkenyl group or a C3-C6 alkynyl group (see WO 13/037717),

[b-23.62] Compounds of Formula (s28):

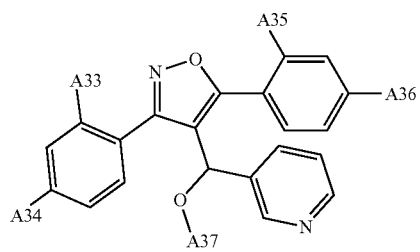

(s28)

wherein A33, A34, A35 and A36 are independent of one another and each represent a hydrogen atom or a halogen atom, and A37 represents a hydrogen atom, acetyl or a benzoyl (see WO 06/031631 and International Patent No. 10/069882),

[b-23.63] Compounds of Formula (s29):

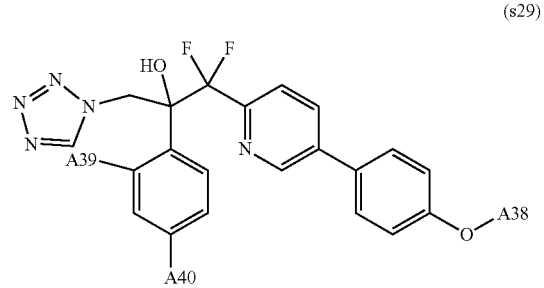

(s29)

wherein A38 represents a C1-C6 alkyl group or a C1-C6 haloalkyl group, and A39 and A40 are independent of one another and each represent a hydrogen atom or a halogen atom (see WO 14/043376),

[b-23.64] Compounds of Formula (s30):

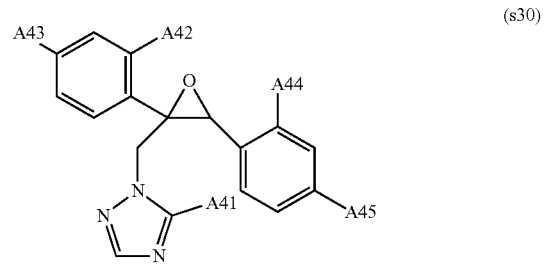

(s30)

wherein A41 represents a hydrogen atom, hydrosulfide (—SH), thiocyanate (—SCN) or a C1-C6 alkylthio, and A42, A43, A44 and A45 are independent of one another and each represent a hydrogen atom or a halogen atom (see WO 09/077443),

[b-23.65] Compounds of Formula (s31) or (s32):

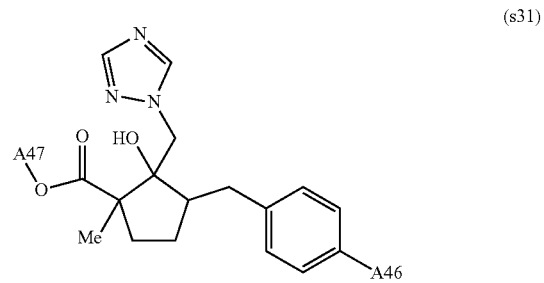

(s31)

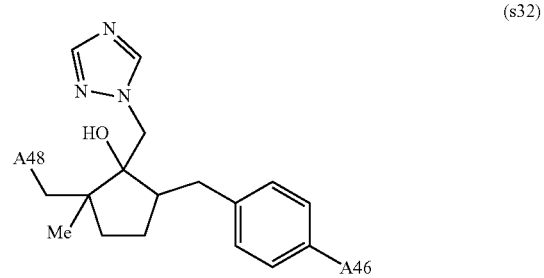

(s32)

wherein A46 represents a hydrogen atom or a halogen atom, A47 represents a C1-C6 alkyl group, and A48 represents a halogen atom (see WO 11/070771),

[b-23.66] Compounds of Formula (s33):

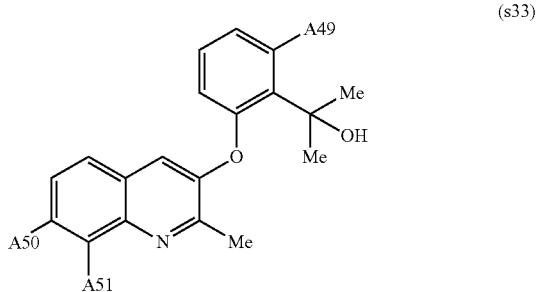

(s33)

wherein A49, A50 and A51 are independent of one another and each represent a hydrogen atom or a halogen atom (see WO 11/081174).

Specific examples of ingredients that may be contained in insecticides and mixed with the inventive compounds are illustrated in the following Group c, and salts, isomers and N-oxides thereof are also encompassed. However, known insecticides are not limited thereto.

Group c:

c-1: Carbamate-Based Acetylcholinesterase (AChE) Inhibitors

Examples of the carbamate-based acetylcholinesterase (AChE) inhibitors include [c-1.1] phosphocarb, [c-1.2] alanycarb, [c-1.3] butocarboxim, [c-1.4] butoxycarboxim, [c-1.5] thiodicarb, [c-1.6] thiofanox, [c-1.7] aldicarb, [c-1.8] bendiocarb, [c-1.9] benfuracarb, [c-1.10] carbaryl, [c-1.11] carbofuran, [c-1.12] carbosulfan, [c-1.13] ethiofencarb, [c-1.14] fenobucarb, [c-1.15] formetanate, [c-1.16] furathiocarb, [c-1.17] isoprocarb, [c-1.18] methiocarb, [c-1.19] methomyl, [c-1.20] oxamyl, [c-1.21] pirimicarb, [c-1.22] propoxur, [c-1.23] trimethacarb, [c-1.24] XMC (3,5-xylyl methylcarbamate), [c-1.25] allyxycarb, [c-1.26] aldoxycarb, [c-1.27] bufencarb, [c-1.28] butacarb, [c-1.29] carbanolate, [c-1.30] metolcarb, [c-1.31] xylylcarb, [c-1.32] fenothiocarb, [c-1.33] xylylcarb, [c-1.34] bendiocarb.

c-2: Organophosphorus-Based Acetylcholinesterase (AChE) Inhibitors

Examples of the organophosphorus-based acetylcholinesterase (AChE) inhibitors include [c-2.1] acephate, [c-2.2] azamethiphos, [c-2.3] azinphos-methyl, [c-2.4] azinphos-ethyl, [c-2.5] ethephon, [c-2.6] cadusafos, [c-2.7] chlorethoxyfos, [c-2.8] chlorfenvinphos, [c-2.9] chlormephos, [c-2.10] chlorpyrifos, [c-2.11] chlorpyrifos-methyl, [c-2.12] coumaphos, [c-2.13] cyanophos, [c-2.14] demeton-S-methyl, [c-2.15] diazinon, [c-2.16] dichlofenthion, [c-2.17] dichlorvos, [c-2.18] dicrotophos, [c-2.19] dimethoate, [c-2.20] dimethylvinphos, [c-2.21] disulfoton, [c-2.22] O-ethyl O-4-nitrophenyl phenylphosphonothioate, [c-2.23] ethion, [c-2.24] ethoprophos, [c-2.25] famphur, [c-2.26] fenamiphos, [c-2.27] fenitrothion, [c-2.28] fenthion, [c-2.29] fosthiazate, [c-2.30] heptenophos, [c-2.31] isofenphos-methyl, [c-2.32] isocarbophos, [c-2.33] isoxathion, [c-2.34] malathion, [c-2.35] mecarbam, [c-2.36] methamidophos, [c-2.37] methidathion, [c-2.38] mevinphos, [c-2.39] monocrotophos, [c-2.40] naled, [c-2.41] omethoate, [c-2.42] oxydemeton-methyl, [c-2.43] parathions, [c-2.44] parathion-methyl, [c-2.45] phenthoate, [c-2.46] phorate, [c-2.47] phosalone, [c-2.48] phosmet, [c-2.49] phosphamidon, [c-2.50] phoxim, [c-2.51] pirimiphos-methyl, [c-2.52] profenofos, [c-2.53] propetamphos, [c-2.54] prothiofos, [c-2.55] pyraclofos, [c-2.56] pyridaphenthion, [c-2.57] quinalphos, [c-2.58] sulfotep, [c-2.59] tebupirimfos, [c-2.60] temephos, [c-2.61] terbufos, [c-2.62] thiometon, [c-2.63] triazophos, [c-2.64] trichlorfon, [c-2.65] vamidothion, [c-2.66] chlorothion, [c-2.67] bromfenvinfos, [c-2.68] bromophos, [c-2.69] bromophos-ethyl, [c-2.70] butathiofos, [c-2.71] carbophenothion, [c-2.72] chlorphoxim, [c-2.73] sulprofos, [c-2.74] diamidafos, [c-2.75] tetrachlorvinphos, [c-2.76] propaphos, [c-2.77] mesulfenfos, [c-2.78] dioxabenzofos, [c-2.79] etrimfos, [c-2.80] oxydeprofos, [c-2.81] formothion, [c-2.82] fensulfothion, [c-2.83] isazofos, [c-2.84] imicyafos, [c-2.85] isamidofos, [c-2.86] thionazin, [c-2.87] fosthietan.

c-3: GABA-Gated Chloride Channel Blockers

Examples of the GABA-gated chloride channel blockers include [c-3.1] chlordane, [c-3.2] endosulfan, [c-3.3] lindane, [c-3.4] dienochlor, [c-3.5] ethiprole, [c-3.6] fipronil, [c-3.7] acetoprole.

c-4: Sodium Channel Modulators

Examples of the sodium channel modulators include [c-4.1] acrinathrin, [c-4.2] allethrin [(1R)-isomer], [c-4.3] bifenthrin, [c-4.4] bioallethrin, [c-4.5] bioallethrin S-cyclopentenyl isomer, [c-4.6] bioresmethrin, [c-4.7] cycloprothrin, [c-4.8] cyfluthrin, [c-4.9] beta-cyfluthrin, [c-4.10] cyhalothrin, [c-4.11] gamma-cyhalothrin, [c-4.12] lambda-cyhalothrin, [c-4.13] cypermethrin, [c-4.14] alpha-cypermethrin, [c-4.15] beta-cypermethrin, [c-4.16] theta-cypermethrin, [c-4.17] zeta-cypermethrin, [c-4.18] cyphenothrin [(1R)-trans-isomer], [c-4.19] deltamethrin, [c-4.20] empenthrin [(EZ)-(1R)-isomer], [c-4.21] esfenvalerate, [c-4.22] ethofenprox, [c-4.23] fenpropathrin, [c-4.24] fenvalerate, [c-4.25] flucythrinate, [c-4.26] flumethrin, [c-4.27] tau-fluvalinate, [c-4.28] halfenprox, [c-4.29] imiprothrin, [c-4.30] methothrin, [c-4.31] metofluthrin, [c-4.32] epsilon-metofluthrin, [c-4.33] momfluorothrin, [c-4.34] epsilon-momfluorothrin, [c-4.35] permethrin, [c-4.36] phenothrin [(1R)-trans-isomer], [c-4.37] prallethrin, [c-4.38] resmethrin, [c-4.39] kadethrin, [c-4.40] silafluofen, [c-4.41] tefluthrin, [c-4.42] tetramethrin, [c-4.43] tetramethrin [(1R)-isomer], [c-4.44] tralomethrin, [c-4.45] transfluthrin, [c-4.46] ZXI8901 (3-(4-bromophenoxy)phenyl]-cyanomethyl 4-(difluoromethoxy)-α-(1-methylethyl)benzene acetate, [c-4.47] biopermethrin, [c-4.48] furamethrin, [c-4.49] profluthrin, [c-4.50] flubrocythrinate, [c-4.51] dimefluthrin, [c-4.52] DDT (dichloro-diphenyl-trichloroethane), [c-4.53] methoxychlor, [c-4.54] phenothrin, [c-4.55] fluvalinate.

c-5: Nicotinic Acetylcholine Receptor (nAChR) Competitive Modulators

Examples of the nicotinic acetylcholine receptor (nAChR) competitive modulators include [c-5.1] acetamiprid, [c-5.2] clothianidin, [c-5.3] dinotefuran, [c-5.4] imidacloprid, [c-5.5] nitenpyram, [c-5.6] thiacloprid, [c-5.7] thiamethoxam, [c-5.8] nicotine, [c-5.9] nicotine sulfate, [c-5.10] sulfoxaflor, [c-5.11] flupyradifurone, [c-5.12] triflumezopyrim.

c-6: Nicotinic Acetylcholine Receptor (nAChR) Allosteric Modulators

Examples of the nicotinic acetylcholine receptor (nAChR) allosteric modulators include [c-6.1] spinosad, [c-6.2] spinetoram.

c-7: Glutamate-Gated Chloride Channel (GluCl) Allosteric Modulators

Examples of the glutamate-gated chloride channel (GluCl) allosteric modulators include [c-7.1] abamectin, [c-7.2] emamectin benzoate, [c-7.3] lepimectin, [c-7.4] milbemectin.

c-8: Juvenile Hormone Analogues

Examples of the juvenile hormone analogues include [c-8.1] hydroprene, [c-8.2] kinoprene, [c-8.3] methoprene, [c-8.4] fenoxycarb, [c-8.5] pyriproxyfen.

c-9: Nonspecific (Multisite) Inhibitors

Examples of the nonspecific (multisite) inhibitors include [c-9.1] methyl bromide, [c-9.2] chloropicrin, [c-9.3] cryolite, [c-9.4] sulfuryl fluoride, [c-9.5] borax, [c-9.6] boric acid, [c-9.7] disodium octaborate, [c-9.8] sodium metaborate, [c-9.9] tartar emetic, [c-9.10] dazomet, [c-9.11] metam, [c-9.12] metam sodium.

c-10: Chordotonal Organ TRPV Channel Modulators

Examples of the chordotonal organ TRPV channel modulators include [c-10.1] pymetrozine, [c-10.2] pyrifluquinazon.

c-11: Mite Growth Inhibitors

Examples of the mite growth inhibitors include [c-11.1] clofentezine, [c-11.2] diflovidazin, [c-11.3] hexythiazox, [c-11.4] etoxazole.

c-12: Mitochondria ATP Synthase Inhibitors

Examples of the mitochondria ATP synthase inhibitors include [c-12.1] diafenthiuron, [c-12.2] azocyclotin, [c-12.3] cyhexatin, [c-12.4] fenbutatin oxide, [c-12.5] propargite, [c-12.6] tetradifon.

c-13: Uncouplers of Oxidative Phosphorylation Via Disruption of Proton Gradient

Examples of the uncouplers of oxidative phosphorylation via disruption of the proton gradient include [c-13.1] chlorfenapyr, [c-13.2] DNOC (dinitro-ortho-cresol), [c-13.3] binapacryl, [c-13.4] sulfluramid.

c-14: Nicotinic Acetylcholine Receptor (nAChR) Channel Blockers

Examples of the nicotinic acetylcholine receptor (nAChR) channel blockers include [c-14.1] bensultap, [c-14.2] cartap hydrochloride, [c-14.3] thiocyclam, [c-14.4] monosultap.

c-15: Chitin Biosynthesis Inhibitors, Type 0

Examples of the chitin biosynthesis inhibitors, type 0, include [c-15.1] bistrifluron, [c-15.2] chlorfluazuron, [c-15.3] diflubenzuron, [c-15.4] flucycloxuron, [c-15.5] flufenoxuron, [c-15.6] hexaflumuron, [c-15.7] lufenuron, [c-15.8] novaluron, [c-15.9] noviflumuron, [c-15.10] teflubenzuron, [c-15.11] triflumuron.

c-16: Chitin Biosynthesis Inhibitors, Type 1

Examples of the chitin biosynthesis inhibitors, type 1, include [c-16.1] buprofezin.

c-17: Dipteran Molting Disruptors

Examples of the dipteran molting disruptors include [c-17.1] cyromazine.

c-18: Molting Hormone (Ecdysone) Receptor Agonists

Examples of the molting hormone (ecdysone) receptor agonists include [c-18.1] chromafenozide, [c-18.2] halofenozide, [c-18.3] methoxyfenozide, [c-18.4] tebufenozide.

c-19: Octopamine Receptor Agonists

Examples of the octopamine receptor agonists include [c-19.1] amitraz.

c-20: Mitochondrial Complex III Electron Transport Inhibitors

Examples of the mitochondrial complex III electron transport inhibitors include [c-20.1] hydrmethylnon, [c-20.2] acequinocyl, [c-20.3] fluacrypyrim, [c-20.4] bifenazate.

c-21: Mitochondrial Complex I Electron Transport Inhibitors (METI)

Examples of the mitochondrial complex I electron transport inhibitors (METI) include [c-21.1] fenazaquin, [c-21.2] fenpyroximate, [c-21.3] pyridaben, [c-21.4] pylimidifen, [c-21.5] tebufenpyrad, [c-21.6] tolfenpyrad, [c-21.7] rotenone.

c-22: Voltage-Dependent Sodium Channel Blockers

Examples of the voltage-dependent sodium channel blockers include [c-22.1] indoxacarb, [c-22.2] metaflumizone.

c-23: Acetyl CoA Carboxylase Inhibitors

Examples of the acetyl CoA carboxylase inhibitors include [c-23.1] spirodiclofen, [c-23.2] spiromesifen, [c-23.3] spirotetramat.

c-24: Mitochondrial Complex IV Electron Transport Inhibitors

Examples of the mitochondrial complex IV electron transport inhibitors include [c-24.1] aluminum phosphide, [c-24.2] calcium phosphide, [c-24.3] phosphine, [c-24.4] zinc phosphide, [c-24.5] calcium cyanide, [c-24.6] potassium cyanide, [c-24.7] sodium cyanide.

c-25: Mitochondrial Complex II Electron Transport Inhibitors

Examples of the mitochondrial complex II electron transport inhibitors include [c-25.1] cyenopyrafen, [c-25.2] cyflumetofen, [c-25.3] pyflubumide.

c-26: Ryanodine Receptor Modulators

Examples of the ryanodine receptor modulators include [c-26.1] chlorantraniliprole, [c-26.2] cyantraniliprole, [c-26.3] flubendiamide.

c-27: Chordotonal Organ Modulators on Undefined Target Sites

Examples of the chordotonal organ modulators on undefined target sites include [c-27.1] flonicamid.

c-28: Other Insecticides

Examples of other insecticides include [c-28.1] azadirachtin, [c-28.2] benzoximate, [c-28.3] phenisobromolate, [c-28.4] chinomethionat, [c-28.5] dicofol, [c-28.6] pyridalyl, [c-28.7] bromopropylate, [c-28.8] triazamate, [c-28.9] dicyclanil, [c-28.10] dinobuton, [c-28.11] dinocap, [c-28.12] hydrogen cyanide, [c-28.13] methyl iodide, [c-28.14] karanjin, [c-28.15] mercury chloride, [c-28.16] methyl isothiocyanate, [c-28.17] pentachlorophenol, [c-28.18] phosphine, [c-28.19] piperonyl butoxide, [c-28.20] polynactins, [c-28.21] sabadilla, [c-28.22] sulcofuron-sodium, [c-28.23] tribufos, [c-28.24] aldrin, [c-28.25] amidithion, [c-28.26] amidothioate, [c-28.27] aminocarb, [c-28.28] amiton, [c-28.29] aramite, [c-28.30] athidathion, [c-28.31] azothoate, [c-28.32] barium polysulphide, [c-28.33] benclothiaz, [c-28.34] 5-(1,3-benzodioxol-5-yl)-3-hexylcyclohex-2-enone, [c-28.35] 1,1-bis(4-chlorophenyl)-2-ethoxyethanol, [c-28.36] butonate, [c-28.37] butopyronoxyl, [c-28.38] 2-(2-butoxyethoxy)ethyl thiocyanate, [c-28.39] camphechlor, [c-28.40] chlorbenside, [c-28.41] chlordecone, [c-28.42] chlordimeform, [c-28.43] chlorfenethol, [c-28.44] chlorfenson, [c-28.45] fluazuron, [c-28.46] metaldehyde, [c-28.47] bialaphos, [c-28.48] levamisol, [c-28.49] amidoflumet, [c-28.50] pyrafluprole, [c-28.51] pyriprole, [c-28.52] tralopyril, [c-28.53] flupyrazofos, [c-28.54] diofenolan, [c-28.55] chlorbenzilate, [c-28.56] flufenzine, [c-28.57] benzomate, [c-28.58] flufenerim, [c-28.59] albendazole, [c-28.60] oxibendazole, [c-28.61] fenbendazole, [c-28.62] metam-sodium, [c-28.63] 1,3-dichloropropene, [c-28.64] flometoquin, [c-28.65] cyclaniliprole, [c-28.66] tetraniliprole, [c-28.67] broflanilide, [c-28.68] dicloromezotiaz, [c-28.69] ethylene dibromide, [c-28.70] acrylonitrile, [c-28.71] bis(2-chloroethyl) ether, [c-28.72] 1-bromo-2-chloroethane, [c-28.73] 3-bromo-1-chloroprop-1-ene, [c-28.74] bromocyclen, [c-28.75] carbon disulfide, [c-28.76] tetrachloromethane,

[c-28.77] nemadectin, [c-28.78] cymiazole, [c-28.79] calcium polysulfide, [c-28.80] cytokinin, [c-28.81] 2-(octylthio)ethanol, [c-28.82] potassium oleate, [c-28.83] sodium oleate, [c-28.84] machine oil, [c-28.85] tar oil, [c-28.86] anabasine, [c-28.87] morantel tartrate, [c-28.88] insect flower pyrethrum, [c-28.89] rape seed oil, [c-28.90] soybean lecithin, [c-28.91] starch, [c-28.92] hydroxypropylstarch, [c-28.93] decanoyloctanoylglycerol, [c-28.94] propylene glycol fatty acid ester, [c-28.95] diatomite, [c-28.96] afoxolaner, [c-28.97] fluazaindolizine, [c-28.98] afidopyropen, [c-28.99] cyhalodiamide, [c-28.100] tioxazafen, [c-28.101] fluhexafon, [c-28.102] fluralaner, [c-28.103] fluxametamide, [c-28.104] tetrachlorantraniliprole, [c-28.105] sarolaner, [c-28.106] lotilaner, [c-28.107] cycloxaprid, [c-28.108] fluensulfone, [c-28.109] TPIC (tripropyl isocyanurate), [c-28.110] D-D (1,3-dichloropropene), [c-28.111] peroxocarbonate, [c-28.112] MB-599 (verbutin), [c-28.113] bis(2, 3,3,3-tetrachloropropyl) ether, [c-28.114] DCIP (bis(2-chloro-1-methylethyl)ether), [c-28.115] ENT-8184 (N-2-(ethylhexyl)bicyclo[2.2.1]hept-5-ene-2,3-dicarboximide), [c-28.116] Bayer 22408 (O,O-diethyl O-naphthalimido phosphorothioate), [c-28.117] Bayer 32394 (tri s(1-dodecyl-3-methyl-2-phenylbenzimidazolium)hexacyanoferrate,

[c-28.118] a Compound of Formula (s34):

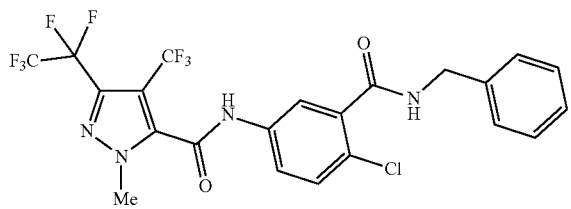

(s34)

(see WO 10/051926),

[c-28.119] a Compound of Formula (s35):

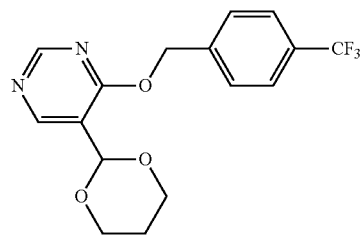

(s35)

(see WO 13/115391),

[c-28.120] a Compound of Formula (s36):

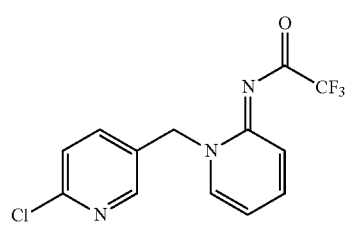

(s36)

(see WO 12/029672),

[c-28.121] a Compound of Formula (s37):

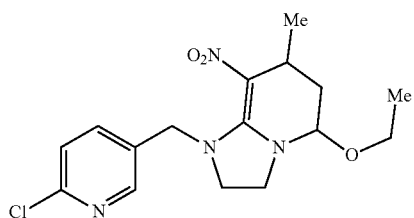

(s37)

(see WO 06/056108),

[c-28.122] a Compound of Formula (s38):

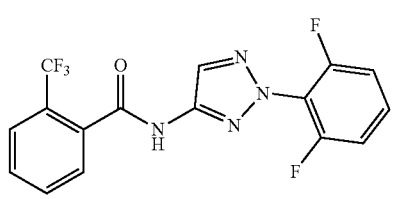

(s38)

(see WO 14/053450 and International Patent No. 15/144683),

[c-28.123] a Compound of Formula (s39):

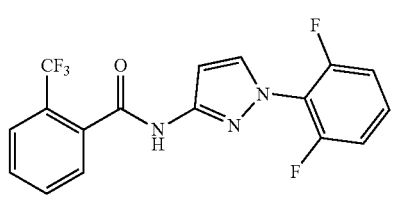

(s39)

(see WO 14/053450 and International Patent No. 15/144683),

[c-28.124] a Compound of Formula (s40):

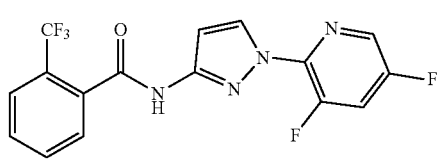

(s40)

(see WO 14/053450 and International Patent No. 15/144683),

[c-28.125] Compounds of Formula (s41):

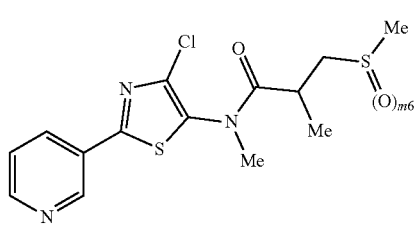

(s41)

wherein m6 represents an integer of 0 to 2 (see WO 10/129497),

[c-28.126] Compounds of Formula (s42):

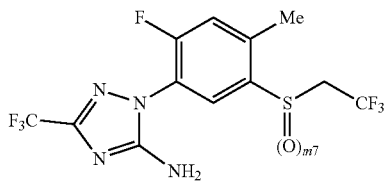

(s42)

wherein m7 represents an integer of 0 to 2 (see WO 11/152320),

[c-28.127] Compounds of Formula (s43):

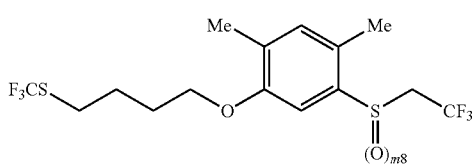

(s43)

wherein m8 represents an integer of 0 to 2 (see JP 2015-160813 A),

[c-28.128] Compounds of Formula (s44):

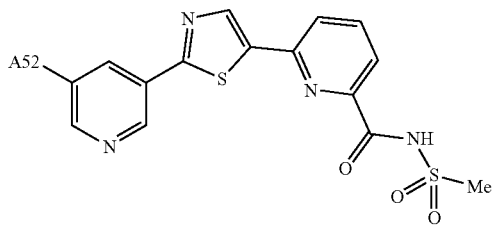

(s44)

wherein A52 represents a hydrogen atom or fluorine atom (see WO 11/134964 and International Patent No. 14/005982),

[c-28.129] Compounds of Formula (s45):

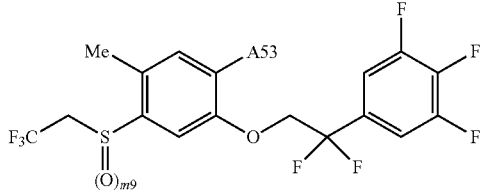

(s45)

wherein m9 represents an integer of 0 to 2, and A53 represents fluorine atom or chlorine atom (see WO 15/025826),

[c-28.130] Compounds of Formula (s46):

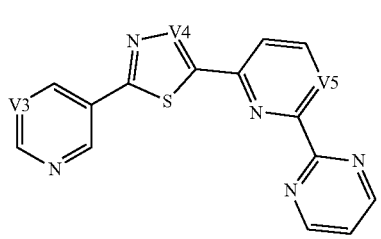

(s46)

wherein V3 represents a nitrogen atom, a carbon atom or C—F, and V4 and V5 are independent of one another and each represent a nitrogen atom or a carbon atom (see WO 11/134964 and WO 14/005982),

[c-28.131] Compounds of Formula (s47):

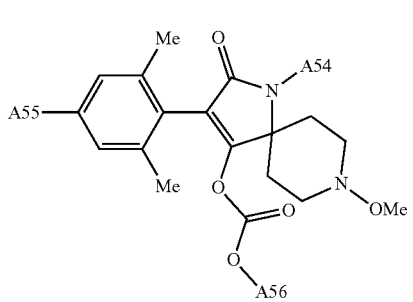

(s47)

wherein A54 represents a hydrogen atom, methyl, methoxy or ethoxy, A55 represents chlorine atom or methyl, and A56 represents methyl or ethyl (see WO 09/049851),

[c-28.132] Compounds of Formula (s48):

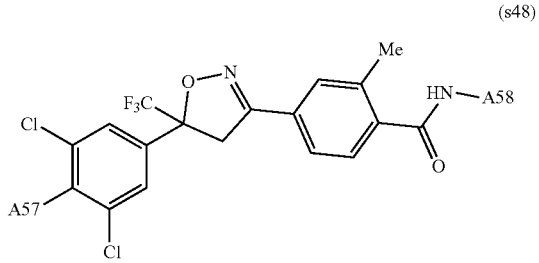

(s48)

wherein A57 represents a hydrogen atom, fluorine atom or chlorine atom, and A58 represents one partial structure selected from the group consisting of:

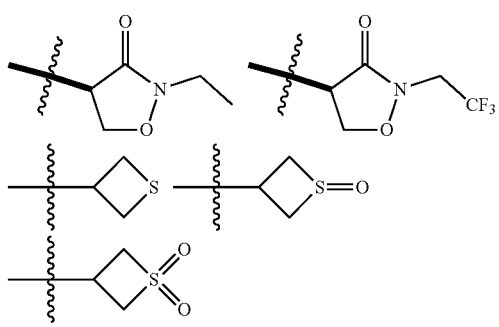

(see WO 11/067272),

[c-28.133] Compounds of Formula (s49):

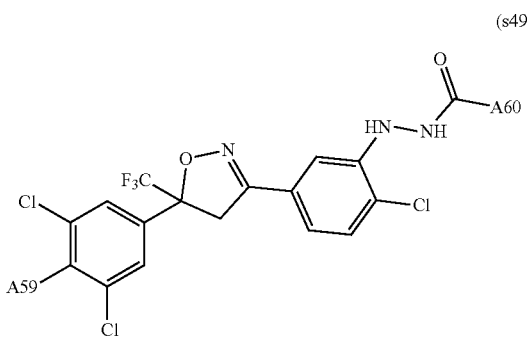

(s49)

wherein A59 represents a hydrogen atom, fluorine atom or chlorine atom, and A60 represents a partial structure selected from the group consisting of:

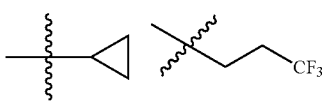

(see WO 10/090344),

[c-28.134] Compounds of Formula (s50):

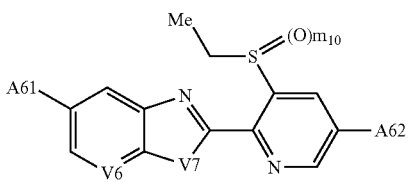

(s50)

wherein m10 represents an integer of 0 to 2, A61 represents trifluoromethyl, trifluoromethylthio, trifluoromethylsulfinyl or trifluoromethylsulfonyl, A62 represents a hydrogen atom or trifluoromethyl, V6 represents a nitrogen atom or a carbon atom, and V7 represents an oxygen atom or a N-methyl (see WO 14/104407),

[c-28.135] Compounds of Formula (s51):

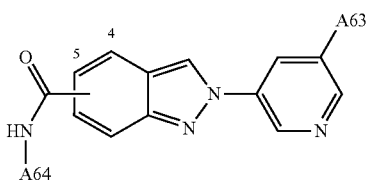

(s51)

wherein A63 represents a hydrogen atom or fluorine atom, the amide group is bonded to 4-position or 5-position, and A64 represents a partial structure selected from the group consisting of:

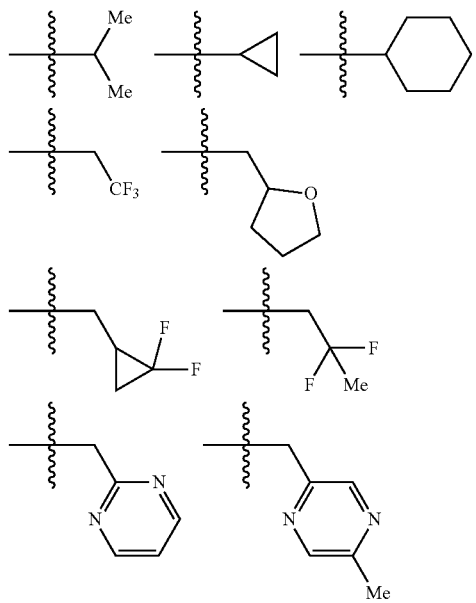

(see WO 15/038503, International Patent No. 16/144351 and International Patent No. 16/144678),

[c-28.136] Compounds of Formula (s52):

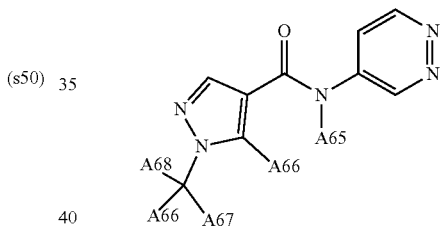

(s52)

wherein A65 represents a hydrogen atom, a C1-C6 alkyl group or a C1-C6 haloalkyl group, A66 represents a hydrogen atom, a halogen atom or a C1-C6 alkyl group, A67 and A68 are independent of one another and each represent a hydrogen atom, a C1-C6 alkyl group optionally substituted with a cyano group, an alkyl group optionally substituted with methoxy, an alkyl group optionally substituted with ethoxy, or a C3-C8 cycloalkyl group, and A69 represents a hydrogen atom, a cyano group, a C1-C6 haloalkyl group optionally substituted with a cyano group, a C1-C6 alkyl group, or a C3-C8 cycloalkyl group (see WO 12/143317 and International Patent No. 16/016369),

[c-28.137] Compounds of Formula (s53) or (s54):

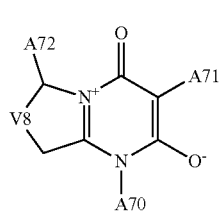

(s53)

-continued (s54)

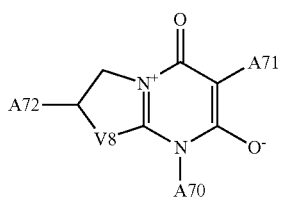

wherein A70 represents methyl, ethyl, isopropyl, 2,2,2-trifluoroethyl or phenyl, A71 represents a partial structure selected from the group consisting of:

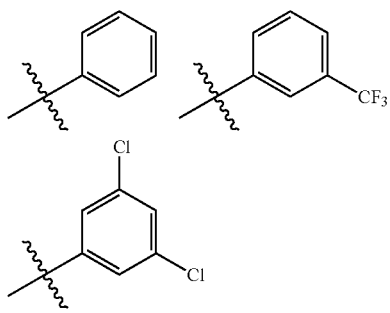

A72 represents a partial structure selected from the group consisting of:

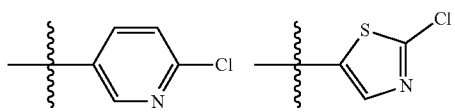 [SMILES: *c1ccc(Cl)nc1 ; *c1cnc(Cl)s1]

and V8 represents an oxygen atom, a sulfur atom, —$CH_2$— or —$CH_2CH_2$— (see WO 14/167084 and International Patent No. 16/055431),

[c-28.138] Compounds of Formula (s55):

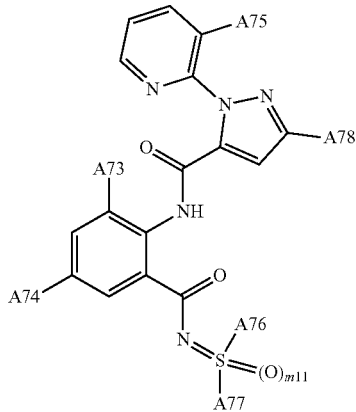

(s55)

wherein m11 represents an integer of 0 to 1, A73 represents chlorine atom, bromine atom, methyl or trifluoromethyl, A74 represents a hydrogen atom, chlorine atom, bromine atom, a cyano group or trifluoromethyl, A75 represents a hydrogen atom, chlorine atom or bromine atom, A76 and A77 are independent of one another and each represent a C1-C6 alkyl group or a C3-C8 cycloalkyl group, and A78 represents chlorine atom, bromine atom, a cyano group, a nitro group, difluoromethyl or trifluoromethyl (see WO 13/024009),

[c-28.139] Compounds of Formula (s56):

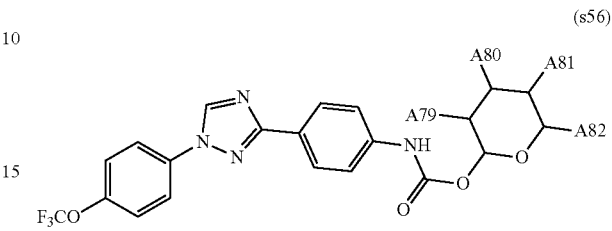

(s56)

wherein A79, A80, A81 and A82 are independent of one another and each represent a hydrogen atom, a halogen atom, a C1-C6 alkyl group, a C1-C6 haloalkyl group, a C1-C6 alkoxy group or a C3-C8 cycloalkoxy group (see WO 12/027521),

[c-28.140] Compounds of Formula (s57):

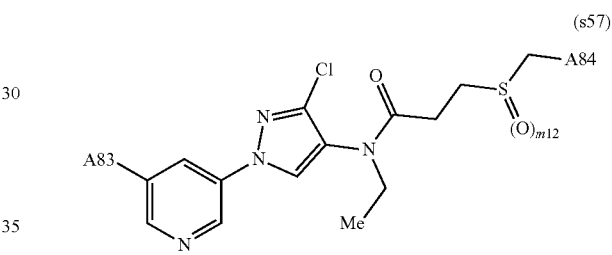

(s57)

wherein m12 represents an integer of 0 to 2, A83 represents a hydrogen atom or fluorine atom, and A84 represents a partial structure selected from the group consisting of:

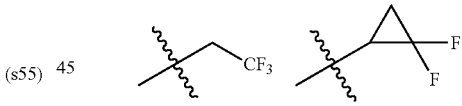

(see WO 13/162715),

[c-28.141] acynonapyr,

[c-28.142] Compounds of Formula (s59):

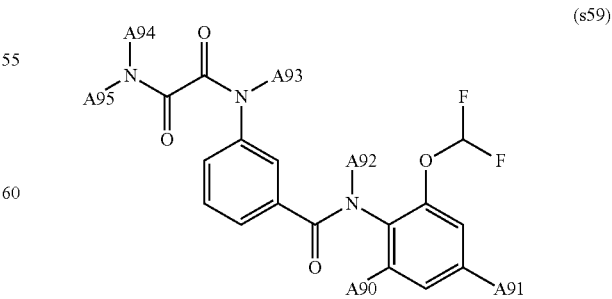

(s59)

wherein A90 represents a halogen atom, a C1-C6 alkyl group or a C1-C6 haloalkyl group, A91 represents a C1-C6 haloalkyl group, A92 and A93 are independent of one another and each represent a hydrogen atom, a C1-C6 alkyl group, acetyl, propionyl, methanesulfonylethyl, methoxycarbonyl or ethoxycarbonyl, and A94 and A95 are independent of one another and each represent a hydrogen atom, a C1-C6 alkyl group or a C1-C6 haloalkyl group (see WO 12/164698).

The inventive compounds and optional agricultural chemicals described above may be mixed together in any ratio without limitation as long as exerting its effects. The weight ratio of the optional agricultural chemical to the inventive compound is usually from 0.001 to 1000, and preferably from 0.01 to 100.

EXAMPLES

The present invention is hereinbelow described in more detail by illustrating Synthetic Examples, Reference Examples and Test Examples. However, the scope of the invention is not limited thereto.

Synthetic Example 1

Synthesis of 1-ethyl-5-isopropyl-6-(2,4,6-trifluorophenyl)-3,4-dihydropyridin-2(1H)-one

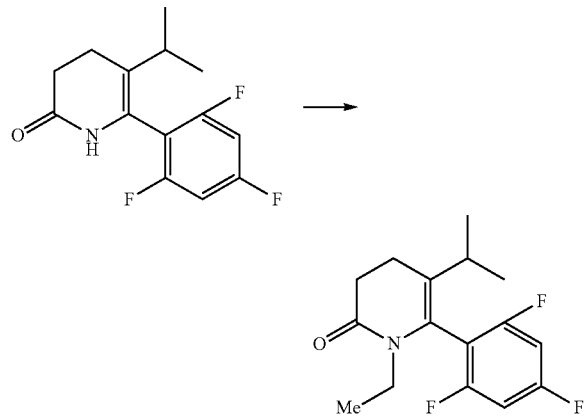

The DMF solution (10 mL) containing 0.80 g of 5-isopropyl-6-(2,4,6-trifluorophenyl)-3,4-dihydropyridin-2(1H)-one, 2.90 g of cesium carbonate and 713 µl of ethyl iodide was stirred at 50° C. for 2 hours. The reaction mixture was cooled to room temperature, before separated by adding water and ethyl acetate. The organic layer thus obtained was sequentially washed with aqueous sodium thiosulfate solution and saturated brine, and was dried over sodium sulfate. The solvent was distilled under reduced pressure, and the residue was purified by silica gel column chromatography. The title compound was obtained as a light yellow oil (0.90 g). The oil, comprising ethyl acetate used in the purification, was directly used for the next reaction.

$^1$H-NMR (CDCl$_3$) δ: 6.75 (2H, dd, J=8.6, 6.7 Hz), 3.29 (2H, q, J=7.0 Hz), 2.53-2.52 (2H, m), 2.31-2.29 (2H, m), 2.17-2.15 (1H, m), 0.93 (6H, d, J=6.7 Hz), 0.92 (3H, t, J=7.0 Hz).

Synthetic Example 2

Synthesis of 1-ethyl-5-isopropyl-6-(2,4,6-trifluorophenyl)pyridin-2(1H)-one (Compound No. 7)

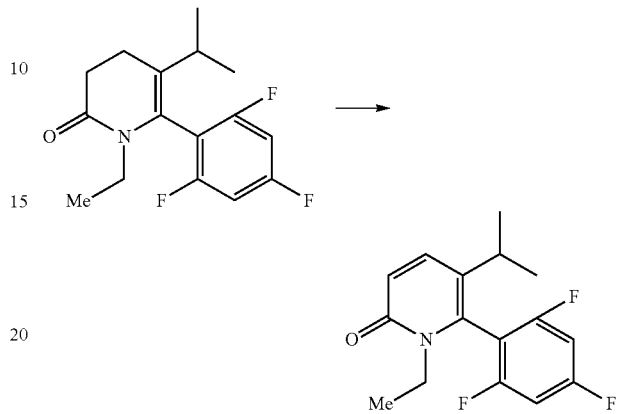

The toluene solution (20 ml) containing 0.90 g of 1-ethyl-5-isopropyl-6-(2,4,6-trifluorophenyl)-3,4-dihydropyridin-2 (1H)-one obtained in Synthetic Example 1 and 2.02 g of 2,3-dichloro-5,6-dicyano-p-benzoquinone was stirred under reflux for 11 hours. Further, 1.01 g of 2,3-dichloro-5,6-dicyano-p-benzoquinone was added, and the mixture was stirred under reflux for 4 hours. The reaction mixture was cooled to room temperature and was purified by silica gel column chromatography. The solid thus obtained was washed with hexane. The title compound was obtained as a white solid (0.76 g).

Synthetic Example 3

Synthesis of 3-chloro-1-ethyl-5-isopropyl-6-(2,4,6-trifluorophenyl)pyridin-2(1H)-one (Compound No. 8)

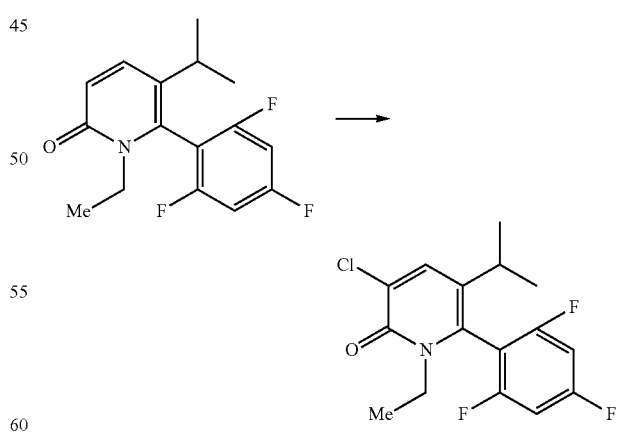

The DMF solution (3 ml) containing 130 mg of 1-ethyl-5-isopropyl-6-(2,4,6-trifluorophenyl)pyridin-2(1H)-one and 71 mg of N-chlorosuccinimide was stirred at 70° C. for 1.5 hours. The reaction mixture was cooled to room temperature, before separated by adding water and ethyl acetate. The organic layer thus obtained was sequentially washed with aqueous sodium thiosulfate solution and saturated brine, and was dried over sodium sulfate. The solvent was distilled under reduced pressure, and the residue was purified by silica gel column chromatography. The title compound was obtained as a white solid (136 mg).

Synthetic Example 4

6-(2,6-Difluoro-4-methoxyphenyl)-1-ethyl-5-isopropylpyridin-2(1H)-one (Compound No. 10)

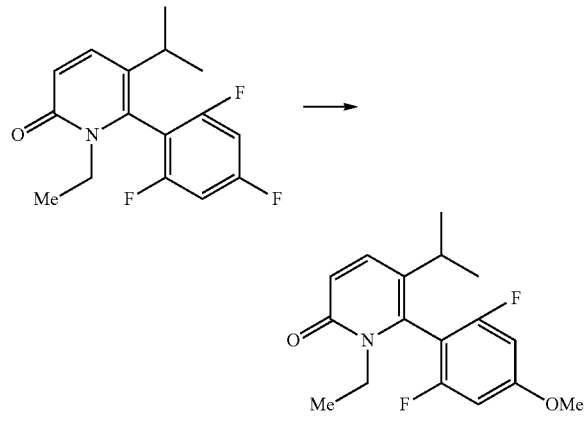

The methanol solution (5 ml) containing 0.38 g of 1-ethyl-5-isopropyl-6-(2,4,6-trifluorophenyl)pyridin-2(1H)-one was added 0.75 g of sodium methoxide (28%, in methanol), and the mixture was stirred under reflux for 4 hours. The mixture was added 0.25 g of sodium methoxide (28%, in methanol), and stirred under reflux for 1.5 hours. Then, 1 N hydrochloric acid was added, before separated by adding ethyl acetate. The organic layer thus obtained was washed with saturated brine and was dried over sodium sulfate. The solvent was distilled under reduced pressure, and the residue was purified by silica gel column chromatography. The title compound was obtained as a transparent gum (0.40 g).

Synthetic Example 5

3-Chloro-6-(2,6-difluoro-4-methoxyphenyl)-1-ethyl-5-isopropylpyridin-2(1H)-one (Compound No. 11)

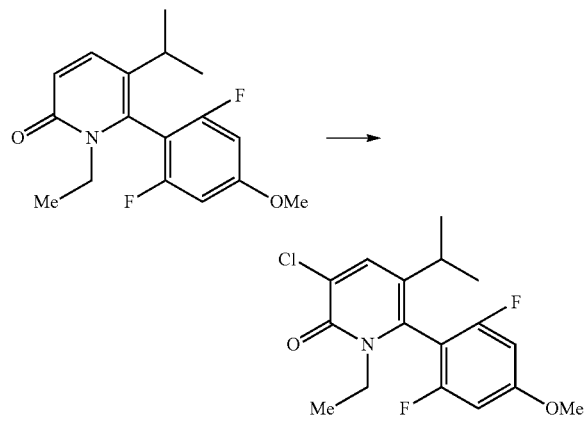

The DMF solution (5 ml) containing 125 mg of 6-(2,6-difluoro-4-methoxyphenyl)-1-ethyl-5-isopropylpyridin-2(1H)-one and 65 mg of N-chlorosuccinimide was stirred at 70° C. for 2 hours. The reaction mixture was cooled to room temperature, before separated by adding water and ethyl acetate. The organic layer thus obtained was sequentially washed with aqueous sodium thiosulfate solution and saturated brine, and was dried over sodium sulfate. The solvent was distilled under reduced pressure, and the residue was purified by silica gel column chromatography. The title compound was obtained as a white solid (129 mg).

Synthetic Example 6

Synthesis of 6-(2,6-difluorophenyl)-1-ethyl-5-methyl-3,4-dihydropyridin-2(1H)-one

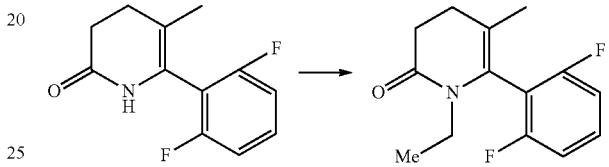

The DMF solution (120 ml) containing 12.40 g of 6-(2,6-difluorophenyl)-5-methyl-3,4-dihydropyridin-2(1H)-one, 54.30 g of cesium carbonate and 25.99 g of ethyl iodide was stirred at 50° C. for 3.5 hours. Next, 27.15 g of cesium carbonate and 13.01 g of ethyl iodide were added. The mixture was stirred at 50° C. for 2 hours and was further stirred at 60° C. for 1.5 hours. The reaction mixture was cooled to room temperature and was filtered to remove insolubles. The filtrate was distilled under reduced pressure to remove the solvent. Ethyl acetate and water were added to the residue, and the resultant liquid mixture was separated. The organic layer thus obtained was sequentially washed with aqueous sodium thiosulfate solution and saturated brine, and was dried over sodium sulfate. The mixture was distilled under reduced pressure to remove the solvent, and the solid obtained was washed with isopropyl ether. The title compound was obtained as a white solid (11.98 g).

$^1$H-NMR (CDCl$_3$) δ: 7.38-7.35 (1H, m), 6.97-6.96 (2H, m), 3.33 (2H, q, J=7.1 Hz), 2.60-2.58 (2H, m), 2.38-2.36 (2H, m), 1.59 (3H, s), 0.91 (3H, t, J=7.1 Hz).

Synthetic Example 7

Synthesis of 6-(2,6-difluorophenyl)-1-ethyl-5-methylpyridin-2(1H)-one (Compound No. 1)

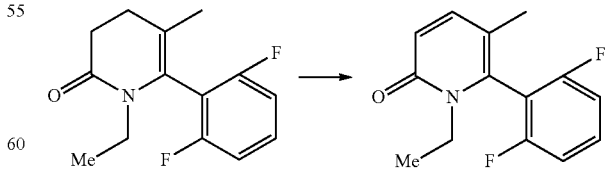

The toluene solution (170 ml) containing 11.98 g of 6-(2,6-difluorophenyl)-1-ethyl-5-methyl-3,4-dihydropyridin-2(1H)-one and 21.65 g of 2,3-dichloro-5,6-dicyano-p-benzoquinone was stirred at 120° C. for 1.5 hours. The reaction mixture was cooled to room temperature and was filtered to remove insolubles. The filtrate was distilled under reduced pressure to remove the solvent, and the residue was purified by silica gel column chromatography. The solid thus obtained was washed with isopropyl ether. The title compound was obtained as a light yellow solid (9.34 g).

Synthetic Example 8

Synthesis of 3-chloro-6-(2,6-difluorophenyl)-1-ethyl-5-methylpyridin-2(1H)-one (Compound No. 2)

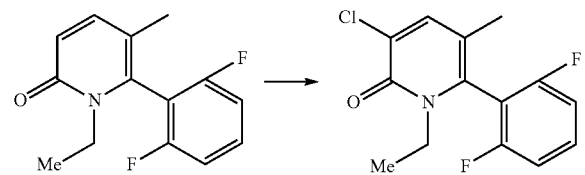 [SMILES: CCn1c(-c2c(F)cccc2F)c(C)ccc1=O ; CCn1c(-c2c(F)cccc2F)c(C)cc(Cl)c1=O]

The DMF solution (110 ml) containing 11.36 g of 6-(2,6-difluorophenyl)-1-ethyl-5-methylpyridin-2(1H)-one and 6.69 g of N-chlorosuccinimide was stirred at 70° C. for 50 minutes. The reaction mixture was cooled to room temperature and was distilled under reduced pressure to remove the solvent. Ethyl acetate and water were added thereto, and the resultant liquid mixture was separated. The organic layer thus obtained was sequentially washed with aqueous sodium thiosulfate solution and saturated brine, and was dried over sodium sulfate. The mixture was distilled under reduced pressure to remove the solvent, and the solid obtained was washed with isopropyl ether. The title compound was obtained as a white solid (11.41 g).

Synthetic Example 9

Synthesis of 3-chloro-5-(dibromomethyl)-6-(2,6-difluorophenyl)-1-ethylpyridin-2(1H)-one (Compound No. 21)

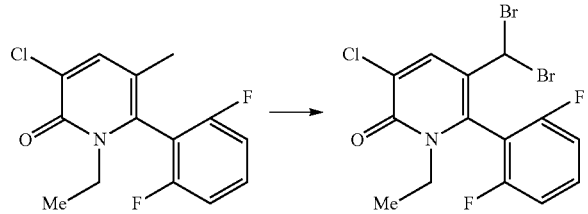 [SMILES: CCn1c(-c2c(F)cccc2F)c(C)cc(Cl)c1=O ; CCn1c(-c2c(F)cccc2F)c(C(Br)Br)cc(Cl)c1=O]

The chlorobenzene solution (230 ml) containing 12.65 g of 3-chloro-6-(2,6-difluorophenyl)-1-ethyl-5-methylpyridin-2(1H)-one were added 16.67 g of N-bromosuccinimide and 366 mg of azobisisobutyronitrile, and the mixture was stirred at 110° C. for 50 minutes. The reaction mixture was cooled to room temperature, before separated by adding water and dichloromethane. The organic layer thus obtained was washed with aqueous sodium thiosulfate solution and was dried over sodium sulfate. The mixture was distilled under reduced pressure to remove the solvent, and the solid obtained was washed with isopropyl ether. The title compound was obtained as a light brown solid (16.88 g).

Synthetic Example 10

Synthesis of 5-chloro-2-(2,6-difluorophenyl)-1-ethyl-6-oxo-1,6-dihydropyridine-3-carbaldehyde (Compound No. 20)

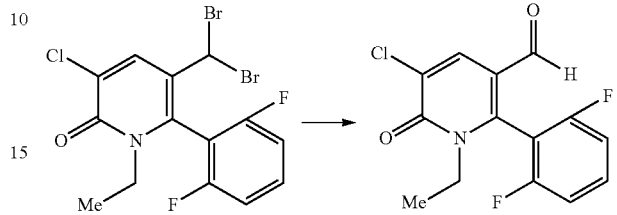

The aqueous solution (190 ml) containing 21.87 g of silver nitrate was added to 380 ml of acetonitrile containing 18.95 g of 3-chloro-5-(dibromomethyl)-6-(2,6-difluorophenyl)-1-ethylpyridin-2(1H)-one. The mixture was stirred at room temperature for 15 minutes. The reaction mixture was filtered to remove insolubles. The filtrate was distilled under reduced pressure to remove the solvent. Water and ethyl acetate were added to the residue, and the resultant mixture was separated. The organic layer thus obtained was washed with 1 N hydrochloric acid and saturated brine, and was dried over sodium sulfate. The mixture was distilled under reduced pressure to remove the solvent, and the solid obtained was washed with isopropyl ether. The title compound was obtained as a light yellow solid (11.37 g).

Synthetic Example 11

Synthesis of 3-chloro-6-(2,6-difluorophenyl)-1-ethyl-5-(1-hydroxypropyl)pyridin-2(1H)-one (Compound No. 24)

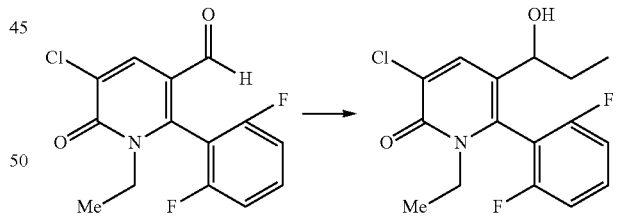

The THF solution (6.05 ml) of ethylmagnesium bromide (1.0 mol/L) was added dropwise, under ice cooling, to the THF solution (12 ml) containing 1.20 g of 5-chloro-2-(2,6-difluorophenyl)-1-ethyl-6-oxo-1,6-dihydropyridine-3-carbaldehyde, and the mixture was stirred for 10 minutes. The reaction mixture was separated by adding 1 N hydrochloric acid and ethyl acetate. The organic layer thus obtained was washed with saturated brine and was dried over sodium sulfate. The solvent was distilled under reduced pressure, and the residue was purified by silica gel column chromatography. The title compound was obtained as a white solid (0.54 g).

Synthetic Example 12

Synthesis of 3-chloro-6-(2,6-difluorophenyl)-1-ethyl-5-(1-methoxypropyl)pyridin-2(1H)-one (Compound No. 25)

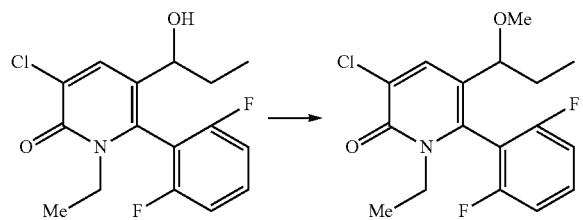 [SMILES: CCC(O)c1cc(Cl)c(=O)n(CC)c1-c1c(F)cccc1F ; CCC(OC)c1cc(Cl)c(=O)n(CC)c1-c1c(F)cccc1F]

The nitromethane solution (3 ml) containing 100 mg of 3-chloro-6-(2,6-difluorophenyl)-1-ethyl-5-(1-hydroxypropyl)pyridin-2(1H)-one, 334 μl of trimethyl orthoformate and 124 μl of methanol was added under ice cooling 3 μl of trifluoromethanesulfonic acid, and the mixture was stirred for 5 minutes. The resulting mixture was separated by adding water and ethyl acetate. The organic layer thus obtained was washed with saturated aqueous sodium hydrogen carbonate solution and was dried over sodium sulfate. The solvent was distilled under reduced pressure, and the residue was purified by silica gel column chromatography. The title compound was obtained as a white solid (94 mg).

Synthetic Example 13

Synthesis of 3-chloro-6-(2,6-difluorophenyl)-1-ethyl-5-propionylpyridin-2(1H)-one (Compound No. 26)

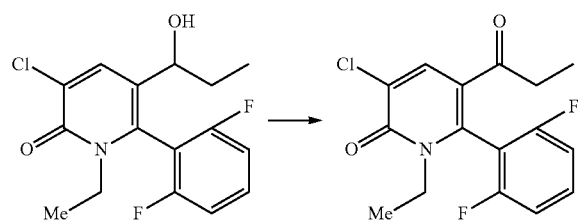 [SMILES: CCC(O)c1cc(Cl)c(=O)n(CC)c1-c1c(F)cccc1F ; CCC(=O)c1cc(Cl)c(=O)n(CC)c1-c1c(F)cccc1F]

The dichloromethane solution (9 ml) containing 900 mg of 3-chloro-6-(2,6-difluorophenyl)-1-ethyl-5-(1-hydroxypropyl)pyridin-2(1H)-one and 3 ml of dimethylsulfoxide were added under ice cooling 1.92 ml of triethylamine and 1.75 g of pyridine-sulfur trioxide complex, and the mixture was stirred for 3 hours. The reaction mixture was separated by adding 1 N hydrochloric acid and ethyl acetate. The organic layer thus obtained was washed sequentially with saturated aqueous sodium hydrogen carbonate solution and saturated brine, and was dried over sodium sulfate. The solvent was distilled under reduced pressure, and the residue was purified by silica gel column chromatography. The title compound was obtained as a white solid (629 mg).

Synthetic Example 14

Synthesis of 3-chloro-6-(2,6-difluorophenyl)-1-ethyl-5-(2-hydroxybutan-2-yl)pyridin-2(1H)-one (Compound No. 27)

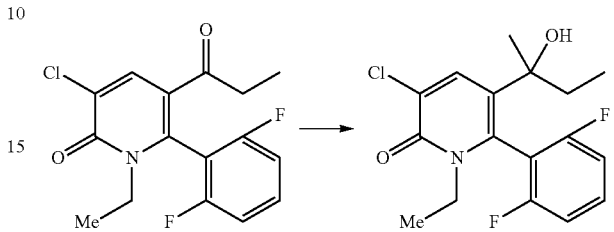

The diethyl ether solution (1.22 ml) of methyllithium(1.1 mol/L) was added dropwise to the THF solution (5 ml) containing 200 mg of 3-chloro-6-(2,6-difluorophenyl)-1-ethyl-5-propionylpyridin-2(1H)-one at −78° C., and the mixture was stirred for 20 minutes. The reaction solution was separated by adding 1 N hydrochloric acid and ethyl acetate. The organic layer thus obtained was washed sequentially with saturated aqueous sodium hydrogen carbonate solution and saturated brine, and was dried over sodium sulfate. The solvent was distilled under reduced pressure, and the residue was purified by silica gel column chromatography. The title compound was obtained as a light yellow solid (178 mg).

Synthetic Example 15

Synthesis of 3-chloro-6-(2,6-difluorophenyl)-1-ethyl-5-(2-methoxybutan-2-yl)pyridin-2(1H)-one (Compound No. 29)

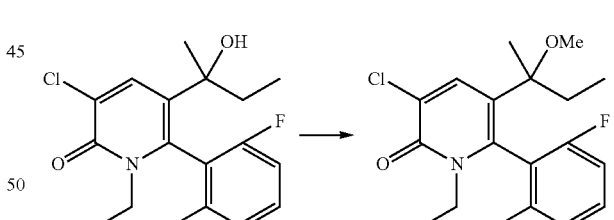

The nitromethane solution (3 ml) containing 80 mg of 3-chloro-6-(2,6-difluorophenyl)-1-ethyl-5-(2-hydroxybutan-2-yl)pyridin-2(1H)-one, 256 μl of trimethyl orthoformate and 95 μl of methanol was added under ice cooling 2 μl of trifluoromethanesulfonic acid, and the mixture was stirred for 10 minutes. The reaction mixture was separated by adding saturated aqueous sodium hydrogen carbonate solution and ethyl acetate. The organic layer thus obtained was washed with saturated brine and was dried over sodium sulfate. The solvent was distilled under reduced pressure, and the residue was purified by silica gel column chromatography. The title compound was obtained as a white solid (80 mg).

Synthetic Example 16

Synthesis of 3-chloro-6-(2,6-difluorophenyl)-1-ethyl-5-(2-fluorobutan-2-yl)pyridin-2(1H)-one (Compound No. 30)

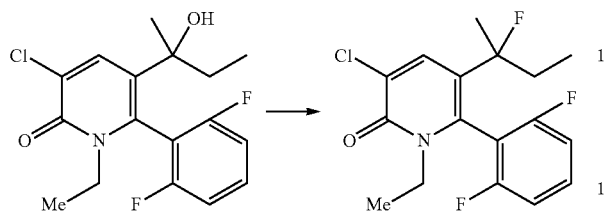

The dichloromethane solution (3 ml) containing 105 mg of 3-chloro-6-(2,6-difluorophenyl)-1-ethyl-5-(2-hydroxybutan-2-yl)pyridin-2(1H)-one was added under ice cooling 50 µl of (diethylamino)sulfur trifluoride, and the mixture was stirred for 15 minutes. The reaction mixture was separated by adding saturated aqueous sodium hydrogen carbonate solution and ethyl acetate. The organic layer thus obtained was washed with saturated brine and was dried over sodium sulfate. The solvent was distilled under reduced pressure, and the residue was purified by silica gel column chromatography. The title compound was obtained as a white solid (102 mg).

Synthetic Example 17

Synthesis of 6-(2-chloro-4-fluorophenyl)-1-ethyl-5-isobutyl-3,4-dihydropyridin-2(1H)-one

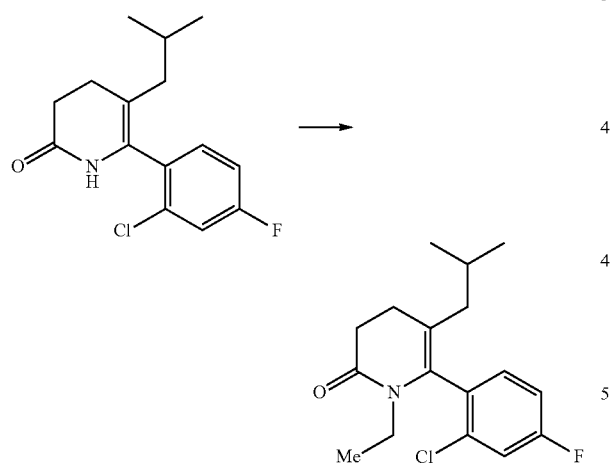

The DMF solution (15 ml) containing 1.48 g of 6-(2-chloro-4-fluorophenyl)-5-isobutyl-3,4-dihydropyridin-2(1H)-one were added 1.26 ml of ethyl iodide and 5.15 g of cesium carbonate, and the mixture was stirred at 50° C. for 6.5 hours. The reaction mixture was cooled to room temperature, before separated by adding water and ethyl acetate. The organic layer thus obtained was washed sequentially with water and saturated brine, and was dried over magnesium sulfate. The solvent was distilled under reduced pressure, and the residue was purified by silica gel column chromatography. The title compound was obtained as a light brown oil (1.43 g).

$^1$H-NMR (CDCl$_3$) δ: 7.23 (1H, dd, J=8.6, 6.1 Hz), 7.20 (1H, dd, J=8.6, 2.6 Hz), 7.06-7.02 (1H, m), 3.70-3.63 (1H, m), 2.87-2.80 (1H, m), 2.61-2.50 (2H, m), 2.42-2.35 (1H, m), 2.27-2.21 (1H, m), 1.83 (1H, dd, J=13.3, 6.3 Hz), 1.75-1.68 (1H, m), 1.60 (1H, dd, J=13.3, 8.0 Hz), 0.90 (3H, t, J=7.0 Hz), 0.78 (3H, d, J=6.4 Hz), 0.77 (3H, d, J=6.4 Hz).

Synthetic Example 18

Synthesis of 6-(2-chloro-4-fluorophenyl)-1-ethyl-5-isobutylpyridin-2(1H)-one (Compound No. 98)

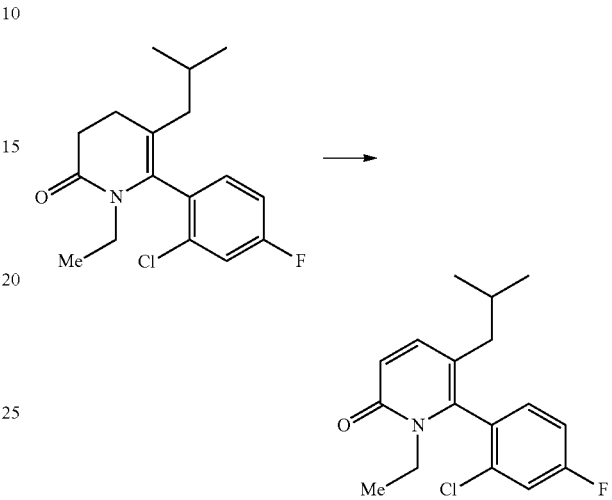

The toluene solution (20 ml) containing 1.43 g of 6-(2-chloro-4-fluorophenyl)-1-ethyl-5-isobutyl-3,4-dihydropyridin-2(1H)-one and 2.10 g of 2,3-dichloro-5,6-dicyano-p-benzoquinone was stirred at 120° C. for 2.5 hours. The reaction mixture was cooled to room temperature and was filtered to remove insolubles. The filtrate was distilled under reduced pressure to remove the solvent, and the residue was purified by silica gel column chromatography. The title compound was obtained as a yellow oil (1.09 g).

Synthetic Example 19

Synthesis of 3-chloro-6-(2-chloro-4-fluorophenyl)-1-ethyl-5-isobutylpyridin-2(1H)-one (Compound No. 99)

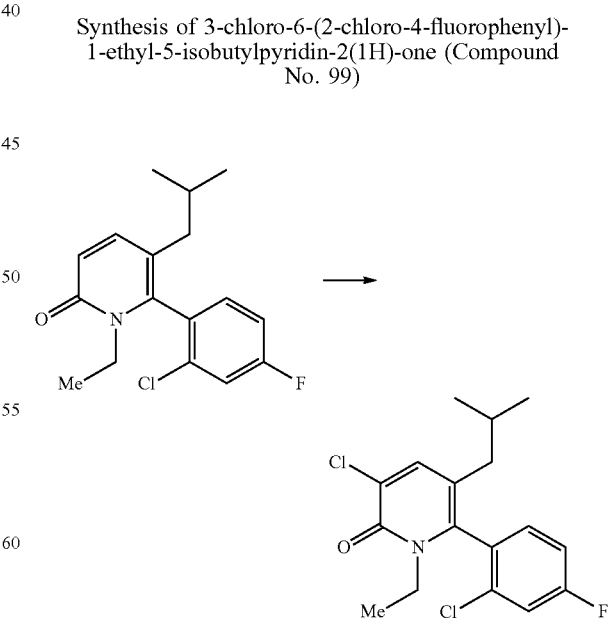

The DMF solution (3 ml) containing 153 mg of 6-(2-chloro-4-fluorophenyl)-1-ethyl-5-isobutylpyridin-2(1H)-one and 87 mg of N-chlorosuccinimide was stirred at 50° C. for 5.5 hours. The reaction mixture was cooled to room temperature, before separated by adding water and ethyl acetate. The organic layer thus obtained was washed sequentially with aqueous sodium thiosulfate solution and saturated brine, and was dried over magnesium sulfate. The solvent was distilled under reduced pressure, and the residue was purified by silica gel column chromatography. The title compound was obtained as a white solid (145 mg).

Synthetic Example 20

Synthesis of 6-(2-chloro-4-fluorophenyl)-1,3-dimethyl-5-propylpyridin-2(1H)-one (Compound No. 339)

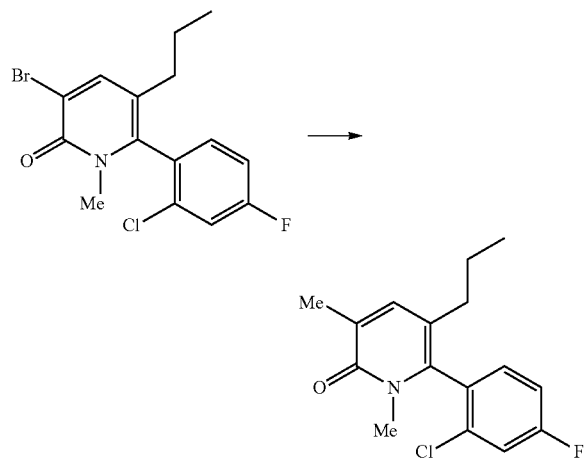

First, 173 mg of 3-bromo-6-(2-chloro-4-fluorophenyl)-1-methyl-5-propylpyridin-2(1H)-one (Compound No. 333) obtained in the same manner as 3-chloro-6-(2-chloro-4-fluorophenyl)-1-ethyl-5-isobutylpyridin-2(1H)-one (Compound No. 99) described in Synthetic Example 19, 116 mg of methylboronic acid, 11 mg of palladium (II) acetate, 360 mg of tripotassium phosphate and 27 mg of tricyclohexylphosphine were dissolved into a mixture of 5 ml toluene and 0.5 ml water. The solution was stirred at 100° C. for 3 hours. The reaction mixture was cooled to room temperature, before separated by adding water and ethyl acetate. The organic layer thus obtained was washed with saturated brine, and was dried over magnesium sulfate. The solvent was distilled under reduced pressure, and the residue was purified by silica gel column chromatography. The title compound was obtained as a yellow solid (54 mg).

Synthetic Example 21

Synthesis of 1-ethyl-5-methyl-6-(2,4,6-trifluorophenyl)-3,4-dihydropyridin-2(1H)-one

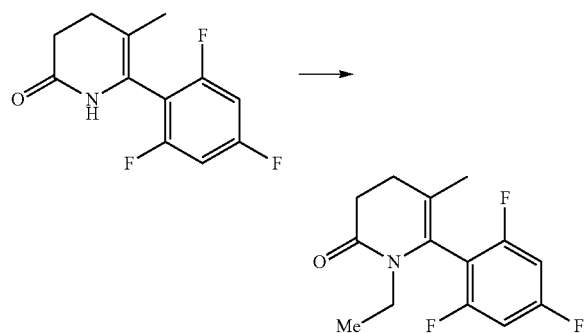

DMF (40 ml) containing 3.86 g of 5-methyl-6-(2,4,6-trifluorophenyl)-3,4-dihydropyridin-2(1H)-one, 5.12 ml of ethyl iodide and 20.85 g of cesium carbonate was stirred at 60° C. for 10 hours. The reaction mixture was cooled to room temperature, before separated by adding water and ethyl acetate. The organic layer thus obtained was washed with saturated brine and was dried over sodium sulfate. The mixture was distilled under reduced pressure to remove the solvent, and the solid obtained was washed with diisopropyl ether. The title compound was obtained as a white solid (4.01 g).

$^1$H-NMR (CDCl$_3$) δ: 6.77-6.72 (2H, m), 3.32 (2H, q, J=7.1 Hz), 2.59-2.56 (2H, m), 2.37-2.35 (2H, m), 0.92 (3H, t, J=7.1 Hz).

Synthetic Example 22

Synthesis of 1-ethyl-5-methyl-6-(2,4,6-trifluorophenyl)pyridin-2(1H)-one

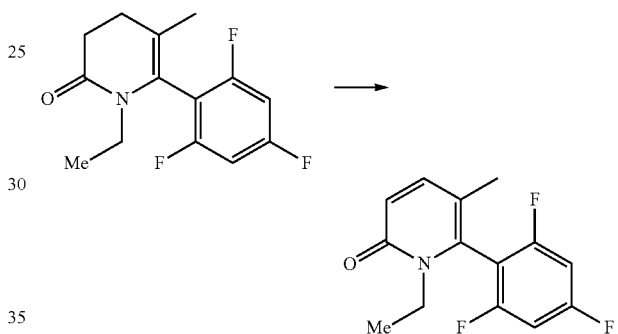

The toluene solution (60 ml) containing 4.00 g of 1-ethyl-5-methyl-6-(2,4,6-trifluorophenyl)-3,4-dihydropyridin-2(1H)-one and 6.75 g of 2,3-dichloro-5,6-dicyano-p-benzoquinone was stirred at 120° C. for 5 hours. The reaction mixture was added 1.69 g of 2,3-dichloro-5,6-dicyano-p-benzoquinone, and was stirred at 120° C. for 2 hours. The reaction mixture was cooled to room temperature and was filtered. The organic layer was distilled under reduced pressure to remove the solvent, and the residue was purified by silica gel column chromatography. The solid was then washed with diisopropyl ether. The title compound was obtained as a white solid (3.50 g).

$^1$H-NMR (CDCl$_3$) δ: 7.26 (1H, d, J=9.5 Hz), 6.88-6.84 (2H, m), 6.64 (1H, d, J=9.5 Hz), 3.82 (2H, q, J=7.1 Hz), 1.81 (3H, s), 1.10 (3H, t, J=7.1 Hz).

Synthetic Example 23

Synthesis of 3-chloro-1-ethyl-5-methyl-6-(2,4,6-trifluorophenyl)pyridin-2(1H)-one

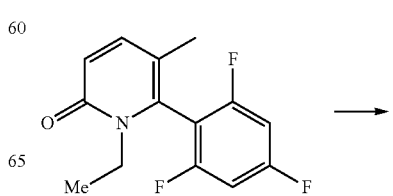

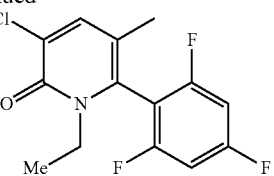

The DMF solution (3 ml) containing 97 mg of 1-ethyl-5-methyl-6-(2,4,6-trifluorophenyl)pyridin-2(1H)-one and 49 mg of N-chlorosuccinimide was stirred at 70° C. for 4 hours. The reaction mixture was added 32 mg of N-chlorosuccinimide, and was stirred at 70° C. for 1 hour. The reaction mixture was cooled to room temperature, before separated by adding water and ethyl acetate. The organic layer thus obtained was washed with saturated brine, and was dried over sodium sulfate. The mixture was distilled under reduced pressure to remove the solvent, and the residue was purified by silica gel column chromatography. The title compound was obtained as a white solid (86 mg).

$^1$H-NMR (CDCl$_3$) δ: 7.50 (1H, s), 6.89-6.85 (2H, m), 3.87 (2H, q, J=7.1 Hz), 1.82 (3H, s), 1.13 (3H, t, J=7.1 Hz).

Synthetic Example 24

Synthesis of 3-chloro-5-(dibromomethyl)-1-ethyl-6-(2,4,6-trifluorophenyl)pyridin-2-one

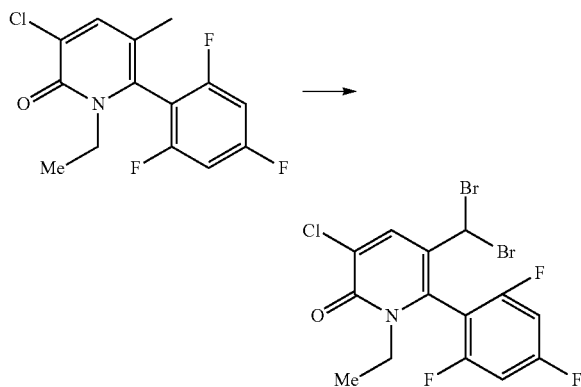

The chlorobenzene solution (70 ml) containing 3.86 g of 3-chloro-1-ethyl-5-methyl-6-(2,4,6-trifluorophenyl)pyridin-2(1H)-one were added 4.78 g of N-bromosuccinimide and 113.9 mg of azobisisobutyronitrile, and the mixture was stirred at 110° C. for 1 hour. The reaction mixture was cooled to room temperature, before separated by adding water and dichloromethane. The organic layer thus obtained was washed sequentially with aqueous sodium thiosulfate solution and saturated brine, and was dried over sodium sulfate. The mixture was distilled under reduced pressure to remove the solvent, and the residue was purified by silica gel column chromatography. The title compound was obtained as a brown oil (5.40 g).

$^1$H-NMR (CDCl$_3$) δ: 8.13 (1H, s), 6.97-6.93 (2H, m), 5.96 (1H, s), 3.81 (2H, q, J=7.1 Hz), 1.14 (3H, t, J=7.1 Hz).

Synthetic Example 25

Synthesis of 5-chloro-1-ethyl-6-oxo-2-(2,4,6-trifluorophenyl)-1,6-dihydropyridine-3-carbaldehyde (Compound No. 289)

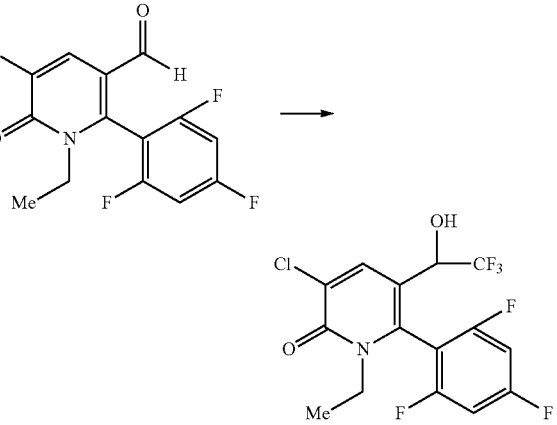

The aqueous solution (47 ml) containing 5.99 g of silver nitrate was added to the acetonitrile solution (95 ml) containing 5.40 g of 3-chloro-5-(dibromomethyl)-1-ethyl-6-(2,4,6-trifluorophenyl)pyridin-2-one, and the mixture was stirred at room temperature for 1 hour. The reaction mixture was filtered through Celite, and was washed with ethyl acetate. The organic layer thus obtained was washed sequentially with water, 1 N hydrochloric acid and saturated brine, and was dried over sodium sulfate. The mixture was distilled under reduced pressure to remove the solvent, and the solid thus obtained was washed with diisopropyl ether. The title compound was obtained as a white solid (3.56 g).

Synthetic Example 26

Synthesis of 3-chloro-1-ethyl-5-(2,2,2-trifluoro-1-hydroxyethyl)-6-(2,4,6-trifluorophenyl)pyridin-2(1H)-one (Compound No. 515)

The DMF solution containing 200 mg of 5-chloro-1-ethyl-6-oxo-2-(2,4,6-trifluorophenyl)-1,6-dihydropyridine-3-carbaldehyde, 280μ of trimethyl(trifluoromethyl)silane and 8 mg of potassium dihydrogen phosphate was stirred at room temperature overnight. The reaction mixture was added approximately 18% hydrochloric acid, and was stirred for 15 minutes. Further, water and ethyl acetate were added, and the resultant liquid mixture was separated. The organic layer thus obtained was washed sequentially with saturated aqueous sodium hydrogen carbonate solution and saturated brine, and was dried over sodium sulfate. The solvent was distilled under reduced pressure, and the residue was purified by silica gel column chromatography. The title compound was obtained as a white substance (150 mg).

Synthetic Example 27

3-Chloro-1-ethyl-5-(2,2,2-trifluoro-1-methoxyethyl)-6-(2,4,6-trifluorophenyl)pyridin-2(1H)-one (Compound No. 516)

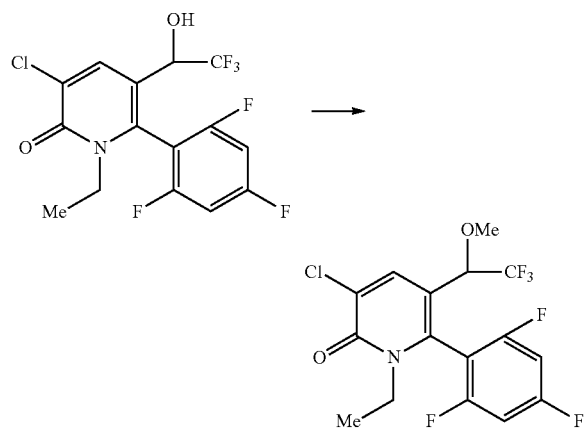

The ethyl acetate solution (3 ml) containing 98 mg of 3-chloro-1-ethyl-5-(2,2,2-trifluoro-1-hydroxyethyl)-6-(2,4,6-trifluorophenyl)pyridin-2(1H)-one, 0.24 g of silver (I) oxide and 0.36 g of methyl iodide was reacted at 60° C. for 5 hours. The reaction mixture was cooled to room temperature and was filtered through Celite. The organic layer thus obtained was washed sequentially with aqueous sodium thiosulfate solution and saturated brine, and was dried over sodium sulfate. The solvent was distilled under reduced pressure, and the residue was purified by silica gel column chromatography. The title compound was obtained as a white solid (86 mg).

Synthetic Example 28

Synthesis of 3-chloro-6-(2,6-difluoro-4-methoxyphenyl)-1-ethyl-5-(2,2,2-trifluoro-1-methoxyethyl)pyridin-2(1H)-one (Compound No. 518)

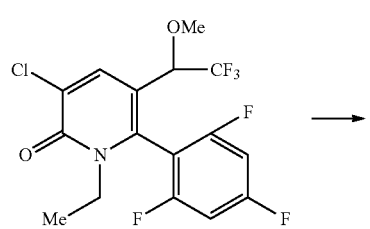

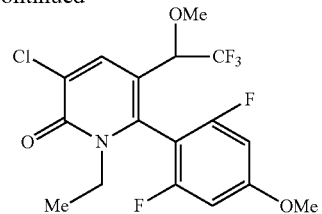

The methanol solution (2 ml) containing 50 mg of 3-chloro-1-ethyl-5-(2,2,2-trifluoro-1-methoxyethyl)-6-(2,4,6-trifluorophenyl)pyridin-2(1H)-one was added 72 mg of sodium methoxide (28%, in methanol), and the mixture was stirred at 60° C. for 8 hours. The reaction mixture was cooled to room temperature, before separated by adding 1 N hydrochloric acid and ethyl acetate. The organic layer thus obtained was washed with saturated brine and was dried over sodium sulfate. The solvent was distilled under reduced pressure, and the residue was purified by silica gel column chromatography. The title compound was obtained as a light gray substance (47 mg).

Synthetic Example 29

Synthesis of 3-chloro-6-(2,6-difluorophenyl)-1-ethyl-5-(1-hydroxy-2-methylpropyl)pyridin-2(1H)-one (Compound No. 53)

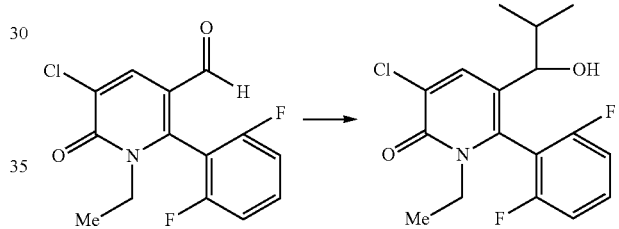

The THF solution (25.4 ml) of isopropyl magnesium chloride-zinc (II) ate complex (iPr3MgZnCl) (0.3 mol/L) was added dropwise to the THF solution (10 ml) containing 1.00 g of 5-chloro-2-(2,6-difluorophenyl)-1-ethyl-6-oxo-1,6-dihydropyridine-3-carbaldehyde at −78° C., and the mixture was stirred for 10 minutes. The reaction mixture was separated by adding saturated aqueous ammonium chloride solution and ethyl acetate. The organic layer thus obtained was washed with saturated brine and was dried over sodium sulfate. The solvent was distilled under reduced pressure, and the residue was purified by silica gel column chromatography. The title compound was obtained as a white solid (0.90 g).

Synthetic Example 30

Synthesis of 3-chloro-6-(2,6-difluorophenyl)-1-ethyl-5-isobutyrylpyridin-2(1H)-one

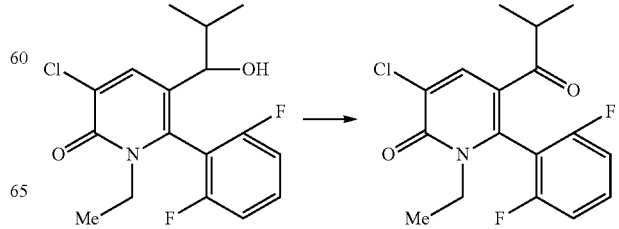

The methylene chloride solution (20 ml) containing 900 mg of 3-chloro-6-(2,6-difluorophenyl)-1-ethyl-5-(1-hydroxy-2-methylpropyl)pyridin-2(1H)-one and 1.23 g of Dess-Martin reagent (1,1,1-triacetoxy-1,1-dihydro-1,2-benziodoxol-3(1H)-one) was stirred at room temperature for 3 hours. The reaction mixture was filtered through Celite. The organic layer thus obtained was washed with aqueous sodium thiosulfate solution and was dried over sodium sulfate. The solvent was distilled under reduced pressure, and the residue was purified by silica gel column chromatography. The title compound was obtained as a white solid (883 mg).

$^1$H-NMR (CDCl$_3$) δ: 7.96 (1H, s), 7.51 (1H, tt, J=8.5, 6.4 Hz), 7.06-7.03 (2H, m), 3.93 (2H, q, J=7.1 Hz), 3.11 (1H, m), 1.16 (3H, t, J=7.1 Hz), 1.04 (6H, t, J=6.8 Hz).

Synthetic Example 31

Synthesis of 3-chloro-6-(2,6-difluorophenyl)-1-ethyl-5-(2-hydroxy-3-methylbutan-2-yl)pyridin-2(1H)-one (Compound No. 183)

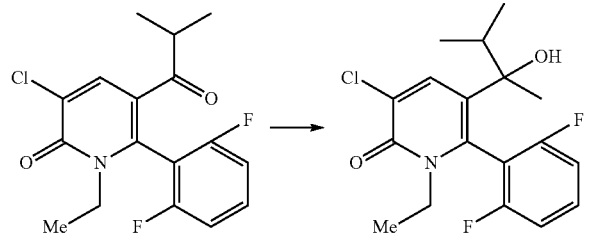 [SMILES: CCn1c(-c2c(F)cccc2F)c(C(=O)C(C)C)cc(Cl)c1=O ; CCn1c(-c2c(F)cccc2F)c(C(C)(O)C(C)C)cc(Cl)c1=O]

The diethyl ether solution (4.73 ml) of methyllithium (1.1 mol/L) was added dropwise to the THF solution (20 ml) containing 883 mg of 3-chloro-6-(2,6-difluorophenyl)-1-ethyl-5-isobutyrylpyridin-2(1H)-one at −78° C., and the mixture was stirred for 20 minutes. The reaction solution was separated by adding saturated aqueous ammonium chloride solution and ethyl acetate. The organic layer thus obtained was washed with saturated brine and was dried over sodium sulfate. The solvent was distilled under reduced pressure, and the residue was purified by silica gel column chromatography. The title compound was obtained as a white solid (530 mg).

Synthetic Example 32

Synthesis of 3-chloro-6-(2,6-difluorophenyl)-1-ethyl-5-(2-methoxy-3-methylbutan-2-yl)pyridin-2(1H)-one (Compound No. 187)

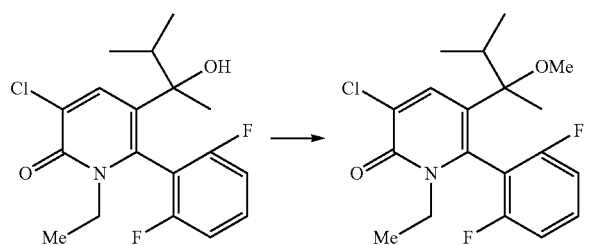 [SMILES: CCn1c(-c2c(F)cccc2F)c(C(C)(O)C(C)C)cc(Cl)c1=O ; CCn1c(-c2c(F)cccc2F)c(C(C)(OC)C(C)C)cc(Cl)c1=O]

The nitromethane solution (3 ml) containing 120 mg of 3-chloro-6-(2,6-difluorophenyl)-1-ethyl-5-(2-hydroxy-3-methylbutan-2-yl)pyridin-2(1H-one, 110 μl of trimethyl orthoformate and 41 μl of methanol was added under ice cooling 3 μl of trifluoromethanesulfonic acid. The mixture was brought to room temperature and was stirred for 30 minutes. The reaction mixture was separated by adding saturated aqueous sodium hydrogen carbonate solution and ethyl acetate. The organic layer thus obtained was washed with saturated brine and was dried over sodium sulfate. The solvent was distilled under reduced pressure, and the residue was purified by silica gel column chromatography. The title compound was obtained as a colorless transparent oil (125 mg).

Synthetic Example 33

Synthesis of 3-chloro-6-(2-chloro-4-fluorophenyl)-1-ethyl-5-(2-methyl-1-propenyl)pyridin-2(1H)-one (Compound No. 300)

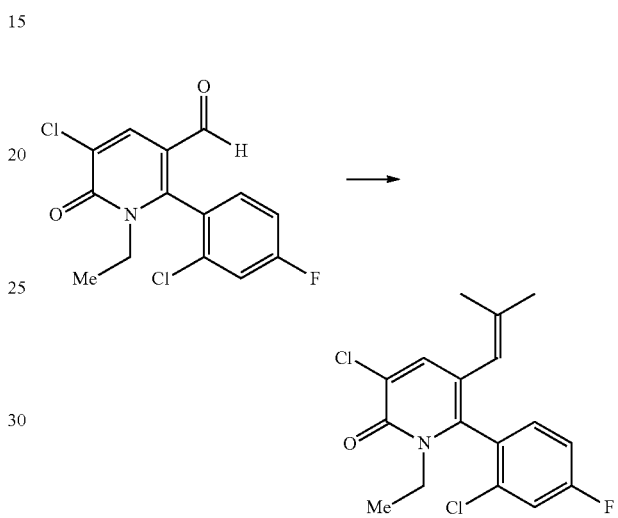

The THF solution (3 ml) containing 322 mg of isopropyltriphenylphosphonium iodide was added under ice cooling 86 mg of potassium t-butoxide, and the mixture was stirred for 1 hour. Next, 80 mg of 5-chloro-2-(2-chloro-4-fluorophenyl)-1-ethyl-6-oxo-1,6-dihydropyridine-3-carbaldehyde, which was obtained in the same manner as 5-chloro-2-(2,6-difluorophenyl)-1-ethyl-6-oxo-1,6-dihydropyridine-3-carbaldehyde (Compound No. 20) described in Synthetic Example 10 was added. The mixture was brought to room temperature and was stirred for 2.5 hours. The reaction solution was separated by adding saturated aqueous ammonium chloride solution and ethyl acetate. The organic layer thus obtained was washed with saturated brine and was dried over magnesium sulfate. The solvent was distilled under reduced pressure, and the residue was purified by silica gel column chromatography. The title compound was obtained as a white solid (54 mg).

Synthetic Example 34

Synthesis of 3-chloro-1-ethyl-5-(hydroxymethyl)-6-(2,4,6-trifluorophenyl)pyridin-2(1H)-one

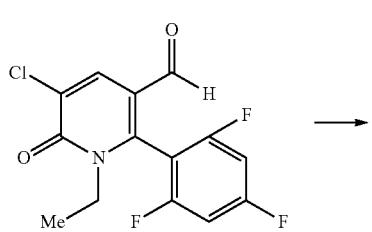

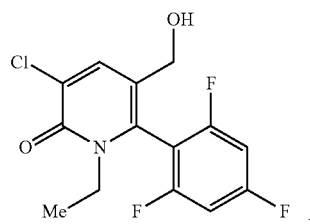

The methanol solution (5 ml) containing 500 mg of 5-chloro-1-ethyl-6-oxo-2-(2,4,6-trifluorophenyl)-1,6-dihydropyridine-3-carbaldehyde was added under ice cooling 0.18 g of sodium borohydride, and the mixture was stirred for 30 minutes. The reaction mixture was separated by adding 1 N hydrochloric acid and ethyl acetate. The organic layer thus obtained was washed with saturated brine and was dried over sodium sulfate. The solvent was distilled under reduced pressure, and the residue was purified by silica gel column chromatography. The title compound was obtained as a light yellow substance (468 mg).

$^1$H-NMR (CDCl$_3$) δ: 7.77 (1H, s), 6.89-6.87 (2H, m), 4.12 (2H, d, J=5.9 Hz), 3.87 (2H, q, J=7.1 Hz), 1.57 (1H, t, J=5.9 Hz), 1.14 (3H, t, J=7.1 Hz).

Synthetic Example 35

Synthesis of 5-(bromomethyl)-3-chloro-1-ethyl-6-(2,4,6-trifluorophenyl)pyridin-2(1H)-one

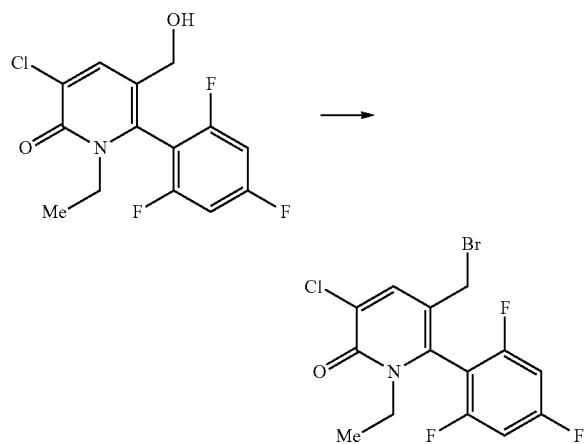

The methylene chloride solution (10 ml) containing 286 mg of 3-chloro-1-ethyl-5-(hydroxymethyl)-6-(2,4,6-trifluorophenyl)pyridin-2(1H)-one, 448 mg of carbon tetrabromide and 354 mg of triphenylphosphine was stirred at room temperature for 3 hours. The reaction mixture was separated by adding water. The organic layer thus obtained was dried over sodium sulfate. The solvent was distilled under reduced pressure, and the residue was purified by silica gel column chromatography. The title compound was obtained as a white solid (411 mg).

$^1$H-NMR (CDCl$_3$) δ: 7.67 (1H, s), 6.93-6.90 (3H, m), 3.95 (2H, s), 3.86 (2H, q, J=7.1 Hz), 1.15 (3H, t, J=7.1 Hz).

Synthetic Example 36

Synthesis of 3-chloro-1-ethyl-5-((methoxy(methyl)amino)methyl)-6-(2,4,6-trifluorophenyl)pyridin-2(1H)-one (Compound No. 89)

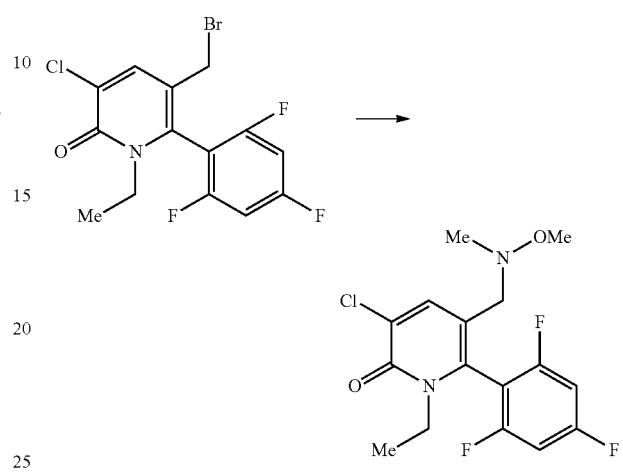

DMF (3 ml) containing 100 mg of 5-(bromomethyl)-3-chloro-1-ethyl-6-(2,4,6-trifluorophenyl)pyridin-2(1H)-one, 39 mg of N,O-dimethylhydroxylamine hydrochloride and 67 μl of diisopropylethylamine was stirred at 80° C. for 2 hours. Further, 193 mg of N,O-dimethylhydroxylamine hydrochloride and 340 μl of diisopropylethylamine were added, and the mixture was stirred at 80° C. for 3 hours. The reaction mixture was cooled to room temperature, before separated by adding water and ethyl acetate. The organic layer thus obtained was washed with saturated brine and was dried over sodium sulfate. The solvent was distilled under reduced pressure, and the residue was purified by silica gel column chromatography. The title compound was obtained as a colorless transparent oil (56 mg).

Synthetic Example 37

Synthesis of 3-chloro-6-(4-ethoxy-2,6-difluorophenyl)-1-ethyl-5-((methoxy(methyl)amino)methyl)pyridin-2(1H)-one (Compound No. 93)

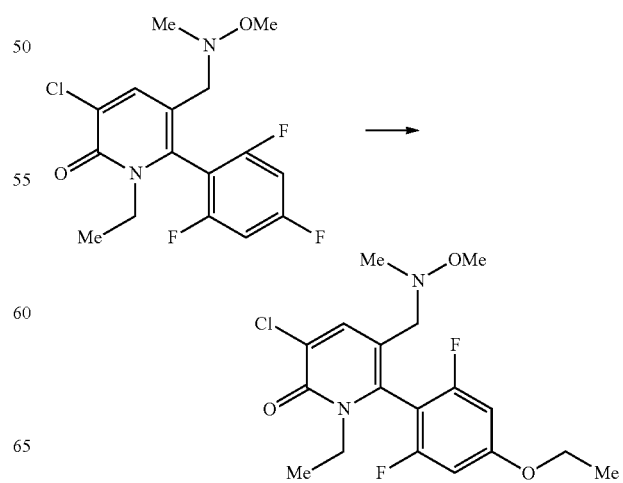

The ethanol solution (3 ml) containing 70 mg of 3-chloro-1-ethyl-5-((methoxy(methyl)amino)methyl)-6-(2,4,6-trifluorophenyl)pyridin-2(1H)-one was added 0.3 ml of sodium ethoxide (20%, in ethanol), and the mixture was stirred at 60° C. for 12 hours. The reaction mixture was cooled to room temperature, before separated by adding water and ethyl acetate. The organic layer thus obtained was washed with saturated brine and was dried over sodium sulfate. The solvent was distilled under reduced pressure, and the residue was purified by silica gel column chromatography. The title compound was obtained as a light yellow solid (67 mg).

Reference Example 1

Synthesis of
3-methyl-1-(2,4,6-trifluorophenyl)butan-1-one

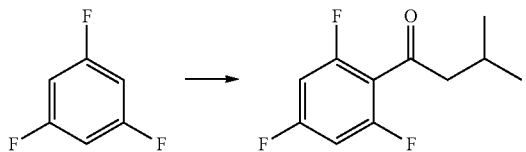

The THF solution (20 ml) containing 2.0 g of 1,3,5-trifluorobenzene was cooled to −78° C., and the hexane solution (5.71 ml) of n-butyllithium (2.65 mol/L) was added dropwise. The mixture was stirred for 1 hour. The THF solution (40 ml) containing 2.06 g of zinc chloride was added dropwise to the reaction liquid at a temperature of not more than −55° C. After the mixture was brought to −10° C., 150 mg of copper (I) chloride and 2.03 ml of isovaleryl chloride were added. The mixture was brought to room temperature and was stirred overnight. The reaction mixture was washed sequentially with 1 N hydrochloric acid, aqueous sodium hydrogen carbonate solution containing ammonia, and saturated brine, and was dried over sodium sulfate. The solvent was distilled under reduced pressure, and the residue was purified by silica gel column chromatography. The title compound was obtained as a transparent oil (3.11 g).

$^1$H-NMR (CDCl$_3$) δ: 6.72-6.68 (2H, m), 2.72 (2H, d, J=7.0 Hz), 2.24-2.23 (1H, m), 0.98 (6H, d, J=6.7 Hz).

Reference Example 2

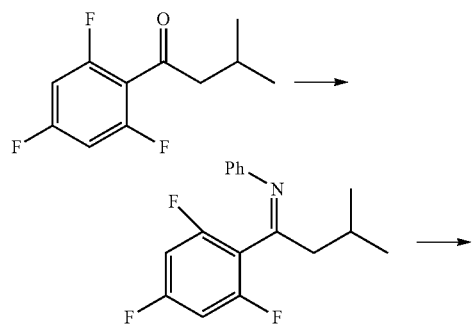

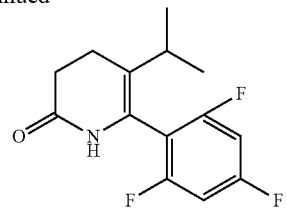

Step 1: Synthesis of 3-methyl-N-phenyl-1-(2,4,6-trifluorophenyl)butane-1-imine

The methylene chloride solution (80 ml) containing 2.00 g of aniline and 3.98 ml of trimethylamine was added dropwise under ice cooling 2.35 ml of titanium tetrachloride. The methylene chloride solution (20 ml) containing 3.09 g of 3-methyl-1-(2,4,6-trifluorophenyl)butan-1-one was added dropwise to the reaction liquid. The mixture under ice cooling was then brought to room temperature, and was stirred for 3 hours. The reaction mixture was separated by adding water. The target layer was dried over sodium sulfate. The solvent was distilled under reduced pressure, and the residue was purified by silica gel column chromatography to obtain an orange oil (3.94 g) comprising the title compound. This product was used for the next reaction without further purification.

Step 2: Synthesis of 5-isopropyl-6-(2,4,6-trifluorophenyl)-3,4-dihydropyridin-2(1H)-one The dioxane solution (50 ml) containing 3.94 g of 3-methyl-N-phenyl-1-(2,4,6-trifluorophenyl)butane-1-imine obtained in Step 1 and 1.80 g of aluminum chloride was added 0.96 g of acrylamide monomer, and the mixture was stirred at 90° C. for 8 hours. The reaction mixture was cooled to room temperature, and was separated by adding 1 N hydrochloric acid and ethyl acetate. The organic layer thus obtained was washed with saturated brine and was dried over sodium sulfate. The solvent was distilled under reduced pressure, and the residue was purified by silica gel column chromatography. The title compound was obtained as a light brown solid (1.05 g).

$^1$H-NMR (CDCl$_3$) δ: 6.75-6.72 (2H, m), 6.42 (1H, br s), 2.55-2.53 (2H, m), 2.43-2.39 (2H, m), 2.25-2.24 (1H, m), 0.97 (6H, d, J=7.0 Hz).

Reference Example 3

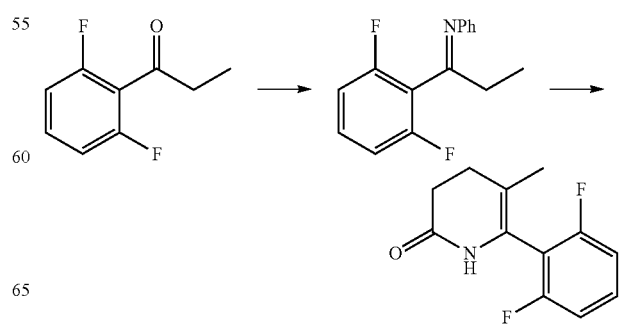

Step 1: Synthesis of 1-(2,6-difluorophenyl)-N-phenylpropane-1-imine

The methylene chloride solution (100 ml) containing 11.74 g of aniline and 17.01 g of trimethylamine was added dropwise under ice cooling the methylene chloride solution (50 ml) containing 23.91 g of titanium tetrachloride. The methylene chloride solution (30 ml) containing 14.30 g of 1-(2,6-difluorophenyl)propan-1-one was added dropwise to the reaction liquid. The mixture under ice cooling was brought to room temperature and was stirred overnight. The reaction mixture was separated by adding 1 N hydrochloric acid. The target layer was dried over sodium sulfate. The mixture was distilled under reduced pressure to remove the solvent, to obtain a dark green oil (21.10 g) comprising the title compound. This product was used for the next reaction without further purification.

Step 2: Synthesis of 6-(2,6-difluorophenyl)-5-methyl-3,4-dihydropyridin-2(1H)-one The dioxane solution (200 ml) containing 21.10 g of 1-(2,6-difluorophenyl)-N-phenylpropane-1-imine obtained in Step 1 and 12.33 g of aluminum chloride was added 6.57 g of acrylamide monomer, and the mixture was stirred at 90° C. for 3 hours. The volume of the reaction mixture was approximately halved by distilling the solvent under reduced pressure. 1 N hydrochloric acid and ethyl acetate were added, and the resultant liquid mixture was separated. The organic layer thus obtained was washed with saturated brine and was dried over sodium sulfate. The solvent was distilled under reduced pressure, and the residue was purified by silica gel column chromatography. The solid thus obtained was washed with isopropyl ether. The title compound was obtained as a white solid (11.65 g).

$^1$H-NMR (CDCl$_3$) δ: 7.36-7.34 (1H, m), 6.97-6.94 (2H, m), 6.52 (1H, br s), 2.61-2.59 (2H, m), 2.48-2.47 (2H, m), 1.63 (3H, s).

Reference Example 4

Synthesis of 2-chloro-4-fluoro-N-methoxy-N-methylbenzamide

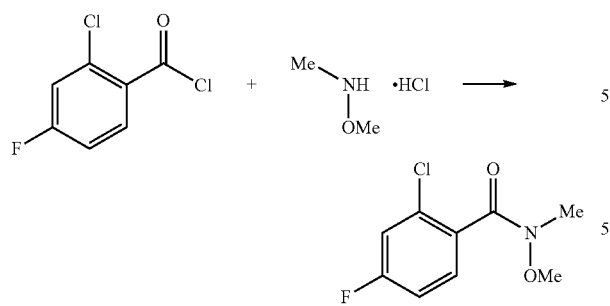

The dichloromethane solution (50 ml) containing 2.53 g of N-methoxy-N-methylamine hydrochloride and 7.22 ml of trimethylamine was added under ice cooling 5.00 g of 2-chloro-4-fluorobenzoyl chloride. The mixture was brought to room temperature and was stirred for 3 hours. The reaction mixture was separated by adding saturated aqueous sodium hydrogen carbonate solution and ethyl acetate. The organic layer thus obtained was washed sequentially with 1 N hydrochloric acid and saturated brine, and was dried over magnesium sulfate. The mixture was distilled under reduced pressure to remove the solvent, to obtain the title compound (5.45 g). The product was used for the next reaction without further purification.

$^1$H-NMR (CDCl$_3$) δ: 7.34 (1H, dd, J=8.5, 6.0 Hz), 7.17 (1H, dd, J=8.5, 2.4 Hz), 7.04 (1H, td, J=8.3, 2.4 Hz), 3.95-3.06 (6H, m).

Reference Example 5

Synthesis of 1-(2-chloro-4-fluorophenyl)-4-methylpentan-1-one

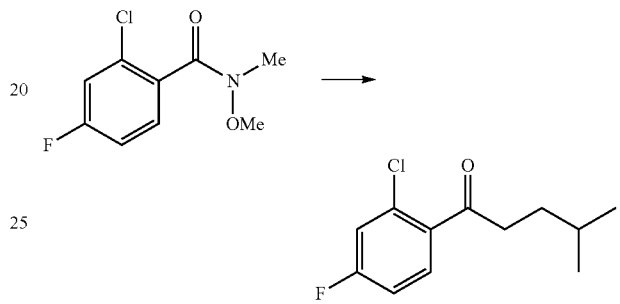

The THF solution (50 ml) containing 5.45 g of 2-chloro-4-fluoro-N-methoxy-N-methylbenzamide obtained in Reference Example 4 was added dropwise under ice cooling the diethyl ether solution (25.1 ml) of isobutylmagnesium bromide (2.0 mol/L). The mixture was brought to room temperature and was stirred for 5 hours. The reaction solution was separated by adding saturated aqueous ammonium chloride solution and ethyl acetate. The organic layer thus obtained was washed with saturated brine and was dried over magnesium sulfate. The mixture was distilled under reduced pressure to remove the solvent, to obtain the title compound as a yellow oil (5.87 g). The oil, comprising ethyl acetate used in the purification, was directly used for the next reaction.

$^1$H-NMR (CDCl$_3$) δ: 7.51 (1H, dd, J=8.5, 6.0 Hz), 7.16 (1H, dd, J=8.5, 2.4 Hz), 7.04 (1H, ddd, J=8.5, 7.8, 2.4 Hz), 2.95-2.90 (2H, m), 1.65-1.56 (3H, m), 0.92 (6H, d, J=6.3 Hz).

Reference Example 6

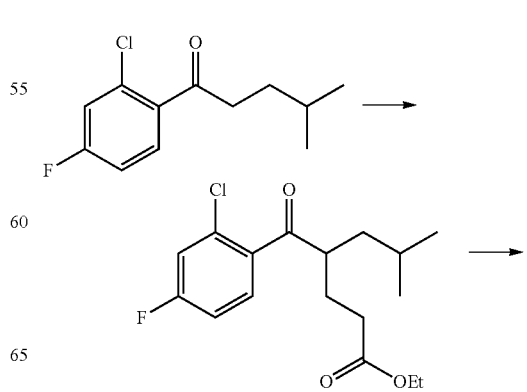

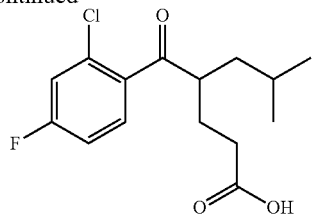

Step 1: Synthesis of ethyl 4-(2-chloro-4-fluorobenzoyl)-6-methylheptanoate

The THF solution (90 ml) containing 5.87 g of 1-(2-chloro-4-fluorophenyl)-4-methylpentan-1-one obtained in Reference Example 5 were added 563 mg of potassium t-butoxide and 2.87 ml of ethyl acrylate, and the mixture was stirred for 20 minutes under ice cooling. 1 N hydrochloric acid and ethyl acetate were added, and the resultant liquid mixture was separated. The organic layer thus obtained was washed with saturated brine and was dried over magnesium sulfate. The mixture was distilled under reduced pressure to remove the solvent, to obtain a residue comprising the title compound. This product was used for the next reaction without further purification.

Step 2: Synthesis of 4-(2-chloro-4-fluorobenzoyl)-6-methylheptanoic acid

The residue, comprising ethyl 4-(2-chloro-4-fluorobenzoyl)-6-methylheptanoate, obtained in Step 1 were added 80 ml of THF and 40 ml of water. Thereafter, 5.25 g of lithium hydroxide monohydrate was added, and the mixture was stirred at 60° C. for 1.5 hours. The reaction mixture was cooled to room temperature and was distilled under reduced pressure to remove THF. Diethyl ether was added to the residue, and the resultant liquid mixture was separated. The aqueous layer was separated by adding 12 N hydrochloric acid and ethyl acetate. The organic layer thus obtained was washed with saturated brine and was dried over magnesium sulfate. The mixture was distilled under reduced pressure to remove the solvent, to obtain the title compound as a white solid (6.26 g).

$^1$H-NMR (CDCl$_3$) δ: 7.47 (1H, dd, J=8.6, 5.8 Hz), 7.17 (1H, dd, J=8.6, 2.4 Hz), 7.07-7.03 (1H, m), 3.47-3.42 (1H, m), 2.48 (1H, ddd, J=16.7, 8.7, 6.0 Hz), 2.39 (1H, ddd, J=16.7, 8.3, 7.0 Hz), 2.11-2.00 (1H, m), 1.90-1.81 (1H, m), 1.67-1.59 (1H, m), 1.57-1.51 (1H, m), 1.33-1.25 (1H, m), 0.86 (6H, d, J=6.4 Hz).

Reference Example 7

Synthesis of 6-(2-chloro-4-fluorophenyl)-5-isobutyl-3,4-dihydropyridin-2(1H)-one

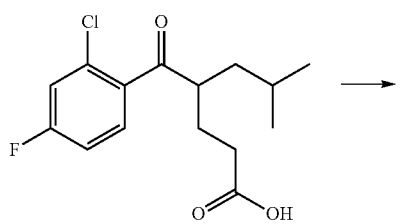

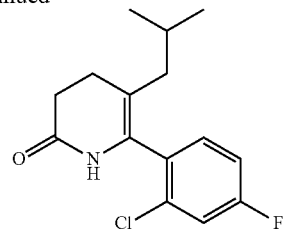

The acetic acid solution (32 ml) containing 6.26 g of 4-(2-chloro-4-fluorobenzoyl)-6-methylheptanoic acid and 96.00 g of ammonium acetate was stirred at 100° C. for 5 hours. The reaction mixture was cooled to room temperature, before separated by adding ethyl acetate and water. Water was added to the organic layer. Potassium carbonate was added until bubbling was stopped, and the liquid mixture was separated. Next, the organic layer was washed with saturated brine and was dried over sodium sulfate. The solvent was distilled under reduced pressure, and the precipitate was washed with diisopropyl ether. The obtained white solid (1.80 g) was identified to be the title compound. Further, the isopropyl ether used for the washing was removed by distillation under reduced pressure, and the residue was purified by silica gel column chromatography. The obtained light yellow solid (1.48 g) was also identified to be the title compound.

$^1$H-NMR (CDCl$_3$) δ: 7.25-7.18 (2H, m), 7.04-7.00 (1H, m), 6.48 (1H, br s), 2.59-2.54 (2H, m), 2.44-2.39 (2H, m), 1.88-1.81 (1H, m), 1.78-1.65 (2H, m), 0.78 (6H, d, J=6.3 Hz).

Reference Example 8

Synthesis of N-phenyl-1-(2,4,6-trifluorophenyl)propane-1-imine

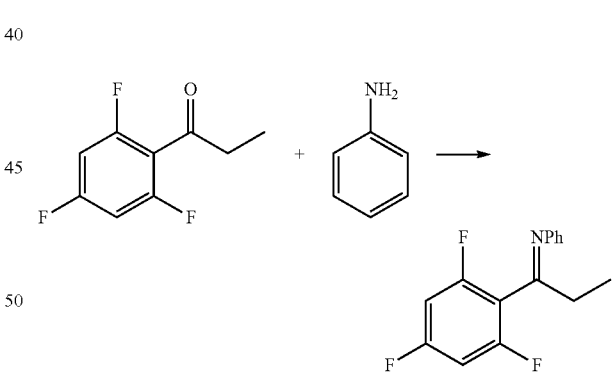

The dichloromethane solution (15 ml) containing 4.37 ml of titanium tetrachloride was added dropwise to the dichloromethane solution (30 ml) containing 3.64 ml of aniline and 7.41 ml of triethylamine at 0° C., and the mixture was stirred for 15 minutes. The dichloromethane solution (10 ml) containing 5.00 g of 1-(2,4,6-trifluorophenyl)propan-1-one was added at 0° C. The mixture was stirred at room temperature for 3.5 hours. The reaction mixture was separated by adding 1 N hydrochloric acid and dichloromethane. The organic layer thus obtained was washed with water and was dried over sodium sulfate. The mixture was distilled under reduced pressure to remove the solvent, to obtain a yellow oil (7.08 g) comprising the title compound.

¹H-NMR (CDCl₃) δ: 7.16-7.11 (2H, m), 6.96-6.92 (1H, m), 6.69-6.67 (2H, m), 6.52-6.49 (2H, m), 2.73 (2H, q, J=7.4 Hz), 1.25 (3H, t, J=7.4 Hz).

Reference Example 9

Synthesis of 5-methyl-6-(2,4,6-trifluorophenyl)-3,4-dihydropyridin-2(1H)-one

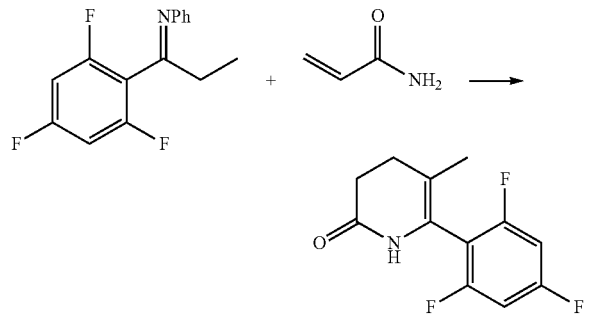

1,4-dioxane (70 ml) containing 7.08 g of N-phenyl-1-(2,4,6-trifluorophenyl)propane-1-imine obtained in Reference Example 8 were added 3.90 g of aluminum chloride and 2.08 g of acrylamide, and the mixture was stirred at 90° C. for 5 hours. The mixture was cooled to room temperature, before separated by adding 1 N hydrochloric acid and ethyl acetate. The organic layer thus obtained was washed with saturated brine and was dried over sodium sulfate. The solvent was distilled under reduced pressure, and the residue was purified by silica gel column chromatography. The title compound was obtained as a white solid (3.86 g).

¹H-NMR (CDCl₃) δ: 6.76-6.72 (2H, m), 6.58 (1H, s), 2.60-2.57 (2H, m), 2.47-2.45 (2H, m), 1.61 (3H, s).

Table 3 lists the compounds synthesized in accordance with Examples described hereinabove. The present invention are not limited thereto.

In Table 3, Structure A is as follows:

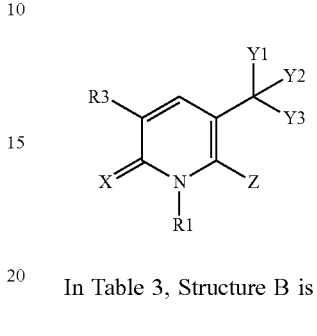

In Table 3, Structure B is as follows:

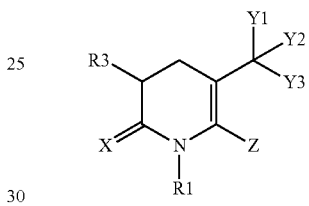

TABLE 3

| Compounds | Z | Y1 | Y2 | Y3 | R1 | R3 | X | Structures |
|---|---|---|---|---|---|---|---|---|
| 1 | 2,6-di-F—Ph | H | H | H | Et | H | O | A |
| 2 | 2,6-di-F—Ph | H | H | H | Et | Cl | O | A |
| 3 | 2,6-di-F—Ph | H | H | H | Me | H | O | A |
| 4 | 2,6-di-F—Ph | H | H | H | Me | Cl | O | A |
| 5 | 2,6-di-F—Ph | Me | Me | H | Et | H | O | A |
| 6 | 2,6-di-F—Ph | Me | Me | H | Et | Cl | O | A |
| 7 | 2,4,6-tri-F—Ph | Me | Me | H | Et | H | O | A |
| 8 | 2,4,6-tri-F—Ph | Me | Me | H | Et | Cl | O | A |
| 9 | 2,4,6-tri-F—Ph | Me | Me | H | Et | Br | O | A |
| 10 | 2,6-di-F-4-MeO—Ph | Me | Me | H | Et | H | O | A |
| 11 | 2,6-di-F-4-MeO—Ph | Me | Me | H | Et | Cl | O | A |
| 12 | 2,6-di-F-4-MeO—Ph | Me | Me | H | Et | Br | O | A |
| 13 | 2,4,6-tri-F—Ph | Me | Me | H | Me | H | O | A |
| 14 | 2,6-di-F-4-MeO—Ph | Me | Me | H | Me | H | O | A |
| 15 | 2,4,6-tri-F—Ph | Me | Me | H | Me | Cl | O | A |
| 16 | 2,6-di-F-4-MeO—Ph | Me | Me | H | Me | Cl | O | A |
| 17 | 2,6-di-F—Ph | Me | HO | H | Et | Cl | O | A |
| 18 | 2,6-di-F—Ph | Me | MeO | H | Et | Cl | O | A |
| 19 | 2,6-di-F—Ph | Me | EtO | H | Et | Cl | O | A |
| 20 | 2,6-di-F—Ph | O= | | H | Et | Cl | O | A |
| 21 | 2,6-di-F—Ph | Br | Br | H | Et | Cl | O | A |
| 22 | 2,6-di-F—Ph | O= | | Me | Et | Cl | O | A |
| 23 | 2,6-di-F—Ph | Me | Me | HO | Et | Cl | O | A |
| 24 | 2,6-di-F—Ph | Et | HO | H | Et | Cl | O | A |
| 25 | 2,6-di-F—Ph | Et | MeO | H | Et | Cl | O | A |
| 26 | 2,6-di-F—Ph | O= | | Et | Et | Cl | O | A |
| 27 | 2,6-di-F—Ph | Et | Me | HO | Et | Cl | O | A |
| 28 | 2,6-di-F—Ph | MeCH= | | Me | Et | Cl | O | A |
|  | 2,6-di-F—Ph | H2C=Me | | Et | Et | Cl | O | A |
| 29 | 2,6-di-F—Ph | Et | Me | MeO | Et | Cl | O | A |
| 30 | 2,6-di-F—Ph | Et | Me | F | Et | Cl | O | A |
| 31 | 2,4,6-tri-F—Ph | Et | Me | H | Et | H | O | A |
| 32 | 2,4,6-tri-F—Ph | Et | Me | H | Et | Br | O | A |
| 33 | 2,4,6-tri-F—Ph | Et | Me | H | Et | Cl | O | A |
| 34 | 2,6-di-F-4-MeO—Ph | Et | Me | H | Et | H | O | A |
| 35 | 2,6-di-F-4-MeO—Ph | Et | Me | H | Et | Cl | O | A |
| 36 | 2,6-di-F-4-MeO—Ph | Et | Me | H | Et | Br | O | B |
| 37 | 2,4,6-tri-F—Ph | iPr | H | H | Et | H | O | A |

TABLE 3-continued

| Compounds | Z | Y1 | Y2 | Y3 | R1 | R3 | X | Structures |
|---|---|---|---|---|---|---|---|---|
| 38 | 2,4,6-tri-F—Ph | iPr | H | H | Et | H | O | A |
| 39 | 2,6-di-F-4-MeO—Ph | iPr | H | H | Et | H | O | A |
| 40 | 2,4,6-tri-F—Ph | iPr | H | H | Et | Br | O | A |
| 41 | 2,4,6-tri-F—Ph | iPr | H | H | Et | Cl | O | A |
| 42 | 2,6-di-F-4-MeO—Ph | iPr | H | H | Et | Cl | O | A |
| 43 | 2,6-di-F-4-MeO—Ph | iPr | H | H | Et | Br | O | A |
| 44 | 2,6-di-F—Ph | HO | H | H | Et | Cl | O | A |
| 45 | 2,6-di-F—Ph | MeO | H | H | Et | Cl | O | A |
| 46 | 2,4,6-tri-F—Ph | Et | HO | H | Et | Cl | O | A |
| 47 | 2,4,6-tri-F—Ph | Et | MeO | H | Et | Cl | O | A |
| 48 | 2,6-di-F-4-MeO—Ph | Et | MeO | H | Et | Cl | O | A |
| 49 | 2,4,6-tri-F—Ph | O= | | Et | Et | Cl | O | A |
| 50 | 2,6-di-F-4-MeO—Ph | Et | HO | H | Et | Cl | O | A |
| 51 | 2,6-di-F-4-MeO—Ph | O= | | Et | Et | Cl | O | A |
| 52 | 2,4,6-tri-F—Ph | Et | Me | HO | Et | Cl | O | A |
| 53 | 2,6-di-F—Ph | iPr | HO | H | Et | Cl | O | A |
| 54 | 2,4,6-tri-F—Ph | Et | Me | MeO | Et | Cl | O | A |
| 55 | 2,6-di-F-4-MeO—Ph | Et | Me | MeO | Et | Cl | O | A |
| 56 | 2,4,6-tri-F—Ph | Et | Me | F | Et | Cl | O | A |
| 57 | 2,6-di-F—Ph | iPrO | H | H | Et | Cl | O | A |
| 58 | 2,4,6-tri-F—Ph | iPrO | H | H | Et | Cl | O | A |
| 59 | 2,6-di-F-4-MeO—Ph | Et | Mr | HO | Et | Cl | O | A |
| 60 | 2,6-di-F-4-MeO—Ph | iPrO | H | H | Et | Cl | O | A |
| 61 | 2,6-di-F-4-MeO—Ph | Et | Me | F | Et | Cl | O | A |
| 62 | 2,6-di-F—Ph | EtO | H | H | Et | Cl | O | A |
| 63 | 2,6-di-F—Ph | iPr | MeO | H | Et | Cl | O | A |
| 64 | 2,4,6-tri-F—Ph | iPr | HO | H | Et | Cl | O | A |
| 65 | 2,4,6-tri-F—Ph | iPr | MeO | H | Et | Cl | O | A |
| 66 | 2,4,6-tri-F—Ph | O= | | iPr | Et | Cl | O | A |
| 67 | 2,4,6-tri-F—Ph | Me | Me | Me | Et | H | O | A |
| 68 | 2,4,6-tri-F—Ph | Me | Me | Me | Me | H | O | A |
| 69 | 2,4,6-tri-F—Ph | Me | Me | Me | Et | Cl | O | A |
| 70 | 2,4,6-tri-F—Ph | Me | Me | Me | Et | Br | O | A |
| 71 | 2,6-di-F-4-MeO—Ph | iPr | MeO | H | Et | Cl | O | A |
| 72 | 2,6-di-F-4-EtO—Ph | iPr | MeO | H | Et | Cl | O | A |
| 73 | 2,6-di-F-4-MeO—Ph | O= | | iPr | Et | Cl | O | A |
| 74 | 2,6-di-F-4-MeO—Ph | Me | Me | Me | Et | Cl | O | A |
| 75 | 2,6-di-F-4-EtO—Ph | Me | Me | Me | Et | Cl | O | A |
| 76 | 2,6-di-F-4-MeO—Ph | Me | Me | Me | Et | Br | O | A |
| 77 | 2,4,6-tri-F—Ph | Me | Me | Me | Me | Cl | O | A |
| 78 | 2,4,6-tri-F—Ph | Me | Me | Me | Me | Br | O | A |
| 79 | 2,6-di-F-4-MeO—Ph | Me | Me | Me | Me | Cl | O | A |
| 80 | 2,6-di-F—Ph | iPr(Me)N— | H | H | Et | Cl | O | A |
| 81 | 2,4,6-tri-F—Ph | iPr(Me)N— | MeO | H | Et | Cl | O | A |
| 82 | 2,6-di-F-4-MeO—Ph | Me | Me | Me | Me | Br | O | A |
| 83 | 2,6-di-F-4-MeOCH2CH2O—Ph | Me | Me | Me | Et | Cl | O | A |
| 84 | 2,6-di-F-4-MeOCH2CH2O—Ph | Me | Me | Me | Me | Cl | O | A |
| 85 | 2,6-di-F-4-MeO—Ph | Me | Me | Me | Me | Cl | O | A |
| 86 | 2,4,6-tri-F—Ph | iPr(Me)N— | H | H | Et | Cl | O | A |
| 87 | 2,6-di-F-4-MeO—Ph | iBu | MeO | H | Et | Cl | O | A |
| 88 | 2,6-di-F-4-MeO—Ph | iPr(Me)N— | H | H | Et | Cl | O | A |
| 89 | 2,4,6-tri-F—Ph | Me(MeO)N— | H | H | Et | Cl | O | A |
| 90 | 2,4,6-tri-F—Ph | iBu | HO | H | Et | Cl | O | A |
| 91 | 2,4,6-tri-F—Ph | Me2N— | H | H | Et | Cl | O | A |
| 92 | 2,6-di-F-4-MeO—Ph | Me2N— | H | H | Et | Cl | O | A |
| 93 | 2,6-di-F-4-EtO—Ph | Me(MeO)N— | H | H | Et | Cl | O | A |
| 94 | 2,6-di-F-4-MeO—Ph | Me(MeO)N— | H | H | Et | Cl | O | A |
| 95 | 2-F-6-MeO—Ph | iPr | H | H | Et | H | O | A |
| 96 | 2-F-6-MeO—Ph | iPr | H | H | Et | Br | O | A |
| 97 | 2-F-6-MeO—Ph | iPr | H | H | Et | Cl | O | A |
| 98 | 2-Cl-4-F—Ph | iPr | H | H | Et | H | O | A |
| 99 | 2-Cl-4-F—Ph | iPr | H | H | Et | Cl | O | A |
| 100 | 2-Cl-4-F—Ph | iPr | H | H | Et | Br | O | A |
| 101 | 2-F-6-HO—Ph | iPr | H | H | Et | Cl | O | A |
| 102 | 2-F-6-HC≡CCH2O—Ph | iPr | H | H | Et | Cl | O | A |
| 103 | 2-F-6-MeOCH2O—Ph | iPr | H | H | Et | Cl | O | A |
| 104 | 2-F-6-H2C=CHCH2O—Ph | iPr | H | H | Et | Cl | O | A |
| 105 | 2-F-6-MeSCH2O—Ph | iPr | H | H | Et | Cl | O | A |
| 106 | 2,4,6-tri-F—Ph | iPr | Me | HO | Et | Cl | O | A |
| 107 | 2,4,6-tri-F—Ph | iPr | Me | MeO | Et | Cl | O | A |
| 108 | 2,6-di-F-4-MeO—Ph | iPr | Me | HO | Et | Cl | O | A |
| 109 | 2,4,6-tri-F—Ph | Me | Me | MeO | Et | Cl | O | A |
| 110 | 2,6-di-F-4-MeO—Ph | iPr | Me | MeO | Et | Cl | O | A |
| 111 | 2-F-4-MeO—Ph | iPr | H | H | Et | H | O | A |
| 112 | 2,4,6-tri-F—Ph | MeONH— | H | H | Et | Cl | O | A |
| 113 | 2,6-di-F-4-MeO—Ph | Me | Me | MeO | Et | Cl | O | A |
| 114 | 2,6-di-F-4-MeO—Ph | MeONH— | H | H | Et | Cl | O | A |
| 115 | 2-F-4-MeO—Ph | iPr | H | H | Et | Cl | O | A |

TABLE 3-continued

| Compounds | Z | Y1 | Y2 | Y3 | R1 | R3 | X | Structures |
|---|---|---|---|---|---|---|---|---|
| 116 | 2-F-4-MeO—Ph | iPr | H | H | Et | Br | O | A |
| 117 | 2,4-di-F—Ph | iPr | H | H | Et | H | O | A |
| 118 | 2-F-4-HO—Ph | iPr | H | H | Et | Cl | O | A |
| 119 | 2,4-di-F—Ph | iPr | H | H | Et | Cl | O | A |
| 120 | 2,4-di-F—Ph | iPr | H | H | Et | Br | O | A |
| 121 | 2-F-4-MeOCH2CH2O—Ph | iPr | H | H | Et | Cl | O | A |
| 122 | 2-F-4-MeOCH2O—Ph | iPr | H | H | Et | Cl | O | A |
| 123 | 2-F-4-EtO—Ph | iPr | H | H | Et | Cl | O | A |
| 124 | 2-F-4-H2C=CHCH2O—Ph | iPr | H | H | Et | Cl | O | A |
| 125 | 2-F-4-HC≡CCH2O—Ph | iPr | H | H | Et | Cl | O | A |
| 126 | 2-F-4-PrO—Ph | iPr | H | H | Et | Cl | O | A |
| 127 | 2-F-4-N≡CCH2O—Ph | iPr | H | H | Et | Cl | O | A |
| 128 | 2-F-4-MeSCH2O—Ph | iPr | H | H | Et | Cl | O | A |
| 129 | 2-F-4-cPrCH2O—Ph | iPr | H | H | Et | Cl | O | A |
| 130 | 2,6-di-F-4-MeO—Ph | Ac(MeO)N— | H | H | Et | Cl | O | A |
| 131 | 2,6-di-F-4-MeO—Ph | MeO(O=)C—N(OMe)— | H | H | Et | Cl | O | A |
| 132 | 2,4,6-tri-F—Ph | Ac(MeO)N— | H | H | Et | Cl | O | A |
| 133 | 2,4,6-tri-F—Ph | MeO(O=)C—N(OMe)— | H | H | Et | Cl | O | A |
| 134 | 2,4-di-Cl—Ph | iPr | H | H | Me | H | O | A |
| 135 | 2,4-di-Cl—Ph | iPr | H | H | Et | H | O | A |
| 136 | 4-Br-2-F—Ph | iPr | H | H | Et | H | O | A |
| 137 | 2,4-di-Cl—Ph | iPr | H | H | Me | Cl | O | A |
| 138 | 2,4-di-Cl—Ph | iPr | H | H | Me | Br | O | A |
| 139 | 2,4-di-Cl—Ph | iPr | H | H | Et | Cl | O | A |
| 140 | 2,4-di-Cl—Ph | iPr | H | H | Et | Br | O | A |
| 141 | 2-F-4-Me—Ph | iPr | H | H | Et | H | O | A |
| 142 | 4-Br-2-F—Ph | iPr | H | H | Et | Br | O | A |
| 143 | 4-Br-2-F—Ph | iPr | H | H | Et | Cl | O | A |
| 144 | 4-F—Ph | iPr | H | H | Et | H | O | A |
| 145 | 4-F—Ph | iPr | H | H | Me | H | O | A |
| 146 | 2-F-4-Me—Ph | iPr | H | H | Et | Cl | O | A |
| 147 | 2-F-4-Me—Ph | iPr | H | H | Et | Br | O | A |
| 148 | 4-F—Ph | iPr | H | H | Et | Br | O | A |
| 149 | 4-F—Ph | iPr | H | H | Et | Cl | O | A |
| 150 | 2,4,6-tri-F—Ph | Me | Me | HO | Et | Cl | O | A |
| 151 | 2,4,6-tri-F—Ph | Et(MeO)N— | H | H | Et | Cl | O | A |
| 152 | 2,6-di-F-4-MeO—Ph | Et(MeO)N— | H | H | Et | Cl | O | A |
| 153 | 2,6-di-F-4-MeO—Ph | iBu | Me | HO | Et | Cl | O | A |
| 154 | 2,4,6-tri-F—Ph | iBu | Me | HO | Et | Cl | O | A |
| 155 | 4-F—Ph | iPr | H | H | Me | Cl | O | A |
| 156 | 4-F—Ph | iPr | H | H | Me | Br | O | A |
| 157 | 2-F-4-Cl—Ph | iPr | H | H | Et | H | O | A |
| 158 | 2-F-4-Cl—Ph | iPr | H | H | Et | Cl | O | A |
| 159 | 2-F-4-Cl—Ph | iPr | H | H | Et | Br | O | A |
| 160 | 2,4,6-tri-F—Ph | O= | | iBu | Et | Cl | O | A |
| 161 | 2,4,6-tri-F—Ph | Me | Me | EtO | Et | Cl | O | A |
| 162 | 2,6-di-F-4-MeO—Ph | Me | Me | EtO | Et | Cl | O | A |
| 163 | 2,4,6-tri-F—Ph | tBu | HO | H | Et | Cl | O | A |
| 164 | 2,4,6-tri-F—Ph | iBu | Me | MeO | Et | Cl | O | A |
| 165 | 2,6-di-F-4-MeO—Ph | iBu | Me | MeO | Et | Cl | O | A |
| 166 | 2,4,6-tri-F—Ph | iPr | Me | F | Et | Cl | O | A |
| 167 | 2,6-di-F-4-MeO—Ph | iPr | Me | F | Et | Cl | O | A |
| 168 | 2,4,6-tri-F—Ph | tBu | MeO | H | Et | Cl | O | A |
| 169 | 2,4,6-tri-F—Ph | tBu | H | H | Et | Cl | O | A |
| 170 | 2,6-di-F-4-MeO—Ph | tBu | MeO | H | Et | Cl | O | A |
| 171 | 2,6-di-F-4-MeO—Ph | iPr | Me | H | Et | Cl | O | A |
| 172 | 2,4,6-tri-F—Ph | tBu | Cl | H | Et | Cl | O | A |
| 173 | 2,4,6-tri-F—Ph | O= | | tBu | Et | Cl | O | A |
| 174 | 2,4,6-tri-F—Ph | tBu | Me | HO | Et | Cl | O | A |
| 175 | 4-Br—Ph | iPr | H | H | Et | H | O | A |
| 176 | 2-Cl-4-F—Ph | -(CH2)5- | | H | Et | H | O | A |
| 177 | 4-Br—Ph | iPr | H | H | Et | Cl | O | A |
| 178 | 4-Br—Ph | iPr | H | H | Et | Br | O | A |
| 179 | 2,6-di-F-4-MeO—Ph | O= | | tBu | Et | Cl | O | A |
| 180 | 2,6-di-F-4-MeO—Ph | tBu | Me | HO | Et | Cl | O | A |
| 181 | 2-Cl-4-F—Ph | -(CH2)5- | | H | Et | Cl | O | A |
| 182 | 2-Cl-4-F—Ph | -(CH2)5- | | H | Et | Br | O | A |
| 183 | 2,6-di-F—Ph | iPr | Me | HO | Et | Cl | O | A |
| 184 | 2,6-di-F—Ph | iPr | Me | F | Et | Cl | O | A |
| 185 | 2-Cl-4-F—Ph | Me | H | H | Et | H | O | A |
| 186 | 2-Cl-4-F—Ph | Me | H | H | Et | Br | O | A |
| 187 | 2,6-di-F—Ph | iPr | Me | MeO | Et | Cl | O | A |
| 188 | 2,6-di-F—Ph | iPr | Me | EtO | Et | Cl | O | A |
| 189 | 2-Cl-4-F—Ph | Me | H | H | Et | Cl | O | A |
| 190 | 2-Cl-4-F—Ph | Et | H | H | Et | H | O | A |
| 191 | 2-Cl-4-F—Ph | Et | H | H | Et | Cl | O | A |
| 192 | 2-Cl-4-F—Ph | Et | H | H | Et | Br | O | A |
| 193 | 4-HO—Ph | iPr | H | H | Et | H | O | A |

TABLE 3-continued

| Compounds | Z | Y1 | Y2 | Y3 | R1 | R3 | X | Structures |
|---|---|---|---|---|---|---|---|---|
| 194 | 4-MeO—Ph | iPr | H | H | Et | H | O | A |
| 195 | 4-MeO—Ph | iPr | H | H | Et | Cl | O | A |
| 196 | 4-MeO—Ph | iPr | H | H | Et | Br | O | A |
| 197 | 2,6-di-F—Ph | CH2= | | iPr | Et | Cl | O | A |
| 198 | 2,6-di-F—Ph | iPr | Me | H | Et | Cl | O | A |
| 199 | 2-Br-4-F—Ph | iPr | H | H | Et | H | O | A |
| 200 | 2-Br-4-F—Ph | iPr | H | H | Et | Cl | O | A |
| 201 | 2-Br-4-F—Ph | iPr | H | H | Et | Br | O | A |
| 202 | 4-F-2-Me—Ph | iPr | H | H | Et | H | O | A |
| 203 | 4-F-2-Me—Ph | iPr | H | H | Et | Cl | O | A |
| 204 | 4-F-2-Me—Ph | iPr | H | H | Et | Br | O | A |
| 205 | 2-Cl-4-F—Ph | Pr | H | H | Et | H | O | A |
| 206 | 2-Cl-4-F—Ph | Pr | H | H | Et | Cl | O | A |
| 207 | 2-Cl-4-F—Ph | Pr | H | H | Et | Br | O | A |
| 208 | 2-Cl-4-F—Ph | Pr | H | H | Et | H | O | A |
| 209 | 2-Cl-4-F—Ph | Bu | H | H | Et | Cl | O | A |
| 210 | 2-Cl-4-F—Ph | Bu | H | H | Et | Br | O | A |
| 211 | 4-F—Ph | iPr | HO | H | Et | Cl | O | A |
| 212 | 4-F—Ph | O= | | iPr | Et | Cl | O | A |
| 213 | 4-F—Ph | iPr | Me | HO | Et | Cl | O | A |
| 214 | 4-F—Ph | iPr | Me | MeO | Et | Cl | O | A |
| 215 | 4-F—Ph | iPr | Me | EtO | Et | Cl | O | A |
| 216 | 4-F—Ph | iPr | Me | PrO | Et | Cl | O | A |
| 217 | 4-F—Ph | iPr | Me | F | Et | Cl | O | A |
| 218 | 2,6-di-F-4-EtO—Ph | O= | | iPr | Et | Cl | O | A |
| 219 | 2-Cl-4-F—Ph | -(CH2)4- | | H | Et | H | O | A |
| 220 | 2-Cl-4-F—Ph | -(CH2)4- | | H | Et | Cl | O | A |
| 221 | 2-Cl-4-F—Ph | -(CH2)4- | | H | Et | Br | O | A |
| 222 | 4-MeO—Ph | O= | | iPr | Et | Cl | O | A |
| 223 | 4-MeO—Ph | iPr | Me | HO | Et | Cl | O | A |
| 224 | 4-MeO—Ph | iPr | Me | MeO | Et | Cl | O | A |
| 225 | 4-Br-2-Cl—Ph | iPr | H | H | Et | H | O | A |
| 226 | 2,6-di-F-4-EtO—Ph | iPr | Me | HO | Et | Cl | O | A |
| 227 | 2,6-di-F-4-EtO—Ph | iPr | Me | MeO | Et | Cl | O | A |
| 228 | 2,4,6-tri-F—Ph | iPr | Me | EtO | Et | Cl | O | A |
| 229 | 2,4,6-tri-F—Ph | iPr | Me | PrO | Et | Cl | O | A |
| 230 | 2,4,6-tri-F—Ph | N= | | | Et | Cl | O | A |
| 231 | 2,4,6-tri-F—Ph | cPent | HO | H | Et | Cl | O | A |
| 232 | 2,4,6-tri-F—Ph | O= | | cPent | Et | Cl | O | A |
| 233 | 4-N≡C—Ph | iPr | HO | H | Et | Cl | O | A |
| 234 | 4-N≡C—Ph | O= | | iPr | Et | Cl | O | A |
| 235 | 4-N≡C—Ph | iPr | Me | HO | Et | Cl | O | A |
| 236 | 4-Br-2-Cl—Ph | iPr | H | H | Et | Cl | O | A |
| 237 | 4-Br-2-Cl—Ph | iPr | H | H | Et | Br | O | A |
| 238 | 2-Cl-4-MeO—Ph | iPr | H | H | Et | H | O | A |
| 239 | 2-Cl-4-MeO—Ph | iPr | H | H | Et | Cl | O | A |
| 240 | 2-Cl-4-MeO—Ph | iPr | H | H | Et | Br | O | A |
| 241 | 2,6-di-F-4-MeO—Ph | iPr | Me | EtO | Et | Cl | O | A |
| 242 | 2,6-di-F-4-MeO—Ph | iPr | Me | PrO | Et | Cl | O | A |
| 243 | 2,4,6-tri-F—Ph | CH2= | | iPr | Et | Cl | O | A |
| 244 | 2,4,6-tri-F—Ph | cPent | Me | HO | Et | Cl | O | A |
| 245 | 2,4,6-tri-F—Ph | cPent | Me | MeO | Et | Cl | O | A |
| 246 | 4-MeO—Ph | iPr | HO | H | Et | Cl | O | A |
| 247 | 4-MeO—Ph | iPr | Me | EtO | Et | Cl | O | A |
| 248 | 4-MeO—Ph | iPr | Me | PrO | Et | Cl | O | A |
| 249 | 4-MeO—Ph | iPr | Me | F | Et | Cl | O | A |
| 250 | 4-N≡C—Ph | iPr | Me | MeO | Et | Cl | O | A |
| 251 | 4-N≡C—Ph | iPr | Me | EtO | Et | Cl | O | A |
| 252 | 4-N≡C—Ph | iPr | Me | PrO | Et | Cl | O | A |
| 253 | 4-N≡C—Ph | iPr | Me | F | Et | Cl | O | A |
| 254 | 2-Cl-4-HO—Ph | iPr | H | H | Et | Cl | O | A |
| 255 | 2-F—Ph | iPr | H | H | Et | Cl | O | A |
| 256 | 2,4,6-tri-F—Ph | cPent | Me | EtO | Et | Cl | O | A |
| 257 | 2,4,6-tri-F—Ph | cPent | Me | PrO | Et | Cl | O | A |
| 258 | 2,4,6-tri-F—Ph | cPr | HO | H | Et | Cl | O | A |
| 259 | 2,4,6-tri-F—Ph | cPr | AcO | H | Et | Cl | O | A |
| 260 | 2,4,6-tri-F—Ph | O= | | cPr | Et | Cl | O | A |
| 261 | 2,4,6-tri-F—Ph | cPr | Me | HO | Et | Cl | O | A |
| 262 | 2-Cl—Ph | iPr | H | H | Et | H | O | A |
| 263 | 2-Et-4-F—Ph | iPr | H | H | Et | Cl | O | A |
| 264 | 2-Cl—Ph | iPr | H | H | Et | Br | O | A |
| 265 | 2-Cl—Ph | iPr | H | H | Et | Cl | O | A |
| 266 | 2-Cl-4-F—Ph | Hex | H | H | Et | H | O | A |
| 267 | 2-Cl-4-F—Ph | Oct | H | H | Et | H | O | B |
| 268 | 2-Cl-4-F—Ph | Hex | H | H | Et | Cl | O | A |
| 269 | 2-Cl-4-F—Ph | Hex | H | H | Et | Br | O | A |
| 270 | 2-Cl-4-F—Ph | Hept | H | H | Et | H | O | A |
| 271 | 2-Cl-4-F—Ph | Hept | H | H | Et | Cl | O | A |

TABLE 3-continued

| Compounds | Z | Y1 | Y2 | Y3 | R1 | R3 | X | Structures |
|---|---|---|---|---|---|---|---|---|
| 272 | 2-Cl-4-F—Ph | Hept | H | H | Et | Br | O | A |
| 273 | 2-Cl-4-F—Ph | Oct | H | H | Et | H | O | A |
| 274 | 2-Cl-4-F—Ph | Oct | H | H | Et | Cl | O | A |
| 275 | 2-Cl-4-F—Ph | Oct | H | H | Et | Br | O | A |
| 276 | 2,4,6-tri-F—Ph | Bu | HO | H | Et | Cl | O | A |
| 277 | 2,4,6-tri-F—Ph | O= | | Bu | Et | Cl | O | A |
| 278 | 2-Cl-4-F—Ph | H | H | H | Et | H | O | B |
| 279 | 2-Cl-4-F—Ph | H | H | H | Et | H | O | A |
| 280 | 2-Cl-4-F—Ph | H | H | H | Et | Cl | O | A |
| 281 | 2-Cl-4-F—Ph | H | H | H | Et | Br | O | A |
| 282 | 2-Cl-4-F—Ph | Pent | H | H | Et | H | O | B |
| 283 | 2,4,6-tri-F—Ph | HC≡C— | HO | H | Et | Cl | O | A |
| 284 | 2,4,6-tri-F—Ph | O= | | HC≡C— | Et | Cl | O | A |
| 285 | 2,4,6-tri-F—Ph | HC≡C— | MeO | H | Et | Cl | O | A |
| 286 | 2,4,6-tri-F—Ph | HC≡C— | F | H | Et | Cl | O | A |
| 287 | 4-MeO—Ph | O= | | H | Et | Cl | O | A |
| 288 | 4-N≡C—Ph | O= | | H | Et | Cl | O | A |
| 289 | 2,4,6-tri-F—Ph | O= | | | Et | Cl | O | A |
| 290 | 4-F—Ph | O= | | H | Et | Cl | O | A |
| 291 | 2-Cl-4-F—Ph | Pent | H | H | Et | H | O | A |
| 292 | 2-Cl-4-F—Ph | Pent | H | H | Et | Cl | O | A |
| 293 | 2-Cl-4-F—Ph | Pent | H | H | Et | Br | O | A |
| 294 | 2-Cl-4-F—Ph | O= | | H | Et | Cl | O | A |
| 295 | 2-Cl-4-F—Ph | CH2= | | H | Et | Cl | O | A |
| 296 | 2,4,6-tri-F—Ph | iPr | H | H | F2CHCH2- | H | O | B |
| 297 | 2,4,6-tri-F—Ph | iPr | H | H | F2CHCH2- | H | O | A |
| 298 | 2-Cl-4-F—Ph | HC(=O) | H | H | Et | Cl | O | A |
| 299 | 2-Cl-4-F—Ph | MeCH= | | H | Et | Cl | O | A |
| 300 | 2-Cl-4-F—Ph | Me2C= | | H | Et | Cl | O | A |
| 301 | 2-Cl-4-F—Ph | Br2C= | | H | Et | Cl | O | A |
| 302 | 2-Cl-4-F—Ph | | HC≡ | | Et | Cl | O | A |
| 303 | 2,4,6-tri-F—Ph | | HC≡ | | Et | Cl | O | A |
| 304 | 2,4,6-tri-F—Ph | iPr | H | H | F2CHCH2- | Cl | O | A |
| 305 | 2,4,6-tri-F—Ph | iPr | H | H | F2CHCH2- | Br | O | A |
| 306 | 2,4,6-tri-F—Ph | iPr | H | H | Et | Me | O | A |
| 307 | 2,4,6-tri-F—Ph | iPr | H | H | F2CHCH2- | Me | O | A |
| 308 | 2,4,6-tri-F—Ph | Ph—O | H | H | Et | Cl | O | A |
| 309 | 2,4,6-tri-F—Ph | ClCH= | | Cl | Et | Cl | O | A |
| 310 | 2,4,6-tri-F—Ph | 4-MeO—Ph—O | H | H | Et | Cl | O | A |
| 311 | 2,4,6-tri-F—Ph | 4-Cl—Ph—O | H | H | Et | Cl | O | A |
| 312 | 2-Cl-4-F—Ph | Me | H | H | Me | H | O | B |
| 313 | 2-Cl-4-F—Ph | Me | H | H | Me | H | S | B |
| 314 | 2-Cl-4-F—Ph | Me | H | H | Me | H | O | A |
| 315 | 2-Cl-4-F—Ph | Et | H | H | Et | H | S | B |
| 316 | 2-Cl-4-F—Ph | Me | H | H | Me | Cl | O | A |
| 317 | 2-Cl-4-F—Ph | Me | H | H | Me | Br | O | A |
| 318 | 2-Cl-4-MeO—Ph | Et | H | H | Et | H | O | A |
| 319 | 2-Cl-4-MeO—Ph | Me | H | H | Et | H | O | A |
| 320 | 2-Cl-4-MeO—Ph | Et | H | H | Et | Cl | O | A |
| 321 | 2-Cl-4-MeO—Ph | Et | H | H | Et | Br | O | A |
| 322 | 2-Cl-4-MeO—Ph | Me | H | H | Me | H | O | A |
| 323 | 2-Cl-4-F—Ph | Et | H | H | Me | H | O | B |
| 324 | 2-Cl-4-MeO—Ph | Me | H | H | Me | Cl | O | A |
| 325 | 2-Cl-4-MeO—Ph | Me | H | H | Me | Br | O | A |
| 326 | 2,4,6-tri-F—Ph | BrCH= | | Br | Et | Cl | O | A |
| 327 | 2-Cl-4-MeO—Ph | Me | H | H | Et | Cl | O | A |
| 328 | 2-Cl-4-MeO—Ph | Me | H | H | Et | Br | O | A |
| 329 | 2-Cl-4-F—Ph | Et | H | H | Me | H | O | A |
| 330 | 2-Cl-4-HO—Ph | Me | H | H | Me | Cl | O | A |
| 331 | 2-Cl-4-F—Ph | Et | H | H | Et | H | S | A |
| 332 | 2-Cl-4-F—Ph | Et | H | H | Me | Cl | O | A |
| 333 | 2-Cl-4-F—Ph | Et | H | H | Me | Br | O | A |
| 334 | 2-Cl-4-MeO—Ph | Et | H | H | Me | H | O | A |
| 335 | 2-Cl-4-MeO—Ph | Et | H | H | Me | Cl | O | A |
| 336 | 2-Cl-4-MeO—Ph | Et | H | H | Me | Br | O | A |
| 337 | 2-Cl-4-EtO—Ph | Me | H | H | Me | Cl | O | A |
| 338 | 2-Br-4-F—Ph | Me | H | H | Et | H | O | B |
| 339 | 2-Cl-4-F—Ph | Et | H | H | Me | Me | O | A |
| 340 | 2-Br-4-F—Ph | Me | H | H | Et | H | O | A |
| 341 | 2-Br-4-F—Ph | Et | H | H | Me | H | O | B |
| 342 | 2-Br-4-F—Ph | Me | H | H | Et | Cl | O | A |
| 343 | 2-Br-4-F—Ph | Me | H | H | Et | Br | O | A |
| 344 | 2-Br-4-MeO—Ph | Me | H | H | Et | H | O | A |
| 345 | 2-Br-4-MeO—Ph | Me | H | H | Et | Cl | O | A |
| 346 | 2-Br-4-MeO—Ph | Me | H | H | Et | Br | O | A |
| 347 | 4-F-2-Me—Ph | Me | H | H | Et | H | O | A |
| 348 | 2-Br-4-F—Ph | Me | H | H | Me | H | O | A |
| 349 | 2-Br-4-F—Ph | Me | H | H | Me | Cl | O | A |

TABLE 3-continued

| Compounds | Z | Y1 | Y2 | Y3 | R1 | R3 | X | Structures |
|---|---|---|---|---|---|---|---|---|
| 350 | 2-Br-4-F—Ph | Me | H | H | Me | Br | O | A |
| 351 | 4-F-2-Me—Ph | Me | H | H | Et | Cl | O | A |
| 352 | 4-F-2-Me—Ph | Me | H | H | Et | Br | O | A |
| 353 | 4-MeO-2-Me—Ph | Me | H | H | Et | H | O | A |
| 354 | 2-Br-4-MeO—Ph | Me | H | H | Me | H | O | A |
| 355 | 4-MeO-2-Me—Ph | Me | H | H | Et | Cl | O | A |
| 356 | 4-MeO-2-Me—Ph | Me | H | H | Et | Br | O | A |
| 357 | 2-Br-4-MeO—Ph | Me | H | H | Me | Cl | O | A |
| 358 | 2-Br-4-MeO—Ph | Me | H | H | Me | Br | O | A |
| 359 | 2-Br-4-F—Ph | Et | H | H | Et | H | O | B |
| 360 | 4-F-2-Me—Ph | Me | H | H | Me | H | O | A |
| 361 | 2-Br-4-F—Ph | Et | H | H | Et | H | O | A |
| 362 | 4-F-2-Me—Ph | Me | H | H | Me | Cl | O | A |
| 363 | 4-F-2-Me—Ph | Me | H | H | Me | Br | O | A |
| 364 | 2,4,6-tri-F—Ph | O= | | H | Et | Br | O | A |
| 365 | 2,4,6-tri-F—Ph | iPr | HO | H | Et | Br | O | A |
| 366 | 2,4,6-tri-F—Ph | O= | | iPr | Et | Br | O | A |
| 367 | 4-MeO-2-Me—Ph | Me | H | H | Me | H | O | A |
| 368 | 2-Br-4-F—Ph | Et | H | H | Et | Cl | O | A |
| 369 | 2-Br-4-F—Ph | Et | H | H | Et | Br | O | A |
| 370 | 2-Br-4-MeO—Ph | Et | H | H | Et | H | O | A |
| 371 | 2,4,6-tri-F—Ph | Et | H | H | Et | H | O | B |
| 372 | 2,4,6-tri-F—Ph | Et | H | H | Et | H | O | A |
| 373 | 2,4,6-tri-F—Ph | Me | H | H | Et | H | O | B |
| 374 | 4-MeO-2-Me—Ph | Me | H | H | Me | Cl | O | A |
| 375 | 4-MeO-2-Me—Ph | Me | H | H | Me | Br | O | A |
| 376 | 2-Br-4-MeO—Ph | Et | H | H | Et | Cl | O | A |
| 377 | 2,4,6-tri-F—Ph | Me | H | H | Et | H | O | A |
| 378 | 2,4,6-tri-F—Ph | Et | H | H | Et | Cl | O | A |
| 379 | 2,4,6-tri-F—Ph | H | H | H | Et | I | O | A |
| 380 | 2,6-di-F-4-MeO—Ph | H | H | H | Et | I | O | A |
| 381 | 2,4,6-tri-F—Ph | iPr | Me | HO | Et | Br | O | A |
| 382 | 2-Br-4-MeO—Ph | Et | H | H | Et | Br | O | A |
| 383 | 2,6-di-F-4-MeO—Ph | Et | H | H | Et | H | O | A |
| 384 | 2,6-di-F-4-MeO—Ph | Et | H | H | Et | Cl | O | A |
| 385 | 2,6-di-F-4-MeO—Ph | Et | H | H | Et | Br | O | A |
| 386 | 2,4,6-tri-F—Ph | Me | H | H | Et | Cl | O | A |
| 387 | 2,4,6-tri-F—Ph | Me | H | H | Et | Br | O | A |
| 388 | 2,6-di-F-4-MeO—Ph | Me | H | H | Et | H | O | A |
| 389 | 2,4,6-tri-F—Ph | Et | H | H | Et | Br | O | A |
| 390 | 2,6-di-F-4-MeO—Ph | Me | H | H | Et | Cl | O | A |
| 391 | 2,6-di-F-4-MeO—Ph | Me | H | H | Et | Br | O | A |
| 392 | 4-F-2-Me—Ph | Et | H | H | Et | H | O | A |
| 393 | 2,4,6-tri-F—Ph | Et | H | H | Me | H | O | B |
| 394 | 2,4,6-tri-F—Ph | Et | H | H | Me | H | O | A |
| 395 | 2,4,6-tri-F—Ph | Me | H | H | Me | H | O | B |
| 396 | 2,4,6-tri-F—Ph | Et | H | H | Me | Cl | O | A |
| 397 | 2,4,6-tri-F—Ph | Et | H | H | Me | Br | O | A |
| 398 | 2,6-di-F-4-MeO—Ph | Et | H | H | Me | H | O | A |
| 399 | 2,6-di-F-4-MeO—Ph | Et | H | H | Me | Cl | O | A |
| 400 | 2,6-di-F-4-MeO—Ph | Et | H | H | Me | Br | O | A |
| 401 | 2,4,6-tri-F—Ph | Me | H | H | Me | H | O | A |
| 402 | 4-F-2-Me—Ph | Et | H | H | Et | Cl | O | A |
| 403 | 4-F-2-Me—Ph | Et | H | H | Et | Br | O | A |
| 404 | 2,4,6-tri-F—Ph | Me | H | H | Me | Cl | O | A |
| 405 | 2,4,6-tri-F—Ph | Me | H | H | Me | Br | O | A |
| 406 | 2,6-di-F-4-MeO—Ph | Me | H | H | Me | H | O | A |
| 407 | 2,6-di-F-4-MeO—Ph | Me | H | H | Me | Cl | O | A |
| 408 | 2,6-di-F-4-MeO—Ph | Me | H | H | Me | Br | O | A |
| 409 | 2,6-di-F—Ph | N═C—CH═ | | H | Et | Cl | O | A |
| 410 | 2-Br-4-F—Ph | Et | H | H | Me | H | O | A |
| 411 | 4-MeO-2-Me—Ph | Et | H | H | Et | H | O | A |
| 412 | 4-MeO-2-Me—Ph | Et | H | H | Et | Cl | O | A |
| 413 | 4-MeO-2-Me—Ph | Et | H | H | Et | Br | O | A |
| 414 | 2-Br-4-F—Ph | Et | H | H | Me | Cl | O | A |
| 415 | 2-Br-4-F—Ph | Et | H | H | Me | Br | O | A |
| 416 | 2-Br-4-MeO—Ph | Et | H | H | Me | H | O | A |
| 417 | 2-Br-4-MeO—Ph | Et | H | H | Me | Cl | O | A |
| 418 | 2-Br-4-MeO—Ph | Et | H | H | Me | Br | O | A |
| 419 | 4-F-2-Me—Ph | Et | H | H | Me | H | O | A |
| 420 | 4-F-2-Me—Ph | Et | H | H | Me | Cl | O | A |
| 421 | 4-F-2-Me—Ph | Et | H | H | Me | Br | O | A |
| 422 | 2,6-di-F—Ph | Et | H | H | Et | H | O | B |
| 423 | 2,4,6-tri-F—Ph | iPr | Me | HO | Me | Br | O | A |
| 424 | 2,4,6-tri-F—Ph | Et | H | H | Et | H | S | B |
| 425 | 4-MeO-2-Me—Ph | Et | H | H | Me | H | O | A |
| 426 | 2,6-di-F—Ph | Et | H | H | Et | H | O | A |
| 427 | 2,4,6-tri-F—Ph | Et | H | H | Et | H | S | A |

TABLE 3-continued

| Compounds | Z | Y1 | Y2 | Y3 | R1 | R3 | X | Structures |
|---|---|---|---|---|---|---|---|---|
| 428 | 2,6-di-F—Ph | Et | H | H | Et | Cl | O | A |
| 429 | 2,6-di-F—Ph | Et | H | H | Et | Br | O | A |
| 430 | 2,4,6-tri-F—Ph | Et | H | H | Et | Cl | S | A |
| 431 | 4-MeO-2-Me—Ph | Et | H | H | Me | Br | O | A |
| 432 | 2,4,6-tri-F—Ph | iPr | Me | MeO | Me | Br | O | A |
| 433 | 4-MeO-2-Me—Ph | Et | H | H | Me | Cl | O | A |
| 434 | 2,4,6-tri-F—Ph | Et | H | H | Et | I | O | A |
| 435 | 2,4,6-tri-F—Ph | Et | H | H | Pr | H | O | B |
| 436 | 2,6-di-F-4-MeO—Ph | Et | H | H | Et | I | O | A |
| 437 | 2,4,6-tri-F—Ph | Et | H | H | Pr | H | O | A |
| 438 | 2,6-di-F-4-HO—Ph | Et | H | H | Et | H | O | A |
| 439 | 2,4,6-tri-F—Ph | Et | H | H | Pr | Cl | O | A |
| 440 | 2,4,6-tri-F—Ph | Et | H | H | Pr | Br | O | A |
| 441 | 2,4,6-tri-F—Ph | Et | H | H | Pr | I | O | A |
| 442 | 2,6-di-F-4-MeO—Ph | Et | H | H | Pr | H | O | A |
| 443 | 2,6-di-F-4-MeO—Ph | Et | H | H | Pr | Cl | O | A |
| 444 | 2,6-di-F-4-MeO—Ph | Et | H | H | Pr | Br | O | A |
| 445 | 2,6-di-F-4-MeO—Ph | Et | H | H | Pr | I | O | A |
| 446 | 2,4,6-tri-F—Ph | EtO=H | | H | Me | Cl | O | A |
| 447 | 2,4,6-tri-F—Ph | iPr | HO | H | Me | Cl | O | A |
| 448 | 2,4,6-tri-F—Ph | O= | | iPr | Me | Cl | O | A |
| 449 | 2,4,6-tri-F—Ph | O= | | H | Et | H | O | A |
| 450 | 2,4,6-tri-F—Ph | iPr | Me | HO | Me | Cl | O | A |
| 451 | 2,4,6-tri-F—Ph | iPr | Me | EtO | Me | Cl | O | A |
| 452 | 2,4,6-tri-F—Ph | iPr | Me | MeO | Me | Cl | O | A |
| 453 | 2,4,6-tri-F—Ph | iPr | HO | H | Et | H | O | A |
| 454 | 2,4,6-tri-F—Ph | O= | | iPr | Et | H | O | A |
| 455 | 2,4,6-tri-F—Ph | iPr | Me | HO | Et | H | O | A |
| 456 | 2,6-di-F-4-EtO—Ph | Et | H | H | Et | H | O | A |
| 457 | 2,6-di-F-4-EtO—Ph | Et | H | H | Et | Cl | O | A |
| 458 | 2,6-di-F-4-EtO—Ph | Et | H | H | Et | Br | O | A |
| 459 | 2,6-di-F-4-HC≡CCH2O—Ph | Et | H | H | Et | H | O | A |
| 460 | 2,6-di-F-4-MeC≡CCH2O—Ph | Et | H | H | Et | H | O | A |
| 461 | 2,6-di-F-4-MeC≡CCH2O—Ph | Et | H | H | Et | Cl | O | A |
| 462 | 2,6-di-F-4-MeC≡CCH2O—Ph | Et | H | H | Et | Br | O | A |
| 463 | 2,6-di-F-4-HC≡CCH2O—Ph | Et | H | H | Et | Cl | O | A |
| 464 | 2,6-di-F-4-HC≡CCH2O—Ph | Et | H | H | Et | Br | O | A |
| 465 | 2,4,6-tri-F—Ph | iPr | Me | MeO | Et | Br | O | A |
| 466 | 2,4,6-tri-F—Ph | iPr | Me | EtO | Et | Br | O | A |
| 467 | 2,6-di-F-4-MeO—Ph | iPr | Me | MeO | Et | Br | O | A |
| 468 | 2,6-di-F-4-MeO—Ph | iPr | Me | EtO | Et | Br | O | A |
| 469 | 2,4,6-tri-F—Ph | Et | HO | H | Et | H | O | A |
| 470 | 2,4,6-tri-F—Ph | Et | H | H | F2CHCH2- | H | O | A |
| 471 | 2,4,6-tri-F—Ph | Et | H | H | F2CHCH2- | Cl | O | A |
| 472 | 2,4,6-tri-F—Ph | Et | H | H | F2CHCH2- | Br | O | A |
| 473 | 2,4,6-tri-F—Ph | Et | H | H | F2CHCH2- | I | O | A |
| 474 | 2,6-di-F-4-MeO—Ph | Et | H | H | F2CHCH2- | H | O | A |
| 475 | 2,6-di-F-4-MeO—Ph | Et | H | H | F2CHCH2- | Cl | O | A |
| 476 | 2,6-di-F-4-MeO—Ph | Et | H | H | F2CHCH2- | Br | O | A |
| 477 | 2,6-di-F-4-MeO—Ph | Et | H | H | F2CHCH2- | I | O | A |
| 478 | 2,4,6-tri-F—Ph | HO | H | H | Et | H | O | A |
| 479 | 2,4,6-tri-F—Ph | iPr | Me | MeO | Et | H | O | A |
| 480 | 2,4,6-tri-F—Ph | O= | | Et | Et | H | O | A |
| 481 | 2,4,6-tri-F—Ph | Et | Me | HO | Et | H | O | A |
| 482 | 2,4,6-tri-F—Ph | Et | Me | HO | Et | Br | O | A |
| 483 | 2,4,6-tri-F—Ph | Et | Me | MeO | Et | Br | O | A |
| 484 | 2,4,6-tri-F—Ph | Et | Me | EtO | Et | Br | O | A |
| 485 | 2,6-di-F-4-MeO—Ph | Et | Me | EtO | Et | Br | O | A |
| 486 | 2,6-di-F-4-MeO—Ph | Et | Me | MeO | Et | Br | O | A |
| 487 | 2,6-di-F-4-MeO—Ph | iPr | Me | HO | Me | Cl | O | A |
| 488 | 2,6-di-F-4-MeO—Ph | iPr | Me | MeO | Me | Cl | O | A |
| 489 | 2,6-di-F-4-MeO—Ph | iPr | Me | EtO | Me | Cl | O | A |
| 490 | 2,4,6-tri-F—Ph | Et | HO | H | Me | Cl | O | A |
| 491 | 2,6-di-F—Ph | Et | H | H | F2CHCH2- | H | O | A |
| 492 | 2,6-di-F—Ph | Et | H | H | F2CHCH2- | Cl | O | A |
| 493 | 2,6-di-F—Ph | Et | H | H | F2CHCH2- | Br | O | A |
| 494 | 2,6-di-F—Ph | Et | H | H | F2CHCH2- | I | O | A |
| 495 | 2,4,6-tri-F—Ph | O= | | Et | Me | Cl | O | A |
| 496 | 2,4,6-tri-F—Ph | iPr | MeO | H | Me | Cl | O | A |
| 497 | 2,4,6-tri-F—Ph | iPr | EtO | H | Me | Cl | O | A |
| 498 | 2,6-di-F-4-MeO—Ph | iPr | MeO | H | Me | Cl | O | A |
| 499 | 2,6-di-F-4-MeO—Ph | iPr | EtO | H | Me | Cl | O | A |
| 500 | 2,6-di-F-4-MeO—Ph | Et | Me | HO | Et | Br | O | A |
| 501 | 2,4,6-tri-F—Ph | iPr | MeO | H | Et | Br | O | A |
| 502 | 2,4,6-tri-F—Ph | Et | MeO | H | Me | Cl | O | A |
| 503 | 2,6-di-F-4-MeO—Ph | iPr | MeO | H | Et | Br | O | A |
| 504 | 2,4,6-tri-F—Ph | Et | MeO | H | Et | Br | O | A |
| 505 | 2,4,6-tri-F—Ph | Et | Me | HO | Me | Cl | O | A |

TABLE 3-continued

| Compounds | Z | Y1 | Y2 | Y3 | R1 | R3 | X | Structures |
|---|---|---|---|---|---|---|---|---|
| 506 | 2,6-di-F-4-MeO—Ph | Et | MeO | H | Me | Cl | O | A |
| 507 | 2,6-di-F-4-MeO—Ph | Et | MeO | H | Et | Br | O | A |
| 508 | 2,4,6-tri-F—Ph | Et | Me | MeO | Me | Cl | O | A |
| 509 | 2,4,6-tri-F—Ph | Et | Me | EtO | Me | Cl | O | A |
| 510 | 2,6-di-F—Ph | O= | | H | Et | H | O | A |
| 511 | 2,6-di-F-4-MeO—Ph | Et | Me | MeO | Me | Cl | O | A |
| 512 | 2,6-di-F-4-MeO—Ph | Et | Me | EtO | Me | Cl | O | A |
| 513 | 2,6-di-F-4-MeO—Ph | Et | Me | HO | Me | Cl | O | A |
| 514 | 2,4,6-tri-F—Ph | Me | HO | H | Et | Cl | O | A |
| 515 | 2,4,6-tri-F—Ph | F3C | HO | H | Et | Cl | O | A |
| 516 | 2,4,6-tri-F—Ph | F3C | MeO | H | Et | Cl | O | A |
| 517 | 2,4,6-tri-F—Ph | CH2= | | H | Et | Cl | O | A |
| 518 | 2,6-di-F-4-MeO—Ph | F3C | MeO | H | Et | Cl | O | A |
| 519 | 2,4,6-tri-F—Ph | Me | MeO | H | Et | Cl | O | A |
| 520 | 2,6-di-F—Ph | iPr | HO | H | Et | Br | O | A |
| 521 | 2,6-di-F—Ph | iPr | Me | HO | Et | H | O | A |
| 522 | 2,6-di-F—Ph | iPr | Me | HO | Et | Br | O | A |
| 523 | 2,6-di-F—Ph | iPr | Me | MeO | Et | Br | O | A |
| 524 | 2,6-di-F—Ph | iPr | Me | EtO | Et | Br | O | A |
| 525 | 2,6-di-F—Ph | iPr | MeO | H | Et | Br | O | A |
| 526 | 2,6-di-F—Ph | iPr | EtO | H | Et | Br | O | A |
| 527 | 2,6-di-F-4-MeO—Ph | Me | MeO | H | Et | Cl | O | A |
| 528 | 2,4,6-tri-F—Ph | Me | EtO | H | Et | Cl | O | A |
| 529 | 2,4,6-tri-F—Ph | Me | F3CCH2O | H | Et | Cl | O | A |
| 530 | 2,6-di-F-4-MeO—Ph | Me | EtO | H | Et | Cl | O | A |
| 531 | 2,6-di-F-4-MeO—Ph | Me | F3CCH2O | H | Et | Cl | O | A |

Table 4 describes the $^1$H-NMR data of the compounds listed in Table 3.

TABLE 4

| Compounds | $^1$H-NMR |
|---|---|
| 1 | $^1$H-NMR (CDCl3) δ: 7.50-7.49 (1H, m), 7.27 (2H, d, J = 9.5 Hz), 7.09-7.06 (2H, m), 6.63 (1H, d, J = 9.5 Hz), 3.83 (2H, q, J = 7.1 Hz), 1.80 (3H, s), 1.10 (3H, t, J = 7.1 Hz). |
| 2 | $^1$H-NMR (CDCl3) δ: 7.53-7.49 (1H, m), 7.50 (1H, s), 7.09-7.07 (2H, m), 3.88 (2H, q, J = 7.1 Hz), 1.81 (3H, s), 1.12 (3H, t, J = 7.1 Hz). |
| 3 | $^1$H-NMR (CDCl3) δ: 7.52-7.45 (1H, m), 7.28 (1H, d, J = 9.2 Hz), 7.10-7.04 (2H, m), 6.64 (1H, d, J = 9.2 Hz), 3.31 (3H, s), 1.84 (3H, s). |
| 4 | $^1$H-NMR (CDCl3) δ: 7.53-7.49 (1H, m), 7.51 (1H, s), 7.09-7.07 (2H, m), 3.37 (3H, s), 1.86 (3H, s). |
| 5 | $^1$H-NMR (CDCl3) δ: 7.50-7.48 (1H, m), 7.40 (1H, d, J = 9.5 Hz), 7.07 (2H, dd, J = 8.5, 7.0 Hz), 6.71 (1H, d, J = 9.5 Hz), 3.79 (2H, q, J = 7.1 Hz), 2.22-2.20 (1H, m), 1.10 (3H, t, J = 7.1 Hz), 1.05 (6H, d, J = 7.0 Hz). |
| 6 | $^1$H-NMR (CDCl3) δ: 7.59 (1H, s), 7.53-7.50 (1H, m), 7.08 (2H, dd, J = 8.5, 7.0 Hz), 3.84 (2H, q, J = 7.1 Hz), 2.23-2.22 (1H, m), 1.12 (3H, t, J = 7.1 Hz), 1.05 (6H, d, J = 6.7 Hz). |
| 7 | $^1$H-NMR (CDCl3) δ: 7.39 (1H, d, J = 9.5 Hz), 6.85 (2H, dd, J = 8.4, 6.9 Hz), 6.71 (1H, d, J = 9.5 Hz), 3.78 (2H, q, J = 7.1 Hz), 2.22-2.17 (1H, m), 1.10 (3H, t, J = 7.1 Hz), 1.05 (6H, d, J = 6.7 Hz). |
| 8 | $^1$H-NMR (CDCl3) δ: 7.58 (1H, s), 6.87-6.85 (2H, m), 3.83 (2H, q, J = 7.2 Hz), 2.23-2.21 (1H, m), 1.13 (3H, t, J = 7.2 Hz), 1.06 (6H, d, J = 6.7 Hz). |
| 9 | $^1$H-NMR (CDCl3) δ: 7.78 (1H, s), 6.87-6.85 (2H, m), 3.83 (2H, q, J = 7.1 Hz), 2.20-2.19 (1H, m), 1.12 (3H, t, J = 7.1 Hz), 1.06 (6H, d, J = 7.0 Hz). |
| 10 | $^1$H-NMR (CDCl3) δ: 7.38 (1H, d, J = 9.5 Hz), 6.69 (1H, d, J = 9.5 Hz), 6.60 (2H, d, J = 8.6 Hz), 3.87 (3H, s), 3.81 (2H, q, J = 7.1 Hz), 2.27-2.26 (1H, m), 1.10 (3H, t, J = 7.1 Hz), 1.04 (6H, d, J = 6.7 Hz). |
| 11 | $^1$H-NMR (CDCl3) δ: 7.56 (1H, s), 6.60 (2H, d, J = 8.9 Hz), 3.88 (3H, s), 3.86 (2H, q, J = 7.0 Hz), 2.29-2.28 (1H, m), 1.12 (3H, t, J = 7.0 Hz), 1.05 (6H, d, J = 7.0 Hz). |
| 12 | $^1$H-NMR (CDCl3) δ: 7.77 (1H, s), 6.60 (2H, d, J = 8.6 Hz), 3.88 (3H, s), 3.86 (2H, q, J = 7.1 Hz), 2.28-2.27 (1H, m), 1.12 (3H, t, J = 7.1 Hz), 1.05 (6H, d, J = 6.7 Hz). |
| 13 | $^1$H-NMR (CDCl3) δ: 7.40 (1H, d, J = 9.5 Hz), 6.85 (2H, dd, J = 8.6, 6.7 Hz), 6.73 (1H, d, J = 9.5 Hz), 3.27 (3H, s), 2.27-2.25 (1H, m), 1.06 (6H, d, J = 6.7 Hz). |
| 14 | $^1$H-NMR (CDCl3) δ: 7.39 (1H, d, J = 9.5 Hz), 6.71 (1H, d, J = 9.5 Hz), 6.60 (2H, d, J = 8.9 Hz), 3.87 (3H, s), 3.28 (3H, s), 2.35-2.32 (1H, m), 1.06 (6H, d, J = 7.0 Hz). |
| 15 | $^1$H-NMR (CDCl3) δ: 7.59 (1H, s), 6.88-6.84 (2H, m), 3.33 (3H, s), 2.29-2.28 (1H, m), 1.07 (6H, d, J = 7.0 Hz). |
| 16 | $^1$H-NMR (CDCl3) δ: 7.58 (1H, s), 6.60 (2H, d, J = 8.9 Hz), 3.87 (3H, s), 3.34 (3H, s), 2.36-2.35 (1H, m), 1.06 (6H, d, J = 6.7 Hz). |
| 17 | $^1$H-NMR (CDCl3) δ: 7.86 (1H, s), 7.56-7.54 (1H, m), 7.13-7.08 (2H, m), 4.25-4.23 (1H, m), 3.89-3.86 (1H, m), 3.81-3.78 (1H, m), 1.65 (1H, d, J = 2.8 Hz), 1.29 (3H, d, J = 6.4 Hz), 1.12 (3H, t, J = 7.0 Hz). |
| 18 | $^1$H-NMR (CDCl3) δ: 7.71 (1H, s), 7.58-7.54 (1H, m), 7.14-7.08 (2H, m), 3.91-3.87 (1H, m), 3.81-3.78 (1H, m), 3.60 (1H, q, J = 6.3 Hz), 3.07 (3H, d, J = 0.7 Hz), 1.24 (3H, d, J = 6.3 Hz), 1.14 (3H, t, J = 7.1 Hz). |
| 19 | $^1$H-NMR (CDCl3) δ: 7.74 (1H, s), 7.56-7.54 (1H, m), 7.12-7.09 (2H, m), 3.89-3.86 (1H, m), 3.81-3.78 (1H, m), 3.71 (1H, q, J = 6.5 Hz), 3.29-3.28 (1H, m), 3.11-3.07 (1H, m), 1.58 (3H, s), 1.24 (3H, d, J = 6.5 Hz), 1.13 (3H, t, J = 7.2 Hz), 1.10 (3H, t, J = 7.0 Hz). |
| 20 | $^1$H-NMR (CDCl3) δ: 9.19 (1H, t, J = 1.0 Hz), 8.13 (1H, s), 7.67-7.63 (1H, m), 7.18-7.16 (2H, m), 3.94 (2H, q, J = 7.1 Hz), 1.19 (3H, t, J = 7.1 Hz). |
| 21 | $^1$H-NMR (CDCl3) δ: 8.13 (1H, s), 7.65-7.63 (1H, m), 7.18 (2H, dd, J = 8.5, 6.8 Hz), 5.96 (1H, s), 3.82 (2H, q, J = 7.1 Hz), 1.13 (3H, t, J = 7.1 Hz). |
| 22 | $^1$H-NMR (CDCl3) δ: 8.07 (1H, s), 7.56-7.52 (1H, m), 7.08 (2H, dd, J = 8.4, 7.2 Hz), 3.93 (2H, q, J = 7.2 Hz), 2.25 (3H, s), 1.16 (3H, t, J = 7.2 Hz). |
| 23 | $^1$H-NMR (CDCl3) δ: 7.89 (1H, s), 7.53-7.48 (1H, m), 7.04 (2H, dd, J = 8.5, 7.1 Hz), 3.79 (2H, q, J = 7.1 Hz), 1.44 (1H, s), 1.35 (6H, s), 1.11 (3H, t, J = 7.1 Hz). |
| 24 | $^1$H-NMR (CDCl3) δ: 7.79 (1H, s), 7.56-7.54 (1H, m), 7.13-7.08 (2H, m), 4.01-3.98 (1H, m), 3.93-3.92 (1H, m), 3.73-3.69 (1H, m), 1.72-1.52 (3H, m), 1.12 (3H, t, J = 7.1 Hz), 0.76 (3H, t, J = 7.4 Hz). |
| 25 | $^1$H-NMR (CDCl3) δ: 7.67 (1H, s), 7.57-7.55 (1H, m), 7.12-7.08 (2H, m), 3.89-3.86 (1H, m), 3.82-3.79 (1H, m), 3.33 (1H, dd, J = 8.1, 5.0 Hz), 3.10 (3H, d, J = 1.2 Hz), 1.65-1.59 (1H, |

TABLE 4-continued

| Compounds | ¹H-NMR |
|---|---|
| | m), 1.48-1.43 (1H, m), 1.14 (3H, t, J = 7.0 Hz), 0.78 (3H, t, J = 7.3 Hz). |
| 26 | ¹H-NMR (CDCl3) δ: 8.05 (1H, s), 7.54-7.52 (1H, m), 7.06 (2H, dd, J = 8.4, 7.2 Hz), 3.93 (2H, q, J = 7.1 Hz), 2.63 (2H, q, J = 7.1 Hz), 1.15 (3H, t, J = 7.1 Hz), 1.02 (3H, t, J = 7.1 Hz). |
| 27 | ¹H-NMR (CDCl3) δ: 7.74 (1H, s), 7.49-7.47 (1H, m), 7.04-7.00 (2H, m), 3.85-3.82 (1H, m), 3.75-3.73 (1H, m), 1.70-1.65 (1H, m), 1.58-1.53 (1H, m), 1.33 (3H, s), 1.26 (1H, s), 1.11 (3H, t, J = 7.0 Hz), 0.81 (3H, t, J = 7.5 Hz). |
| 28 | ¹H-NMR (CDCl3) δ: 7.48-7.41 (2H, m, mixture), 7.01-6.97 (2H, m, mixture), 5.27-5.26 (1H, m, endo), 4.88-4.87 (1H, m, exo), 4.80 (1H, s, exo), 3.88 (2H, q, J = 7.0 Hz, mixture), 2.01 (2H, q, J = 7.4 Hz, exo), 1.59 (3H, s, endo), 1.44-1.43 (1H, m, endo), 1.12 (3H, t, J = 7.0 Hz, mixture), 0.90 (3H, t, J = 7.3 Hz, exo). endo/exo = 75/25 |
| 28 | ¹H-NMR (CDCl3) δ: 7.81 (1H, s), 7.52-7.50 (1H, m), 7.06-7.01 (2H, m), 3.78 (2H, q, J = 7.1 Hz), 3.00 (3H, s), 1.54-1.50 (2H, m), 1.11 (3H, t, J = 7.1 Hz), 1.02 (3H, s), 0.75 (3H, t, J = 7.1 Hz). |
| 30 | ¹H-NMR (CDCl3) δ: 7.52 (1H, d, J = 1.2 Hz), 7.49-7.47 (1H, m), 7.04-7.01 (2H, m), 3.88-3.85 (1H, m), 3.77-3.74 (1H, m), 1.81-1.68 (1H, m), 1.43 (3H, d, J = 22.9 Hz), 1.12 (3H, dd, J = 9.0, 5.4 Hz), 0.83 (3H, t, J = 7.4 Hz). |
| 31 | ¹H-NMR (CDCl3) δ: 7.32 (1H, d, J = 9.5 Hz), 6.88-6.81 (2H, m), 6.71 (1H, d, J = 9.5 Hz), 3.94-3.87 (1H, m), 3.69-3.65 (1H, m), 1.90-1.89 (1H, m), 1.47-1.39 (2H, m), 1.11 (3H, t, J = 7.1 Hz), 1.04 (3H, d, J = 7.1 Hz), 0.68 (3H, td, J = 7.4, 0.9 Hz). |
| 32 | ¹H-NMR (CDCl3) δ: 7.72 (1H, s), 6.89-6.81 (2H, m), 3.97-3.94 (1H, m), 3.75-3.71 (1H, m), 1.92-1.88 (1H, m), 1.47-1.39 (2H, m), 1.13 (3H, t, J = 7.1 Hz), 1.05 (3H, d, J = 7.1 Hz), 0.69 (3H, td, J = 7.4, 0.8 Hz). |
| 33 | ¹H-NMR (CDCl3) δ: 7.51 (1H, s), 6.88-6.83 (2H, m), 3.97-3.94 (1H, m), 3.74-3.71 (1H, m), 1.93-1.90 (1H, m), 1.46-1.40 (2H, m), 1.13 (3H, t, J = 7.2 Hz), 1.05 (3H, d, J = 7.0 Hz), 0.69 (3H, td, J = 7.4, 0.8 Hz). |
| 34 | ¹H-NMR (CDCl3) δ: 7.31 (1H, d, J = 9.5 Hz), 6.69 (1H, d, J = 9.5 Hz), 6.60-6.58 (2H, m), 3.97-3.90 (1H, m), 3.88 (3H, s), 3.72-3.69 (1H, m), 1.98-1.96 (1H, m), 1.46-1.38 (2H, m), 1.11 (3H, t, J = 7.1 Hz), 1.03 (3H, d, J = 6.8 Hz), 0.68 (3H, t, J = 7.3 Hz). |
| 35 | ¹H-NMR (CDCl3) δ: 7.50 (1H, s), 6.60-6.59 (2H, m), 4.00-3.94 (1H, m), 3.88 (3H, s), 3.77-3.74 (1H, m), 2.00-1.97 (1H, m), 1.45-1.39 (2H, m), 1.13 (3H, t, J = 7.0 Hz), 1.04 (3H, d, J = 6.7 Hz), 0.69 (3H, t, J = 7.2 Hz). |
| 36 | ¹H-NMR (CDCl3) δ: 7.70 (1H, s), 6.60-6.58 (2H, m), 3.99-3.96 (1H, m), 3.88 (3H, s), 3.77-3.75 (1H, m), 1.98-1.97 (1H, m), 1.45-1.39 (2H, m), 1.12 (3H, t, J = 7.0 Hz), 1.04 (3H, d, J = 7.0 Hz), 0.69 (3H, t, J = 7.2 Hz). |
| 37 | ¹H-NMR (CDCl3) δ: 6.74 (2H, dd, J = 8.7, 6.9 Hz), 3.31 (2H, q, J = 7.2 Hz), 2.56-2.54 (2H, m), 2.35-2.33 (2H, m), 1.72-1.71 (3H, m), 0.92 (3H, t, J = 7.2 Hz), 0.76 (6H, d, J = 6.4 Hz). |
| 38 | ¹H-NMR (CDCl3) δ: 7.27 (1H, d, J = 9.5 Hz), 6.84 (2H, dd, J = 8.5, 6.8 Hz), 6.66 (1H, d, J = 9.5 Hz), 3.81 (2H, q, J = 7.1 Hz), 1.92 (2H, d, J = 7.3 Hz), 1.63-1.61 (1H, m), 1.10 (3H, t, J = 7.1 Hz), 0.76 (6H, d, J = 6.6 Hz). |
| 39 | ¹H-NMR (CDCl3) δ: 7.25 (3H, d, J = 9.3 Hz), 6.63 (1H, d, J = 9.3 Hz), 6.60-6.58 (2H, m), 3.88 (3H, s), 3.83 (2H, q, J = 7.1 Hz), 1.94 (2H, d, J = 7.3 Hz), 1.67-1.57 (1H, m), 1.10 (3H, t, J = 7.1 Hz), 0.76 (6H, d, J = 6.6 Hz). |
| 40 | ¹H-NMR (CDCl3) δ: 7.70 (1H, s), 6.86-6.85 (2H, m), 3.85 (2H, q, J = 7.1 Hz), 1.92 (2H, d, J = 7.3 Hz), 1.64-1.61 (1H, m), 1.12 (3H, t, J = 7.1 Hz), 0.77 (6H, d, J = 6.7 Hz). |
| 41 | ¹H-NMR (CDCl3) δ: 7.50 (1H, s), 6.87-6.85 (2H, m), 3.85 (2H, q, J = 7.2 Hz), 1.92 (2H, d, J = 7.3 Hz), 1.66-1.61 (1H, m), 1.12 (3H, t, J = 7.2 Hz), 0.77 (6H, d, J = 6.4 Hz). |
| 42 | ¹H-NMR (CDCl3) δ: 7.48 (1H, s), 6.61-6.58 (2H, m), 3.88 (3H, s), 3.88 (2H, q, J = 7.1 Hz), 1.94 (2H, d, J = 7.3 Hz), 1.66-1.61 (1H, m), 1.12 (3H, t, J = 7.1 Hz), 0.76 (6H, d, J = 6.7 Hz). |
| 43 | ¹H-NMR (CDCl3) δ: 7.69 (1H, s), 6.60-6.58 (2H, m), 3.88 (3H, s), 3.88 (2H, q, J = 7.0 Hz), 1.94 (2H, d, J = 7.3 Hz), 1.68-1.59 (1H, m), 1.11 (3H, t, J = 7.0 Hz), 0.76 (6H, d, J = 6.4 Hz). |
| 44 | ¹H-NMR (CDCl3) δ: 7.78 (1H, s), 7.56-7.53 (1H, m), 7.12-7.08 (2H, m), 4.11 (2H, d, J = 6.0 Hz), 3.88 (2H, q, J = 7.1 Hz), 1.51 (1H, t, J = 6.0 Hz), 1.14 (3H, t, J = 7.1 Hz). |
| 45 | ¹H-NMR (CDCl3) δ: 7.71 (1H, s), 756.-7.53 (1H, m), 7.09 (2H, dd, J = 8.5, 7.1 Hz), 3.88 (2H, q, J = 7.1 Hz), 3.87 (2H, s), 3.16 (3H, s), 1.14 (3H, t, J = 7.1 Hz). |
| 46 | ¹H-NMR (CDCl3) δ: 7.78 (1H, s), 6.89-6.87 (2H, m), 3.97-3.93 (2H, m), 3.71 (1H, td, J = 13.8, 7.0 Hz), 1.71-1.67 (2H, m), 1.59-.51 (1H, m), 1.13 (3H, t, J = 7.0 Hz), 0.77 (3H, t, J = 7.4 Hz). |
| 47 | ¹H-NMR (CDCl3) δ: 7.66 (1H, s), 6.90-6.88 (2H, m), 3.88-3.86 (1H, m), 3.83-3.78 (1H, m), 3.33 (1H, dd, J = 8.1, 5.0 Hz), 3.10 (3H, d, J = 1.2 Hz), 1.64-1.61 (1H, m), 1.47-1.42 (1H, m), 1.14 (3H, t, J = 7.0 Hz), 0.79 (3H, t, J = 7.3 Hz). |
| 48 | ¹H-NMR (CDCl3) δ: 7.65 (1H, s), 6.63-6.60 (2H, m), 3.93-3.81 (5H, m), 3.39 (1H, dd, J = 8.0, 5.2 Hz), 3.10 (3H, d, J = 1.2 Hz), 1.66-1.58 (1H, m), 1.47-1.44 (1H, m), 1.14 (3H, t, J = 7.0 Hz), 0.79 (3H, t, J = 7.3 Hz). |
| 49 | ¹H-NMR (CDCl3) δ: 8.05 (1H, s), 6.84-6.82 (2H, m), 3.93 (2H, q, J = 7.1 Hz), 2.70 (2H, q, J = 7.1 Hz), 1.16 (3H, t, J = 7.1 Hz), 1.05 (3H, t, J = 7.1 Hz). |
| 50 | ¹H-NMR (CDCl3) δ: 7.77 (1H, s), 6.65-6.59 (2H, m), 4.03-3.96 (2H, m), 3.89 (3H, s), 3.73 (1H, dq, J = 13.9, 7.1 Hz), 1.69-1.65 (3H, m), 1.13 (3H, t, J = 7.1 Hz), 0.77 (3H, t, J = 7.4 Hz). |
| 51 | ¹H-NMR (CDCl3) δ: 8.03 (1H, s), 6.59 (2H, dd, J = 11.1, 2.1 Hz), 3.95 (2H, q, J = 7.1 Hz), 3.87 (3H, s), 2.59 (2H, q, J = 7.2 Hz), 1.15 (3H, t, J = 7.1 Hz), 1.03 (3H, t, J = 7.2 Hz). |
| 52 | ¹H-NMR (CDCl3) δ: 7.69 (1H, s), 6.79-6.78 (2H, m), 3.85 (1H, dq, J = 13.8, 7.2 Hz), 3.74 (1H, dq, J = 13.8, 7.2 Hz), 1.70 (1H, dq, J = 14.3, 7.2 Hz), 1.55 (1H, dq, J = 14.3, 7.2 Hz), 1.36 (3H, s), 1.36 (1H, br s), 1.11 (3H, t, J = 7.2 Hz), 0.81 (3H, t, J = 7.2 Hz). |
| 53 | ¹H-NMR (CDCl3) δ: 7.76 (1H, s), 7.56 (1H, tt, J = 8.4, 6.4 Hz), 7.14-7.07 (2H, m), 4.10 (1H, dq, J = 13.7, 7.1 Hz), 3.66-3.57 (2H, m), 1.84-1.80 (1H, m) 1.78 (1H, d, J = 3.4 Hz), 1.12 (3H, t, J = 7.1 Hz), 0.94 (3H, d, J = 6.3 Hz), 0.63 (3H, dd, J = 6.8, 0.7 Hz). |
| 54 | ¹H-NMR (CDCl3) δ: 7.76 (1H, s), 6.85-6.78 (2H, m), 3.82-3.76 (1H, m), 2.98 (3H, s), 1.58-1.54 (2H, m), 1.11 (3H, t, J = 7.7 Hz), 1.09 (3H, s), 0.75 (3H, t, J = 7.4 Hz). |
| 55 | ¹H-NMR (CDCl3) δ: 7.82 (1H, s), 6.59-6.55 (2H, m), 3.88 (3H, s), 3.81 (2H, q, J = 7.1 Hz), 3.03 (3H, s), 1.58-1.51 (2H, m), 1.12 (3H, t, J = 7.1 Hz), 1.04 (3H, s), 0.76 (3H, t, J = 7.3 Hz). |
| 56 | ¹H-NMR (CDCl3) δ: 7.46 (1H, s), 6.81-6.78 (2H, m), 3.89-3.86 (1H, m), 3.77-3.74 (1H, m), 1.84-1.69 (2H, m), 1.46 (3H, d, J = 22.6 Hz), 1.13 (3H, t, J = 7.0 Hz), 0.83 (3H, t, J = 7.3 Hz). |
| 57 | ¹H-NMR (CDCl3) δ: 7.71 (1H, s), 7.54 (1H, tt, J = 8.4, 6.4 Hz), 7.11-7.07 (2H, m), 3.90-3.86 (4H, m), 3.38-3.33 (1H, m), 1.14 (3H, t, J = 7.0 Hz), 1.00 (6H, d, J = 6.1 Hz). |
| 58 | ¹H-NMR (CDCl3) δ: 7.69 (1H, s), 6.88-6.85 (2H, m), 3.89-3.84 (4H, m), 3.38 (1H, dq, J = 6.1, 6.1 Hz), 1.14 (3H, t, J = 7.1 Hz), 1.03 (6H, d, J = 6.1 Hz). |
| 59 | ¹H-NMR (CDCl3) δ: 7.79 (1H, s), 6.58-6.53 (2H, m), 3.90-3.73 (2H, m), 3.86 (3H, s), 1.70-1.48 (2H, m), 1.37 (1H, s), 1.32 (3H, s), 1.11 (3H, t, J = 7.1 Hz), 0.80 (3H, t, J = 7.4 Hz). |
| 60 | ¹H-NMR (CDCl3) δ: 7.70 (1H, s), 6.62-6.61 (2H, m), 3.92 (2H, s), 3.89-3.88 (5H, m), 3.40 (1H, dq, J = 6.1, 6.1 Hz), 1.13 (3H, t, J = 7.0 Hz), 1.04 (6H, d, J = 6.1 Hz). |
| 61 | ¹H-NMR (CDCl3) δ: 7.57 (1H, s), 6.57-6.55 (2H, m), 3.90-3.85 (4H, m), 3.79 (1H, dq, J = 13.6, 7.0 Hz), 1.75-1.70 (2H, m), 1.42 (3H, d, J = 23.2 Hz), 1.12 (3H, t, J = 7.0 Hz), 0.83 (3H, t, J = 7.3 Hz). |
| 62 | ¹H-NMR (CDCl3) δ: 7.71 (1H, s), 7.54 (1H, tt, J = 8.4, 6.4 Hz), 7.11-7.07 (2H, m), 3.91 (2H, s), 3.88 (2H, q, J = 7.0 Hz), 3.27 (2H, q, J = 7.0 Hz), 1.14 (3H, t, J = 7.0 Hz), 1.10 (3H, t, J = 7.0 Hz). |
| 63 | ¹H-NMR (CDCl3) δ: 7.66 (1H, s), 7.56 (1H, tt, J = 8.6, 6.4 Hz), 7.13-7.07 (2H, m), 4.00 (1H, dq, J = 13.9, 7.1 Hz), 3.70 (1H, dq, J = 13.9, 7.1 Hz), 3.12-3.09 (4H, m), 1.72-1.67 (1H, m), 1.14 (3H, t, J = 7.1 Hz), 0.88 (3H, d, J = 6.9 Hz), 0.67 (3H, dd, J = 6.9, 1.4 Hz). |
| 64 | ¹H-NMR (CDCl3) δ: 7.75 (1H, s), 6.90-6.87 (2H, m), 4.13-4.07 (1H, m), 3.63-3.56 (2H, m), 1.83-1.80 (1H, m), 1.70 (1H, d, J = 2.9 Hz), 1.12 (3H, t, J = 7.1 Hz), 0.96 (3H, d, J = 6.8 Hz), 0.64 (3H, d, J = 6.8 Hz). |
| 65 | ¹H-NMR (CDCl3) δ: 7.65 (1H, s), 6.89-6.87 (2H, m), 3.99 (1H, dq, J = 13.7, 6.8 Hz), 3.68 (1H, dq, J = 13.7, 6.8 Hz), |

TABLE 4-continued

| Compounds | ¹H-NMR |
|---|---|
| | 3.11 (3H, s), 3.09 (1H, d, J = 7.6 Hz), 1.69-1.68 (1H, m), 1.14 (3H, t, J = 7.2 Hz), 0.90 (3H, d, J = 6.6 Hz), 0.67 (3H, dd, J = 7.0, 1.3 Hz). |
| 66 | ¹H-NMR (CDCl3) δ: 7.96 (1H, s), 6.84-6.79 (2H, m), 3.93 (2H, q, J = 7.1 Hz), 3.16 (1H, dq, J = 6.8, 6.8 Hz), 1.17 (3H, t, J = 7.1 Hz), 1.06 (6H, d, J = 6.8 Hz). |
| 67 | ¹H-NMR (CDCl3) δ: 7.60 (1H, d, J = 9.8 Hz), 6.82 (2H, dd, J = 8.6, 7.0 Hz), 6.67 (1H, d, J = 9.8 Hz), 3.71 (2H, q, J = 7.0 Hz), 1.08 (3H, t, J = 7.0 Hz), 1.06 (9H, s). |
| 68 | ¹H-NMR (CDCl3) δ: 7.60 (1H, d, J = 10.1 Hz), 6.85-6.80 (2H, m), 6.68 (1H, d, J = 10.1 Hz), 3.18 (3H, s), 1.07 (9H, s). |
| 69 | ¹H-NMR (CDCl3) δ: 7.81 (1H, s), 6.86-6.80 (2H, m), 3.75 (2H, q, J = 7.1 Hz), 1.10 (3H, t, J = 7.1 Hz), 1.07 (9H, s). |
| 70 | ¹H-NMR (CDCl3) δ: 8.01 (1H, s), 6.86-6.80 (2H, m), 3.75 (2H, q, J = 7.1 Hz), 1.09 (3H, t, J = 7.1 Hz), 1.07 (9H, s). |
| 71 | ¹H-NMR (CDCl3) δ: 7.64 (1H, s), 6.62-6.60 (2H, m), 4.00 (1H, dq, J = 13.6, 6.9 Hz), 3.90 (3H, s), 3.72 (1H, dq, J = 13.6, 6.9 Hz), 3.15 (1H, d, J = 7.3 Hz), 3.11 (3H, d, J = 1.8 Hz), 1.72-1.66 (1H, m), 1.14 (3H, t, J = 6.9 Hz), 0.90 (3H, d, J = 6.7 Hz), 0.67 (3H, dd, J = 7.0, 1.2 Hz). |
| 72 | ¹H-NMR (CDCl3) δ: 7.63 (1H, s), 6.60-6.57 (2H, m), 4.09 (2H, q, J = 6.9 Hz), 4.01 (1H, dq, J = 13.6, 7.0 Hz), 3.72 (1H, dq, J = 13.6, 7.0 Hz), 3.16 (1H, d, J = 7.3 Hz), 3.11 (3H, d, J = 1.8 Hz), 1.70-1.69 (1H, m), 1.48 (3H, t, J = 7.0 Hz), 1.14 (3H, t, J = 7.0 Hz), 0.89 (3H, d, J = 6.4 Hz), 0.67 (3H, dd, J = 7.0, 1.2 Hz). |
| 73 | ¹H-NMR (CDCl3) δ: 7.93 (1H, s), 6.59-6.55 (2H, m), 3.95 (2H, q, J = 7.1 Hz), 3.86 (3H, s), 3.11-3.04 (1H, m), 1.16 (3H, t, J = 7.1 Hz), 1.04 (6H, d, J = 6.8 Hz). |
| 74 | ¹H-NMR (CDCl3) δ: 7.80 (1H, s), 6.57 (2H, d, J = 8.8 Hz), 3.88 (3H, s), 3.78 (2H, q, J = 7.1 Hz), 1.10 (3H, t, J = 7.1 Hz), 1.07 (9H, s). |
| 75 | ¹H-NMR (CDCl3) δ: 7.80 (1H, s), 6.55 (2H, d, J = 8.9 Hz), 4.08 (2H, q, J = 6.9 Hz), 3.78 (2H, q, J = 7.1 Hz), 1.47 (3H, t, J = 6.9 Hz), 1.10 (3H, t, J = 7.1 Hz), 1.08 (9H, s). |
| 76 | ¹H-NMR (CDCl3) δ: 8.00 (1H, s), 6.57 (2H, d, J = 8.9 Hz), 3.88 (3H, s), 3.78 (2H, q, J = 7.0 Hz), 1.09 (3H, t, J = 7.0 Hz), 1.07 (9H, s). |
| 77 | ¹H-NMR (CDCl3) δ: 7.81 (1H, s), 6.86-6.81 (2H, m), 3.24 (3H, s), 1.08 (9H, s). |
| 78 | ¹H-NMR (CDCl3) δ: 8.01 (1H, s), 6.86-6.81 (2H, m), 3.25 (3H, s), 1.08 (9H, s). |
| 79 | ¹H-NMR (CDCl3) δ: 7.80 (1H, s), 6.60-6.55 (2H, m), 3.87 (3H, s), 3.25 (3H, s), 1.09 (9H, s). |
| 80 | ¹H-NMR (CDCl3) δ: 7.78 (1H, s), 7.51 (1H, tt, J = 8.6, 6.4 Hz), 7.07-7.05 (2H, m), 3.86 (2H, q, J = 7.0 Hz), 2.91 (2H, s), 2.65 (1H, dq, J = 6.7, 6.7 Hz), 1.96 (3H, s), 1.13 (3H, t, J = 7.0 Hz), 0.84 (6H, d, J = 6.7 Hz). |
| 81 | ¹H-NMR (CDCl3) δ: 7.68 (1H, s), 6.93-6.85 (2H, m), 3.84 (2H, q, J = 7.2 Hz), 3.46 (1H, dd, J = 10.0, 2.7 Hz), 3.08 (3H, d, J = 0.7 Hz), 1.71-1.59 (2H, m), 1.15 (3H, t, J = 7.1 Hz), 1.04-0.99 (1H, m), 0.82 (3H, d, J = 6.6 Hz), 0.60 (3H, d, J = 6.6 Hz). |
| 82 | ¹H-NMR (CDCl3) δ: 8.00 (1H, s), 6.59-6.55 (2H, m), 3.87 (3H, s), 3.26 (3H, s), 1.09 (9H, s). |
| 83 | ¹H-NMR (CDCl3) δ: 7.80 (1H, s), 6.63-6.58 (2H, m), 4.17-4.15 (2H, m), 3.80-3.75 (4H, m), 3.48 (3H, s), 1.09 (3H, t, J = 7.1 Hz), 1.07 (9H, s). |
| 84 | ¹H-NMR (CDCl3) δ: 7.80 (1H, s), 6.63-6.59 (2H, m), 4.17-4.14 (2H, m), 3.80-3.78 (2H, m), 3.47 (3H, s), 3.25 (3H, s), 1.08 (9H, s). |
| 85 | ¹H-NMR (CDCl3) δ: 7.80 (1H, s), 6.58-6.53 (2H, m), 4.07 (2H, q, J = 7.0 Hz), 3.25 (3H, s), 1.47 (3H, t, J = 7.0 Hz), 1.09 (9H, s). |
| 86 | ¹H-NMR (CDCl3) δ: 7.75 (1H, s), 6.85-6.82 (2H, m), 3.85 (2H, q, J = 7.2 Hz), 2.91 (2H, s), 2.64 (1H, dq, J = 6.3, 6.3 Hz), 1.96 (3H, s), 1.13 (3H, t, J = 7.2 Hz), 0.86 (6H, d, J = 6.3 Hz). |
| 87 | ¹H-NMR (CDCl3) δ: 7.67 (1H, s), 6.63-6.61 (2H, m), 3.89 (3H, s), 3.87 (2H, q, J = 7.2 Hz), 3.53 (1H, dd, J = 9.9, 2.8 Hz), 3.08 (3H, d, J = 1.0 Hz), 1.68-1.63 (2H, m), 1.14 (3H, t, J = 7.2 Hz), 1.06-1.04 (1H, m), 0.82 (3H, d, J = 6.6 Hz), 0.61 (3H, d, J = 6.6 Hz). |
| 88 | ¹H-NMR (CDCl3) δ: 7.78 (1H, s), 6.60-6.57 (2H, m), 3.90 (3H, s), 3.88 (2H, q, J = 7.2 Hz), 2.93 (2H, s), 2.69 (1H, dq, J = 6.6, 6.6 Hz), 1.97 (3H, s), 1.12 (3H, t, J = 7.2 Hz), 0.88 (6H, d, J = 6.6 Hz). |
| 89 | ¹H-NMR (CDCl3) δ: 7.78 (1H, s), 6.60-6.57 (2H, m), 3.90 (3H, s), 3.88 (2H, q, J = 7.2 Hz), 2.93 (2H, s), 2.69 (1H, dq, J = 6.6, 6.6 Hz), 1.97 (3H, s), 1.12 (3H, t, J = 7.2 Hz), 0.88 (6H, d, J = 6.6 Hz) |
| 90 | ¹H-NMR (CDCl3) δ: 7.81 (1H, s), 6.93-6.85 (2H, m), 4.13-4.07 (1H, m), 3.95 (1H, dq, J = 13.8, 6.9 Hz), 3.74 (1H, dq, J = 13.8, 6.9 Hz), 1.67-1.59 (3H, m), 1.21-1.20 (1H, m), 1.13 (3H, t, J = 7.2 Hz), 0.81 (3H, d, J = 6.4 Hz), 0.67 (3H, d, J = 6.4 Hz). |
| 91 | ¹H-NMR (CDCl3) δ: 7.77 (1H, s), 6.85 (2H, td, J = 8.6, 1.8 Hz), 3.86 (2H, q, J = 7.1 Hz), 2.80 (2H, s), 2.06 (6H, s), 1.13 (3H, t, J = 7.1 Hz). |
| 92 | ¹H-NMR (CDCl3) δ: 7.79 (1H, s), 6.60-6.59 (2H, m), 3.89-3.87 (5H, m), 2.83 (2H, s), 2.06 (6H, s), 1.13 (3H, t, J = 7.0 Hz). |
| 93 | ¹H-NMR (CDCl3) δ: 7.74 (1H, s), 6.56 (2H, dd, J = 12.0, 2.7 Hz), 4.07 (2H, q, J = 7.0 Hz), 3.90 (2H, q, J = 7.1 Hz), 3.30 (3H, s), 2.83 (2H, s), 2.41 (3H, s), 1.47 (3H, t, J = 7.0 Hz), 1.13 (3H, t, J = 7.1 Hz). |
| 94 | ¹H-NMR (CDCl3) δ: 7.74 (1H, s), 6.59 (2H, dd, J = 12.0, 2.8 Hz), 3.91 (2H, q, J = 7.1 Hz), 3.87 (3H, s), 3.30 (3H, s), 3.20 (2H, s), 2.41 (3H, s), 1.14 (3H, t, J = 7.1 Hz). |
| 95 | ¹H-NMR (CDCl3) δ: 7.43 (1H, td, J = 8.4, 6.7 Hz), 7.27-7.25 (1H, m), 6.84-6.78 (2H, m), 6.61 (1H, d, J = 9.3 Hz), 4.00-3.91 (1H, m), 3.78 (3H, s), 3.67-3.58 (1H, m), 1.93-1.83 (2H, m), 1.63-1.53 (1H, m), 1.06 (3H, t, J = 7.1 Hz), 0.73 (3H, d, J = 6.6 Hz), 0.70 (3H, d, J = 6.6 Hz). |
| 96 | ¹H-NMR (CDCl3) δ: 7.69 (1H, s), 7.45 (1H, td, J = 8.4, 6.6 Hz), 6.83 (1H, td, J = 8.4, 0.8 Hz), 6.81-6.79 (1H, m), 4.03-3.96 (1H, m), 3.78 (3H, s), 3.72-3.63 (1H, m), 1.92-1.83 (2H, m), 1.63-1.55 (1H, m), 1.08 (3H, t, J = 7.0 Hz), 0.74 (3H, d, J = 6.4 Hz), 0.71 (3H, d, J = 6.7 Hz). |
| 97 | ¹H-NMR (CDCl3) δ: 7.48 (1H, s), 7.45 (1H, td, J = 8.4, 6.5 Hz), 6.83 (1H, td, J = 8.4, 0.9 Hz), 6.81-6.79 (1H, m), 4.03-3.96 (1H, m), 3.78 (3H, s), 3.71-3.63 (1H, m), 1.93-1.84 (2H, m), 1.63-1.55 (1H, m), 1.08 (3H, t, J = 7.2 Hz), 0.74 (3H, d, J = 6.4 Hz), 0.71 (3H, d, J = 6.4 Hz). |
| 98 | ¹H-NMR (CDCl3) δ: 7.31-7.24 (3H, m), 7.14 (1H, ddd, J = 8.5, 7.8, 2.7 Hz), 6.63 (1H, d, J = 9.5 Hz), 4.15-4.03 (1H, m), 3.47-3.38 (1H, m), 1.97 (1H, dd, J = 13.9, 6.8 Hz), 1.75 (1H, dd, J = 13.9, 7.8 Hz), 1.68-1.57 (1H, m), 1.09 (3H, t, J = 7.0 Hz), 0.79 (3H, d, J = 6.6 Hz), 0.73 (3H, d, J = 6.6 Hz). |
| 99 | ¹H-NMR (CDCl3) δ: 7.49 (1H, s), 7.30 (1H, dd, J = 8.3, 2.4 Hz), 7.25 (1H, dd, J = 8.5, 5.9 Hz), 7.15 (1H, ddd, J = 8.5, 7.8, 2.4 Hz), 4.15-4.07 (1H, m), 3.52-3.43 (1H, m), 1.98 (1H, dd, J = 14.2, 6.8 Hz), 1.75 (1H, dd, J = 14.2, 8.1 Hz), 1.69-1.59 (1H, m), 1.11 (3H, t, J = 7.1 Hz), 0.80 (3H, d, J = 6.6 Hz), 0.74 (3H, d, J = 6.6 Hz). |
| 100 | ¹H-NMR (CDCl3) δ: 7.69 (1H, s), 7.30 (1H, dd, J = 8.3, 2.5 Hz), 7.25 (1H, dd, J = 8.5, 5.9 Hz), 7.15 (1H, ddd, J = 8.5, 7.8, 2.5 Hz), 4.15-4.06 (1H, m), 3.52-3.43 (1H, m), 1.98 (1H, dd, J = 14.2, 6.8 Hz), 1.74 (1H, dd, J = 14.2, 7.9 Hz), 1.68-1.59 (1H, m), 1.11 (3H, t, J = 7.0 Hz), 0.80 (3H, d, J = 6.6 Hz), 0.73 (3H, d, J = 6.6 Hz). |
| 101 | ¹H-NMR (CDCl3) δ: 8.36 (1H, br s), 7.54 (1H, s), 7.34 (1H, td, J = 8.2, 6.7 Hz), 7.05-7.02 (1H, m), 6.74-6.69 (1H, m), 4.04-3.95 (1H, m), 3.83-3.74 (1H, m), 2.05-1.95 (2H, m), 1.70-1.60 (1H, m), 1.08 (3H, t, J = 7.1 Hz), 0.76 (6H, t, J = 6.5 Hz). |
| 102 | ¹H-NMR (CDCl3) δ: 7.50-7.44 (2H, m), 6.95 (1H, d, J = 8.5 Hz), 6.88 (1H, td, J = 8.4, 0.8 Hz), 4.69 (2H, d, J = 2.4 Hz), 4.04-3.95 (1H, m), 3.73-3.65 (1H, m), 2.49 (1H, t, J = 2.4 Hz), 1.89 (2H, d, J = 7.3 Hz), 1.64-1.57 (1H, m), 1.10 (3H, t, J = 7.1 Hz), 0.73 (6H, t, J = 6.7 Hz). |
| 103 | ¹H-NMR (CDCl3) δ: 7.49 (1H, s), 7.43 (1H, td, J = 8.4, 6.7 Hz), 7.07 (1H, d, J = 8.4 Hz), 6.88 (1H, td, J = 8.4, 0.7 Hz), 5.15 (1H, d, J = 7.1 Hz), 5.10 (1H, d, J = 7.1 Hz), 4.12-4.03 (1H, m), 3.70-3.61 (1H, m), 3.40 (3H, s), 1.95-1.86 (2H, m), 1.64-1.56 (1H, m), 1.11 (3H, t, J = 7.1 Hz), 0.74 (6H, dd, J = 6.6, 3.2 Hz). |
| 104 | ¹H-NMR (CDCl3) δ: 7.49 (1H, s), 7.43 (1H, td, J = 8.4, 6.6 Hz), 6.83 (1H, td, J = 8.4, 0.7 Hz), 6.79 (1H, d, J = 8.4 Hz), 5.91-5.83 (1H, m), 5.25-5.23 (1H, m), 5.21 (1H, t, J = 1.7 Hz), 4.56-4.47 (2H, m), 4.04-3.98 (1H, m), 3.73-3.66 (1H, m), 1.93-1.86 (2H, m), 1.65-1.56 (1H, m), 1.09 (3H, t, J = 7.0 Hz), 0.74-0.71 (6H, m). |

TABLE 4-continued

| Compounds | $^1$H-NMR |
|---|---|
| 105 | $^1$H-NMR (CDCl3) δ: 7.49 (1H, s), 7.46 (1H, td, J = 8.6, 6.7 Hz), 6.88 (1H, td, J = 8.6, 0.7 Hz), 6.84 (1H, d, J = 8.6 Hz), 5.15 (1H, d, J = 12.2 Hz), 5.11 (1H, d, J = 12.2 Hz), 4.13-4.06 (1H, m), 3.68-3.61 (1H, m), 2.15 (3H, s), 1.90 (2H, d, J = 7.0 Hz), 1.64-1.56 (1H, m), 1.10 (3H, t, J = 7.0 Hz), 0.74 (6H, d, J = 6.4 Hz). |
| 106 | $^1$H-NMR (CDCl3) δ: 7.64 (1H, s), 6.78-6.76 (2H, m), 3.90-3.87 (1H, m), 3.73-3.68 (1H, m), 1.86 (1H, dq, J = 6.7, 6.7 Hz), 1.36 (3H, s), 1.11-1.10 (4H, m), 0.86 (3H, d, J = 6.7 Hz), 0.78 (3H, d, J = 6.7 Hz). |
| 107 | $^1$H-NMR (CDCl3) δ: 7.76 (1H, s), 6.86-6.79 (2H, m), 3.80-3.74 (2H, m), 3.02 (3H, d, J = 1.0 Hz), 1.73 (1H, dq, J = 6.8, 6.8 Hz), 1.12 (3H, t, J = 7.1 Hz), 0.98 (3H, s), 0.83 (3H, d, J = 6.8 Hz), 0.72 (3H, d, J = 6.8 Hz). |
| 108 | $^1$H-NMR (CDCl3) δ: 7.75 (1H, s), 6.55-6.54 (2H, m), 3.89-3.86 (4H, m), 3.77-3.71 (1H, m), 1.83 (1H, dq, J = 6.7, 6.7 Hz), 1.31 (3H, s), 1.22 (1H, s), 1.11 (3H, t, J = 7.0 Hz), 0.85 (3H, d, J = 6.7 Hz), 0.78 (3H, d, J = 6.7 Hz). |
| 109 | $^1$H-NMR (CDCl3) δ: 7.85 (1H, s), 6.84-6.82 (2H, m), 3.79 (2H, q, J = 7.1 Hz), 3.01 (3H, s), 1.19 (6H, s), 1.12 (3H, t, J = 7.1 Hz). |
| 110 | 1H-NMR (CDCl3) δ: 7.79 (1H, s), 6.59-6.54 (2H, m), 3.88 (3H, s), 3.84 (1H, dd, J = 13.8, 7.0 Hz), 3.74 (1H, dd, J = 13.8, 7.0 Hz), 3.03 (3H, s), 1.75 (1H, dq, J = 6.6, 6.6 Hz), 1.11 (3H, t, J = 7.0 Hz), 0.94 (3H, s), 0.83 (3H, d, J = 6.6 Hz), 0.72 (3H, d, J = 6.6 Hz). |
| 111 | $^1$H-NMR (CDCl3) δ: 7.24 (1H, d, J = 9.3 Hz), 7.09 (1H, t, J = 8.4 Hz), 6.81 (1H, dd, J = 8.4, 2.4 Hz), 6.74 (1H, dd, J = 11.0, 2.4 Hz), 6.61 (1H, d, J = 9.3 Hz), 3.92 (4H, td, J = 13.2, 6.3 Hz), 3.71 (1H, td, J = 13.6, 6.9 Hz), 1.92 (2H, dq, J = 28.6, 7.1 Hz), 1.66-1.57 (5H, m), 1.08 (3H, t, J = 7.0 Hz), 0.74 (6H, d, J = 6.6 Hz). |
| 112 | $^1$H-NMR (CDCl3) δ: 7.74 (1H, s), 6.86-6.85 (2H, m), 5.49 (1H, br s), 3.87 (2H, q, J = 7.1 Hz), 3.46 (2H, s), 3.36 (3H, s), 1.14 (3H, t, J = 7.1 Hz). |
| 113 | $^1$H-NMR (CDCl3) δ: 7.87 (1H, s), 6.59-6.57 (2H, m), 3.88 (3H, s), 3.81 (2H, q, J = 7.1 Hz), 3.04 (3H, s), 1.17 (6H, s), 1.12 (3H, t, J = 7.1 Hz). |
| 114 | $^1$H-NMR (CDCl3) δ: 7.74 (1H, s), 6.62-6.58 (2H, m), 5.47 (1H, br s), 3.90 (2H, q, J = 7.1 Hz), 3.87 (3H, s), 3.49 (2H, s), 3.40 (3H, s), 1.13 (3H, t, J = 7.2 Hz). |
| 115 | $^1$H-NMR (CDCl3) δ: 7.47 (1H, s), 7.08 (1H, t, J = 8.4 Hz), 6.82 (1H, dd, J = 8.4, 2.6 Hz), 6.75 (1H, dd, J = 11.0, 2.6 Hz), 4.01-3.92 (1H, m), 3.89 (3H, s), 3.80-3.71 (1H, m), 1.99-1.87 (2H, m), 1.67-1 .57 (1H, m), 1.10 (3H, t, J = 7.0 Hz), 0.75 (6H, d, J = 6.6 Hz). |
| 116 | $^1$H-NMR (CDCl3) δ: 7.68 (1H, s), 7.08 (1H, t, J = 8.4 Hz), 6.82 (1H, dd, J = 8.4, 2.4 Hz), 6.74 (1H, dd, J = 11.0, 2.4 Hz), 4.01-3.90 (1H, m), 3.89 (3H, s), 3.80-3.71 (1H, m), 1.99-1.86 (2H, m), 1.67-1.56 (1H, m), 1.10 (3H, t, J = 7.1 Hz), 0.75 (6H, d, J = 6.6 Hz). |
| 117 | $^1$H-NMR (CDCl3) δ: 7.25 (1H, d, J = 9.5 Hz), 7.21 (1H, td, J = 8.3, 6.3 Hz), 7.06-6.96 (2H, m), 6.63 (1H, d, J = 9.5 Hz), 3.94-3.86 (1H, m), 3.72-3.63 (1H, m), 1.95-1.83 (2H, m), 1.66-1.55 (1H, m), 1.08 (3H, t, J = 7.1 Hz), 0.75 (6H, d, J = 6.6 Hz). |
| 118 | $^1$H-NMR (CDCl3) δ: 7.63 (1H, s), 7.52 (1H, s), 7.00 (1H, t, J = 8.3 Hz), 6.84 (1H, dd, J = 8.3, 2.3 Hz), 6.81 (1H, dd, J = 10.5, 2.3 Hz), 4.05-3.98 (1H, m), 3.84-3.77 (1H, m), 2.00 (1H, dd, J = 14.1, 7.3 Hz), 1.93 (1H, dd, J = 14.1, 7.3 Hz), 1.67-1.58 (1H, m), 1.12 (3H, t, J = 7.0 Hz), 0.76 (6H, d, J = 6.7 Hz). |
| 119 | $^1$H-NMR (CDCl3) δ: 7.48 (1H, s), 7.20 (1H, td, J = 8.3, 6.2 Hz), 7.07-7.03 (1H, m), 6.99 (1H, td, J = 8.9, 2.4 Hz), 3.98-3.91 (1H, m), 3.76-3.69 (1H, m), 1.93 (1H, dd, J = 14.1, 7.3 Hz), 1.87 (1H, dd, J = 14.1, 7.3 Hz), 1.66-1.57 (1H, m), 1.10 (3H, t, J = 7.0 Hz), 0.76 (6H, d, J = 6.7 Hz). |
| 120 | $^1$H-NMR (CDCl3) δ: 7.69 (1H, s), 7.20 (1H, td, J = 8.3, 6.2 Hz), 7.07-7.03 (1H, m), 6.99 (1H, td, J = 8.9, 2.4 Hz), 3.98-3.91 (1H, m), 3.76-3.69 (1H, m), 1.93 (1H, dd, J = 14.2, 7.2 Hz), 1.86 (1H, dd, J = 14.2, 7.2 Hz), 1.65-1.57 (1H, m), 1.10 (3H, t, J = 7.0 Hz), 0.76 (6H, d, J = 6.7 Hz). |
| 121 | $^1$H-NMR (CDCl3) δ: 7.46 (1H, s), 7.07 (1H, t, J = 8.4 Hz), 6.84 (1H, dd, J = 8.4, 2.4 Hz), 6.77 (1H, dd, J = 11.0, 2.4 Hz), 4.19-4.17 (2H, m), 3.96 (1H, td, J = 13.5, 6.8 Hz), 3.81-3.70 (3H, m), 3.48 (3H, s), 1.98-1.85 (2H, m), 1.66-1.56 (1H, m), 1.09 (3H, t, J = 7.1 Hz), 0.75 (6H, d, J = 6.6 Hz). |
| 122 | $^1$H-NMR (CDCl3) δ: 7.47 (1H, s), 7.08 (1H, t, J = 8.2 Hz), 6.95-6.89 (2H, m), 5.24 (2H, s), 4.01-3.92 (1H, m), 3.80-3.71 (1H, m), 3.54 (3H, s), 1.99-1.86 (2H, m), 1.67-1.57 (1H, m), 1.11 (3H, t, J = 7.0 Hz), 0.76 (6H, d, J = 6.6 Hz). |
| 123 | $^1$H-NMR (CDCl3) δ: 7.48 (1H, s), 7.07 (1H, t, J = 8.4 Hz), 6.82-6.80 (1H, m), 6.73 (1H, dd, J = 11.2, 2.3 Hz), 4.10 (2H, q, J = 7.0 Hz), 4.01-3.94 (1H, m), 3.80-3.73 (1H, m), 1.97 (1H, dd, J = 14.0, 7.3 Hz), 1.90 (1H, dd, J = 14.0, 7.3 Hz), 1.66-1.58 (1H, m), 1.48 (3H, t, J = 7.0 Hz), 1.11 (3H, t, J = 7.0 Hz), 0.76 (6H, d, J = 6.6 Hz). |
| 124 | $^1$H-NMR (CDCl3) δ: 7.47 (1H, s), 7.07 (1H, t, J = 8.4 Hz), 6.83 (1H, dd, J = 8.4, 2.4 Hz), 6.76 (1H, dd, J = 11.0, 2.4 Hz), 6.13-6.03 (1H, m), 5.47 (1H, dq, J = 17.3, 1.5 Hz), 5.36 (1H, dq, J = 10.5, 1.5 Hz), 4.60 (2H, dt, J = 5.4, 1.5 Hz), 4.01-3.92 (1H, m), 3.79-3.71 (1H, m), 1.99-1.86 (2H, m, ). 1.66-1.56 (1H, m), 1.10 (3H, t, J = 7.1 Hz), 0.75 (6H, d, J = 6.6 Hz). |
| 125 | $^1$H-NMR (CDCl3) δ: 7.47 (1H, s), 7.10 (1H, t, J = 8.4 Hz), 6.90 (1H, dd, J = 8.4, 2.6 Hz), 6.85 (1H, dd, J = 11.0, 2.6 Hz), 4.77 (2H, d, J = 2.4 Hz), 4.01-3.92 (1H, m), 3.79-3.71 (1H, m), 2.61 (1H, t, J = 2.4 Hz), 1.98-1.86 (2H, m), 1.67-1.56 (1H, m), 1.10 (3H, t, J = 7.1 Hz), 0.75 (6H, d, J = 6.8 Hz). |
| 126 | $^1$H-NMR (CDCl3) δ: 7.47 (1H, s), 7.05 (1H, t, J = 8.4 Hz), 6.80 (1H, dd, J = 8.4, 2.4 Hz), 6.73 (1H, dd, J = 11.2, 2.4 Hz), 4.01-3.92 (3H, m), 3.80-3.71 (1H, m), 1.99-1.82 (4H, m), 1.67-1.57 (1H, m), 1.12-1.06 (6H, m), 0.75 (6H, d, J = 6.6 Hz). |
| 127 | $^1$H-NMR (CDCl3) δ: 7.48 (1H, s), 7.19 (1H, t, J = 8.4 Hz), 6.93 (1H, dd, J = 8.4, 2.4 Hz), 6.87 (1H, dd, J = 10.2, 2.4 Hz), 4.87 (2H, s), 3.98-3.91 (1H, m), 3.77-3.69 (1H, m), 1.94 (1H, dd, J = 14.1, 7.3 Hz), 1.88 (1H, dd, J = 14.1, 7.3 Hz), 1.66-1.58 (1H, m), 1.11 (3H, t, J = 7.0 Hz), 0.76 (6H, d, J = 6.7 Hz). |
| 128 | $^1$H-NMR (CDCl3) δ: 7.47 (1H, s), 7.10 (1H, t, J = 8.4 Hz), 6.88-6.85 (1H, m), 6.81 (1H, dd, J = 10.9, 2.3 Hz), 5.20 (2H, s), 4.01-3.92 (1H, m), 3.80-3.71 (1H, m), 2.32 (3H, s), 1.99-1.86 (2H, m), 1.66-1.57 (1H, m), 1.11 (3H, t, J = 7.1 Hz), 0.76 (6H, d, J = 6.6 Hz). |
| 129 | $^1$H-NMR (CDCl3) δ: 7.47 (1H, s), 7.05 (1H, t, J = 8.4 Hz), 6.80 (1H, dd, J = 8.4, 2.4 Hz), 6.73 (1H, dd, J = 11.1, 2.4 Hz), 4.00-3.92 (1H, m), 3.86 (2H, d, J = 6.8 Hz), 3.79-3.71 (1H, m), 1.99-1.86 (2H, m), 1.67-1.57 (1H, m), 1.36-1.27 (1H, m), 1.10 (3H, t, J = 7.0 Hz), 0.75 (6H, d, J = 6.6 Hz), 0.72-0.68 (2H, m), 0.42-0.38 (2H, m) |
| 130 | $^1$H-NMR (CDCl3) δ: 7.65 (1H, s), 6.63-6.62 (2H, m), 4.28 (2H, s), 3.89 (2H, q, J = 7.0 Hz), 3.88 (3H, s), 3.48 (3H, s), 2.12 (3H, s), 1.13 (3H, t, J = 7.0 Hz). |
| 131 | $^1$H-NMR (CDCl3) δ: 7.71 (1H, s), 6.62-6.60 (2H, m), 4.12 (2H, s), 3.91 (2H, q, J = 7.1 Hz), 3.87 (3H, s), 3.73 (3H, s), 3.49 (3H, s), 1.14 (3H, t, J = 7.1 Hz). |
| 132 | $^1$H-NMR (CDCl3) δ: 7.67 (1H, s), 6.89 (2H, td, J = 8.6, 1.8 Hz), 4.25 (2H, s), 3.87 (2H, q, J = 7.0 Hz), 3.50 (3H, s), 2.11 (3H, s), 1.4 (3H, t, J = 7.0 Hz). |
| 133 | $^1$H-NMR (CDCl3) δ: 7.72 (1H, s), 6.88-6.86 (2H, m), 4.10 (2H, s), 3.88 (2H, q, J = 7.1 Hz), 3.73 (3H, s), 3.50 (3H, s), 1.14 (3H, t, J = 7.1 Hz). |
| 134 | $^1$H-NMR (CDCl3) δ: 7.57 (1H, d, J = 2.1 Hz), 7.41 (1H, dd, J = 8.2, 2.1 Hz), 7.29 (1H, d, J = 9.3 Hz), 7.17 (1H, d, J = 8.2 Hz), 6.65 (1H, d, J = 9.3 Hz), 3.20 (3H, s), 2.00 (1H, dd, J = 14.2, 7.1 Hz), 1.82 (1H, dd, J = 14.2, 7.8 Hz), 1.70-1.57 (1H, m), 0.79 (3H, d, J = 6.6 Hz), 0.75 (3H, d, J = 6.6 Hz). |
| 135 | $^1$H-NMR (CDCl3) δ: 7.56 (1H, d, J = 2.0 Hz), 7.40 (1H, dd, J = 8.2, 2.0 Hz), 7.26 (1H, d, J = 9.3 Hz), 7.21 (1H, d, J = 8.2 Hz), 6.63 (1H, d, J = 9.3 Hz), 4.11-4.02 (1H, m), 3.46-3.38 (1H, m), 1.97 (1H, dd, J = 14.2, 6.8 Hz), 1.75 (1H, dd, J = 14.2, 7.8 Hz), 1.69-1.58 (1H, m), 1.09 (3H, t, J = 7.1 Hz), 0.79 (3H, d, J = 6.6 Hz), 0.73 (3H, d, J = 6.6 Hz). |
| 136 | $^1$H-NMR (CDCl3) δ: 7.46-7.41 (2H, m), 7.25 (1H, d, J = 9.5 Hz), 7.13-7.09 (1H, m), 6.63 (1H, d, J = 9.5 Hz), 3.94-3.85 (1H, m), 3.71-3.62 (1H, m), 1.95-1.83 (2H, m), 1.66-1.56 (1H, m), 1.08 (3H, t, J = 7.1 Hz), 0.75 (6H, d, J = 6.6 Hz). |
| 137 | $^1$H-NMR (CDCl3) δ: 7.58 (1H, d, J = 2.1 Hz), 7.50 (1H, s), 7.42 (1H, dd, J = 8.0, 2.1 Hz), 7.15 (1H, d, J = 8.0 Hz), 3.26 (3H, s), 2.00 (1H, dd, J = 14.1, 7.0 Hz), 1.82 (1H, dd, J = 14.1, 7.8 Hz), 1.69-1.61 (1H, m), 0.79 (3H, d, J = 6.4 Hz), 0.76 (3H, d, J = 6.4 Hz). |
| 138 | $^1$H-NMR (CDCl3) δ: 7.71 (1H, s), 7.58 (1H, d, J = 2.1 Hz), 7.42 (1H, dd, J = 8.3, 2.1 Hz), 7.15 (1H, d, J = 8.3 Hz), 3.27 (3H, s), 2.00 (1H, dd, J = 14.1, 7.0 Hz), 1.81 (1H, dd, J = |

TABLE 4-continued

| Compounds | ¹H-NMR |
|---|---|
| | 14.1, 8.0 Hz), 1.69-1.61 (1H, m), 0.79 (3H, d, J = 6.7 Hz), 0.76 (3H, d, J = 6.7 Hz). |
| 139 | ¹H-NMR (CDCl3) δ: 7.57 (1H, d, J = 2.0 Hz), 7.49 (1H, s), 7.41 (1H, dd, J = 8.3, 2.0 Hz), 7.20 (1H, d, J = 8.3 Hz), 4.15-4.06 (1H, m), 3.51-3.42 (1H, m), 1.98 (1H, dd, J = 14.2, 6.8 Hz), 1.75 (1H, dd, J = 14.2, 7.9 Hz), 1.70-1.60 (1H, m), 1.11 (3H, t, J = 7.1 Hz), 0.80 (3H, d, J = 6.6 Hz), 0.74 (3H, d, J = 6.6 Hz). |
| 140 | ¹H-NMR (CDCl3) δ: 7.69 (1H, s), 7.57 (1H, d, J = 2.0 Hz), 7.41 (1H, dd, J = 8.3, 2.0 Hz), 7.20 (1H, d, J = 8.3 Hz), 4.15-4.06 (1H, m), 3.51-3.43 (1H, m), 1.98 (1H, dd, J = 14.2, 6.7 Hz), 1.74 (1H, dd, J = 14.2, 8.1 Hz), 1.70-1.61 (1H, m), 1.11 (3H, t, J = 7.1 Hz), 0.80 (3H, d, J = 6.6 Hz), 0.74 (3H, d, J = 6.3 Hz). |
| 141 | ¹H-NMR (CDCl3) δ: 7.25 (1H, d, J = 9.3 Hz), 7.09-7.05 (2H, m), 7.03-7.00 (1H, m), 6.60 (1H, d, J = 9.3 Hz), 3.95-3.87 (1H, m), 3.74-3.65 (1H, m), 2.45 (3H, s), 1.97-1.84 (2H, m), 1.65-1.56 (1H, m), 1.08 (3H, t, J = 7.1 Hz), 0.74 (6H, d, J = 6.6 Hz). |
| 142 | ¹H-NMR (CDCl3) δ: 7.68 (1H, s), 7.47-7.42 (2H, m), 7.12-7.07 (1H, m), 3.98-3.89 (1H, m), 3.75-3.66 (1H, m), 1.96-1.84 (2H, m), 1.67-1.58 (1H, m), 1.10 (3H, t, J = 7.0 Hz), 0.76 (6H, d, J = 6.6 Hz). |
| 143 | ¹H-NMR (CDCl3) δ: 7.48-7.41 (3H, m), 7.11-7.07 (1H, m), 3.98-3.89 (1H, m), 3.75-3.67 (1H, m), 1.96-1.84 (2H, m), 1.68-1.58 (1H, m), 1.10 (3H, t, J = 7.1 Hz), 0.76 (6H, d, J = 6.6 Hz). |
| 144 | ¹H-NMR (CDCl3) δ: 7.25-7.16 (5H, m), 6.59 (1H, d, J = 9.3 Hz), 3.77 (2H, q, J = 7.0 Hz), 1.88 (2H, d, J = 7.3 Hz), 1.63-1.54 (1H, m), 1.08 (3H, t, J = 7.0 Hz), 0.74 (6H, d, J = 6.6 Hz). |
| 145 | ¹H-NMR (CDCl3) δ 7.97 (1H, d, J = 9.3 Hz), 7.22-7.16 (4H, m), 6.62 (1H, d, J = 9.3 Hz), 3.19 (3H, s), 1.94 (2H, d, J = 7.3 Hz), 1.65-1.55 (1H, m), 0.74 (6H, d, J = 6.6 Hz). |
| 146 | ¹H-NMR (CDCl3) δ: 7.47 (1H, s), 7.09-7.01 (3H, m), 3.99-3.91 (1H, m), 3.78-3.70 (1H, m), 2.45 (3H, s), 1.98-1.85 (2H, m), 1.67-1.57 (1H, m), 1.10 (3H, t, J = 7.1 Hz), 0.75 (6H, d, J = 6.6 Hz). |
| 147 | ¹H-NMR (CDCl3) δ: 7.68 (1H, s), 7.09-7.00 (3H, m), 3.99-3.91 (1H, m), 3.78-3.70 (1H, m), 2.45 (3H, s), 1.97-1.84 (2H, m), 1.67-1.57 (1H, m), 1.10 (3H, t, J = 7.1 Hz), 0.74 (6H, d, J = 6.6 Hz). |
| 148 | ¹H-NMR (CDCl3) δ: 7.67 (1H, s), 7.21-7.17 (4H, m), 3.81 (2H, q, J = 7.1 Hz), 1.88 (2H, d, J = 7.3 Hz), 1.65-1.55 (1H, m), 1.10 (3H, t, J = 7.1 Hz), 0.75 (6H, d, J = 6.6 Hz). |
| 149 | ¹H-NMR (CDCl3) δ: 7.46 (1H s), 7.22-7.17 (4H, m), 3.81 (2H, q, J = 7.1 Hz), 1.88 (2H, d, J = 7.6 Hz), 1.66-1.56 (1H, m), 1.10 (3H, t, J = 7.1 Hz), 0.75 (6H, d, J = 6.6 Hz). |
| 150 | ¹H-NMR (CDCl3) δ: 7.82 (1H, s), 6.82-6.80 (2H, m), 3.80 (2H, q, J = 7.0 Hz), 1.41 (1H, s), 1.38 (6H, s), 1.12 (3H, t, J = 7.0 Hz). |
| 151 | ¹H-NMR (CDCl3) δ: 7.73 (1H, s), 6.87-6.82 (2H, m), 3.90-3.86 (2H, m), 3.25 (3H, s), 3.18 (2H, s), 2.52 (2H, q, J = 7.0 Hz), 1.14 (3H, t, J = 7.0 Hz), 0.98 (3H, t, J = 7.0 Hz). |
| 152 | ¹H-NMR (CDCl3) δ: 7.74 (1H, s), 6.58 (2H, dd, J = 11.8, 2.8 Hz), 3.90 (2H, q, J = 7.1 Hz), 3.87 (3H, s), 3.28 (3H, s), 3.22 (2H, s), 2.52 (2H, q, J = 7.1 Hz), 1.14 (3H, t, J = 7.1 Hz), 0.99 (3H, t, J = 7.1 Hz). |
| 153 | ¹H-NMR (CDCl3) δ: 7.80 (1H, s), 6.57-6.54 (2H, m), 3.89-3.87 (4H, m), 3.77-3.74 (1H, m), 1.65-1.63 (2H, m), 1.43 (1H, dd, J = 14.4, 6.4 Hz), 1.32 (3H, s), 1.28 (1H, s), 1.11 (3H, t, J = 7.2 Hz), 0.89 (3H, d, J = 6.4 Hz), 0.83 (3H, d, J = 6.4 Hz). |
| 154 | ¹H-NMR (CDCl3) δ: 7.67 (1H, s), 6.79-6.77 (2H, m), 3.88 (1H, dq, J = 13.8, 7.0 Hz), 3.72 (1H, dq, J = 13.8, 7.0 Hz), 1.66-1.64 (2H, m), 1.45-1.41 (1H, m), 1.37 (3H, s), 1.18 (1H, s), 1.11 (3H, t, J = 7.2 Hz), 0.88 (3H, d, J = 6.4 Hz), 0.83 (3H, d, J = 6.4 Hz). |
| 155 | ¹H-NMR (CDCl3) δ: 7.49 (1H, s), 7.23-7.16 (4H, m), 3.25 (3H, s), 1.95 (2H, d, J = 7.6 Hz), 1.64-1.58 (1H, m), 0.75 (6H, d, J = 6.7 Hz). |
| 156 | ¹H-NMR (CDCl3) δ: 7.69 (1H, s), 7.24-7.14 (4H, m), 3.25 (3H, s), 1.94 (2H, d, J = 7.3 Hz), 1.66-1.56 (1H, m), 0.75 (6H, d, J = 6.6 Hz). |
| 157 | ¹H-NMR (CDCl3) δ: 7.30-7.24 (3H, m), 7.17 (1H, t, J = 8.0 Hz), 6.63 (1H, d, J = 9.2 Hz), 3.93-3.86 (1H, m), 3.70-3.63 (1H, m), 1.95-1.84 (2H, m), 1.65-1.57 (1H, m), 1.08 (3H, t, J = 7.0 Hz), 0.75 (6H, d, J = 6.4 Hz). |
| 158 | ¹H-NMR (CDCl3) δ: 7.48 (1H, s), 7.32-7.26 (2H, m), 7.16 (1H, t, J = 7.8 Hz), 3.98-3.90 (1H, m), 3.76-3.67 (1H, m), 1.96-1.84 (2H, m), 1.68-1.57 (1H, m), 1.11 (3H, t, J = 7.0 Hz), 0.76 (6H, d, J = 6.6 Hz). |
| 159 | ¹H-NMR (CDCl3) δ: 7.69 (1H, s), 7.32-7.26 (2H, m), 7.16 (1H, t, J = 7.9 Hz), 3.98-3.89 (1H, m), 3.76-3.67 (1H, m), 1.96-1.84 (2H, m), 1.67-1.59 (1H, m), 1.10 (3H, t, J = 7.0 Hz), 0.76 (6H, d, J = 6.6 Hz). |
| 160 | ¹H-NMR (CDCl3) δ: 7.99 (1H, s), 6.85-6.81 (2H, m), 3.93 (2H, q, J = 7.1 Hz), 2.53 (2H, d, J = 6.7 Hz), 2.11-2.06 (1H, m), 1.16 (3H, t, J = 7.2 Hz), 0.87 (6H, d, J = 6.7 Hz). |
| 161 | ¹H-NMR (CDCl3) δ: 7.92 (1H, s), 6.84-6.82 (2H, m), 3.78 (2H, q, J = 7.1 Hz), 3.20 (2H, q, J = 7.1 Hz), 1.17 (6H, s), 1.11 (3H, t, J = 7.1 Hz), 1.09 (3H, t, J = 7.1 Hz). |
| 162 | ¹H-NMR (CDCl3) δ: 7.94 (1H, s), 6.57 (2H, d, J = 8.9 Hz), 3.88 (3H, s), 3.80 (2H, q, J = 7.0 Hz), 3.21 (2H, q, J = 7.0 Hz), 1.15 (6H, s), 1.13 (3H, t, J = 7.0 Hz), 1.11 (3H, t, J = 7.0 Hz). |
| 163 | ¹H-NMR (CDCl3) δ: 7.85 (1H, s), 6.92-6.83 (2H, m), 4.30 (1H, dq, J = 13.7, 7.1 Hz), 3.81-3.78 (1H, m), 3.45 (1H, dq, J = 13.7, 7.1 Hz), 1.76 (1H, d, J = 3.2 Hz), 1.09 (3H, t, J = 7.1 Hz), 0.81 (9H, s). |
| 164 | ¹H-NMR (CDCl3) δ: 7.76 (1H, s), 6.84-6.78 (2H, m), 3.84 (1H, dq, J = 13.6, 7.2 Hz), 3.74 (1H, dq, J = 13.6, 7.2 Hz), 2.94 (3H, s), 1.65-1.62 (1H, m), 1.47-1.47 (2H, m), 1.11 (3H, t, J = 7.2 Hz), 1.09 (3H, s), 0.82 (6H, d, J = 6.4 Hz). |
| 165 | ¹H-NMR (CDCl3) δ: 7.84 (1H, s), 6.59-6.55 (2H, m), 3.88 (3H, s), 3.85-3.75 (2H, m), 3.00 (3H, s), 1.66-1.59 (1H, m), 1.43 (2H, d, J = 5.9 Hz), 1.11 (3H, t, J = 7.1 Hz), 1.02 (3H, s), 0.84 (3H, d, J = 6.4 Hz), 0.82 (3H, d, J = 6.4 Hz). |
| 166 | ¹H-NMR (CDCl3) δ: 7.45 (1H, d, J = 1.2 Hz), 6.81-6.76 (2H, m), 3.93 (1H, dq, J = 13.6, 6.9 Hz), 3.70 (1H, dq, J = 13.6, 6.9 Hz), 1.95-1.87 (1H, m), 1.47 (3H, d, J = 23.2 Hz), 1.12 (3H, t, J = 6.9 Hz), 0.92 (3H, d, J = 6.7 Hz), 0.81 (3H, d, J = 6.7 Hz). |
| 167 | ¹H-NMR (CDCl3) δ: 7.53 (1H, d, J = 1.0 Hz), 6.56-6.53 (2H, m), 3.91 (1H, dq, J = 13.6, 7.0 Hz), 3.87 (3H, s), 3.74 (1H, dq, J = 13.6, 7.0 Hz), 1.85 (1H, dq, J = 26.4, 6.8 Hz), 1.43 (3H, d, J = 23.4 Hz), 1.12 (3H, t, J = 7.0 Hz), 0.91 (3H, d, J = 6.8 Hz), 0.82 (3H, d, J = 6.8 Hz). |
| 168 | ¹H-NMR (CDCl3) δ: 7.72 (1H, s), 6.92-6.82 (2H, m), 4.22 (1H, dq, J = 13.7, 7.1 Hz), 3.50 (1H, dq, J = 13.7, 7.1 Hz), 3.18 (1H, d, J = 1.7 Hz), 3.15 (3H, d, J = 2.4 Hz), 1.11 (3H, t, J = 7.1 Hz), 0.77 (9H, s). |
| 169 | ¹H-NMR (CDCl3) δ: 7.52 (1H, s), 6.85-6.83 (2H, m), 3.89 (2H, q, J = 7.2 Hz), 2.05 (2H, s), 1.09 (3H, t, J = 7.2 Hz), 0.78 (9H, s). |
| 170 | ¹H-NMR (CDCl3) δ: 7.70 (1H, s), 6.63-6.57 (2H, m), 4.23 (1H, dq, J = 13.5, 7.0 Hz), 3.89 (3H, s), 3.54 (1H, dq, J = 13.5, 7.0 Hz), 3.25 (1H, d, J = 1.5 Hz), 3.15 (3H, d, J = 2.4 Hz), 1.11 (3H, t, J = 7.0 Hz), 0.77 (9H, s). |
| 171 | ¹H-NMR (CDCl3) δ: 7.50 (1H, s), 6.60-6.59 (2H, m), 4.04 (1H, dq, J = 13.8, 7.0 Hz), 3.88 (3H, s), 3.69 (1H, dq, J = 13.8, 7.0 Hz), 1.69 (1H, dq, J = 9.3, 6.7 Hz), 1.60-1., 57 (1H, m), 1.12 (3H t, J = 7.0 Hz), 1.06 (3H, d, J = 6.7 Hz), 0.86 (3H, d, J = 6.7 Hz), 0.66 (3H, d, J = 6.7 Hz). |
| 172 | ¹H-NMR (CDCl3) δ: 7.86 (1H, s), 6.94 (1H, tt, J = 8.3, 2.1 Hz), 6.88 (1H, tt, J = 8.3, 2.1 Hz), 4.21 (1H, dq, J = 13.8, 7.0 Hz), 4.08 (1H, s), 3.49 (1H, dq, J = 13.8, 7.0 Hz), 1.11 (3H, t, J = 7.0 Hz), 0.94 (9H, s). |
| 173 | ¹H-NMR (CDCl3) δ: 7.75 (1H, s), 6.81-6.78 (2H, m), 3.90 (2H, q, J = 7.1 Hz), 1.17 (3H, t, J = 7.1 Hz), 1.16 (9H, s). |
| 174 | ¹H-NMR (CDCl3) δ: 7.60 (1H, s), 6.77-6.70 (2H, m), 4.07 (1H, dq, J = 13.8, 7.0 Hz), 3.54 (1H, dq, J = 13.8, 7.0 Hz), 1.50 (3H, s), 1.19 (1H, s), 1.08 (3H, t, J = 7.0 Hz), 0.90 (9H, s). |
| 175 | ¹H-NMR (CDCl3) δ: 7.64-7.62 (2H, m), 7.24 (1H, d, J = 9.2 Hz), 7.13-7.10 (2H, m), 6.60 (1H, d, J = 9.2 Hz), 3.76 (2H, q, J = 7.0 Hz), 1.88 (2H, d, J = 7.6 Hz), 1.64-1.56 (1H, m), 1.08 (3H, t, J = 7.0 Hz), 0.74 (6H, d, J = 6.4 Hz). |
| 176 | ¹H-NMR (CDCl3) δ: 7.37 (1H, d, J = 9.5 Hz), 7.31 (1H, dd, J = 8.3, 2.4 Hz), 7.24 (1H, dd, J = 8.4, 6.0 Hz), 7.14 (1H, ddd, J = 8.4, 7.6, 2.4 Hz), 6.66 (1H, d, J = 9.5 Hz), 4.09-4.02 (1H, m), 3.42-3.35 (1H, m), 1.73-1.59 (5H, m), 1.50-1.46 (1H, m), 1.37-1.21 (2H, m), 1.18-0.95 (6H, m). |
| 177 | ¹H-NMR (CDCl3) δ: 7.66-7.63 (2H, m), 7.46 (1H, s), 7.12-7.09 (2H, m), 3.80 (2H, q, J = 7.0 Hz), 1.89 (2H, d, J = 7.3 |

| Compounds | ¹H-NMR |
|---|---|
| | Hz), 1.66-1.58 (1H, m), 1.10 (3H, t, J = 7.0 Hz), 0.75 (6H, d, J = 6.7 Hz). |
| 178 | ¹H-NMR (CDCl3) δ: 7.67 (1H, s), 7.66-7.63 (2H, m), 7.12-7.09 (2H, m), 3.80 (2H, q, J = 7.0 Hz), 1.88 (2H, d, J = 7.3 Hz), 1.65-1.57 (1H, m), 1.10 (3H, t, J = 7.0 Hz), 0.75 (6H, d, J = 6.7 Hz). |
| 179 | ¹H-NMR (CDCl3) δ: 7.69 (1H, s), 6.55-6.53 (2H, m), 3.92 (2H, q, J = 7.1 Hz), 3.84 (3H, s), 1.16 (3H, t, J = 7.1 Hz), 1.14 (9H, s). |
| 180 | ¹H-NMR (CDCl3) δ: 7.65 (1H, s), 6.53-6.50 (2H, m), 4.04 (1H, dq, J = 13.6, 7.2 Hz), 3.85 (3H, s), 3.60 (1H, dd, J = 13.5, 7.3 Hz), 1.47 (3H, s), 1.25 (1H, s), 1.08 (3H, t, J = 7.2 Hz), 0.90 (9H, s). |
| 181 | ¹H-NMR (CDCl3) δ: 7.57 (1H, s), 7.32 (1H, dd, J = 8.3, 2.4 Hz), 7.23 (1H, dd, J = 8.6, 5.8 Hz), 7.15 (1H, ddd, J = 8.6, 7.6, 2.4 Hz), 4.13-4.06 (1H, m), 3.47-3.40 (1H, m), 1.74-1.62 (4H, m), 1.49 (1H, d, J = 13.1 Hz), 1.36-1.22 (3H, m), 1.19-0.95 (6H, m). |
| 182 | ¹H-NMR (CDCl3) δ: 7.77 (1H, s), 7.32 (1H, dd, J = 8.3, 2.4 Hz), 7.23 (1H, dd, J = 8.4, 6.0 Hz), 7.15 (1H, ddd, J = 8.4, 8.0, 2.4 Hz), 4.12-4.05 (1H, m), 3.48-3, 41 (1H, m), 1.74-1.61 (5H, m), 1.51-1.47 (1H, m), 1.36-1.22 (2H, m), 1.19-0.94 (6H, m). |
| 183 | ¹H-NMR (CDCl3) δ: 7.71 (1H, s), 7.47 (1H, tt, J = 8.4, 6.4 Hz), 7.02-7.00 (2H, m), 3.88-3.82 (1H, m), 3.74-3.68 (1H, m), 1.86 (1H, dq, J = 6.7, 6.7 Hz), 1.33 (3H, s), 1.14 (1H, s), 1.10 (3H, t, J = 7.1 Hz), 0.85 (3H, d, J = 6.7 Hz), 0.78 (3H, d, J = 6.7 Hz). |
| 184 | ¹H-NMR (CDCl3) δ: 7.50 (1H, d, J = 1.2 Hz), 7.49-7.46 (1H, m), 7.04-6.99 (2H, m), 3.91-3.88 (1H, m), 3.75-3.68 (1H, m), 1.92-1.86 (1H, m), 1.44 (3H, d, J = 23.2 Hz), 1.11 (3H, t, J = 7.1 Hz), 0.91 (3H, d, J = 6.8 Hz), 0.82 (3H, d, J = 6.8 Hz). |
| 185 | ¹H-NMR (CDCl3) δ: 7.32-7.28 (3H, m), 7.14 (1H, ddd, J = 8.6, 8.0, 2.4 Hz), 6.65 (1H, d, J = 9.2 Hz), 4.11-4.04 (1H, m), 3.44-3.37 (1H, m), 2.08-2.00 (1H, m), 1.97-1.90 (1H, m), 1.09 (3H, t, J = 7.0 Hz), 0.97 (3H, t, J = 7.6 Hz). |
| 186 | ¹H-NMR (CDCl3) δ: 773 (1H, s), 731 (1H, dd, J = 8.3, 2.4 Hz), 7.28-7.25 (1H, m), 7.15 (1H, ddd, J = 8.6, 8.0, 2.4 Hz), 4.15-4.07 (1H, m), 3.50-3.43 (1H, m), 2.08-2.00 (1H, m), 1.98-1.91 (1H, m), 1.11 (3H, t, J = 7.0 Hz), 0.99 (3H, t, J = 7.6 Hz). |
| 187 | ¹H-NMR (CDCl3) δ: 7.80 (1H, s), 7.52 (1H, tt, J = 8.6, 6.4 Hz), 7.07-7.01 (2H, m), 3.84-3.70 (2H, m), 3.03 (3H, s), 1.76 (1H, dq, J = 6.7, 6.7 Hz), 1.11 (3H, t, J = 7.0 Hz), 0.91 (3H, s), 0.83 (3H, d, J = 6.7 Hz), 0.72 (3H, d, J = 6.7 Hz). |
| 188 | ¹H-NMR (CDCl3) δ: 7.88 (1H, s), 7.52 (1H, tt, J = 8.4, 6.4 Hz), 7.05-7.02 (2H, m), 3.84-3.77 (1H, m), 3.74-3.67 (1H, m), 3.33 (1H, dq, J = 9.0, 7.1 Hz), 3.07 (1H, dq, J = 9.0, 7.1 Hz), 1.76 (1H, dq, J = 6.8, 6.8 Hz), 1.11-1.10 (6H, m), 0.85 (3H, d, J = 6.8 Hz), 0.81 (3H, s), 0.72 (3H, d, J = 6.8 Hz). |
| 189 | ¹H-NMR (CDCl3) δ: 7.53 (1H, d, J = 3.7 Hz), 7.31 (1H, dd, J = 8.3, 2.4 Hz), 7.27 (1H, dd, J = 8.6, 5.8 Hz), 7.15 (1H, ddd, J = 8.6, 8.0, 2.4 Hz), 4.14-4.07 (1H, m), 3.49-3.42 (1H, m), 2.08-2.01 (1H, m), 1.98-1.91 (1H, m), 1.11 (3H, t, J = 7.0 Hz), 0.99 (3H, t, J = 7.6 Hz). |
| 190 | ¹H-NMR (CDCl3) δ: 7.31-7.26 (3H, m), 7.14 (1H, ddd, J = 8.6, 8.0, 2.4 Hz), 6.63 (1H, d, J = 9.5 Hz), 4.11-4.04 (1H, m), 3.44-3.37 (1H, m), 2.01 (1H, ddd, J = 14.1, 9.5, 5.8 Hz), 1.86 (1H, ddd, J = 14.1, 9.5, 6.4 Hz), 1.45-1.31 (2H, m), 1.09 (3H, t, J = 7.2 Hz), 0.78 (3H, t, J = 7.3 Hz). |
| 191 | ¹H-NMR (CDCl3) δ: 7.51 (1H, s), 7.26 (1H, dd, J = 8.5, 5.9 Hz), 7.15 (1H, ddd, J = 8.5, 7.8, 2.4 Hz), 4.15-4.07 (1H, m), 3.50-3.42 (1H, m), 2.05-1.98 (1H, m), 1.87 (1H, ddd, J = 14.2, 9.3, 6.3 Hz), 1.47-1.31 (2H, m), 1.11 (3H, t, J = 7.1 Hz), 0.79 (3H, t, J = 7.3 Hz). |
| 192 | ¹H-NMR (CDCl3) δ: 7.72 (1H, s), 7.31 (1H, dd, J = 8.2, 2.4 Hz), 7.26 (1H, dd, J = 8.5, 5.9 Hz), 7.15 (1H, ddd, J = 8.5, 7.8, 2.4 Hz), 4.15-4.08 (1H, m), 3.51-3.42 (1H, m), 2.05-1.97 (1H, m), 1.87 (1H, ddd, J = 14.2, 9.3, 6.6 Hz), 1.47-1.30 (2H, m), 1.11 (3H, t, J = 7.0 Hz), 0.79 (3H, t, J = 7.3 Hz). |
| 193 | ¹H-NMR (CDCl3) δ: 8.15 (1H, s), 7.29 (1H, d, J = 9.3 Hz), 7.08-7.00 (4H, m), 6.65 (1H, d, J = 9.3 Hz), 3.87 (2H, q, J = 7.0 Hz), 1.95 (2H, d, J = 7.3 Hz), 1.64-1.57 (1H, m), 1.11 (3H, t, J = 7.0 Hz), 0.74 (6H, d, J = 6.6 Hz). |
| 194 | ¹H-NMR (CDCl3) δ: 7.23 (1H, d, J = 9.3 Hz), 7.15-7.11 (2H, m), 7.00-6.97 (2H, m), 6.57 (1H, d, J = 9.3 Hz), 3.88 (3H, s), 3.79 (2H, q, J = 7.1 Hz), 1.90 (2H, d, J = 7.3 Hz), 1.65-1.55 (1H, m), 1.08 (3H, t, J = 7.1 Hz), 0.74 (6H, d, J = 6.6 Hz). |
| 195 | ¹H-NMR (CDCl3) δ: 7.45 (1H, s), 7.13-7.10 (2H, m), 7.01-6.97 (2H, m), 3.89 (3H, s), 3.83 (2H, q, J = 7.0 Hz), 1.91 (2H, d, J = 7.3 Hz), 1.64-1.57 (1H, m), 1.10 (3H, t, J = 7.0 Hz), 0.75 (6H, d, J = 6.6 Hz). |
| 196 | ¹H-NMR (CDCl3) δ: 7.66 (1H, s), 7.13-7.10 (2H, m), 7.01-6.97 (2H, m), 3.89 (3H, s), 3.84 (2H, q, J = 7.0 Hz), 1.91 (2H, d, J = 7.3 Hz), 1.66-1.55 (1H, m), 1.10 (3H, t, J = 7.0 Hz), 0.74 (6H, d, J = 6.6 Hz). |
| 197 | ¹H-NMR (CDCl3) δ: 7.49-7.43 (2H, m), 7.01-6.98 (2H, m), 4.92-4.91 (1H, m), 4.91-4.89 (1H, m), 3.87 (2H, q, J = 7.1 Hz), 2.09 (1H, dq, J = 7.0, 7.0 Hz), 1.14 (3H, t, J = 7.1 Hz), 0.87 (6H, d, J = 7.0 Hz) |
| 198 | ¹H-NMR (CDCl3) δ: 7.53-7.50 (2H, m), 7.10-7.05 (2H, m), 4.03-4.00 (1H, m), 3.68-3.66 (1H, m), 1.63-1.57 (2H, m), 1.12 (3H, t, J = 7.2 Hz), 1.06 (3H, d, J = 6.4 Hz), 0.84 (3H, d, J = 6.4 Hz), 0.66 (3H, dd, J = 6.3, 1.1 Hz). |
| 199 | ¹H-NMR (CDCl3) δ: 7.47 (1H, dd, J = 8.0, 2.4 Hz), 7.28-7.25 (2H, m), 7.18 (1H, ddd, J = 8.6, 8.0, 2.4 Hz), 6.63 (1H, d, J = 9.5 Hz), 4.15-4.08 (1H, m), 3.41-3.34 (1H, m), 1.99 (1H, dd, J = 14.1, 6.6 Hz), 1.72 (1H, dd, J = 14.1, 8.3 Hz), 1.68-1.61 (1H, m), 1.10 (3H, t, J = 7.0 Hz), 0.81 (3H, d, J = 6.4 Hz), 0.72 (3H, d, J = 6.4 Hz). |
| 200 | ¹H-NMR (CDCl3) δ: 7.50-7.47 (2H, m), 7.27-7.24 (1H, m), 7.19 (1H, ddd, J = 8.6, 7.6, 2.4 Hz), 4.18-4.11 (1H, m), 3.47-3.40 (1H, m), 2.00 (1H, dd, J = 13.9, 6.4 Hz), 1.72 (1H, dd, J = 13.9, 8.1 Hz), 1.69-1.62 (1H, m), 1.12 (3H, t, J = 7.0 Hz), 0.82 (3H, d, J = 6.7 Hz), 0.73 (3H, d, J = 6.7 Hz). |
| 201 | ¹H-NMR (CDCl3) δ: 7.70 (1H, s), 7.48 (1H, dd, J = 8.0, 2.4 Hz), 7.27-7.24 (1H, m), 7.19 (1H, ddd, J = 8.6, 7.6, 2.4 Hz), 4.18-4.11 (1H, m), 3.47-3.40 (1H, m), 2.00 (1H, dd, J = 13.8, 6.4 Hz), 1.74-1.61 (2H, m), 1.12 (3H, t, J = 7.2 Hz), 0.82 (3H, d, J = 6.4 Hz), 0.73 (3H, d, J = 6.4 Hz). |
| 202 | ¹H-NMR (CDCl3) δ: 7.26 (1H, d, J = 9.3 Hz), 7.13 (1H, dd, J = 8.3, 5.6 Hz), 7.05-6.98 (2H, m), 6.60 (1H, d, J = 9.3 Hz), 4.15-4.06 (1H, m), 3.38-3.29 (1H, m), 2.07 (3H, s), 1.95 (1H, dd, J = 13.9, 6.8 Hz), 1.71 (1H, dd, J = 13.9, 7.9 Hz), 1.65-1.55 (1H, m), 1.06 (3H, t, J = 7.0 Hz), 0.78 (3H, d, J = 6.6 Hz), 0.71 (3H, d, J = 6.6 Hz). |
| 203 | ¹H-NMR (CDCl3) δ: 7.49 (1H, s), 7.11 (1H, dd, J = 8.3, 5.9 Hz), 7.06-6.99 (2H, m), 4.19-4.10 (1H, m), 3.43-3.34 (1H, m), 2.06 (3H, s), 1.96 (1H, dd, J = 13.9, 6.6 Hz), 1.71 (1H, dd, J = 13.9, 8.1 Hz), 1.66-1.57 (1H, m), 1.08 (3H, t, J = 7.0 Hz), 0.79 (3H, d, J = 6.3 Hz), 0.72 (3H, d, J = 6.6 Hz). |
| 204 | ¹H-NMR (CDCl3) δ: 7.69 (1H, s), 7.11 (1H, dd, J = 8.3, 5.6 Hz), 7.06-6.99 (2H, m), 4.18-4.10 (1H, m), 3.49-3.35 (1H, m), 2.06 (3H, s), 1.96 (1H, dd, J = 13.9, 6.6 Hz), 1.70 (1H, dd, J = 13.9, 7.9 Hz), 1.66-1.56 (1H, m), 1.08 (3H, t, J = 7.0 Hz), 0.79 (3H, d, J = 6.6 Hz), 0.72 (3H, d, J = 6.6 Hz). |
| 205 | ¹H-NMR (CDCl3) δ: 7.31-7.26 (3H, m), 7.14 (1H, td, J = 8.2, 2.4 Hz), 6.63 (1H, d, J = 9.3 Hz), 4.15-4.03 (1H, m), 3.45-3.36 (1H, m), 2.06-1.98 (1H, m), 1.88 (1H, ddd, J = 13.9, 9.5, 6.3 Hz), 1.42-1.24 (2H, m), 1.21-1.12 (2H, m), 1.09 (3H, t, J = 7.1 Hz), 0.78 (3H, t, J = 7.3 Hz). |
| 206 | ¹H-NMR (CDCl3) δ: 7.72 (1H, s), 7.31 (1H, dd, J = 8.3, 2.4 Hz), 7.28-7.25 (1H, m), 7.15 (1H, ddd, J = 8.6, 8.0, 2.4 Hz), 4.14-4.08 (1H, m), 3.49-3.43 (1H, m), 2.02 (1H, ddd, J = 14.4, 9.8, 5.8 Hz), 1.89 (1H, ddd, J = 14.4, 10.1, 6.1 Hz), 1.42-1.25 (2H, m), 1.21-1.13 (2H, m), 1.11 (3H, t, J = 7.0 Hz), 0.78 (3H, t, J = 7.2 Hz). |
| 207 | ¹H-NMR (CDCl3) δ: 7.72 (1H, s), 7.31 (1H, dd, J = 8.3, 2.4 Hz), 7.28-7.25 (1H, m), 7.15 (1H, ddd, J = 8.6, 8.0, 2.4 Hz), 4.14-4.08 (1H, m), 3.49-3.43 (1H, m), 2.02 (1H, ddd, J = 14.4, 9.8, 5.8 Hz), 1.89 (1H, ddd, J = 14.4, 10.1, 6.1 Hz), 1.42-1.25 (2H, m), 1.21-1.13 (2H, m), 1.11 (3H, t, J = 7.0 Hz), 0.78 (3H, t, J = 7.2 Hz). |
| 208 | ¹H-NMR (CDCl3) δ: 7.31-7.25 (3H, m), 7.16-7.12 (1H, m), 6.63 (1H, d, J = 9.3 Hz), 4.13-4.03 (1H, m), 3.45-3.36 (1H, m), 2.05-1.97 (1H, m), 1.87 (1H, ddd, J = 14.2, 9.8, 6.1 Hz), 1.43-1.24 (2H, m), 1.21-1.07 (7H, m), 0.81 (3H, t, J = 7.1 Hz). |
| 209 | ¹H-NMR (CDCl3) δ: 7.51 (1H, s), 7.31 (1H, dd, J = 8.3, 2.8 Hz), 7.26 (2H, dd, J = 8.6, 5.8 Hz), 7.16 (1H, ddd, J = 8.6, 7.6, 2.8 Hz), 4.15-4.08 (1H, m), 3.49-3.42 (1H, m), 2.02 (1H, ddd, J = 14.4, 10.1, 5.8 Hz), 1.88 (1H, ddd, J = 14.4, 10.1, 6.1 Hz), 1.43-1.28 (2H, m), 1.22-1.09 (7H, m), 0.82 (3H, t, J = 7.2 Hz). |
| 210 | ¹H-NMR (CDCl3) δ: 7.72 (1H, s), 7.31 (1H, dd, J = 8.3, 2.8 Hz), 7.26 (1H, dd, J = 8.6, 5.8 Hz), 7.17-7.13 (1H, m), 4.15-4.08 (1H, m), 3.49-3.43 (1H, m), 2.01 (1H, ddd, J = 14.1, 10.1, |

TABLE 4-continued

| Compounds | ¹H-NMR |
|---|---|
| | 5.8 Hz), 1.88 (1H, ddd, J = 14.1, 10.1, 6.1 Hz), 1.43-1.26 (2H, m), 1.21-1.09 (7H, m), 0.81 (3H, t, J = 7.2 Hz). |
| 211 | ¹H-NMR (CDCl3) δ: 7.72 (1H, s), 7.33-7.30 (1H, m), 7.24-7.17 (3H, m), 3.87 (1H, dq, J = 13.5, 6.7 Hz), 3.73 (1H, dq, J = 13.5, 6.7 Hz), 3.60 (1H, d, J = 8.3 Hz), 1.84-1.80 (1H, m), 1.68 (1H, br s), 1.10 (3H, t, J = 6.7 Hz), 0.93 (3H, d, J = 6.7 Hz), 0.66 (3H, d, J = 6.7 Hz). |
| 212 | ¹H-NMR (CDCl3) δ: 7.80 (1H, s), 7.30-7.18 (4H, m), 3.89 (2H, q, J = 7.1 Hz), 2.56-2.55 (1H, m), 1.15 (3H, t, J = 7.1 Hz), 0.91 (6H, d, J = 6.6 Hz). |
| 213 | ¹H-NMR (CDCl3) δ: 7.82 (1H, s), 7.27-7.25 (2H, m), 7.20-7.16 (2H, m), 3.70 (2H, q, J = 7.0 Hz), 1.76 (1H, dq, J = 6.7, 6.7 Hz), 1.20 (3H, s), 1.07 (3H, t, J = 7.0 Hz), 1.03 (1H, s), 0.83 (3H, d, J = 6.7 Hz), 0.78 (3H, d, J = 6.7 Hz). |
| 214 | ¹H-NMR (CDCl3) δ: 7.78 (1H, s), 7.26-7.12 (4H, m), 3.70 (2H, q, J = 7.1 Hz), 3.00 (3H, s), 1.78 (1H, dq, J = 6.8, 6.8 Hz), 1.07 (3H, t, J = 7.1 Hz), 0.83 (3H, d, J = 6.8 Hz), 0.73 (3H, s), 0.72 (3H, d, J = 6.8 Hz). |
| 215 | ¹H-NMR (CDCl3) δ: 7.85 (1H, s), 7.26-7.19 (2H, m), 7.18-7.14 (2H, m), 3.69 (2H, q, J = 7.0 Hz), 3.30-3.27 (1H, m), 3.04-3.01 (1H, m), 1.77 (1H, dq, J = 6.7, 6.7 Hz), 1.12 (3H, t, J = 7.0 Hz), 1.07 (3H, t, J = 7.0 Hz), 0.85 (3H, d, J = 6.7 Hz), 0.72 (3H, d, J = 6.7 Hz), 0.64 (3H, s). |
| 216 | ¹H-NMR (CDCl3) δ: 7.85 (1H, s), 7.27-7.13 (4H, m), 3.70 (2H, q, J = 7.0 Hz), 3.15 (1H, dt, J = 11.8, 4.3 Hz), 2.94 (1H, dt, J = 11.3, 4.3 Hz), 1.78 (1H, dq, J = 6.8, 6.8 Hz), 1.55-1.49 (2H, m), 1.07 (3H, t, J = 7.0 Hz), 0.91 (3H, t, J = 7.4 Hz), 0.85 (3H, d, J = 6.8 Hz), 0.72 (3H, d, J = 6.8 Hz), 0.62 (3H, s). |
| 217 | ¹H-NMR (CDCl3) δ: 7.62 (1H, d, J = 0.7 Hz), 7.24-7.20 (2H, m), 7.17-7.15 (2H, m), 3.72 (2H, q, J = 7.0 Hz), 1.76 (1H, ddq, J = 25.6, 6.8, 6.8 Hz), 1.31 (3H, d, J = 23.7 Hz), 1.08 (3H, t, J = 7.0 Hz), 0.86 (3H, d, J = 6.8 Hz), 0.82 (3H, d, J = 6.8 Hz). |
| 218 | ¹H-NMR (CDCl3) δ: 7.92 (1H, s), 6.55-6.54 (2H, m), 4.06 (2H, q, J = 7.0 Hz), 3.95 (2H, q, J = 7.0 Hz), 3.09-3.04 (1H, m), 1.45 (3H, t, J = 7.0 Hz), 1.15 (3H, t, J = 7.0 Hz), 1.04 (6H, d, J = 6.7 Hz). |
| 219 | ¹H-NMR (CDCl3) δ: 7.36 (1H, d, J = 9.5 Hz), 7.31-7.26 (2H, m), 7.15-7.12 (1H, m), 6.67 (1H, d, J = 9.5 Hz), 4.08-4.01 (1H, m), 3.42-3.35 (1H, m), 2.17-2.09 (1H, m), 1.82-1.77 (1H, m), 1.73-1.63 (3H, m), 1.53-1.34 (4H, m), 1.09 (3H, t, J = 7.0 Hz). |
| 220 | ¹H-NMR (CDCl3) δ: 7.55 (1H, s), 7.31 (1H, dd, J = 8.3, 2.4 Hz), 7.26 (1H, dd, J = 8.6, 5.8 Hz), 7.17-7.13 (1H, m), 4.12-4.05 (1H, m), 3.47-3.41 (1H, m), 2.18-2.11 (1H, m), 1.85-1.79 (1H, m), 1.75-1.65 (3H, m), 1.53-1.36 (4H, m), 1.11 (3H, t, J = 7.0 Hz). |
| 221 | ¹H-NMR (CDCl3) δ: 7.76 (1H, s), 7.30 (1H, dd, J = 8.3, 2.4 Hz), 7.25 (1H, dd, J = 8.6, 5.8 Hz), 7.15 (1H, ddd, J = 8.6, 7.6, 2.4 Hz), 4.12-4.05 (1H, m), 3.48-3.41 (1H, m), 2.17-2.10 (1H, m), 1.84-1.79 (1H, m), 1.76-1.64 (3H, m), 1.53-1.34 (4H, m), 1.11 (3H, t, J = 7.0 Hz). |
| 222 | ¹H-NMR (CDCl3) δ: 7.75 (1H, s), 7.20 (2H, ddd, J = 9.3, 2.4, 1.2 Hz), 7.01 (2H, ddd, J = 9.3, 2.4, 1.2 Hz), 3.93 (2H, q, J = 7.0 Hz), 3.88 (3H, s), 2.38-2.32 (1H, m), 1.15 (3H, d, J = 7.0 Hz), 0.86 (6H, d, J = 6.7 Hz). |
| 223 | ¹H-NMR (CDCl3) δ: 7.83 (1H, s), 7.20-7.15 (2H, m), 6.99-6.98 (2H, m), 3.88 (3H, s), 3.72 (2H, q, J = 6.9 Hz), 1.80-1.75 (1H, m), 1.20 (3H, s), 1.15 (3H, s), 1.07 (3H, t, J = 6.9 Hz), 0.82 (3H, d, J = 6.7 Hz), 0.77 (3H, d, J = 6.7 Hz). |
| 224 | ¹H-NMR (CDCl3) δ: 7.79 (1H, s), 7.15-7.10 (2H, m), 6.96-6.95 (2H, m), 3.88 (3H, s), 3.73 (2H, q, J = 6.9 Hz), 3.01 (3H, S), 1.82-1.77 (1H, m), 1.07 (3H, t, J = 6.9 Hz), 0.83 (3H, d, J = 6.7 Hz), 0.73 (3H, d, J = 7.0 Hz), 0.71 (3H, s). |
| 225 | ¹H-NMR (CDCl3) δ: 7.71 (1H, d, J = 1.8 Hz), 7.55 (1H, dd, J = 8.3, 1.8 Hz), 7.26 (1H, d, J = 9.5 Hz), 7.15 (1H, d, J = 8.3 Hz), 6.63 (1H, d, J = 9.5 Hz), 4.10-4.03 (1H, m), 3.44-3.37 (1H, m), 1.97 (1H, dd, J = 14.1, 6.7 Hz), 1.74 (1H, dd, J = 14.1, 8.0 Hz), 1.69-1.59 (1H, m), 1.09 (3H, t, J = 7.0 Hz), 0.79 (3H, d, J = 6.4 Hz), 0.73 (3H, d, J = 6.7 Hz). |
| 226 | ¹H-NMR (CDCl3) δ: 7.76 (1H, s), 6.54-6.50 (2H, m), 4.06 (2H, q, J = 7.0 Hz), 3.90-3.83 (1H, m), 3.75-3.72 (1H, m), 1.86-1.79 (1H, m), 1.46 (3H, t, J = 7.0 Hz), 1.31 (3H, s), 1.22 (1H, s), 1.11 (3H, t, J = 7.0 Hz), 0.85 (3H, d, J = 6.7 Hz), 0.78 (3H, d, J = 6.7 Hz). |
| 227 | ¹H-NMR (CDCl3) δ: 7.79 (1H, s), 6.57-6.49 (2H, m), 4.07 (2H, q, J = 7.0 Hz), 3.84-3.78 (1H, m), 3.03 (3H, s), 1.76 (1H, dq, J = 6.7, 6.7 Hz), 1.47 (3H, t, J = 7.0 Hz), 1.11 (3H, t, J = 7.0 Hz), 0.93 (3H, s), 0.83 (3H, d, J = 6.7 Hz), 0.71 (3H, d, J = 6.7 Hz). |
| 228 | ¹H-NMR (CDCl3) δ: 7.86 (1H, s), 6.85-6.80 (2H, m), 3.81 (1H, dq, J = 13.8, 7.0 Hz), 3.70 (1H, dq, J = 13.8, 7.0 Hz), 3.34-3.31 (1H, m), 3.07-3.04 (1H, m), 1.77-1.71 (1H, m), 1.11 (6H, t, J = 7.0 Hz), 0.86 (3H, s), 0.86 (3H, d, J = 6.7 Hz), 0.72 (3H, dd, J = 6.7, 0.9 Hz). |
| 229 | ¹H-NMR (CDCl3) δ: 7.87 (1H, s), 6.86-6.80 (2H, m), 3.83-3.77 (1H, m), 3.74-3.68 (1H, m), 3.20-3.18 (1H, m), 2.98-2.95 (1H, m), 1.78-1.73 (1H, m), 1.54-1.47 (2H, m), 1.11 (3H, t, J = 7.0 Hz), 0.90 (3H, t, J = 7.0 Hz), 0.86 (3H, d, J = 6.7 Hz), 0.84 (3H, s), 0.72 (3H, dd, J = 6.7, 1.1 Hz). |
| 230 | ¹H-NMR (CDCl3) δ: 7.70 (1H, s), 6.97-6.91 (2H, m), 3.96 (2H, q, J = 7.2 Hz), 1.19 (3H, t, J = 7.2 Hz). |
| 231 | ¹H-NMR (CDCl3) δ: 7.78 (1H, s), 6.92-6.86 (2H, m), 4.08 (1H, dq, J = 13.9, 7.0 Hz), 3.69 (1H, dd, J = 9.3, 2.8 Hz), 3.62 (1H, dq, J = 13.9, 7.0 Hz), 2.15-2.10 (1H, m), 1.87-1.86 (1H, m), 1.68 (1H, dd, J = 2.8 Hz), 1.58-1.39 (5H, m), 1.33-1.25 (1H, m), 1.12 (3H, t, J = 7.0 Hz), 0.82-0.78 (1H, m). |
| 232 | ¹H-NMR (CDCl3) δ: 8.02 (1H, s), 6.83-6.80 (2H, m), 3.93 (2H, q, J = 7.0 Hz), 3.36-3.33 (1H, m), 1.82-1.80 (2H, m), 1.70-1.67 (2H, m), 1.63-1.57 (4H, m), 1.16 (3H, t, J = 7.2 Hz). |
| 233 | ¹H-NMR (CDCl3) δ: 7.86-7.82 (2H, m), 7.72 (1H, s), 7.50-7.48 (1H, m), 7.38-7.35 (1H, m), 3.85-3.82 (1H, m), 3.72-3.66 (1H, m), 3.49 (1H, dd, J = 8.5, 4.3 Hz), 1.84-1.81 (1H, m), 1.64 (1H, dd, J = 3.4 Hz), 1.10 (3H, t, J = 7.1 Hz), 0.93 (3H, d, J = 6.3 Hz), 0.66 (3H, d, J = 6.8 Hz). |
| 234 | ¹H-NMR (CDCl3) δ: 7.90 (1H, s), 7.81-7.79 (2H, m), 7.38-7.37 (2H, m), 3.82 (2H, q, J = 7.0 Hz), 2.95-2.90 (1H, m), 1.14 (3H, t, J = 7.0 Hz), 0.99 (6H, d, J = 6.7 Hz). |
| 235 | ¹H-NMR (CDCl3) δ: 7.76-7.75 (1H, m), 7.69 (1H, s), 7.43-7.38 (2H, m), 3.68-3.63 (2H, m), 1.83-1.78 (1H, m), 1.27 (3H, s), 1.06 (3H, t, J = 6.9 Hz), 0.84 (3H, d, J = 6.7 Hz), 0.83 (1H, br s), 0.78 (3H, d, J = 7.0 Hz). |
| 236 | ¹H-NMR (CDCl3) δ: 7.72 (1H, d, J = 1.8 Hz), 7.56 (1H, dd, J = 8.3, 1.8 Hz), 7.49 (1H, s), 7.13 (1H, d, J = 8.3 Hz), 4.14-4.07 (1H, m), 3.50-3.42 (1H, m), 1.98 (1H, dd, J = 14.1, 6.9 Hz), 1.75 (1H, dd, J = 14.1, 8.0 Hz), 1.69-1.61 (1H, m), 1.11 (3H, t, J = 7.0 Hz), 0.80 (3H, d, J = 6.7 Hz), 0.74 (3H, d, J = 6.7 Hz). |
| 237 | ¹H-NMR (CDCl3) δ: 7.72 (1H, d, J = 1.8 Hz), 7.69 (1H, s), 7.56 (1H, dd, J = 8.3, 1.8 Hz), 7.13 (1H, d, J = 8.3 Hz), 4.14-4.07 (1H, m), 3.50-3.43 (1H, m), 1.98 (1H, dd, J = 14.1, 6.7 Hz), 1.74 (1H, dd, J = 14.1, 8.0 Hz), 1.69-1.60 (1H, m), 1.11 (3H, t, J = 7.0 Hz), 0.80 (3H, d, J = 6.7 Hz), 0.74 (3H, d, J = 6.4 Hz). |
| 238 | ¹H-NMR (CDCl3) δ: 7.27-7.24 (1H, m), 7.15 (1H, d, J = 8.5 Hz), 7.05 (1H, d, J = 2.5 Hz), 6.92 (1H, dd, J = 8.5, 2.5 Hz), 6.60 (1H, d, J = 9.5 Hz), 4.12-4.03 (1H, m), 3.89 (3H, s), 3.52-3.43 (1H, m), 1.99 (1H, dd, J = 14.0, 6.8 Hz), 1.78 (1H, dd, J = 14.0, 7.9 Hz), 1.68-1.58 (1H, m), 1.09 (3H, t, J = 7.0 Hz), 0.79 (3H, d, J = 6.6 Hz), 0.72 (3H, d, J = 6.6 Hz). |
| 239 | ¹H-NMR (CDCl3) δ: 7.48 (1H, s), 7.13 (1H, d, J = 8.6 Hz), 7.05 (1H, d, J = 2.6 Hz), 6.92 (1H, dd, J = 8.6, 2.6 Hz), 4.14-4.08 (1H, m), 3.89 (3H, s), 3.56-3.49 (1H, m), 1.99 (1H, dd, J = 14.1, 6.7 Hz ), 1.78 (1H, dd, J = 14.1, 8.1 Hz), 1.65 (1H, dq, J = 17.4, 5.6 Hz), 1.10 (3H, t, J = 7.0 Hz), 0.79 (3H, d, J = 6.7 Hz), 0.73 (3H, d, J = 6.7 Hz). |
| 240 | ¹H-NMR (CDCl3) δ: 7.69 (1H, s), 7.13 (1H, d, J = 8.6 Hz), 7.05 (1H, d, J = 2.4 Hz), 6.92 (1H, dd, J = 8.6, 2.4 Hz), 4.14-4.08 (2H, m), 3.89 (3H, s), 3.56-3.49 (1H, m), 1.99 (1H, dd, J = 14.1, 6.7 Hz), 1.77 (1H, dd, J = 14.1, 8.0 Hz), 1.67-1.61 (1H, m), 1.10 (3H, t, J = 7.0 Hz), 0.79 (3H, d, J = 6.4 Hz), 0.73 (3H, d, J = 6.4 Hz). |
| 241 | ¹H-NMR (CDCl3) δ: 7.87 (1H, s), 6.58-6.54 (2H, m), 3.88 (3H, s), 3.87-3.83 (1H, m), 3.74-3.72 (1H, m), 3.33-3.32 (1H, m), 3.06-3.05 (1H, m), 1.75 (1H, dq, J = 6.7, 6.7 Hz), 1.12 (3H, t, J = 7.0 Hz), 1.11 (3H, t, J = 7.0 Hz), 0.86 (3H, s), 0.85 (3H, d, J = 7.0 Hz), 0.72 (3H, dd, J = 7.0, 0.9 Hz). |
| 242 | ¹H-NMR (CDCl3) δ: 7.87 (1H, s), 6.55-6.54 (2H, m), 3.87 (3H, s), 3.86-3.82 (1H, m), 3.73 (1H, dq, J = 13.6, 7.0 Hz), 3.19 (1H, dt, J = 8.9, 6.7 Hz), 2.97 (1H, dt, J = 8.9, 6.7 Hz), 1.79-1.73 (1H, m), 1.53-1.50 (2H, m), 1.11 (3H, t, J = 7.0 Hz), 0.91 (3H, t, J = 7.0 Hz), 0.86 (3H, d, J = 6.7 Hz), 0.84 (3H, s), 0.72 (3H, dd, J = 6.7, 1.1 Hz). |
| 243 | ¹H-NMR (CDCl3) δ: 7.45 (1H, s), 6.79-6.77 (2H, m), 4.95-4.94 (1H, m), 4.89-4.87 (1H, m), 3.87 (2H, q, J = 7.0 Hz), |

TABLE 4-continued

| Compounds | ¹H-NMR |
|---|---|
| | 2.10-2.06 (1H, m), 1.15 (3H, t, J = 7.0 Hz), 0.90 (6H, d, J = 6.8 Hz). |
| 244 | ¹H-NMR (CDCl3) δ: 7.71 (1H, s), 6.80-6.76 (2H, m), 3.87 (1H, dq, J = 13.5, 7.0 Hz), 3.71 (1H, dq, J = 13.5, 7.0 Hz), 2.21-2.20 (1H, m), 1.65-1.42 (6H, m), 1.36-1.32 (1H, m), 1.34 (1H, s), 1.23-1.20 (1H, m), 1.11 (1H, s), 1.11 (3H, t, J = 7.0 Hz). |
| 245 | ¹H-NMR (CDCl3) δ: 7.83 (1H, s), 6.88-6.80 (2H, m), 3.80-3.73 (2H, m), 3.06 (3H, s), 1.87-1.85 (1H, m), 1.60-1.56 (3H, m), 1.50-1.26 (5H, m), 1.12 (3H, t, J = 7.1 Hz), 0.99 (3H, s). |
| 246 | ¹H-NMR (CDCl3) δ: 7.70 (1H, s), 7.22-7.20 (1H, m), 7.10-7.09 (1H, m), 7.02-7.00 (2H, m), 3.90-3.87 (4H, m), 3.78-3.74 (1H, m), 3.66 (1H, dd, J = 8.7, 2.0 Hz), 1.84-1.80 (1H, m), 1.60 (1H, br s), 1.10 (3H, t, J = 7.0 Hz), 0.93 (3H, d, J = 6.7 Hz), 0.66 (3H, d, J = 6.7 Hz). |
| 247 | ¹H-NMR (CDCl3) δ: 7.85 (1H, s), 7.15-7.09 (2H, m), 6.96-6.95 (2H, m), 3.88 (3H, s), 3.73-3.71 (2H, m), 3.30-3.27 (1H, m), 3.07-3.01 (1H, m), 1.81-1.76 (1H, m), 1.12 (3H, t, J = 7.0 Hz), 1.07 (3H, t, J = 7.0 Hz), 0.85 (3H, d, J = 6.7 Hz), 0.72 (3H, d, J = 7.0 Hz), 0.64 (3H, s). |
| 248 | ¹H-NMR (CDCl3) δ: 7.85 (1H, s), 7.16-7.14 (1H, m), 7.11-7.09 (1H, m), 6.96-6.94 (2H, m), 3.88 (3H, s), 3.72 (2H, q, J = 7.0 Hz), 3.16-3.14 (1H, m), 2.96-2.93 (1H, m), 1.82-1.76 (1H, m), 1.54-1.48 (2H, m), 1.07 (3H, t, J = 7.0 Hz), 0.91 (3H, t, J = 7.3 Hz), 0.85 (3H, d, J = 6.7 Hz), 0.72 (3H, d, J = 6.7 Hz), 0.63 (3H, s). |
| 249 | ¹H-NMR (CDCl3) δ: 7.71 (1H, s), 7.16-7.11 (2H, m), 6.97-6.96 (2H, m), 3.88 (3H, s), 3.77-3.70 (2H, m), 1.75-1.71 (1H, m), 1.26 (3H, d, J = 24.2 Hz), 1.08 (3H, t, J = 6.9 Hz), 0.85 (3H, d, J = 6.7 Hz), 0.82 (3H, t, J = 7.0 Hz). |
| 250 | ¹H-NMR (CDCl3) δ: 7.79-7.76 (2H, m), 7.72 (1H, s), 7.42-7.40 (2H, m), 3.65-3.64 (2H, m), 2.97 (3H, s), 1.77-1.71 (1H, m), 1.07 (3H, t, J = 6.9 Hz), 0.82-0.81 (6H, m), 0.73 (3H, d, J = 7.0 Hz). |
| 251 | ¹H-NMR (CDCl3) δ: 7.83 (1H, s), 7.78-7.77 (2H, m), 7.42-7.40 (2H, m), 3.64-3.63 (2H, m), 3.30-3.28 (1H, m), 3.03-3.01 (1H, m), 1.76-1.75 (1H, m), 1.10-1.05 (6H, m), 0.85 (3H, d, J = 6.7 Hz), 0.72 (3H, d, J = 7.0 Hz), 0.67 (3H, s). |
| 252 | ¹H-NMR (CDCl3) δ: 7.84 (1H, s), 7.79-7.77 (2H, m), 7.42-7.40 (2H, m), 3.64 (2H, q, J = 7.0 Hz), 3.16-3.13 (1H, m), 2.95-2.92 (1H, m), 1.80-1.73 (1H, m), 1.51-1.44 (2H, m), 1.06 (3H, t, J = 7.0 Hz) 0.90 (3H, t J = 7.4 Hz), 0.85 (3H, d, J = 6.8 Hz) 0.72 (3H, d, J = 6.8 Hz), 0.64 (3H, s). |
| 253 | ¹H-NMR (CDCl3) δ: 7.76-7.75 (2H, m), 7.46 (1H, d, J = 0.9 Hz), 7.39-7.37 (2H, m), 3.72-3.63 (2H, m), 1.89-1.80 (1H, m), 1.41 (3H, d, J = 22.9 Hz), 1.08 (3H, t, J = 6.9 Hz), 0.88 (3H, d, J = 6.7 Hz), 0.81 (3H, d, J = 6.7 Hz). |
| 254 | ¹H-NMR (CDCl3) δ: 7.53 (1H, s), 7.24 (1H, br s), 7.15-7.13 (1H, m), 7.08 (1H, d, J = 8.4 Hz), 6.95 (1H, dd, J = 8.4, 2.4 Hz), 4.19-4.10 (1H, m), 3.63-3.54 (1H, m), 2.05-1.99 (1H, m), 1.82 (1H, dd, J = 14.2, 8.1 Hz), 1.70-1.60 (1H, m), 1.13 (3H, t, J = 7.1 Hz), 0.80 (3H, d, J = 6.6 Hz), 0.74 (3H, d, J = 6.6 Hz). |
| 255 | ¹H-NMR (CDCl3) δ: 7.55-7.47 (2H, m), 7.29 (1H, td, J = 7.5, 1.1 Hz), 7.25-7.18 (2H, m), 4.00-3.91 (1H, m), 3.78-3.69 (1H, m), 1.97-1.84 (2H, m), 1.66-1.56 (1H, m), 1.11 (3H, t, J = 7.0 Hz), 0.74 (6H, d, J = 6.6 Hz). |
| 256 | ¹H-NMR (CDCl3) δ: 7.90 (1H, s), 6.87-6.80 (2H, m), 3.77-3.73 (2H, m), 3.37 (1H, dq, J = 8.9, 7.0 Hz), 3.08 (1H, dq, J = 8.9, 7.0 Hz), 1.80-1.79 (1H, m), 1.59-1.57 (2H, m), 1.47-1.33 (6H, m), 1.14 (3H, t, J = 7.0 Hz), 1.11 (3H, t, J = 7.0 Hz), 0.93 (3H, s). |
| 257 | ¹H-NMR (CDCl3) δ: 7.91 (1H, s), 6.85-6.82 (2H, m), 3.78-3.73 (2H, m), 3.23 (1H, dt, J = 8.6, 6.7 Hz), 3.01 (1H, dt, J = 8.6, 6.7 Hz), 1.81-1.77 (1H, m), 1.61-1.51 (5H, m), 1.50-1.32 (5H, m), 1.11 (3H, t, J = 7.0 Hz), 0.93 (3H, t, J = 7.0 Hz), 0.92 (3H, s). |
| 258 | ¹H-NMR (CDCl3) δ: 7.92 (1H, s), 6.90-6.84 (2H, m), 3.96-3.93 (1H, m), 3.74-3.71 (1H, m), 3.36 (1H, d, J = 7.8 Hz), 1.71-1.71 (1H, m), 1.15-1.07 (1H, m), 1.13 (3H, t, J = 7.0 Hz), 0.64-0.57 (1H, m), 0.53-0.46 (1H, m), 0.35-0.33 (1H, m), −0.01-−0.03 (1H, m). |
| 259 | ¹H-NMR (CDCl3) δ: 7.85 (1H, s), 6.88-6.85 (2H, m), 4.65 (1H, d, J = 8.3 Hz), 3.86-3.80 (2H, m), 2.00 (3H, s), 1.19-1.12 (1H, m), 1.13 (3H, t, J = 7.0 Hz), 0.58-0.55 (2H, m), 0.45-0.42 (1H, m), 0.09-0.07 (1H, m). |
| 260 | ¹H-NMR (CDCl3) δ: 8.13 (1H, s), 6.83-6.81 (2H, m), 3.94 (2H, q, J = 7.1 Hz), 2.13-2.09 (1H, m), 1.16 (3H, t, J = 7.1 Hz), 1.04-1.02 (2H, m), 0.92-0.90 (2H, m). |
| 261 | ¹H-NMR (CDCl3) δ: 7.96 (1H, s), 6.81-6.75 (2H, m), 3.80 (2H, q, J = 7.1 Hz), 1.21 (3H, s), 1.16-1.10 (1H, m), 1.15 (3H, s), 1.12 (3H, t, J = 7.1 Hz), 0.56-0.50 (1H, m), 0.47-0.40 (2H, m), 0.37-0.34 (1H, m). |
| 262 | ¹H-NMR (CDCl3) δ: 7.53 (1H, dd, J = 7.8, 1.4 Hz), 7.46-7.43 (1H, m), 7.41-7.38 (1H, m), 7.28-7.26 (2H, m), 6.62 (1H, d, J = 9.2 Hz), 4.14-4.04 (1H, m), 3.48-3.41 (1H, m), 1.97 (1H, dd, J = 14.1, 6.7 Hz), 1.75 (1H, dd, J = 14.1, 8.0 Hz), 1.67-1.59 (2H, m), 1.09 (3H, t, J = 7.2 Hz), 0.77 (3H, d, J = 6.7 Hz), 0.71 (3H, d, J = 6.4 Hz). |
| 263 | ¹H-NMR (CDCl3) δ: 7.48 (1H, s), 7.12-7.09 (2H, m), 7.03-7.00 (1H, m), 4.20-4.12 (1H, m), 3.36-3.29 (1H, m), 2.32 (2H, q, J = 7.6 Hz), 1.96 (1H, dd, J = 13.6, 6.3 Hz), 1.71-1.59 (2H, m), 1.15 (3H, t, J = 7.6 Hz), 1.09 (3H, t, J = 7.0 Hz), 0.81 (3H, d, J = 6.4 Hz), 0.71 (3H, d, J = 6.4 Hz). |
| 264 | ¹H-NMR (CDCl3) δ: 7.70 (1H, s), 7.55-7.53 (1H, m), 7.48-7.45 (1H, m), 7.41 (1H, td, J = 7.5, 1.3 Hz), 7.26-7.24 (1H, m), 4.15-4.08 (1H, m), 3.53-3.46 (1H, m), 1.98 (1H, dd, J = 14.3, 6.9 Hz), 1.75 (1H, dd, J = 14.3, 8.0 Hz), 1.67-1.59 (1H, m), 1.11 (3H, t, J = 7.0 Hz), 0.78 (3H, d, J = 6.4 Hz).0.72 (3H, d, J = 6.4 Hz). |
| 265 | ¹H-NMR (CDCl3) δ: 7.54 (1H, dd, J = 7.8, 1.4 Hz), 7.49 (1H, s), 7.48-7.45 (1H, m), 7.42-7.39 (1H, m), 7.26-7.25 (1H, m), 4.15-4.08 (1H, m), 3.53-3.46 (1H, m), 1.98 (1H, dd, J = 14.1, 6.7 Hz), 1.76 (1H, dd, J = 14.1, 8.0 Hz), 1.68-1.60 (1H, m), 1.11 (3H, t, J = 7.0 Hz), 0.78 (3H, d, J = 6.7 Hz), 0.72 (3H, d, J = 6.7 Hz). |
| 266 | ¹H-NMR (CDCl3) δ: 7.30-7.27 (3H, m), 7.16-7.12 (1H, m), 6.63 (1H, d, J = 9.2 Hz), 4.11-4.04 (1H, m), 3.44-3.37 (1H, m), 2.01 (1H, ddd, J = 14.1, 9.8, 5.5 Hz), 1.87 (1H, ddd, J = 14.1, 9.8, 6.1 Hz), 1.40-1.14 (10H, m), 1.09 (3H, t, J = 7.0 Hz), 0.85 (3H, t, J = 7.0 Hz). |
| 267 | ¹H-NMR (CDCl3) δ: 7.24-7.19 (2H, m), 7.06-7.02 (1H, m), 3.67-3.60 (1H, m), 2.88-2.81 (1H, m), 2.60-2.50 (2H, m), 2.43-2.36 (1H, m), 2.25 (1H, dt, J = 15.9, 6.1 Hz), 1.84 (1H, ddd, J = 13.5, 9.8, 5.8 Hz), 1.72 (1H, ddd, J = 13.5, 9.5, 6.4 Hz), 1.33-1.13 (14H, m), 0.90 (3H, t, J = 7.0 Hz), 0.87 (3H, t, J = 7.0 Hz). |
| 268 | ¹H-NMR (CDCl3) δ: 7.51 (1H, s), 7.31 (1H, dd, J = 8.3, 2.4 Hz), 7.28-7.24 (1H, m), 7.15 (1H, ddd, J = 8.5, 7.8, 2.4 Hz), 4.16-4.07 (1H, m), 3.50-3.41 (1H, m), 2.04-1.98 (1H, m), 1.88 (1H, ddd, J = 14.2, 9.8, 6.1 Hz), 1.44-1.09 (14H, m), 0.85 (3H, t, J = 7.1 Hz). |
| 269 | ¹H-NMR (CDCl3) δ: 7.71 (1H, s), 7.31 (1H, dd, J = 8.3, 2.4 Hz), 7.28-7.24 (1H, m), 7.15 (1H, ddd, J = 8.5, 7.8, 2.4 Hz), 4.15-4.07 (1H, m), 3.50-3.42 (1H, m), 2.05-1.97 (1H, m), 1.88 (1H, ddd, J = 14.2, 9.8, 6.1 Hz), 1.40-1.09 (14H, m), 0.85 (3H, t, J = 7.1 Hz). |
| 270 | ¹H-NMR (CDCl3) δ: 7.31-7.25 (3H, m), 7.16-7.12 (1H, m), 6.63 (1H, d, J = 9.3 Hz), 4.12-4.03 (1H, m), 3.45-3.36 (1H, m), 2.05-1.97 (1H, m), 1.87 (1H, ddd, J = 13.9, 9.8, 6.1 Hz), 1.41-1.13 (12H, m), 1.09 (3H, t, J = 7.1 Hz), 0.86 (3H, t, J = 7.1 Hz). |
| 271 | ¹H-NMR (CDCl3) δ: 7.51 (1H, s), 7.31 (1H, dd, J = 8.3, 2.4 Hz), 7.28-7.24 (1H, m), 7.15 (1H, ddd, J = 8.3, 7.8, 2.4 Hz), 4.16-4.07 (1H, m), 3.50-3.41 (1H, m), 2.05-1.98 (1H, m), 1.92-1.84 (1H, m), 1.42-1.09 (15H, m), 0.87 (3H, t, J = 7.1 Hz). |
| 272 | ¹H-NMR (CDCl3) δ: 7.71 (1H, s), 7.31 (1H, dd, J = 8.3, 2.7 Hz), 7.26 (1H, dd, J = 8.5, 5.9 Hz), 7.15 (1H, ddd, J = 8.5, 7.8, 2.7 Hz), 4.15-4.07 (1H, m), 3.50-3.42 (1H, m), 2.04-1.97 (1H, m), 1.91-1.84 (1H, m), 1.42-1.09 (15H, m), 0.87 (3H, t, J = 7.1 Hz). |
| 273 | ¹H-NMR (CDCl3) δ: 7.31-7.26 (3H, m), 7.14 (1H, ddd, J = 8.6, 8.0, 2.4 Hz), 6.63 (1H, d, J = 9.5 Hz), 4.11-4.04 (1H, m), 3.44-3.37 (1H, m), 2.01 (1H, ddd, J = 14.1, 9.8, 5.8 Hz), 1.87 (1H, ddd, J = 14.1, 10.1, 6.1 Hz), 1.40-1.13 (15H, m), 1.09 (3H, t, J = 7.0 Hz), 0.87 (3H, t, J = 7.1 Hz). |
| 274 | ¹H-NMR (CDCl3) δ: 7.51 (1H, s), 7.31 (1H, dd, J = 8.3, 2.4 Hz), 7.26 (2H, dd, J = 8.6, 5.8 Hz), 7.15 (1H, ddd, J = 8.6, 8.0, 2.4 Hz), 4.15-4.08 (1H, m), 3.49-3.42 (1H, m), 2.01 (1H, ddd, J = 14.4, 9.8, 5.5 Hz), 1.88 (1H, ddd, J = 14.4, 10.1, 6.1 Hz), 1.41-1.09 (17H, m), 0.87 (3H, t, J = 7.2 Hz). |

TABLE 4-continued

| Compounds | ¹H-NMR |
|---|---|
| 275 | ¹H-NMR (CDCl3) δ: 7.71 (1H, s), 7.31 (1H, dd, J = 8.2, 2.6 Hz), 7.26 (2H, dd, J = 8.5, 5.9 Hz), 7.15 (1H, ddd, J = 8.5, 7.8, 2.6 Hz), 4.15-4.07 (1H, m), 3.50-3.41 (1H, m), 2.05-1.97 (1H, m), 1.87 (1H, ddd, J = 13.9, 10.0, 6.3 Hz), 1.42-1.09 (17H, m), 0.87 (3H, t, J = 7.0 Hz). |
| 276 | ¹H-NMR (CDCl3) δ: 7.79 (1H, s), 6.92-6.85 (2H, m), 3.99-3.95 (2H, m), 3.73-3.67 (1H, m), 1.71-1.62 (2H, m), 1.51-1.47 (1H, m), 1.25-1.13 (7H, m), 0.83 (3H, t, J = 7.2 Hz). |
| 277 | ¹H-NMR (CDCl3) δ: 8.02 (1H, s), 6.86-6.79 (2H, m), 3.93 (2H, q, J = 7.1 Hz), 2.66 (2H, t, J = 7.3 Hz), 1.54-1.50 (2H, m), 1.30-1.26 (2H, m), 1.16 (3H, t, J = 7.1 Hz), 0.88 (3H, t, J = 7.3 Hz). |
| 278 | ¹H-NMR (CDCl3) δ: 7.25-7.20 (2H, m), 7.06-7.03 (1H, m), 3.59-3.52 (1H, m), 2.98-2.91 (1H, m), 2.63-2.52 (2H, m), 2.43-2.36 (1H, m), 2.31-2.25 (1H, m), 1.53 (3H, s), 0.90 (3H, t, J = 7.0 Hz). |
| 279 | ¹H-NMR (CDCl3) δ: 7.31 (1H, dd, J = 8.3, 2.4 Hz), 7.28-7.24 (2H, m), 7.15 (1H, ddd, J = 8.5, 8.1, 2.4 Hz), 6.61 (1H, d, J = 9.3 Hz), 4.08-3.99 (1H, m), 3.53-3.44 (1H, m), 1.72 (3H, s), 1.10 (3H, t, J = 7.1 Hz). |
| 280 | ¹H-NMR (CDCl3) δ: 7.49 (1H, s), 7.32 (1H, dd, J = 8.3, 2.4 Hz), 7.26 (1H, dd, J = 8.6, 5.8 Hz), 7.16 (1H, ddd, J = 8.6, 7.6, 2.4 Hz), 4.11-4.04 (1H, m), 3.57-3.50 (1H, m), 1.74 (3H, s), 1.12 (3H, t, J = 7.0 Hz). |
| 281 | ¹H-NMR (CDCl3) δ: 7.70 (1H, s), 7.32 (1H, dd, J = 8.3, 2.4 Hz), 7.25 (1H, dd, J = 8.6, 5.8 Hz), 7.16 (1H, ddd, J = 8.6, 8.0, 2.4 Hz), 4.11-4.04 (1H, m), 3.57-3.50 (1H, m), 1.73 (3H, s), 1.12 (3H, t, J = 7.0 Hz). |
| 282 | ¹H-NMR (CDCl3) δ: 7.24-17.19 (2H, m), 7.04 (1H, td, J = 8.2, 2.4 Hz), 3.67-3.60 (1H, m), 2.88-2.81 (1H, m), 2.60-2.50 (2H, m), 2.43-2.36 (1H, m), 2.26 (1H, dt, J = 15.9, 6.1 Hz), 1.85 (1H, ddd, J = 13.5, 9.5, 5.8 Hz), 1.73 (1H, ddd, J = 13.5, 9.2, 6.4 Hz), 1.35-1.18 (4H, m), 1.17-1.09 (4H, m), 0.90 (3H, t, J = 7.2 Hz), 0.83 (3H, t, J = 7.2 Hz). |
| 283 | ¹H-NMR (CDCl3) δ: 8.00 (1H, s), 6.90-6.88 (2H, m), 4.80 (1H, dd, J = 4.6, 2.4 Hz), 3.87-3.85 (2H, m), 2.64 (1H, d, J = 2.4 Hz), 2.00 (1H, d, J = 4.6 Hz), 1.15 (3H, t, J = 7.2 Hz). |
| 284 | ¹H-NMR (CDCl3) δ: 8.40 (1H, s), 6.88-6.83 (2H, m), 3.96 (2H, q, J = 7.2 Hz), 3.31 (1H, s), 1.18 (3H, t, J = 7.2 Hz). |
| 285 | ¹H-NMR (CDCl3) δ: 7.93 (1H, s), 6.92-6.86 (2H, m), 4.32 (1H, d, J = 2.2 Hz), 3.94-3.78 (2H, m), 3.20 (3H, s), 2.62 (1H, d, J = 2.2 Hz), 1.15 (3H, t, J = 7.1 Hz). |
| 286 | ¹H-NMR (CDCl3) δ: 7.98 (1H, s), 6.92-6.90 (2H, m), 5.35 (1H, dd, J = 47.5, 2.3 Hz), 3.89-3.85 (2H, m), 2.89 (1H, dd, J = 5.2, 2.3 Hz), 1.16 (3H, t, J = 7.0 Hz). |
| 287 | ¹H-NMR (CDCl3) δ: 9.12 (1H, s), 8.10 (1H, s), 7.29 (2H, dt, J = 9.3, 2.6 Hz), 7.07 (2H, dt, J = 9.3, 2.6 Hz), 3.95-3.90 (5H, m), 1.18 (3H, t, J = 7.0 Hz). |
| 288 | ¹H-NMR (CDCl3) δ: 9.04 (1H, s), 8.12 (1H, s), 7.92 (2H, dt, J = 8.3, 1.8 Hz), 7.57 (2H, dt, J = 8.3, 1.8 Hz), 3.86 (2H, q, J = 7.0 Hz), 1.19 (3H, t, J = 7.0 Hz). |
| 289 | ¹H-NMR (CDCl3) δ: 9.23 (1H, s), 8.12 (1H, s), 6.97-6.95 (2H, m), 3.94 (2H, q, J = 7.2 Hz), 1.20 (3H, t, J = 7.2 Hz). |
| 290 | ¹H-NMR (CDCl3) δ: 9.09 (1H, s), 8.11 (1H, s), 7.41-7.39 (2H, m), 7.33-7.28 (2H, m), 3.90 (2H, q, J = 7.0 Hz), 1.18 (3H, t, J = 7.0 Hz). |
| 291 | ¹H-NMR (CDCl3) δ: 7.31-7.26 (3H, m), 7.14 (1H, ddd, J = 8.6, 8.0, 2.8 Hz), 6.63 (1H, d, J = 9.5 Hz), 4.11-4.04 (1H, m), 3.44-3.37 (1H, m), 2.01 (1H, ddd, J = 14.1, 9.8, 5.8 Hz), 1.88 (1H, ddd, J = 14.1, 10.1, 6.1 Hz), 1.39-1.25 (2H, m), 1.23-1.19 (2H, m), 1.17-1.12 (4H, m), 1.09 (3H, t, J = 7.0 Hz), 0.83 (3H, t, J = 7.3 Hz). |
| 292 | ¹H-NMR (CDCl3) δ: 7.51 (1H, s), 7.31 (1H, dd, J = 8.3, 2.8 Hz), 7.26 (2H, dd, J = 8.6, 5.8 Hz), 7.15 (1H, ddd, J = 8.6, 8.0, 2.8 Hz), 4.15-4.08 (1H, m), 3.49-3.42 (1H, m), 2.01 (1H, ddd, J = 14.1, 9.8, 5.8 Hz), 1.88 (1H, ddd, J = 14.1, 9.8, 6.4 Hz), 1.41-1.29 (2H, m), 1.23-1.18 (2H, m), 1.15-1.09 (7H, m), 0.83 (3H, t, J = 7.2 Hz). |
| 293 | ¹H-NMR (CDCl3) δ: 7.71 (1H, s), 7.31 (1H, dd, J = 8.3, 2.4 Hz), 7.26 (2H, dd, J = 8.5, 5.9 Hz), 7.17-7.13 (1H, m), 4.15-4.07 (1H, m), 3.50-3.42 (1H, m), 2.01 (1H, ddd, J = 14.2, 10.0, 5.6 Hz), 1.88 (1H, ddd, J = 14.2, 9.8, 6.1 Hz), 1.42-1.28 (2H, m), 1.26-1.17 (2H, m), 1.16-1.09 (7H, m), 0.83 (3H, t, J = 7.1 Hz). |
| 294 | ¹H-NMR (CDCl3) δ: 9.06 (1H, s), 8.12 (1H, s), 7.43-7.38 (2H, m), 7.27-7.23 (2H, m), 4.18-4.11 (1H, m), 3.63-3.56 (1H, m), 1.18 (3H, t, J = 7.2 Hz). |
| 295 | ¹H-NMR (CDCl3) δ: 7.87 (1H, s), 7.33 (1H, dd, J = 8.3, 2.4 Hz), 7.28 (1H, dd, J = 8.7, 6.0 Hz), 7.17 (1H, ddd, J = 8.7, 8.0, 2.4 Hz), 5.79 (1H, dd, J = 17.4, 11.0 Hz), 5.44 (1H, d, J = 17.4 Hz), 5.04 (1H, d, J = 11.0 Hz), 4.15-4.08 (1H, m), 3.55-3.48 (1H, m), 1.13 (3H, t, J = 7.0 Hz). |
| 296 | ¹H-NMR (CDCl3) δ: 6.78-9-6.74 (2H, m), 5.86 (1H, tt, J = 56.6, 4.5 Hz), 3.58 (2H, td, J = 13.6, 4.5 Hz), 2.60 (2H, dd, J = 8.8, 6.2 Hz), 2.39 (2H, dd, J = 8.8, 6.2 Hz), 1.75-1.71 (3H, m), 0.77 (3H, s), 0.76 (3H, s). |
| 297 | ¹H-NMR (CDCl3) δ: 7.35 (1H, d, J = 9.5 Hz), 6.85 (2H, dd, J = 8.6, 7.0 Hz), 6.68 (1H, d, J = 9.5 Hz), 6.10 (1H, tt, J = 56.7, 4.5 Hz), 4.06 (2H, td, J = 13.1, 4.5 Hz), 1.96 (2H, d, J = 7.3 Hz), 1.66-1.61 (1H, m), 0.76 (3H, s), 0.75 (3H, s). |
| 298 | ¹H-NMR (CDCl3) δ: 9.54 (1H, t, J = 1.2 Hz), 7.45 (1H, s), 7.32 (1H, dd, J = 8.1, 2.4 Hz), 7.25 (3H, dd, J = 8.6, 5.8 Hz), 7.15 (1H, ddd, J = 8.6, 7.6, 2.4 Hz), 4.14-4.07 (1H, m), 3.54-3.47 (1H, m), 3.24 (1H, dd, J = 17.9, 1.2 Hz), 3.07 (1H, dd, J = 18.0, 1.2 Hz), 1.13 (3H, t, J = 7.0 Hz). |
| 299 | E-isomer: ¹H-NMR (CDCl3) δ: 7.82 (1H, s), 7.33 (1H, dd, J = 8.3, 2.4 Hz), 7.17-7.11 (2H, m), 5.93 (1H, dq, J = 15.6, 6.8 Hz), 5.43 (1H, dq, J = 15.6, 1.7 Hz), 4.16-4.06 (1H, m), 3.60-3.44 (1H, m), 1.69 (3H, dd, J = 6.8, 1.7 Hz), 1.11 (3H, t, J = 7.1 Hz).<br>Z-isomer: ¹H-NMR (CDCl3) δ: 7.61 (1H, s), 7.30-7.19 (3H, m), 5.59-5.48 (2H, m), 4.16-4.06 (1H, m), 3.60-3.44 (1H, m), 1.74 (3H, dd, J = 6.3, 1.0 Hz), 1.14 (3H, t, J = 7.1 Hz).<br>E/Z = 59/41 |
| 300 | ¹H-NMR (CDCl3) δ: 7.52 (1H, s), 7.29-7.26 (1H, m), 7.20 (1H, dd, J = 8.4, 6.0 Hz), 7.12 (1H, ddd, J = 8.4, 7.8, 2.4 Hz), 5.31-5.30 (1H, m), 4.15-4.06 (1H, m), 3.59-3.50 (1H, m), 1.70 (3H, d, J = 1.2 Hz), 1.63 (3H, d, J = 1.5 Hz), 1.13 (3H, t, J = 7.1 Hz). |
| 301 | ¹H-NMR (CDCl3) δ: 7.91 (1H, s), 7.34 (1H, dd, J = 8.1, 2.4 Hz), 7.27 (2H, dd, J = 8.6, 5.8 Hz), 7.19 (1H, ddd, J = 8.6, 7.6, 2.4 Hz), 6.52 (1H, s), 4.13-4.06 (1H, m), 3.59-3.52 (1H, m), 1.14 (3H, t, J = 7.0 Hz). |
| 302 | ¹H-NMR (CDCl3) δ: 7.65 (1H, s), 7.35-7.30 (2H, m), 7.16 (1H, ddd, J = 8.5, 7.8, 2.4 Hz), 4.20-4.11 (1H, m), 3.61-3.53 (1H, m), 2.82 (1H, s), 1.14 (3H, t, J = 7.1 Hz). |
| 303 | ¹H-NMR (CDCl3) δ: 7.66 (1H, s), 6.89-6.83 (2H, m), 3.92 (2H, q, J = 7.2 Hz), 2.88 (1H, s), 1.16 (3H, t, J = 7.2 Hz). |
| 304 | ¹H-NMR (CDCl3) δ: 7.57 (1H, s), 6.86 (2H, dd, J = 8.5, 7.1 Hz), 6.12 (1H, tt, J = 56.6, 4.5 Hz), 4.10 (2H, td, J = 12.9, 4.5 Hz), 1.97 (2H, d, J = 7.3 Hz), 1.70-1.60 (1H, m), 0.77 (6H, d, J = 6.6 Hz). |
| 305 | ¹H-NMR (CDCl3) δ: 7.77 (1H, s), 6.86 (2H, dd, J = 8.3, 7.1 Hz), 6.12 (1H, tt, J = 56.6, 4.4 Hz), 4.10 (2H, td, J = 12.9, 4.4 Hz), 1.96 (2H, d, J = 7.3 Hz), 1.70-1.60 (1H, m), 0.77 (6H, d, J = 6.6 Hz). |
| 306 | ¹H-NMR (CDCl3) δ: 7.15 (1H, d, J = 1.2 Hz), 6.85-6.80 (2H, m), 3.81 (2H, q, J = 7.0 Hz), 2.21 (3H, d, J = 1.2 Hz), 1.89 (2H, d, J = 7.3 Hz), 1.68-1.60 (1H, m), 1.09 (3H, t, J = 7.0 Hz), 0.75 (6H, d, J = 6.4 Hz). |
| 307 | ¹H-NMR (CDCl3) δ: 7.22 (1H, d, J = 1.1 Hz), 6.84-6.82 (2H, m), 6.11 (1H, tt, J = 56.7, 4.5 Hz), 4.06 (2H, td, J = 13.0, 4.5 Hz), 2.21 (3H, d, J = 1.1 Hz), 1.94 (2H, d, J = 7.3 Hz), 1.67-1.62 (1H, m), 0.75 (6H, d, J = 6.7 Hz). |
| 308 | ¹H-NMR (CDCl3) δ: 7.75 (1H, s), 7.26-7.23 (2H, m), 6.96 (1H, tt, J = 7.4, 1.0 Hz), 6.87-6.80 (2H, m), 6.77-6.75 (2H, m), 4.44 (2H, s), 3.89 (2H, q, J = 7.2 Hz), 1.16 (3H, t, J = 7.2 Hz). |
| 309 | E-isomer: ¹H-NMR (CDCl3) δ: 7.58 (1H, s), 6.87-6.84 (2H, m), 6.26 (1H, s), 3.89 (2H, q, J = 7.2 Hz), 1.16 (3H, t, J = 7.2 Hz). E/Z = >99/<1 |
| 310 | ¹H-NMR (CDCl3) δ: 7.74 (1H, s), 6.86-6.82 (2H, m), 6.78-6.77 (2H, m), 6.70-6.68 (2H, m), 4.39 (2H, s), 3.89 (2H, q, J = 7.2 Hz), 3.75 (3H, s), 1.16 (3H, t, J = 7.2 Hz). |
| 311 | ¹H-NMR (CDCl3) δ: 7.72 (1H, s), 7.19 (2H, dt, J = 9.8, 2.8 Hz), 6.87-6.81 (2H, m), 6.69 (2H, dt, J = 9.9, 2.8 Hz), 4.41 (2H, s), 3.89 (2H, q, J = 7.2 Hz), 1.16 (3H, t, J = 7.2 Hz). |
| 312 | ¹H-NMR (CDCl3) δ: 7.22-7.19 (2H, m), 7.04 (1H, td, J = 8.3, 2.4 Hz), 2.70 (3H, s), 2.60-2.57 (2H, m), 2.45-2.38 (1H, m), 2.30 (1H, dt, J = 16.0, 6.7 Hz), 1.90-1.75 (2H, m), 0.92 (3H, t, J = 7.5 Hz). |
| 313 | ¹H-NMR (CDCl3) δ: 7.25-7.20 (2H, m), 7.08 (1H, ddd, J = 8.5, 7.8, 2.7 Hz), 3.25-3.18 (1H, m), 3.20 (3H, s), 3.12-3.03 (1H, m), 2.38-2.30 (1H, m), 2.25-2.18 (1H, m), 1.95-1.79 (2H, m), 0.94 (3H, t, J = 7.4 Hz). |

TABLE 4-continued

| Compounds | ¹H-NMR |
|---|---|
| 314 | ¹H-NMR (CDCl3) δ: 7.34-7.30 (2H, m), 7.23 (1H, dd, J = 8.4, 6.0 Hz), 7.17-7.13 (1H, m), 6.67 (1H, d, J = 9.2 Hz), 3.70 (3H, s), 2.11-1.95 (2H, m), 0.98 (3H, t, J = 7.6 Hz). |
| 315 | ¹H-NMR (CDCl3) δ: 7.28-7.22 (2H, m), 7.10-7.05 (1H, m), 4.42-4.33 (1H, m), 3.44-3.36 (1H, m), 3.21 (1H, ddd, J = 16.1, 6.1, 5.1 Hz), 3.02 (1H, ddd, J = 16.1, 12.9, 5.9 Hz), 2.30 (1H, ddd, J = 16.1, 12.9, 5.1 Hz), 2.15 (1H, dt, J = 16.4, 5.9 Hz), 1.88 (1H, ddd, J = 13.7, 8.8, 6.1 Hz), 1.76 (1H, ddd, J = 13.7, 8.8, 6.6 Hz), 1.44-1.29 (2H, m), 1.02 (3H, t, J = 7.1 Hz), 0.79 (3H, t, J = 7.4 Hz). |
| 316 | ¹H-NMR (CDCl3) δ: 7.54 (1H, s), 7.32 (1H, dd, J = 8.3, 2.4 Hz), 7.22 (1H, dd, J = 8.3, 5.9 Hz), 7.16 (1H, ddd, J = 8.5, 7.8, 2.4 Hz), 3.26 (3H, s), 2.13-1.95 (2H, m), 1.00 (3H, t, J = 7.6 Hz). |
| 317 | ¹H-NMR (CDCl3) δ: 7.75 (1H, s), 7.32 (1H, dd, J = 8.2, 2.6 Hz), 7.22 (1H, dd, J = 8.5, 5.9 Hz), 7.16 (1H, ddd, J = 8.5, 7.8, 2.6 Hz), 3.27 (3H, s), 2.04 (2H, dtd, J = 37.8, 14.1, 6.5 Hz), 1.00 (3H, t, J = 7.6 Hz). |
| 318 | ¹H-NMR (CDCl3) δ: 7.28 (1H, d, J = 9.3 Hz), 7.16 (1H, d, J = 8.5 Hz), 7.05 (1H, d, J = 2.6 Hz), 6.92 (1H, dd, J = 8.5, 2.6 Hz), 6.61 (1H, d, J = 9.3 Hz), 4.12-4.03 (1H, m), 3.88 (3H, s), 3.50-3.41 (1H, m), 2.03 (1H, ddd, J = 14.2, 9.5, 6.1 Hz), 1.89 (1H, ddd, J = 14.2, 9.3, 6.6 Hz), 1.47-1.28 (2H, m), 1.09 (3H, t, J = 7.1 Hz), 0.78 (3H, t, J = 7.3 Hz). |
| 319 | ¹H-NMR (CDCl3) δ: 7.30 (1H, d, J = 9.3 Hz), 7.17 (1H, d, J = 8.5 Hz), 7.06 (1H, d, J = 2.7 Hz), 6.93 (1H, dd, J = 8.5, 2.7 Hz), 6.63 (1H, d, J = 9.3 Hz), 4.12-4.03 (1H, m), 3.88 (3H, s), 3.50-3.41 (1H, m), 2.10-1.91 (2H, m), 1.09 (3H, t, J = 7.0 Hz), 0.97 (3H, t, J = 7.6 Hz). |
| 320 | ¹H-NMR (CDCl3) δ: 7.50 (1H, s), 7.14 (1H, d, J = 8.6 Hz), 7.06 (1H, d, J = 2.8 Hz), 6.93 (1H, dd, J = 8.6, 2.8 Hz), 4.15-4.08 (1H, m), 3.89 (3H, s), 3.54-3.47 (1H, m), 2.03 (1H, ddd, J = 14.1, 9.5, 5.8 Hz), 1.90 (1H, ddd, J = 14.1, 9.5, 6.4 Hz), 1.46-1.32 (2H, m), 1.11 (3H, t, J = 7.0 Hz), 0.78 (3H, t, J = 7.3 Hz). |
| 321 | ¹H-NMR (CDCl3) δ: 7.71 (1H, s), 7.14 (1H, d, J = 8.6 Hz), 7.06 (1H, d, J = 2.8 Hz), 6.93 (1H, dd, J = 8.6, 2.8 Hz), 4.15-4.08 (1H, m), 3.89 (3H, s), 3.55-3.48 (1H, m), 2.03 (1H, ddd, J = 14.4, 9.5, 5.8 Hz), 1.90 (1H, ddd, J = 14.4, 9.5, 6.4 Hz), 1.46-1.31 (2H, m), 1.11 (3H, t, J = 7.2 Hz), 0.78 (3H, t, J = 7.3 Hz). |
| 322 | ¹H-NMR (CDCl3) δ: 7.32 (1H, d, J = 9.3 Hz), 7.12 (1H, d, J = 8.5 Hz), 7.07 (1H, d, J = 2.4 Hz), 6.93 (1H, dd, J = 8.5, 2.4 Hz), 6.64 (1H, d, J = 9.3 Hz), 3.87 (3H, s), 3.22 (3H, s), 2.15-1.96 (2H, m), 0.98 (3H, t, J = 7.6 Hz). |
| 323 | ¹H-NMR (CDCl3) δ: 7.22-7.18 (2H, m), 7.07-7.02 (1H, m), 2.70 (3H, s), 2.59-2.55 (2H, m), 2.45-2.36 (1H, m), 2.28 (1H, dt, J = 16.0, 6.5 Hz), 1.89-1.82 (1H, m), 1.78-1.70 (1H, m), 1.43-1.26 (2H, m), 0.79 (3H, t, J = 7.3 Hz). |
| 324 | ¹H-NMR (CDCl3) δ: 7.53 (1H, s), 7.10 (1H, d, J = 8.6 Hz), 7.07 (1H, d, J = 2.4 Hz), 6.94 (1H, dd, J = 8.6, 2.4 Hz), 3.88 (3H, s), 3.27 (3H, s), 2.14-1.98 (2H, m), 0.99 (3H, t, J = 7.5 Hz). |
| 325 | ¹H-NMR (CDCl3) δ: 7.73 (1H, s), 7.09 (1H, d, J = 8.5 Hz), 7.06 (1H, d, J = 2.7 Hz), 6.93 (1H, dd, J = 8.5, 2.7 Hz), 3.87 (3H, s), 3.27 (3H, s), 2.14-1.96 (2H, m), 0.98 (3H, t, J = 7.6 Hz). |
| 326 | E-isomer: ¹H-NMR (CDCl3) δ: 7.56 (1H, s), 6.86-6.84 (2H, m), 6.74 (1H, s), 3.89 (2H, q, J = 7.1 Hz), 1.16 (3H, t, J = 7.1 Hz). E/Z = >99/<1 |
| 327 | ¹H-NMR (CDCl3) δ: 7.53 (1H, s), 7.17 (1H, d, J = 8.6 Hz), 7.07 (1H, d, J = 2.6 Hz), 6.94 (1H, dd, J = 8.6, 2.6 Hz), 4.16-4.08 (1H, m), 3.89 (3H, s), 3.55-3.48 (1H, m), 2.11-2.03 (1H, m), 2.02-1.94 (1H, m), 1.12 (3H, t, J = 7.0 Hz), 0.99 (3H, t, J = 7.6 Hz). |
| 328 | ¹H-NMR (CDCl3) δ: 7.72 (1H, s), 7.15 (1H, d, J = 8.6 Hz), 7.06 (1H, d, J = 2.6 Hz), 6.93 (1H, dd, J = 8.6, 2.6 Hz), 4.14-4.08 (1H, m), 3.88 (3H, s), 3.55-3.48 (1H, m), 2.10-2.02 (1H, m), 2.00-1.93 (1H, m), 1.11 (3H, t, J = 7.0 Hz), 0.98 (3H, t, J = 7.5 Hz). |
| 329 | ¹H-NMR (CDCl3) δ: 7.32-7.29 (2H, m), 7.22 (1H, dd, J = 8.5, 5.9 Hz), 7.15 (1H, ddd, J = 8.5, 7.8, 2.4 Hz), 6.65 (1H, d, J = 9.3 Hz), 3.20 (3H, s), 2.05 (1H, ddd, J = 14.2, 9.0, 6.1 Hz), 1.92 (1H, ddd, J = 14.2, 9.0, 6.6 Hz), 1.48-1.29 (2H, m), 0.79 (3H, t, J = 7.3 Hz). |
| 330 | ¹H-NMR (CDCl3) δ: 7.65 (1H, s), 7.59 (1H, s), 7.15 (1H, d, J = 2.3 Hz), 7.04 (1H, d, J = 8.4 Hz), 6.97 (1H, dd, J = 8.4, 2.3 Hz), 3.33 (3H, s), 2.18-2.01 (2H, m), 1.00 (3H, t, J = 7.4 Hz). |
| 331 | ¹H-NMR (CDCl3) δ: 7.76 (1H, d, J = 8.8 Hz), 7.33 (1H, dd, J = 8.3, 2.4 Hz), 7.28 (1H, dd, J = 8.5, 5.9 Hz), 7.18 (1H, ddd, J = 8.5, 7.8, 2.4 Hz), 7.12 (1H, d, J = 8.8 Hz), 4.92-4.83 (1H, m), 4.03-3.94 (1H, m), 2.06 (1H, ddd, J = 14.2, 9.3, 6.1 Hz), 1.90 (1H, ddd, J = 14.2, 9.3, 6.3 Hz), 1.49-1.32 (2H, m), 1.23 (3H, t, J = 7.0 Hz), 0.79 (3H, t, J = 7.3 Hz). |
| 332 | ¹H-NMR (CDCl3) δ: 7.52 (1H, s), 7.32 (1H, dd, J = 8.3, 2.4 Hz), 7.21 (1H, dd, J = 8.5, 6.1 Hz), 7.16 (1H, ddd, J = 8.5, 7.8, 2.4 Hz), 3.26 (3H, s), 2.05 (1H, ddd, J = 14.2, 9.3, 6.1 Hz), 1.93 (1H, ddd, J = 14.2, 9.0, 6.6 Hz), 1.47-1.32 (2H, m), 0.79 (3H, t, J = 7.3 Hz). |
| 333 | ¹H-NMR (CDCl3) δ: 7.73 (1H, s), 7.31 (1H, dd, J = 8.3, 2.4 Hz), 7.21 (1H, dd, J = 8.5, 6.0 Hz), 7.16 (1H, ddd, J = 8.5, 7.8, 2.4 Hz), 3.27 (3H, s), 2.05 (1H, ddd, J = 14.2, 9.3, 6.1 Hz), 1.92 (1H, ddd, J = 14.2, 9.0, 6.6 Hz), 1.47-1.32 (2H, m), 0.79 (3H, t, J = 7.3 Hz). |
| 334 | ¹H-NMR (CDCl3) δ: 7.30 (1H, d, J = 9.3 Hz), 7.11 (1H, d, J = 8.5 Hz), 7.06 (1H, d, J = 2.6 Hz), 6.93 (1H, dd, J = 8.5, 2.6 Hz), 6.63 (1H, d, J = 9.3 Hz), 3.88 (3H, s), 3.21 (3H, s), 2.07 (1H, ddd, J = 14.2, 9.0, 6.3 Hz), 1.95 (1H, ddd, J = 14.2, 9.0, 6.6 Hz), 1.46-1.31 (2H, m) 0.79 (3H, t, J = 7.3 Hz). |
| 335 | ¹H-NMR (CDCl3) δ: 7.52 (1H, s), 7.09 (1H, d, J = 8.6 Hz), 7.07 (1H, d, J = 2.4 Hz), 6.94 (1H, dd, J = 8.6, 2.4 Hz), 3.88 (3H, s), 3.27 (3H, s), 2.07 (1H, ddd, J = 14.1, 9.5, 6.1 Hz), 1.96 (1H, ddd, J = 14.1, 9.2, 6.4 Hz), 1.46-1.33 (2H, m), 0.79 (3H, t, J = 7.3 Hz). |
| 336 | ¹H-NMR (CDCl3) δ: 7.72 (1H, s), 7.09 (1H, d, J = 8.5 Hz), 7.07 (1H, d, J = 2.4 Hz), 6.94 (1H, dd, J = 8.5, 2.4 Hz), 3.88 (3H, s), 3.28 (3H, s), 2.07 (1H, ddd, J = 14.2, 9.3, 6.1 Hz), 1.95 (1H, ddd, J = 14.2, 9.0, 6.6 Hz), 1.47-1.32 (2H, m), 0.79 (3H, t, J = 7.3 Hz). |
| 337 | ¹H-NMR (CDCl3) δ: 7.53 (1H, s), 7.08 (1H, d, J = 8.5 Hz), 7.05 (1H, d, J = 2.4 Hz), 6.92 (1H, dd, J = 8.5, 2.4 Hz), 4.09 (2H, q, J = 7.0 Hz), 3.27 (3H, s), 2.15-1.97 (2H, m), 1.46 (3H, t, J = 7.0 Hz), 0.99 (3H, t, J = 7.6 Hz). |
| 338 | ¹H-NMR (CDCl3) δ: 7.39 (1H, dd, J = 8.2, 2.6 Hz), 7.24 (1H, dd, J = 8.5, 6.1 Hz), 7.09 (1H, td, J = 8.2, 2.6 Hz), 3.73-3.64 (1H, m), 2.84-2.74 (1H, m), 2.64-2.51 (2H, m), 2.46-2.38 (1H, m), 2.26 (1H, dt, J = 15.9, 6.0 Hz), 1.90-1.71 (2H, m), 0.91 (6H, t, J = 7.4 Hz). |
| 339 | ¹H-NMR (CDCl3) δ: 7.29 (1H, dd, J = 8.4, 2.4 Hz), 7.22-7.18 (2H, m), 7.13 (1H, ddd, J = 8.6, 7.6, 2.4 Hz), 3.21 (3H, s), 2.21 (3H, d, J = 1.2 Hz), 2.03 (1H, ddd, J = 14.1, 9.5, 5.8 Hz), 1.90 (1H, ddd, J = 14.1, 9.2, 6.4 Hz), 1.44-1.33 (2H, m), 0.78 (3H, t, J = 7.3 Hz). |
| 340 | ¹H-NMR (CDCl3) δ: 7.48 (1H, dd, J = 8.1, 2.4 Hz), 7.31 (1H, d, J = 9.3 Hz), 7.29 (1H, dd, J = 8.5, 5.9 Hz), 7.19 (1H, ddd, J = 8.5, 7.8, 2.4 Hz), 6.65 (1H, d, J = 9.3 Hz), 4.17-4.08 (1H, m), 3.39-3.30 (1H, m), 2.09-1.99 (1H, m), 1.97-1.88 (1H, m), 1.10 (3H, t, J = 7.0 Hz), 0.99 (3H, t, J = 7.6 Hz). |
| 341 | ¹H-NMR (CDCl3) δ: 7.39 (1H, dd, J = 8.2, 2.4 Hz), 7.21 (1H, dd, J = 8.4, 6.0 Hz), 7.09 (1H, ddd, J = 8.4, 7.8, 2.4 Hz), 2.70 (3H, s), 2.61-2.55 (2H, m), 2.47-2.39 (1H, m), 2.29 (1H, dt, J = 16.0, 6.4 Hz), 1.91-1.73 (2H, m), 0.92 (3H, t, J = 7.4 Hz). |
| 342 | ¹H-NMR (CDCl3) δ: 7.53 (1H, s), 7.49 (1H, dd, J = 8.1, 2.4 Hz), 7.27 (1H, dd, J = 8.5, 5.6 Hz), 7.20 (1H, ddd, J = 8.5, 7.8, 2.4 Hz), 4.20-4.11 (1H, m), 3.45-3.36 (1H, m), 2.10-2.00 (1H, m), 1.99-1.89 (1H, m), 1.12 (3H, t, J = 7.1 Hz), 1.00 (3H, t, J = 7.6 Hz). |
| 343 | ¹H-NMR (CDCl3) δ: 7.73 (1H, s), 7.49 (1H, dd, J = 8.1, 2.4 Hz), 7.27 (1H, dd, J = 8.5, 5.9 Hz), 7.20 (1H, ddd, J = 8.5, 7.8, 2.4 Hz), 4.20-4.11 (1H, m), 3.45-3.37 (1H, m), 2.09-2.00 (1H, m), 1.98-1.89 (1H, m), 1.12 (3H, t, J = 7.0 Hz), 1.00 (3H, t, J = 7.6 Hz). |
| 344 | ¹H-NMR (CDCl3) δ: 7.30 (1H, d, J = 9.3 Hz), 7.24 (1H, d, J = 2.4 Hz), 7.18 (1H, d, J = 8.5 Hz), 6.97 (1H, dd, J = 8.5, 2.4 Hz), 6.63 (1H, d, J = 9.3 Hz), 4.17-4.08 (1H, m), 3.88 (3H, s), 3.45-3.36 (1H, m), 2.11-2.01 (1H, m), 2.00-1.91 (1H, m), 1.10 (3H, t, J = 7.0 Hz), 0.98 (3H, t, J = 7.6 Hz). |
| 345 | ¹H-NMR (CDCl3) δ: 7.52 (1H, s), 7.24 (1H, d, J = 2.7 Hz), 7.16 (1H, d, J = 8.5 Hz), 6.97 (1H, dd, J = 8.5, 2.7 Hz), 4.20-4.10 (1H, m), 3.88 (3H, s), 3.50-3.42 (1H, m), 2.11-1.92 (2H, m), 1.12 (3H, t, J = 7.1 Hz), 0.99 (3H, t, J = 7.6 Hz). |

| Compounds | ¹H-NMR |
|---|---|
| 346 | ¹H-NMR (CDCl3) δ: 7.72 (1H, s), 7.24 (1H, d, J = 2.4 Hz), 7.16 (1H, d, J = 8.5 Hz), 6.97 (1H, dd, J = 8.5, 2.4 Hz), 4.20-4.10 (1H, m), 3.88 (3H, s), 3.51-3.42 (1H, m), 2.11-2.02 (1H, m), 2.01-1.91 (1H, m), 1.12 (3H, t, J = 7.1 Hz), 0.99 (3H, t, J = 7.6 Hz). |
| 347 | ¹H-NMR (CDCl3) δ: 7.31 (1H, d, J = 9.3 Hz), 7.15 (1H, dd, J = 8.3, 5.6 Hz), 7.06-6.99 (2H, m), 6.62 (1H, d, J = 9.3 Hz), 4.17-4.09 (1H, m), 3.34-3.25 (1H, m), 2.09 (3H, s), 2.07-1.98 (1H, m), 1.95-1.85 (1H, m), 1.06 (3H, t, J = 7.0 Hz), 0.94 (3H, t, J = 7.6 Hz). |
| 348 | ¹H-NMR (CDCl3) δ: 7.49 (1H, dd, J = 8.4, 2.4 Hz), 7.33 (1H, d, J = 9.2 Hz), 7.24-7.18 (2H, m), 6.67 (1H, d, J = 9.2 Hz), 3.20 (3H, s), 2.11-2.04 (1H, m), 2.01-1.94 (1H, m), 1.00 (3H, t, J = 7.5 Hz). |
| 349 | ¹H-NMR (CDCl3) δ: 7.54 (1H, s), 7.50-7.48 (1H, m), 7.22-7.20 (2H, m), 3.26 (3H, s), 2.12-2.04 (1H, m), 2.03-195 (1H, m) 1.01 (3H, t, J = 7.6 Hz). |
| 350 | ¹H-NMR (CDCl3) δ: 7.75 (1H, s), 7.51-7.48 (1H, m), 7.22-7.20 (2H, m), 3.26 (3H, s), 2.13-1.94 (2H, m), 1.01 (3H, t, J = 7.6 Hz). |
| 351 | ¹H-NMR (CDCl3) δ: 7.53 (1H, s), 7.14 (1H, dd, J = 8.3, 5.8 Hz), 7.07-7.01 (2H, m), 4.20-4.12 (1H, m), 3.39-3.32 (1H, m), 2.08 (3H, s), 2.07-2.00 (1H, m), 1.95-1.88 (1H, m), 1.08 (3H, t, J = 7.0 Hz), 0.96 (3H, t, J = 7.5 Hz). |
| 352 | ¹H-NMR (CDCl3) δ: 7.73 (1H, s), 7.14 (1H, dd, J = 8.3, 5.8 Hz), 7.07-7.00 (2H, m), 4.20-4.10 (1H, m), 3.39-3.32 (1H, m), 2.08 (3H, s), 2.07-2.00 (1H, m), 1.95-1.87 (1H, m), 108 (3H, t, J = 7.0 Hz), 0.96 (3H, t, J = 7.5 Hz). |
| 353 | ¹H-NMR (CDCl3) δ: 7.31 (1H, d, J = 9.3 Hz), 7.15 (1H, dd, J = 8.3, 5.9 Hz), 7.06-6.99 (2H, m), 6.62 (1H, d, J = 9.3 Hz), 4.17-4.08 (1H, m), 3.34-3.25 (1H, m), 2.08 (3H, s), 2.07-1.98 (1H, m), 1.95-1.85 (1H, m), 1.06 (3H, t, J = 7.1 Hz), 0.94 (3H, t, J = 7.6 Hz). |
| 354 | ¹H-NMR (CDCl3) δ: 7.32 (1H, d, J = 9.3 Hz), 7.25 (1H, d, J = 2.7 Hz), 7.12 (1H, d, J = 8.5 Hz), 6.98 (1H, dd, J = 8.5, 2.7 Hz), 6.65 (1H, d, J = 9.3 Hz), 3.87 (3H, s), 3.21 (3H, s), 2.15-1.96 (2H, m), 0.99 (3H, t, J = 7.6 Hz). |
| 355 | ¹H-NMR (CDCl3) δ: 7.52 (1H, s), 7.14 (1H, dd, J = 8.3, 5.6 Hz), 7.07-7.00 (2H, m), 4.21-4.11 (1H, m), 3.39-3.31 (1H, m), 2.10-1.99 (1H, m), 2.08 (3H, s), 1.96-1.87 (1H, m), 1.08 (3H, t, J = 7.1 Hz), 0.96 (3H, t, J = 7.6 Hz). |
| 356 | ¹H-NMR (CDCl3) δ: 7.73 (1H, s), 7.14 (1H, dd, J = 8.3, 5.6 Hz), 7.07-7.00 (2H, m), 4.20-4.12 (1H, m), 3.40-3.32 (1H, m), 2.08 (3H, s), 2.06-1.99 (1H, m), 1.96-1.86 (1H, m), 1.08 (3H, t, J = 7.0 Hz), 0.96 (3H, t, J = 7.6 Hz). |
| 357 | ¹H-NMR (CDCl3) δ: 7.53 (1H, s), 7.25 (1H, d, J = 2.4 Hz), 7.10 (1H, d, J = 8.6 Hz), 6.98 (1H, dd, J = 8.6, 2.4 Hz), 3.87 (3H, s), 3.27 (3H, s), 2.14-2.07 (1H, m), 2.05-1.98 (1H, m), 1.00 (3H, t, J = 7.6 Hz). |
| 358 | ¹H-NMR (CDCl3) δ: 7.74 (1H, s), 7.25 (1H, d, J = 2.4 Hz), 7.10 (1H, d, J = 8.6 Hz), 6.98 (1H, dd, J = 8.6, 2.4 Hz), 3.87 (3H, s), 3.27 (3H, s), 2.14-2.06 (1H, m), 2.05-1.97 (1H, m), 1.00 (3H, t, J = 7.6 Hz). |
| 359 | ¹H-NMR (CDCl3) δ: 7.39 (1H, dd, J = 8.3, 2.4 Hz), 7.24 (1H, dd, J = 8.4, 6.0 Hz), 7.11-7.07 (1H, m), 3.73-3.66 (1H, m), 2.81-2.75 (1H, m), 2.62-2.51 (2H, m), 2.41 (1H, ddd, J = 16.0, 12.5, 5.9 Hz), 2.24 (1H, dt, J = 16.0, 5.9 Hz), 1.85 (1H, ddd, J = 13.8, 9.2, 5.5 Hz), 1.71 (1H, ddd, J = 13.8, 9.2, 6.4 Hz), 1.42-1.26 (2H, m), 0.91 (3H, t, J = 7.0 Hz), 0.79 (3H, t, J = 7.3 Hz). |
| 360 | ¹H-NMR (CDCl3) δ: 7.33 (1H, d, J = 9.3 Hz), 7.10-7.00 (3H, m), 6.64 (1H, d, J = 9.3 Hz), 3.15 (3H, s), 2.12-2.02 (1H, m), 2.08 (3H, s), 2.00-1.90 (1H, m), 0.95 (3H, t, J = 7.6 Hz). |
| 361 | ¹H-NMR (CDCl3) δ: 7.48 (1H, dd, J = 8.1, 2.4 Hz), 7.30-7.27 (2H, m), 7.18 (1H, ddd, J = 8.6, 8.0, 2.4 Hz), 6.64 (1H, d, J = 9.5 Hz), 4.15-4.09 (1H, m), 3.39-3.32 (1H, m), 2.01 (1H, ddd, J = 14.1, 9.8, 5.8 Hz), 1.85 (1H, ddd, J = 14.1, 9.5, 6.4 Hz), 1.47-1.31 (2H, m), 1.10 (3H, t, J = 7.2 Hz), 0.79 (3H, t, J = 7.3 Hz). |
| 362 | ¹H-NMR (CDCl3) δ: 7.54 (1H, s), 7.09-7.01 (3H, m), 3.21 (3H, s), 2.11-2.04 (1H, m), 2.08 (3H, s), 2.00-1.93 (1H, m), 0.97 (3H, t, J = 7.6 Hz). |
| 363 | ¹H-NMR (CDCl3) δ: 7.75 (1H, s), 7.09-7.01 (3H, m), 3.22 (3H, s), 2.11-2.04 (1H, m), 2.08 (3H, s), 1.99-1.92 (1H, m), 0.97 (3H, t, J = 7.5 Hz). |
| 364 | ¹H-NMR (CDCl3) δ: 9.21 (1H, t, J = 1.0 Hz), 8.33 (1H, s), 6.98-6.93 (2H, m), 3.94 (2H, q, J = 7.1 Hz), 1.19 (3H, t, J = 7.1 Hz). |
| 365 | ¹H-NMR (CDCl3) δ: 7.96 (1H, s), 6.90-6.87 (2H, m), 4.09 (1H, dq, J = 13.7, 7.0 Hz), 3.62-3.59 (2H, m), 1.82 (1H, ddq, J = 8.7, 6.8, 6.8 Hz), 1.67 (1H, d, J = 2.7 Hz), 1.12 (3H, t, J = 7.0 Hz), 0.96 (3H, d, J = 6.8 Hz), 0.64 (3H, dd, J = 6.8, 0.7 Hz). |
| 366 | ¹H-NMR (CDCl3) δ: 8.16 (1H, s), 6.82-6.80 (2H, m), 3.93 (2H, q, J = 7.0 Hz), 3.16 (1H, dq, J = 6.8, 6.8 Hz), 1.16 (3H, t, J = 7.0 Hz), 1.06 (6H, d, J = 6.8 Hz). |
| 367 | ¹H-NMR (CDCl3) δ: 7.33 (1H, d, J = 9.2 Hz), 7.10-7.00 (3H, m), 6.64 (1H, d, J = 9.2 Hz), 3.15 (3H, s), 2.11-2.03 (1H, m), 2.08 (3H, s), 1.99-1.91 (1H, m), 0.95 (3H, t, J = 7.5 Hz). |
| 368 | ¹H-NMR (CDCl3) δ: 7.51 (1H, s), 7.49 (1H, dd, J = 8.1, 2.4 Hz), 7.26 (2H, dd, J = 8.5, 5.9 Hz), 7.19 (1H, ddd, J = 8.5, 7.8, 2.4 Hz), 4.20-4.11 (1H, m), 3.45-3.37 (1H, m), 2.02 (1H, ddd, J = 14.2, 9.8, 5.9 Hz), 1.86 (1H, ddd, J = 14.2, 9.5, 6.6 Hz), 1.51-1.31 (2H, m), 1.12 (3H, t, J = 7.1 Hz), 0.79 (3H, t, J = 7.3 Hz). |
| 369 | ¹H-NMR (CDCl3) δ: 7.72 (1H, s), 7.48 (1H, dd, J = 7.9, 2.4 Hz), 7.26 (1H, dd, J = 8.5, 5.9 Hz), 7.19 (1H, ddd, J = 8.5, 7.8, 2.4 Hz), 4.19-4.11 (1H, m), 3.46-3.37 (1H, m), 2.02 (1H, ddd, J = 14.2, 9.5, 5.9 Hz), 1.85 (1H, ddd, J = 14.2, 9.5, 6.3 Hz), 1.51-1.29 (2H, m), 1.12 (3H, t, J = 7.0 Hz), 0.79 (3H, t, J = 7.3 Hz). |
| 370 | ¹H-NMR (CDCl3) δ: 7.28 (1H, d, J = 9.5 Hz), 7.24 (1H, d, J = 2.4 Hz), 7.17 (1H, d, J = 8.6 Hz), 6.97 (1H, dd, J = 8.6, 2.4 Hz), 6.62 (1H, d, J = 9.5 Hz), 4.15-4.08 (1H, m), 3.88 (3H, s), 3.45-3.38 (1H, m), 2.03 (1H, ddd, J = 14.4, 9.8, 5.8 Hz), 1.88 (1H, ddd, J = 14.4, 9.8, 6.4 Hz), 1.47-1.31 (2H, m), 1.10 (3H, t, J = 7.0 Hz), 0.79 (3H, t, J = 7.3 Hz). |
| 371 | ¹H-NMR (CDCl3) δ: 6.77-6.72 (2H, m), 3.31 (2H, q, J = 7.3 Hz), 2.57-2.54 (2H, m), 2.36-2.33 (2H, m), 1.81 (2H, dd, J = 8.0, 7.3 Hz), 1.40-1.33 (2H, m), 0.92 (3H, t, J = 7.2 Hz), 0.78 (3H, t, J = 7.3 Hz). |
| 372 | ¹H-NMR (CDCl3) δ: 7.29 (1H, d, J = 9.5 Hz), 6.88-6.81 (2H, m), 6.66 (1H, d, J = 9.5 Hz), 3.80 (2H, q, J = 7.1 Hz), 2.05-1.99 (2H, m), 1.44-1.34 (2H, m), 1.10 (3H, t, J = 7.1 Hz), 0.79 (3H, t, J = 7.3 Hz). |
| 373 | ¹H-NMR (CDCl3) δ: 6.78-6.72 (2H, m), 3.31 (2H, q, J = 7.0 Hz), 2.58-2.55 (2H, m), 2.38-2.35 (2H, m), 1.85 (2H, q, J = 7.6 Hz), 0.93 (3H, t, J = 7.6 Hz), 0.92 (3H, t, J = 7.0 Hz). |
| 374 | ¹H-NMR (CDCl3) δ: 7.54 (1H, s), 7.09-7.00 (3H, m), 3.21 (3H, s), 2.12-2.03 (1H, m), 2.08 (3H, s), 2.01-1.92 (1H, m), 0.97 (3H, t, J = 7.6 Hz). |
| 375 | ¹H-NMR (CDCl3) δ: 7.75 (1H, s), 7.09-7.00 (3H, m), 3.22 (3H, s), 2.12-2.03 (1H, m), 2.08 (3H, s), 2.00-1.91 (1H, m), 0.97 (3H, t, J = 7.6 Hz). |
| 376 | ¹H-NMR (CDCl3) δ: 7.50 (1H, s), 7.24 (1H, d, J = 2.4 Hz), 7.15 (1H, d, J = 8.6 Hz), 6.97 (1H, dd, J = 8.6, 2.4 Hz), 4.19-4.12 (1H, m), 3.88 (3H, s), 3.50-3.43 (1H, m), 2.04 (1H, ddd, J = 14.1, 9.5, 5.8 Hz), 1.89 (1H, ddd, J = 14.1, 9.5, 6.4 Hz), 1.48-1.32 (2H, m), 1.12 (3H, t, J = 7.0 Hz), 0.79 (3H, t, J = 7.3 Hz). |
| 377 | ¹H-NMR (CDCl3) δ: 7.31 (1H, d, J = 9.2 Hz), 6.88-6.83 (2H, m), 6.68 (1H, d, J = 9.2 Hz), 3.80 (2H, q, J = 7.1 Hz), 2.06 (2H, q, J = 7.5 Hz), 1.11 (3H, t, J = 7.1 Hz), 0.99 (3H, t, J = 7.5 Hz). |
| 378 | ¹H-NMR (CDCl3) δ: 7.52 (1H, s), 6.89-6.83 (2H, m), 3.85 (2H, q, J = 7.1 Hz), 2.03-2.00 (2H, m), 1.45-1.36 (2H, m), 1.13 (3H, t, J = 7.1 Hz), 0.80 (3H, t, J = 7.4 Hz). |
| 379 | ¹H-NMR (CDCl3) δ: 7.96 (1H, s), 6.87-6.85 (2H, m), 3.87 (2H, q, J = 7.1 Hz), 1.80 (3H, s), 1.12 (3H, t, J = 7.1 Hz). |
| 380 | ¹H-NMR (CDCl3) δ: 7.95 (1H, s), 6.62-6.58 (2H, m), 3.90 (2H, q, J = 7.1 Hz), 3.87 (3H, s), 1.80 (3H, s), 1.11 (3H, t, J = 7.1 Hz). |
| 381 | ¹H-NMR (CDCl3) δ: 7.85 (1H, s), 6.78-6.76 (2H, m), 3.87 (1H, dq, J = 13.7, 7.0 Hz), 3.70 (1H, dq, J = 13.7, 7.0 Hz), 1.85 (1H, dq, J = 6.8, 6.8 Hz), 1.35 (3H, s), 1.11 (1H, s), 1.10 (3H, t, J = 7.0 Hz), 0.86 (3H, d, J = 6.8 Hz), 0.78 (3H, d, J = 6.8 Hz). |
| 382 | ¹H-NMR (CDCl3) δ: 7.71 (1H, s), 7.24 (1H, d, J = 2.8 Hz), 7.15 (1H, d, J = 8.6 Hz), 6.97 (1H, dd, J = 8.6, 2.8 Hz), 4.19-4.10 (1H, m), 3.88 (3H, s), 3.50-3.43 (1H, m), 2.03 (1H, ddd, J = 14.4, 9.5, 5.8 Hz), 1.89 (1H, ddd, J = 144, 9.5, 6.4 Hz), |

TABLE 4-continued

| Compounds | ¹H-NMR |
|---|---|
| | 1.49-1.30 (2H, m), 1.11 (3H, t, J = 7.2 Hz), 0.79 (3H, t, J = 7.3 Hz). |
| 383 | ¹H-NMR (CDCl3) δ: 7.28 (1H, d, J = 9.5 Hz), 6.64 (1H, d, J = 9.5 Hz), 6.61-6.57 (2H, m), 3.88 (3H, s), 3.83 (2H, q, J = 7.1 Hz), 2.05-2.01 (2H, m), 1.43-1.35 (2H, m), 1.10 (3H, t, J = 7.1 Hz), 0.79 (3H, t, J = 7.3 Hz). |
| 384 | ¹H-NMR (CDCl3) δ: 7.51 (1H, s), 6.62-6.57 (2H, m), 3.90-3.85 (2H, m), 3.88 (3H, s), 2.06-2.02 (2H, m), 1.45-1.35 (2H, m), 1.12 (3H, t, J = 7.1 Hz), 0.79 (3H, t, J = 7.3 Hz). |
| 385 | ¹H-NMR (CDCl3) δ: 7.71 (1H, s), 6.62-6.58 (2H, m), 3.90-3.85 (2H, m), 3.88 (3H, s), 2.05-2.02 (2H, m), 1.44-1.36 (2H, m), 1.12 (3H, t, J = 7.2 Hz), 0.79 (3H, t, J = 7.3 Hz). |
| 386 | ¹H-NMR (CDCl3) δ: 7.54 (1H, s), 6.89-6.84 (2H, m), 3.85 (2H, q, J = 7.0 Hz), 2.07 (2H, q, J = 7.6 Hz), 1.13 (3H, t, J = 7.0 Hz), 1.01 (3H, t, J = 7.6 Hz). |
| 387 | ¹H-NMR (CDCl3) δ: 7.74 (1H, s), 6.89-6.84 (2H, m), 3.85 (2H, q, J = 7.1 Hz), 2.06 (2H, q, J = 7.5 Hz), 1.13 (3H, t, J = 7.1 Hz), 1.01 (3H, t, J = 7.5 Hz). |
| 388 | ¹H-NMR (CDCl3) δ: 7.30 (1H, d, J = 9.2 Hz), 6.65 (1H, d, J = 9.2 Hz), 6.62-6.58 (2H, m), 3.87 (3H, s), 3.83 (2H, q, J = 7.1 Hz), 2.08 (2H, q, J = 7.6 Hz), 1.11 (3H, t, J = 7.1 Hz), 0.99 (3H, t, J = 7.6 Hz). |
| 389 | ¹H-NMR (CDCl3) δ: 7.73 (1H, s), 6.89-6.83 (2H, m), 3.85 (2H, q, J = 7.1 Hz), 2.03-2.00 (2H, m), 1.44-1.36 (2H, m), 1.12 (3H, t, J = 7.1 Hz), 0.80 (3H, t, J = 7.3 Hz). |
| 390 | ¹H-NMR (CDCl3) δ: 7.52 (1H, s), 6.63-6.58 (2H, m), 3.90-3.85 (2H, m), 3.88 (3H, s), 2.09 (2H, q, J = 7.6 Hz), 1.13 (3H, t, J = 7.1 Hz), 1.00 (3H, t, J = 7.6 Hz). |
| 391 | ¹H-NMR (CDCl3) δ: 7.73 (1H, s), 6.62-6.57 (2H, m), 3.90-3.85 (2H, m), 3.88 (3H, s), 2.08 (2H, q, J = 7.6 Hz), 1.12 (3H, t, J = 7.1 Hz), 1.00 (3H, t, J = 7.6 Hz). |
| 392 | ¹H-NMR (CDCl3) δ: 7.28 (1H, d, J = 9.3 Hz), 7.14 (1H, dd, J = 8.3, 5.9 Hz), 7.06-6.98 (2H, m), 6.60 (1H, d, J = 9.3 Hz), 4.16-4.08 (1H, m), 3.35-3.26 (1H, m), 2.08 (3H, s), 2.00 (1H, ddd, J = 13.9, 9.0, 6.3 Hz), 1.83 (1H, ddd, J = 13.9, 9.0, 6.8 Hz), 1.40-1.30 (2H, m), 1.06 (3H, t, J = 7.0 Hz), 0.77 (3H, t, J = 7.3 Hz). |
| 393 | ¹H-NMR (CDCl3) δ: 6.78-6.72 (2H, m), 2.78 (3H, s), 2.59-2.56 (2H, m), 2.38-2.35 (2H, m), 1.84-1.81 (2H, m), 1.41-1.33 (2H, m), 0.79 (3H, t, J = 7.5 Hz). |
| 394 | ¹H-NMR (CDCl3) δ: 7.30 (1H, d, J = 9.3 Hz), 6.88-6.82 (2H, m), 6.68 (1H, d, J = 9.3 Hz), 3.28 (3H, s), 2.08-2.04 (2H, m), 1.45-1.35 (2H, m), 0.78 (3H, t, J = 7.4 Hz). |
| 395 | ¹H-NMR (CDCl3) δ: 6.78-6.71 (2H, m), 2.78 (3H, s), 2.60-2.56 (2H, m), 2.40-2.37 (2H, m), 1.86 (2H, q, J = 7.4 Hz), 0.94 (3H, t, J = 7.4 Hz). |
| 396 | ¹H-NMR (CDCl3) δ: 7.52 (1H, s), 6.89-6.83 (2H, m), 3.34 (3H, s), 2.09-2.05 (2H, m), 1.46-1.37 (2H, m), 0.79 (3H, t, J = 7.3 Hz). |
| 397 | ¹H-NMR (CDCl3) δ: 7.73 (1H, s), 6.89-6.83 (2H, m), 3.35 (3H, s), 2.08-2.04 (2H, m), 1.46-1.37 (2H, m), 0.79 (3H, t, J = 7.3 Hz). |
| 398 | ¹H-NMR (CDCl3) δ: 7.29 (1H, d, J = 9.5 Hz), 6.66 (1H, d, J = 9.5 Hz), 6.61-6.57 (2H, m), 3.87 (3H, s), 3.30 (3H, s), 2.10-2.07 (2H, m), 1.43-1.36 (2H, m), 0.78 (3H, t, J = 7.5 Hz). |
| 399 | ¹H-NMR (CDCl3) δ: 7.51 (1H, s), 6.62-6.57 (2H, m), 3.87 (3H, s), 3.35 (3H, s), 2.11-2.07 (2H, m), 1.46-1.36 (2H, m), 0.79 (3H, t, J = 7.3 Hz). |
| 400 | ¹H-NMR (CDCl3) δ: 7.72 (1H, s), 6.62-6.58 (2H, m), 3.87 (3H, s), 3.36 (3H, s), 2.10-2.07 (2H, m), 1.44-1.37 (2H, m), 0.79 (3H, t, J = 7.3 Hz). |
| 401 | ¹H-NMR (CDCl3) δ: 7.33 (1H, d, J = 9.2 Hz), 6.88-6.83 (2H, m), 6.69 (1H, d, J = 9.2 Hz), 3.28 (3H, s), 2.10 (2H, q, J = 7.5 Hz), 1.00 (3H, t, J = 7.5 Hz). |
| 402 | ¹H-NMR (CDCl3) δ: 7.51 (1H, s), 7.12 (1H, dd, J = 8.3, 5.9 Hz), 7.07-7.00 (2H, m), 4.20-4.11 (1H, m), 3.40-3.32 (1H, m), 2.07 (3H, s), 2.00 (1H, ddd, J = 14.2, 9.0, 6.3 Hz), 1.84 (1H, ddd, J = 14.2, 9.0, 6.6 Hz), 1.43-1.29 (2H, m), 1.08 (3H, t, J = 7.1 Hz), 0.77 (3H, t, J = 7.3 Hz). |
| 403 | ¹H-NMR (CDCl3) δ: 7.71 (1H, s), 7.12 (1H, dd, J = 8.4, 5.7 Hz), 7.07-6.99 (2H, m), 4.20-4.11 (1H, m), 3.41-3.32 (1H, m), 2.00 (1H, ddd, J = 13.9, 9.0, 6.3 Hz), 1.83 (1H, ddd, J = 13.9, 9.0, 6.6 Hz), 1.43-1.29 (2H, m), 1.08 (3H, t, J = 7.0 Hz), 0.77 (3H, t, J = 7.3 Hz). |
| 404 | ¹H-NMR (CDCl3) δ: 7.55 (1H, s), 6.89-6.84 (2H, m), 3.35 (3H, s), 2.12 (2H, q, J = 7.5 Hz), 1.02 (3H, t, J = 7.5 Hz). |
| 405 | ¹H-NMR (CDCl3) δ: 7.75 (1H, s), 6.90-6.83 (2H, m), 3.35 (3H, s), 2.11 (2H, q, J = 7.6 Hz), 1.02 (3H, t, J = 7.6 Hz). |
| 406 | ¹H-NMR (CDCl3) δ: 7.32 (1H, d, J = 9.5 Hz), 6.67 (1H, d, J = 9.5 Hz), 6.62-6.58 (2H, m), 3.30 (3H, s), 2.13 (2H, q, J = 7.5 Hz), 1.00 (3H, t, J = 7.5 Hz). |
| 407 | ¹H-NMR (CDCl3) δ: 7.53 (1H, s), 6.63-6.58 (2H, m), 3.87 (3H, s), 3.36 (3H, s), 2.14 (2H, q, J = 7.6 Hz), 1.01 (3H, t, J = 7.6 Hz). |
| 408 | ¹H-NMR (CDCl3) δ: 7.74 (1H, s), 6.62-6.58 (2H, m), 3.87 (3H, s), 3.36 (3H, s), 2.13 (2H, q, J = 7.5 Hz), 1.01 (3H, t, J = 7.5 Hz). |
| 409 | E-isomer: ¹H-NMR (CDCl3) δ: 7.78 (1H, s), 7.69-7.61 (1H, m), 7.20-7.14 (2H, m), 6.58 (1H, d, J = 16.4 Hz), 5.59 (1H, d, J = 16.4 Hz), 3.89 (2H, q, J = 7.1 Hz), 1.15 (3H, t, J = 7.1 Hz). E/Z = >99/<1 |
| 410 | ¹H-NMR (CDCl3) δ: 7.49-7.47 (1H, m), 7.31 (1H, d, J = 9.2 Hz), 7.24-7.17 (2H, m), 6.66 (1H, d, J = 9.2 Hz), 3.20 (3H, s), 2.05 (1H, ddd, J = 14.1, 9.5, 5.8 Hz), 1.91 (1H, ddd, J = 14.1, 9.5, 6.4 Hz), 1.49-1.31 (2H, m), 0.80 (3H, t, J = 7.3 Hz). |
| 411 | ¹H-NMR (CDCl3) δ: 7.28 (1H, d, J = 9.3 Hz), 7.06 (1H, d, J = 8.3 Hz), 6.84-6.80 (2H, m), 6.58 (1H, d, J = 9.3 Hz), 4.16-4.08 (1H, m), 3.86 (3H, s), 3.40-3.31 (1H, m), 2.04 (3H, s), 2.03-1.97 (1H, m), 1.86 (1H, ddd, J = 13.9, 8.8, 7.1 Hz), 1.40-1.30 (2H, m), 1.06 (3H, t, J = 7.1 Hz), 0.76 (3H, t, J = 7.3 Hz). |
| 412 | ¹H-NMR (CDCl3) δ: 7.50 (1H, s), 7.04 (1H, d, J = 8.3 Hz), 6.85-6.81 (2H, m), 4.19-4.12 (1H, m), 3.86 (3H, s), 3.44-3.37 (1H, m), 2.04-1.99 (1H, m), 2.03 (3H, s), 1.87 (1H, ddd, J = 14.1, 8.9, 6.7 Hz), 1.40-1.31 (2H, m), 1.08 (3H, t, J = 7.0 Hz), 0.77 (3H, t, J = 7.3 Hz). |
| 413 | ¹H-NMR (CDCl3) δ: 7.70 (1H, s), 7.04 (1H, d, J = 8.3 Hz), 6.84-6.81 (2H, m), 4.19-4.10 (1H, m), 3.86 (3H, s), 3.45-3.38 (1H, m), 2.03 (3H, s), 2.04-1.98 (1H, m), 1.87 (1H, ddd, J = 14.1, 9.2, 6.7 Hz), 1.40-1.32 (2H, m), 1.08 (3H, t, J = 6.9 Hz), 0.77 (3H, t, J = 7.3 Hz). |
| 414 | ¹H-NMR (CDCl3) δ: 7.53 (1H, s), 7.51-7.48 (1H, m), 7.22-7.19 (2H, m), 3.26 (3H, s), 2.05 (1H, ddd, J = 14.2, 9.3, 6.1 Hz), 1.91 (1H, ddd, J = 14.2, 9.3, 6.6 Hz), 1.49-1.33 (2H, m), 0.80 (3H, t, J = 7.3 Hz). |
| 415 | ¹H-NMR (CDCl3) δ: 7.73 (1H, s), 7.50-7.48 (1H, m), 7.21-7.19 (2H, m), 3.26 (3H, s), 2.05 (1H, ddd, J = 14.4, 9.5, 5.9 Hz), 1.91 (1H, ddd, J = 14.4, 9.5, 6.3 Hz), 1.51-1.31 (2H, m), 0.80 (3H, t, J = 7.3 Hz). |
| 416 | ¹H-NMR (CDCl3) δ: 7.30 (1H, d, J = 9.3 Hz), 7.24 (1H, d, J = 2.7 Hz), 7.11 (1H, d, J = 8.5 Hz), 6.97 (1H, dd, J = 8.5, 2.7 Hz), 6.63 (1H, d, J = 9.3 Hz), 3.87 (3H, s), 3.21 (3H, s), 2.07 (1H, ddd, J = 14.2, 9.3, 5.9 Hz), 1.94 (1H, ddd, J = 14.2, 9.3, 6.3 Hz), 1.48-1.32 (2H, m), 0.79 (3H, t, J = 7.3 Hz). |
| 417 | ¹H-NMR (CDCl3) δ: 7.52 (1H, s), 7.25 (1H, d, J = 2.4 Hz), 7.09 (1H, d, J = 8.6 Hz), 6.98 (1H, dd, J = 8.6, 2.4 Hz), 3.88 (3H, s), 3.27 (3H, s), 2.07 (1H, ddd, J = 14.1, 9.5, 5.8 Hz), 1.94 (1H, ddd, J = 14.1, 9.5, 6.4 Hz), 1.48-1.34 (2H, m), 0.80 (3H, t, J = 7.3 Hz). |
| 418 | ¹H-NMR (CDCl3) δ: 7.72 (1H, s), 7.24 (1H, d, J = 2.4 Hz), 7.09 (1H, d, J = 8.6 Hz), 6.98 (1H, dd, J = 8.6, 2.4 Hz), 3.88 (3H, s), 3.27 (3H, s), 2.07 (1H, ddd, J = 14.1, 9.5, 5.8 Hz), 1.94 (1H, ddd, J = 14.1, 9.5, 6.1 Hz), 1.49-1.32 (2H, m), 0.80 (3H, t, J = 7.3 Hz). |
| 419 | ¹H-NMR (CDCl3) δ: 7.32 (1H, d, J = 9.2 Hz), 7.09-7.00 (3H, m), 6.63 (1H, d, J = 9.2 Hz), 3.15 (3H, s), 2.08 (3H, s), 2.07-2.01 (1H, m), 1.88 (1H, ddd, J = 14.1, 8.9, 6.7 Hz), 1.38-1.33 (2H, m), 0.77 (3H, t, J = 7.3 Hz). |
| 420 | ¹H-NMR (CDCl3) δ: 7.53 (1H, s), 7.08-7.01 (3H, m), 3.21 (3H, s), 2.07 (3H, s), 2.07-2.01 (1H, m), 1.89 (1H, ddd, J = 14.1, 8.9, 6.7 Hz), 1.41-1.33 (2H, m), 0.78 (3H, t, J = 7.3 Hz). |
| 421 | ¹H-NMR (CDCl3) δ: 7.74 (1H, s), 7.08-7.01 (3H, m), 3.22 (3H, s), 2.07 (3H, s), 2.06-2.01 (1H, m), 1.88 (1H, ddd, J = 14.1, 8.9, 6.7 Hz), 1.41-1.33 (2H, m), 0.78 (3H, t, J = 7.3 Hz). |
| 422 | ¹H-NMR (CDCl3) δ: 7.40-7.33 (1H, m), 6.99-6.93 (2H, m), 3.31 (2H, q, J = 7.1 Hz), 2.58-2.55 (2H, m), 2.37-2.33 (2H, m), 1.84-1.80 (2H, m), 1.41-1.31 (2H, m), 0.92 (3H, t, J = 7.1 Hz), 0.77 (3H, t, J = 7.4 Hz). |
| 423 | ¹H-NMR (CDCl3) δ: 7.86 (1H, s), 6.80-6.76 (2H, m), 3.27 (3H, s), 1.86 (1H, dq, J = 6.8, 6.8 Hz), 1.36 (3H, s), 1.16 (1H, s), 0.86 (3H, d, J = 6.8 Hz), 0.77 (3H, d, J = 6.8 Hz). |
| 424 | ¹H-NMR (CDCl3) δ: 6.81-6.74 (2H, m), 3.94 (2H, q, J = 7.1 Hz), 3.13-3.09 (2H, m), 2.27-2.23 (2H, m), 1.86-1.82 (2H, m), |

TABLE 4-continued

| Compounds | ¹H-NMR |
|---|---|
| | 1.43-1.34 (2H, m), 1.04 (3H, t, J = 7.1 Hz), 0.79 (3H, t, J = 7.3 Hz). |
| 425 | ¹H-NMR (CDCl3) δ: 7.31 (1H, d, J = 9.2 Hz), 7.09-7.00 (3H, m), 6.62 (1H, d, J = 9.2 Hz), 3.15 (3H, s), 2.08 (3H, s), 2.04 (1H, ddd, J = 14.1, 8.9, 6.4 Hz), 1.88 (1H, ddd, J = 14.1, 8.9, 7.0 Hz), 1.41-1.31 (2H, m), 0.77 (3H, t, J = 7.3 Hz). |
| 426 | ¹H-NMR (CDCl3) δ: 7.53-7.47 (1H, m), 7.30 (1H, d, J = 9.3 Hz), 7.09-7.04 (2H, m), 6.66 (1H, d, J = 9.3 Hz), 3.81 (2H, q, J = 7.1 Hz), 2.02-1.99 (2H, m), 1.42-1.35 (2H, m), 1.10 (3H, t, J = 7.1 Hz), 0.77 (3H, t, J = 7.3 Hz). |
| 427 | ¹H-NMR (CDCl3) δ: 7.78 (1H, d, J = 8.9 Hz), 7.12 (1H, d, J = 8.9 Hz), 6.91-6.86 (2H, m), 4.51-4.47 (2H, m), 2.07-2.04 (2H, m), 1.46-1.38 (2H, m), 1.23 (3H, t, J = 7.0 Hz), 0.80 (3H, t, J = 7.3 Hz). |
| 428 | ¹H-NMR (CDCl3) δ: 7.56-7.48 (2H, m), 7.11-7.05 (2H, m), 3.85 (2H, q, J = 7.1 Hz), 2.04-1.99 (2H, m), 1.45-1.35 (2H, m), 1.12 (3H, t, J = 7.1 Hz), 0.78 (3H, t, J = 7.4 Hz). |
| 429 | ¹H-NMR (CDCl3) δ: 7.73 (1H, s), 7.55-7.49 (1H, m), 7.10-7.05 (2H, m), 3.86 (2H, q, J = 7.1 Hz), 2.03-1.99 (2H, m), 1.43-1.36 (2H, m), 1.12 (3H, t, J = 7.1 Hz), 0.78 (3H, t, J = 7.3 Hz). |
| 430 | ¹H-NMR (CDCl3) δ: 7.60 (1H, s), 6.93-6.87 (2H, m), 4.62-4.57 (2H, m), 2.08-2.04 (2H, m), 1.48-1.39 (2H, m), 1.25 (3H, t, J = 7.0 Hz), 0.82 (3H, t, J = 7.3 Hz). |
| 431 | ¹H-NMR (CDCl3) δ: 7.73 (1H, s), 7.08-7.01 (3H, m), 3.22 (3H, s), 2.07 (3H, s), 2.07-2.01 (1H, m), 1.88 (1H, ddd, J = 14.1, 8.9, 6.7 Hz), 1.41-1.33 (2H, m), 0.78 (3H, t, J = 7.3 Hz). |
| 432 | ¹H-NMR (CDCl3) δ: 7.96 (1H, s), 6.85-6.80 (2H, m), 3.27 (3H, s), 3.02 (3H, d, J = 1.0 Hz), 1.75 (1H, dq, J = 6.8, 6.8 Hz), 1.00 (3H, s), 0.84 (3H, d, J = 6.8 Hz), 0.71 (3H, d, J = 6.8 Hz). |
| 433 | ¹H-NMR (CDCl3) δ: 7.53 (1H, s), 7.08-7.01 (3H, m), 3.21 (3H, s), 2.07 (3H, s), 2.07-2.01 (1H, m), 1.89 (1H, ddd, J = 14.1, 7.0 Hz), 1.41-1.33 (2H, m), 0.78 (3H, t, J = 7.3 Hz). |
| 434 | ¹H-NMR (CDCl3) δ: 7.97 (1H, s), 6.88-6.83 (2H, m), 3.84 (2H, q, J = 7.1 Hz), 2.00-1.97 (2H, m), 1.43-1.35 (2H, m), 1.11 (3H, t, J = 7.1 Hz), 0.79 (3H, t, J = 7.3 Hz). |
| 435 | ¹H-NMR (CDCl3) δ: 6.77-6.71 (2H, m), 3.22-3.19 (2H, m), 2.57-2.54 (2H, m), 2.36-2.33 (2H, m), 1.84-1.81 (2H, m), 1.40-1.30 (4H, m), 0.78 (3H, t, J = 7.5 Hz), 0.72 (3H, t, J = 7.3 Hz). |
| 436 | ¹H-NMR (CDCl3) δ: 7.96 (1H, s), 6.62-6.57 (2H, m), 3.90-3.84 (2H, m), 3.88 (3H, s), 2.03-1.99 (2H, m), 1.43-1.34 (2H, m), 1.11 (3H, t, J = 7.1 Hz), 0.79 (3H, t, J = 7.4 Hz). |
| 437 | ¹H-NMR (CDCl3) δ: 7.28 (1H, d, J = 9.2 Hz), 6.87-6.82 (2H, m), 6.66 (1H, d, J = 9.2 Hz), 3.69-3.66 (2H, m), 2.03-1.99 (2H, m), 1.55-1.48 (2H, m), 1.42-1.35 (2H, m), 0.80-0.74 (6H, m). |
| 438 | ¹H-NMR (CDCl3) δ: 10.34 (1H, br s), 7.40 (1H, d, J = 9.3 Hz), 6.73 (1H, d, J = 9.3 Hz), 6.69-6.64 (2H, m), 3.93 (2H, q, J = 7.1 Hz), 2.13-2.09 (2H, m), 1.45-1.36 (2H, m), 1.15 (3H, t, J = 7.1 Hz), 0.80 (3H, t, J = 7.3 Hz). |
| 439 | ¹H-NMR (CDCl3) δ: 7.51 (1H, s), 6.88-6.83 (2H, m), 3.74-3.70 (2H, m), 2.03-2.00 (2H, m), 1.56-1.50 (2H, m), 1.44-1.36 (2H, m), 0.81-0.74 (6H, m). |
| 440 | ¹H-NMR (CDCl3) δ: 7.72 (1H, s), 6.88-6.83 (2H, m), 3.73-3.70 (2H, m), 2.03-2.00 (2H, m), 1.57-1.49 (2H, m), 1.43-1.36 (2H, m), 0.79 (3H, t, J = 7.3 Hz), 0.76 (3H, t, J = 7.5 Hz). |
| 441 | ¹H-NMR(CDCl3) δ: 7.96 (1H, s), 6.87-6.83 (2H, m), 3.73-3.70 (2H, m), 2.01-1.97 (2H, m), 1.56-1.49 (2H, m), 1.43-1.35 (2H, m), 0.79 (3H, t, J = 7.3 Hz), 0.75 (3H, t, J = 7.5 Hz). |
| 442 | ¹H-NMR (CDCl3) δ: 7.27 (1H, d, J = 9.3 Hz), 6.63 (1H, d, J = 9.3 Hz), 6.61-6.56 (2H, m), 3.88 (3H, s), 3.72-3.68 (2H, m), 2.05-2.01 (2H, m), 1.57-1.47 (2H, m), 1.43-1.33 (2H, m), 0.78 (3H, t, J = 7.3 Hz), 0.75 (3H, t, J = 7.5 Hz). |
| 443 | ¹H-NMR (CDCl3) δ: 7.50 (1H, s), 6.61-6.57 (2H, m), 3.88 (3H, s), 3.76-3.73 (2H, m), 2.05-2.02 (2H, m), 1.58-1.50 (2H, m), 1.43-1.36 (2H, m), 0.79 (3H, t, J = 7.5 Hz), 0.75, (3H, t, J = 7.5 Hz). |
| 444 | ¹H-NMR (CDCl3) δ: 7.71 (1H, s), 6.61-6.57 (2H, m), 3.88 (3H, s), 3.76-3.73 (2H, m), 2.05-2.02 (2H, m), 1.58-1.50 (2H, m), 1.43-1.35 (2H, m), 0.79 (3H, t, J = 7.3 Hz), 0.75 (3H, t, J = 7.3 Hz). |
| 445 | ¹H-NMR (CDCl3) δ: 7.95 (1H, s), 6.61-6.57 (2H, m), 3.88 (3H, s), 3.76-3.73 (2H, m), 2.03-2.00 (2H, m), 1.57-1.49 (2H, m), 1.42-1.35 (2H, m), 0.78 (3H, t, J = 7.3 Hz), 0.75 (3H, t, J = 7.3 Hz). |
| 446 | ¹H-NMR (CDCl3) δ: 9.26 (1H, t, J = 1.2 Hz), 8.10 (1H, s), 6.95-6.92 (2H, m), 3.41 (3H, s). |
| 447 | ¹H-NMR (CDCl3) δ: 7.74 (1H, s), 6.93-6.83 (2H, m), 3.62 (1H, d, J = 8.1 Hz), 3.32 (3H, s), 1.80-1.76 (2H, m), 0.94 (3H, d, J = 6.6 Hz), 0.60 (3H, d, J = 6.6 Hz). |
| 448 | ¹H-NMR (CDCl3) δ: 7.96 (1H, s), 6.82-6.78 (2H, m), 3.39 (3H, s), 3.17-3.09 (1H, m), 1.05 (6H, d, J = 6.7 Hz). |
| 449 | ¹H-NMR (CDCl3) δ: 9.22-9.22 (1H, m), 7.91 (1H, d, J = 9.5 Hz), 6.95-6.89 (2H, m), 6.70 (1H, dd, J = 9.5, 0.7 Hz), 3.86 (2H, q, J = 7.2 Hz), 1.14 (3H, t, J = 7.2 Hz). |
| 450 | ¹H-NMR (CDCl3) δ: 7.66 (1H, s), 6.80-6.76 (2H, m), 3.27 (3H, s), 1.86 (1H, dq, J = 6.7, 6.7 Hz), 1.36 (3H, s), 1.16 (1H, s), 0.86 (3H, d, J = 6.7 Hz), 0.77 (3H, d, J = 6.7 Hz). |
| 451 | ¹H-NMR (CDCl3) δ: 7.86 (1H, s), 6.86-6.80 (2H, m), 3.36-3.31 (1H, m), 3.25 (3H, s), 3.07-3.03 (1H, m), 1.76 (1H, dq, J = 6.8, 6.8 Hz), 1.10 (3H, t, J = 7.0 Hz), 0.90 (3H, s), 0.86 (3H, d, J = 6.8 Hz), 0.71 (3H, dd, J = 6.8, 1.0 Hz). |
| 452 | ¹H-NMR (CDCl3) δ: 7.76 (1H, s), 6.86-6.79 (2H, m), 3.26 (3H, s), 3.02 (3H, d, J = 1.0 Hz), 1.75 (1H, dq, J = 6.8, 6.8 Hz), 1.00 (3H, s), 0.84 (3H, d, J = 6.6 Hz), 0.71 (3H, d, J = 6.8 Hz). |
| 453 | ¹H-NMR (CDCl3) δ: 7.55 (1H, d, J = 9.5 Hz), 6.89-6.86 (2H, m), 6.77 (1H, d, J = 9.5 Hz), 4.06 (1H, td, J = 13.9, 7.0 Hz), 3.57-3.54 (1H, m), 1.84 (1H, ddq, J = 7.8, 6.8, 6.8 Hz), 1.67 (1H, t, J = 2.9 Hz), 1.10 (3H, t, J = 7.0 Hz), 0.96 (3H, d, J = 6.8 Hz), 0.63 (3H, dd, J = 6.8, 0.7 Hz). |
| 454 | ¹H-NMR (CDCl3) δ: 7.76 (1H, d, J = 9.8 Hz), 6.82-6.80 (2H, m), 6.70 (1H, d, J = 9.8 Hz), 3.88 (2H, q, J = 7.1 Hz), 3.19 (1H, dq, J = 6.8, 6.8 Hz), 1.14 (3H, t, J = 7.1 Hz), 1.05 (6H, d, J = 6.8 Hz). |
| 455 | ¹H-NMR (CDCl3) δ: 7.39 (1H, d, J = 9.8 Hz), 6.77-6.75 (2H, m), 6.65 (1H, d, J = 9.8 Hz), 3.85 (1H, dq, J = 13.5, 7.0 Hz), 3.64 (1H, dd, J = 13.5, 7.0 Hz), 1.89 (1H, dq, J = 6.8, 6.8 Hz), 1.35 (3H, s), 1.10 (1H, s), 1.09 (3H, t, J = 7.0 Hz), 0.85 (3H, d, J = 6.8 Hz), 0.77 (3H, d, J = 6.8 Hz). |
| 456 | ¹H-NMR (CDCl3) δ: 7.28 (1H, d, J = 9.5 Hz), 6.64 (1H, d, J = 9.5 Hz), 6.59-6.55 (2H, m), 4.08 (2H, q, J = 7.0 Hz), 3.83 (2H, q, J = 7.0 Hz), 2.05-2.02 (2H, m), 1.47 (3H, t, J = 7.0.Hz), 1.42-1.35 (2H, m), 1.10 (3H, t, J = 7.0 Hz), 0.78 (3H, t, J = 7.3 Hz). |
| 457 | ¹H-NMR (CDCl3) δ: 7.50 (1H, s), 6.60-6.55 (2H, m), 4.08 (2H, q, J = 7.0 Hz), 3.87 (2H, q, J = 7.1 Hz), 2.06-2.02 (2H, m), 1.47 (3H, t, J = 7.0 Hz), 1.44-1.35 (2H, m), 1.12 (3H, t, J = 7.1 Hz), 0.79 (3H, t, J = 7.3 Hz). |
| 458 | ¹H-NMR (CDCl3) δ: 7.71 (1H, s), 6.59-6.56 (2H, m), 4.08 (2H, q, J = 7.0 Hz), 3.87 (2H, q, J = 7.1 Hz), 2.05-2.02 (2H, m), 1.47 (3H, t, J = 7.0 Hz), 1.43-1.36 (2H, m), 1.12 (3H, t, J = 7.1 Hz), 0.79 (3H, t, J = 7.3 Hz). |
| 459 | ¹H-NMR (CDCl3) δ: 7.28 (1H, d, J = 9.5 Hz), 6.72-6.67 (2H, m), 6.65 (1H, d, J = 9.5 Hz), 4.76 (2H, d, J = 2.4 Hz), 3.82 (2H, q, J = 7.1 Hz), 2.64 (1H, t, J = 2.4 Hz), 2.05-2.01 (3H, m), 1.44-1.34 (2H, m), 1.10 (3H, t, J = 7.1 Hz), 0.78 (3H, t, J = 7.3 Hz). |
| 460 | ¹H-NMR (CDCl3) δ: 7.28 (1H, d, J = 9.5 Hz), 6.70-6.63 (3H, m), 4.71 (2H, q, J = 2.4 Hz), 3.83 (2H, q, J = 7.1 Hz), 2.05-2.01 (2H, m), 1.91 (3H, t, J = 2.4 Hz), 1.43-1.34 (2H, m), 1.11 (3H, t, J = 7.1 Hz), 0.79 (3H, t, J = 7.3 Hz). |
| 461 | ¹H-NMR (CDCl3) δ: 7.51 (1H, s), 6.71-6.66 (2H, m), 4.71 (2H, q, J = 2.3 Hz), 3.87 (2H, q, J = 7.1 Hz), 2.06-2.02 (2H, m), 1.91 (3H, t, J = 2.3 Hz), 1.45-1.36 (2H, m), 1.13 (3H, t, J = 7.1 Hz), 0.79 (3H, t, J = 7.4 Hz). |
| 462 | ¹H-NMR (CDCl3) δ: 7.71 (1H, s), 6.70-6.65 (2H, m), 4.71 (2H, q, J = 2.4 Hz), 3 88 (2H, q, J = 71 Hz), 2.05-2.01 (2H, m), 1.91 (3H, t, J = 2.4 Hz), 1.45-1.35 (2H, m), 1.12 (3H, t, J = 7.1 Hz), 0.79 (3H, t, J = 7.4 Hz). |
| 463 | ¹H-NMR (CDCl3) δ: 7.51 (1H, s), 6.72-6.68 (2H, m), 4.76 (2H, d, J = 2.4 Hz), 3.87 (2H, q, J = 7.1 Hz), 2.64 (1H, t, J = 2.4 Hz), 2.05-2.01 (2H, m), 1.45-1.35 (2H, m), 1.13 (3H, t, J = 7.1 Hz), 0.79 (3H, t, J = 7.3 Hz). |
| 464 | ¹H-NMR (CDCl3) δ: 7.72 (1H, s), 6.72-6.67 (2H, m), 4.76 (2H, d, J = 2.4 Hz), 3.87 (2H, q, J = 7.1 Hz), 2.64 (1H, t, J = 2.4 Hz), 2.05-2.01 (2H, m), 1.45-1.35 (2H, m), 1.12 (3H, t, J = 7.1 Hz), 0.79 (3H, t, J = 7.3 Hz). |
| 465 | ¹H-NMR (CDCl3) δ: 7.96 (1H, s), 6.84-6.80 (2H, m), 3.80-3.74 (2H, m), 3.02 (3H, d, J = 1.0 Hz), 1.73 (1H, dq, J = 6.8, |

| Compounds | ¹H-NMR |
|---|---|
| | 6.8 Hz), 1.11 (3H, t, J = 7.1 Hz), 0.97 (3H, s), 0.83 (3H, d, J = 6.8 Hz), 0.71 (3H, d, J = 6.8 Hz). |
| 466 | ¹H-NMR (CDCl3) δ: 8.07 (1H, s), 6.86-6.79 (2H, m), 3.86-3.67 (2H, m), 3.36-3.29 (1H, m), 3.07-3.03 (1H, m), 1.74 (1H, dq, J = 6.8, 6.8 Hz), 1.11 (6H, t, J = 7.0 Hz), 0.86-0.85 (6H, m), 0.72 (3H, d, J = 6.8 Hz). |
| 467 | ¹H-NMR (CDCl3) δ: 7.99 (1H, s), 6.57-6.54 (2H, m), 3.88 (3H, s), 3.85-3.83 (1H, m), 3.76-3.73 (1H, m), 3.03 (3H, s), 1.76 (1H, dq, J = 6.6, 6.6 Hz), 1.11 (3H, t, J = 7.0 Hz), 0.93 (3H, s), 0.84 (3H, d, J = 6.6 Hz), 0.72 (3H, d, J = 6.6 Hz). |
| 468 | ¹H-NMR (CDCl3) δ: 8.08 (1H, s), 6.56-6.53 (2H, m), 3.89 (3H, s), 3.85-3.83 (1H, m), 3.74-3.71 (1H, m), 3.34-3.29 (1H, m), 3.07-3.05 (1H, m), 1.75-1.73 (1H, m), 1.12 (3H, t, J = 7.0 Hz), 1.10 (3H, t, J = 7.0 Hz), 0.86-0.85 (6H, m), 0.72 (3H, dd, J = 6.8, 1.0 Hz). |
| 469 | ¹H-NMR (CDCl3) δ: 7.57 (1H, d, J = 9.5 Hz), 6.91-6.84 (2H, m), 6.74 (1H, d, J = 9.5 Hz), 3.96-3.89 (2H, m), 3.70-3.63 (1H, m), 1.78 (1H, d, J = 2.4 Hz), 1.73-1.66 (1H, m), 1.59-1.55 (1H, m), 1.11 (3H, t, J = 7.1 Hz), 0.76 (3H, t, J = 7.1 Hz). |
| 470 | ¹H-NMR (CDCl3) δ: 7.37 (1H, d, J = 9.5 Hz), 6.88-6.83 (2H, m), 6.69 (1H, d, J = 9.5 Hz), 6.11 (1H, tt, J = 56.8, 4.5 Hz), 4.05 (2H, td, J = 13.0, 4.5 Hz), 2.07-2.03 (2H, m), 1.45-1.36 (2H, m), 0.79 (3H, t, J = 7.3 Hz). |
| 471 | ¹H-NMR (CDCl3) δ: 7.59 (1H, s), 6.88-6.84 (2H, m), 6.13 (1H, tt, J = 56.5, 4.6 Hz), 4.09 (2H, td, J = 12.8, 4.6 Hz), 2.08-2.04 (2H, m), 1.47-1.31 (2H, m), 0.80 (3H, t, J = 7.3 Hz). |
| 472 | ¹H-NMR (CDCl3) δ: 7.80 (1H, s), 6.89-6.83 (2H, m), 6.13 (1H, tt, J = 56.6, 4.5 Hz), 4.09 (2H, td, J = 12.9, 4.5 Hz), 2.08-2.04 (2H, m), 1.47-1.37 (2H, m), 0.80 (3H, t, J = 7.4 Hz). |
| 473 | ¹H-NMR (CDCl3) δ: 8.04 (1H, s), 6.88-6.84 (2H, m), 6.12 (1H, tt, J = 56.6, 4.4 Hz), 4.08 (2H, td, J = 12.9, 4.4 Hz), 2.05-2.01 (2H, m), 1.46-1.36 (2H, m), 0.79 (3H, t, J = 7.3 Hz). |
| 474 | ¹H-NMR (CDCl3) δ: 7.36 (1H, d, J = 9.3 Hz), 6.66 (1H, d, J = 9.3 Hz), 6.62-6.57 (2H, m), 6.11 (1H, tt, J = 56.8, 4.5 Hz), 4.08 (2H, td, J = 13.2, 4.5 Hz), 3.88 (3H, s), 2.09-2.05 (2H, m), 1.45-1.35 (2H, m), 0.79 (3H, t, J = 7.4 Hz). |
| 475 | ¹H-NMR (CDCl3) δ: 7.57 (1H, s), 6.63-6.58 (2H, m), 6.14 (1H, tt, J = 56.6, 4.6 Hz), 4.12 (2H, td, J = 12.9, 4.6 Hz), 3.88 (3H, s), 2.10-2.06 (2H, m), 1.46-1.37 (2H, m), 0.79 (3H, t, J = 7.3 Hz). |
| 476 | ¹H-NMR (CDCl3) δ: 7.78 (1H, s), 6.62-6.58 (2H, m), 6.14 (1H, tt, J = 56.6, 4.6 Hz), 4.12 (2H, td, J = 12.9, 4.6 Hz), 3.88 (3H, s), 2.10-2.06 (2H, m), 1.46-1.37 (2H, m), 0.79 (3H, t, J = 7.3 Hz). |
| 477 | ¹H-NMR (CDCl3) δ: 8.02 (1H, s), 6.61-6.58 (2H, m), 6.13 (2H, tt, J = 56.7, 4.6 Hz), 4.12 (2H, td, J = 12.8, 4.6 Hz), 3.88 (3H, s), 2.07-2.04 (2H, m), 1.44-1.37 (2H, m), 0.79 (3H, t, J = 7.5 Hz). |
| 478 | ¹H-NMR (CDCl3) δ: 7.52 (1H, d, J = 9.5 Hz), 6.89-6.85 (2H, m), 6.70 (1H, ddq, J = 9.5 Hz), 4.11 (2H, s), 3.82 (2H, q, J = 7.0 Hz), 1.12 (3H, t, J = 7.0 Hz). |
| 479 | ¹H-NMR (CDCl3) δ: 7.55 (1H, d, J = 9.8 Hz), 6.85-6.78 (2H, m), 6.69 (1H, d, J = 9.8 Hz), 3.80-3.66 (2H, m), 3.01 (3H, s), 1.79-1.72 (1H, m), 1.10 (1H, t, J = 7.1 Hz), 0.98 (3H, s), 0.83 (3H, d, J = 6.8 Hz), 0.71 (3H, d, J = 6.8 Hz). |
| 480 | ¹H-NMR (CDCl3) δ: 7.84 (1H, d, J = 9.8 Hz), 6.82 (2H, td, J = 8.7, 1.6 Hz), 6.71 (1H, d, J = 9.8 Hz), 3.88 (2H, q, J = 7.2 Hz), 2.71 (2H, q, J = 7.2 Hz), 1.14 (3H, t, J = 7.2 Hz), 1.04 (3H, t, J = 7.2 Hz). |
| 481 | ¹H-NMR (CDCl3) δ: 7.41 (1H, d, J = 9.8 Hz), 6.79-6.76 (2H, m), 6.66 (1H, d, J = 9.8 Hz), 3.84-3.68 (2H, m), 1.76-1.69 (1H, m), 1.57-1.53 (1H, m), 1.37 (3H, s), 1.18 (1H, s), 1.09 (3H, t, J = 7.3 Hz), 0.79 (3H, t, J = 7.1 Hz). |
| 482 | ¹H-NMR (CDCl3) δ: 7.88 (1H, s), 6.81-6.76 (2H, m), 3.85-3.75 (2H, m), 1.73-1.67 (1H, m), 1.59-1.53 (1H, m), 1.36 (3H, s), 1.25 (1H, s), 1.11 (3H, t, J = 7.2 Hz), 0.81 (3H, t, J = 7.2 Hz). |
| 483 | ¹H-NMR (CDCl3) δ: 7.96 (1H, s), 6.84-6.78 (2H, m), 3.82-3.76 (2H, m), 2.98 (3H, s), 1.58-1.51 (2H, m), 1.11 (6H, s), 0.75 (3H, t, J = 7.4 Hz). |
| 484 | ¹H-NMR (CDCl3) δ: 7.99 (1H, s), 6.82-6.77 (2H, m), 3.81-3.73 (2H, m), 3.25-3.20 (1H, m), 3.12-3.08 (1H, m), 1.57-1.56 (2H, m), 1.10 (3H, t, J = 7.0 Hz), 1.07 (3H, s), 0.97 (3H, t, J = 7.0 Hz), 0.74 (3H, t, J = 7.5 Hz). |
| 485 | ¹H-NMR (CDCl3) δ: 8.08 (1H, s), 6.58-6.53 (2H, m), 3.87 (3H, s), 3.80-3.79 (2H, m), 3.29-3.27 (1H, m), 3.11-3.09 (1H, m), 1.57-1.50 (2H, m), 1.12-1.06 (6H, m), 1.00 (3H, s), 0.75 (3H, t, J = 7.4 Hz). |
| 486 | ¹H-NMR (CDCl3) δ: 8.02 (1H, s), 6.59-6.54 (2H, m), 3.88 (3H, s), 3.81 (2H, q, J = 7.1 Hz), 3.03 (3H, 8), 1.55-1.52 (2H, m), 1.11 (3H, t, J = 7.1 Hz), 1.04 (3H, s), 0.76 (3H, t, J = 7.4 Hz). |
| 487 | ¹H-NMR (CDCl3) δ: 7.76 (1H, s), 6.57-6.54 (2H, m), 3.86 (3H, s), 3.27 (3H, s), 1.82 (1H, dq, J = 6.9, 6.9 Hz), 1.33 (3H, s), 1.27 (1H, s), 0.85 (3H, d, J = 6.9 Hz), 0.77 (3H, d, J = 6.9 Hz). |
| 488 | ¹H-NMR (CDCl3) δ: 7.79 (1H, s), 6.58-6.56 (2H, m), 3.87 (3H, s), 3.27 (3H, s), 3.03 (3H, s), 1.78 (1H, dq, J = 6.9, 6.9 Hz), 0.96 (3H, s), 0.84 (3H, d, J = 6.9 Hz), 0.71 (3H, d, J = 6.9 Hz). |
| 489 | ¹H-NMR (CDCl3) δ: 7.87 (1H, s), 6.59-6.52 (2H, m), 3.87 (3H, s), 3.35-3.30 (1H, m), 3.26 (3H, s), 3.06-3.05 (1H, m), 1.76 (1H, dq, J = 6.9, 6.9 Hz), 1.12 (3H, t, J = 6.9 Hz), 0.89 (3H, s), 0.86 (3H, d, J = 6.9 Hz), 0.71 (3H, dd, J = 6.9, 0.9 Hz). |
| 490 | ¹H-NMR (CDCl3) δ: 7.79 (1H, s), 6.92-6.85 (2H, m), 3.98 (1H, t, J = 6.8 Hz), 3.34 (3H, s), 1.77-1.52 (3H, m), 0.77 (3H, t, J = 7.3 Hz). |
| 491 | ¹H-NMR (CDCl3) δ: 7.56-7.49 (1H, m), 7.37 (1H, d, J = 9.5 Hz), 7.10-7.04 (2H, m), 6.68 (1H, d, J = 9.5 Hz), 6.12 (1H, tt, J = 56.8, 4.5 Hz), 4.06 (2H, td, J = 13.0, 4.5 Hz), 2.07-2.03 (2H, m), 1.45-1.35 (2H, m), 0.77 (3H, t, J = 7.4 Hz). |
| 492 | ¹H-NMR (CDCl3) δ: 7.59 (1H, s), 7.58-7.52 (1H, m), 7.10-7.07 (2H, m), 6.14 (1H, tt, J = 56.6, 4.5 Hz), 4.10 (2H, td, J = 12.8, 4.5 Hz), 2.08-2.05 (2H, m), 1.45-1.38 (2H, m), 0.78 (3H, t, J = 7.3 Hz). |
| 493 | ¹H-NMR (CDCl3) δ: 7.80 (1H, s), 7.58-7.52 (1H, m), 7.08 (2H, dd, J = 8.6, 7.0 Hz), 6.14 (1H, tt, J = 56.6, 4.6 Hz), 4.10 (2H, td, J = 12.8, 4.6 Hz), 2.08-2.05 (2H, m), 1.45-1.37 (2H, m), 0.78 (3H, t, J = 7.3 Hz). |
| 494 | ¹H-NMR (CDCl3) δ: 8.04 (1H, s), 7.57-7.59.(1H, m), 7.10-7.07 (2H, m), 6.13 (1H, tt, J = 56.7, 4.5 Hz), 4.10 (2H, td, J = 12.8, 4.5 Hz), 2.05-2.02 (2H, m), 1.44-1.37 (2H, m), 0.77 (3H, t, J = 7.3 Hz). |
| 495 | ¹H-NMR (CDCl3) δ: 8.06 (1H, s), 6.85-6.82 (2H, m), 3.41 (3H, s), 2.71 (2H, q, J = 7.2 Hz), 1.06 (3H, t, J = 7.2 Hz). |
| 496 | ¹H-NMR (CDCl3) δ: 7.65 (1H, s), 6.92-6.84 (2H, m), 3.34 (3H, s), 3.15 (1H, d, J = 7.6 Hz), 3.12 (3H, d, J = 2.0 Hz), 1.70 (1H, ddd, J = 7.6, 7.0, 6.6 Hz), 0.89 (3H, d, J = 6.6 Hz), 0.66 (3H, dd, J = 7.0, 1.3 Hz). |
| 497 | ¹H-NMR (CDCl3) δ: 7.69 (1H, s), 6.91-6.84 (2H, m), 3.39-3.34 (1H, m), 3.33 (3H, s), 3.25 (1H, d, J = 7.6 Hz), 3.11-3.09 (1H, m), 1.70-1.66 (1H, m), 1.11 (3H, t, J = 7.1 Hz), 0.90 (3H, d, J = 6.6 Hz), 0.65 (3H, dd, J = 6.8, 1.5 Hz). |
| 498 | ¹H-NMR (CDCl3) δ: 7.65 (1H, s), 6.63-6.60 (2H, m), 3.89 (3H, s), 3.35 (3H, s), 3.22 (1H, d, J = 7.6 Hz), 3.12 (3H, d, J = 1.8 Hz), 1.70 (1H, ddq, J = 7.6, 6.9, 6.9 Hz), 0.90 (3H, d, J = 6.9 Hz), 0.66 (3H, dd, J = 6.9, 1.8 Hz). |
| 499 | ¹H-NMR (CDCl3) δ: 7.68 (1H, s), 6.63-6.58 (2H, m), 3.88 (3H, s), 3.38-3.36 (1H, m), 3.34 (3H, s), 3.32 (1H, d, J = 7.6 Hz), 3.12-3.11 (1H, m), 1.69 (1H, ddq, J = 7.6, 6.9, 6.9 Hz), 1.11 (3H, t, J = 7.0 Hz), 0.90 (3H, d, J = 6.9 Hz), 0.65 (3H, dd, J = 6.9, 0.9 Hz). |
| 500 | ¹H-NMR (CDCl3) δ: 7.99 (1H, s), 6.56-6.55 (2H, m), 3.88-3.82 (4H, m), 3.82-3.75 (1H, m), 1.67-1.62 (1H, m), 1.56-1.53 (1H, m), 1.35 (1H, s), 1.32 (3H, s), 1.11 (3H, t, J = 7.1 Hz), 0.80 (3H, t, J = 7.3 Hz). |
| 501 | ¹H-NMR (CDCl3) δ: 7.85 (1H, s), 6.89-6.86 (2H, m), 4.01-3.95 (1H, m), 3.70-3.67 (1H, m), 3.11 (3H, d, J = 1.5 Hz), 3.08 (1H, d, J = 7.3 Hz), 1.68 (1H, ddq, J = 7.3, 6.7, 6.7 Hz), 1.14 (3H, t, J = 7.0 Hz), 0.90 (3H, d, J = 6.7 Hz), 0.67 (3H, dd, J = 6.7, 1.5 Hz). |
| 502 | ¹H-NMR (CDCl3) δ: 7.67 (1H, s), 6.92-6.86 (2H, m), 3.40 (1H, dd, J = 7.8, 5.4 Hz), 3.34 (3H, s), 3.10 (3H, d, J = 1.2 Hz), 1.68-1.62 (1H, m), 1.48-1.43 (1H, m), 0.79 (3H, t, J = 7.5 Hz). |
| 503 | ¹H-NMR (CDCl3) δ: 7.83 (1H, s), 6.62-6.57 (2H, m), 3.99 (1H, dq, J = 13.8, 7.1 Hz), 3.88 (3H, s), 3.71 (1H, dq, J = 13.8, 7.1 Hz), 3.13 (1H, d, J = 7.6 Hz), 3.10 (3H, d, J = 1.71 Hz), 1.12 (3H, t, J = 7.1 Hz), 0.88 (3H, d, J = 6.6 Hz), 0.66 (3H, dd, J = 6.6, 1.3 Hz). |
| 504 | ¹H-NMR (CDCl3) δ: 7.87 (1H, s), 6.92-6.85 (2H, m), 3.90-3.77 (2H, m), 3.32 (1H, dd, J = 8.1, 5.1 Hz), 3.10 (3H, d, J = |

TABLE 4-continued

| Compounds | ¹H-NMR |
|---|---|
| | 1.2 Hz), 1.66-1.62 (1H, m), 1.48-1.41 (1H, m), 1.14 (3H, t, J = 7.1 Hz), 0.79 (3H, t, J = 7.3 Hz). |
| 505 | ¹H-NMR (CDCl3) δ: 7.68 (1H, s), 6.80-6.78 (2H, m), 3.27 (3H, s), 1.73-1.68 (1H, m), 1.60-1.53 (1H, m), 1.37 (3H, s), 1.26 (1H, s), 0.81 (3H, t, J = 7.3 Hz). |
| 506 | ¹H-NMR (CDCl3) δ: 7.67 (1H, s), 6.64-6.59 (2H, m), 3.89 (3H, s), 3.46 (1H, dd, J = 7.8, 5.4 Hz), 3.35 (3H, s), 3.10 (3H, d, J = 1.2 Hz), 1.68-1.61 (1H, m), 1.50-1.43 (1H, m), 0.79 (3H, t, J = 7.3 Hz). |
| 507 | ¹H-NMR (CDCl3) δ: 7.86 (1H, s), 6.64-6.59 (2H, m), 3.90-3.83 (5H, m), 3.38 (1H, dd, J = 8.1, 5.1 Hz), 3.10 (3H, d, J = 1.2 Hz), 1.66-1.61 (1H, m), 1.49-1.42 (1H, m), 1.14 (3H, t, J = 7.1 Hz), 0.79 (3H, t, J = 7.3 Hz). |
| 508 | ¹H-NMR (CDCl3) δ: 7.76 (1H, s), 6.83-6.81 (2H, m), 3.28 (3H, s), 2.98 (3H, s), 1.58-1.54 (2H, m), 1.12 (3H, s), 0.75 (3H, t, J = 7.4 Hz). |
| 509 | ¹H-NMR (CDCl3) δ: 7.78 (1H, s), 6.83-6.78 (2H, m), 3.25-3.22 (4H, m), 3.12-3.08 (1H, m), 1.62-1.56 (2H, m), 1.11 (3H, s), 0.96 (3H, t, J = 7.0 Hz), 0.73 (3H, t, J = 7.4 Hz). |
| 510 | ¹H-NMR (CDCl3) δ: 9.21 (1H, q, J = 1.0 Hz), 7.94 (1H, d, J = 9.5 Hz), 7.63 (1H, tt, J = 8.6, 6.4 Hz), 7.17-7.14 (2H, m), 6.72, (1H, dd, J = 9.5, 0.9 Hz), 3.89 (2H, q, J = 7.1 Hz), 1.16 (3H, t, J = 7.1 Hz). |
| 511 | ¹H-NMR (CDCl3) δ: 7.82 (1H, s), 6.59-6.55 (2H, m), 3.87 (3H, s), 3.28 (3H, s), 3.03 (3H, s), 1.56-1.53 (2H, m), 1.07 (3H, s), 0.76 (3H, t, J = 7.3 Hz). |
| 512 | ¹H-NMR (CDCl3) δ: 7.87 (1H, s), 6.57-6.55 (2H, m), 3.87 (3H, s), 3.30-3.24 (4H, m), 3.11-3.09 (1H, m), 1.57-1.53 (2H, m), 1.07 (3H, t, J = 7.0 Hz), 1.04 (3H, s), 0.75 (3H, t, J = 7.4 Hz). |
| 513 | ¹H-NMR (CDCl3) δ: 7.80 (1H, s), 6.57-6.56 (2H, m), 3.86 (3H, s), 3.28 (3H, s), 1.68-1.54 (2H, m), 1.40 (1H, s), 1.33 (3H, s), 0.80 (3H, t, J = 7.4 Hz). |
| 514 | ¹H-NMR (CDCl3) δ: 7.85 (1H, s), 6.91-6.86 (2H, m), 4.25-4.23 (1H, m), 3.85-3.81 (2H, m), 1.67 (1H, s), 1.30 (3H, d, J = 6.4 Hz), 1.13 (3H, dd, J = 9.6, 4.7 Hz). |
| 515 | ¹H-NMR (CDCl3) δ: 7.90 (1H, d, J = 1.0 Hz), 6.92-6.89 (2H, m), 4.39-4.37 (1H, m), 4.06-4.03 (1H, m), 3.67-3.64 (1H, m), 2.81 (1H, d, J = 4.4 Hz), 1.14 (3H, t, J = 7.2 Hz). |
| 516 | ¹H-NMR (CDCl3) δ: 7.77 (1H, d, J = 0.9 Hz), 6.94-6.90 (2H, m), 4.03-4.00 (1H, m), 3.85-3.83 (1H, m), 3.70-3.67 (1H, m), 3.32 (3H, d, J = 0.9 Hz), 1.16 (3H, t, J = 7.0 Hz). |
| 517 | ¹H-NMR (CDCl3) δ: 7.87 (1H, s), 6.89-6.86 (2H, m), 5.90 (1H, dt, J = 17.3, 11.0 Hz), 5.50 (1H, d, J = 17.3 Hz), 5.12 (1H, d, J = 11.0 Hz), 3.88 (2H, q, J = 7.2 Hz), 1.14 (3H, t, J = 7.2 Hz). |
| 518 | ¹H-NMR (CDCl3) δ: 7.75 (1H, d, J = 0.6 Hz), 6.66-6.63 (2H, m), 4.04-4.01 (1H, m), 3.93-3.89 (1H, m), 3.90 (3H, s), 3.74-3.72 (1H, m), 3.31 (3H, s), 1.15 (3H, t, J = 7.0 Hz). |
| 519 | ¹H-NMR (CDCl3) δ: 7.70 (1H, s), 6.92-6.86 (2H, m), 3.89-3.87 (1H, m), 3.80-3.78 (1H, m), 3.60 (1H, q, J = 6.4 Hz), 3.07 (3H, d, J = 0.6 Hz), 1.24 (3H, d, J = 6.4 Hz), 1.14 (3H, t, J = 7.0 Hz). |
| 520 | ¹H-NMR (CDCl3) δ: 7.97 (1H, s), 7.56 (1H, tt, J = 8.4, 6.4 Hz), 7.12-7.08 (2H, m), 4.10 (1H, dq, J = 13.8, 7.0 Hz), 3.62 (1H, dq, J = 13.8, 7.0 Hz), 3.57 (1H, dd, J = 8.7, 2.0 Hz), 1.83-1.81 (1H, m), 1.70 (1H, d, J = 3.1 Hz), 1.12 (3H, t, J = 7.0 Hz), 0.94 (3H, d, J = 6.7 Hz), 0.63 (3H, d, J = 6.7 Hz). |
| 521 | ¹H-NMR (CDCl3) δ: 7.48-7.41 (2H, m), 7.02-6.97 (2H, m), 6.65 (1H, d, J = 9.8 Hz), 3.83 (1H, dq, J = 13.7, 7.1 Hz), 3.64 (1H, dq, J = 13.7, 7.1 Hz), 1.93-1.86 (1H, m), 1.33 (3H, s), 1.09 (1H, s), 1.08 (3H, t, J = 7.1 Hz), 0.84 (3H, d, J = 6.8 Hz), 0.77 (3H, d, J = 6.8 Hz). |
| 522 | ¹H-NMR (CDCl3) δ: 7.91 (1H, s), 7.47 (1H, tt, J = 8.4, 6.4 Hz), 7.03-6.98 (2H, m), 3.88-3.81 (1H, m), 3.75-3.68 (1H, m), 1.89-1.82 (1H, m), 1.32 (3H, s), 1.15 (1H, s), 1.10 (3H, t, J = 7.1 Hz), 0.85 (3H, d, J = 6.6 Hz), 0.78 (3H, d, J = 6.8 Hz). |
| 523 | ¹H-NMR (CDCl3) δ: 8.00 (1H, s), 7.52 (1H, tt, J = 8.4, 6.4 Hz), 7.05-7.02 (2H, m), 3.82-3.72 (2H, m), 3.03 (3H, d, J = 0.7 Hz), 1.76 (1H, dq, J = 6.8, 6.8 Hz), 1.11 (3H, t, J = 7.1 Hz), 0.90 (3H, s), 0.83 (3H, d, J = 6.8 Hz), 0.72 (3H, d, J = 6.8 Hz). |
| 524 | ¹H-NMR (CDCl3) δ: 8.09 (1H, s), 7.52 (1H, tt, J = 8.6, 6.4 Hz), 7.07-7.01 (2H, m), 3.84-3.68 (2H, m), 3.34-3.31 (1H, m), 3.09-3.06 (1H, m), 1.79-1.73 (1H, m), 1.11-1.10 (6H, m), 0.85 (3H, d, J = 6.9 Hz), 0.81 (3H, s), 0.72 (3H, dd, J = 6.9, 1.1 Hz). |
| 525 | ¹H-NMR (CDCl3) δ: 7.86 (1H, s), 7.56 (1H, tt, J = 8.6, 6.4 Hz), 7.11-7.08 (2H, m), 3.99 (1H, dq, J = 13.6, 7.0 Hz), 3.70 (1H, dq, J = 13.6, 7.0 Hz), 3.12 (3H, d, J = 1.8 Hz), 3.09 (1H, d, J = 7.3 Hz), 1.69-1.65 (1H, m), 1.14 (3H, t, J = 7.0 Hz), 0.88 (3H, d, J = 6.9 Hz), 0.67 (3H, dd, J = 6.9, 1.4 Hz). |
| 526 | ¹H-NMR (CDCl3) δ: 7.89 (1H, s), 7.55 (1H, tt, J = 8.4, 6.4 Hz), 7.11-7.06 (2H, m), 3.99 (1H, dq, J = 13.6, 7.0 Hz), 3.69 (1H, dq, J = 13.6, 7.0 Hz), 3.40-3.37 (1H, m), 3.19 (1H, d, J = 7.3 Hz), 3.10-3.08 (1H, m), 1.69-1.65 (1H, m), 1.13 (3H, t, J = 7.1 Hz), 1.10 (3H, t, J = 7.1 Hz), 0.88 (3H, d, J = 6.3 Hz), 0.66 (3H, dd, J = 7.0, 1.3 Hz). |
| 527 | ¹H-NMR (CDCl3) δ: 7.69 (1H, s), 6.64-6.60 (2H, m), 3.92-3.90 (1H, m), 3.89 (3H, s), 3.83-3.80 (1H, m), 3.66 (1H, q, J = 6.4 Hz), 3.07 (3H, d, J = 0.9 Hz), 1.24 (3H, d, J = 6.4 Hz), 1.14 (3H, t, J = 7.0 Hz). |
| 528 | ¹H-NMR (CDCl3) δ: 7.73 (1H, s), 6.90-6.86 (2H, m), 3.87-3.85 (1H, m), 3.80-3.79 (1H, m), 3.70 (1H, q, J = 6.4 Hz), 3.28-3.26 (1H, m), 3.10-3.08 (1H, m), 1.24 (3H, d, J = 6.4 Hz), 1.14 (3H, t, J = 7.2 Hz), 1.11 (3H, t, J = 6.7 Hz). |
| 529 | ¹H-NMR (CDCl3) δ: 7.70 (1H, s), 6.92-6.90 (2H, m), 3.92 (1H, q, J = 6.4 Hz), 3.86-3.80 (2H, m), 3.66-3.61 (1H, m), 3.50-3.46 (1H, m), 1.32 (3H, d, J = 6.4 Hz), 1.14 (3H, t, J = 7.0 Hz). |
| 530 | ¹H-NMR (CDCl3) δ: 7.72 (1H, s), 6.63-6.59 (2H, m), 3.92-3.86 (1H, m), 3.89 (3H, s), 3.85-3.79 (1H, m), 3.76 (1H, q, J = 6.4 Hz), 3.29-3.27 (1H, m), 3.11-3.09 (1H, m), 1.23 (3H, d, J = 6.4 Hz), 1.13 (3H, t, J = 6.7 Hz), 1.11 (3H, t, J = 7.0 Hz). |
| 531 | ¹H-NMR (CDCl3) δ: 7.69 (1H, s), 6.66-6.61 (2H, m), 3.97 (1H, q, J = 6.4 Hz), 3.89 (3H, s), 3.87-3.83 (2H, m), 3.65-3.61 (1H, m), 3.51-3.43 (1H, m), 1.31 (3H, d, J = 6.4 Hz), 1.14 (3H, t, J = 7.2 Hz). |

The following specifically illustrates the effectiveness of the inventive compounds on plant diseases without limiting the scope of the invention to such examples.

[Test Example A] Blast on Rice

Seeds of a test plant (rice variety: Sachikaze) were planted and cultivated until the second leaves appeared. In the test, the inventive compounds were dissolved into dimethyl sulfoxide-methanol mixture solution (volume ratio: 9/1), and the resultant solutions were diluted with well water to a concentration of 250 ppm to obtain the drug solutions. The drug solutions were sprayed to the test plant (2.5 ml/pot). After the drug solutions dried, a conidial suspension (1-2× $10^5$ conidia/ml) of *Magnaporthe grisea* was inoculated to the plant by spraying. After the inoculation, the plant was kept in a mist chamber at room temperature of 20 to 23° C. for about 24 hours to promote the onset of disease. The degrees of disease development were investigated 6 to 10 days after the inoculation, and the effectiveness of the drug solutions was evaluated.

[Test Example B] Gray Mold on Tomato

Seeds of a test plant (tomato variety: Oogata Fukuju) were planted and cultivated until three to five first leaves (true leaves) appeared. In the test, the inventive compounds were dissolved into dimethyl sulfoxide-methanol mixture solution (volume ratio: 9/1), and the resultant solutions were diluted with well water to a concentration of 250 ppm to obtain the drug solutions. The drug solutions were sprayed to the test plant (2.5 ml/pot). After the drug solutions dried, a conidial suspension (4-8×10$^5$ conidia/ml) of *Botrytis cinerea* was inoculated to the plant by spraying. After the inoculation, the plant was kept in a mist chamber at room temperature of 20 to 23° C. for about 48 hours to promote the onset of disease. The degrees of disease development were investigated 2 to 3 days after the inoculation, and the effectiveness of the drug solutions was evaluated.

[Test Example C] *Alternaria* Sooty Spot on Cabbage

Seeds of a test plant (cabbage variety: Shikidori) were planted and cultivated until the cotyledons extended. In the test, the inventive compounds were dissolved into dimethyl sulfoxide-methanol mixture solution (volume ratio: 9/1), and the resultant solutions were diluted with well water to a concentration of 250 ppm to obtain the drug solutions. The drug solutions were sprayed to the test plant (2.5 ml/pot). After the drug solutions dried, a conidial suspension (4-8×10$^5$ conidia/ml) of *Alternaia brassicicola* was inoculated to the plant by spraying. After the inoculation, the plant was kept in a mist chamber at room temperature of 20 to 23° C. for about 48 hours to promote the onset of disease. The degrees of disease development were investigated 2 to 3 days after the inoculation, and the effectiveness of the drug solutions was evaluated.

[Test Example D] Powdery Mildew on Barley

Seeds of a test plant (barley variety: Akashinriki) were planted and cultivated until the first leaves appeared. In the test, the inventive compounds were dissolved into dimethyl sulfoxide-methanol mixture solution (volume ratio: 9/1), and the resultant solutions were diluted with well water to a concentration of 250 ppm to obtain the drug solutions. The drug solutions were sprayed to the test plant (2.5 ml/pot). After the drug solutions dried, conidia of *Blumeria graminis* f. sp. *hordei* were inoculated to the plant by shaking off. The degrees of disease development were investigated 6 to 10 days after the inoculation, and the effectiveness of the drug solutions was evaluated.

[Test Example E] Brown Rust on Wheat

Seeds of a test plant (wheat variety: Norin 61) were planted and cultivated until the first leaves appeared. In the test, the inventive compounds were dissolved into dimethyl sulfoxide-methanol mixture solution (volume ratio: 9/1), and the resultant solutions were diluted with well water to a concentration of 250 ppm to obtain the drug solutions. The drug solutions were sprayed to the test plant (2.5 ml/pot). After the drug solutions dried, a urediniospore suspension (1-2×10$^5$ urediniospores/ml) of *Puccinia recondita* was inoculated to the plant by spraying. After the inoculation, the plant was kept in a mist chamber at room temperature of 20 to 23° C. for about 24 hours to promote the onset of disease. The degrees of disease development were investigated 7 to 10 days after the inoculation, and the effectiveness of the drug solutions was evaluated.

[Test Example F] Late Blight on Tomato

Seeds of a test plant (tomato variety: Oogata Fukuju) were planted and cultivated until three to five first leaves appeared. In the test, the inventive compounds were dissolved into dimethyl sulfoxide-methanol mixture solution (volume ratio: 9/1), and the resultant solutions were diluted with well water to a concentration of 250 ppm to obtain the drug solutions. The drug solutions were sprayed to the test plant (2.5 ml/pot). After the drug solutions dried, a zoosporangia suspension (4-8×10$^3$ zoosporangia/ml) of *Phytophthora infestans* was inoculated to the plant by spraying. After the inoculation, the plant was kept in a mist chamber at room temperature of 20° C. for about 24 hours to promote the onset of disease. The degrees of disease development were investigated 5 to 10 days after the inoculation, and the effectiveness of the drug solutions was evaluated.

[Test Example G] Downy Mildew on Vine

Seeds of a test plant (grape variety: Neomuscat) were planted and cultivated until three to four first leaves appeared. In the test, the inventive compounds were dissolved into dimethyl sulfoxide-methanol mixture solution (volume ratio: 9/1), and the resultant solutions were diluted with well water to a concentration of 250 ppm to obtain the drug solutions. The drug solutions were sprayed to the test plant (2.5 ml/pot). After the drug solutions dried, a zoosporangia suspension (1-2×10$^4$ zoosporangia/ml) of *Plasmopara viticola* was inoculated to the plant by spraying. After the inoculation, the plant was kept in a mist chamber at room temperature of 20° C. for about 24 hours to promote the onset of disease. The degrees of disease development were investigated 7 to 10 days after the inoculation, and the effectiveness of the drug solutions was evaluated.

[Test Example H] Anthracnose on Cucumber

Seeds of a test plant (cucumber variety: Sagami Hanjiro) were planted and cultivated until the first leaf appeared. In the test, the inventive compounds were dissolved into dimethyl sulfoxide-methanol mixture solution (volume ratio: 9/1), and the resultant solutions were diluted with well water to a concentration of 250 ppm to obtain the drug solutions. The drug solutions were sprayed to the test plant (2.5 ml/pot). After the drug solutions dried, a conidial suspension (2-4×10$^5$ conidia/ml) of *Colletotrichum orbiculare* was inoculated to the plant by spraying. After the inoculation, the plant was kept in a mist chamber at room temperature of 20 to 23° C. for about 24 hours to promote the onset of disease. The degrees of disease development were investigated 6 to 10 days after the inoculation, and the effectiveness of the drug solutions was evaluated.

In Test Examples described above, the degrees of disease development were evaluated in increments of 0.05 from 0 (as no incidence of disease) to 3 (as the degree of disease development in an untreated plant group). Further, control values were calculated using the following equation based on the degree of disease development.

<Control Value>

Control value=$100\{1-(n/3)\}$ n=Degree of disease development in each treated group The results of the above tests are described in Table 5. In the table, H: more than 50% control value, L: 50% or less control value, and nt: not tested.

TABLE 5

| Compounds | Test A | Test B | Test C | Test D | Test E | Test F | Test G | Test H |
|---|---|---|---|---|---|---|---|---|
| 1 | H | L | L | L | L | L | L | L |
| 2 | H | L | L | H | L | H | L | H |
| 3 | L | L | H | L | L | L | L | L |
| 4 | H | L | H | L | L | H | L | L |
| 5 | H | H | H | H | H | L | L | H |
| 6 | H | H | H | H | H | L | L | H |
| 7 | H | H | H | H | H | L | H | H |
| 8 | H | H | H | H | H | L | L | H |
| 9 | H | H | H | H | H | L | H | H |
| 10 | H | H | H | H | H | L | L | H |
| 11 | H | H | H | H | H | L | L | H |
| 12 | H | H | H | H | H | L | H | H |
| 13 | H | H | L | H | L | L | L | L |
| 14 | H | H | H | H | H | H | L | H |
| 15 | H | H | H | H | H | L | L | H |
| 16 | H | H | H | H | H | L | H | H |
| 17 | L | H | H | L | H | H | H | H |
| 18 | H | H | H | H | H | H | H | H |
| 19 | H | H | H | H | H | L | H | H |
| 20 | H | H | L | L | H | L | H | L |
| 21 | L | H | L | H | H | L | H | L |
| 22 | L | H | H | L | H | L | H | H |
| 23 | H | H | H | H | H | L | L | H |
| 24 | H | H | H | H | H | L | L | H |
| 25 | H | H | H | H | H | L | H | H |
| 26 | H | H | H | H | H | L | H | H |
| 27 | H | H | H | H | H | L | H | H |
| 28 | H | H | H | H | H | L | H | H |
| 29 | H | H | H | H | H | L | H | H |
| 30 | H | H | H | H | H | L | H | H |
| 31 | H | H | H | H | H | L | H | H |
| 32 | H | H | H | H | H | L | L | H |
| 33 | H | H | H | H | H | L | L | H |
| 34 | H | H | H | H | H | L | H | H |
| 35 | H | H | H | H | H | L | L | H |
| 36 | H | H | H | H | H | L | H | H |
| 37 | H | L | L | L | L | L | L | L |
| 38 | H | L | L | H | H | L | L | L |
| 39 | H | H | H | H | H | L | H | H |
| 40 | H | H | H | H | H | L | L | H |
| 41 | H | H | H | H | H | L | H | H |
| 42 | H | H | H | H | H | L | H | H |
| 43 | H | H | H | H | H | L | H | H |
| 44 | L | H | H | L | H | L | L | L |
| 45 | H | H | H | H | H | L | L | L |
| 46 | H | H | H | H | H | L | L | H |
| 47 | H | H | H | H | H | L | H | H |
| 48 | H | H | H | H | H | L | H | H |
| 49 | H | H | H | H | H | L | L | H |
| 50 | H | H | H | L | H | L | H | H |
| 51 | H | H | H | H | H | L | L | H |
| 52 | H | H | H | H | H | L | H | H |
| 53 | H | H | H | H | H | L | H | H |
| 54 | H | H | H | H | H | L | L | H |
| 55 | H | H | H | H | H | L | L | H |
| 56 | H | H | H | H | H | L | H | H |
| 57 | L | H | H | H | H | L | L | H |
| 58 | H | H | H | H | H | L | L | H |
| 59 | H | H | H | H | H | L | H | H |
| 60 | H | H | H | H | H | L | H | H |
| 61 | H | H | H | H | H | L | H | H |
| 62 | H | H | H | H | H | L | H | H |
| 63 | H | H | H | H | H | L | H | H |
| 64 | H | H | H | H | H | L | H | H |
| 65 | H | H | H | H | H | L | L | H |
| 66 | H | H | H | H | H | L | L | H |
| 67 | L | H | H | H | H | L | L | H |
| 68 | L | L | H | L | H | L | L | H |
| 69 | H | H | L | H | H | L | L | L |
| 70 | H | H | H | H | H | L | L | H |
| 71 | H | H | H | H | H | L | L | H |
| 72 | H | H | H | H | H | L | H | H |
| 73 | H | H | H | H | H | L | H | H |
| 74 | H | H | H | L | H | L | H | H |
| 75 | L | H | H | L | H | L | L | H |

TABLE 5-continued

| Compounds | Test A | Test B | Test C | Test D | Test E | Test F | Test G | Test H |
|---|---|---|---|---|---|---|---|---|
| 76 | H | H | H | L | H | L | L | H |
| 77 | L | H | H | H | H | L | L | L |
| 78 | H | H | H | H | H | L | L | H |
| 79 | H | H | H | H | H | L | L | H |
| 80 | L | H | L | L | L | H | L | H |
| 81 | H | H | L | L | L | L | L | L |
| 82 | L | H | H | L | H | L | H | H |
| 83 | H | H | H | L | H | L | H | H |
| 84 | L | L | H | L | L | L | L | H |
| 85 | H | H | H | L | H | L | L | H |
| 86 | L | L | H | L | L | L | L | L |
| 87 | L | H | H | H | H | L | L | H |
| 88 | L | H | H | H | H | L | L | L |
| 89 | H | H | H | H | H | L | L | H |
| 90 | H | H | H | H | H | L | H | H |
| 91 | L | L | L | L | H | L | L | H |
| 92 | H | L | H | L | H | L | L | H |
| 93 | H | H | H | H | H | L | H | H |
| 94 | H | H | H | H | H | H | H | H |
| 95 | L | H | L | H | H | H | L | L |
| 96 | L | H | H | H | H | L | L | H |
| 97 | H | H | H | H | H | L | L | H |
| 98 | H | H | H | H | H | L | L | L |
| 99 | H | H | H | H | H | H | H | H |
| 100 | H | H | H | H | H | L | H | H |
| 101 | L | H | L | L | H | H | H | L |
| 102 | H | H | H | H | H | L | H | H |
| 103 | H | H | H | H | H | L | H | H |
| 104 | H | H | L | H | L | L | H | H |
| 105 | H | H | H | L | L | L | H | H |
| 106 | H | H | H | H | H | H | H | H |
| 107 | H | H | H | H | H | L | H | H |
| 108 | H | H | H | H | H | L | H | H |
| 109 | H | H | H | H | H | L | L | H |
| 110 | H | H | H | H | H | L | H | H |
| 111 | H | H | H | H | H | L | H | H |
| 112 | L | H | H | H | H | L | L | H |
| 113 | H | H | H | L | H | L | L | H |
| 114 | L | H | H | H | H | L | L | H |
| 115 | H | H | H | H | H | L | L | H |
| 116 | H | H | H | H | H | L | H | H |
| 117 | H | H | H | H | H | L | L | H |
| 118 | L | H | H | L | H | L | L | L |
| 119 | H | H | H | H | H | L | H | H |
| 120 | H | H | H | H | H | L | L | H |
| 121 | H | H | H | H | H | L | L | H |
| 122 | H | H | H | H | H | L | H | H |
| 123 | H | H | H | H | H | L | H | H |
| 124 | H | H | H | H | H | L | L | H |
| 125 | H | H | H | H | H | L | H | H |
| 126 | L | H | H | H | H | L | H | H |
| 127 | L | H | H | H | H | L | H | H |
| 128 | H | H | H | H | H | L | H | H |
| 129 | L | H | H | H | H | L | H | L |
| 130 | H | L | H | L | H | L | H | H |
| 131 | H | H | H | H | H | L | H | H |
| 132 | H | L | H | L | L | L | L | L |
| 133 | H | H | H | H | H | L | H | H |
| 134 | H | H | L | H | H | L | H | L |
| 135 | H | H | H | H | H | L | H | H |
| 136 | H | H | L | H | H | L | H | L |
| 137 | H | H | H | H | H | L | H | H |
| 138 | H | H | H | L | H | L | L | H |
| 139 | H | H | H | H | H | L | H | H |
| 140 | H | H | H | H | H | L | H | H |
| 141 | H | H | H | H | H | L | H | L |
| 142 | H | H | H | H | H | L | H | H |
| 143 | H | H | H | H | H | L | H | H |
| 144 | L | L | H | H | H | L | H | L |
| 145 | L | L | H | L | H | L | L | L |
| 146 | H | H | H | H | H | L | H | L |
| 147 | H | H | H | H | H | L | H | L |
| 148 | H | H | H | H | H | L | H | H |
| 149 | H | H | H | H | H | L | H | H |
| 150 | H | H | H | H | H | L | H | H |

TABLE 5-continued

| Compounds | Test A | Test B | Test C | Test D | Test E | Test F | Test G | Test H |
|---|---|---|---|---|---|---|---|---|
| 151 | H | H | H | H | H | L | H | H |
| 152 | H | H | H | H | H | L | H | H |
| 153 | L | H | H | H | H | L | H | H |
| 154 | H | H | H | H | H | L | H | H |
| 155 | L | H | H | H | H | L | H | L |
| 156 | H | H | H | H | H | L | L | L |
| 157 | H | H | H | H | H | L | H | L |
| 158 | H | H | H | H | H | L | H | H |
| 159 | H | H | H | H | H | L | H | H |
| 160 | L | H | H | H | H | L | H | H |
| 161 | H | H | H | H | H | L | H | H |
| 162 | H | H | H | H | H | L | H | H |
| 163 | H | H | H | H | H | L | H | H |
| 164 | H | H | H | H | H | L | H | L |
| 165 | H | H | H | H | H | L | H | H |
| 166 | H | H | H | H | H | H | H | H |
| 167 | H | H | H | H | H | H | H | H |
| 168 | H | H | H | H | H | L | L | L |
| 169 | H | H | H | H | H | H | H | H |
| 170 | H | H | H | H | H | H | H | H |
| 171 | H | H | H | H | H | L | H | H |
| 172 | H | H | H | H | H | H | H | H |
| 173 | L | H | H | H | H | L | L | H |
| 174 | H | H | H | H | H | L | L | L |
| 175 | L | H | L | H | H | L | L | L |
| 176 | H | H | H | H | H | H | L | L |
| 177 | L | H | H | L | H | L | L | L |
| 178 | L | H | H | L | H | L | L | L |
| 179 | H | H | H | H | H | L | L | H |
| 180 | H | H | H | L | L | L | L | L |
| 181 | H | H | H | H | H | L | H | H |
| 182 | H | H | H | H | H | L | L | L |
| 183 | H | H | H | H | H | H | H | H |
| 184 | H | H | H | H | H | L | H | H |
| 185 | L | H | H | H | H | L | L | L |
| 186 | H | H | H | H | H | L | H | H |
| 187 | H | H | H | H | H | L | H | H |
| 188 | H | H | H | H | H | H | H | H |
| 189 | H | H | H | H | H | L | H | H |
| 190 | H | H | H | H | H | L | H | L |
| 191 | H | H | H | H | H | L | H | H |
| 192 | H | H | H | H | H | L | L | H |
| 193 | L | L | H | L | L | L | L | L |
| 194 | H | H | L | H | H | L | L | L |
| 195 | H | H | H | H | H | L | L | H |
| 196 | H | H | H | L | H | L | L | H |
| 197 | H | H | H | H | H | L | H | H |
| 198 | H | H | H | H | H | L | L | H |
| 199 | H | H | H | H | H | H | H | H |
| 200 | H | H | H | H | H | H | H | H |
| 201 | H | H | H | H | H | L | H | H |
| 202 | H | H | L | H | H | L | H | L |
| 203 | H | H | H | H | H | H | H | H |
| 204 | H | H | H | H | H | L | H | H |
| 205 | H | H | H | H | H | L | H | L |
| 206 | H | H | H | H | H | H | H | H |
| 207 | H | H | H | H | H | L | H | H |
| 208 | H | H | H | H | H | L | L | L |
| 209 | H | H | H | H | H | L | H | H |
| 210 | H | H | H | H | H | L | L | H |
| 211 | L | H | H | L | H | L | L | L |
| 212 | L | H | H | H | H | L | L | L |
| 213 | H | H | H | H | H | L | H | H |
| 214 | H | H | H | H | H | L | L | L |
| 215 | L | L | L | H | L | L | L | L |
| 216 | L | L | L | H | L | L | L | L |
| 217 | H | H | H | H | H | L | L | H |
| 218 | H | H | H | H | H | L | H | H |
| 219 | H | H | H | H | H | L | L | H |
| 220 | H | H | H | H | H | L | H | H |
| 221 | H | H | H | H | H | L | L | L |
| 222 | L | H | H | H | H | L | L | L |
| 223 | L | H | H | L | H | L | L | L |
| 224 | L | H | L | L | H | L | L | L |
| 225 | L | H | H | H | H | L | L | L |

TABLE 5-continued

| Compounds | Test A | Test B | Test C | Test D | Test E | Test F | Test G | Test H |
|---|---|---|---|---|---|---|---|---|
| 226 | H | H | H | L | H | L | L | H |
| 227 | H | H | H | H | H | L | H | H |
| 228 | H | H | H | H | H | L | H | H |
| 229 | H | H | H | H | H | L | H | H |
| 230 | L | L | L | L | L | L | H | L |
| 231 | H | H | H | H | H | H | H | H |
| 232 | H | H | H | H | H | L | L | L |
| 233 | L | L | H | L | L | L | L | L |
| 234 | L | L | H | L | L | L | L | L |
| 235 | L | L | H | L | H | L | L | L |
| 236 | H | H | H | H | H | L | L | L |
| 237 | L | H | H | H | H | L | L | L |
| 238 | H | H | H | H | H | L | H | H |
| 239 | H | H | H | H | H | L | L | H |
| 240 | H | H | H | H | H | L | H | H |
| 241 | H | H | H | H | H | L | L | H |
| 242 | L | L | H | L | L | L | L | L |
| 243 | H | H | H | H | H | L | L | H |
| 244 | H | H | H | H | H | L | L | H |
| 245 | L | L | H | L | L | L | L | L |
| 246 | L | L | H | L | H | L | L | L |
| 247 | L | H | L | H | L | L | L | L |
| 248 | H | L | L | L | L | L | L | L |
| 249 | L | H | H | L | H | L | L | H |
| 250 | L | H | L | L | H | L | L | L |
| 251 | L | L | H | L | L | L | L | L |
| 252 | H | L | L | L | L | L | L | L |
| 253 | L | H | H | L | L | L | L | L |
| 254 | L | H | H | L | H | H | L | H |
| 255 | H | H | H | H | H | L | L | H |
| 256 | L | L | L | H | H | L | H | L |
| 257 | L | L | H | L | L | L | L | H |
| 258 | H | H | H | H | H | L | H | H |
| 259 | H | H | H | H | H | L | H | H |
| 260 | H | H | H | H | H | H | L | H |
| 261 | H | H | H | H | H | L | H | H |
| 262 | L | H | H | H | H | L | L | H |
| 263 | H | H | H | H | H | L | H | H |
| 264 | L | H | H | H | H | L | L | H |
| 265 | H | H | H | H | H | L | H | H |
| 266 | L | L | L | H | H | L | L | H |
| 267 | L | L | L | H | L | L | L | H |
| 268 | L | L | L | H | L | L | L | L |
| 269 | L | L | L | H | L | L | L | L |
| 270 | L | L | L | H | L | L | L | L |
| 271 | L | L | L | H | L | L | L | L |
| 272 | L | L | L | L | H | L | L | L |
| 273 | L | L | L | H | L | L | L | L |
| 274 | L | L | L | H | L | L | L | L |
| 275 | L | L | L | H | L | L | L | L |
| 276 | H | H | H | H | H | L | H | L |
| 277 | H | H | H | H | H | L | H | H |
| 278 | L | L | L | L | L | H | L | H |
| 279 | L | L | L | H | L | L | L | L |
| 280 | L | H | L | H | H | L | L | H |
| 281 | L | H | L | H | H | L | L | H |
| 282 | L | L | L | H | L | L | L | L |
| 283 | L | H | H | L | H | L | L | H |
| 284 | L | H | H | H | H | H | H | H |
| 285 | H | H | H | H | H | L | L | H |
| 286 | L | H | H | L | H | L | L | H |
| 287 | L | L | H | L | L | L | L | L |
| 288 | L | L | H | L | L | L | L | L |
| 289 | L | H | H | L | H | L | L | H |
| 290 | L | L | H | L | L | H | L | L |
| 291 | L | L | L | H | H | L | L | H |
| 292 | L | H | H | H | L | L | L | L |
| 293 | L | L | H | H | L | L | L | L |
| 294 | L | H | H | L | H | L | H | L |
| 295 | L | H | H | H | H | H | L | L |
| 296 | L | L | H | L | H | L | L | L |
| 297 | L | H | H | H | H | L | H | L |
| 298 | L | L | H | L | L | L | L | H |
| 299 | L | H | H | H | H | L | H | H |
| 300 | H | H | H | H | H | L | L | H |

TABLE 5-continued

| Compounds | Test A | Test B | Test C | Test D | Test E | Test F | Test G | Test H |
|---|---|---|---|---|---|---|---|---|
| 301 | H | H | H | H | H | L | L | H |
| 302 | H | H | L | L | H | L | L | H |
| 303 | L | H | H | H | H | L | L | H |
| 304 | H | H | H | H | H | L | L | H |
| 305 | H | H | H | H | H | L | L | H |
| 306 | H | H | H | H | H | L | H | H |
| 307 | L | H | H | H | H | L | L | H |
| 308 | H | L | H | L | L | L | L | L |
| 309 | H | H | H | H | H | L | H | H |
| 310 | L | H | H | H | H | L | H | L |
| 311 | L | L | L | L | H | L | L | L |
| 312 | L | L | H | L | L | L | L | L |
| 313 | L | L | L | L | L | L | H | L |
| 314 | L | L | L | H | H | L | L | L |
| 315 | L | L | L | H | L | L | L | L |
| 316 | L | H | H | L | H | H | H | H |
| 317 | L | H | H | L | H | H | H | H |
| 318 | L | H | H | H | H | H | L | H |
| 319 | L | H | H | H | H | L | L | H |
| 320 | H | H | H | H | H | H | H | H |
| 321 | H | H | H | H | H | L | H | H |
| 322 | L | H | L | L | H | L | L | H |
| 323 | L | H | L | L | L | L | L | L |
| 324 | L | H | H | L | H | L | H | H |
| 325 | L | H | H | L | H | L | H | H |
| 326 | H | H | H | H | H | L | L | H |
| 327 | H | H | H | L | H | H | H | H |
| 328 | H | H | H | L | H | L | H | H |
| 329 | L | H | L | H | H | L | L | L |
| 330 | L | H | L | L | L | L | H | L |
| 331 | L | H | L | H | H | L | L | H |
| 332 | H | H | H | H | H | L | L | H |
| 333 | H | H | H | L | H | L | L | H |
| 334 | L | H | L | H | H | L | L | L |
| 335 | H | H | H | H | H | L | H | H |
| 336 | H | H | H | L | H | L | H | H |
| 337 | L | H | L | L | H | L | L | H |
| 338 | L | L | H | L | L | L | L | L |
| 339 | H | H | L | H | H | L | H | H |
| 340 | L | H | H | H | H | L | L | L |
| 341 | L | L | L | L | L | L | L | H |
| 342 | H | H | H | H | H | L | L | H |
| 343 | H | H | H | H | H | L | H | H |
| 344 | L | H | H | L | H | L | L | L |
| 345 | H | H | H | L | H | L | H | H |
| 346 | H | H | H | L | H | L | H | H |
| 347 | L | H | H | L | L | L | L | L |
| 348 | L | H | L | H | H | L | L | L |
| 349 | L | H | H | H | H | L | H | L |
| 350 | L | H | H | L | H | L | H | L |
| 351 | L | H | H | H | H | L | L | H |
| 352 | H | H | H | H | H | L | L | H |
| 353 | L | L | L | H | H | L | L | L |
| 354 | L | L | L | L | H | L | L | H |
| 355 | H | H | H | H | H | L | L | H |
| 356 | H | H | H | H | H | L | L | H |
| 357 | H | H | L | L | H | L | L | H |
| 358 | L | H | L | H | H | L | L | L |
| 359 | L | L | L | H | L | L | L | L |
| 360 | L | L | L | L | L | H | L | L |
| 361 | H | H | L | H | H | L | L | L |
| 362 | H | H | L | H | H | L | L | L |
| 363 | H | H | L | L | H | L | H | L |
| 364 | L | H | H | L | H | L | H | L |
| 365 | H | H | H | H | H | L | H | H |
| 366 | H | H | H | H | H | L | H | H |
| 367 | L | L | L | H | L | L | L | H |
| 368 | H | H | H | H | H | H | H | H |
| 369 | H | H | H | H | H | H | H | H |
| 370 | L | H | H | H | H | H | H | H |
| 371 | L | H | L | L | L | L | L | L |
| 372 | L | H | H | H | H | L | H | H |
| 373 | L | L | H | L | L | L | L | H |
| 374 | L | H | H | H | H | L | L | L |
| 375 | L | H | H | H | H | H | H | L |

TABLE 5-continued

| Compounds | Test A | Test B | Test C | Test D | Test E | Test F | Test G | Test H |
|---|---|---|---|---|---|---|---|---|
| 376 | H | H | H | H | H | H | H | H |
| 377 | L | L | L | H | L | L | L | H |
| 378 | H | H | H | H | H | L | L | H |
| 379 | L | H | H | H | H | L | L | H |
| 380 | H | H | H | H | H | H | L | H |
| 381 | H | H | H | H | H | H | H | H |
| 682 | H | H | H | L | H | H | H | H |
| 383 | H | H | H | H | H | L | H | H |
| 384 | H | H | H | H | H | L | H | H |
| 385 | H | H | H | H | H | L | H | H |
| 386 | H | H | H | H | H | L | H | H |
| 387 | H | H | H | H | H | L | H | H |
| 388 | H | H | H | L | H | L | L | H |
| 389 | H | H | H | H | H | L | L | H |
| 390 | H | H | H | H | H | L | H | H |
| 391 | H | H | H | L | H | L | L | H |
| 392 | L | H | H | L | L | L | L | L |
| 393 | L | H | L | L | L | L | L | L |
| 394 | L | H | H | L | L | L | L | L |
| 395 | L | H | L | L | L | L | L | L |
| 396 | H | H | H | H | H | L | L | H |
| 397 | H | H | H | H | H | L | H | H |
| 398 | L | H | H | H | H | L | L | H |
| 399 | H | H | H | H | H | L | H | H |
| 400 | H | H | H | L | H | L | H | H |
| 401 | L | L | L | L | L | L | L | H |
| 402 | H | H | H | H | H | L | H | H |
| 403 | H | H | H | H | H | L | L | H |
| 404 | L | H | L | L | H | L | L | H |
| 405 | H | H | L | L | H | L | H | H |
| 406 | L | H | L | H | H | L | L | H |
| 407 | H | H | H | L | H | L | H | H |
| 408 | H | H | H | L | H | L | L | H |
| 409 | L | L | H | L | H | L | L | L |
| 410 | L | L | L | H | H | L | L | L |
| 411 | L | H | L | H | H | L | L | L |
| 412 | H | H | H | H | H | H | L | H |
| 413 | H | H | H | L | H | L | L | H |
| 414 | H | H | H | H | H | L | L | H |
| 415 | H | H | H | L | H | L | L | L |
| 416 | L | L | L | L | H | L | L | L |
| 417 | L | H | H | L | H | L | L | H |
| 418 | L | H | L | H | H | L | L | H |
| 419 | L | L | H | L | L | L | L | H |
| 420 | L | H | L | H | H | L | L | L |
| 421 | L | H | H | H | H | L | L | H |
| 422 | L | L | H | H | L | L | L | L |
| 423 | H | H | H | H | H | H | H | H |
| 424 | L | H | L | L | L | L | L | L |
| 425 | H | nt | L | nt | nt | L | L | H |
| 426 | H | H | H | L | L | L | L | H |
| 427 | L | H | H | L | L | L | L | H |
| 428 | H | H | H | H | H | L | H | H |
| 429 | H | H | H | H | H | L | H | H |
| 430 | H | H | H | H | H | L | L | H |
| 431 | H | H | H | H | H | L | H | H |
| 432 | H | H | H | H | H | L | L | H |
| 433 | L | H | H | H | H | L | H | H |
| 434 | H | H | H | H | H | L | L | H |
| 435 | L | L | H | L | L | H | L | L |
| 436 | H | H | H | H | H | L | L | H |
| 437 | L | L | L | H | L | L | L | H |
| 438 | L | H | H | L | H | L | L | L |
| 439 | H | L | L | L | L | L | L | H |
| 440 | H | L | L | L | L | L | L | L |
| 441 | L | L | L | L | L | L | L | H |
| 442 | H | L | L | H | H | L | H | H |
| 443 | L | H | H | L | H | H | H | H |
| 444 | L | H | H | L | H | L | H | H |
| 445 | L | H | H | L | H | L | L | H |
| 446 | H | H | L | L | L | L | L | L |
| 447 | H | H | H | H | H | L | H | H |
| 448 | L | H | L | L | L | L | L | L |
| 449 | L | H | L | L | L | L | L | L |
| 450 | H | H | H | H | H | H | H | H |

TABLE 5-continued

| Compounds | Test A | Test B | Test C | Test D | Test E | Test F | Test G | Test H |
|---|---|---|---|---|---|---|---|---|
| 451 | H | L | L | H | L | L | L | L |
| 452 | H | H | H | H | H | L | H | H |
| 453 | L | H | H | H | H | L | H | H |
| 454 | L | H | H | H | H | L | L | H |
| 455 | L | H | H | H | H | L | H | H |
| 456 | H | H | H | H | H | L | H | H |
| 457 | H | H | H | H | H | L | L | H |
| 458 | H | H | H | H | H | L | H | H |
| 459 | H | H | H | H | H | L | H | H |
| 460 | H | H | H | H | H | L | H | H |
| 461 | H | H | H | H | H | L | H | H |
| 462 | L | H | H | L | H | H | L | H |
| 463 | H | H | H | H | H | L | H | H |
| 464 | L | H | H | H | H | L | L | H |
| 465 | H | H | H | H | H | L | H | H |
| 466 | L | L | H | H | L | L | L | L |
| 467 | H | H | H | H | H | L | H | H |
| 468 | H | H | H | H | H | H | H | H |
| 469 | L | H | H | L | L | L | L | H |
| 470 | L | L | H | L | L | L | L | H |
| 471 | H | H | H | H | H | L | H | H |
| 472 | H | H | H | H | H | L | H | H |
| 473 | H | H | H | H | H | L | L | L |
| 474 | H | H | H | H | H | L | H | H |
| 475 | H | H | H | H | H | L | H | H |
| 476 | H | H | H | H | H | L | H | H |
| 477 | H | H | H | H | H | L | L | H |
| 478 | L | L | H | H | L | L | L | L |
| 479 | H | H | H | H | H | L | H | H |
| 480 | L | H | L | H | L | L | L | H |
| 481 | L | H | L | H | H | L | L | H |
| 482 | H | H | H | H | H | L | H | H |
| 483 | H | H | H | H | H | L | H | H |
| 484 | H | H | L | H | H | L | H | H |
| 485 | H | H | H | L | H | L | L | H |
| 486 | H | H | H | H | H | L | L | H |
| 487 | H | H | H | H | H | H | H | H |
| 488 | H | H | H | L | H | L | L | H |
| 489 | H | H | H | H | H | L | L | H |
| 490 | L | L | L | L | H | L | H | L |
| 491 | L | H | H | H | H | L | L | L |
| 492 | H | H | H | H | H | L | H | H |
| 493 | H | H | H | H | H | L | H | H |
| 494 | H | H | H | H | H | L | H | H |
| 495 | L | H | H | H | H | L | L | L |
| 496 | H | H | H | H | H | L | H | H |
| 497 | H | H | H | H | H | L | H | H |
| 498 | H | H | H | L | H | L | L | H |
| 499 | H | H | H | H | H | L | H | H |
| 500 | H | H | H | L | H | L | H | H |
| 501 | H | H | H | H | H | L | L | H |
| 502 | H | H | H | H | H | L | H | H |
| 503 | H | H | H | H | H | L | H | H |
| 504 | H | H | H | H | H | L | H | H |
| 505 | H | H | H | H | H | L | H | H |
| 506 | H | H | H | H | H | L | H | H |
| 507 | H | H | H | H | H | L | H | H |
| 508 | H | H | H | H | H | L | H | H |
| 509 | H | L | L | H | H | L | H | H |
| 510 | H | L | L | L | L | L | L | L |
| 511 | H | H | H | L | H | L | H | H |
| 519 | H | H | H | L | H | L | H | H |
| 513 | H | H | H | H | H | L | H | H |
| 514 | L | H | H | H | H | L | H | H |
| 515 | H | H | L | L | H | L | H | H |
| 516 | H | H | H | H | H | L | H | H |
| 517 | L | nt | H | nt | nt | L | H | H |
| 518 | H | H | H | H | H | L | L | H |
| 519 | H | H | H | H | H | L | H | H |
| 520 | H | H | H | H | H | L | H | H |
| 521 | L | H | H | H | H | L | H | L |
| 522 | H | H | H | H | H | H | H | H |
| 523 | H | H | H | H | H | L | H | H |
| 524 | H | H | H | H | H | L | H | H |
| 525 | H | H | H | H | H | L | H | H |

TABLE 5-continued

| Compounds | Test A | Test B | Test C | Test D | Test E | Test F | Test G | Test H |
|---|---|---|---|---|---|---|---|---|
| 526 | H | H | L | H | L | L | L | H |
| 527 | H | H | H | H | H | L | H | H |
| 528 | H | H | H | H | H | L | L | H |
| 529 | H | L | H | H | H | L | L | L |
| 530 | H | H | H | H | H | L | L | H |
| 531 | H | H | H | H | H | L | L | H |

INDUSTRIAL APPLICABILITY

The pyridone compounds of the invention are novel compounds capable of controlling plant diseases, and are valuable as agricultural chemicals, for example, agricultural and horticultural pest control agents, in particular, agricultural and horticultural fungicides.

The entire contents of Japanese Patent Application No. 2017-77801 (filed Apr. 10, 2017) are incorporated herein by reference.

All publications, patent applications and technical standards mentioned in the present specification are herein incorporated by reference to the same extent as if each individual publication, patent application or technical standard was specifically and individually indicated to be incorporated by reference.

The invention claimed is:

1. A compound of formula (1), or a salt thereof:

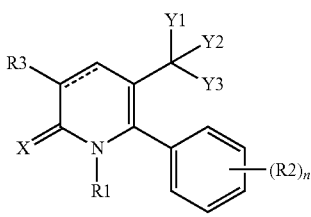

(1)

wherein R1 represents:
a C1-C6 alkyl group optionally substituted with one substituent A, or
a C1-C6 haloalkyl group;
R2 represents:
a hydroxy group,
a cyano group,
a halogen atom,
a C1-C6 alkyl group optionally substituted with one substituent B,
a C1-C6 alkoxy group optionally substituted with one substituent B,
a C2-C6 alkenyloxy group optionally substituted with one substituent B, or
a C3-C6 alkynyloxy group optionally substituted with one substituent B;
R3 represents:
a hydrogen atom,
a halogen atom, or
a C1-C6 alkyl group optionally substituted with one substituent A;
Y1, Y2 and Y3 are independent of one another and each represent:
a hydrogen atom,
a hydroxy group,
a halogen atom,
a C1-C9 alkyl group optionally substituted with one substituent B,
a C1-C6 haloalkyl group,
a C3-C8 cycloalkyl group optionally substituted with one substituent B,
a C2-C6 alkynyl group optionally substituted with one substituent B,
a C1-C6 alkoxy group optionally substituted with one substituent B,
a C1-C6 haloalkoxy group,
RdC(═O)— wherein Rd is a hydrogen atom, a C1-C6 alkyl group optionally substituted with one substituent C, a C1-C6 haloalkyl group, a C3-C8 cycloalkyl group, a C1-C6 alkoxy group, a C1-C6 haloalkoxy group, a C3-C8 cycloalkoxy group, or RaRbN— wherein Ra and Rb are independent of one another and each represent a hydrogen atom, a C1-C6 alkyl group optionally substituted with one substituent C, a C1-C6 haloalkyl group, or a C3-C8 cycloalkyl group, or Ra and Rb, together with the nitrogen atom to which they are bonded, form aziridinyl, azetidinyl, pyrrolidinyl, piperidinyl, homopiperidinyl or azocanyl,
RdC(═O)O— wherein Rd is the same as defined hereinabove, an aryloxy group optionally substituted with 0 to 5 substituent(s) D,
RaRbN— wherein Ra and Rb are the same as defined hereinabove,
Rg(RhO)N— wherein Rg and Rh are independent of one another and each represent a hydrogen atom, a C1-C6 alkyl group optionally substituted with one substituent C, a C1-C6 haloalkyl group, or a C3-C8 cycloalkyl group, or
ReC(═O)N(Rf)— wherein Re and Rf are independent of one another and each represent a hydrogen atom, a C1-C6 alkyl group optionally substituted with one substituent C, a C1-C6 haloalkyl group, a C3-C8 cycloalkyl group, a C1-C6 alkoxy group, a C1-C6 haloalkoxy group, a C3-C8 cycloalkoxy group, or RaRbN— wherein Ra and Rb are the same as defined hereinabove,
or Y1 and Y2, together with the carbon atom to which Y1, Y2 and Y3 are bonded, form:
a carbonyl group,
a C2-C6 alkenyl group optionally substituted with one substituent B,
a C2-C6 haloalkenyl group, or
a C3-C8 cycloalkyl group optionally substituted with one substituent B, and
Y3 represents:
a hydrogen atom,
a halogen atom,
a C1-C9 alkyl group optionally substituted with one substituent B,
a C3-C8 cycloalkyl group optionally substituted with one substituent B, or a C2-C6 alkynyl group optionally substituted with one substituent B, or or Y1, Y2 and Y3, together with the carbon atom to which Y1, Y2 and Y3 are bonded, represent:
  a cyano group, or
  a C2-C6 alkynyl group optionally substituted with one substituent B;

n represents an integer of 1 to 5 with the proviso that when n is 2 or greater, the two or more substituents R2 are independent of one another;

X represents an oxygen atom or a sulfur atom;

the bond with the broken line represents a double bond or a single bond;

the substituent A is independently selected from the group consisting of hydroxy group, cyano group, C3-C8 cycloalkyl groups, C1-C6 alkoxy groups, C1-C6 haloalkoxy groups, C3-C8 cycloalkoxy groups, RaRbN— wherein Ra and Rb are the same as defined hereinabove and Rc-L- wherein Rc and L are the same as defined hereinabove;

the substituent B is independently selected from the group consisting of hydroxy group, cyano group, C3-C8 cycloalkyl groups, C1-C6 alkoxy groups, C1-C6 haloalkoxy groups, C3-C8 cycloalkoxy groups, C2-C6 alkoxyalkoxy groups, RaRbN— wherein Ra and Rb are the same as defined hereinabove), Rc-L- wherein Rc and L are the same as defined hereinabove, RdC (=O)— wherein Rd is the same as defined hereinabove and 3 to 6-membered ring groups containing 1 to 2 oxygen atoms;

the substituent C is independently selected from the group consisting of cyano group, C1-C6 alkoxy groups, C1-C6 haloalkoxy groups and C3-C8 cycloalkoxy groups; and the substituent D is independently selected from the group consisting of halogen atoms, hydroxy group, cyano group, nitro group, C1-C6 alkyl groups optionally substituted with one substituent C, C1-C6 haloalkyl groups, C3-C8 cycloalkyl groups, C1-C6 alkoxy groups, C1-C6 haloalkoxy groups and C3-C8 cycloalkoxy groups.

2. An agricultural and horticultural pest control agent comprising the compound according to claim 1 or a salt thereof as an active ingredient.

3. An agricultural and horticultural fungicide comprising the compound according to claim 1 or a salt thereof as an active ingredient.

4. A method for controlling a plant disease, comprising applying the agricultural and horticultural pest control agent according to claim 2 to a plant, a plant seed or a soil on which a plant is or is to be cultivated.

5. A method for controlling a plant disease, comprising applying the agricultural and horticultural fungicide according to claim 3 to a plant, a plant seed or a soil on which a plant is or is to be cultivated.

* * * * *